US009663502B2

(12) United States Patent
Aicher et al.

(10) Patent No.: US 9,663,502 B2
(45) Date of Patent: May 30, 2017

(54) 2-ACYLAMIDOMETHYL AND SULFONYLAMIDOMETHYL BENZOXAZINE CARBAMATES FOR INHIBITION OF RORGAMMA ACTIVITY AND THE TREATMENT OF DISEASE

(71) Applicants: Merck Sharp & Dohme Corp., Rahway, NJ (US); Lycera Corporation, Ann Arbor, MI (US)

(72) Inventors: Thomas D. Aicher, Ann Arbor, MI (US); Chad A. VanHuis, Hartland, MI (US); John MacLean, Brookline, MA (US); Brian M. Andresen, Boston, MA (US); Kenneth J. Barr, Boston, MA (US); Corey Bienstock, Natick, MA (US); Neville J. Anthony, Northborough, MA (US); Matthew Daniels, Somerville, MA (US); Yuan Liu, Billerica, MA (US); Catherine White, Boston, MA (US); Blair T. Lapointe, Boston, MA (US); Nunzio Sciammetta, Boston, MA (US); Vladimir Simov, Boston, MA (US); Wesley B. Trotter, Boston, MA (US); Kun Liu, Boston, MA (US)

(73) Assignees: Lycera Corporation, Ann Arbor, MI (US); Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 15/103,407

(22) PCT Filed: Dec. 19, 2014

(86) PCT No.: PCT/US2014/071656
§ 371 (c)(1),
(2) Date: Jun. 10, 2016

(87) PCT Pub. No.: WO2015/095788
PCT Pub. Date: Jun. 25, 2015

(65) Prior Publication Data
US 2016/0304505 A1 Oct. 20, 2016

Related U.S. Application Data

(60) Provisional application No. 61/919,107, filed on Dec. 20, 2013.

(51) Int. Cl.
C07D 265/36 (2006.01)
C07D 413/12 (2006.01)
(Continued)

(52) U.S. Cl.
CPC .......... *C07D 413/12* (2013.01); *A61K 31/538* (2013.01); *A61K 45/06* (2013.01);
(Continued)

(58) Field of Classification Search
CPC .................................................. C07D 265/36
(Continued)

(56) References Cited

U.S. PATENT DOCUMENTS 5,583,152 A * 12/1996 Bernstein ............. C07D 209/18
514/224.2
5,985,903 A 11/1999 Assmann et al.
(Continued)

FOREIGN PATENT DOCUMENTS

EP 0882718 A1 12/1998
EP 1820515 A1 8/2007
(Continued)

OTHER PUBLICATIONS

International Search Report and Written Opinion for PCT/US2014/071656 dated Mar. 12, 2015 (8 pages).
International Search Report and Written Opinion for PCT/US2014/071671 dated Apr. 28, 2015 (10 pages).
Annunziato et al., "Type 17 T helper cells-origins, features and possible roles in rheumatic disease," 5 Nat. Rev. Rheumatol. 325-31 (2009).
Boaventura et al., "Human mucosal leishmaniasis: Neutrophils infiltrate areas of tissue damage that express high levels of Th17-related cytokines," 40 Eur. J. Immunol. 2830-36 (2010).
Buonocore et al., "Innate lymphoid cells drive interleukin-23-dependent innate intestinal pathology," 464 Nature 1371-75 (2010).
(Continued)

*Primary Examiner* — Niloofar Rahmani
(74) *Attorney, Agent, or Firm* — Goodwin Procter LLP

(57) ABSTRACT

The invention provides certain benzoxazine compounds of the Formula (I) or pharmaceutically acceptable salts thereof, wherein $R^1$, $R^2$, $R^a$, $R^b$, $R^c$, $R^d$, $R^g$, and Cy are as defined herein. The invention also provides pharmaceutical compositions comprising such compounds of the Formula (I) or pharmaceutically acceptable salts thereof, and methods of using the compounds of the Formula (I) or pharmaceutically acceptable salts thereof or pharmaceutical compositions comprising the same for treating diseases or conditions mediated by RORgammaT.

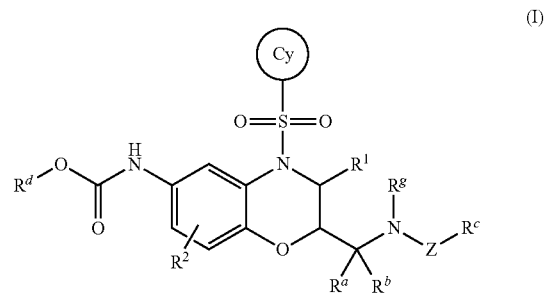

26 Claims, No Drawings

(51) Int. Cl.
    *C07D 471/04*     (2006.01)
    *A61K 31/538*     (2006.01)
    *A61K 45/06*     (2006.01)
    *C07D 413/14*     (2006.01)
    *C07D 417/12*     (2006.01)
    *C07D 487/04*     (2006.01)
    *C07D 498/04*     (2006.01)
    *C07D 513/04*     (2006.01)

(52) U.S. Cl.
    CPC ......... *C07D 265/36* (2013.01); *C07D 413/14* (2013.01); *C07D 417/12* (2013.01); *C07D 471/04* (2013.01); *C07D 487/04* (2013.01); *C07D 498/04* (2013.01); *C07D 513/04* (2013.01)

(58) Field of Classification Search
    USPC ....................................................... 544/105
    See application file for complete search history.

(56) References Cited

U.S. PATENT DOCUMENTS

| | | | |
|---|---|---|---|
| 6,020,354 | A | 2/2000 | Assmann et al. |
| 6,037,367 | A | 3/2000 | Christensen, IV et al. |
| 6,160,001 | A | 12/2000 | Assmann et al. |
| 6,172,092 | B1 | 1/2001 | Assmann et al. |
| 6,180,643 | B1 | 1/2001 | Zablocki et al. |
| 6,348,032 | B1 | 2/2002 | Sperl et al. |
| 6,352,985 | B1 | 3/2002 | Yamasaki et al. |
| 6,387,939 | B1 | 5/2002 | Assmann et al. |
| 6,440,973 | B1 | 8/2002 | Zablocki et al. |
| 6,534,535 | B1 | 3/2003 | Zhu et al. |
| 6,605,634 | B2 | 8/2003 | Zablocki et al. |
| 6,638,960 | B2 | 10/2003 | Assmann et al. |
| 6,683,091 | B2 | 1/2004 | Asberom et al. |
| 6,828,344 | B1 | 12/2004 | Seehra et al. |
| 7,084,176 | B2 | 8/2006 | Morie et al. |
| 7,115,750 | B1 | 10/2006 | Kato et al. |
| 7,138,401 | B2 | 11/2006 | Kasibhatla et al. |
| 7,329,675 | B2 | 2/2008 | Cox et al. |
| 7,420,059 | B2 | 9/2008 | O'Connor et al. |
| 7,482,342 | B2 | 1/2009 | D'Orchymont et al. |
| 7,569,571 | B2 | 8/2009 | Dong et al. |
| 7,696,200 | B2 | 4/2010 | Ackermann et al. |
| 7,713,996 | B2 | 5/2010 | Ackermann et al. |
| 7,741,495 | B2 | 6/2010 | Liou et al. |
| 7,799,933 | B2 | 9/2010 | Ceccarelli et al. |
| 9,266,827 | B2 | 2/2016 | Aicher et al. |
| 9,512,111 | B2 | 12/2016 | Glick et al. |
| 2006/0004000 | A1 | 1/2006 | D'Orchymont et al. |
| 2006/0100230 | A1 | 5/2006 | Bischoff et al. |
| 2007/0010537 | A1 | 1/2007 | Hamamura et al. |
| 2007/0010670 | A1 | 1/2007 | Hirata et al. |
| 2007/0049556 | A1 | 3/2007 | Zhang et al. |
| 2007/0060567 | A1 | 3/2007 | Ackermann et al. |
| 2007/0154487 | A1 | 7/2007 | Littman et al. |
| 2007/0191603 | A1 | 8/2007 | Ackermann et al. |
| 2007/0197782 | A1 | 8/2007 | Clough et al. |
| 2007/0281922 | A1 | 12/2007 | Liu et al. |
| 2008/0027100 | A1 | 1/2008 | McCormick et al. |
| 2008/0058386 | A1 | 3/2008 | Liou et al. |
| 2008/0153805 | A1 | 6/2008 | Ceccarelli et al. |
| 2008/0305169 | A1 | 12/2008 | Miki et al. |
| 2009/0005410 | A1 | 1/2009 | Charvat et al. |
| 2009/0075973 | A1 | 3/2009 | Newcom et al. |
| 2009/0247502 | A1 | 10/2009 | Newcom et al. |
| 2009/0275586 | A1 | 11/2009 | Govek et al. |
| 2010/0022515 | A1 | 1/2010 | Alper et al. |
| 2010/0130484 | A1 | 5/2010 | Ackermann et al. |
| 2010/0234340 | A1 | 9/2010 | Schunk et al. |
| 2011/0053915 | A1 | 3/2011 | Ivaschenko et al. |
| 2011/0112070 | A1 | 5/2011 | Baldwin et al. |
| 2011/0118246 | A1 | 5/2011 | Baldwin et al. |
| 2011/0130384 | A1 | 6/2011 | Setoh et al. |
| 2011/0178063 | A1 | 7/2011 | Baldwin et al. |
| 2014/0088094 | A1 | 3/2014 | Glick et al. |
| 2015/0111877 | A1 | 4/2015 | Aicher et al. |
| 2015/0126493 | A1 | 5/2015 | Aicher et al. |
| 2016/0304476 | A1 | 10/2016 | Aicher et al. |
| 2016/0311787 | A1 | 10/2016 | Aicher et al. |

FOREIGN PATENT DOCUMENTS

| | | |
|---|---|---|
| EP | 2181710 A1 | 5/2010 |
| JP | 6-250441 A | 9/1994 |
| JP | 2004307487 A | 11/2004 |
| WO | WO-92/13856 A1 | 8/1992 |
| WO | WO-97/01561 A1 | 1/1997 |
| WO | WO-97/48697 A1 | 12/1997 |
| WO | WO-98/22457 A1 | 5/1998 |
| WO | WO-00/17202 A1 | 3/2000 |
| WO | WO-01/12600 A1 | 2/2001 |
| WO | WO-02/100819 A1 | 12/2002 |
| WO | WO-03/014075 A2 | 2/2003 |
| WO | WO-2004/056830 A1 | 7/2004 |
| WO | WO-2005/028434 A2 | 3/2005 |
| WO | WO-2005/037834 A1 | 4/2005 |
| WO | WO-2006/007486 A2 | 1/2006 |
| WO | WO-2006/057460 A1 | 6/2006 |
| WO | WO-2007/024944 A1 | 3/2007 |
| WO | WO-2007/031429 A1 | 3/2007 |
| WO | WO-2007/093507 A1 | 8/2007 |
| WO | WO-2007/125405 A2 | 11/2007 |
| WO | WO-2007/138998 A1 | 12/2007 |
| WO | WO-2008/003703 A1 | 1/2008 |
| WO | WO-2008/045664 A2 | 4/2008 |
| WO | WO-2008/062740 A1 | 5/2008 |
| WO | WO-2008/074692 A1 | 6/2008 |
| WO | WO-2008/097428 A2 | 8/2008 |
| WO | WO-2008/150827 A1 | 12/2008 |
| WO | WO-2009/032667 A1 | 3/2009 |
| WO | WO-2009/035997 A2 | 3/2009 |
| WO | WO-2009/077956 A2 | 6/2009 |
| WO | WO-2009/147187 A1 | 12/2009 |
| WO | WO-2009/149819 A1 | 12/2009 |
| WO | WO-2009/149820 A1 | 12/2009 |
| WO | WO-2009/157196 A1 | 12/2009 |
| WO | WO-2010/017827 A1 | 2/2010 |
| WO | WO-2010/038901 A1 | 4/2010 |
| WO | WO-2010/057101 A2 | 5/2010 |
| WO | WO-2010/059602 A2 | 5/2010 |
| WO | WO-2010/071853 A1 | 6/2010 |
| WO | WO-2010/102958 A1 | 9/2010 |
| WO | WO-2010/117425 A1 | 10/2010 |
| WO | WO-2010/123139 A1 | 10/2010 |
| WO | WO-2010/125082 A1 | 11/2010 |
| WO | WO-2011/019634 A2 | 2/2011 |
| WO | WO-2011/059839 A1 | 5/2011 |
| WO | WO-2011/067364 A1 | 6/2011 |
| WO | WO-2011/067365 A1 | 6/2011 |
| WO | WO-2011/067366 A1 | 6/2011 |
| WO | WO-2011/109059 A1 | 9/2011 |
| WO | WO-2012/032065 A1 | 3/2012 |
| WO | WO-2012/032067 A1 | 3/2012 |
| WO | WO-2012/037108 A1 | 3/2012 |
| WO | WO-2012/064744 A2 | 5/2012 |
| WO | WO-2012/139775 A1 | 10/2012 |
| WO | WO-2013/169704 A2 | 11/2013 |

OTHER PUBLICATIONS

Eberl et al., "An essential function for the nuclear receptor RORγt in the generation of fetal lymphoid tissue inducer cells," 5(1) Nat. Immunol. 64-73 (2004).

Figueroa-Vega et al., "Increased Circulating Pro-Inflammatory Cytokines and Th17 Lymphocytes in Hashimoto's Thyroiditis," 95(2) J. Clin. Endocrinol. Metab. 953-62 (2010).

Gennaro (ed.), Remington: The Science and Practice of Pharmacy, 20th edition (2000).

He et al., "RORγt, a Novel Isoform of an Orphan Receptor, Negatively Regulates Fas Ligand Expression and IL-2 Production in T Cells," 9 Immunity 797-806 (1998).

(56) References Cited

OTHER PUBLICATIONS

Hirose et al., "RORγ: the third member of ROR/RZR orphan receptor subfamily that is highly expressed in skeletal muscle," 205 Biochem. Biophys. Res. Comm. 1976-83 (1994).
Hueber et al., "Cutting Edge: Mast Cells Express IL-17A in Rheumatoid Arthritis Synovium," 184 J. Immunol. 3336-40 (2010).
Ivanov et al., "The Orphan Nuclear Receptor RORγt Directs the Differentiation Program of Proinflammatory IL-17+ T Helper Cells," 126 Cell 1121-33 (2006).
Jia et al., "The T helper type 17/regulatory T cell imbalance in patients with acute Kawasaki disease," 162 Clin. Exp. Immunol. 131-37 (2010).
Jin et al., "Structural Basis for Hydroxycholesterols as Natural Ligands of Orphans Nuclear Receptor RORγ," 24(5) Mol. Endocrinol. 923-29 (2010).
Kastelein et al., "Discovery and Biology of IL-23 and IL-27: Related but Functionally Distinct Regulators of Inflammation," 25 Annu. Rev. Immunol. 221-42 (2007).
Kurebayashi et al., "Selective LXXLL peptides antagonize transcriptional activation by the retinoid-related orphan receptor RORγ," 315 Biochem. Biophys. Res. Comm. 919-27 (2004).
Louten et al., "Development and function of TH17 cells in health and disease," 123(5) J. Allergy Clin. Immunol. 1004-11 (2009).
Miossec et al., "Interleukin-17 and Type 17 Helper T Cells," 361(9) New Eng. J. Med. 888-98 (2009).
Sun et al., "Requirement for RORγ in Thymocyte Survival and Lymphoid Organ Development," 288 Science 2369-72 (2000).
Sutton et al., "Interleukin-1 and IL-23 Induce Innate IL-17 Production from γδ T Cells, Amplifying Th17 Responses and Autoimmunity," 31 Immunity 331-41 (2009).
Wang et al., "Identification of SR1078, a Synthetic Agonist for the Orphan Nuclear Receptors RORα and RORγ," 5(11) ACS Chem. Biol. 1029-34 (2010).
Wang et al., "Modulation of Retinoic Acid Receptor-related Orphan Receptor α and γ Activity by 7-Oxygenated Sterol Ligands," 285(7) J. Bio. Chem. 5013-25 (2010).
Xie et al., "RORγt Recruits Steroid Receptor Coactivators to Ensure Thymocyte Survival," 175(6) J. Immunol. 3800-09 (2005).
Yang et al., "T Helper 17 Lineage Differentiation is programmed by Orphan Nuclear Receptors RORα and RORγ," 28 Immunity 29-39 (2008).
André et al., "Disruption of retinoid-related orphan receptor β changes circadian behaviour, causes retinal degeneration and leads to vacillans phenotype in mice," 17(14) The EMBO J. 3867-77 (1998).
Becker-André et al., "Identification of nuclear receptor mRNAs by RT-PCR amplification of conserved zinc-finger motif sequences," 194(3) Biochem. Biophys. Res. Comm. 1371-79 (1993).
Burris et al., "Targeting Orphan Nuclear Receptors for Treatment of Metabolic Diseases and Autoimmunity," 19(1) Chem. Biol. 51-59 (2012).
Cai, et al., "Pivotal Role of Dermal IL-17-Producing γδ T Cells in Skin Inflammation", Immunity (2011) vol. 35, pp. 596-610.
Carlberg et al., "RZRs, a new family of retinoid-related orphan receptors that function as both monomers and homodimers," 8 Mol. Endocrinol. 757-70 (1994).
D. van der Heijde, et al., "Secukinumab Provides Significant and Sustained Inhibition of Joint Structural Damage in a Phase III Study of Active Psoriatic Arthritis" Arthritis & Rheumatology Brief Report, Accepted Article DOI: 10.1002/art.39685, American College of Rheumatology, (2016) pp. 1-27.
Baeten, et al., "Secukinumab, an Interleukin-17A Inhibitor, in Ankylosing Spondylitis", The New England Journal of Medicine, (2015) vol. 373, pp. 2534-2548.
Dussault et al., "Orphan nuclear receptor RORα-deficient mice display the cerebellar defects of staggerer," 70 Mech. Develop. 147-53 (1998).
Giguère et al., "Isoform-specific amino-terminal domains dictate DNA-binding properties of RORα, a novel family of orphan hormone nuclear receptors," 8 Genes & Develop. 538-53 (1994).

Huh et al., "Small molecule inhibitors of RORγt: Targeting Th17 cells and other applications," 42 Eur. J. Immunol. 2232-2237 (2012).
Krueger, "A welcome surprise in psoriasis", Nature Medicine, (2012) vol. 18, No. 12, pp. 1750-1751.
Leonardi, et al., "Anti-Interleukin-17 Monoclonal Antibody Ixekizumab in Chronic Plaque Psoriasis", The New England Journal of Medicine, (2012) vol. 366, Iss. 13, pp. 1-10.
Martinez, "Th17-biased RORγt transgenic mice become susceptible to a viral model for multiple sclerosis", Brain, Behavior, and Immunity, (2014) vol. 43, pp. 86-97.
Medvedev et al., "Cloning of a cDNA encoding the murine orphan receptor RZR/RORγ and characterization of its response element," 181 Gene 199-206 (1996).
Nakajima, et al., "IL-17A as an Inducer for Th2 Immune Responses in Murine Atopic Dermatitis Models", Journal of Investigative Dermatology, (2014) vol. 134, pp. 2122-2130.
Ortiz et al., "TOR: a new orphan receptor expressed in the thymus that can modulate retinoid and thyroid hormone signals," 9 Mol. Endocrinol. 1679-91 (1995).
Papp, et al. "Brodalumab, an Anti-Interleukin-17-Receptor Antibody for Psoriasis", The New England Journal of Medicine, (2012) vol. 366, Iss. 13, 9 pgs.
Skepner, et al., "Pharmacologic Inhibition of RORγt RegulatesTh17 Signature Gene Expression and Suppresses Cutaneous Inflammation in Vivo", The Journal of Immunology, (2014) pp. 1-12.
Smith, "The Bench-to-Bedside Story of IL-17 and the Therapeutic Efficacy of its Targeting in Spondyloarthritis", Curr Rheumatol Rep. (2016) vol. 18, pp. 1-10.
Solt et al., "Action of RORs and their ligands in (patho)physiology," 23(12) Trends in Endocrinology and Metabolism. 619-627 (2012).
Tlustochowicz, et al. "Efficacy and Safety of Subcutaneous and Intravenous Loading Dose Regimens of Secukinumab in Patients with Active Rheumatoid Arthritis: Results from a Randomized Phase II Study" The Journal of Rheumatology, (2016) vol. 43, No. 3, pp. 495-503.
Villey et al., "RORγT, a thymus-specific isoform of the orphan nuclear receptor RORγ/TOR, is up-regulated by signaling through the pre-T cell receptor and binds to the TEA promoter," 29 Eur. J. Immunol. 4072-80 (1999).
Wiesenberg et al., "Transcriptional activation of the nuclear receptor RZRα by the pineal gland hormone melatonin and identification of CGP 52608 as a synthetic ligand," 23(3) Nucl. Acids Res. 327-33 (1995).
Xiao, et al., "Small-Molecule RORγt Antagonists Inhibit T Helper 17 Cell Transcriptional Network by Divergent Mechanisms", Immunity (2014) vol. 40, pp. 477-489.
Arisawa et al., "Development of Isomerization and Cycloisomerization with Use of a Ruthenium Hydride with N-Heterocyclic Carbene and Its Application to the Synthesis of Heterocycles," 71 J. Org. Chem. 4255-61 (2006).
Berge et al., "Pharmaceutical salts," 66(1) J. Pharm. Sci. 1-19 (1977).
Bhagawanth et al., "Room-Temperature Pd-Catalyzed Amidation of Aryl Bromides Using tert-Butyl Carbamate," 74 J. Org. Chem. 4634-37 (2009).
Boger et al., "Regiocontrolled Nucleophilic Addition to Selectively Activated p-Quinone Diimines: Alternative Preparation of a Key Intermediate Employed in the Preparation of the CC-1065 Lefthand Subunit," 55 J. Org. Chem. 1379-90 (1990).
Carroll et al., "Synthesis, Nicotinic Acetylcholine Receptor Binding, and Antinociceptive Properties of 2-exo-2-(2',3'-Disubstituted 5'-pyridinyl)-y-azabicyclo[2.2.1]heptanes: Epibatidine Analogues," 45 J. Med. Chem. 4755-61 (2002).
Chang et al., "7-Aroyl-aminoindoline-1-sulfonamides as a Novel Class of Potent Antitubulin Agents," 49 J. Med. Chem. 6656-59 (2006).
Colbon et al., "Double Arylation of Allyl Alcohol via a One-Pot Heck Arylation—Isomerization—Acylation Cascade," 13 Org. Lett. 5456-59 (2011).
De et al., Methods in Molecular Biology 1184, second edition, Human Press (2014).

(56) References Cited

OTHER PUBLICATIONS

Gould, "Salt selection for basic drugs," 33 Int'l J. Pharmaceutics 201-217 (1986).
Grasa et al., "Amination Reactions of Aryl Halides with Nitrogen-Containing Reagents Mediated by Palladium/Imidazolium Salt Systems," 66 J. Org. Chem. 7729-37 (2001).
Greene & Wuts, Protective Groups in Organic Synthesis, 2d Edition (1991).
Guimond et al., "Rhodium(III)-Catalyzed Isoquinolone Synthesis: The N—O Bond as a Handle for C—N Bond Formation and Catalyst Turnover," 132(20) J. Am. Chem. Soc. 6908-09 (2010).
Hanessian et al., "A versatile protocol for the stereocontrolled elaboration of vicinal secondary and tertiary centers of relevance to natural product synthesis," 52(6) J. Org. Chem. 1170-72 (1987).
Hauser et al., "Relative Ease of Cyclization of 2-, 3-, and 4-Aminopyridine Derivatives. Synthesis of Naphthyridines," 15 J. Org. Chem. 1224-32 (1950).
International Search Report and Written Opinion for PCT/US2011/059788 dated May 23, 2012 (23 pages).
International Search Report and Written Opinion for PCT/US2013/039422 dated Oct. 11, 2013 (9 pages).
International Search Report and Written Opinion for PCT/US2013/039839 dated Oct. 18, 2013 (8 pages).
International Search Report and Written Opinion for PCT/US2013/040085 dated Oct. 23, 2013 (9 pages).
Ishikura et al., "An Efficient Synthesis of 3-Heteroarylpyridines via Diethyl-(3-pyridyl)-borane," Synthesis 936-38 (1984).
Jayashree et al., "Design and synthesis of 2-quinolones as antioxidants and antimicrobials: a rational approach," 19 Med. Chem. Res. 193-209 (2010).
Jiang et al., "Synthesis and Cytotoxicity Evaluation of Novel Indolylpyrimidines and Indolylpyrazines as Potential Antitumor Agents," 9 Bioorg. Med. Chem. 1149-54 (2001).
Li et al., "Chemical Libraries via Sequential C—H Functionalization of Phenols," 10 J. Comb. Chem. 170-74 (2008).
Li et al., "Synthesis and Resolution of a Novel Chiral Diamine Ligand and Application to Asymmetric Lithiation-Substitution," 2 Org. Lett. 875-78 (2000).
Liu et al., "1-Sulfonylindazoles as potent and selective 5-HT6 ligands," 19 Bioorg. Med. Chem. Lett. 2413-15 (2009).
Murase et al., "A New Concise Synthesis of Arcyriacyanin A and Its Unique Inhibitory Activity against a Panel of Human Cancer Cell Line," 48(1) Chem. Pharm. Bull. 81-84 (2000).
Ninomiya et al., "Phosphorous in Organic Synthesis—VII: Diphenyl Phosphorazidate (DPPA). A New Convenient Reagent for a Modified Curtius Reaction," 30 Tetrahedron 2151-57 (1975).
Nyrkova et al., "Synthesis of a New Heterocyclic System—3,4-Diazaphenoxazine," 1(9) J. Org. Chem. USSR, 1711-14, translating 1(9) Zh. Org. Khimii, 1688-91 (1965).
Santilli et al., "Synthesis of 5,6,7,8-Tetrahydro-5-oxopyrido[2,3-*d*] pyrimidine-6-carbonitriles and -6-carboxylic Acid Esters," 12 J. Het. Chem. 311-16 (1975).
Skraup, "Eine Synthese des Chinolins," 13 Berichte 2086-87 (1880).
Stefko et al., "General and Modular Synthesis of Isomeric 5-Substituted Pyridin-2-yl and 6-Substituted Pyridin-3-yl C-Ribonucleosides Bearing Diverse Alkyl, Aryl, Hetaryl, Amino, Carbamoyl, and Hydroxy Groups," 76 J. Org. Chem. 6619-35 (2011).
STN Columbus, pp. 1-40 (2011).
Takano et al., "A new synthesis of a steroid side chain via stereocontrolled protonation: synthesis of (−)-desmosterol," 14 J. Chem. Soc., Chem. Commun. 760-61 (1983).
Van Heerden et al., "Dibutylboron triflate promoted conjugate addition of benzylic and allylic organocopper reagents to chiral α,β-unsaturated N-acyl imidazolidinones" 38(10) Tet. Lett. 182-124 (1997).
Wang et al., "Synthesis of new carbon-11-labeled 7-aroyl-aminoindoline-1-sulfonamides as potential PET agents for imaging of tubulin polymerization in cancers," 51(1) J. Label. Compd. Radiopharm. 6-11 (2008).
Yeh et al., "Practical Cu-catalyzed amination of functionalized heteroaryl halides," 47(34) Tetrahedron Lett. 6011-16 (2006).
Zhu et al., "The Direct Formulation of Functionalized Alkyl(aryl)zinc halides by Oxidative Addition of Highly Reactive Zinc with Organic Halides and Their Reactions with Acid Chlorides, α,β-Unsaturated Ketones, and Allylic, Aryl, and Vinyl Halides," 56 J. Org. Chem. 1445-53 (1991).
International Search Report and Written Opinion for PCT/US2014/071663 dated Apr. 17, 2015 (6 pages).
U.S. Appl. No. 14/398,061, Tetrahydronaphthyridine and Related Bicyclic Compounds for Inhibition of RORgamma Activity and the Treatment of Disease, filed Oct. 30, 2014.
U.S. Appl. No. 15/103,409, Carbamate Benzoxazine Propionic Acids and Acid Derivatives for Modulation of RORgamma Activity and the Treatment of Disease, filed Jun. 10, 2016.
U.S. Appl. No. 15/103,414, Tetrahydronaphthyridine, Benzoxazine, Aza-Benzoxazine and Related Bicyclic Compounds for Inhibition of RORgamma Activity and the Treatment of Disease, filed Jun. 10, 2016.

* cited by examiner

2-ACYLAMIDOMETHYL AND SULFONYLAMIDOMETHYL BENZOXAZINE CARBAMATES FOR INHIBITION OF RORGAMMA ACTIVITY AND THE TREATMENT OF DISEASE

CROSS-REFERENCE TO RELATED APPLICATIONS

This application is the national stage of International (PCT) Patent Application Serial No. PCT/US2014/071656, filed Dec. 19, 2014 which claims the benefit of and priority to U.S. Provisional Patent Application Ser. No. 61/919,107, filed Dec. 20, 2013, the contents of each of which are hereby incorporated by reference in their entirety.

FIELD OF THE INVENTION

The present invention relates to certain substituted phenyl compounds of the Formula (I) (also referred to herein as the "compounds of the Formula (I)" or "compounds of Formula (I)") which are antagonists of a Thymocyte/T cell specific variant of Retinoic Acid Receptor-related Orphan Receptor (ROR), RORgammaT. The present invention also provides compositions comprising such compounds, and methods of using such compounds for treating conditions or disorders associated with inappropriate RORgammaT activity, in particular in the treatment and prevention of disease states mediated by RORgammaT. Such disease states may include immune and inflammatory disorders such as rheumatoid arthritis, psoriasis, multiple sclerosis, inflammatory bowel disease, and asthma.

BACKGROUND OF THE INVENTION

Upon activation by antigen-presenting cells, naïve T helper cells undergo clonal expansion and will ultimately differentiate into cytokine secreting effector T cells, such as Th1 and Th2 subtypes. A third and distinct effector subset has been identified, which plays a key role in providing immunity to bacteria and fungi at mucosal surfaces (Kastelein et al., *Annu. Rev. Immunol.* 25: 221-242, 2007). This effector T helper cell subset can be distinguished based on its ability to produce large quantities of IL-17/F, IL-21 and IL-22, and is named Th17 (Miossec et al., *New Eng. J. Med.* 361: 888-898, 2009).

Different T helper subsets are characterized by the expression of lineage specific master transcription factors. Th1 and Th2 effector cells express Tbet and GATA3, respectively. A Thymocyte/T cell specific variant of Retinoic Acid Receptor-related Orphan Receptor (ROR), RORgammaT, is highly expressed in Th17 cells (He et al., *Immunity* 9: 797-806, 1998). RORgammaT belongs to the nuclear hormone receptor superfamily (Hirose et al., *Biochem. Biophys. Res. Comm.* 205: 1976-1983, 1994). RORgammaT is a truncated form of RORgamma, lacking the first N-terminal 21 amino acids and is, in contrast to RORgamma which is expressed in multiple tissues (heart, brain, kidney, lung, liver, and muscle), exclusively expressed in cells of the lymphoid lineage and embryonic lymphoid tissue inducers (Sun et al., *Science* 288: 2369-2372, 2000; Eberl et al., *Nat Immunol.* 5: 64-73, 2004).

Studies using heterozygous knock-in mice replacing the RORgammaT open reading frame with GFP (green fluorescent protein) revealed a constitutive expression of GFP in approximately 10% of the CD4+ T cells in the small intestinal lamina propria (LP), co-expressing the Th17 cytokines IL-17/F and IL-22 (Ivanov et al., *Cell* 126: 1121-1133, 2006). In mice deficient for RORgammaT, the number of Th17 cells was markedly decreased in the LP; and in vitro stimulation of CD4+ T cells under Th17 polarizing conditions resulted in a drastic decrease of IL-17 expression. These results were further substantiated via forced expression of RORgammaT in naïve CD4+ T cells, which resulted in an induction of IL-17/F and IL-22 (Ivanov et al., *Cell* 126: 1121-1133, 2006). The foregoing studies demonstrate the importance of RORgammaT in differentiation and stabilization of the Th17 lineage. In addition, a ROR family member, RORalpha, has been demonstrated to be involved in Th17 differentiation and stabilization (Yang et al., *Immunity* 28: 29-39, 2008).

Recently, RORgammaT was shown to play a crucial role in non-Th17 lymphoid cells. In these studies, RORgammaT was critically important in innate lymphoid cells expressing Thy1, SCA-1, and IL-23R proteins. Genetic disruption of RORgamma in a mouse colitis model dependent on these innate lymphoid cells prevented colitis development (Buonocore et al., *Nature* 464: 1371-1375, 2010). In addition, RORgammaT was shown to play a crucial role in other non-Th17 cells, such as mast cells (Hueber et al., *J. Immunol.* 184: 3336-3340, 2010). Finally, RORgammaT expression and secretion of Th17-type of cytokines was reported for Lymphoid Tissue Inducer cells, NK T-cells, NK cells (Eberl et al., *Nat. Immunol.* 5: 64-73, 2004) and gamma-delta T-cells (Sutton et al., *Immunity.* 31: 331-341, 2009; Louten et al., *J. Allergy Clin. Immunol.* 123: 1004-1011, 2009), suggesting an important function for RORgammaT in these subtypes of cells.

Based on the role of IL-17 producing cells (either Th17 or non-Th17 cells) RORgammaT has been identified as a key mediator in the pathogenesis of several diseases (Louten et al., *J. Allergy Clin. Immunol.* 123: 1004-1011, 2009; Annunziato et al., *Nat. Rev. Rheumatol.* 5: 325-331, 2009). This was confirmed using several disease models representative of autoimmune diseases. Genetic ablation of the RORgamma gene in mice prevented the development of experimental autoimmune diseases, such as experimental autoimmune encephalomyelitis (EAE) and colitis (Ivanov et al., *Cell* 126:1121-33, 2006; Buonocore et al., *Nature* 464: 1371-1375, 2010).

With RORgammaT being a critical mediator in Th17-cells and non-Th17 cells, antagonism of the transcriptional activity of RORgammaT is expected to have a beneficial effect on autoimmune diseases, such as but not limited to rheumatoid arthritis, psoriasis, multiple sclerosis, inflammatory bowel disease (e.g., Crohn's disease, ulcerative colitis), and asthma (Annunziato et al., *Nat. Rev. Rheumatol.* 5: 325-331, 2009; Louten et al., *J. Allergy Clin. Immunol.* 123: 1004-1011, 2009). Antagonism of RORgammaT may also be beneficial in other diseases that are characterized by increased levels of Th17 cells and/or elevated levels of Th17 hallmark cytokines such as IL-17, IL-22 and IL-23. Examples of such diseases are Kawasaki Disease (Jia et al., *Clin. Exp. Immunol.* 162: 131-137, 2010) and Hashimoto's thyroiditis (Figueroa-Vega et al., *J. Clin. Endocrinol. Metab.* 95: 953-62, 2010). Another example includes infectious diseases, such as but not limited to mucosal leishmaniasis (Boaventura et al., *Eur. J. Immunol.* 40: 2830-2836, 2010). In each of the above examples the inhibition may be enhanced by simultaneous inhibition of RORalpha.

In another aspect, compounds of Formula (I) can be used in the treatment of cancer. Those skilled in the art will recognize the term "cancer" to be a name for diseases in which the body's cells become abnormal and divide without control. The term cancer includes, but is not limited to, colorectal, lung, and pancreatic cancer.

Compounds modulating RORgammaT have been reported. Examples of agonists include T0901317 and SR1078 (Wang et al., *ACS Chem. Biol.* 5:1029-1034, 2010). In addition, antagonists have been reported such as 7-oxygenated sterols (Wang et al., *J. Biol. Chem.* 285: 5013-5025, 2010) and the compounds described in EP 2181710 A1.

Numerous immune and inflammatory disorders continue to afflict millions of patients worldwide. Although significant advances have been made in treating these disorders, current therapies do not provide satisfactory results for all patients due to, for example, detrimental side effects or insufficient efficacy. One exemplary immune disorder in need of better therapy is psoriasis. Various therapeutics have been developed in an attempt to treat psoriasis. However, the traditional therapies for psoriasis often have toxic adverse effects. An exemplary inflammatory disorder in need of better treatment is rheumatoid arthritis. Numerous therapeutics have been developed in an attempt to treat this disorder. However, some patients develop resistance to current therapies.

Accordingly, a need exists for improved treatments for immune disorders and inflammatory disorders. The present invention addresses this need and provides other related advantages.

SUMMARY OF THE INVENTION

The present invention provides compounds that alter the interaction of coregulator proteins with RORgammaT and thereby antagonize RORgammaT-mediated transcriptional activity; pharmaceutical compositions comprising such compounds and pharmaceutically acceptable excipients; and use of such compounds or such pharmaceutical compositions for the treatment of RORgammaT-mediated diseases or conditions, in particular autoimmune diseases and inflammatory diseases.

DETAILED DESCRIPTION OF THE INVENTION

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "fluoroalkyl," "—O-alkyl," etc.

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "therapeutically effective amount" as used herein refers to an amount of the compound of Formula (I) and/or an additional therapeutic agent, or a composition thereof that is effective in producing the desired therapeutic, ameliorative, inhibitory, or preventative effect when administered to a patient suffering from a disease or condition mediated by RORgammaT. In the combination therapies of the present invention, a therapeutically effective amount can refer to each individual agent or to the combination as a whole, wherein the amounts of all agents administered are together effective, but wherein the component agent of the combination may not be present individually in an effective amount.

The term "preventing," as used herein with respect to cancer or an inflammatory disease or disorder, refers to reducing the likelihood of an autoimmune or inflammatory disease or disorder.

The term "alkyl," as used herein, refers to an aliphatic hydrocarbon group having one of its hydrogen atoms replaced with a bond having the specified number of carbon atoms. In different embodiments, an alkyl group contains from 1 to 6 carbon atoms ($C_1$-$C_6$ alkyl) or from 1 to 3 carbon atoms ($C_1$-$C_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl, and neohexyl. In one embodiment, an alkyl group is linear. In another embodiment, an alkyl group is branched.

The term "fluoroalkyl," as used herein, refers to an alkyl group as defined above, wherein one or more of the alkyl group's hydrogen atoms has been replaced with a fluorine. In one embodiment, a fluoroalkyl group has from 1 to 6 carbon atoms. In another embodiment, a fluoroalkyl group has from 1 to 3 carbon atoms. In another embodiment, a fluoroalkyl group is substituted with from 1 to 3 fluorine atoms. Non-limiting examples of fluoroalkyl groups include —$CH_2F$, —$CHF_2$, and —$CF_3$. The term "$C_1$-$C_3$ fluoroalkyl" refers to a fluoroalkyl group having from 1 to 3 carbon atoms.

The term "alkylene," as used herein, refers to an alkyl group, as defined above, wherein one of the alkyl group's hydrogen atoms has been replaced with a bond. Non-limiting examples of alkylene groups include —$CH_2$—, —$CH_2CH_2$—, —$CH_2CH_2CH_2$—, —$CH_2CH_2CH_2CH_2$—, —$CH(CH_3)CH_2CH_2$—, —$CH(CH_3)$—, and —$CH_2CH(CH_3)CH_2$—. In one embodiment, an alkylene group has from 1 to about 6 carbon atoms ($C_1$-$C_6$ alkylene). In another embodiment, an alkylene group has from 1 to 3 carbon atoms ($C_1$-$C_3$ alkylene). In another embodiment, an alkylene group is branched. In another embodiment, an alkylene group is linear. In one embodiment, an alkylene group is —$CH_2$—. The term "$C_1$-$C_3$ alkylene" refers to an alkylene group having from 1 to 3 carbon atoms. Unless otherwise indicated, an alkylene group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to 4 carbon atoms. Non-limiting examples of alkenyl groups include ethenyl, propenyl, n-butenyl, 3-methylbut-2-enyl, n-pentenyl, octenyl, and decenyl. The term "$C_2$-$C_6$ alkenyl" refers to an alkenyl group having from 2 to 6 carbon atoms. The term "$C_2$-$C_4$ alkenyl" refers to an alkenyl group having from 2 to 4 carbon atoms. Unless otherwise indicated, an alkenyl group is unsubstituted.

The term "alkoxy," as used herein, refers to an —O-alkyl group, wherein an alkyl group is as defined above. Non-limiting examples of alkoxy groups include methoxy, ethoxy, n-propoxy, isopropoxy, n-butoxy, and tert-butoxy. An alkoxy group is bonded via its oxygen atom to the rest of the molecule.

The term "aryl," as used herein, refers to an aromatic monocyclic or multicyclic ring system comprising from about 6 to about 14 carbon atoms. In one embodiment, an aryl group contains from about 6 to 10 carbon atoms ($C_6$-$C_{10}$ aryl). In another embodiment an aryl group is phenyl. Non-limiting examples of aryl groups include phenyl and naphthyl.

The term "carbocycle," as used herein, refers to a fully saturated, partially unsaturated, or an aromatic monocyclic or multicyclic ring system comprising from about 6 to 14 carbon atoms. In one embodiment, an aryl group contains from 3 to 10 carbon atoms ($C_3$-$C_{10}$ carbocycle). Non-limiting examples of carbocyclic groups include cycloalkyl and aryl groups, as defined herein. In specific embodiments, the carbocyclic groups are selected from cyclopropyl, cyclobutyl, cyclopentyl, cyclohexyl, phenyl, indanyl, naphthyl, and tetrahydronaphthyl.

The term "cycloalkyl," as used herein, refers to a saturated ring containing the specified number of ring carbon atoms, and no heteroatom. In a like manner the term "$C_3$-$C_6$ cycloalkyl" refers to a saturated ring having from 3 to 6 ring carbon atoms. Non-limiting examples of monocyclic cycloalkyls include cyclopropyl, cyclobutyl, cyclopentyl, and cyclohexyl.

The term "halo," as used herein, means —F, —Cl, —Br or —I. In one embodiment, a halo group is —F or —Cl. In another embodiment, a halo group is —F.

"Heterocyclyl" refers to a 4-, 5-, 6-, or 7-membered monocyclic ring or 8-, 9-, or 10-membered bicyclic ring, or 13- or 14-membered tricyclic ring, saturated, unsaturated or aromatic, containing 1, 2, 3, or 4 heteroatoms selected from O, N, or S, and the heterocyclyl may optionally be substituted with one to four substituents. The nitrogen or sulfur atom of the heterocyclyl can be optionally oxidized to the corresponding N-oxide, S-oxide, or S,S-dioxide. A heterocyclyl group can be joined to the rest of the molecule via a ring carbon or ring nitrogen atom. Representative heterocyclyls are as follows: azetidinyl, pyrrolidinyl, pyrrolyl, tetrahydrofuran, imidazolyl, imidazolinyl, 1,3-oxazolidinyl, 1,2-oxazolidinyl, isoxazolyl, 1,2,4-oxadiazolyl, 1,3,4-oxadiazolyl, tetrahydropyranyl, piperidinyl, piperazinyl, morpholinyl, pyrimidinyl, pyrrolopyrazine, pyrrolopyridine, and indolyl.

The term "substituted" means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation from a reaction mixture to a useful degree of purity, and formulation into an efficacious therapeutic agent.

When any substituent or variable occurs more than one time in any constituent or in the compound of Formula (I), its definition on each occurrence is independent of its definition at every other occurrence, unless otherwise indicated.

When an integer defining the presence of a certain number of atoms in a group is equal to zero, it means that the atoms adjacent thereto are connected directly by a bond; for example, in the structure

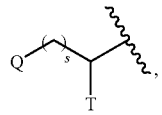

wherein s is an integer equal to zero, 1 or 2, the structure is

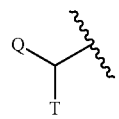

when s is zero; or it means that the indicated atom is absent; for example, —S(O)$_0$— means —S—.

The term "in purified form," as used herein, refers to the physical state of a compound after the compound has been isolated through a synthetic process (e.g., from a reaction mixture), from a natural source, or a combination thereof. The term "in purified form" also refers to the physical state of a compound after the compound has been obtained from a purification process or processes described herein or well-known to the skilled artisan (e.g., chromatography, recrystallization, and the like), in sufficient purity to be characterizable by standard analytical techniques described herein or well-known to the skilled artisan.

It should also be noted that any carbon as well as heteroatom with unsatisfied valences in the text, schemes, examples, and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves various degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of Formula (I) may contain one or more stereogenic centers and can thus occur as racemates, racemic mixtures, single enantiomers, diastereomeric mixtures, and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures, or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers, and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention.

All stereoisomers (for example, geometric isomers, optical isomers, and the like) of the present compounds (including stereoisomers of salts and solvates of the present compounds as well as stereoisomers of salts, solvates, and esters of prodrugs of the present compounds), such as those that may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

The compounds of Formula (I) can form salts which are also within the scope of this invention. Reference to a compound of Formula (I) herein is understood to include reference to salts thereof, unless otherwise indicated. The term "salt(s)," as employed herein, denotes acidic salts formed with inorganic and/or organic acids, as well as basic salts formed with inorganic and/or organic bases. In addition, when a compound of Formula (I) contains both a basic moiety, such as but not limited to a pyridine or imidazole, and an acidic moiety, such as but not limited to a carboxylic acid, zwitterions ("inner salts") may be formed and are included within the term "salt(s)" as used herein. Such acidic and basic salts used within the scope of the invention are pharmaceutically acceptable (i.e., non-toxic, physiologically acceptable) salts. Salts of the compounds of Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates), and the like. Additionally, acids that are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine, and the like. Basic nitrogen-containing groups may be quaternized with agents such as lower alkyl halides (e.g., methyl, ethyl, and butyl chlorides, bromides, and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

The present invention further includes the compounds of Formula (I) in all their isolated forms. For example, the above-identified compounds are intended to encompass all forms of the compounds, such as any solvates, hydrates, stereoisomers, and tautomers thereof.

As used herein, the term "composition" is intended to encompass a product comprising the specified ingredients in the specified amounts, as well as any product that results, directly or indirectly, from combination of the specified ingredients in the specified amounts.

In the compounds of generic Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I). For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. In light of the present disclosure, isotopically-enriched compounds within generic Formula (I) can be prepared without undue experimentation by conventional techniques well known to those skilled in the art or by processes analogous to those described in the examples herein using appropriate isotopically-enriched reagents and/or intermediates.

Compounds of the Invention

The present invention provides a compound of Formula (I) or a pharmaceutically acceptable salt thereof, wherein $R^1$, $R^2$, $R^a$, $R^b$, $R^c$, $R^d$, $R^g$, and Cy are as defined below. Described below are embodiments of the compound of Formula (I). The compounds of the Formulas (IA), (IB), and (IC), shown below, are embodiments of the compound of Formula (I).

In embodiment no. 1, the invention provides a compound of Formula (I),

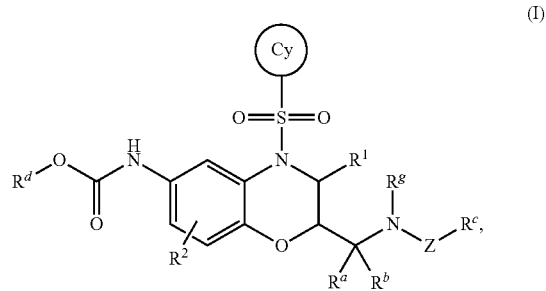

or a pharmaceutically acceptable salt thereof, wherein:
$R^1$ is H or $C_1$-$C_3$ alkyl,
$R^2$ is H, halo, or $C_1$-$C_3$ alkyl;

$R^a$ and $R^b$ are independently selected from the group consisting of H, $C_1$-$C_6$ alkyl, trifluoromethyl, and cyclopropyl, Z is —C(O)— or —SO$_2$—;

$R^c$ is selected from the group consisting of
- (a.) $C_1$-$C_6$ alkyl, wherein said $C_1$-$C_6$ alkyl of $R^c$ is unsubstituted or independently substituted by 1 to 6 hydroxy, amino, oxo, $C_1$-$C_3$ alkylamino, $C_1$-$C_3$ alkoxy, $C_1$-$C_3$ dialkylamino, or fluoro;
- (b.) $C_3$-$C_9$ mono- or bicycloalkyl, wherein said $C_3$-$C_9$ mono- or bicycloalkyl of $R^c$ is unsubstituted or independently substituted by 1 to 4 $C_1$-$C_3$ alkyl, $C_1$-$C_3$ alkoxy, fluoro, trifluoromethyl, cyano, amino, $C_1$-$C_3$ alkylamino, or $C_1$-$C_3$ dialkylamino;
- (c.) a ring $C^c$ of the formula

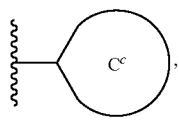

wherein ring $C^c$ is a 3- to 6-membered heterocyclyl, wherein said heterocyclyl is a saturated, partially saturated, or aromatic ring system containing 1 to 3 heteroatoms independently selected from the group consisting of N, O, and S, and is unsubstituted or independently substituted by 1 to 3 $C_1$-$C_6$ alkyl, $C_1$-$C_3$ alkoxy, fluoro, hydroxyl, oxo, cyano, amino, $C_1$-$C_3$ alkylamino, or $C_1$-$C_3$ dialkylamino;
- (d.) phenyl, wherein said phenyl of $R^c$ is unsubstituted or independently substituted by 1 to 4 $C_1$-$C_3$ alkylsulfonyl;

$R^g$ is H or methyl;

$R^d$ is
- (a.) $C_1$-$C_8$ alkyl, wherein said $C_1$-$C_8$ alkyl of $R^d$ is unsubstituted or independently substituted by 1 to 6 halo, $C_1$-$C_3$ alkoxy, hydroxy, cyano, trimethylsilyl, or methylsulfonyl;
- (b.) $C_2$-$C_8$ alkenyl, wherein said $C_2$-$C_8$ alkenyl of $R^d$ is unsubstituted or independently substituted by 1 to 6 fluoro or cyano;
- (c.) a group of the formula -M-$R^{CH}$;
  M is
  - (i.) a bond; or
  - (ii.) $C_1$-$C_6$ alkylene, wherein said $C_1$-$C_6$ alkylene of M is unsubstituted or substituted by 1 to 6 fluoro;

$R^{CH}$ is a ring selected from the group consisting of
  - (i.) $C_3$-$C_9$ mono- or bicycloalkyl;
  - (ii.) phenyl; and
  - (iii.) a 3- to 6-membered heterocyclyl, wherein said heterocyclyl of $R^{CH}$ is a saturated or partially saturated ring system containing 1 to 2 heteroatoms independently selected from the group consisting of N, O, and S;

wherein $R^{CH}$ is unsubstituted or independently substituted by 1 to 4 halo, $C_1$-$C_3$ alkyl, $C_1$-$C_3$ trifluoroalkyl, cyano, $C_1$-$C_4$ alkylcarbonylamino, or oxo;

Cy is
- (a.) phenyl;
- (b.) a 5- to 7-membered, monocyclic heterocyclyl, wherein said heterocyclyl of Cy is a saturated, partially saturated, or aromatic ring system containing 1 to 3 heteroatoms independently selected from the group consisting of N, O, and S; or
- (c.) $C_3$-$C_6$ cycloalkyl;

wherein Cy is unsubstituted or independently substituted by 1 to 4 $R^k$ moieties selected from the group consisting of:
- (i.) $C_1$-$C_6$ alkyl, wherein said $C_1$-$C_6$ alkyl is unsubstituted or independently substituted by 1 to 3 hydroxy or fluoro;
- (ii.) $C_1$-$C_6$ alkoxy, wherein said $C_1$-$C_6$ alkoxy is unsubstituted or independently substituted by 1 to 3 fluoro, hydroxy, methoxy, or phenyl;
- (iii.) —N($R^e$)$_2$;
- (iv.) —O(CH$_2$)$_{n1}$C(O)N($R^e$)$_2$;
- (v.) —O(CH$_2$)$_{n2}$CO$_2$$R^f$;
- (vi.) hydroxyl;
- (vii.) oxo;
- (viii.) halo;
- (ix.) $C_1$-$C_3$ alkylsulfonyl;
- (x.) cyano; and
- (xi.) oxetanyl;

or alternatively, two $R^k$ moieties, when substituted on adjacent ring atoms of Cy, form a second ring, wherein said second ring is a 5- to 7-membered saturated, partially saturated, or aromatic ring system containing 0, 1, or 2 heteroatoms independently selected from the group consisting of N, O, and S; wherein said second ring is unsubstituted or substituted by 1 to 3 $R^k$ moieties independently selected from (i)-(xi);

each $R^e$ is independently H or $C_1$-$C_3$ alkyl, $R^f$ is H or $C_1$-$C_3$ alkyl;

the subscript n1 is 1, 2, or 3; and the subscript n2 is 1, 2, or 3.

In embodiment no. 2, the invention provides a compound of Formula (I) wherein Z is —C(O)—, and the remaining variables are as set forth in embodiment no. 1.

In embodiment no. 3, the invention provides a compound of Formula (I) wherein Z is —SO$_2$—, and the remaining variables are as set forth in embodiment no. 1.

In embodiment no. 4, the invention provides a compound of Formula (I), wherein $R^1$ is H, and the remaining variables are as set forth in embodiment no. 1.

In embodiment no. 5, the invention provides a compound of Formula (I), wherein $R^1$ is methyl, and the remaining variables are as set forth in embodiment no. 1.

In embodiment no. 6, the invention provides a compound of Formula (I), wherein Cy is a group of the formula

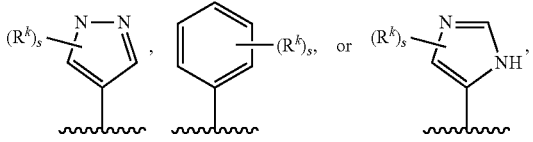

wherein the subscript s is 0, 1, 2, or 3, and the remaining variables are as set forth in embodiment no. 1.

In embodiment no. 7, the invention provides a compound of Formula (I) wherein Cy is a group of the formula

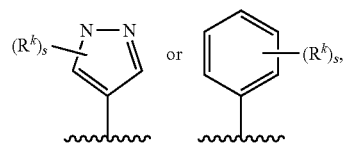

wherein the subscript s is 0, 1, 2, or 3, and the remaining variables are as set forth in embodiment no. 1.

In embodiment no. 8, the invention provides a compound of Formula (I) wherein $R^d$ is a group of the formula

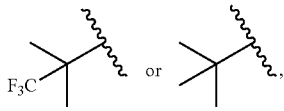

and the remaining variables are as set forth in embodiment no. 1.

In embodiment no. 9, the invention provides a compound of Formula (I), wherein $R^g$ is H, and the remaining variables are as set forth in embodiment no. 1.

In embodiment no. 10, the invention provides a compound of Formula (I), wherein
$R^d$ is a group of the formula -M-$R^{CH}$;
M is
(i.) a bond; or
(ii.) $C_1$-$C_6$ alkylene, wherein said $C_1$-$C_6$ alkylene of M is unsubstituted or substituted by 1 to 6 fluoro;
$R^{CH}$ is a ring selected from the group consisting of
(i.) $C_3$-$C_9$ mono- or bicycloalkyl, wherein said cycloalkyl of $R^{CH}$ is unsubstituted or independently substituted by 1 to 4 fluoro, $C_1$-$C_3$ alkyl, or $C_1$-$C_3$ trifluoroalkyl;
(ii.) phenyl, wherein said phenyl of $R^{CH}$ is unsubstituted or independently substituted by 1 to 3 halo or cyano; and
(iii.) a 3- to 6-membered heterocyclyl, wherein said heterocyclyl of $R^{CH}$ is a saturated or partially saturated ring system containing 1 to 2 heteroatoms independently selected from the group consisting of N, O, and S, wherein said heterocyclyl is unsubstituted or independently substituted by 1 to 2 $C_1$-$C_3$ alkyl, trifluoromethyl, $C_1$-$C_4$ alkylcarbonylamino, or oxo; and
the remaining variables are as set forth in embodiment no. 1.

In embodiment no. 11, the invention provides a compound of Formula (I), wherein $R^c$ is $C_1$-$C_6$ alkyl, wherein said $C_1$-$C_6$ alkyl of $R^c$ is unsubstituted or independently substituted by 1 to 6 hydroxy, amino, oxo, $C_1$-$C_3$ alkylamino, $C_1$-$C_3$ alkoxy, $C_1$-$C_3$ dialkylamino or fluoro; and the remaining variables are as set forth in embodiment no. 1.

In embodiment no. 12, the invention provides a compound of Formula (I), wherein $R^c$ is $C_1$-$C_6$ alkyl, wherein said $C_1$-$C_6$ alkyl is unsubstituted or substituted by hydroxy; and the remaining variables are as set forth in embodiment no. 1.

In embodiment no. 13, the invention provides a compound of Formula (I), wherein
$R^1$ is H;
Cy is a group of the formula

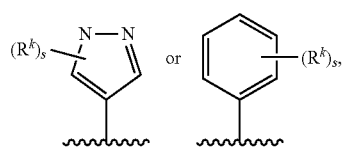

wherein the subscript s is 0, 1, 2, or 3;
$R^c$ is $C_1$-$C_6$ alkyl, wherein said $C_1$-$C_6$ alkyl is unsubstituted or substituted by hydroxyl;

$R^d$ is a group of the formula

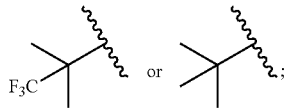

$R^g$ is H, and
the remaining variables are as set forth in embodiment no. 1.

In embodiment no. 14, the invention provides a compound of Formula (I), wherein
Z is —C(O)—;
$R^1$, Cy, $R^c$, $R^d$, and $R^g$ are as set forth in embodiment no. 13; and
the remaining variables are as set forth in embodiment no. 1.

In embodiment no. 15, the invention provides a compound of Formula (I), wherein
Z is —$SO_2$—;
$R^1$, Cy, $R^c$, $R^d$, and $R^g$ are as set forth in embodiment no. 13; and
the remaining variables are as set forth in embodiment no. 1.

In embodiment no. 16, the invention provides a compound of Formula (I) as set forth in any one of embodiments nos. 1-15, wherein the compound of Formula (I) has the Formula (IA)

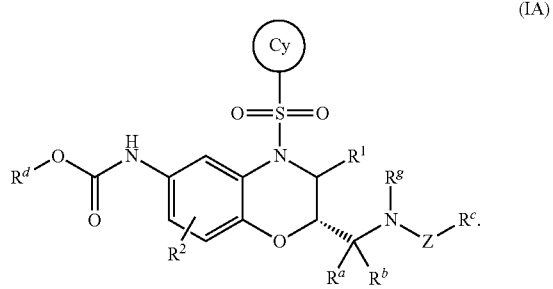

(IA)

In embodiment no. 17, the invention provides a compound of Formula (IB),

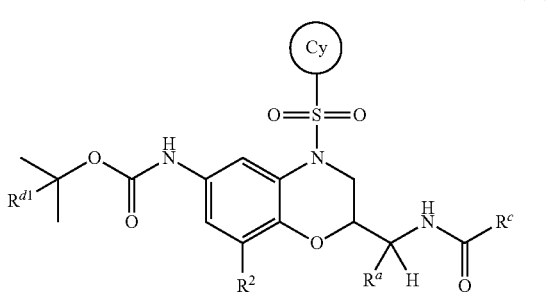

(IB)

wherein
Cy is

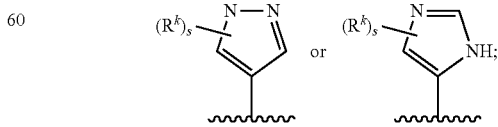

$R^2$ is H or F;
the subscript s is 0, 1, 2, or 3;

$R^{d1}$ is $CH_3$, $CHF_2$, $CH_2F$, or $CF_3$;
$R^a$ is H or $C_1$-$C_3$ alkyl; and
$R^c$ is
  (a.) $C_1$-$C_6$ alkyl, wherein said $C_1$-$C_6$ alkyl is unsubstituted or independently substituted by 1 to 4 fluoro or hydroxyl; and
  (b.) cyclopropyl, wherein said cyclopropyl is unsubstituted or substituted by 1 to 2 fluoro; and
$R^k$ is as set forth in embodiment no. 1.

In embodiment no. 18, the invention provides a compound of Formula (IB), wherein each $R^k$ is independently:
  (i.) $C_1$-$C_6$ alkyl, wherein said $C_1$-$C_6$ alkyl is unsubstituted or independently substituted by 1 to 3 hydroxy or fluoro;
  (ii.) $C_1$-$C_6$ alkoxy, wherein said $C_1$-$C_6$ alkoxy is unsubstituted or independently substituted by 1 to 3 fluoro, hydroxy, methoxy, or phenyl;
  (iii.) a halo selected from fluoro or chloro; or
alternatively, two $R^k$ moieties, when substituted on adjacent ring atoms of Cy, form said second ring, wherein said second ring is a 5- to 6-membered partially saturated or aromatic ring system that contains 0 or 1 N atom; wherein said second ring is unsubstituted or substituted by 1 to 2 $R^k$ moieties independently selected from (i)-(iii); and
the remaining variables are as set forth as in embodiment no. 17.

In embodiment no. 19, the invention provides a compound of Formula (IB), wherein Cy is:

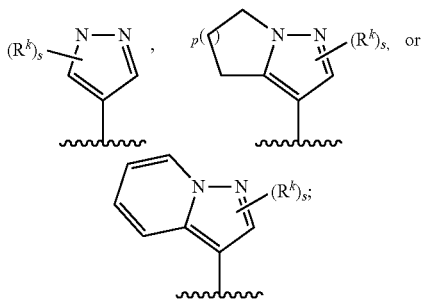

wherein
  the subscript p is 1 or 2;
  the subscript s is 0, 1, or 2;
  $R^k$ is as set forth in embodiment no. 1; and
  the remaining variables are as set forth in embodiment no. 17.

In embodiment no. 20, the invention provides a compound of Formula (IB), wherein
Cy is

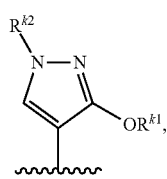

wherein
  $R^{k1}$ is $C_1$-$C_6$ alkyl or $CH_2CH_2OH$;
  $R^{k2}$ is $C_1$-$C_3$ alkyl or $CHF_2$; and
  the remaining variables are as set forth in embodiment no. 17.

In embodiment no. 21, the invention provides a compound of Formula (IB), wherein
Cy is

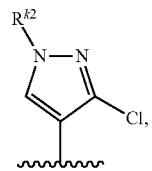

wherein
  $R^{k2}$ is $C_1$-$C_3$ alkyl or $CHF_2$; and
  the remaining variables are as set forth in embodiment no. 17.

In embodiment no. 22, the invention provides a compound of Formula (IB), wherein Cy is:

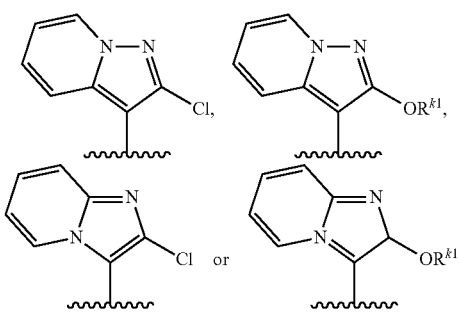

wherein
  $R^{k1}$ is $C_1$-$C_6$ alkyl or $CH_2CH_2OH$; and
  the remaining variables are as set forth in embodiment no. 17.

In embodiment no. 23, the invention provides a compound of Formula (IB), wherein Cy is:

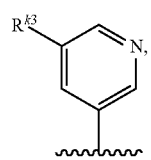

wherein
  $R^{k3}$ is $C_1$-$C_3$ alkyl or $C_1$-$C_3$ fluoroalkyl; and
  the remaining variables are as set forth in embodiment no. 17.

In embodiment no. 24, the invention provides a compound as set forth in any one of embodiment nos. 17-23, wherein the compound of Formula (IB) has the Formula (IC):

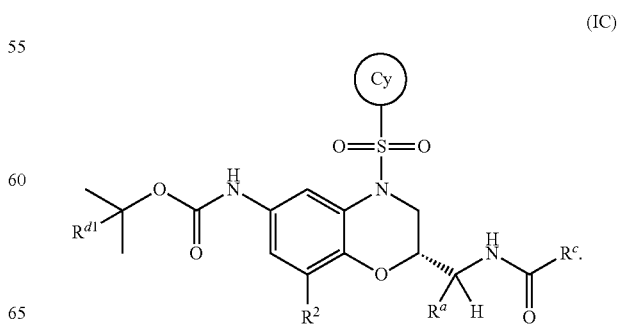

(IC)

In embodiment no. 25, the invention provides a compound as set forth in embodiment no. 1, wherein Cy is unsubstituted or independently substituted by 1 to 4 $R^k$ moieties selected from the group consisting of:
- (i.) $C_1$-$C_6$ alkyl, wherein said $C_1$-$C_6$ alkyl is unsubstituted or independently substituted by 1 to 3 hydroxy or fluoro;
- (ii.) $C_1$-$C_6$ alkoxy, wherein said $C_1$-$C_6$ alkoxy is unsubstituted or independently substituted by 1 to 3 fluoro, hydroxy, methoxy, or phenyl;
- (iii.) —N($R^e$)$_2$;
- (iv.) —O(CH$_2$)$_{n1}$C(O)N($R^e$)$_2$;
- (v.) —O(CH$_2$)$_{n2}$CO$_2$$R^f$;
- (vi.) hydroxyl;
- (vii.) oxo;
- (viii.) halo;
- (ix.) $C_1$-$C_3$ alkylsulfonyl;
- (x.) cyano;
- (xi.) oxetanyl;
- (xii.) cyclopropyl;
- (xiii.) —(CH$_2$)$_{n1}$N(H)C(O)O—($C_1$-$C_6$ alkyl); and
- (xiv.) —SF$_5$;

or alternatively, two $R^k$ moieties, when substituted on adjacent ring atoms of Cy, form a second ring, wherein said second ring is a 5- to 7-membered saturated, partially saturated, or aromatic ring system containing 0, 1, or 2 heteroatoms independently selected from the group consisting of N, O, and S; wherein said second ring is unsubstituted or substituted by 1 to 3 $R^k$ moieties independently selected from (i)-(xiv); and $R^1$, $R^2$, $R^a$, $R^b$, $R^c$, $R^d$, $R^e$, $R^f$, $R^g$, and the subscripts n1 and n2 are as set forth in embodiment no. 1.

In embodiment no. 26, the compound is selected from any one of the compounds described in Example Nos. 1-54 (or a pharmaceutically acceptable salt thereof), which are set forth in the Examples below.

In embodiment no. 27, the compound is selected from any one of the following compounds (or a pharmaceutically acceptable salt thereof):

(S)-tert-butyl (2-(aminomethyl)-4-((4-fluorophenyl)sulfonyl)-3,4-dihydro-2H-benzo[b][1,4]oxazin-6-yl)carbamate;

(S)-tert-butyl (2-(acetamidomethyl)-4-((1-ethyl-3-methyl-1H-pyrazol-4-yl)sulfonyl)-3,4-dihydro-2H-benzo[b][1,4]oxazin-6-yl)carbamate;

(S)-tert-butyl (2-(acetamidomethyl)-4-((1,5-dimethyl-1H-pyrazol-4-yl)sulfonyl)-3,4-dihydro-2H-benzo[b][1,4]oxazin-6-yl)carbamate;

(S)-tert-butyl (2-(acetamidomethyl)-4-(imidazo[1,2-a]pyridin-6-ylsulfonyl)-3,4-dihydro-2H-benzo[b][1,4]oxazin-6-yl)carbamate;

(S)-tert-butyl (2-(acetamidomethyl)-4-(imidazo[1,2-a]pyridin-5-ylsulfonyl)-3,4-dihydro-2H-benzo[b][1,4]oxazin-6-yl)carbamate;

(S)-tert-butyl (2-(acetamidomethyl)-4-((3-cyano-4-methylphenyl)sulfonyl)-3,4-dihydro-2H-benzo[b][1,4]oxazin-6-yl)carbamate;

(S)-tert-butyl (2-(acetamidomethyl)-4-((5-bromo-2-chlorophenyl)sulfonyl)-3,4-dihydro-2H-benzo[b][1,4]oxazin-6-yl)carbamate;

(S)-tert-butyl (2-(acetamidomethyl)-4-((1-(difluoromethyl)-5-methyl-1H-pyrazol-4-yl)sulfonyl)-3,4-dihydro-2H-benzo[b][1,4]oxazin-6-yl)carbamate;

(S)-tert-butyl (2-(acetamidomethyl)-4-((3-chloro-1-ethyl-1H-pyrazol-4-yl)sulfonyl)-3,4-dihydro-2H-benzo[b][1,4]oxazin-6-yl)carbamate;

(S)-tert-butyl (2-(acetamidomethyl)-4-((2-methyl-6,7-dihydro-5H-pyrazolo[5,1-b][1,3]oxazin-3-yl)sulfonyl)-3,4-dihydro-2H-benzo[b][1,4]oxazin-6-yl)carbamate;

(S)-tert-butyl (2-(acetamidomethyl)-4-((5-methoxy-1,3-dimethyl-1H-pyrazol-4-yl)sulfonyl)-3,4-dihydro-2H-benzo[b][1,4]oxazin-6-yl)carbamate;

(S)-tert-butyl (2-(acetamidomethyl)-4-((2-methyl-4,5,6,7-tetrahydropyrazolo[1,5-a]pyridin-3-yl)sulfonyl)-3,4-dihydro-2H-benzo[b][1,4]oxazin-6-yl)carbamate;

(S)-tert-butyl (2-(acetamidomethyl)-4-((3-methoxy-1,5-dimethyl-1H-pyrazol-4-yl)sulfonyl)-3,4-dihydro-2H-benzo[b][1,4]oxazin-6-yl)carbamate;

(S)-tert-butyl (2-(acetamidomethyl)-4-(imidazo[2,1-b]thiazol-5-ylsulfonyl)-3,4-dihydro-2H-benzo[b][1,4]oxazin-6-yl)carbamate;

(S)-tert-butyl (2-(acetamidomethyl)-4-((2,3-dichlorophenyl)sulfonyl)-3,4-dihydro-2H-benzo[b][1,4]oxazin-6-yl)carbamate (S)-tert-butyl (2-(acetamidomethyl)-4-((2-methylimidazo[1,2-a]pyrimidin-3-yl)sulfonyl)-3,4-dihydro-2H-benzo[b][1,4]oxazin-6-yl)carbamate;

(S)-tert-butyl (2-(acetamidomethyl)-4-((6,7-dihydro-5H-pyrazolo[5,1-b][1,3]oxazin-3-yl)sulfonyl)-3,4-dihydro-2H-benzo[b][1,4]oxazin-6-yl)carbamate;

(S)-tert-butyl (2-(acetamidomethyl)-4-((2-methylpyrazolo[1,5-a]pyrimidin-3-yl)sulfonyl)-3,4-dihydro-2H-benzo[b][1,4]oxazin-6-yl)carbamate;

(S)-tert-butyl (2-(acetamidomethyl)-4-((4-chlorophenyl)sulfonyl)-3,4-dihydro-2H-benzo[b][1,4]oxazin-6-yl)carbamate;

(S)-tert-butyl (2-(acetamidomethyl)-4-((2-chloro-4-fluorophenyl)sulfonyl)-3,4-dihydro-2H-benzo[b][1,4]oxazin-6-yl)carbamate;

(S)-tert-butyl (2-(acetamidomethyl)-4-((3-chlorophenyl)sulfonyl)-3,4-dihydro-2H-benzo[b][1,4]oxazin-6-yl)carbamate;

(S)-tert-butyl (2-(acetamidomethyl)-4-((3-(trifluoromethyl)phenyl)sulfonyl)-3,4-dihydro-2H-benzo[b][1,4]oxazin-6-yl)carbamate;

(S)-tert-butyl (2-(acetamidomethyl)-4-((3-cyanophenyl)sulfonyl)-3,4-dihydro-2H-benzo[b][1,4]oxazin-6-yl)carbamate;

(S)-tert-butyl (2-(acetamidomethyl)-4-((3-(methylsulfonyl)phenyl)sulfonyl)-3,4-dihydro-2H-benzo[b][1,4]oxazin-6-yl)carbamate;

5U (S)-tert-butyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-tert-butyl (2-(acetamidomethyl)-4-((3-cyano-4-fluorophenyl)sulfonyl)-3,4-dihydro-2H-benzo[b][1,4]oxazin-6-yl)carbamate;

(S)-tert-butyl (2-(acetamidomethyl)-4-((4-fluoro-3-methylphenyl)sulfonyl)-3,4-dihydro-2H-benzo[b][1,4]oxazin-6-yl)carbamate;

(S)-tert-butyl (2-(acetamidomethyl)-4-((2-chloro-5-(trifluoromethyl)pyridin-3-yl)sulfonyl)-3,4-dihydro-2H-benzo[b][1,4]oxazin-6-yl)carbamate;

(S)-tert-butyl (2-(acetamidomethyl)-4-((2-chloro-5-methylpyridin-3-yl)sulfonyl)-3,4-dihydro-2H-benzo[b][1,4]oxazin-6-yl)carbamate;

(S)-tert-butyl (2-(acetamidomethyl)-4-((5-methyl-2-oxo-1,2-dihydropyridin-3-yl)sulfonyl)-3,4-dihydro-2H-benzo[b][1,4]oxazin-6-yl)carbamate;

(S)-tert-butyl (2-(acetamidomethyl)-4-((5-methylpyridin-3-yl)sulfonyl)-3,4-dihydro-2H-benzo[b][1,4]oxazin-6-yl)carbamate;

(S)-tert-butyl (2-(acetamidomethyl)-4-((3,4-difluorophenyl)sulfonyl)-3,4-dihydro-2H-benzo[b][1,4]oxazin-6-yl)carbamate;

(S)-tert-butyl (2-(acetamidomethyl)-4-((3-chloro-4-fluorophenyl)sulfonyl)-3,4-dihydro-2H-benzo[b][1,4]oxazin-6-yl)carbamate;

(S)-tert-butyl (2-(acetamidomethyl)-4-((4-fluoro-3-methoxyphenyl)sulfonyl)-3,4-dihydro-2H-benzo[b][1,4]oxazin-6-yl)carbamate;

(S)-tert-butyl (2-(acetamidomethyl)-4-((4-fluoro-3-(trifluoromethyl)phenyl)sulfonyl)-3,4-dihydro-2H-benzo[b][1,4]oxazin-6-yl)carbamate;

(S)-tert-butyl (2-(acetamidomethyl)-4-((5-(trifluoromethyl)pyridin-3-yl)sulfonyl)-3,4-dihydro-2H-benzo[b][1,4]oxazin-6-yl)carbamate;

(S)-tert-butyl (2-(acetamidomethyl)-4-((4-chloro-3-cyanophenyl)sulfonyl)-3,4-dihydro-2H-benzo[b][1,4]oxazin-6-yl)carbamate;

(S)-tert-butyl (2-(acetamidomethyl)-4-((5-cyano-2-methylphenyl)sulfonyl)-3,4-dihydro-2H-benzo[b][1,4]oxazin-6-yl)carbamate;

(S)-tert-butyl (2-(acetamidomethyl)-4-((1-isopropyl-3,5-dimethyl-1H-pyrazol-4-yl)sulfonyl)-3,4-dihydro-2H-benzo[b][1,4]oxazin-6-yl)carbamate;

(S)-tert-butyl (2-(acetamidomethyl)-4-(imidazo[1,2-a]pyridin-3-ylsulfonyl)-3,4-dihydro-2H-benzo[b][1,4]oxazin-6-yl)carbamate;

(S)-tert-butyl (2-(acetamidomethyl)-4-((2-methylimidazo[1,2-a]pyridin-3-yl)sulfonyl)-3,4-dihydro-2H-benzo[b][1,4]oxazin-6-yl)carbamate;

(S)-tert-butyl (2-(acetamidomethyl)-4-((6-methylimidazo[2,1-b]thiazol-5-yl)sulfonyl)-3,4-dihydro-2H-benzo[b][1,4]oxazin-6-yl)carbamate;

(S)-tert-butyl (2-(acetamidomethyl)-4-((2-methoxy-4,5,6,7-tetrahydropyrazolo[1,5-a]pyridin-3-yl)sulfonyl)-3,4-dihydro-2H-benzo[b][1,4]oxazin-6-yl)carbamate;

(S)-tert-butyl (2-(acetamidomethyl)-4-((2-methoxy-5,6-dihydro-4H-pyrrolo[1,2-b]pyrazol-3-yl)sulfonyl)-3,4-dihydro-2H-benzo[b][1,4]oxazin-6-yl)carbamate;

(S)-tert-butyl (2-(acetamidomethyl)-4-((2-chloro-4,5,6,7-tetrahydropyrazolo[1,5-a]pyridin-3-yl)sulfonyl)-3,4-dihydro-2H-benzo[b][1,4]oxazin-6-yl)carbamate;

(S)-tert-butyl (2-(acetamidomethyl)-4-((6-(trifluoromethyl)pyridin-2-yl)sulfonyl)-3,4-dihydro-2H-benzo[b][1,4]oxazin-6-yl)carbamate;

(S)-tert-butyl (2-(acetamidomethyl)-4-((1-ethyl-3-methoxy-1H-pyrazol-4-yl)sulfonyl)-3,4-dihydro-2H-benzo[b][1,4]oxazin-6-yl)carbamate;

(S)-tert-butyl (2-(acetamidomethyl)-4-((3-ethoxy-1-ethyl-1H-pyrazol-4-yl)sulfonyl)-3,4-dihydro-2H-benzo[b][1,4]oxazin-6-yl)carbamate;

(S)-methyl 2-((4-((2-(acetamidomethyl)-6-((tert-butoxycarbonyl)amino)-2H-benzo[b][1,4]oxazin-4(3H)-yl)sulfonyl)-1-ethyl-1H-pyrazol-3-yl)oxy)acetate;

(S)-tert-butyl (2-(acetamidomethyl)-4-((3-(2,2-difluoroethoxy)-1-ethyl-1H-pyrazol-4-yl)sulfonyl)-3,4-dihydro-2H-benzo[b][1,4]oxazin-6-yl)carbamate;

(S)-2-((4-((2-(acetamidomethyl)-6-((tert-butoxycarbonyl)amino)-2H-benzo[b][1,4]oxazin-4(3H)-yl)sulfonyl)-1-ethyl-1H-pyrazol-3-yl)oxy)acetic acid;

(S)-tert-butyl (2-(acetamidomethyl)-4-((1-ethyl-3-(2-(methylamino)-2-oxoethoxy)-1H-pyrazol-4-yl)sulfonyl)-3,4-dihydro-2H-benzo[b][1,4]oxazin-6-yl)carbamate;

(S)-tert-butyl (2-(acetamidomethyl)-4-((1-ethyl-3-(2,2,2-trifluoroethoxy)-1H-pyrazol-4-yl)sulfonyl)-3,4-dihydro-2H-benzo[b][1,4]oxazin-6-yl)carbamate;

(S)-tert-butyl (2-(acetamidomethyl)-4-((1-ethyl-3-(2-hydroxyethoxy)-1H-pyrazol-4-yl)sulfonyl)-3,4-dihydro-2H-benzo[b][1,4]oxazin-6-yl)carbamate;

(S)-tert-butyl (2-(acetamidomethyl)-4-((2-chloro-5,6-dihydro-4H-pyrrolo[1,2-b]pyrazol-3-yl)sulfonyl)-3,4-dihydro-2H-benzo[b][1,4]oxazin-6-yl)carbamate;

(S)-tert-butyl (2-(acetamidomethyl)-4-((1-ethyl-3-(ethylamino)-1H-pyrazol-4-yl)sulfonyl)-3,4-dihydro-2H-benzo[b][1,4]oxazin-6-yl)carbamate;

(S)-tert-butyl (2-(acetamidomethyl)-4-((3-cyclopropyl-1-ethyl-1H-pyrazol-4-yl)sulfonyl)-3,4-dihydro-2H-benzo[b][1,4]oxazin-6-yl)carbamate;

(S)-tert-butyl (2-(acetamidomethyl)-4-((3-(difluoromethoxy)-1-ethyl-1H-pyrazol-4-yl)sulfonyl)-3,4-dihydro-2H-benzo[b][1,4]oxazin-6-yl)carbamate;

(S)-tert-butyl (2-(acetamidomethyl)-4-((3-(dimethylamino)-1-ethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-ethyl-3-hydroxy-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-ethyl-3-isopropoxy-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3-chloro-4-fluorophenyl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3,4-difluorophenyl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((4-fluoro-3-(trifluoromethyl)phenyl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((4-fluoro-3-methylphenyl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((4-fluoro-3-methoxyphenyl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((4-chlorophenyl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3-cyanophenyl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((4-chloro-3-cyanophenyl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((5-cyano-2-methylphenyl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3-(methylsulfonyl)phenyl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((2-chloro-5-cyanophenyl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((3-chloro-5-cyanophenyl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((1-(difluoromethyl)-5-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((3-chloro-1-ethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((1-methyl-3-(trifluoromethyl)-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((2,4-dimethylthiazol-5-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((3-ethoxy-4-fluorophenyl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((3-(difluoromethoxy)phenyl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((3-(trifluoromethoxy)phenyl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((3-bromophenyl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((3-bromo-4-fluorophenyl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((2-methylthiazol-5-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((1-ethyl-5-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((1-ethyl-3,5-dimethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((3-methyl-1-propyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((2-methyl-4-(trifluoromethyl)thiazol-5-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-(3,5-dimethyl-1-propyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((3,5-dimethyl-1-(2,2,2-trifluoroethyl)-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((1-(2,2-difluoroethyl)-3,5-dimethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((1-ethyl-3-(trifluoromethyl)-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((1-ethyl-3-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((1,5-dimethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (4-((1,5-dimethyl-1H-pyrazol-4-yl)sulfonyl)-2-(methylsulfonamidoethyl)-3,4-dihydro-2H-benzo[b][1,4]oxazin-6-yl)carbamate;

(S)-1,1,1-trifluoro-2-methylpropan-2-yl (2-(acetamidoethyl)-4-((2-methoxy-5,6-dihydro-4H-pyrrolo[1,2-b]pyrazol-3-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((2-methoxy-4,5,6,7-tetrahydropyrazolo[1,5-a]pyridin-3-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((1-(difluoromethyl)-3,5-dimethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((1-ethyl-3-methoxy-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((3-ethoxy-1-ethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((5-cyclopropylpyridin-3-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((2-chloro-4,5,6,7-tetrahydropyrazolo[1,5-a]pyridin-3-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((3-methoxy-1,5-dimethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((2-chloro-5,6-dihydro-4H-pyrrolo[1,2-b]pyrazol-3-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((3-(2,2-difluoroethoxy)-1-ethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((1-(2,2-difluoroethyl)-3-ethoxy-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((3-cyclopropyl-1-ethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((3-(difluoromethoxy)-1-ethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((1-ethyl-3-(methylamino)-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidoethyl)-4-((1-ethyl-3-(ethylamino)-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-cyclopropyl-3-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-cyclopropyl-5-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-(difluoromethyl)-3-ethoxy-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-(imidazo[1,2-a]pyridin-3-ylsulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3-(benzyloxy)-1-ethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3-(3-(benzyloxy)propoxy)-1-ethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-ethyl-3-(3-hydroxypropoxy)-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3-methyl-1-propyl-1H-pyrazol-5-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-(2-methoxyethyl)-3-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-(2-methoxyethyl)-5-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-isopropyl-3-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-isopropyl-5-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((2-(2-hydroxyethoxy)-4,5,6,7-tetrahydropyrazolo[1,5-a]pyridin-3-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3-chloro-1-(difluoromethyl)-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3-methyl-1-(oxetan-3-yl)-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((5-methyl-1-(oxetan-3-yl)-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-(2-hydroxyethyl)-3-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-(2-hydroxyethyl)-5-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-(2-hydroxy-2-methylpropyl)-3-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-(2-hydroxy-2-methylpropyl)-5-methyl-1H-pyrazol-4-yl)sulfonyl)-3,4-dihydro-2H-benzo[b][1,4]oxazin-6-yl)carbamate;

(S)-2-((4-((2-(acetamidomethyl)-6-(((((1,1,1-trifluoro-2-methylpropan-2-yl)oxy)carbonyl)amino)-2,3-dihydro-4H-benzo[b][1,4]oxazin-4-yl)sulfonyl)-1-ethyl-1H-pyrazol-3-yl)oxy)acetic acid;

(S)-1,1,1-trifluoro-2-methylpropan-2-yl (2-(cyclopropanecarboxamidomethyl)-4-((1-ethyl-3-(2-hydroxyethoxy)-1H-pyrazol-4-yl)sulfonyl)-3,4-dihydro-2H-benzo[b][1,4]oxazin-6-yl)carbamate;

1,1,1-trifluoro-2-methylpropan-2-yl ((S)-4-((1-ethyl-3-(2-hydroxyethoxy)-1H-pyrazol-4-yl)sulfonyl)-2-((1S,2S)-2-fluorocyclopropanecarboxamido)methyl)-3,4-dihydro-2H-benzo[b][1,4]oxazin-6-yl)carbamate;

(S)-1,1,1-trifluoro-2-methylpropan-2-yl (4-((1-ethyl-3-(2-hydroxyethoxy)-1H-pyrazol-4-yl)sulfonyl)-2-((2-hydroxy-2-methylpropanamido)methyl)-3,4-dihydro-2H-benzo[b][1,4]oxazin-6-yl)carbamate;

1,1,1-trifluoro-2-methylpropan-2-yl ((2S)-4-((1-ethyl-3-(2-hydroxyethoxy)-1H-pyrazol-4-yl)sulfonyl)-2-((3,3,3-trifluoro-2-hydroxy-2-methylpropanamido)methyl)-3,4-dihydro-2H-benzo[b][1,4]oxazin-6-yl)carbamate;

1,1,1-trifluoro-2-methylpropan-2-yl ((2S)-2-((2-amino-3,3,3-trifluoro-2-methylpropanamido)methyl)-4-((1-ethyl-3-(2-hydroxyethoxy)-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (4-((1-ethyl-3-(2-hydroxyethoxy)-1H-pyrazol-4-yl)sulfonyl)-2-((2,2,2-trifluoroethylsulfonamido)methyl)-3,4-dihydro-2H-benzo[b][1,4]oxazin-6-yl)carbamate;

(S)-1,1,1-trifluoro-2-methylpropan-2-yl (4-((1-ethyl-3-(2-hydroxyethoxy)-1H-pyrazol-4-yl)sulfonyl)-2-(methylsulfonamidomethyl)-3,4-dihydro-2H-benzo[b][1,4]oxazin-6-yl)carbamate;

(S)-1,1,1-trifluoro-2-methylpropan-2-yl (2-(acetamidomethyl)-4-((3-cyclopropyl-4-fluorophenyl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3-cyclopropylphenyl)sulfonyl)-3,4-dihydro-2H-benzo[b][1,4]oxazin-6-yl)carbamate;

1,1,1-trifluoro-2-methylpropan-2-yl ((R)-2-((R)-1-acetamidoethyl)-4-((3-chloro-4-fluorophenyl)sulfonyl)-3,4-dihydro-2H-benzo[b][1,4]oxazin-6-yl)carbamate;

1,1,1-trifluoro-2-methylpropan-2-yl ((R)-2-((S)-1-acetamidoethyl)-4-((3-chloro-4-fluorophenyl)sulfonyl)-3,4-dihydro-2H-benzo[b][1,4]oxazin-6-yl)carbamate;

1,1,1-trifluoro-2-methylpropan-2-yl ((R)-2-((R or S)-1-acetamidoethyl)-4-((1-(difluoromethyl)-3-methyl-1H-pyrazol-4-yl)sulfonyl)-3,4-dihydro-2H-benzo[b][1,4]oxazin-6-yl)carbamate;

1,1,1-trifluoro-2-methylpropan-2-yl ((R)-2-((S or R)-1-acetamidoethyl)-4-((1-(difluoromethyl)-3-methyl-1H-pyrazol-4-yl)sulfonyl)-3,4-dihydro-2H-benzo[b][1,4]oxazin-6-yl)carbamate;

1,1,1-trifluoro-2-methylpropan-2-yl ((R)-2-((R or S)-1-acetamidoethyl)-4-((3,4-difluorophenyl)sulfonyl)-3,4-dihydro-2H-benzo[b][1,4]oxazin-6-yl)carbamate;

1,1,1-trifluoro-2-methylpropan-2-yl ((R)-2-((S or R)-1-acetamidoethyl)-4-((3,4-difluorophenyl)sulfonyl)-3,4-dihydro-2H-benzo[b][1,4]oxazin-6-yl)carbamate;

1,1,1-trifluoro-2-methylpropan-2-yl ((R)-2-((R or S)-1-acetamidoethyl)-4-((3-chloro-1-ethyl-1H-pyrazol-4-yl)sulfonyl)-3,4-dihydro-2H-benzo[b][1,4]oxazin-6-yl)carbamate;

1,1,1-trifluoro-2-methylpropan-2-yl ((R)-2-((S or R)-1-acetamidoethyl)-4-((3-chloro-1-ethyl-1H-pyrazol-4-yl)sulfonyl)-3,4-dihydro-2H-benzo[b][1,4]oxazin-6-yl)carbamate;

1,1,1-trifluoro-2-methylpropan-2-yl ((R)-2-((R or S)-1-acetamidoethyl)-4-((3-methoxy-1,5-dimethyl-1H-pyrazol-4-yl)sulfonyl)-3,4-dihydro-2H-benzo[b][1,4]oxazin-6-yl)carbamate;

1,1,1-trifluoro-2-methylpropan-2-yl ((R)-2-((S)-1-acetamidoethyl)-4-((3-methoxy-1,5-dimethyl-1H-pyrazol-4-yl)sulfonyl)-3,4-dihydro-2H-benzo[b][1,4]oxazin-6-yl)carbamate;

1,1,1-trifluoro-2-methylpropan-2-yl ((R or S)-2-((S or R)-1-acetamidoethyl)-4-((4-fluorophenyl)sulfonyl)-3,4-dihydro-2H-benzo[b][1,4]oxazin-6-yl)carbamate;

1,1,1-trifluoro-2-methylpropan-2-yl ((S or R)-2-((S or R)-1-acetamidoethyl)-4-((4-fluorophenyl)sulfonyl)-3,4-dihydro-2H-benzo[b][1,4]oxazin-6-yl)carbamate;

1,1,1-trifluoro-2-methylpropan-2-yl ((R or S)-2-((S or R)-1-acetamidoethyl)-4-((4-fluorophenyl)sulfonyl)-3,4-dihydro-2H-benzo[b][1,4]oxazin-6-yl)carbamate;

1,1,1-trifluoro-2-methylpropan-2-yl ((R or S)-2-((R or S)-1-acetamidoethyl)-4-((4-fluorophenyl)sulfonyl)-3,4-dihydro-2H-benzo[b][1,4]oxazin-6-yl)carbamate;

1,1,1-trifluoro-2-methylpropan-2-yl ((R)-2-((R or S)-acetamido(cyclopropyl)methyl)-4-((4-fluorophenyl)sulfonyl)-3,4-dihydro-2H-benzo[b][1,4]oxazin-6-yl)carbamate 1,1,1-trifluoro-2-methylpropan-2-yl ((R)-2-((S or R)-acetamido(cyclopropyl)methyl)-4-((4-fluorophenyl)sulfonyl)-3,4-dihydro-2H-benzo[b][1,4]oxazin-6-yl)carbamate;

(R)-tert-butyl (2-(2-acetamidopropan-2-yl)-4-((4-fluorophenyl)sulfonyl)-3,4-dihydro-2H-benzo[b][1,4]oxazin-6-yl)carbamate;

(S)-tert-butyl (2-(2-acetamidopropan-2-yl)-4-((4-fluorophenyl)sulfonyl)-3,4-dihydro-2H-benzo[b][1,4]oxazin-6-yl)carbamate;

(R)-1,1,1-trifluoro-2-methylpropan-2-yl (2-(2-acetamidopropan-2-yl)-4-((3-chloro-4-fluorophenyl)sulfonyl)-3,4-dihydro-2H-benzo[b][1,4]oxazin-6-yl)carbamate;

(S)-1,1,1-trifluoro-2-methylpropan-2-yl (2-(2-acetamidopropan-2-yl)-4-((3-chloro-4-fluorophenyl)sulfonyl)-3,4-dihydro-2H-benzo[b][1,4]oxazin-6-yl)carbamate;

(R)-1,1,1-trifluoro-2-methylpropan-2-yl (2-(2-acetamidopropan-2-yl)-4-((4-fluorophenyl)sulfonyl)-3,4-dihydro-2H-benzo[b][1,4]oxazin-6-yl)carbamate;

(R)-1,1,1-trifluoro-2-methylpropan-2-yl (4-((3-chloro-4-fluorophenyl)sulfonyl)-2-(2-(methylsulfonamido)propan-2-yl)-3,4-dihydro-2H-benzo[b][1,4]oxazin-6-yl)carbamate;

(R)-1,1,1-trifluoro-2-methylpropan-2-yl (4-((3-chloro-4-fluorophenyl)sulfonyl)-2-(2-(cyclopropanesulfonamido)propan-2-yl)-3,4-dihydro-2H-benzo[b][1,4]oxazin-6-yl)carbamate;

(R)-1,1,1-trifluoro-2-methylpropan-2-yl (4-((3,4-difluorophenyl)sulfonyl)-2-(2-(methylsulfonamido)propan-2-yl)-3,4-dihydro-2H-benzo[b][1,4]oxazin-6-yl)carbamate;

(R)-1,1,1-trifluoro-2-methylpropan-2-yl (4-((4-fluorophenyl)sulfonyl)-2-(2-(methylsulfonamido)propan-2-yl)-3,4-dihydro-2H-benzo[b][1,4]oxazin-6-yl)carbamate;

(R)-1,1,1-trifluoro-2-methylpropan-2-yl (2-(2-(2-(dimethylamino)-2-oxoacetamido)propan-2-yl)-4-((4-fluorophenyl)sulfonyl)-3,4-dihydro-2H-benzo[b][1,4]oxazin-6-yl)carbamate;

(R)-1,1,1-trifluoro-2-methylpropan-2-yl (2-(2-(cyclopropanesulfonamido)propan-2-yl)-4-((4-fluorophenyl)sulfonyl)-3,4-dihydro-2H-benzo[b][1,4]oxazin-6-yl)carbamate;

(R or S)-1,1,1-trifluoro-2-methylpropan-2-yl (2-(2-acetamidopropan-2-yl)-4-((3-chloro-1-ethyl-1H-pyrazol-4-yl)sulfonyl)-3,4-dihydro-2H-benzo[b][1,4]oxazin-6-yl)carbamate;

(R or S)-1,1,1-trifluoro-2-methylpropan-2-yl (2-(2-acetamidopropan-2-yl)-4-((1-(difluoromethyl)-3-methyl-1H-pyrazol-4-yl)sulfonyl)-3,4-dihydro-2H-benzo[b][1,4]oxazin-6-yl)carbamate;

(R or S)-1,1,1-trifluoro-2-methylpropan-2-yl (2-(2-acetamidopropan-2-yl)-4-((4-fluoro-3-(trifluoromethyl)phenyl)sulfonyl)-3,4-dihydro-2H-benzo[b][1,4]oxazin-6-yl)carbamate;

(R or S)-1,1,1-trifluoro-2-methylpropan-2-yl (2-(2-acetamidopropan-2-yl)-4-((3-methoxy-1,5-dimethyl-1H-pyrazol-4-yl)sulfonyl)-3,4-dihydro-2H-benzo[b][1,4]oxazin-6-yl)carbamate;

(R or S)-1,1,1-trifluoro-2-methylpropan-2-yl (2-(2-acetamidopropan-2-yl)-4-((3-chloro-1-ethyl-1H-pyrazol-4-yl)sulfonyl)-3,4-dihydro-2H-benzo[b][1,4]oxazin-6-yl)carbamate;

(R or S)-1,1,1-trifluoro-2-methylpropan-2-yl (2-(2-acetamidopropan-2-yl)-4-((1-(difluoromethyl)-3-methyl-1H-pyrazol-4-yl)sulfonyl)-3,4-dihydro-2H-benzo[b][1,4]oxazin-6-yl)carbamate;

(R or S)-1,1,1-trifluoro-2-methylpropan-2-yl (2-(2-acetamidopropan-2-yl)-4-((4-fluoro-3-(trifluoromethyl)phenyl)sulfonyl)-3,4-dihydro-2H-benzo[b][1,4]oxazin-6-yl)carbamate;

(R or S)-1,1,1-trifluoro-2-methylpropan-2-yl (2-(2-acetamidopropan-2-yl)-4-((3-methoxy-1,5-dimethyl-1H-pyrazol-4-yl)sulfonyl)-3,4-dihydro-2H-benzo[b][1,4]oxazin-6-yl)carbamate;

1,1,1-trifluoro-2-methylbutan-2-yl ((S)-2-(acetamidomethyl)-4-((4-fluorophenyl)sulfonyl)-3,4-dihydro-2H-benzo[b][1,4]oxazin-6-yl)carbamate;

(S)-tert-pentyl (2-(acetamidomethyl)-4-((4-fluorophenyl)sulfonyl)-3,4-dihydro-2H-benzo[b][1,4]oxazin-6-yl)carbamate;

(S)-2,3-dimethylbutan-2-yl (2-(acetamidomethyl)-4-((4-fluorophenyl)sulfonyl)-3,4-dihydro-2H-benzo[b][1,4]oxazin-6-yl)carbamate;

(S)-2,3,3-trimethylbutan-2-yl (2-(acetamidomethyl)-4-((4-fluorophenyl)sulfonyl)-3,4-dihydro-2H-benzo[b][1,4]oxazin-6-yl)carbamate;

2-cyano-1,1,1-trifluoropropan-2-yl ((S)-2-(acetamidomethyl)-4-((4-fluorophenyl)sulfonyl)-3,4-dihydro-2H-benzo[b][1,4]oxazin-6-yl)carbamate;

(S)-1-methylcyclobutyl (2-(acetamidomethyl)-4-((4-fluorophenyl)sulfonyl)-3,4-dihydro-2H-benzo[b][1,4]oxazin-6-yl)carbamate;

(S)-1-methylcyclopropyl (2-(acetamidomethyl)-4-((4-fluorophenyl)sulfonyl)-3,4-dihydro-2H-benzo[b][1,4]oxazin-6-yl)carbamate;

(S)-3,3,4,4,4-pentafluoro-2-methylbutan-2-yl (2-(acetamidomethyl)-4-((4-fluorophenyl)sulfonyl)-3,4-dihydro-2H-benzo[b][1,4]oxazin-6-yl)carbamate;

(S)-2,2,3,3,3-pentafluoropropyl (2-(acetamidomethyl)-4-((4-fluorophenyl)sulfonyl)-3,4-dihydro-2H-benzo[b][1,4]oxazin-6-yl)carbamate;
1-cyclopropyl-2,2,2-trifluoroethyl ((S)-2-(acetamidomethyl)-4-((4-fluorophenyl)sulfonyl)-3,4-dihydro-2H-benzo[b][1,4]oxazin-6-yl)carbamate;
1,1,1-trifluoro-3-methyl-3-phenylbutan-2-yl ((S)-2-(acetamidomethyl)-4-((4-fluorophenyl)sulfonyl)-3,4-dihydro-2H-benzo[b][1,4]oxazin-6-yl)carbamate;
2,2,2-trifluoro-1-(1-methylcyclohexyl)ethyl ((S)-2-(acetamidomethyl)-4-((4-fluorophenyl)sulfonyl)-3,4-dihydro-2H-benzo[b][1,4]oxazin-6-yl)carbamate;
1-cyclohexyl-2,2,2-trifluoroethyl ((S)-2-(acetamidomethyl)-4-((4-fluorophenyl)sulfonyl)-3,4-dihydro-2H-benzo[b][1,4]oxazin-6-yl)carbamate;
1-cyclohexyl-2,2,3,3,3-pentafluoropropyl ((S)-2-(acetamidomethyl)-4-((4-fluorophenyl)sulfonyl)-3,4-dihydro-2H-benzo[b][1,4]oxazin-6-yl)carbamate;
(R)-3,3,4,4,4-pentafluorobutan-2-yl ((S)-2-(acetamidomethyl)-4-((4-fluorophenyl)sulfonyl)-3,4-dihydro-2H-benzo[b][1,4]oxazin-6-yl)carbamate;
(S)-3,3,4,4,4-pentafluorobutan-2-yl ((S)-2-(acetamidomethyl)-4-((4-fluorophenyl)sulfonyl)-3,4-dihydro-2H-benzo[b][1,4]oxazin-6-yl)carbamate;
(S)-1,1,1,3,3,3-hexafluoropropan-2-yl (2-(acetamidomethyl)-4-((4-fluorophenyl)sulfonyl)-3,4-dihydro-2H-benzo[b][1,4]oxazin-6-yl)carbamate;
(S)-1-(trifluoromethyl)cyclohexyl (2-(acetamidomethyl)-4-((4-fluorophenyl)sulfonyl)-3,4-dihydro-2H-benzo[b][1,4]oxazin-6-yl)carbamate;
(S)-4,4-dimethyl-1-(trifluoromethyl)cyclohexyl (2-(acetamidomethyl)-4-((4-fluorophenyl)sulfonyl)-3,4-dihydro-2H-benzo[b][1,4]oxazin-6-yl)carbamate;
2,2,2-trifluoro-1-phenylethyl ((S)-2-(acetamidomethyl)-4-((4-fluorophenyl)sulfonyl)-3,4-dihydro-2H-benzo[b][1,4]oxazin-6-yl)carbamate;
1-(4-chlorophenyl)-2,2,2-trifluoroethyl ((S)-2-(acetamidomethyl)-4-((4-fluorophenyl)sulfonyl)-3,4-dihydro-2H-benzo[b][1,4]oxazin-6-yl)carbamate;
2,2,3,3,3-pentafluoro-1-phenylpropyl ((S)-2-(acetamidomethyl)-4-((4-fluorophenyl)sulfonyl)-3,4-dihydro-2H-benzo[b][1,4]oxazin-6-yl)carbamate;
1,1,1-trifluoro-2-phenylpropan-2-yl ((S)-2-(acetamidomethyl)-4-((4-fluorophenyl)sulfonyl)-3,4-dihydro-2H-benzo[b][1,4]oxazin-6-yl)carbamate;
1,1,1,2,2-pentafluoropentan-3-yl ((S)-2-(acetamidomethyl)-4-((4-fluorophenyl)sulfonyl)-3,4-dihydro-2H-benzo[b][1,4]oxazin-6-yl)carbamate;
1,1,1-trifluoro-3-phenylpropan-2-yl ((S)-2-(acetamidomethyl)-4-((4-fluorophenyl)sulfonyl)-3,4-dihydro-2H-benzo[b][1,4]oxazin-6-yl)carbamate;
(S)-2,2,2-trifluoroethyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;
(S)-(1-(trifluoromethyl)cyclopropyl)methyl (2-(acetamidomethyl)-4-((4-fluorophenyl)sulfonyl)-3,4-dihydro-2H-benzo[b][1,4]oxazin-6-yl)carbamate;
(S)-(1-(trifluoromethyl)cyclopropyl)methyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;
(S)-(1-(trifluoromethyl)cyclopropyl)methyl (2-(cyclopropanecarboxamidomethyl)-4-((4-fluorophenyl)sulfonyl)-3,4-dihydro-2H-benzo[b][1,4]oxazin-6-yl)carbamate;
(S)-(1-(trifluoromethyl)cyclopropyl)methyl (2-(acetamidomethyl)-4-((3,4-difluorophenyl)sulfonyl)-3,4-dihydro-2H-benzo[b][1,4]oxazin-6-yl)carbamate;
(S)-(1-(trifluoromethyl)cyclopropyl)methyl (2-(acetamidomethyl)-4-((4-fluoro-3-methoxyphenyl)sulfonyl)-3,4-dihydro-2H-benzo[b][1,4]oxazin-6-yl)carbamate;
(S)-(1-(trifluoromethyl)cyclopropyl)methyl (2-(acetamidomethyl)-4-((4-fluoro-3-methylphenyl)sulfonyl)-3,4-dihydro-2H-benzo[b][1,4]oxazin-6-yl)carbamate;
(S)-(1-(trifluoromethyl)cyclopropyl)methyl (2-(acetamidomethyl)-4-((3-chloro-4-fluorophenyl)sulfonyl)-3,4-dihydro-2H-benzo[b][1,4]oxazin-6-yl)carbamate;
(S)-4,4-difluorocyclohexyl (2-(acetamidomethyl)-4-((4-fluorophenyl)sulfonyl)-3,4-dihydro-2H-benzo[b][1,4]oxazin-6-yl)carbamate;
(2,2-difluorocyclopropyl)methyl ((S)-2-(acetamidomethyl)-4-((4-fluorophenyl)sulfonyl)-3,4-dihydro-2H-benzo[b][1,4]oxazin-6-yl)carbamate;
(S)-cyclopentyl (2-(acetamidomethyl)-4-((4-fluorophenyl)sulfonyl)-3,4-dihydro-2H-benzo[b][1,4]oxazin-6-yl)carbamate;
(S)-cyclopentyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;
(S)-cyclohexyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;
2-(trifluoromethyl)cyclohexyl ((S)-2-(acetamidomethyl)-4-((4-fluorophenyl)sulfonyl)-3,4-dihydro-2H-benzo[b][1,4]oxazin-6-yl)carbamate;
(2S)-bicyclo[2.2.1]heptan-2-yl ((S)-2-(acetamidomethyl)-4-((4-fluorophenyl)sulfonyl)-3,4-dihydro-2H-benzo[b][1,4]oxazin-6-yl)carbamate;
6-(2,2,2-trifluoroethyl)bicyclo[3.1.0]hexan-6-yl ((S)-2-(acetamidomethyl)-4-((4-fluorophenyl)sulfonyl)-3,4-dihydro-2H-benzo[b][1,4]oxazin-6-yl)carbamate;
(1R,2S)-2-(trifluoromethyl)cyclohexyl ((S)-2-(acetamidomethyl)-4-((4-fluorophenyl)sulfonyl)-3,4-dihydro-2H-benzo[b][1,4]oxazin-6-yl)carbamate;
(1S,2R)-2-(trifluoromethyl)cyclohexyl ((S)-2-(acetamidomethyl)-4-((4-fluorophenyl)sulfonyl)-3,4-dihydro-2H-benzo[b][1,4]oxazin-6-yl)carbamate;
3,3-dimethylbutan-2-yl ((S)-2-(acetamidomethyl)-4-((4-fluorophenyl)sulfonyl)-3,4-dihydro-2H-benzo[b][1,4]oxazin-6-yl)carbamate;
1,1,1-trifluoropropan-2-yl ((S)-2-(acetamidomethyl)-4-((4-fluorophenyl)sulfonyl)-3,4-dihydro-2H-benzo[b][1,4]oxazin-6-yl)carbamate;
(R)-3,3-dimethylbutan-2-yl ((S)-2-(acetamidomethyl)-4-((4-fluorophenyl)sulfonyl)-3,4-dihydro-2H-benzo[b][1,4]oxazin-6-yl)carbamate;
(S)-3,3-dimethylbutan-2-yl ((S)-2-(acetamidomethyl)-4-((4-fluorophenyl)sulfonyl)-3,4-dihydro-2H-benzo[b][1,4]oxazin-6-yl)carbamate;
(S)-3,3-dimethylbutan-2-yl ((S)-2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;
(R)-1,1,1-trifluoro-3,3-dimethylbutan-2-yl ((S)-2-(acetamidomethyl)-4-((4-fluorophenyl)sulfonyl)-3,4-dihydro-2H-benzo[b][1,4]oxazin-6-yl)carbamate;
(S)-1,1,1-trifluoro-3,3-dimethylbutan-2-yl ((S)-2-(acetamidomethyl)-4-((4-fluorophenyl)sulfonyl)-3,4-dihydro-2H-benzo[b][1,4]oxazin-6-yl)carbamate;
(R)-3,3-dimethylbutan-2-yl ((S)-2-(cyclopropanecarboxamidomethyl)-4-((4-fluorophenyl)sulfonyl)-3,4-dihydro-2H-benzo[b][1,4]oxazin-6-yl)carbamate;
(S)-3,3-dimethylbutan-2-yl ((S)-2-(cyclopropanecarboxamidomethyl)-4-((4-fluorophenyl)sulfonyl)-3,4-dihydro-2H-benzo[b][1,4]oxazin-6-yl)carbamate;

(R)-3,3-dimethylbutan-2-yl ((S)-2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-2,2-difluoro-2-phenylethyl (2-(acetamidomethyl)-4-((4-fluorophenyl)sulfonyl)-3,4-dihydro-2H-benzo[b][1,4]oxazin-6-yl)carbamate;

(2,2,3,3-tetrafluorocyclobutyl)methyl ((S)-2-(acetamidomethyl)-4-((4-fluorophenyl)sulfonyl)-3,4-dihydro-2H-benzo[b][1,4]oxazin-6-yl)carbamate;

(S)-2-cyano-2-methylpropyl (2-(acetamidomethyl)-4-((4-fluorophenyl)sulfonyl)-3,4-dihydro-2H-benzo[b][1,4]oxazin-6-yl)carbamate;

(S)-4-((2-(acetamidomethyl)-6-(((neopentyloxy)carbonyl)amino)-2H-benzo[b][1,4]oxazin-4(3H)-yl)sulfonyl)-1-(difluoromethyl)-3-methyl-1H-pyrazole;

(S)-isobutyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-isobutyl (2-(acetamidomethyl)-4-((4-fluorophenyl)sulfonyl)-3,4-dihydro-2H-benzo[b][1,4]oxazin-6-yl)carbamate;

(S)-(1-methylcyclopropyl)methyl (2-(acetamidomethyl)-4-((4-fluorophenyl)sulfonyl)-3,4-dihydro-2H-benzo[b][1,4]oxazin-6-yl)carbamate;

sec-butyl ((S)-2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-(1-methylcyclopentyl)methyl (2-(acetamidomethyl)-4-((4-fluorophenyl)sulfonyl)-3,4-dihydro-2H-benzo[b][1,4]oxazin-6-yl)carbamate;

(S)-tert-butyl 3-((((2-(acetamidomethyl)-4-((4-fluorophenyl)sulfonyl)-3,4-dihydro-2H-benzo[b][1,4]oxazin-6-yl)carbamoyl)oxy)methyl)-3-methylazetidine-1-carboxylate;

(S)-benzyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-2-chlorobenzyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-2,2-difluoro-3,3-dimethylpentyl (2-(acetamidomethyl)-4-((4-fluorophenyl)sulfonyl)-3,4-dihydro-2H-benzo[b][1,4]oxazin-6-yl)carbamate;

(S)-2,2-difluoro-3,3-dimethylpent-4-en-1-yl (2-(acetamidomethyl)-4-((4-fluorophenyl)sulfonyl)-3,4-dihydro-2H-benzo[b][1,4]oxazin-6-yl)carbamate;

(2,2-difluoro-1-phenylcyclopropyl)methyl ((S)-2-(acetamidomethyl)-4-((4-fluorophenyl)sulfonyl)-3,4-dihydro-2H-benzo[b][1,4]oxazin-6-yl)carbamate;

(S)-3,3,3-trifluoropropyl (2-(acetamidomethyl)-4-((4-fluorophenyl)sulfonyl)-3,4-dihydro-2H-benzo[b][1,4]oxazin-6-yl)carbamate;

(S)-2-(trimethylsilyl)ethyl (2-(acetamidomethyl)-4-((4-fluorophenyl)sulfonyl)-3,4-dihydro-2H-benzo[b][1,4]oxazin-6-yl)carbamate;

(S)-2,2,2-trichloroethyl (2-(acetamidomethyl)-4-((4-fluorophenyl)sulfonyl)-3,4-dihydro-2H-benzo[b][1,4]oxazin-6-yl)carbamate;

(S)-2,2,2-trichloroethyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-2,2,2-trichloroethyl (2-(cyclopropanecarboxamidomethyl)-4-((4-fluorophenyl)sulfonyl)-3,4-dihydro-2H-benzo[b][1,4]oxazin-6-yl)carbamate;

(S)-methyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-isopropyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-phenyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-4-chlorophenyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-2-chlorophenyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-cyclopropylmethyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-neopentyl (2-(acetamidomethyl)-4-((4-fluorophenyl)sulfonyl)-3,4-dihydro-2H-benzo[b][1,4]oxazin-6-yl)carbamate;

(S)-cyclopropylmethyl (2-(acetamidomethyl)-4-((4-fluorophenyl)sulfonyl)-3,4-dihydro-2H-benzo[b][1,4]oxazin-6-yl)carbamate;

(S)-2-(methylsulfonyl)ethyl (2-(acetamidomethyl)-4-((4-fluorophenyl)sulfonyl)-3,4-dihydro-2H-benzo[b][1,4]oxazin-6-yl)carbamate;

1-cyclopropylethyl ((S)-2-(acetamidomethyl)-4-((4-fluorophenyl)sulfonyl)-3,4-dihydro-2H-benzo[b][1,4]oxazin-6-yl)carbamate;

3,3,4,4,4-pentafluorobutan-2-yl ((S)-2-(acetamidomethyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((1-fluorocyclopropanecarboxamido)methyl)-4-((4-fluorophenyl)sulfonyl)-3,4-dihydro-2H-benzo[b][1,4]oxazin-6-yl)carbamate;

(S)-tert-butyl (4-((4-fluorophenyl)sulfonyl)-2-(pivalamidomethyl)-3,4-dihydro-2H-benzo[b][1,4]oxazin-6-yl)carbamate;

(S)-tert-butyl (4-((4-fluorophenyl)sulfonyl)-2-((1-methylcyclopropanecarboxamido)methyl)-3,4-dihydro-2H-benzo[b][1,4]oxazin-6-yl)carbamate (S)-tert-butyl (4-((4-fluorophenyl)sulfonyl)-2-(propionamidomethyl)-3,4-dihydro-2H-benzo[b][1,4]oxazin-6-yl)carbamate;

(S)-tert-butyl (2-(butyramidomethyl)-4-((4-fluorophenyl)sulfonyl)-3,4-dihydro-2H-benzo[b][1,4]oxazin-6-yl)carbamate;

(S)-tert-butyl (4-((4-fluorophenyl)sulfonyl)-2-(isobutyramidomethyl)-3,4-dihydro-2H-benzo[b][1,4]oxazin-6-yl)carbamate;

(S)-tert-butyl (2-(cyclopropanecarboxamidomethyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-(cyclopropanecarboxamidomethyl)-4-((4-fluorophenyl)sulfonyl)-3,4-dihydro-2H-benzo[b][1,4]oxazin-6-yl)carbamate;

(S)-tert-butyl (2-(cyclopropanecarboxamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-neopentyl (2-(cyclopropanecarboxamidomethyl)-4-((4-fluorophenyl)sulfonyl)-3,4-dihydro-2H-benzo[b][1,4]oxazin-6-yl)carbamate (S)-neopentyl (2-(cyclopropanecarboxamidomethyl)-4-((1-(difluoromethyl)-3-methyl-1H-pyrazol-4-yl)sulfonyl)-3,4-dihydro-2H-benzo[b][1,4]oxazin-6-yl)carbamate;

1,1,1-trifluoro-2-methylpropan-2-yl ((S)-2-(((1S,2S)-2-fluorocyclopropanecarboxamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((3-fluorocyclobutanecarboxamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((3,3-difluorocyclobutanecarboxamido)methyl)-4-((4-fluorophenyl)sulfonyl)-3,4-dihydro-2H-benzo[b][1,4]oxazin-6-yl)carbamate;

1,1,1-trifluoro-2-methylpropan-2-yl ((2S)-4-((4-fluorophenyl)sulfonyl)-2-((2-methylcyclopropanecarboxamido)methyl)-3,4-dihydro-2H-benzo[b][1,4]oxazin-6-yl)carbamate;

1,1,1-trifluoro-2-methylpropan-2-yl ((2S)-2-((2,2-difluorocyclopropanecarboxamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((bicyclo[1.1.1]pentane-1-carboxamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((1-methylcyclopropanecarboxamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((3-methylcyclobutanecarboxamido)methyl)-3,4-dihydro-2H-benzo[b][1,4]oxazin-6-yl)carbamate;

1,1,1-trifluoro-2-methylpropan-2-yl ((2S)-2-((2,2-dimethylcyclopropanecarboxamido)methyl)-4-((4-fluorophenyl)sulfonyl)-3,4-dihydro-2H-benzo[b][1,4]oxazin-6-yl)carbamate;

1,1,1-trifluoro-2-methylpropan-2-yl ((S)-2-(((1R,2S)-2-fluorocyclopropanecarboxamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((1-(dimethylamino)cyclopropanecarboxamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((1-methylcyclobutanecarboxamido)methyl)-3,4-dihydro-2H-benzo[b][1,4]oxazin-6-yl)carbamate;

(S)-1,1,1-trifluoro-2-methylpropan-2-yl (2-((2-amino-2-methylpropanamido)methyl)-4-((4-fluorophenyl)sulfonyl)-3,4-dihydro-2H-benzo[b][1,4]oxazin-6-yl)carbamate;

1,1,1-trifluoro-2-methylpropan-2-yl ((2S)-4-((4-fluorophenyl)sulfonyl)-2-((3,3,3-trifluoro-2-hydroxypropanamido)methyl)-3,4-dihydro-2H-benzo[b][1,4]oxazin-6-yl)carbamate;

1,1,1-trifluoro-2-methylpropan-2-yl ((2S)-2-((2-amino-3,3,3-trifluoro-2-methylpropanamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((1-aminocyclopentanecarboxamido)methyl)-4-((4-fluorophenyl)sulfonyl)-3,4-dihydro-2H-benzo[b][1,4]oxazin-6-yl)carbamate;

1,1,1-trifluoro-2-methylpropan-2-yl ((2S)-2-((2-amino-3-fluoro-3-methylbutanamido)methyl)-4-((4-fluorophenyl)sulfonyl)-3,4-dihydro-2H-benzo[b][1,4]oxazin-6-yl)carbamate;

1,1,1-trifluoro-2-methylpropan-2-yl ((2S)-2-((2-amino-3,3,3-trifluoropropanamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((1-aminocyclopropanecarboxamido)methyl)-4-((4-fluorophenyl)sulfonyl)-3,4-dihydro-2H-benzo[b][1,4]oxazin-6-yl)carbamate;

1,1,1-trifluoro-2-methylpropan-2-yl ((2S)-4-((4-fluorophenyl)sulfonyl)-2-((3,3,3-trifluoro-2-hydroxy-2-methylpropanamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((2-hydroxy-2-methylpropanamido)methyl)-3,4-dihydro-2H-benzo[b][1,4]oxazin-6-yl)carbamate;

1,1,1-trifluoro-2-methylpropan-2-yl ((2S)-2-((2-(dimethylamino)propanamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((2-(dimethylamino)-2-oxoacetamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((2-(dimethylamino)-2-methylpropanamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((2-methyl-2-(methylamino)propanamido)methyl)-3,4-dihydro-2H-benzo[b][1,4]oxazin-6-yl)carbamate;

1,1,1-trifluoro-2-methylpropan-2-yl ((2S)-2-((1-(tert-butyl)azetidine-2-carboxamido)methyl)-4-((4-fluorophenyl)sulfonyl)-3,4-dihydro-2H-benzo[b][1,4]oxazin-6-yl)carbamate;

1,1,1-trifluoro-2-methylpropan-2-yl ((2S)-4-((4-fluorophenyl)sulfonyl)-2-((spiro[2.3]hexane-1-carboxamido)methyl)-3,4-dihydro-2H-benzo[b][1,4]oxazin-6-yl)carbamate;

1,1,1-trifluoro-2-methylpropan-2-yl ((2S)-2-((2,2-difluoro-1-methylcyclopropanecarboxamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((oxetane-3-carboxamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((3-methyloxetane-3-carboxamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((1-methylazetidine-3-carboxamido)methyl)-3,4-dihydro-2H-benzo[b][1,4]oxazin-6-yl)carbamate;

(S)-1,1,1-trifluoro-2-methylpropan-2-yl (2-((3-aminooxetane-3-carboxamido)methyl)-4-((4-fluorophenyl)sulfonyl)-3,4-dihydro-2H-benzo[b][1,4]oxazin-6-yl)carbamate;

1,1,1-trifluoro-2-methylpropan-2-yl ((2S)-4-((4-fluorophenyl)sulfonyl)-2-((tetrahydro-2H-pyran-3-carboxamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((2-(tetrahydro-2H-pyran-4-yl)acetamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((tetrahydro-2H-pyran-4-carboxamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((1-methyl-1H-pyrazole-4-carboxamido)methyl)-3,4-dihydro-2H-benzo[b][1,4]oxazin-6-yl)carbamate;

(S)-1,1,1-trifluoro-2-methylpropan-2-yl (2-((1H-pyrazole-4-carboxamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((1-(trifluoromethyl)cyclopropanecarboxamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((1-methyl-1H-pyrrole-2-carboxamido)methyl)-3,4-dihydro-2H-benzo[b][1,4]oxazin-6-yl)carbamate;

(S)-1,1,1-trifluoro-2-methylpropan-2-yl (2-((1-cyanocyclopropanecarboxamido)methyl)-4-((4-fluorophenyl)sulfonyl)-3,4-dihydro-2H-benzo[b][1,4]oxazin-6-yl)carbamate;

(S)-5-(((4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)carbamoyl)isoxazole;

(S)-4-(((4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)carbamoyl)-1H-imidazole;

(S)-1,1,1-trifluoro-2-methylpropan-2-yl (4-((4-fluorophenyl)sulfonyl)-2-((1-hydroxycyclopropanecarboxamido)methyl)-3,4-dihydro-2H-benzo[b][1,4]oxazin-6-yl)carbamate;

(S)-2-(((4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)carbamoyl)-1H-imidazole;

(S)-3-(((4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)carbamoyl)-1H-1,2,4-triazole;

(S)-5-(((4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)carbamoyl)-1H-1,2,3-triazole;

(S)-1,1,1-trifluoro-2-methylpropan-2-yl (4-((4-fluorophenyl)sulfonyl)-2-((furan-2-carboxamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((furan-2-carboxamido)methyl)-3,4-dihydro-2H-benzo[b][1,4]oxazin-6-yl)carbamate;

(S)-3-(((4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)carbamoyl)azetidine;

1,1,1-trifluoro-2-methylpropan-2-yl ((2S)-4-((4-fluorophenyl)sulfonyl)-2-((tetrahydrofuran-2-carboxamido)methyl)-3,4-dihydro-2H-benzo[b][1,4]oxazin-6-yl)carbamate 1,1,1-trifluoro-2-methylpropan-2-yl ((2S)-4-((4-fluorophenyl)sulfonyl)-2-((2-methyl-5-oxopyrrolidine-2-carboxamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((1-hydroxycyclobutanecarboxamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((3-methoxycyclobutanecarboxamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((1-isopropylazetidine-3-carboxamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((1-methylcyclopentanecarboxamido)methyl)-3,4-dihydro-2H-benzo[b][1,4]oxazin-6-yl)carbamate;

1,1,1-trifluoro-2-methylpropan-2-yl ((2S)-4-((4-fluorophenyl)sulfonyl)-2-((oxetane-2-carboxamido)methyl)-3,4-dihydro-2H-benzo[b][1,4]oxazin-6-yl)carbamate;

(S)-1,1,1-trifluoro-2-methylpropan-2-yl (2-((4H-1,2,4-triazole-3-carboxamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((2-hydroxy-2-methylpropanamido)methyl)-3,4-dihydro-2H-benzo[b][1,4]oxazin-6-yl)carbamate;

(S)-1,1,1-trifluoro-2-methylpropan-2-yl (2-((2-(3,5-dimethylisoxazol-4-yl)acetamido)methyl)-4-((4-fluorophenyl)sulfonyl)-3,4-dihydro-2H-benzo[b][1,4]oxazin-6-yl)carbamate;

1,1,1-trifluoro-2-methylpropan-2-yl ((S)-2-(((1R,2S)-2-cyanocyclopropanecarboxamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((1H-pyrrole-2-carboxamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((3,5-dimethylisoxazole-4-carboxamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((4-methyl-1H-imidazole-5-carboxamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((2-methyl-1H-imidazole-4-carboxamido)methyl)-3,4-dihydro-2H-benzo[b][1,4]oxazin-6-yl)carbamate;

(S)-1,1,1-trifluoro-2-methylpropan-2-yl (2-((3-(ethylsulfonyl)benzamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((4-(ethylsulfonyl)benzamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((2-(4-(ethylsulfonyl)phenyl)acetamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((2-methoxy-2-methylpropanamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((tetrahydro-2H-pyran-4-carboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((oxetane-3-carboxamido)methyl)-3,4-dihydro-2H-benzo[b][1,4]oxazin-6-yl)carbamate;

(S)-1,1,1-trifluoro-2-methylpropan-2-yl (4-((1-ethyl-3-methoxy-1H-pyrazol-4-yl)sulfonyl)-2-((oxetane-3-carboxamido)methyl)-3,4-dihydro-2H-benzo[b][1,4]oxazin-6-yl)carbamate;

(S)-1,1,1-trifluoro-2-methylpropan-2-yl (4-((2-methoxy-5,6-dihydro-4H-pyrrolo[1,2-b]pyrazol-3-yl)sulfonyl)-2-((oxetane-3-carboxamido)methyl)-3,4-dihydro-2H-benzo[b][1,4]oxazin-6-yl)carbamate;

1,1,1-trifluoro-2-methylpropan-2-yl ((S)-4-((3-chloro-4-fluorophenyl)sulfonyl)-2-(((1S,2S)-2-fluorocyclopropanecarboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((3-methyloxetane-3-carboxamido)methyl)-3,4-dihydro-2H-benzo[b][1,4]oxazin-6-yl)carbamate;

(S)-1,1,1-trifluoro-2-methylpropan-2-yl (2-((3-aminooxetane-3-carboxamido)methyl)-4-((3-chloro-4-fluorophenyl)sulfonyl)-3,4-dihydro-2H-benzo[b][1,4]oxazin-6-yl)carbamate;

1,1,1-trifluoro-2-methylpropan-2-yl ((2S)-4-((3-chloro-4-fluorophenyl)sulfonyl)-2-((2-methyltetrahydrofuran-2-carboxamido)methyl)-3,4-dihydro-2H-benzo[b][1,4]oxazin-6-yl)carbamate;

1,1,1-trifluoro-2-methylpropan-2-yl ((2S)-4-((3-chloro-4-fluorophenyl)sulfonyl)-2-((2-isopropyltetrahydro-2H-pyran-4-carboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((4-cyanotetrahydro-2H-pyran-4-carboxamido)methyl)-3,4-dihydro-2H-benzo[b][1,4]oxazin-6-yl)carbamate;

1,1,1-trifluoro-2-methylpropan-2-yl ((2S)-4-((3-chloro-4-fluorophenyl)sulfonyl)-2-((2-methyltetrahydro-2H-pyran-2-carboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((1-methyl-1H-pyrazole-4-carboxamido)methyl)-3,4-dihydro-2H-benzo[b][1,4]oxazin-6-yl)carbamate;

(S)-1,1,1-trifluoro-2-methylpropan-2-yl (2-((1H-pyrazole-4-carboxamido)methyl)-4-((3-chloro-4-fluorophenyl)sulfonyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((1-(trifluoromethyl)cyclopropanecarboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((1-methylcyclopropanecarboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((1-cyanocyclopropanecarboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((1-hydroxycyclopropanecarboxamido)methyl)-3,4-dihydro-2H-benzo[b][1,4]oxazin-6-yl)carbamate;

(S)-1,1,1-trifluoro-2-methylpropan-2-yl (2-((1H-imidazole-2-carboxamido)methyl)-4-((3-chloro-4-fluorophenyl)sulfonyl)-3,4-dihydro-2H-benzo[b][1,4]oxazin-6-yl)carbamate;

1,1,1-trifluoro-2-methylpropan-2-yl ((2S)-4-((3-chloro-4-fluorophenyl)sulfonyl)-2-((2-methylcyclopropanecarboxamido)methyl)-3,4-dihydro-2H-benzo[b][1,4]oxazin-6-yl)carbamate;

1,1,1-trifluoro-2-methylpropan-2-yl ((S)-4-((3-chloro-4-fluorophenyl)sulfonyl)-2-(((S)-tetrahydrofuran-2-carboxamido)methyl)-3,4-dihydro-2H-benzo[b][1,4]oxazin-6-yl)carbamate;

1,1,1-trifluoro-2-methylpropan-2-yl ((2S)-4-((3-chloro-4-fluorophenyl)sulfonyl)-2-((tetrahydrofuran-2-carboxamido)methyl)-3,4-dihydro-2H-benzo[b][1,4]oxazin-6-yl)carbamate;

1,1,1-trifluoro-2-methylpropan-2-yl ((S)-4-((3-chloro-4-fluorophenyl)sulfonyl)-2-(((1R,2S)-2-cyanocyclopropanecarboxamido)methyl)-3,4-dihydro-2H-benzo[b][1,4]oxazin-6-yl)carbamate;

1,1,1-trifluoro-2-methylpropan-2-yl ((2S)-4-((3-chloro-4-fluorophenyl)sulfonyl)-2-((2-methyl-5-oxopyrrolidine-2-carboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((1-hydroxycyclobutanecarboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((3-methoxycyclobutanecarboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((3,3-difluorocyclobutanecarboxamido)methyl)-3,4-dihydro-2H-benzo[b][1,4]oxazin-6-yl)carbamate;

(S)-1,1,1-trifluoro-2-methylpropan-2-yl (2-((bicyclo[1.1.1]pentane-1-carboxamido)methyl)-4-((3-chloro-4-fluorophenyl)sulfonyl)-3,4-dihydro-2H-benzo[b][1,4]oxazin-6-yl)carbamate;

1,1,1-trifluoro-2-methylpropan-2-yl ((2S)-4-((3-chloro-4-fluorophenyl)sulfonyl)-2-((tetrahydro-2H-pyran-3-carboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((1-methylcyclopentanecarboxamido)methyl)-3,4-dihydro-2H-benzo[b][1,4]oxazin-6-yl)carbamate;

1,1,1-trifluoro-2-methylpropan-2-yl ((S)-4-((3-chloro-4-fluorophenyl)sulfonyl)-2-(((1R,2S)-2-fluorocyclopropanecarboxamido)methyl)-3,4-dihydro-2H-benzo[b][1,4]oxazin-6-yl)carbamate;

1,1,1-trifluoro-2-methylpropan-2-yl ((2S)-4-((3-chloro-4-fluorophenyl)sulfonyl)-2-((2,2-dimethyltetrahydro-2H-pyran-4-carboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((4-methyltetrahydro-2H-pyran-4-carboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((3-ethyloxetane-3-carboxamido)methyl)-3,4-dihydro-2H-benzo[b][1,4]oxazin-6-yl)carbamate (S)-1,1,1-trifluoro-2-methylpropan-2-yl (4-((3-chloro-4-fluorophenyl)sulfonyl)-2-((4-fluorotetrahydro-2H-pyran-4-carboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((1-methylcyclobutanecarboxamido)methyl)-3,4-dihydro-2H-benzo[b][1,4]oxazin-6-yl)carbamate;

(S)-1,1,1-trifluoro-2-methylpropan-2-yl (4-((1-ethyl-3-methyl-1H-pyrazol-4-yl)sulfonyl)-2-((oxetane-3-carboxamido)methyl)-3,4-dihydro-2H-benzo[b][1,4]oxazin-6-yl)carbamate;

(S)-1,1,1-trifluoro-2-methylpropan-2-yl (4-((3,4-difluorophenyl)sulfonyl)-2-((oxetane-3-carboxamido)methyl)-3,4-dihydro-2H-benzo[b][1,4]oxazin-6-yl)carbamate;

1,1,1-trifluoro-2-methylpropan-2-yl ((S)-2-(((1R,2S)-2-cyanocyclopropanecarboxamido)methyl)-4-((3,4-difluorophenyl)sulfonyl)-3,4-dihydro-2H-benzo[b][1,4]oxazin-6-yl)carbamate;

1,1,1-trifluoro-2-methylpropan-2-yl ((S)-2-(((1R,2S)-2-cyanocyclopropanecarboxamido)methyl)-4-((1-ethyl-3-methyl-1H-pyrazol-4-yl)sulfonyl)-3,4-dihydro-2H-benzo[b][1,4]oxazin-6-yl)carbamate;

1,1,1-trifluoro-2-methylpropan-2-yl ((S)-4-((3,4-difluorophenyl)sulfonyl)-2-(((1R,2S)-2-fluorocyclopropanecarboxamido)methyl)-3,4-dihydro-2H-benzo[b][1,4]oxazin-6-yl)carbamate;

(S)-1,1,1-trifluoro-2-methylpropan-2-yl (4-((3-chloro-1-ethyl-1H-pyrazol-4-yl)sulfonyl)-2-((oxetane-3-carboxamido)methyl)-3,4-dihydro-2H-benzo[b][1,4]oxazin-6-yl)carbamate;

1,1,1-trifluoro-2-methylpropan-2-yl ((2S)-4-((3-chloro-4-fluorophenyl)sulfonyl)-2-((2-(tetrahydro-2H-pyran-3-yl)acetamido)methyl)-3,4-dihydro-2H-benzo[b][1,4]oxazin-6-yl)carbamate;

1,1,1-trifluoro-2-methylpropan-2-yl ((2S)-4-((3-chloro-4-fluorophenyl)sulfonyl)-2-((2-methyltetrahydrofuran-3-carboxamido)methyl)-3,4-dihydro-2H-benzo[b][1,4]oxazin-6-yl)carbamate;

(S)-1,1,1-trifluoro-2-methylpropan-2-yl (4-((3-ethoxy-1-ethyl-1H-pyrazol-4-yl)sulfonyl)-2-((oxetane-3-carboxamido)methyl)-3,4-dihydro-2H-benzo[b][1,4]oxazin-6-yl)carbamate;

1,1,1-trifluoro-2-methylpropan-2-yl ((S)-4-((3-(difluoromethoxy)-1-ethyl-1H-pyrazol-4-yl)sulfonyl)-2-((1S,2S)-2-fluorocyclopropanecarboxamido)methyl)-3,4-dihydro-2H-benzo[b][1,4]oxazin-6-yl)carbamate;

(S)-1,1,1-trifluoro-2-methylpropan-2-yl (4-((3-(difluoromethoxy)-1-ethyl-1H-pyrazol-4-yl)sulfonyl)-2-((2-hydroxy-2-methylpropanamido)methyl)-3,4-dihydro-2H-benzo[b][1,4]oxazin-6-yl)carbamate;

1,1,1-trifluoro-2-methylpropan-2-yl ((2S)-2-((2-amino-3,3,3-trifluoro-2-methylpropanamido)methyl)-4-((3-(difluoromethoxy)-1-ethyl-1H-pyrazol-4-yl)sulfonyl)-3,4-dihydro-2H-benzo[b][1,4]oxazin-6-yl)carbamate;

1,1,1-trifluoro-2-methylpropan-2-yl ((S)-4-((1-(difluoromethyl)-3-ethoxy-1H-pyrazol-4-yl)sulfonyl)-2-(((1S,2S)-2-fluorocyclopropanecarboxamido)methyl)-3,4-dihydro-2H-benzo[b][1,4]oxazin-6-yl)carbamate (S)-1,1,1-trifluoro-2-methylpropan-2-yl (4-((1-(difluoromethyl)-3-ethoxy-1H-pyrazol-4-yl)sulfonyl)-2-((2-hydroxy-2-methylpropanamido)methyl)-3,4-dihydro-2H-benzo[b][1,4]oxazin-6-yl)carbamate;

1,1,1-trifluoro-2-methylpropan-2-yl ((2S)-2-((2-amino-3,3,3-trifluoro-2-methylpropanamido)methyl)-4-((1-(difluoromethyl)-3-ethoxy-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (4-((3-(2,2-difluoroethoxy)-1-ethyl-1H-pyrazol-4-yl)sulfonyl)-2-((2-hydroxy-2-methylpropanamido)methyl)-3,4-dihydro-2H-benzo[b][1,4]oxazin-6-yl)carbamate;

(S)-1,1,1-trifluoro-2-methylpropan-2-yl (4-((1-(2,2-difluoroethyl)-3-ethoxy-1H-pyrazol-4-yl)sulfonyl)-2-((2-hydroxy-2-methylpropanamido)methyl)-3,4-dihydro-2H-benzo[b][1,4]oxazin-6-yl)carbamate;

(S)-1,1,1-trifluoro-2-methylpropan-2-yl (4-((1-ethyl-3-methyl-1H-pyrazol-4-yl)sulfonyl)-2-((2-hydroxy-2-methylpropanamido)methyl)-3,4-dihydro-2H-benzo[b][1,4]oxazin-6-yl)carbamate;

(S)-1,1,1-trifluoro-2-methylpropan-2-yl (2-((2-hydroxy-2-methylpropanamido)methyl)-4-((2-methoxy-5,6-dihydro-4H-pyrrolo[1,2-b]pyrazol-3-yl)sulfonyl)-3,4-dihydro-2H-benzo[b][1,4]oxazin-6-yl)carbamate;

(S)-1,1,1-trifluoro-2-methylpropan-2-yl (2-(cyclopropanesulfonamidomethyl)-4-((4-fluorophenyl)sulfonyl)-3,4-dihydro-2H-benzo[b][1,4]oxazin-6-yl)carbamate;

(S)-4-((2-(cyclopropanesulfonamidomethyl)-6-((((1,1,1-trifluoro-2-methylpropan-2-yl)oxy)carbonyl)amino)-2H-benzo[b][1,4]oxazin-4(3H)-yl)sulfonyl)-1-(difluoromethyl)-3-methyl-1H-pyrazole;

(S)-1,1,1-trifluoro-2-methylpropan-2-yl (2-(cyclopropanesulfonamidomethyl)-4-((3,4-difluorophenyl)sulfonyl)-3,4-dihydro-2H-benzo[b][1,4]oxazin-6-yl)carbamate;

(S)-1,1,1-trifluoro-2-methylpropan-2-yl (2-(cyclopropanesulfonamidomethyl)-4-((3-ethoxy-4-fluorophenyl)sulfonyl)-3,4-dihydro-2H-benzo[b][1,4]oxazin-6-yl)carbamate;

(S)-tert-butyl (2-(cyclopropanesulfonamidomethyl)-4-((1-(difluoromethyl)-5-methyl-1H-pyrazol-4-yl)sulfonyl)-3,4-dihydro-2H-benzo[b][1,4]oxazin-6-yl)carbamate;

(S)-4-((6-((tert-butoxycarbonyl)amino)-2-(cyclopropanesulfonamidomethyl)-2H-benzo[b][1,4]oxazin-4(3H)-yl)sulfonyl)-3-chloro-1-ethyl-1H-pyrazole;

(S)-1,1,1-trifluoro-2-methylpropan-2-yl (2-(cyclopropanesulfonamidomethyl)-4-((3-(methylsulfonyl)phenyl)sulfonyl)-3,4-dihydro-2H-benzo[b][1,4]oxazin-6-yl)carbamate;

(S)-1,1,1-trifluoro-2-methylpropan-2-yl (2-(cyclopropanesulfonamidomethyl)-4-((4-fluoro-3-methoxyphenyl)sulfonyl)-3,4-dihydro-2H-benzo[b][1,4]oxazin-6-yl)carbamate;

(S)-tert-butyl (2-(cyclopropanesulfonamidomethyl)-4-((3,4-difluorophenyl)sulfonyl)-3,4-dihydro-2H-benzo[b][1,4]oxazin-6-yl)carbamate;

(S)-tert-butyl (2-(cyclopropanesulfonamidomethyl)-4-((4-fluoro-3-methoxyphenyl)sulfonyl)-3,4-dihydro-2H-benzo[b][1,4]oxazin-6-yl)carbamate;

(S)-1,1,1-trifluoro-2-methylpropan-2-yl (4-((3-cyanophenyl)sulfonyl)-2-cyclopropanesulfonamidomethyl)-3,4-dihydro-2H-benzo[b][1,4]oxazin-6-yl)carbamate;

(S)-tert-butyl (2-(cyclopropanesulfonamidomethyl)-4-((4-fluorophenyl)sulfonyl)-3,4-dihydro-2H-benzo[b][1,4]oxazin-6-yl)carbamate;

(S)-tert-butyl (4-((3-cyanophenyl)sulfonyl)-2-(cyclopropanesulfonamidomethyl)-3,4-dihydro-2H-benzo[b][1,4]oxazin-6-yl)carbamate;

(S)-tert-butyl (2-(cyclopropanesulfonamidomethyl)-4-((3-(methylsulfonyl)phenyl)sulfonyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-(cyclopropanesulfonamidomethyl)-3,4-dihydro-2H-benzo[b][1,4]oxazin-6-yl)carbamate;

(S)-tert-butyl (4-((3-chloro-4-fluorophenyl)sulfonyl)-2-(cyclopropanesulfonamidomethyl)-3,4-dihydro-2H-benzo[b][1,4]oxazin-6-yl)carbamate (S)-(1-(trifluoromethyl)cyclopropyl)methyl (2-(cyclopropanesulfonamidomethyl)-4-((4-fluorophenyl)sulfonyl)-3,4-dihydro-2H-benzo[b][1,4]oxazin-6-yl)carbamate;

(S)-4-((6-((tert-butoxycarbonyl)amino)-2-(cyclopropanesulfonamidomethyl)-2H-benzo[b][1,4]oxazin-4(3H)-yl)sulfonyl)-1-(difluoromethyl)-3-methyl-1H-pyrazole;

3-(((S)-2-(cyclopropanesulfonamidomethyl)-6-((((1,1,1-trifluoro-2-methylpropan-2-yl)oxy)carbonyl)amino)-2H-benzo[b][1,4]oxazin-4(3H)-yl)sulfonyl)-2-methoxy-5,6,7,8-tetrahydro-4H-pyrazolo[1,5-a]pyridine;

4-(((S)-2-(cyclopropanesulfonamidomethyl)-6-((((1,1,1-trifluoro-2-methylpropan-2-yl)oxy)carbonyl)amino)-2H-benzo[b][1,4]oxazin-4(3H)-yl)sulfonyl)-1-ethyl-3-methoxy-1H-pyrazole;

3-(((S)-2-(cyclopropanesulfonamidomethyl)-6-((((1,1,1-trifluoro-2-methylpropan-2-yl)oxy)carbonyl)amino)-2H-benzo[b][1,4]oxazin-4(3H)-yl)sulfonyl)-2-methoxy-4,5,6,7-tetrahydropyrrolo[1,2-b]pyrazole;

(S)-1,1,1-trifluoro-2-methylpropan-2-yl (2-(cyclopropanesulfonamidomethyl)-4-((1-ethyl-3-methyl-1H-pyrazol-4-yl)sulfonyl)-3,4-dihydro-2H-benzo[b][1,4]oxazin-6-yl)carbamate;

(S)-4-((2-(cyclopropanesulfonamidomethyl)-6-((((1,1,1-trifluoro-2-methylpropan-2-yl)oxy)carbonyl)amino)-2H-benzo[b][1,4]oxazin-4(3H)-yl)sulfonyl)-3-ethoxy-1-ethyl-1H-pyrazole;

(S)-3-chloro-4-((2-(cyclopropanesulfonamidomethyl)-6-((((1,1,1-trifluoro-2-methylpropan-2-yl)oxy)carbonyl)amino)-2H-benzo[b][1,4]oxazin-4(3H)-yl)sulfonyl)-1-ethyl-1H-pyrazole;

(S)-4-((2-(cyclopropanesulfonamidomethyl)-6-((((1,1,1-trifluoro-2-methylpropan-2-yl)oxy)carbonyl)amino)-2H-benzo[b][1,4]oxazin-4(3H)-yl)sulfonyl)-1-(difluoromethyl)-3-ethoxy-1H-pyrazole;

(S)-4-((2-(cyclopropanesulfonamidomethyl)-6-((((1,1,1-trifluoro-2-methylpropan-2-yl)oxy)carbonyl)amino)-2H-benzo[b][1,4]oxazin-4(3H)-yl)sulfonyl)-3-(difluoromethoxy)-1-ethyl-1H-pyrazole;

(S)-4-((2-(cyclopropanesulfonamidomethyl)-6-((((1,1,1-trifluoro-2-methylpropan-2-yl)oxy)carbonyl)amino)-2H-benzo[b][1,4]oxazin-4(3H)-yl)sulfonyl)-1-ethyl-3-(2-methoxy-2-oxoethoxy)-1H-pyrazole;

(S)-tert-butyl (4-((3,4-difluorophenyl)sulfonyl)-2-(methylsulfonamidomethyl)-3,4-dihydro-2H-benzo[b][1,4]oxazin-6-yl)carbamate;

(S)-tert-butyl (2-(methylsulfonamidomethyl)-4-((3-(methylsulfonyl)phenyl)sulfonyl)-3,4-dihydro-2H-benzo[b][1,4]oxazin-6-yl)carbamate;

(S)-tert-butyl (4-((4-fluoro-3-methoxyphenyl)sulfonyl)-2-(methylsulfonamidomethyl)-3,4-dihydro-2H-benzo[b][1,4]oxazin-6-yl)carbamate;

(S)-4-((6-((tert-butoxycarbonyl)amino)-2-(methylsulfonamidomethyl)-2H-benzo[b][1,4]oxazin-4(3H)-yl)sulfonyl)-1-(difluoromethyl)-3-methyl-1H-pyrazole;

(S)-tert-butyl (4-((3-cyanophenyl)sulfonyl)-2-(methylsulfonamidomethyl)-3,4-dihydro-2H-benzo[b][1,4]oxazin-6-yl)carbamate;

(S)-tert-butyl (4-((4-fluorophenyl)sulfonyl)-2-(methylsulfonamidomethyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-(methylsulfonamidomethyl)-3,4-dihydro-2H-benzo[b][1,4]oxazin-6-yl)carbamate;

(S)-tert-butyl (4-((3-chloro-4-fluorophenyl)sulfonyl)-2-(methylsulfonamidomethyl)-3,4-dihydro-2H-benzo[b][1,4]oxazin-6-yl)carbamate;

(S)-1,1,1-trifluoro-2-methylpropan-2-yl (4-((1-ethyl-3-methyl-1H-pyrazol-4-yl)sulfonyl)-2-(methylsulfonamidomethyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-(methylsulfonamidomethyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((pyridine-3-sulfonamido)methyl)-3,4-dihydro-2H-benzo[b][1,4]oxazin-6-yl)carbamate;

(S)-5-(N-((4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)sulfamoyl)-2-methylthiazole;

(S)-1,1,1-trifluoro-2-methylpropan-2-yl (4-((4-fluorophenyl)sulfonyl)-2-((1-methyl-1H-imidazole-4-sulfonamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((thiophene-2-sulfonamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((1-methylcyclopropanesulfonamido)methyl)-3,4-dihydro-2H-benzo[b][1,4]oxazin-6-yl)carbamate (S)-1,1,1-trifluoro-2-methylpropan-2-yl (2-(ethylsulfonamidomethyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((2,2,2-trifluoroethylsulfonamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((trifluoromethylsulfonamido)methyl)-3,4-dihydro-2H-benzo[b][1,4]oxazin-6-yl)carbamate;

(S)-5-(N-((4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)sulfamoyl)-2,4-dimethylthiazole;

(S)-1,1,1-trifluoro-2-methylpropan-2-yl (2-((cyclohexylmethylsulfonamido)methyl)-4-((4-fluorophenyl)sulfonyl)-3,4-dihydro-2H-benzo[b][1,4]oxazin-6-yl)carbamate;

(S)-4-(N-((4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)sulfamoyl)-3,5-dimethylisoxazole;

(S)-1,1,1-trifluoro-2-methylpropan-2-yl (4-((4-fluorophenyl)sulfonyl)-2-(propylsulfonamidomethyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-(phenylsulfonamidomethyl)-3,4-dihydro-2H-benzo[b][1,4]oxazin-6-yl)carbamate;

(S)-1,1,1-trifluoro-2-methylpropan-2-yl (2-((chloromethylsulfonamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((5-chlorothiophene-2-sulfonamido)methyl)-4-((4-fluorophenyl)sulfonyl)-3,4-dihydro-2H-benzo[b][1,4]oxazin-6-yl)carbamate;

(S)-2-((N-((4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)sulfamoyl)methyl)pyridine;

(S)-3-((N-((4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)sulfamoyl)methyl)pyridine;

(S)-1,1,1-trifluoro-2-methylpropan-2-yl (4-((4-fluorophenyl)sulfonyl)-2-((2-methylpropylsulfonamido)methyl)-3,4-dihydro-2H-benzo[b][1,4]oxazin-6-yl)carbamate;

(S)-4-(N-((4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)sulfamoyl)-1-methyl-3-(trifluoromethyl)-1H-pyrazole;

(S)-1,1,1-trifluoro-2-methylpropan-2-yl (4-((4-fluorophenyl)sulfonyl)-2-((phenylmethylsulfonamido)methyl)-3,4-dihydro-2H-benzo[b][1,4]oxazin-6-yl)carbamate (S)-1,1,1-trifluoro-2-methylpropan-2-yl (2-((2-cyanophenylsulfonamido)methyl)-4-((4-fluorophenyl)sulfonyl)-3,4-dihydro-2H-benzo[b][1,4]oxazin-6-yl)carbamate;

(S)-1-(difluoromethyl)-4-(N-((4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)sulfamoyl)-5-methyl-1H-pyrazole;

(S)-1,1,1-trifluoro-2-methylpropan-2-yl (4-((3-chloro-4-fluorophenyl)sulfonyl)-2-((2,2,2-trifluoroethylsulfonamido)methyl)-3,4-dihydro-2H-benzo[b][1,4]oxazin-6-yl)carbamate;

1,1,1-trifluoro-2-methylpropan-2-yl ((2S)-2-((2-ethylcyclopropanesulfonamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((2-ethoxyethylsulfonamido)methyl)-4-((4-fluorophenyl)sulfonyl)-3,4-dihydro-2H-benzo[b][1,4]oxazin-6-yl)carbamate;

1,1,1-trifluoro-2-methylpropan-2-yl ((2S)-4-((4-fluorophenyl)sulfonyl)-2-((((tetrahydro-2H-pyran-2-yl)methylsulfonamido)methyl)-3,4-dihydro-2H-benzo[b][1,4]oxazin-6-yl)carbamate;

(S)-1,1,1-trifluoro-2-methylpropan-2-yl (2-((cyclopropylmethylsulfonamido)methyl)-4-((4-fluorophenyl)sulfonyl)-3,4-dihydro-2H-benzo[b][1,4]oxazin-6-yl)carbamate;

1,1,1-trifluoro-2-methylpropan-2-yl ((2S)-4-((3-chloro-4-fluorophenyl)sulfonyl)-2-((2-ethylcyclopropanesulfonamido)methyl)-3,4-dihydro-2H-benzo[b][1,4]oxazin-6-yl)carbamate;

(S)-4-(N-((4-((3-chloro-4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)sulfamoyl)-3,5-dimethylisoxazole;

(S)-1,1,1-trifluoro-2-methylpropan-2-yl (4-((3-chloro-4-fluorophenyl)sulfonyl)-2-(propylsulfonamidomethyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-(phenylsulfonamidomethyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((2-methylpropylsulfonamido)methyl)-3,4-dihydro-2H-benzo[b][1,4]oxazin-6-yl)carbamate;

(S)-1,1,1-trifluoro-2-methylpropan-2-yl (4-((3-ethoxy-1-ethyl-1H-pyrazol-4-yl)sulfonyl)-2-((2,2,2-trifluoroethylsulfonamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((N-methylmethylsulfonamido)methyl)-3,4-dihydro-2H-benzo[b][1,4]oxazin-6-yl)carbamate;

(S)-1,1,1-trifluoro-2-methylpropan-2-yl (2-((1,1-dioxidoisothiazolidin-2-yl)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((N-methylmethylsulfonamido)methyl)-3,4-dihydro-2H-benzo[b][1,4]oxazin-6-yl)carbamate;

(S)-tert-butyl (2-(acetamidomethyl)-4-((4-(trifluoromethyl)piperidin-1-yl)sulfonyl)-3,4-dihydro-2H-benzo[b][1,4]oxazin-6-yl)carbamate;

tert-butyl ((2S)-2-(acetamidomethyl)-4-((3-(trifluoromethyl)pyrrolidin-1-yl)sulfonyl)-3,4-dihydro-2H-benzo[b][1,4]oxazin-6-yl)carbamate;

tert-butyl ((2S)-2-(acetamidomethyl)-4-((3-(trifluoromethyl)piperidin-1-yl)sulfonyl)-3,4-dihydro-2H-benzo[b][1,4]oxazin-6-yl)carbamate;

(S)-tert-butyl (2-(acetamidomethyl)-4-((4-fluoropiperidin-1-yl)sulfonyl)-3,4-dihydro-2H-benzo[b][1,4]oxazin-6-yl)carbamate;

(S)-tert-butyl (2-(acetamidomethyl)-8-fluoro-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-8-fluoro-4-((4-fluorophenyl)sulfonyl)-3,4-dihydro-2H-benzo[b][1,4]oxazin-6-yl)carbamate;

(S)-4-((6-((tert-butoxycarbonyl)amino)-8-fluoro-2-(methylsulfonamidomethyl)-2H-benzo[b][1,4]oxazin-4(3H)-yl)sulfonyl)-1-(difluoromethyl)-3-methyl-1H-pyrazole;

(S)-tert-butyl (2-(cyclopropanesulfonamidomethyl)-8-fluoro-4-((4-fluorophenyl)sulfonyl)-3,4-dihydro-2H-benzo[b][1,4]oxazin-6-yl)carbamate;

(S)-tert-butyl (2-(cyclopropanesulfonamidomethyl)-4-((1-(difluoromethyl)-3-methyl-1H-pyrazol-4-yl)sulfonyl)-8-fluoro-3,4-dihydro-2H-benzo[b][1,4]oxazin-6-yl)carbamate;

(S)-tert-butyl (8-fluoro-4-((4-fluorophenyl)sulfonyl)-2-(methylsulfonamidomethyl)-3,4-dihydro-2H-benzo[b][1,4]oxazin-6-yl)carbamate;

(S)-tert-butyl (2-(acetamidomethyl)-4-((3,4-difluorophenyl)sulfonyl)-8-fluoro-3,4-dihydro-2H-benzo[b][1,4]oxazin-6-yl)carbamate;

(S)-1,1,1-trifluoro-2-methylpropan-2-yl (2-(acetamidomethyl)-4-((3,4-difluorophenyl)sulfonyl)-8-fluoro-3,4-dihydro-2H-benzo[b][1,4]oxazin-6-yl)carbamate;

(S)-1,1,1-trifluoro-2-methylpropan-2-yl (2-(acetamidomethyl)-8-chloro-4-((4-fluorophenyl)sulfonyl)-3,4-dihydro-2H-benzo[b][1,4]oxazin-6-yl)carbamate;

(S)-1,1,1-trifluoro-2-methylpropan-2-yl (8-chloro-4-((4-fluorophenyl)sulfonyl)-2-(methylsulfonamidomethyl)-3,4-dihydro-2H-benzo[b][1,4]oxazin-6-yl)carbamate tert-butyl (cis-2-(acetamidomethyl)-4-((4-fluorophenyl)sulfonyl)-3-methyl-3,4-dihydro-2H-benzo[b][1,4]oxazin-6-yl)carbamate;

(R,S) 1,1,1-trifluoro-2-methylpropan-2-yl (cis-2-(acetamidomethyl)-4-((4-fluorophenyl)sulfonyl)-3-methyl-3,4-dihydro-2H-benzo[b][1,4]oxazin-6-yl)carbamate;

(S,R) 1,1,1-trifluoro-2-methylpropan-2-yl (cis-2-(acetamidomethyl)-4-((4-fluorophenyl)sulfonyl)-3-methyl-3,4-dihydro-2H-benzo[b][1,4]oxazin-6-yl)carbamate;

tert-butyl-2-(acetamidomethyl)-4-(4-fluorophenylsulfonyl)-3-methyl-3,4-dihydro-2H-benzo[b][1,4]oxazin-6-ylcarbamate;

1,1,1-trifluoro-2-methylpropan-2-yl ((2S,3S)-2-(acetamidomethyl)-4-((4-fluorophenyl)sulfonyl)-3-methyl-3,4-dihydro-2H-benzo[b][1,4]oxazin-6-yl)carbamate;

1,1,1-trifluoro-2-methylpropan-2-yl (2R,3R)-2-(acetamidomethyl)-4-((4-fluorophenyl)sulfonyl)-3-methyl-3,4-dihydro-2H-benzo[b][1,4]oxazin-6-yl)carbamate;

1,1,1-trifluoro-2-methylpropan-2-yl (2-(acetamidomethyl)-3-ethyl-4-((4-fluorophenyl)sulfonyl)-3,4-dihydro-2H-benzo[b][1,4]oxazin-6-yl)carbamate;

1,1,1-trifluoro-2-methylpropan-2-yl ((2S,3R or 2R, 3S)-2-(acetamidomethyl)-4-((3-ethoxy-1-ethyl-1H-pyrazol-4-yl)sulfonyl)-3-methyl-3,4-dihydro-2H-benzo[b][1,4]oxazin-6-yl)carbamate;

1,1,1-trifluoro-2-methylpropan-2-yl ((2R,3S or 2S,3R)-2-(acetamidomethyl)-4-((1-(difluoromethyl)-3-methyl-1H-pyrazol-4-yl)sulfonyl)-3-methyl-3,4-dihydro-2H-benzo[b][1,4]oxazin-6-yl)carbamate;

1,1,1-trifluoro-2-methylpropan-2-yl ((2S,3R or 2R,3S)-4-((4-fluorophenyl)sulfonyl)-2-((2-hydroxy-2-methylpropanamido)methyl)-3-methyl-3,4-dihydro-2H-benzo[b][1,4]oxazin-6-yl)carbamate;

1,1,1-trifluoro-2-methylpropan-2-yl ((2S,3R)-2-(acetamidomethyl)-4-((1-(difluoromethyl)-3-methyl-1H-pyrazol-4-yl)sulfonyl)-3-methyl-3,4-dihydro-2H-benzo[b][1,4]oxazin-6-yl)carbamate;

1,1,1-trifluoro-2-methylpropan-2-yl ((2R,3S or 2S,3R)-2-(acetamidomethyl)-4-((1-(difluoromethyl)-3-methyl-1H-pyrazol-4-yl)sulfonyl)-3-methyl-3,4-dihydro-2H-benzo[b][1,4]oxazin-6-yl)carbamate;

1,1,1-trifluoro-2-methylpropan-2-yl ((2S,3R or 2R,3S)-4-((4-fluorophenyl)sulfonyl)-2-((2-hydroxy-2-methylpropanamido)methyl)-3-methyl-3,4-dihydro-2H-benzo[b][1,4]oxazin-6-yl)carbamate;

1,1,1-trifluoro-2-methylpropan-2-yl ((2S,3R)-2-(acetamidomethyl)-4-((1-(difluoromethyl)-3-methyl-1H-pyrazol-4-yl)sulfonyl)-3-methyl-3,4-dihydro-2H-benzo[b][1,4]oxazin-6-yl)carbamate;

2,2,2-trifluoro-1,1-dimethylethyl [(2S)-2-[({[(1R,2S)-2-cyanocyclopropyl]carbonyl}amino)methyl]-4-{[1-(difluoromethoxy)-3-(2-hydroxyethoxy)-1H-pyrazol-4-yl]sulfonyl}-3,4-dihydro-2H-1,4-benzoxazin-6-yl]carbamate;

2,2,2-trifluoro-1,1-dimethylethyl [(2S)-4-{[1-(difluoromethyl)-3-(2-hydroxyethoxy)-1H-pyrazol-4-yl]sulfonyl}-2-({[(2,2,2-trifluoroethyl)sulfonyl]amino}methyl)-3,4-dihydro-2H-1,4-benzoxazin-6-yl]carbamate;

2,2,2-trifluoro-1,1-dimethylethyl [(2S)-4-{[1-(difluoromethyl)-3-(2-hydroxyethoxy)-1H-pyrazol-4-yl]sulfonyl}-2-{[(2-hydroxy-2-methylpropanoyl)amino]methyl}-3,4-dihydro-2H-1,4-benzoxazin-6-yl]carbamate;

2,2,2-trifluoro-1,1-dimethylethyl [(2S)-2-{[(2S and 2R-amino-3,3,3-trifluoro-2-methylpropanoyl)amino]methyl}-4-{[1-(difluoromethyl)-3-(2-hydroxyethoxy)-1H-pyrazol-4-yl]sulfonyl}-3,4-dihydro-2H-1,4-benzoxazin-6-yl]carbamate;

2,2,2-trifluoro-1,1-dimethylethyl {(2S)-4-{[1-(difluoromethyl)-3-(2-hydroxyethoxy)-1H-pyrazol-4-yl]sulfonyl}-2-[({[(1R,2R)-2-fluorocyclopropyl]carbonyl}amino)methyl]-3,4-dihydro-2H-1,4-benzoxazin-6-yl}carbamate;

2,2,2-trifluoro-1,1-dimethylethyl [(2S)-4-{[3-(2-hydroxyethoxy)-1-(1-methylethyl)-1H-pyrazol-4-yl]sulfonyl}-2-{[(2-hydroxy-2-methylpropanoyl)amino]methyl}-3,4-dihydro-2H-1,4-benzoxazin-6-yl]carbamate;

2,2,2-trifluoro-1,1-dimethylethyl [(2S)-2-[(acetylamino)methyl]-4-{[1-cyclopropyl-3-(2-hydroxyethoxy)-1H-pyrazol-4-yl]sulfonyl}-3,4-dihydro-2H-1,4-benzoxazin-6-yl]carbamate;

2,2,2-trifluoro-1,1-dimethylethyl [(2S)-4-{[1-cyclopropyl-3-(2-hydroxyethoxy)-1H-pyrazol-4-yl]sulfonyl}-2-{[(2-hydroxy-2-methylpropanoyl)amino]methyl}-3,4-dihydro-2H-1,4-benzoxazin-6-yl]carbamate;

2,2,2-trifluoro-1,1-dimethylethyl [(2S)-4-{[2-(2-hydroxyethoxy)pyrazolo[1,5-a]pyridin-3-yl]sulfonyl}-2-{[(2-hydroxy-2-methylpropanoyl)amino]methyl}-3,4-dihydro-2H-1,4-benzoxazin-6-yl]carbamate;

2,2,2-trifluoro-1,1-dimethylethyl [(2S)-4-{[1-ethyl-3-(2-hydroxyethoxy)-1H-pyrazol-4-yl]sulfonyl}-2-{[(oxetan-3-ylcarbonyl)amino]methyl}-3,4-dihydro-2H-1,4-benzoxazin-6-yl]carbamate;

2,2,2-trifluoro-1,1-dimethylethyl [(2S)-2-{[(cyclopropylsulfonyl)amino]methyl}-4-{[1-ethyl-3-(2-hydroxyethoxy)-1H-pyrazol-4-yl]sulfonyl}-3,4-dihydro-2H-1,4-benzoxazin-6-yl]carbamate;

2,2,2-trifluoro-1,1-dimethylethyl [(2S)-2-[(acetylamino)methyl]-4-{[1-(difluoromethyl)-3-(2-hydroxyethoxy)-1H-pyrazol-4-yl]sulfonyl}-3,4-dihydro-2H-1,4-benzoxazin-6-yl]carbamate;

2,2,2-trifluoro-1,1-dimethylethyl [(2S)-2-[(acetylamino)methyl]-4-{[3-(2-hydroxyethoxy)-1-(1-methylethyl)-1H-pyrazol-4-yl]sulfonyl}-3,4-dihydro-2H-1,4-benzoxazin-6-yl]carbamate;

2,2,2-trifluoro-1,1-dimethylethyl [(2S)-2-[(acetylamino)methyl]-4-{[2-(2-hydroxyethoxy)pyrazolo[1,5-a]pyridin-3-yl]sulfonyl}-3,4-dihydro-2H-1,4-benzoxazin-6-yl]carbamate;

methyl 2-((4-(((R)-2-((R or S)-acetamido(cyclopropyl)methyl)-6-(((((1,1,1-trifluoro-2-methylpropan-2-yl)oxy)carbonyl)amino)-2H-benzo[b][1,4]oxazin-4(3H)-yl)sulfonyl)-1-ethyl-1H-pyrazol-3-yl)oxy)acetate;

1,1,1-trifluoro-2-methylpropan-2-yl ((R)-2-((R or S)-acetamido(cyclopropyl)methyl)-4-((1-ethyl-3-(2-hydroxyethoxy)-1H-pyrazol-4-yl)sulfonyl)-3,4-dihydro-2H-benzo[b][1,4]oxazin-6-yl)carbamate;

methyl 2-((4-(((R)-2-((R or S)-acetamido(cyclopropyl)methyl)-6-(((((1,1,1-trifluoro-2-methylpropan-2-yl)oxy)carbonyl)amino)-2H-benzo[b][1,4]oxazin-4(3H)-yl)sulfonyl)-1-ethyl-1H-pyrazol-3-yl)oxy)acetate;

1,1,1-trifluoro-2-methylpropan-2-yl ((R)-2-((R or S)-acetamido(cyclopropyl)methyl)-4-((1-ethyl-3-(2-hydroxyethoxy)-1H-pyrazol-4-yl)sulfonyl)-3,4-dihydro-2H-benzo[b][1,4]oxazin-6-yl)carbamate;

1,1,1-trifluoro-2-methylpropan-2-yl ((R)-2-((R or S)-cyclopropyl(2-hydroxy-2-methylpropanamido)methyl)-4-((1-ethyl-3-(2-hydroxyethoxy)-1H-pyrazol-4-yl)sulfonyl)-3,4-dihydro-2H-benzo[b][1,4]oxazin-6-yl)carbamate;

1,1,1-trifluoro-2-methylpropan-2-yl ((R)-2-((R or S)-cyclopropyl(2-hydroxy-2-methylpropanamido)methyl)-4-((1-ethyl-3-(2-hydroxyethoxy)-1H-pyrazol-4-yl)sulfonyl)-3,4-dihydro-2H-benzo[b][1,4]oxazin-6-yl)carbamate;

methyl 2-((4-(((R)-2-((R or S)-cyclopropyl(2-hydroxy-2-methylpropanamido)methyl)-6-(((((1,1,1-trifluoro-2-methylpropan-2-yl)oxy)carbonyl)amino)-2H-benzo[b][1,4]oxazin-4(3H)-yl)sulfonyl)-1-ethyl-1H-pyrazol-3-yl)oxy)acetate;

methyl 2-((4-(((R)-2-((R or S)-cyclopropyl(2-hydroxy-2-methylpropanamido)methyl)-6-(((((1,1,1-trifluoro-2-methylpropan-2-yl)oxy)carbonyl)amino)-2H-benzo[b][1,4]oxazin-4(3H)-yl)sulfonyl)-1-ethyl-1H-pyrazol-3-yl)oxy)acetate;

2,2,2-trifluoro-1,1-dimethylethyl [(2R)-2-[(1S or 1R)-1-(acetylamino)ethyl]-4-{[1-(difluoromethyl)-3-(2-hydroxyethoxy)-1H-pyrazol-4-yl]sulfonyl}-3,4-dihydro-2H-1,4-benzoxazin-6-yl]carbamate;

1,1,1-trifluoro-2-methylpropan-2-yl ((R)-2-((R or S)-1-acetamidopropyl)-4-((4-fluorophenyl)sulfonyl)-3,4-dihydro-2H-benzo[b][1,4]oxazin-6-yl)carbamate;

1,1,1-trifluoro-2-methylpropan-2-yl ((R)-2-((R or S)-1-acetamidopropyl)-4-((4-fluorophenyl)sulfonyl)-3,4-dihydro-2H-benzo[b][1,4]oxazin-6-yl)carbamate;

2,2,2-trifluoro-1,1-dimethylethyl [(2R)-2-[(1R or S)-1-(acetylamino)ethyl]-4-{[1-(difluoromethyl)-3-ethoxy-1H-pyrazol-4-yl]sulfonyl}-3,4-dihydro-2H-1,4-benzoxazin-6-yl]carbamate;

2,2,2-trifluoro-1,1-dimethylethyl [(2R)-2-[(1R or S)-1-(acetylamino)ethyl]-4-{[1-(difluoromethyl)-3-ethoxy-1H-pyrazol-4-yl]sulfonyl}-3,4-dihydro-2H-1,4-benzoxazin-6-yl]carbamate;

2,2,2-trifluoro-1,1-dimethylethyl [(2R)-2-[(1R or S)-1-(acetylamino)ethyl]-4-{[1-ethyl-3-(2-hydroxyethoxy)-1H-pyrazol-4-yl]sulfonyl}-3,4-dihydro-2H-1,4-benzoxazin-6-yl]carbamate;

2,2,2-trifluoro-1,1-dimethylethyl [(2R)-2-[(1R or S)-1-(acetylamino)ethyl]-4-{[1-ethyl-3-(2-hydroxyethoxy)-1H-pyrazol-4-yl]sulfonyl}-3,4-dihydro-2H-1,4-benzoxazin-6-yl]carbamate;

(S)-1,1,1-trifluoro-2-methylpropan-2-yl (2-((2-hydroxy-2-methylpropanamido)methyl)-4-((1-isopropyl-3-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-((2-hydroxy-2-methylpropanamido)methyl)-4-((1-isopropyl-5-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (4-((1-cyclopropyl-3-methyl-1H-pyrazol-4-yl)sulfonyl)-2-((2-hydroxy-2-methylpropanamido)methyl)-3,4-dihydro-2H-benzo[b][1,4]oxazin-6-yl)carbamate;

(S)-1,1,1-trifluoro-2-methylpropan-2-yl (4-((1-cyclopropyl-5-methyl-1H-pyrazol-4-yl)sulfonyl)-2-((2-hydroxy-2-methylpropanamido)methyl)-3,4-dihydro-2H-benzo[b][1,4]oxazin-6-yl)carbamate;

2,2,2-trifluoro-1,1-dimethylethyl [(2S)-4-[(6-chloroimidazo[2,1-b][1,3]thiazol-5-yl)sulfonyl]-2-{[(2-hydroxy-2-methylpropanoyl)amino]methyl}-3,4-dihydro-2H-1,4-benzoxazin-6-yl]carbamate;

2,2,2-trifluoro-1,1-dimethylethyl [(2S)-2-{[(2-hydroxy-2-methylpropanoyl)amino]methyl}-4-{[3-(pentafluoro-lambda~6~-sulfanyl)phenyl]sulfonyl}-3,4-dihydro-2H-1,4-benzoxazin-6-yl]carbamate;

2,2,2-trifluoro-1,1-dimethylethyl {(2S)-2-{[(2-hydroxy-2-methylpropanoyl)amino]methyl}-4-[(1-methyl-1H-pyrazol-5-yl)sulfonyl]-3,4-dihydro-2H-1,4-benzoxazin-6-yl}carbamate;

2,2,2-trifluoro-1,1-dimethylethyl [(2S)-4-{[1-ethyl-3-(ethylamino)-1H-pyrazol-4-yl]sulfonyl}-2-{[(2-hydroxy-2-methylpropanoyl)amino]methyl}-3,4-dihydro-2H-1,4-benzoxazin-6-yl]carbamate;

2,2,2-trifluoro-1,1-dimethylethyl [(2S)-4-{[1-(difluoromethyl)-3-methyl-1H-pyrazol-4-yl]sulfonyl}-2-{[(2-hydroxy-2-methylpropanoyl)amino]methyl}-3,4-dihydro-2H-1,4-benzoxazin-6-yl]carbamate;

2,2,2-trifluoro-1,1-dimethylethyl [(2S)-2-{[(cyclopropylsulfonyl)amino]methyl}-4-{[3-(pentafluoro-lambda~6~-sulfanyl)phenyl]sulfonyl}-3,4-dihydro-2H-1,4-benzoxazin-6-yl]carbamate;

2,2,2-trifluoro-1,1-dimethylethyl {(2S,3R)-2-[(acetylamino)methyl]-4-[(3-ethoxy-1-ethyl-1H-pyrazol-4-yl)sulfonyl]-3-methyl-3,4-dihydro-2H-1,4-benzoxazin-6-yl}carbamate;

2,2,2-trifluoro-1,1-dimethylethyl [(2S,3R)-4-{[1-(difluoromethyl)-3-methyl-1H-pyrazol-4-yl]sulfonyl}-3-methyl-2-{[(methylsulfonyl)amino]methyl}-3,4-dihydro-2H-1,4-benzoxazin-6-yl]carbamate;

2,2,2-trifluoro-1,1-dimethylethyl [(2S,3R)-4-{[1-(difluoromethyl)-3-methyl-1H-pyrazol-4-yl]sulfonyl}-2-{[(ethylsulfonyl)amino]methyl}-3-methyl-3,4-dihydro-2H-1,4-benzoxazin-6-yl]carbamate;

2,2,2-trifluoro-1,1-dimethylethyl [(2S,3R)-2-{[(cyclopropylsulfonyl)amino]methyl}-4-{[1-(difluoromethyl)-3-methyl-1H-pyrazol-4-yl]sulfonyl}-3-methyl-3,4-dihydro-2H-1,4-benzoxazin-6-yl]carbamate;

2,2,2-trifluoro-1,1-dimethylethyl [(2S,3R)-4-{[1-(difluoromethyl)-3-methyl-1H-pyrazol-4-yl]sulfonyl}-3-methyl-2-({[(2,2,2-trifluoroethyl)sulfonyl]amino}methyl)-3,4-dihydro-2H-1,4-benzoxazin-6-yl]carbamate;

2,2,2-trifluoro-1,1-dimethylethyl [(2S,3R)-4-{[1-(difluoromethyl)-3-methyl-1H-pyrazol-4-yl]sulfonyl}-2-{[(2-hydroxy-2-methylpropanoyl)amino]methyl}-3-methyl-3,4-dihydro-2H-1,4-benzoxazin-6-yl]carbamate;

2,2,2-trifluoro-1,1-dimethylethyl {(2S,3R)-4-{[1-(difluoromethyl)-3-methyl-1H-pyrazol-4-yl]sulfonyl}-2-[({[(1R,2R)-2-fluorocyclopropyl]carbonyl}amino)methyl]-3-methyl-3,4-dihydro-2H-1,4-benzoxazin-6-yl}carbamate;

2,2,2-trifluoro-1,1-dimethylethyl [(2S,3R)-2-{[((2R and 2S-amino-3,3,3-trifluoro-2-methylpropanoyl)amino]methyl}-4-{[1-(difluoromethyl)-3-methyl-1H-pyrazol-4-yl]sulfonyl}-3-methyl-3,4-dihydro-2H-1,4-benzoxazin-6-yl]carbamate;

1,1,1-trifluoro-2-methylpropan-2-yl ((2S,3R)-4-((1-(difluoromethyl)-3-methyl-1H-pyrazol-4-yl)sulfonyl)-3-methyl-2-((R and S)-3,3,3-trifluoro-2-hydroxy-2-methylpropanamido)methyl)-3,4-dihydro-2H-benzo[b][1,4]oxazin-6-yl)carbamate;

2,2,2-trifluoro-1,1-dimethylethyl [(2S,3R)-2-[({[(1S,2S)-2-cyanocyclopropyl]carbonyl}amino)methyl]-4-{[1-(difluoromethyl)-3-methyl-1H-pyrazol-4-yl]sulfonyl}-3-methyl-3,4-dihydro-2H-1,4-benzoxazin-6-yl]carbamate;

2,2,2-trifluoro-1,1-dimethylethyl [(2S,3R)-2-{[(cyclopropylcarbonyl)amino]methyl]-4-{[1-(difluoromethyl)-3-methyl-1H-pyrazol-4-yl]sulfonyl}-3-methyl-3,4-dihydro-2H-1,4-benzoxazin-6-yl]carbamate;

2,2,2-trifluoro-1,1-dimethylethyl {(2S,3R)-4-{[1-(difluoromethyl)-3-(2-hydroxyethoxy)-1H-pyrazol-4-yl]sulfonyl}-2-[({[(1R,2R)-2-fluorocyclopropyl]carbonyl}amino)methyl]-3-methyl-3,4-dihydro-2H-1,4-benzoxazin-6-yl}carbamate;

2,2,2-trifluoro-1,1-dimethylethyl [(2S,3R)-4-{[1-(difluoromethyl)-3-(2-hydroxyethoxy)-1H-pyrazol-4-yl]sulfonyl}-3-methyl-2-{[(methylsulfonyl)amino]methyl}-3,4-dihydro-2H-1,4-benzoxazin-6-yl]carbamate;

2,2,2-trifluoro-1,1-dimethylethyl [(2S,3R)-4-[(3-ethoxy-1-ethyl-1H-pyrazol-4-yl)sulfonyl]-3-methyl-2-{[(methylsulfonyl)amino]methyl}-3,4-dihydro-2H-1,4-benzoxazin-6-yl]carbamate;

2,2,2-trifluoro-1,1-dimethylethyl {(2S,3R)-4-[(3-ethoxy-1-ethyl-1H-pyrazol-4-yl)sulfonyl]-2-[({[(1R,2R)-2-fluorocyclopropyl]carbonyl}amino)methyl]-3-methyl-3,4-dihydro-2H-1,4-benzoxazin-6-yl}carbamate;

2,2,2-trifluoro-1,1-dimethylethyl {(2S,3R)-2-[({[(1R,2S)-2-cyanocyclopropyl]carbonyl}amino)methyl]-4-[(3- ethoxy-1-ethyl-1H-pyrazol-4-yl)sulfonyl]-3-methyl-3,4-dihydro-2H-1,4-benzoxazin-6-yl}carbamate;

2,2,2-trifluoro-1,1-dimethylethyl [(2S,3R)-4-[(3-ethoxy-1-ethyl-1H-pyrazol-4-yl)sulfonyl]-2-{[(2-hydroxy-2-methylpropanoyl)amino]methyl}-3-methyl-3,4-dihydro-2H-1,4-benzoxazin-6-yl]carbamate;

2,2,2-trifluoro-1,1-dimethylethyl [(2S,3R)-4-{[1-ethyl-3-(2-hydroxyethoxy)-1H-pyrazol-4-yl]sulfonyl}-3-methyl-2-{[(methylsulfonyl)amino]methyl}-3,4-dihydro-2H-1,4-benzoxazin-6-yl]carbamate;

2,2,2-trifluoro-1,1-dimethylethyl {(2S,3R)-4-{[1-ethyl-3-(2-hydroxyethoxy)-1H-pyrazol-4-yl]sulfonyl}-2-[({[(1R,2R)-2-fluorocyclopropyl]carbonyl}amino)methyl]-3-methyl-3,4-dihydro-2H-1,4-benzoxazin-6-yl}carbamate;

2,2,2-trifluoro-1,1-dimethylethyl [(2S,3R)-2-[({[(1R,2S)-2-cyanocyclopropyl]carbonyl}amino)methyl]-4-{[1-ethyl-3-(2-hydroxyethoxy)-1H-pyrazol-4-yl]sulfonyl}-3-methyl-3,4-dihydro-2H-1,4-benzoxazin-6-yl]carbamate;

2,2,2-trifluoro-1,1-dimethylethyl [(2S,3R)-4-{[1-ethyl-3-(2-hydroxyethoxy)-1H-pyrazol-4-yl]sulfonyl}-2-{[(2-hydroxy-2-methylpropanoyl)amino]methyl}-3-methyl-3,4-dihydro-2H-1,4-benzoxazin-6-yl]carbamate;

2,2,2-trifluoro-1,1-dimethylethyl [(2S,3R)-2-[(acetylamino)methyl]-4-{[1-ethyl-3-(2-hydroxyethoxy)-1H-pyrazol-4-yl]sulfonyl}-3-methyl-3,4-dihydro-2H-1,4-benzoxazin-6-yl]carbamate;

1,1,1-trifluoro-2-methylpropan-2-yl ((2S,3R)-2-((S)-1-acetamidoethyl)-4-((3,4-difluorophenyl)sulfonyl)-3-methyl-3,4-dihydro-2H-benzo[b][1,4]oxazin-6-yl)carbamate;

1,1,1-trifluoro-2-methylpropan-2-yl ((R)-2-((S)-1-acetamido-2,2,2-trifluoroethyl)-4-((4-fluorophenyl)sulfonyl)-3,4-dihydro-2H-benzo[b][1,4]oxazin-6-yl)carbamate;

1,1,1-trifluoro-2-methylpropan-2-yl ((R)-2-((R)-1-acetamido-2,2,2-trifluoroethyl)-4-((4-fluorophenyl)sulfonyl)-3,4-dihydro-2H-benzo[b][1,4]oxazin-6-yl)carbamate;

1,1,1-trifluoro-2-methylpropan-2-yl ((S)-2-((S)-1-acetamido-2,2,2-trifluoroethyl)-4-((4-fluorophenyl)sulfonyl)-3,4-dihydro-2H-benzo[b][1,4]oxazin-6-yl)carbamate; and 1,1,1-trifluoro-2-methylpropan-2-yl ((S)-2-((R)-1-acetamido-2,2,2-trifluoroethyl)-4-((4-fluorophenyl)sulfonyl)-3,4-dihydro-2H-benzo[b][1,4]oxazin-6-yl)carbamate.

The invention also provides a compound of Formula (I) or a pharmaceutically acceptable salt thereof in purified form.

Uses of the Compounds

Compounds of Formula (I) alter the interaction of coregulator proteins with Retinoic Acid Receptor-related Orphan Receptor gamma t (RORgammaT) and thereby antagonize RORgammaT-mediated transcriptional activity, and as such are useful in the treatment of diseases and conditions in which inhibition of RORgammaT is desirable, such as autoimmune and inflammatory diseases and disorders.

Accordingly, another embodiment of the present invention provides a method for treating a disease or condition mediated by RORgammaT in a subject comprising administering to the subject an amount of a compound of Formula (I) that is effective for treating the disease or condition mediated by RORgammaT in the subject.

The compounds according to the invention can be used in therapy.

A further aspect of the invention resides in the use of compounds of Formula (I) for the treatment of RORgammaT-mediated diseases or RORgammaT-mediated conditions.

Another aspect of the invention resides in the use of a compound of Formula (I) in the manufacture of a medicament for the treatment of a disease or condition mediated by RORgammaT.

Another aspect of the invention resides in the use of compounds of Formula (I) for the treatment of autoimmune diseases, in particular those diseases in which Th17 cells and non-Th17 cells, which express Th17 hallmark cytokines, play a prominent role. These include, but are not limited to, the treatment of rheumatoid arthritis, psoriasis, inflammatory bowel disease (e.g., Crohn's disease, ulcerative colitis), ankylosing spondylitis, and multiple sclerosis.

In another aspect, compounds of Formula (I) can be used for treatment of inflammatory diseases in which Th17 cells and/or non-Th17 cells, which express Th17 hallmark cytokines, play a prominent role, such as but not limited to respiratory diseases, osteoarthritis, and asthma. Also, compounds of Formula (I) can be used for treatment of infectious diseases in which Th17 cells and/or non-Th17 cells, which express Th17 hallmark cytokines, play a prominent role, such as but not limited to mucosal leishmaniasis.

Compounds of Formula (I) can also be used for treatment of other diseases in which Th17 cells and/or non-Th17 cells, which express Th17 hallmark cytokines, play a prominent role, such as but not limited to Kawasaki disease and Hashimoto's thyroiditis.

In one aspect, the disease or condition is an autoimmune disease or inflammatory disease. The disease or condition includes, but is not limited to, multiple sclerosis, inflammatory bowel disease (e.g., Crohn's disease, ulcerative colitis), psoriasis, rheumatoid arthritis, asthma, osteoarthritis, Kawasaki disease, Hashimoto's thyroiditis, and mucosal leishmaniasis.

In another aspect, the compounds of Formula (I) can be used in therapies to treat or prevent multiple sclerosis, inflammatory bowel disease (e.g., Crohn's disease, ulcerative colitis), psoriasis, rheumatoid arthritis, asthma, osteoarthritis, Kawasaki disease, Hashimoto's thyroiditis, and mucosal leishmaniasis.

In another aspect, the compounds of Formula (I) can be used to treat or prevent psoriasis.

In yet another aspect, the compounds of Formula (I) can be used to treat inflammatory bowel disease (e.g., Crohn's disease, ulcerative colitis).

In another aspect, the compound of Formula (I) can be used to treat colorectal cancer.

In another aspect, the compound of Formula (I) can be used to treat lung cancer.

In another aspect, the compound of Formula (I) can be used to treat pancreatic cancer.

Route of Administration/Dosage

The compounds of this invention can be administered for the treatment or prevention of afflictions, diseases, and illnesses according to the invention by any means that effects contact of the active ingredient compound with the site of action in the body of a warm-blooded animal. For example, administration can be oral, topical, including transdermal, ocular, buccal, intranasal, inhalation, intravaginal, rectal, intracisternal, and parenteral. The term "parenteral" as used herein refers to modes of administration that include subcutaneous, intravenous, intramuscular, intraarticular injection or infusion, intrasternal and intraperitoneal. For the purpose of this disclosure, a warm-blooded animal is a member of the animal kingdom possessed of a homeostatic mechanism and includes mammals and birds.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health, and weight of the recipient; the extent of disease; kind of concurrent treatment, if any; frequency of treatment; and the nature of the effect desired. Usually, a daily dosage of active ingredient compound will be from about 1.0-2000 milligrams per day. Ordinarily, from 10 to 500 milligrams per day in one or more applications is effective to obtain desired results. These dosages are the effective amounts for the treatment and prevention of afflictions, diseases, and illnesses described above, e.g., autoimmune and inflammatory diseases and disorders.

Compositions include those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g., injection liquids in predetermined amounts, for example in sealed vials and ampoules, and may also be stored in a freeze dried (lyophilized) condition requiring only the addition of sterile liquid carrier, e.g., water, prior to use.

Mixed with such pharmaceutically acceptable auxiliaries, e.g., as described in the standard reference, Gennaro, A. R. et al., Remington: The Science and Practice of Pharmacy (20th Edition, Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g., as an injection preparation, in the form of a solution, suspension, emulsion, or as a spray, e.g., a nasal spray.

For making solid dosage units, the use of conventional additives such as fillers, colorants, polymeric binders, and the like is contemplated. In general any pharmaceutically acceptable additive that does not interfere with the function of the active compounds can be used. Suitable carriers with which the active agent of the invention can be administered as solid compositions include lactose, starch, cellulose derivatives, and the like, or mixtures thereof, used in suitable amounts. For parenteral administration, aqueous suspensions, isotonic saline solutions, and sterile injectable solutions may be used, containing pharmaceutically acceptable dispersing agents and/or wetting agents, such as propylene glycol or butylene glycol.

Pharmaceutical Compositions

Another aspect of the present invention provides pharmaceutical compositions comprising a compound of Formula (I) or a pharmaceutically acceptable salt thereof and one or more pharmaceutically acceptable excipients. The term "excipient" and "carrier" may be used interchangeably. The term "composition," as in pharmaceutical composition, is intended to encompass a product comprising the active ingredient(s), and the inert ingredient(s) (pharmaceutically acceptable excipients) that make up the carrier, as well as any product that results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula (I), additional active ingredient(s), and pharmaceutically acceptable excipients.

The pharmaceutical compositions of the present invention comprise a compound represented by Formula (I) (or pharmaceutically acceptable salts thereof) as an active ingredient, a pharmaceutically acceptable carrier, and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy in light of the present disclosure.

The active ingredient can be administered orally in solid dosage forms, such as capsules, tablets, troches, dragées, granules, and powders, or in liquid dosage forms, such as elixirs, syrups, emulsions, dispersions, and suspensions. The active ingredient can also be administered parenterally, in sterile liquid dosage forms, such as dispersions, suspensions, or solutions. Other dosages forms that can also be used to administer the active ingredient as an ointment, cream, drops, transdermal patch, or powder for topical administration, as an ophthalmic solution or suspension formation, i.e., eye drops, for ocular administration, as an aerosol spray or powder composition for inhalation or intranasal administration, or as a cream, ointment, spray, or suppository for rectal or vaginal administration.

Gelatin capsules can contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours, for example. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in Remington's Pharmaceutical Sciences, A. Osol, a standard reference text in this field.

For administration by inhalation, the compounds of Formula (I) may be conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula (I) in suitable propellants, such as fluorocarbons or hydrocarbons.

For ocular administration, an ophthalmic preparation may be formulated with an appropriate weight percent solution or suspension of the compounds of Formula (I) in an appropriate ophthalmic vehicle, such that the compound is maintained in contact with the ocular surface for a sufficient time period to allow the compound to penetrate the corneal and internal regions of the eye.

Useful pharmaceutical dosage forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil, or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contains 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term "coadministration" is understood to include the administration of the two agents concomitantly or sequentially, or alternatively as a fixed dose combination of the two active components.

The present invention also relates to a pharmaceutical composition comprising compounds of Formula (I) or pharmaceutically acceptable salts thereof in admixture with pharmaceutically acceptable auxiliaries and optionally other therapeutic agents. The auxiliaries must be "acceptable" in the sense of being compatible with the other ingredients of the composition and not deleterious to the recipients thereof.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general, parenteral administration requires lower dosages than other methods of administration which are more dependent upon absorption. However, a dosage for humans preferably contains 0.0001-100 mg per kg body weight. The desired dose may be presented as one dose or as multiple subdoses administered at appropriate intervals throughout the day. The dosage as well as the regimen of administration may differ between a female and a male recipient.

Combination Therapy

Compounds of Formula (I), and pharmaceutically acceptable salts and physiologically functional derivatives (e.g., prodrugs) thereof, may be employed alone or in combination with other therapeutic agents for the treatment of diseases and conditions associated with inappropriate IL-17 pathway activity. Combination therapies according to the present invention thus comprise the administration of at least one compound of Formula (I) or a pharmaceutically acceptable salt thereof, or a physiologically functional derivative thereof, and the use of at least one other pharmaceutically active agent. The compound(s) of Formula (I) and the other pharmaceutically active agent(s) may be administered together or separately and, when administered separately, this may occur simultaneously or sequentially in any order. The amounts of the compound(s) of Formula (I) and the other pharmaceutically active agent(s) and the relative timings of administration will be selected in order to achieve the desired combined therapeutic effect.

For the treatment of the inflammatory and autoimmune diseases, rheumatoid arthritis, psoriasis, inflammatory bowel disease, ankylosing spondylitis, SLE (systemic lupus erythematosus), uveitis, atopic dermatitis, COPD, asthma, and allergic rhinitis, a compound of Formula (I) may be combined with one or more other active agents such as: (1) TNF-a inhibitors; (2) non-selective COX-1/COX-2 inhibitors; (3) COX-2 inhibitors; (4) other agents for treatment of inflammatory and autoimmune diseases including glucocorticoids, methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist; (6) LTD4 receptor antagonist; (7) PDE4 inhibitor; (8) antihistamine HI receptor antagonists; (9) a1- and a2-adrenoceptor agonist; (10) anticholinergic agents; (11) β-adrenoceptor agonists; (12) insulin-like growth factor type I (IGF-1) mimetic; (13) glucocorticosteroids; (14) kinase inhibitors such as inhibitors of the Janus Kinases (JAK1 and/or JAK2 and/or JAK3 and/or TYK2), p38 MAPK and IKK2; (15) B-cell targeting biologics such as rituximab; (16) selective costimulation modulators such as abatacept; (17) interleukin inhibitors, such as IL-1 inhibitor anakinra, IL-6 inhibitor tocilizumab, and IL12/IL-23 inhibitor ustekinumab. The compound of Formula (I) may also be combined with anti-IL17 antibodies to obtain additive/synergistic responses for the treatment of inflammatory and autoimmune diseases.

For the treatment of cancer, the compounds of Formula (I) can be combined with other therapeutic, chemotherapeutic, and anti-cancer agents. Combinations of the compounds of Formula (I) with other therapeutic, chemotherapeutic, and anti-cancer agents are within the scope of the invention. Examples of such agents can be found in *Cancer Principles and Practice of Oncology* by V. T. Devita and S. Hellman (editors), 6th edition (Feb. 15, 2001), Lippincott Williams & Wilkins Publishers. In light of the present disclosure, a person of ordinary skill in the art would be able to discern which combinations of the compounds of Formula (I) with the other therapeutic, chemotherapeutic, and anti-cancer agents would be useful based on the particular characteristics of the drugs and the cancer involved. The compounds of Formula (I) may also be useful when co-administered with radiation therapy. The compounds of Formula (I) can be present in the same dosage unit as the other therapeutic, chemotherapeutic, and anti-cancer agents. The compounds of Formula (I) and the other therapeutic, chemotherapeutic, and anti-cancer agents can also be present in separate dosage units.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimize the activity and/or stability and/or physical characteristics, such as solubility, of the therapeutic ingredient. It will be clear also that, where appropriate, the other therapeutic ingredients may be used in optically pure form.

The combinations referred to above may conveniently be presented for use in the form of a pharmaceutical composition and thus, pharmaceutical compositions comprising a combination as defined above together with a pharmaceutically acceptable diluent or carrier represent a further aspect of the invention. These combinations are of particular interest in respiratory diseases and are conveniently adapted for inhaled or intranasal delivery.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

Accordingly, the pharmaceutical compositions of the present invention include those that also comprise at least one additional therapeutically active agent, in addition to the compound of Formula (I).

The invention further includes a compound of Formula (I) in combination with one or more other drug(s).

Methods of Preparing the Compounds of Formula (I)

The compounds of this invention may be made by a variety of methods, including standard chemistry in light of the present disclosure. Illustrative general synthetic methods are set out below and then specific compounds of the Formula (I) are prepared in the Examples.

Compounds of Formula (I) may be prepared in light of the present disclosure via techniques known in the art of organic synthesis, examples of which are set forth in the following synthesis schemes. It would be well understood by those skilled in the art in light of the present disclosure that in all of the schemes described below, protecting groups for sensitive or reactive groups should be employed where necessary in accordance with general principles of chemistry. Protecting groups can be manipulated according to standard methods of organic synthesis (T. W. Green and P. G. M. Wuts (1991) Protecting Groups in Organic Synthesis, John Wiley & Sons). These groups can be removed at a convenient stage of the compound synthesis using methods that are readily apparent to those skilled in the art. The selection of protecting groups as well as the reaction conditions and order of reaction steps shall be consistent with the preparation of compounds of Formula (I). Those skilled in the art will recognize in light of the present disclosure whether a stereocenter exists in compounds of Formula (I). When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994).

The following solvents, reagents, protecting groups, moieties, and other designations may be referred to by their abbreviations:

Me=methyl; Et=ethyl; Pr=propyl; iPr=isopropyl, Bu=butyl; t-Bu=tert-butyl; Ph=phenyl, and Ac=acetyl
μl=microliters
AcOH or HOAc=acetic acid
APCI=atmospheric-pressure chemical ionization
aq=aqueous
Bn=benzyl
Boc or BOC=tert-butoxycarbonyl
Bz=benzoyl
Cbz=benzyloxycarbonyl
DBU=1,8-diazabicyclo[5.4.0] undec-7-ene
DCM=dichloromethane:
DMAP=4-Dimethylaminopyridine
DIBAL=diisobutylaluminum hydride
DIAD=diisopropyl azodicarboxylate
DIEA or Hünig's Base=N,N-diisopropylethylamine
DMF=dimethylformamide
DMSO=dimethyl sulfoxide
EDC=1-ethyl-3-(3-dimethylaminopropyl)carbodiimide
EDTA=ethylenediamine tetraacetic acid
ESI=electrospray ionization
EtOAc=ethyl acetate
g=grams
GST=glutathione S-transferase
h=hour
HMDS=1,1,1,3,3,3-hexamethyldisilazane
HATU=N,N,N',N'-tetramethyl-O-(7-azabenzotriazol-1-yl)uronium hexafluorophosphate
Hex=hexanes
HPLC=high-performance liquid chromatography
HOBt=1-hydroxybenzotriazole
LDA=lithium diisopropylamide
LCMS=liquid chromatography mass spectrometry
LRMS=low resolution mass spectroscopy
min=minute
mg=milligrams
mL=milliliters
mmol=millimoles
MeOH=methanol
MPLC=medium pressure liquid chromatography
MTBE=methyl tert-butyl ether
MS=mass spectrometry
NBS=N-bromosuccinimide
NMO=4-methylmorpholine N-oxide
NMR=nuclear magnetic resonance spectroscopy rac=racemic mixture
RT or rt=room temperature (ambient, about 25° C.)
sat=saturated
SFC=supercritical fluid chromatography
TBSCl=t-butyldimethylsilyl chloride
TBS=t-butyldimethyl silyl
TEA=triethylamine (Et$_3$N)
TFA=trifluoroacetic acid
TFAA=trifluoroacetic anhydride
THF=tetrahydrofuran
TLC=thin layer chromatography
TMS=trimethylsilyl
TPAP=tetrapropylammonium perruthenate
TsOH=p-toluenesulfonic acid General Methods Methods for preparing compounds described herein are illustrated in the following synthetic schemes. The schemes are given for the purpose of illustrating the invention, but not for limiting the scope or spirit of the invention. Starting materials shown in the schemes can be obtained from commercial sources or be prepared based on procedures described in the literature.

The synthetic route illustrated in Scheme 1 is a general method for preparing various carbamates. Reaction of a starting amine A with a carbamoylating agent of structure B where X is a leaving group which includes halides, electron deficient phenols, imidazole, triazoles, or other moieties well-known to those trained in the art affords the target carbamate C.

The reaction procedures in Scheme 1 are contemplated to be amenable to preparing a wide variety of carbamoyl-substituted benzoxazines having different substituents at the R$^1$, R$^2$, R$^a$, R$^b$, R$^c$, R$^g$, and Cy positions. A wide variety of alcohol starting materials necessary to prepare the carbamoylating reagent B are commercially available or readily prepared via known methods. Furthermore, if a functional group that is part of the R$^1$, R$^2$, R$^a$, R$^b$, R$^c$, R$^g$, or Cy group would not be amenable to a reaction condition described in Scheme 1, it is contemplated that the functional group can first be protected using standard protecting group chemistry and strategies, and then the protecting group is removed after completing the desired synthetic transformation. In certain other embodiments, a functional group in substituents R$^1$, R$^2$, R$^a$, R$^b$, R$^c$, R$^g$, or Cy in the benzoxazine compounds can be converted to another functional group using standard functional group manipulation procedures known in the art. See, for example, "Comprehensive Organic Synthesis" (B. M. Trost & I. Fleming, eds., 1991-1992).

SCHEME 1

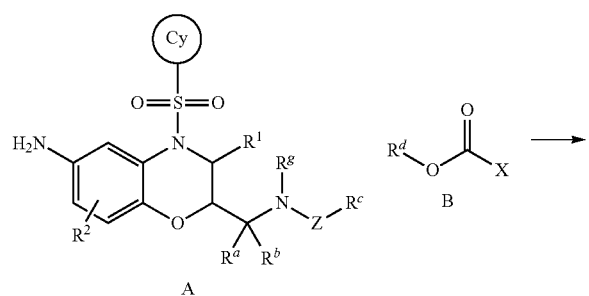

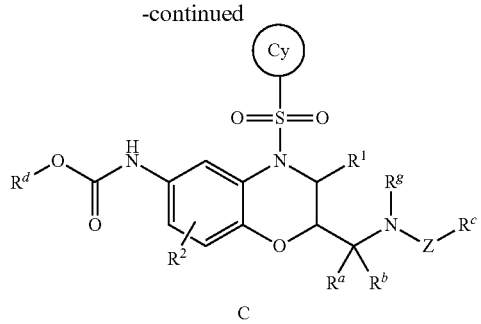

C

Scheme 2 illustrates a different general method for preparing carbamates. Treatment of the amine A with phosgene, triphosgene, or other reagents known to convert aromatic or heteroaromatic amines to isocyanates, affords the isocyanate B which when treated with an alcohol C either without or with a catalyst (a base which includes but is not limited to triethyl amine, DBU, Hunig's base, or a metal catalyst such as a dibutyl tin dilaurate and numerous others known to those trained in the art) affords the carbamate D.

SCHEME 2

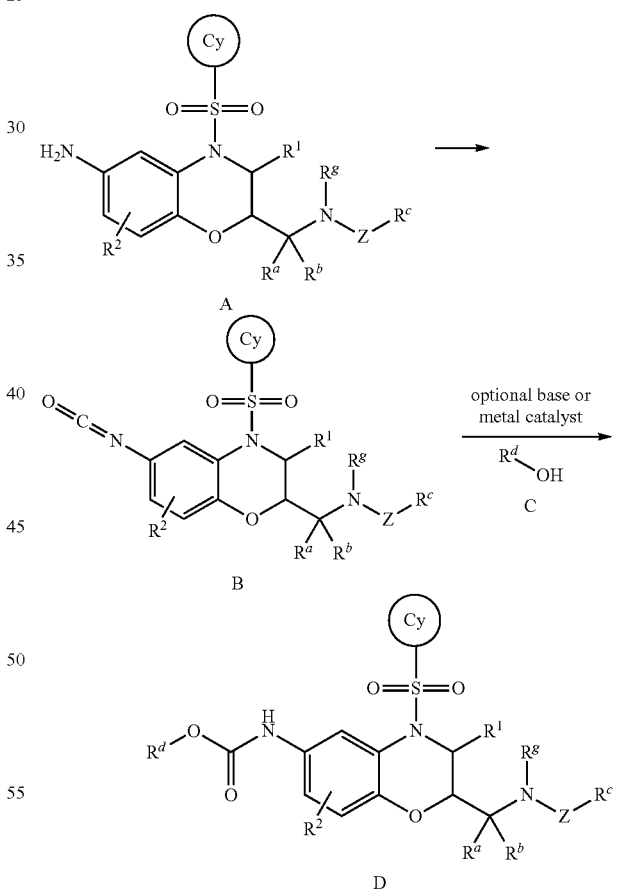

Scheme 3 illustrates a different general method for preparing carbamates. Treatment of the carboxylic acid A with conditions suitable to prepare an acyl azide (diphenyl phosphoryl azide, or isobutyl chloroformate and sodium azide, or other similar conditions known to those trained in the art) afford the acyl azide, which upon heating rearranges to form the isocyanate B. Treatment of the isocyanate with an alcohol C affords the carbamate D.

SCHEME 3

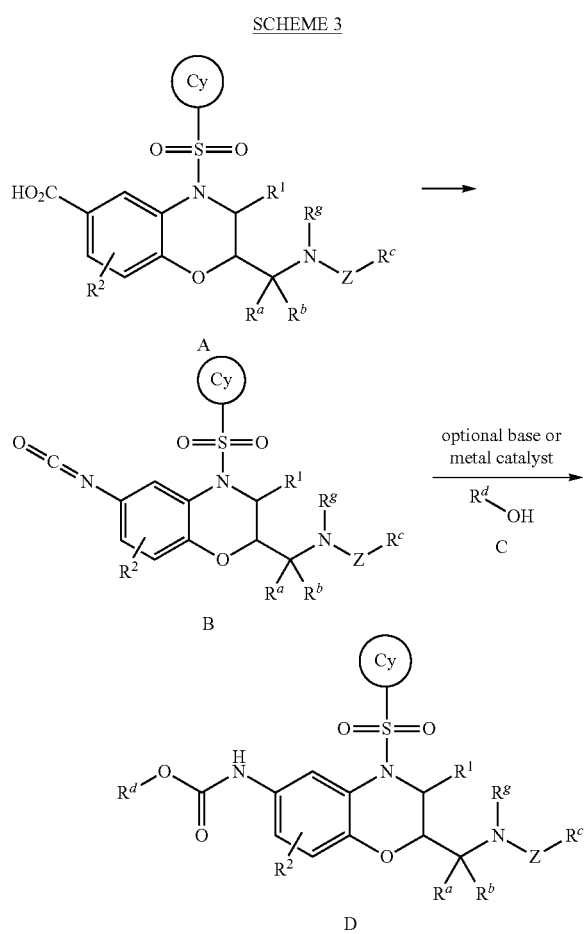

Scheme 4 illustrates another general method for preparing carbamates of the invention. Treatment of a halide or triflate (X=OTf) A with Pd-mediated coupling conditions with a unsubstituted carbamate C, affords the carbamate D. The unsubstituted carbamate C can be prepared from alcohols B via treatment with either potassium isocyanate and acid or with sulfurisocyanatidic chloride.

Scheme 5 illustrates a general method for preparing alcohols and carbamoylating reagents suitable for Scheme 1 and other general schemes below wherein $R^d$ is a group of the formula $(R^{fs})(R^{hs})(R^{gs})C-$. Treatment of a ketone or aldehyde A with a Grignard reagent, $R^{hs}Li$, a $R^{hs}$ metal, or a trialkylsilyl reagent (i.e., trimethyl silyl trifluoromethane) affords the alcohol B, which can be reacted with p-nitrochloroformate, carbonyldiimide, or phosgene to afford the carbamoylating reagents.

SCHEME 5

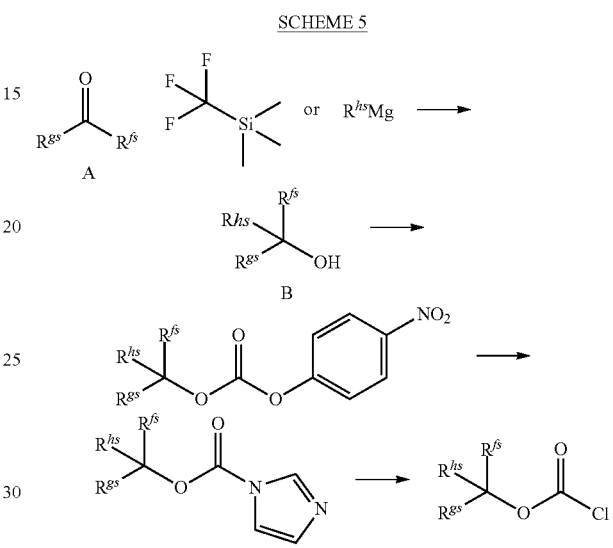

The synthetic route in Scheme 6 is a general method for preparing various carbamoyl-substituted benzoxazine compounds having a acylamidomethyl or sulfonylamidomethyl side-chain. Reaction of nitro-aryl aniline A with an epoxide provides benzoxazine B. The nitro group in benzoxazine B can be reduced in the presence of $Boc_2O$ to a Boc carbamate group to provide Boc benzoxazine C. Mitsunobu reaction of benzoxazine C, followed by hydrolysis of the phthalimide provides aminomethyl benzoxazine E. Functionalization of the aminomethyl group and sulfonylation of the benzoxazine leads to Boc-carbamate G. Removal of the Boc carbamate

SCHEME 4

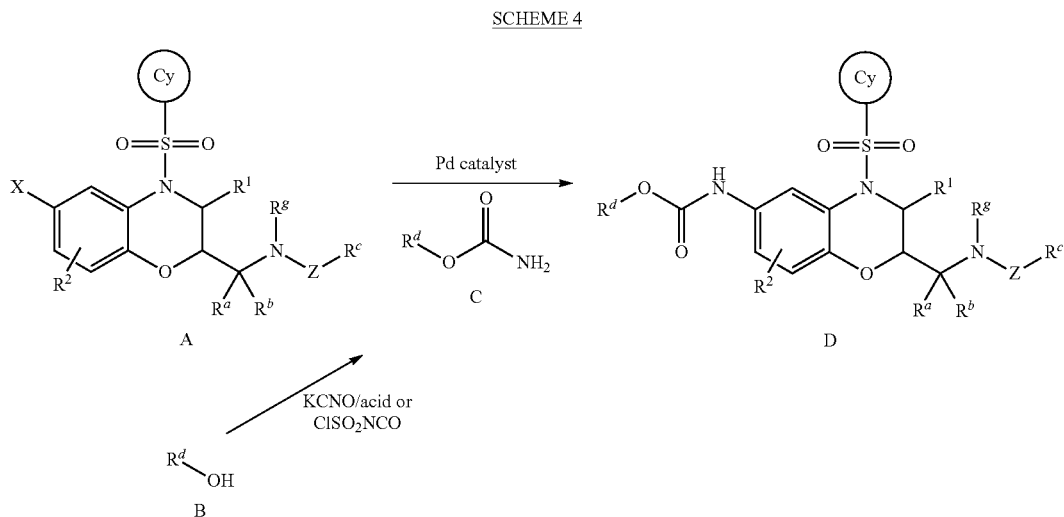

group under acidic conditions and subsequent installation of the desired carbamate affords acylamidomethyl or sulfonylamidomethyl benzoxazine carbamate H.

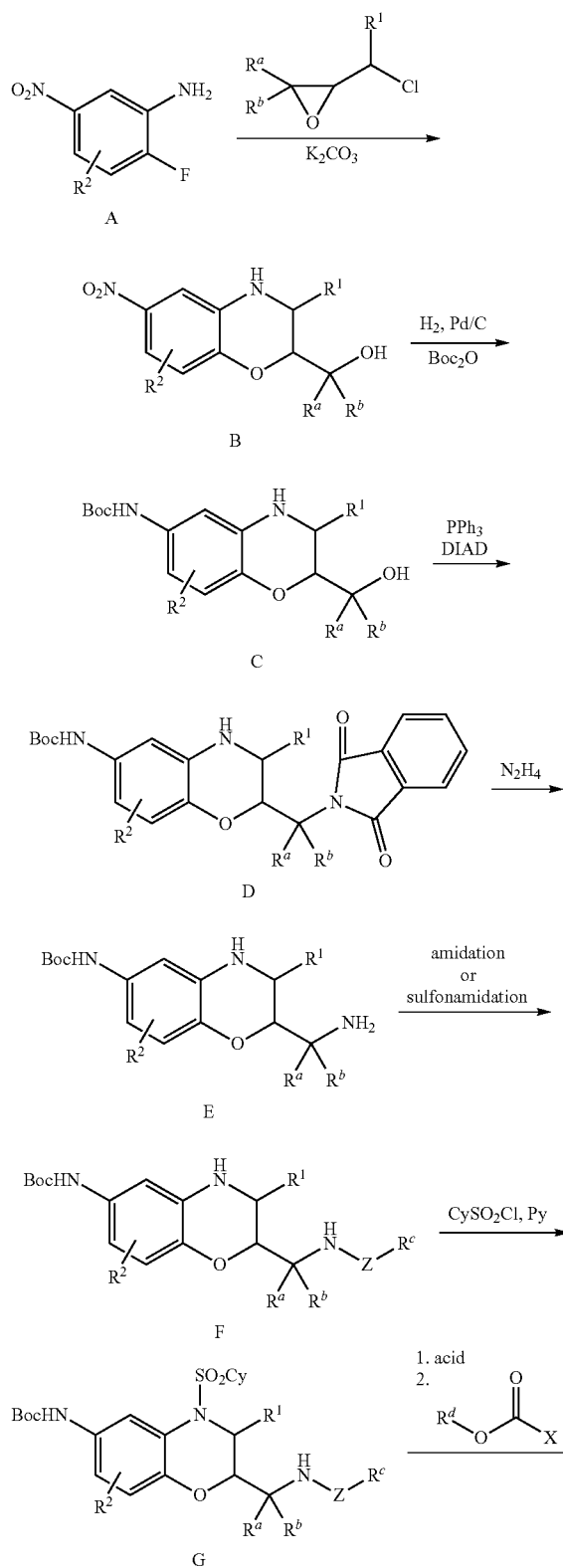

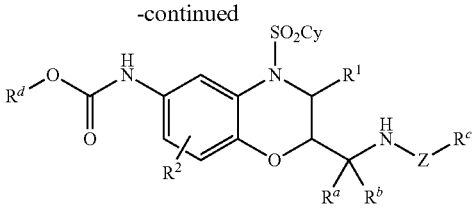

Scheme 7 provides an alternative general method for preparing various carbamoyl-substituted benzoxazine compounds. Reaction of fluoro-dinitrobenzene A with α-hydroxyester B, followed by reduction of the nitro moieties and subsequent acid-mediated cyclization, provides benzoxazinone C. The amide group in benzoxazinone C can be reduced using, for example, lithium aluminum hydride (LiAlH$_4$) to provide benzoxazine D. Carbamate coupling of benzoxazine D with a carbamoylating reagent, followed by removal of the aminomethyl side-chain protecting group affords the carbamate F which can be further functionalized as shown above.

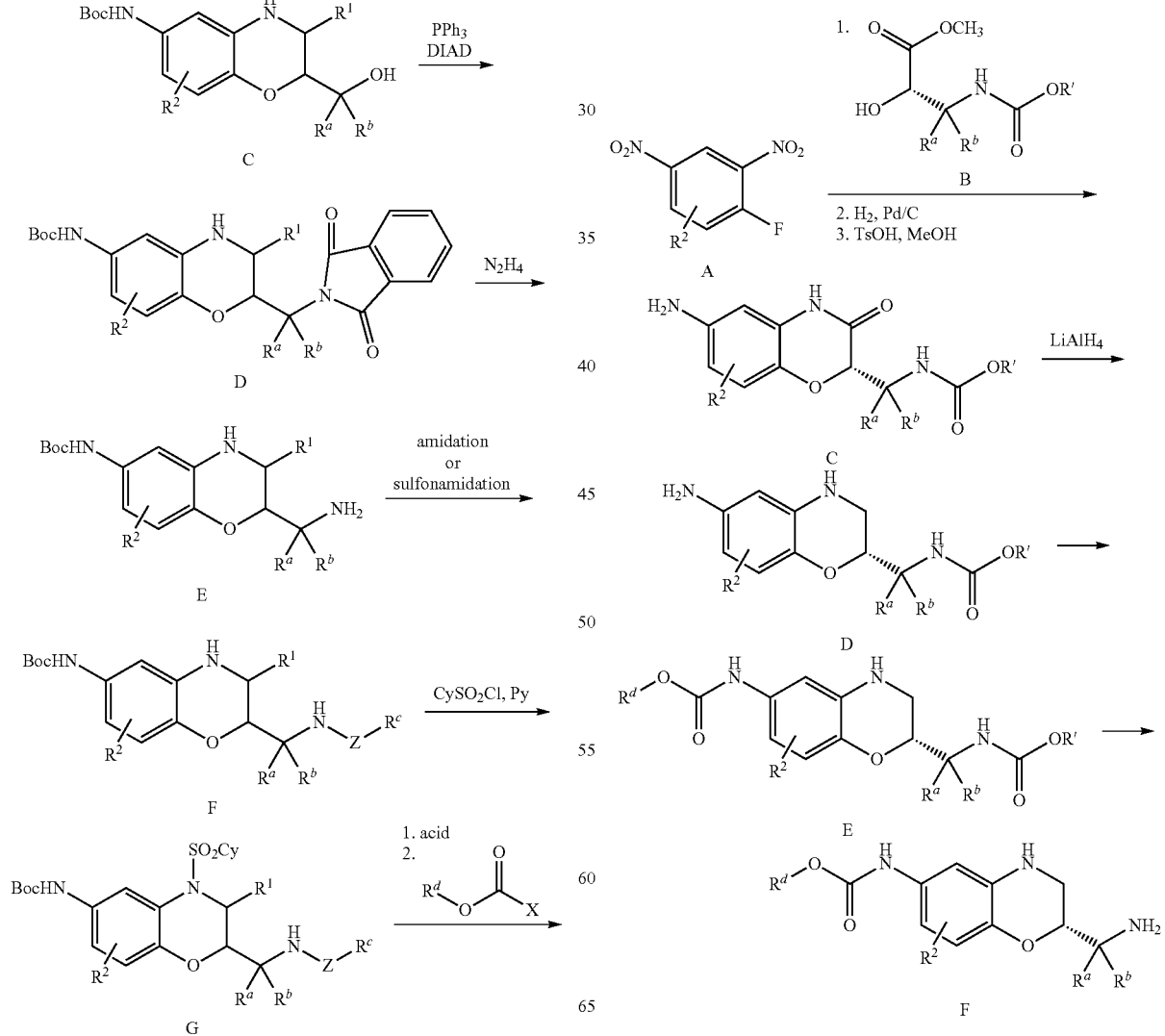

Scheme 8 shows the synthesis of 3-substituted benzoxazines. Condensation of amino phenol A with chloro ketone B leads to imine C, which upon reduction (e.g., NaBH$_4$) affords alcohol D. Bis-sulfonylation, followed by S$_N$2 displacement of the activated methyl alcohol moiety with NaN$_3$ gives azide G. Lastly, reduction of the azide, functionalization of the corresponding amine as the amide or sulfonamide and replacing of the Boc-carbamate with a suitable carbamate yields 3-substituted benzoxazine carbamate I.

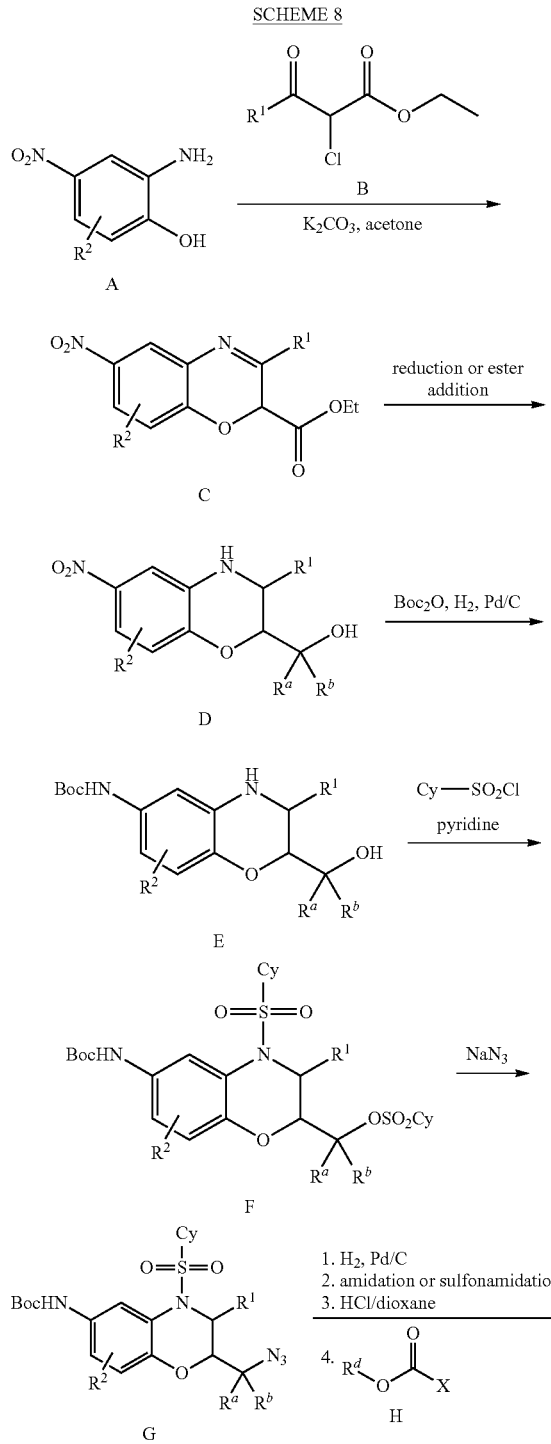

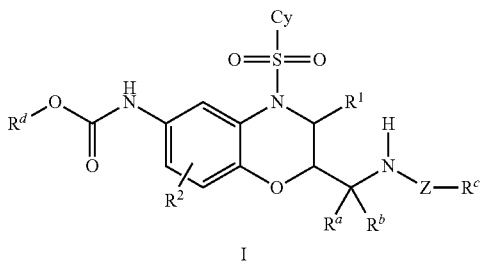

Scheme 9 shows an alternative synthesis of branched side-chain benzoxazines utilizing a common Weinreb amide intermediate. Oxidation of the previously described alcohol C to the corresponding acid, followed by Weinreb amide formation and subsequent addition of an alkyl lithium or Grignard reagent afforded alkyl ketone E. Reductive amination of the ketone, followed by functionalization of the corresponding intermediate F as described before led to the branched side-chain benzoxazine H.

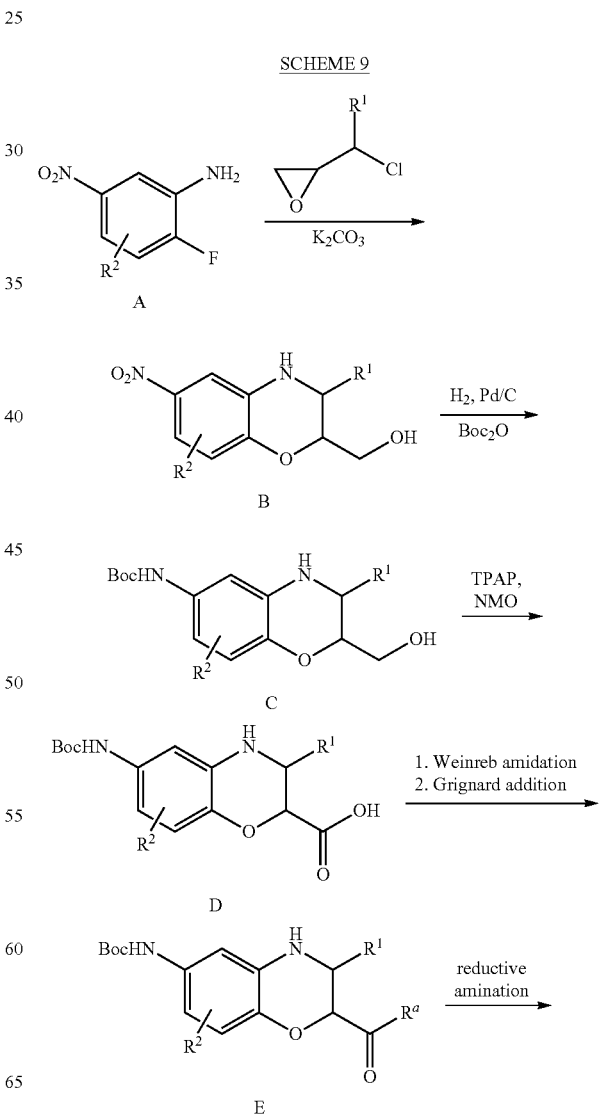

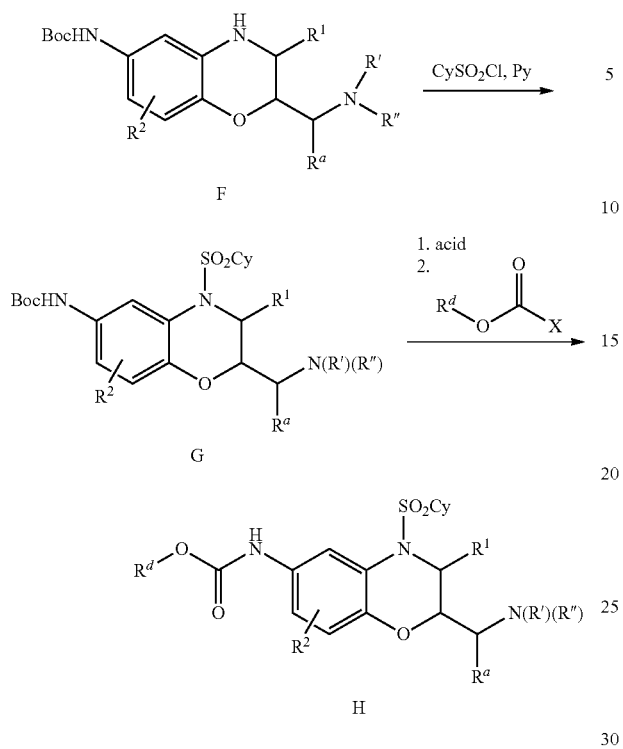

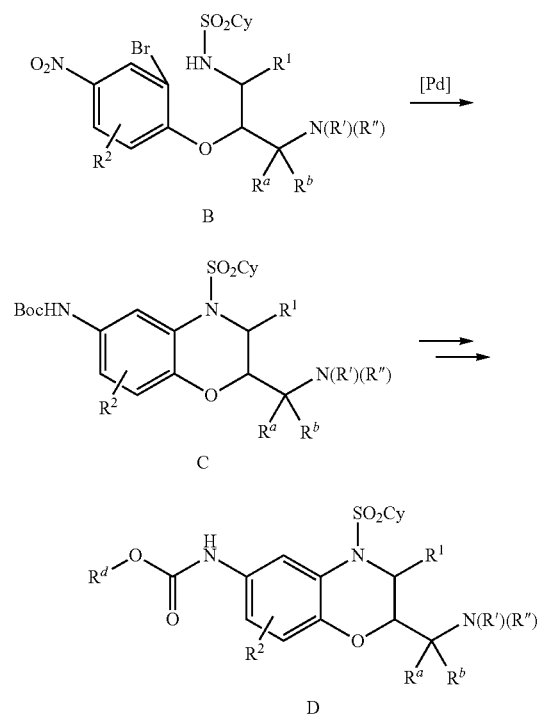

Scheme 10 shows an alternative approach to substituted benzoxazines starting from fluoride A and sulfonylated amino alcohol B via a two-step S$_N$Ar/Pd-mediated C—N coupling sequence to afford substituted benzoxazine C. Subsequent functionalization as described in Scheme 6 gives substituted benzoxazine D.

An alternative method for preparing substituted benzoxazines stereoselectively [shown as (R,R,S), but not limited to] can be seen in Scheme 11. Addition of an enolate of the oxazolidinone A to the Boc-protected aldehyde B can afford a variety of (S,S,R) beta-hydroxycarboxylic acids C diastereoselectively (see *J. Am. Chem. Soc.* (2003) 125, 8218-8227). Protection of the alcohol moiety with a silyl group, followed by a Curtius rearrangement in the presence of benzyl alcohol and subsequent desilylation, can afford the bis-carbamate D. This alcohol is added in via an SnAr displacement of the p-nitrophenyl halide of compound E, to afford the phenolic ether F. Exchange of the Boc-moiety with an SO$_2$Cy affords the sulfonamide G, which via a Pd-mediated intramolecular cyclization can afford the benzoxazine H. This can be converted to the aniline I, and carbamoylated via the procedures within Schemes 1 and 6 to afford the bis-carbamate J. Exchange of the benzoyl carbamate moiety with an appropriate amine protecting group affords the final compounds K. The other diastereomers can also be prepared using the same route, but starting with the other enantiomers of compound A and/or B.

SCHEME 10

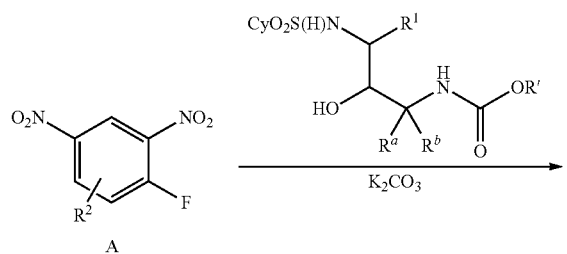

SCHEME 11

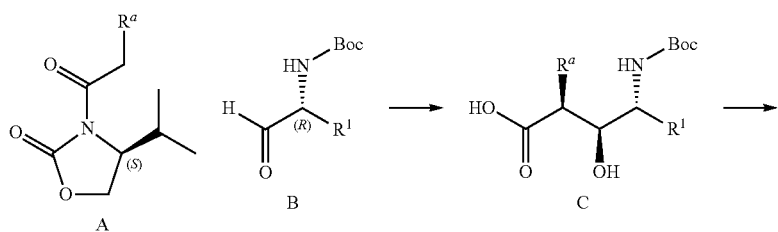

-continued

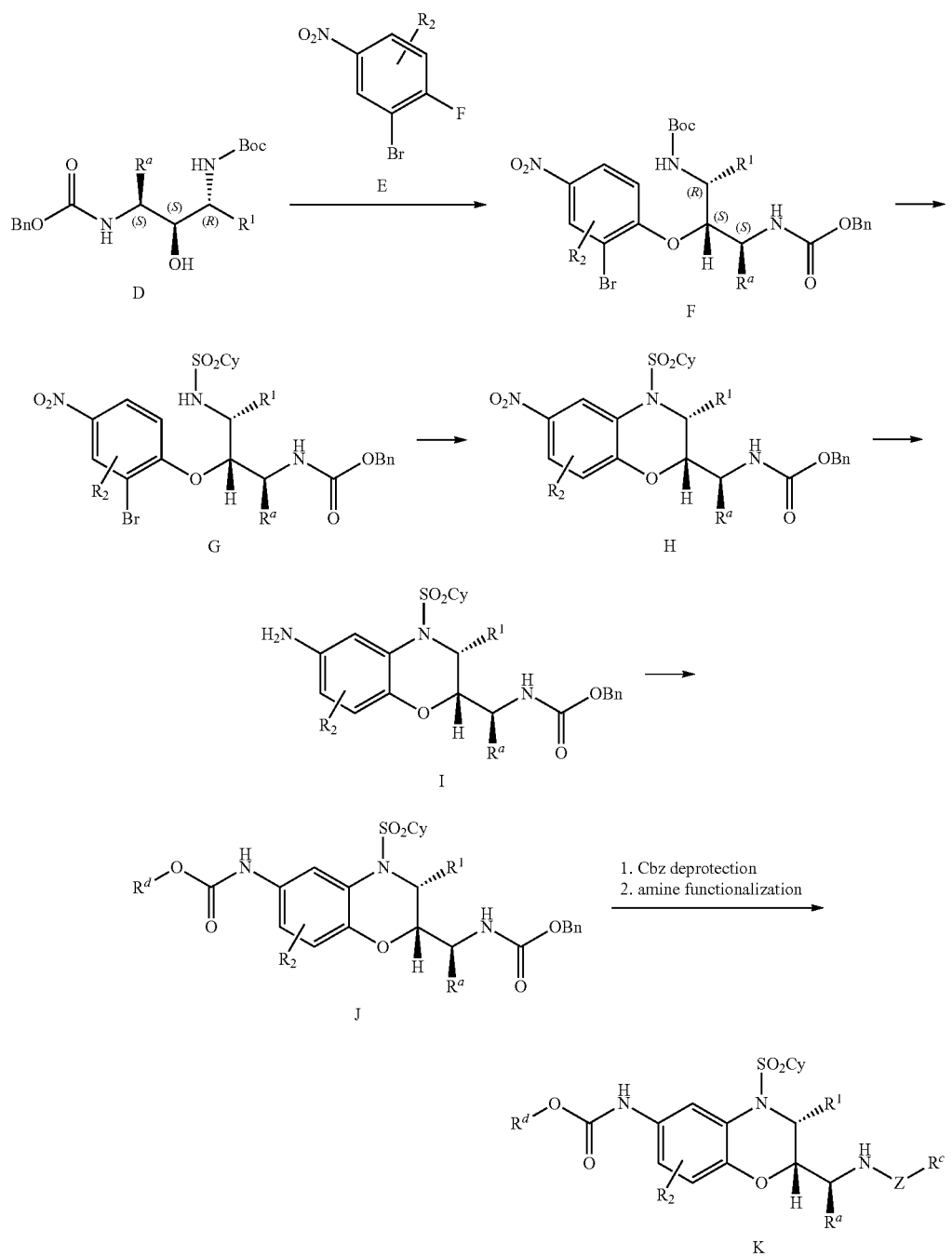

INTERMEDIATES

The following experimental procedures detail the preparation of chemical materials used in the synthesis of Examples of the instant invention. The exemplified procedures are for illustrative purposes only, and are not intended to limit the scope of the instant invention in any way.

Intermediate 1—Synthesis of methyl 2-((4-(chlorosulfonyl)-1-ethyl-1H-pyrazol-3-yl)oxy)acetate

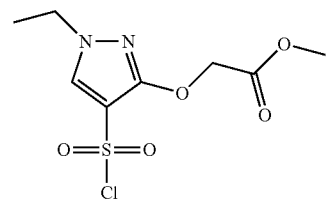 [SMILES: CCn1cc(S(=O)(=O)Cl)c(OCC(=O)OC)n1]

Step 1—Synthesis of methyl 2-((1-ethyl-1H-pyrazol-3-yl)oxy)acetate

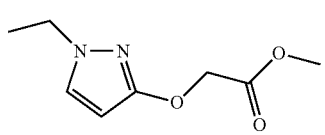

To a solution of 1-ethyl-1,2-dihydro-3H-pyrazol-3-one (13.8 g, 124 mmol) in N,N-dimethylformamide (75 mL) was added potassium carbonate (25.5 g, 185 mmol) followed by methyl bromoacetate (16.3 mL, 172 mmol). The reaction was stirred at ambient temperature overnight. The solution was partitioned between ethyl acetate and water, washed with brine, dried with sodium sulfate, filtered and concentrated in vacuo. The residue was purified by column chromatography eluting with a gradient of ethyl acetate in hexanes. The pure fractions were combined and concentrated in vacuo to yield the title compound.

Step 2—Synthesis of methyl 2-((4-(chlorosulfonyl)-1-ethyl-1H-pyrazol-3-yl)oxy)acetate

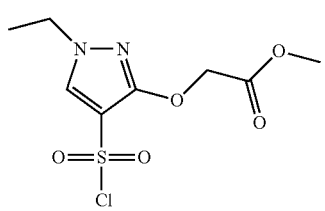 [SMILES: CCn1cc(S(=O)(=O)Cl)c(OCC(=O)OC)n1]

To a suspension of sulfur trioxide dimethylformamide complex (0.42 g, 2.7 mmol) in dichloromethane (10 mL) under nitrogen at 0° C. was added a solution of methyl 2-((1-ethyl-1H-pyrazol-3-yl)oxy)acetate (0.5 g, 2.7 mmol) in dichloromethane (1 mL). The reaction was allowed to warm to ambient temperature and stirred for 1 hour. The solution was recooled to 0° C., and anhydrous pyridine was added (0.65 mL, 8.1 mmol), followed by phosphorus pentachloride (0.62 g, 3 mmol) in portions. After 30 minutes the cooling bath was removed, and the mixture was stirred at ambient temperature overnight. The reaction was concentrated in the presence of silica. The residue was purified by column chromatography eluting with a gradient of 10-60% ethyl acetate in hexanes. The pure fractions were combined and concentrated in vacuo to yield the title compound.

Intermediate 2—Preparation of 3-Ethoxy-1-ethyl-1H-pyrazole-4-sulfonyl chloride

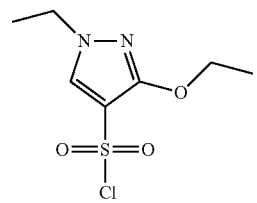

Step 1—Synthesis of 1-ethyl-1,2-dihydro-3H-pyrazol-3-one

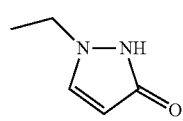

To methyl 2-chloroprop-2-enoate (5 mL, 49.8 mmol) in anhydrous tetrahydrofuran (75 mL) was added ethylhydrazine oxalate (11.2 g, 74.7 mmol) followed by triethylamine (13.9 mL, 99.6 mmol). The reaction was stirred at ambient temperature overnight. The solids were filtered off, then the filtrates were concentrated. The residue was purified by column chromatography eluting with a gradient of methanol in dichloromethane. The pure fractions were combined and concentrated in vacuo to yield the title compound.

Step 2—Synthesis of 3-ethoxy-1-ethyl-1H-pyrazole

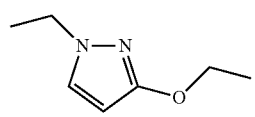

To a solution of 1-ethyl-1,2-dihydro-3H-pyrazol-3-one (1.55 g, 13.8 mmol) in N,N-dimethylformamide (15 mL) was added potassium carbonate (3.8 g, 27.6 mmol) followed by ethyl bromide (2.1 mL, 27.6 mmol). The reaction was stirred at ambient temperature for 3 hours. The solution was diluted with ethyl acetate, washed with water, brine, dried with sodium sulfate, filtered and concentrated in vacuo to yield the title compound.

Step 3—Synthesis of 3-Ethoxy-1-ethyl-1H-pyrazole-4-sulfonyl chloride

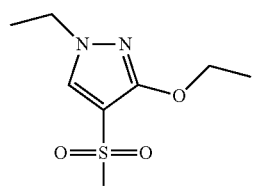

To 3-ethoxy-1-ethyl-1H-pyrazole (3.14 g, 22.4 mmol) in chloroform (25 mL) at 0° C. was added chlorosulfonic acid (15 mL, 224 mmol) dropwise. The resulting solution was stirred for 3 hours at 70° C. The solution was cooled in an ice bath and then quenched by pouring into ice water. The resulting suspension was extracted with dichloromethane and the combined organic layers were dried over anhydrous sodium sulfate and concentrated under vacuum to yield the title compound as an oil.

Intermediate 3—Synthesis of
5-ethoxy-2-ethylthiazole-4-sulfonyl chloride

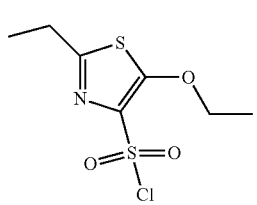

Step 1—Synthesis of ethyl 2-propionamidoacetate

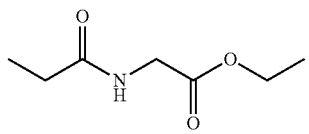

Into a 500-mL 3-necked round-bottom flask, was placed a solution of ethyl 2-aminoacetate hydrochloride (21 g, 150.45 mmol, 1.00 equiv) in saturated sodium bicarbonate/tetrahydrofuran (75/150 mL), followed by the addition of propanoyl chloride (20 g, 216.16 mmol, 1.50 equiv) dropwise with stirring at 0° C. The resulting solution was stirred for 2 h at room temperature. The resulting solution was extracted with 3×200 mL of ethyl acetate and the organic layers combined. The resulting mixture was washed with 2×500 mL of water. The mixture was dried over anhydrous sodium sulfate and concentrated under vacuum to afford ethyl 2-propanamidoacetate as yellow oil.

Step 2—Synthesis of 5-ethoxy-2-ethylthiazole

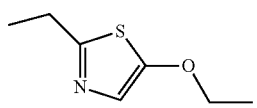

Into a 250-mL round-bottom flask, was placed a solution of ethyl 2-propanamidoacetate (6 g, 37.69 mmol, 1.00 equiv) in dioxane (150 mL) and $P_2S_5$ (17 g, 76.48 mmol, 2.00 equiv). The resulting solution was stirred overnight at 60° C. The reaction was then quenched by the addition of 50 mL of sodium hydroxide. The resulting solution was extracted with 3×100 mL of dichloromethane and the organic layers combined and dried over anhydrous sodium sulfate and concentrated under vacuum. The crude product was applied onto a silica gel column eluting with petroleum ether/ether (3:2) to afford 5-ethoxy-2-ethyl-1,3-thiazole as yellow oil.

Step 3—Synthesis of
5-ethoxy-2-ethylthiazole-4-sulfonic acid

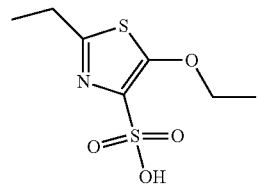

Into a 25-mL round-bottom flask, was placed a solution of 5-ethoxy-2-ethyl-1,3-thiazole (300 mg, 1.91 mmol, 1.00 equiv) in chloroform (5 mL), followed by the addition of sulfonoperoxoyl chloride (1.1 g, 9.44 mmol, 5.00 equiv) dropwise with stirring at room temperature. The resulting solution was stirred for 2 h at 60° C. The resulting mixture was concentrated under vacuum to afford 5-ethoxy-2-ethyl-1,3-thiazole-4-sulfonic acid as a yellow oil.

Step 4—Synthesis of
5-ethoxy-2-ethylthiazole-4-sulfonyl chloride

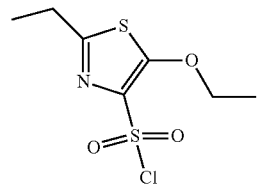

Into a 250-mL round-bottom flask, was placed 5-ethoxy-2-ethyl-1,3-thiazole-4-sulfonic acid (2.7 g, 11.38 mmol, 1.00 equiv) and thionyl chloride (20 mL, 5.00 equiv). The resulting solution was stirred for 2 h at 78° C. in an oil bath. The reaction was then quenched by the addition of 100 mL of water/ice. The resulting solution was extracted with 2×100 mL of dichloromethane and the organic layers combined and dried over anhydrous sodium sulfate and concentrated under vacuum. The crude product was applied onto a silica gel column eluting with ether/petroleum ether (3:1) to afford 5-ethoxy-2-ethyl-1,3-thiazole-4-sulfonyl chloride as a brown solid. MS ESI calculated for $C_7H_{11}ClNO_3S_2$ $(M+H)^+$ 256. found 256 $(M+H)^+$; $^1$H-NMR (300 MHz, CDCl$_3$): δ 4.38-4.28 (q, 2H), 2.99-2.92 (q, 2H), 1.61-1.53 (t, 3H), 1.45-1.34 (t, 3H).

Intermediate 4—Synthesis of
2-cyclopropyl-5-ethoxythiazole-4-sulfonyl chloride

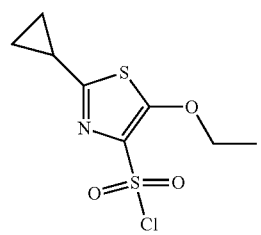

Step 1—Synthesis of ethyl 2-(cyclopropanecarboxamido)acetate

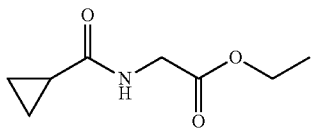

Into a 250-mL round-bottom flask, was placed a solution of ethyl 2-aminoacetate hydrochloride (10 g, 71.64 mmol, 1.00 equiv) in saturated sodium bicarbonate/tetrahydrofuran (50/50 mL). This was followed by the addition of a solution of cyclopropanecarbonyl chloride (9.0 g, 86.10 mmol, 1.20 equiv) in tetrahydrofuran (50 mL) dropwise with stirring at room temperature. The resulting solution was stirred overnight at room temperature. The resulting solution was extracted with 2×100 mL of ethyl acetate and the organic layers concentrated under vacuum. The crude product was applied onto a silica gel column eluting with ethyl acetate/petroleum ether (1:20 to 1:5) to afford ethyl 2-(cyclopropylformamido)acetate as a white solid.

Step 2—Synthesis of 2-cyclopropyl-5-ethoxythiazole

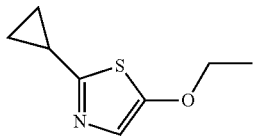

Into a 50-mL round-bottom flask, was placed ethyl 2-(cyclopropylformamido)acetate (171 mg, 1.00 mmol, 1.00 equiv) and $P_2S_5$ (333 mg, 1.50 mmol, 1.50 equiv) in 1,4-dioxane (5 mL). The resulting solution was stirred overnight at 70° C. The reaction was quenched with 10 mL of water and the resulting solution extracted with 2×10 mL of ethyl acetate. The organic layers were combined and concentrated under vacuum. The crude product was applied onto a silica gel column eluting with petroleum ether:ethyl acetate (30:1 to 10:1) to afford 2-cyclopropyl-5-ethoxy-1,3-thiazole as a yellow oil.

Step 3—Synthesis of 2-cyclopropyl-5-ethoxythiazole-4-sulfonyl chloride

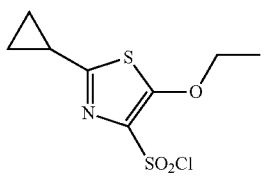

Into a 25-mL round-bottom flask, was placed 2-cyclopropyl-5-ethoxy-1,3-thiazole (600 mg, 3.55 mmol, 1.00 equiv) and $HSO_3Cl$ (1.65 g, 14.22 mmol, 4.00 equiv) in chloroform (10 mL). The resulting solution was heated to reflux for 2 h. The reaction was concentrated under vacuum and the crude residue was dissolved in thionyl chloride (10 mL). The resulting solution was heated to 80° C. for 3 h. The reaction was then quenched by the addition of 30 mL of water. The resulting solution was extracted with 2×30 mL of ethyl acetate and the organic layers combined and concentrated under vacuum. The crude product was applied onto a silica gel column eluting with ethyl acetate/petroleum ether (1:20 to 1:5) to afford 2-cyclopropyl-5-ethoxy-1,3-thiazole-4-sulfonyl chloride as a brown solid. MS ESI calculated for $C_8H_{11}ClNO_3S_2$ $(M+H)^+$ 267. found 267; $^1$H-NMR (400 MHz, $CDCl_3$): δ 4.27-4.33 (m, 2H), 2.17-2.23 (m, 1H), 1.52-1.56 (t, 3H), 1.11-1.17 (m, 4H).

Intermediate 5—Synthesis of 5-ethoxy-2-(trifluoromethyl)thiazole-4-sulfonyl chloride

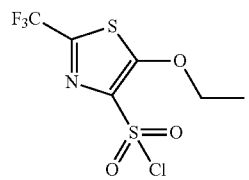 [SMILES: CCOc1sc(C(F)(F)F)nc1S(=O)(=O)Cl]

Step 1—Synthesis of ethyl 2-(2,2,2-trifluoroacetamido)acetate

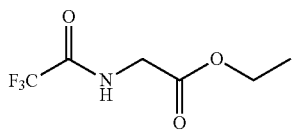

Into a 250-mL round-bottom flask, was placed a solution of trifluoroacetamide (20.3 g, 179.58 mmol, 2.00 equiv) in acetonitrile (150 mL), TEBA (1.5 g, 6.60 mmol, 0.07 equiv), potassium carbonate (24.8 g, 179.44 mmol, 2.00 equiv) and ethyl 2-bromoacetate (15 g, 89.82 mmol, 1.00 equiv). The resulting solution was heated to reflux for 1 h. The solids were filtered out and the filtrate was concentrated under vacuum. The crude product was applied onto a silica gel column eluting with ethyl acetate/petroleum ether (1:20 to 1:1) to afford ethyl 2-(trifluoroacetamido)acetate as a colorless solid.

Step 2—Synthesis of 5-ethoxy-2-(trifluoromethyl)thiazole

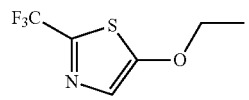

Into a 25-mL round-bottom flask, was placed ethyl 2-(trifluoroacetamido)acetate (10 g, 50.22 mmol, 1.00 equiv), $P_2S_5$ (16.7 g, 75.13 mmol, 1.50 equiv) and toluene (150 mL). The resulting solution was heated to reflux overnight, then diluted with 100 mL of water. The resulting mixture was extracted with 3×100 mL of ethyl acetate and the organic layers combined and concentrated under vacuum. The residue was applied onto a silica gel column eluting with ethyl acetate/petroleum ether (1:30 to 1:5) to afford 5-ethoxy-2-(trifluoromethyl)-1,3-thiazole as a yellow liquid.

Step 3—Synthesis of 4-bromo-5-ethoxy-2-(trifluoromethyl)thiazole

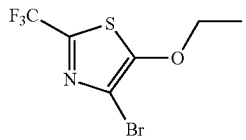

Into a 50-mL round-bottom flask, was placed a solution of 5-ethoxy-2-(trifluoromethyl)-1,3-thiazole (1 g, 5.07 mmol, 1.00 equiv) in chloroform (20 mL), followed by the addition of NBS (1.17 mg, 1.30 equiv). The resulting solution was heated to reflux overnight, then concentrated under vacuum. The crude product was applied onto a silica gel column eluting with ethyl acetate/petroleum ether (1:30 to 1:10) to afford 4-bromo-5-ethoxy-2-(trifluoromethyl)-1,3-thiazole as a yellow liquid.

Step 4—Synthesis of 5-ethoxy-2-(trifluoromethyl)thiazole-4-sulfonyl chloride

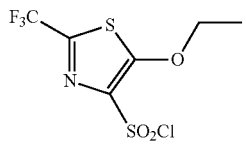

Into a 50-mL 3-necked round-bottom flask, purged and maintained under an inert atmosphere of nitrogen, was placed 4-bromo-5-ethoxy-2-(trifluoromethyl)-1,3-thiazole (1 g, 3.62 mmol, 1.00 equiv) in tetrahydrofuran (20 mL), followed by the addition of n-BuLi (2.9 mL, 2.00 equiv) dropwise with stirring at −78° C. The resulting solution was stirred for 30 min at −78° C. and followed by the addition of $SO_2$ (460 mg, 7.19 mmol, 2.00 equiv) at −78° C. The resulting solution was stirred for 30 more minutes at room temperature and then concentrated under vacuum. The crude intermediate was dissolved in dichloromethane (20 mL) and treated with NCS (1.44 g, 10.78 mmol, 3.00 equiv). The resulting solution was stirred for 30 min at room temperature, then concentrated under vacuum. The crude product was applied onto a silica gel column eluting with ethyl acetate/petroleum ether (1:20 to 1:2) to afford 5-ethoxy-2-(trifluoromethyl)-1,3-thiazole-4-sulfonyl chloride as a yellow solid. MS ESI calculated for $C_6H_5F_3NO_3S_2$ (M-Cl)$^+$ 260. found 260 (M-Cl)$^+$; $^1$H-NMR (400 MHz, CDCl$_3$): δ 4.38-4.49 (m, 2H), 1.60-1.69 (m, 3H).

Intermediate 6—Synthesis of 2-methoxy-5,6-dihydro-4H-pyrrolo[1,2-b]pyrazole-3-sulfonyl chloride

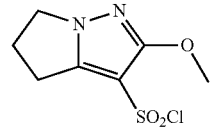

Step 1—Synthesis of ethyl 6-chloro-3-oxohexanoate

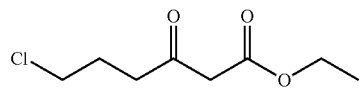

Into a 1000-mL 3-necked round-bottom flask purged and maintained under an inert atmosphere of nitrogen, was placed tetrahydrofuran (160 mL), followed by the addition of lithium diisopropylamide (86 mL, 2.00 equiv) at −78° C. A solution of ethyl 3-oxobutanoate (11.2 g, 86.06 mmol, 1.00 equiv) in tetrahydrofuran (6 mL) was next added dropwise with stirring at −78° C., followed by the addition of a solution of 1-bromo-2-chloroethane (12.2 g, 85.07 mmol, 1.00 equiv) in tetrahydrofuran (6 mL) dropwise with stirring at 0° C. After stirring for 1 h at 0° C., the pH value of the solution was adjusted to 7 with hydrogen chloride (2 N). The resulting mixture was extracted with ethyl acetate (3×) and the organic layers combined and dried over anhydrous sodium sulfate and concentrated under vacuum to afford ethyl 6-chloro-3-oxohexanoate as a colorless liquid.

Step 2—Synthesis of 5,6-dihydro-4H-pyrrolo[1,2-b]pyrazol-2-ol

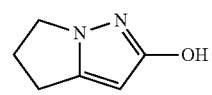

Into a 20 mL sealed tube was placed ethyl 6-chloro-3-oxohexanoate (9.0 g, 46.72 mmol, 1.00 equiv), ethanol (20 mL) and hydrazine hydrate (3.0 mL). The reaction mixture was heated in a microwave for 2 h at 120° C., cooled to room temperature and concentrated under vacuum. The resulting solution was extracted with ethyl acetate and the organic layers combined, dried over anhydrous sodium sulfate, filtered and concentrated under vacuum. The crude product was applied onto a silica gel column eluting with dichloromethane/methanol (10:1) to afford the title compound as a light yellow solid.

Step 3—Synthesis of 2-methoxy-5,6-dihydro-4H-pyrrolo[1,2-b]pyrazole

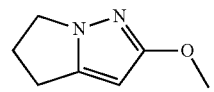

Into a 50 mL round-bottom flask was placed 5,6-dihydro-4H-pyrrolo[1,2-b]pyrazol-2-ol (1.0 g, 8.06 mmol, 1.00 equiv), acetone (20 mL) and potassium carbonate (2.2 g, 15.92 mmol, 2.00 equiv). The mixture was stirred for 5 min, followed by the addition of iodomethane (2.3 g, 16.20 mmol, 2.00 equiv) dropwise with stirring. The resulting solution was stirred overnight at room temperature. The solids were filtered and the resulting filtrate was concentrated under vacuum. The crude product was applied onto a silica gel column eluting with dichloromethane/methanol (10:1) to afford 2-methoxy-5,6-dihydro-4H-pyrrolo[1,2-b]pyrazole as a yellow liquid.

Step 4—Synthesis of 2-methoxy-5,6-dihydro-4H-pyrrolo[1,2-b]pyrazole-3-sulfonyl chloride

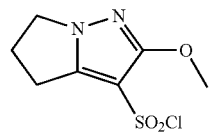

To a 25-mL round-bottom flask was added 2-methoxy-5,6-dihydro-4H-pyrrolo[1,2-b]pyrazole (300 mg, 2.17 mmol, 1.00 equiv) and chloroform (3.0 mL), followed by the addition of chlorosulfonic acid (1.5 mL) dropwise with stirring at −78° C. The resulting solution was stirred for 3 h at 60° C. and then cooled to 0° C. with a water/ice bath. The reaction was quenched by the addition of water/ice and the resulting solution was extracted with dichloromethane. The organic layers were combined, dried over anhydrous sodium sulfate and concentrated under vacuum to afford 2-methoxy-5,6-dihydro-4H-pyrrolo[1,2-b]pyrazole-3-sulfonyl chloride as a yellow liquid.

Intermediate 7—Synthesis of 2-chloro-5,6-dihydro-4H-pyrrolo[1,2-b]pyrazole-3-sulfonyl chloride

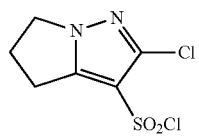 [SMILES: O=S(=O)(Cl)c1c(Cl)nn2c1CCC2]

Step 1—Synthesis of 2-chloro-5,6-dihydro-4H-pyrrolo[1,2-b]pyrazole

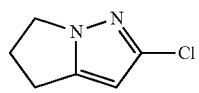

To a 30 mL sealed tube was added 5,6-dihydro-4H-pyrrolo[1,2-b]pyrazol-2-ol (1.8 g, 14.50 mmol, 1.00 equiv) and POCl₃ (10 mL). The resulting solution was stirred for 8 h at 200° C., cooled to room temperature with a water/ice bath and then quenched by the addition of water/ice. The resulting solution was extracted with dichloromethane (3×) and the organic layers combined, dried over anhydrous sodium sulfate and concentrated under vacuum. The crude product was applied onto a silica gel column eluting with dichloromethane/methanol (100:0 to 10:1) to afford the title compound as a brown oil.

Step 2—Synthesis of 2-chloro-5,6-dihydro-4H-pyrrolo[1,2-b]pyrazole-3-sulfonyl chloride

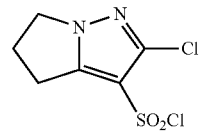

To a 25 mL round-bottom flask was added 2-chloro-5,6-dihydro-4H-pyrrolo[1,2-b]pyrazole (100 mg, 0.70 mmol, 1.00 equiv) and chloroform (2.0 mL), followed by the addition of chlorosulfonic acid (1.0 mL) at −78° C. The resulting solution was stirred for 12 h at 60° C., then cooled to 25° C. The reaction was quenched by the addition of water/ice and the resulting mixture was extracted with dichloromethane (3×). The organic layers were combined, dried over anhydrous sodium sulfate and concentrated under vacuum. The crude product was applied onto a silica gel column eluting with ethyl acetate/petroleum ether (1:10 to 1:1) to afford 2-chloro-5,6-dihydro-4H-pyrrolo[1,2-b]pyrazole-3-sulfonyl chloride as a white solid.

Intermediate 8—Synthesis of 2-methoxy-4,5,6,7-tetrahydropyrazolo[1,5-a]pyridine-3-sulfonyl chloride

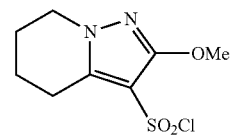

Step 1—Synthesis of ethyl 7-chloro-3-oxoheptanoate

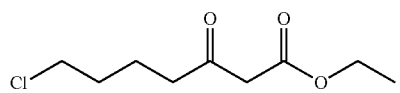

To a 1000-mL 3-necked round-bottom flask purged and maintained under an inert atmosphere of nitrogen was added tetrahydrofuran (160 mL), followed by the addition of lithium diisopropylamide (100 mL) at −78° C. A solution of ethyl 3-oxobutanoate (13 g, 99.89 mmol, 1.00 equiv) in tetrahydrofuran (6 mL) was next added dropwise with stirring at −78° C., followed by a solution of 1-bromo-3-chloropropane (15.7 g, 99.72 mmol, 1.00 equiv) in tetrahydrofuran (6 mL) dropwise with stirring at 0° C. The resulting solution was stirred for 1 h at 0° C. The pH value of the reaction was adjusted to 7 with 2 N hydrogen chloride and the resulting solution was extracted with ethyl acetate (3×). The organic layers were combined and concentrated under vacuum to afford ethyl 7-chloro-3-oxoheptanoate as a colorless liquid.

Step 2—Synthesis of 4,5,6,7-tetrahydropyrazolo[1,5-a]pyridin-2-ol

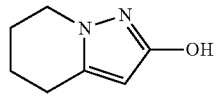

To a 10 mL sealed tube was added ethyl 7-chloro-3-oxoheptanoate (900 mg, 4.35 mmol, 1.00 equiv), ethanol (5.0 mL) and hydrazine hydrate (0.5 mL). The reaction mixture was irradiated with microwave radiation for 2 h at 120° C., cooled to room temperature and concentrated under vacuum. The crude product was applied onto a silica gel column eluting with dichloromethane/methanol (10:1) to afford 4,5,6,7-tetrahydropyrazolo[1,5-a]pyridin-2-ol.

Step 3—Synthesis of 2-methoxy-4,5,6,7-tetrahydropyrazolo[1,5-a]pyridine

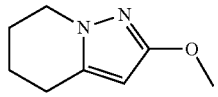

To a 50 mL round-bottom flask was added 4,5,6,7-tetrahydropyrazolo[1,5-c]pyridin-2-ol (250 mg, 1.81 mmol, 1.00 equiv), acetone (5.0 mL) and potassium carbonate (500 mg, 3.62 mmol, 2.00 equiv). The reaction mixture was stirred for 5 min at room temperature, followed by the addition of $CH_3I$ (511 mg, 3.60 mmol, 2.00 equiv) dropwise with stirring. The resulting solution was stirred overnight at room temperature and quenched with 20 mL of water. The resulting mixture was extracted with ethyl acetate (3×), the combined organic layers dried over anhydrous sodium sulfate and concentrated under vacuum. The crude product was applied onto a silica gel column eluting with dichloromethane/methanol (10:1) to afford the title compound as a yellow liquid.

Step 4—Synthesis of 2-methoxy-4,5,6,7-tetrahydropyrazolo[1,5-a]pyridine-3-sulfonyl chloride

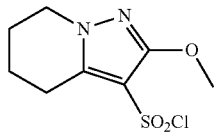

To a 50 mL round-bottom flask was added 2-methoxy-4,5,6,7-tetrahydropyrazolo[1,5-a]pyridine (150 mg, 0.99 mmol, 1.00 equiv) and chloroform (1.5 mL), followed by the addition of chlorosulfonic acid (0.5 mL) dropwise with stirring at −78° C. The resulting solution was stirred for 3 h at 60° C., then cooled to room temperature with a water/ice bath. The reaction was quenched by the addition of water/ice and the resulting mixture was extracted with dichloromethane (3×). The organic layers were combined, dried over anhydrous sodium sulfate and concentrated under vacuum to afford the title compound as a yellow liquid. $^1$H-NMR (400 MHz, $CDCl_3$): δ 4.03 (s, 3H), 4.02 (m, 2H), 3.06 (m, 2H), 2.05 (m, 2H), 1.95 (m, 2H).

Intermediate 9—Synthesis of 2-chloro-4,5,6,7-tetrahydropyrazolo[1,5-a]pyridine-3-sulfonyl chloride

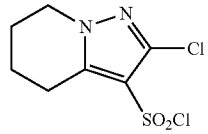 [SMILES: O=S(=O)(Cl)c1c(Cl)nn2c1CCCC2]

Step 1—Synthesis of 2-chloro-4,5,6,7-tetrahydropyrazolo[1,5-a]pyridine

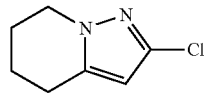

To a 30 mL sealed tube was added 4,5,6,7-tetrahydropyrazolo[1,5-a]pyridin-2-ol (3.0 g, 21.71 mmol, 1.00 equiv) and $POCl_3$ (12.0 mL). The resulting solution was stirred for 8 h at 200° C., then cooled to room temperature. The reaction was quenched by the addition of water/ice and the resulting solution was extracted with dichloromethane (3×). The combined organic layers were dried over anhydrous sodium sulfate and concentrated under vacuum. The residue was applied onto a silica gel column eluting with dichloromethane/methanol (100:0 to 10:1) to afford the title compound as a colorless liquid.

Step 2—Synthesis of 2-chloro-4,5,6,7-tetrahydropyrazolo[1,5-a]pyridine-3-sulfonyl chloride

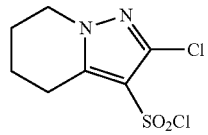 [SMILES: O=S(=O)(Cl)c1c(Cl)nn2c1CCCC2]

To a 25-mL round-bottom flask was added 2-chloro-4,5,6,7-tetrahydropyrazolo[1,5-a]pyridine (350 mg, 2.23 mmol, 1.00 equiv) and chloroform (3.5 mL), followed by the addition of sulfonoperoxoyl chloride (1.5 mL) at −78° C. The resulting solution was stirred for 12 h at 60° C., then cooled to room temperature. The reaction was quenched by the addition of water/ice and the resulting solution was extracted with dichloromethane (3×). The combined organic layers were dried over anhydrous sodium sulfate and concentrated under vacuum. The crude product was applied onto a silica gel column eluting with ethyl acetate/petroleum ether (0:100 to 1:1) to afford the title compound as a brown solid. $^1$H-NMR (400 MHz, $CDCl_3$): δ 4.19 (m, 2H), 3.11 (m, 2H), 2.12 (m, 2H), 2.05 (m, 2H), 1.92 (m, 2H).

Intermediate 10—Synthesis of 3-(difluoromethoxy)-1-ethyl-1H-pyrazole-4-sulfonyl chloride

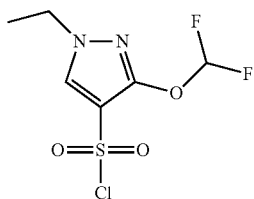

Step 1—Synthesis of 1H-pyrazol-3-ol

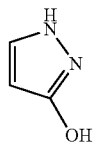

To a 100 mL round-bottom flask was added methyl (2E)-3-methoxyprop-2-enoate (11.6 g, 99.90 mmol, 1.00 equiv) and methanol (10.0 mL), followed by the addition of hydrazine hydrate (7.8 mL) dropwise with stirring. The resulting solution was stirred for 90 min at 85° C., then concentrated under vacuum to afford crude 1H-pyrazol-3-ol as a white solid.

Step 2—Synthesis of 1-(3-hydroxy-1H-pyrazol-1-yl)ethanone

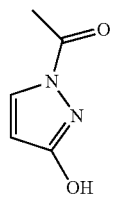

To a 250 mL round-bottom flask was added 1H-pyrazol-3-ol (8.5 g, 101.10 mmol, 1.00 equiv), and pyridine (50 mL), followed by the addition of a solution of acetic anhydride (47.5 mL) in pyridine (10.0 mL) dropwise with stirring over 15 min at 95° C. The resulting solution was stirred for 1 h at 95° C. and then concentrated under vacuum. The crude product was applied onto a silica gel column eluting with ethyl acetate/petroleum ether (1:100 to 1:1) to afford the title compound as a white solid.

Step 3—Synthesis of 1-(3-(difluoromethoxy)-1H-pyrazol-1-yl)ethanone

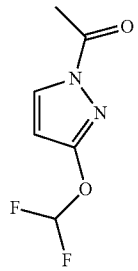

To a 250 mL round-bottom flask was added 1-(3-hydroxy-1H-pyrazol-1-yl)ethanone (5.0 g, 39.65 mmol, 1.00 equiv), N,N-dimethylformamide (50.0 mL), potassium carbonate (11.0 g, 79.02 mmol, 2.00 equiv) and ethyl 2-chloro-2,2-difluoroacetate (7.5 g, 47.31 mmol, 1.20 equiv). The resulting solution was stirred for 12 h at 60° C., then diluted with water. The resulting mixture was extracted with ethyl ether (3×) and the combined organic layers washed with water, dried over anhydrous sodium sulfate and concentrated under vacuum. The crude product was applied onto a silica gel column eluting with ethyl ether/hexanes (0:100 to 1:1) to afford the title compound as colorless oil. $^1$H-NMR (400 MHz, CDCl$_3$): δ 8.15 (d, 1H), 7.02 (t, 1H), 6.14 (d, 1H), 2.62 (s, 3H).

Step 4—Synthesis of 3-(difluoromethoxy)-1H-pyrazole

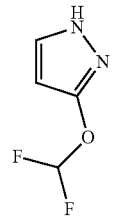

To a 25 mL round-bottom flask was added 1-[3-(difluoromethoxy)-1H-pyrazol-1-yl]ethan-1-one (110 mg, 0.62 mmol, 1.00 equiv), methanol (2.0 mL), tetrahydrofuran (2.0 mL) and sodium hydroxide (2.0 mL, 1 M). The resulting solution was stirred for 1 h at 25° C., then diluted with water. The resulting mixture was extracted with dichloromethane (3×) and the combined organic layers dried over anhydrous sodium sulfate and concentrated under vacuum to afford the title compound as a colorless liquid. $^1$H-NMR (400 MHz, CDCl$_3$): δ 7.48 (d, 1H), 6.74 (t, 1H), 5.99 (d, 1H).

Step 5—Synthesis of 3-(difluoromethoxy)-1-ethyl-1H-pyrazole

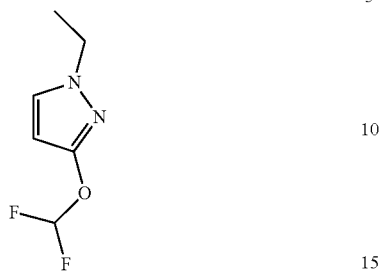

To a 100 mL round-bottom flask was added 3-(difluoromethoxy)-1H-pyrazole (500 mg, 3.73 mmol, 1.00 equiv) and N,N-dimethylformamide (15 mL), followed by the addition of sodium hydride (360 mg, 15.00 mmol, 4.00 equiv). The mixture was stirred for 10 min before the addition of bromoethane (1620 mg, 15.00 mmol, 4.00 equiv). The resulting solution was stirred for 12 h at 25° C., then quenched by the addition of water. The resulting mixture was extracted with ethyl ether and the combined organic layers washed with water, dried over anhydrous sodium sulfate and concentrated under vacuum. The crude product was applied onto a silica gel column eluting with ethyl ether/hexane (0:100 to 1:1) to afford 3-(difluoromethoxy)-1-ethyl-1H-pyrazole as a colorless liquid.

Step 6—Synthesis of 3-(difluoromethoxy)-1-ethyl-1H-pyrazole-4-sulfonyl chloride

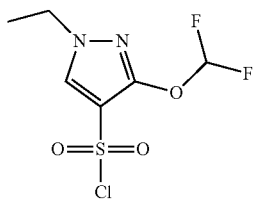

To a 250 mL round-bottom flask was added 3-(difluoromethoxy)-1-ethyl-1H-pyrazole (3.0 g, 18.50 mmol, 1.00 equiv) and chloroform (20.0 mL), followed by the addition of sulfonoperoxoyl chloride (8.0 mL) at −78° C. The mixture was stirred for 2 h at 60° C., then concentrated under vacuum. To the resulting residue was added sulfuroyl dichloride (20.0 mL) and the solution was stirred for 2 h at 85° C. The reaction mixture was cooled to room temperature and then quenched by the addition of water/ice. The resulting mixture was extracted with ethyl acetate (3×) and the combined organic layers dried over anhydrous sodium sulfate and concentrated under vacuum. The crude product was applied onto a silica gel column eluting with ethyl acetate/petroleum ether (0:100 to 100:0) to afford 3-(difluoromethoxy)-1-ethyl-1H-pyrazole-4-sulfonyl chloride as a brown liquid. MS ESI calculated for $C_6H_8ClF_2N_2O_3S$ $(M+H)^+$ 260.6. found 260.8 $(M+H)^+$; $^1$H-NMR (300 MHz, $CDCl_3$): δ 7.91 (s, 1H), 7.05 (t, J=71.7 Hz, 1H), 4.12 (q, J=7.5 Hz, 2H), 1.53 (t, J=7.2 Hz, 3H); F-NMR (300 MHz, $CDCl_3$): δ −85.82.

Intermediate 11—Synthesis of 1-(difluoromethyl)-3-ethoxy-1H-pyrazole-4-sulfonyl chloride

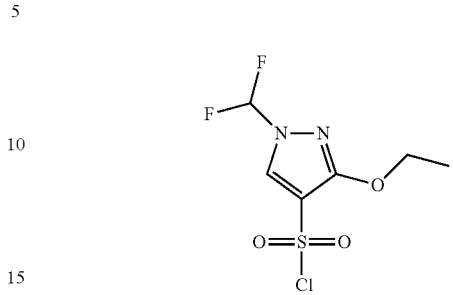

Step 1—Synthesis of 1-(3-ethoxy-1H-pyrazol-1-yl)ethanone

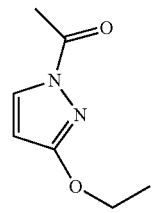

To a 100 mL round-bottom flask was added 1-(3-hydroxy-1H-pyrazol-1-yl)ethan-1-one (2.0 g, 15.86 mmol, 1.00 equiv), N,N-dimethylformamide (20.0 mL) and potassium carbonate (4.4 g, 31.61 mmol, 2.00 equiv), followed by the addition of bromoethane (2.4 mL, 2.00 equiv) dropwise with stirring. The resulting solution was stirred for 12 h at 25° C., then diluted with ethyl acetate. The resulting solution was washed with water and the organic layer dried over anhydrous sodium sulfate and concentrated under vacuum. The crude product was applied onto a silica gel column eluting with ethyl acetate/petroleum ether (0:100 to 1:1) to afford 1-(3-ethoxy-1H-pyrazol-1-yl)ethanone as a white solid. $^1$H-NMR (300 MHz, $CDCl_3$): δ 8.05 (d, 1H), 5.95 (d, 1H), 4.32 (q, 2H), 2.58 (s, 3H), 1.43 (t, 3H).

Step 2—Synthesis of 3-ethoxy-1H-pyrazole

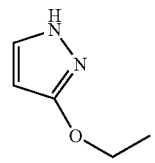

To a 100 mL round-bottom flask was added 1-(3-ethoxy-1H-pyrazol-1-yl)ethan-1-one (1.26 g, 8.17 mmol, 1.00 equiv), methanol (15 mL), tetrahydrofuran (10 mL) and sodium hydroxide aqueous (12 mL, 1 M). The resulting solution was stirred for 1 h at 25° C., then diluted with $H_2O$. The resulting mixture was extracted with dichloromethane (3×) and the combined organic layers dried over anhydrous sodium sulfate and concentrated under vacuum. The crude product was applied onto a silica gel column eluting with dichloromethane/methanol (0:100 to 1:10) to afford 3-ethoxy-1H-pyrazole as a colorless liquid. ¹H-NMR (300 MHz, CDCl₃): δ 7.36 (d, 1H), 5.72 (d, 1H), 4.22 (q, 2H), 1.43 (t, 3H).

Step 3—Synthesis of 1-(difluoromethyl)-3-ethoxy-1H-pyrazole

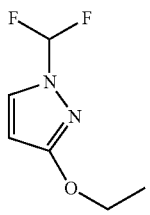

To a 100 mL round-bottom flask was added 3-ethoxy-1H-pyrazole (2.0 g, 17.84 mmol, 1.00 equiv), N,N-dimethylformamide (30 mL) and potassium carbonate (4.9 g, 35.45 mmol, 2.00 equiv), followed by the addition of ethyl 2-chloro-2,2-difluoroacetate (3.4 g, 21.45 mmol, 1.20 equiv) dropwise with stirring. The resulting solution was stirred for 12 h at 60° C., then diluted with H₂O. The resulting mixture was extracted with dichloromethane (3×) and the combined organic layers washed with water, dried over anhydrous sodium sulfate and concentrated under vacuum. The crude product was applied onto a silica gel column with ethyl ether/hexane (0:100 to 1:1) to afford 1-(difluoromethyl)-3-ethoxy-1H-pyrazole as a colorless liquid. ¹H-NMR (300 MHz, CDCl₃): δ 7.56 (d, 1H), 7.17 (t, 1H), 5.86 (d, 1H), 4.29 (q, 2H), 1.39 (t, 3H).

Step 4—Synthesis of 1-(difluoromethyl)-3-ethoxy-1H-pyrazole-4-sulfonic acid

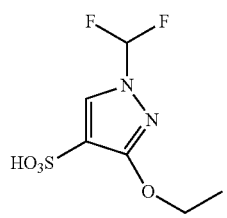

To a 25 mL round-bottom flask was added 1-(difluoromethyl)-3-ethoxy-1H-pyrazole (600 mg, 3.70 mmol, 1.00 equiv) and trichloromethane (2.0 mL), followed by the addition of chlorosulfonic acid (1.0 mL) at −78° C. The resulting solution was stirred for 2 h at 60° C. and then concentrated under vacuum to afford 1-(difluoromethyl)-3-ethoxy-1H-pyrazole-4-sulfonic acid as colorless oil, which was used in the next step without further purification.

Step 5—Synthesis of 1-(difluoromethyl)-3-ethoxy-1H-pyrazole-4-sulfonyl chloride

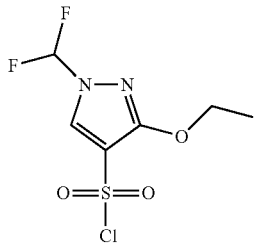

To a 25 mL round-bottom flask was added 1-(difluoromethyl)-3-ethoxy-1H-pyrazole-4-sulfonic acid (800 mg, 3.30 mmol, 1.00 equiv) and sulfuroyl dichloride (3.0 mL). The resulting solution was stirred for 2 h at 85° C. and then quenched by the addition of water/ice. The resulting mixture was extracted with dichloromethane (3×) and the combined organic layers dried over anhydrous sodium sulfate and concentrated under vacuum. The crude product was applied onto a silica gel column eluting with ethyl acetate/petroleum ether (0:100 to 100:0) to afford 1-(difluoromethyl)-3-ethoxy-1H-pyrazole-4-sulfonyl chloride as brown liquid. ¹H-NMR (300 MHz, CDCl₃): δ 8.23 (s, 1H), 7.01 (t, J=60.6 Hz, 1H), 4.44 (q, J=7.2 Hz, 2H), 1.48 (t, J=7.2 Hz, 1H); F-NMR (300 MHz, CDCl₃): δ −96.34

Intermediate 12—Synthesis of 1-cyclopropyl-3-methyl-1H-pyrazole-4-sulfonyl chloride (P1) and 1-cyclopropyl-5-methyl-1H-pyrazole-4-sulfonyl chloride (P2)

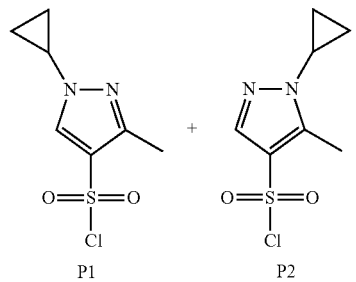

Step 1—Synthesis of 1-cyclopropyl-3-methyl-1H-pyrazole and 1-cyclopropyl-5-methyl-1H-pyrazole

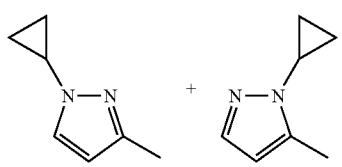

To a mixture of 3-methyl-1H-pyrazole (1 g, 12.2 mmol), potassium cyclopropyltrifluoroborate (3.6 g, 24.4 mmol) and Na₂CO₃ (2.6 g, 24.4 mmol) in dichloroethane (20 mL) were added Cu(OAc)₂ (2.2 g, 12.2 mmol) and 2,2'-bipyridine (1.9 g, 12.2 mmol). The mixture was stirred at 70° C. for 18 h. The reaction was diluted with water and extracted with DCM. The combined organic layers were washed with brine, dried over Na₂SO₄ and concentrated. The crude product was purified by column chromatography (petroleum ether:EtOAc=10:1) to give the mixture of 1-cyclopropyl-3-methyl-1H-pyrazole and 1-cyclopropyl-5-methyl-1H-pyrazole (1:1 by NMR). ¹H-NMR (CDCl₃, 400 MHz) δ 7.24 (1H, s), 5.83-5.95 (1H, s), 3.19-3.47 (1H, s), 2.16-2.33 (3H, s), 0.88-1.08 (1H, m), 0.88-1.01 (2H, m), 0.85-0.94 (1H, m).

Step 2—Synthesis of 1-cyclopropyl-3-methyl-1H-pyrazole-4-sulfonyl chloride & 1-cyclopropyl-5-methyl-1H-pyrazole-4-sulfonyl chloride (P1+P2)

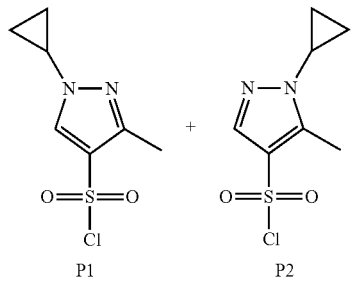

To a 1:1 mixture of 1-cyclopropyl-3-methyl-1H-pyrazole and 1-cyclopropyl-5-methyl-1H-pyrazole (3 g, 24 mmol) in was added HSO₃Cl (1 mL). The reaction was stirred at 80° C. for 3 h, then poured into ice water and extracted with EtOAc. The combined organic layers were washed with brine, dried over Na₂SO₄ and concentrated. The crude product was purified by column chromatography (petroleum ether:EtOAc=10:1) to afford a mixture of 1-cyclopropyl-3-methyl-1H-pyrazole-4-sulfonyl chloride (P1) and 1-cyclopropyl-5-methyl-1H-pyrazole-4-sulfonyl chloride (P2) (1:1 from NMR), which was directly used in next step without further separation. ¹H-NMR (CDCl₃, 400 MHz) δ 8.00 (1H, s), 7.77-7.85 (1H, m), 3.58-3.62 (1H, m), 3.36-3.47 (1H, m), 2.48 (3H, s), 2.03 (3H, s), 1.14-1.18 (4H, m), 1.07-1.13 (4H, m).

EXAMPLES

The invention now being generally described will be more readily understood by reference to the following examples, which are included for purposes of illustration of certain aspects and embodiments of the present invention, and are not intended to limit the invention. Starting materials useful for preparing the compounds of Formula (I) can be obtained from commercial sources or are readily prepared from commercially available materials using transformations which are known to those of skill in the art of organic chemistry.

Example 1—Synthesis of (S)-tert-butyl (2-(aminomethyl)-4-((4-fluorophenyl)sulfonyl)-3,4-dihydro-2H-benzo[b][1,4]oxazin-6-yl)carbamate (1)

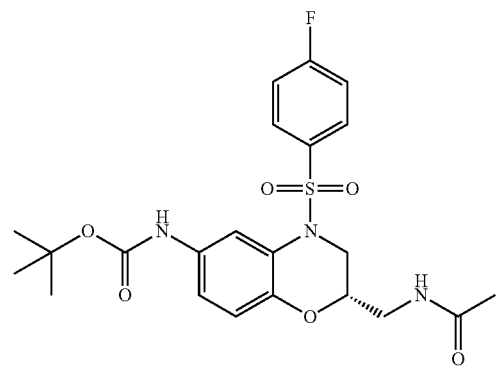 [SMILES: CC(=O)NC[C@H]1CN(S(=O)(=O)c2ccc(F)cc2)c2cc(NC(=O)OC(C)(C)C)ccc2O1]

The title compound was prepared according to the procedures described below.

Step 1—Synthesis of 2-[[(2S)-3-chloro-2-hydroxypropyl]amino]-4-nitrophenol

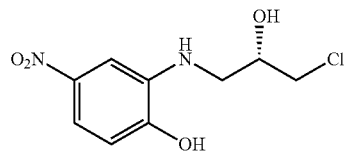 [SMILES: O=[N+]([O-])c1ccc(O)c(NC[C@H](O)CCl)c1]

A solution of 2-amino-4-nitrophenol (250.0 g, 1.62 mol, 1.00 equiv) and (2S)-2-(chloromethyl)oxirane (330.0 g, 3.57 mol, 2.20 equiv) in ethanol/water (2500/25 mL) was stirred for twelve hours at 60° C. in an oil bath. The resulting mixture was cooled and concentrated to afford 2-[[(2S)-3-chloro-2-hydroxypropyl]amino]-4-nitrophenol as a brown oil.

Step 2—Synthesis of [(2R)-6-nitro-3,4-dihydro-2H-1,4-benzoxazin-2-yl]methanol

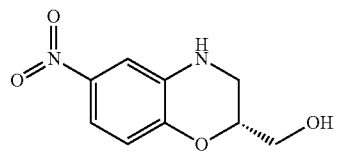 [SMILES: O=[N+]([O-])c1ccc2c(c1)NC[C@H](CO)O2]

A solution of 2-[[(2S)-3-chloro-2-hydroxypropyl]amino]-4-nitrophenol (400 g, 1.62 mol) in ethanol (2.5 L) and potassium carbonate (134.5 g, 973 mmol) was stirred for twelve hours at 90° C. in an oil bath. The mixture was filtered and the filtrate was concentrated. The residue was diluted with water (1.5 L) and extracted three times with ethyl acetate (1 L). The combined organic layers were washed with brine, dried (Na₂SO₄), and concentrated. The residue was purified via MPLC over silica gel eluting with ethyl acetate/petroleum ether (1:1) to afford [(2R)-6-nitro-3,4-dihydro-2H-1,4-benzoxazin-2-yl]methanol as a red solid.

Step 3—Synthesis of ((R)-2-hydroxymethyl-3,4-dihydro-2H-benzo[1,4]oxazin-6-yl)-carbamic acid tert-butyl ester

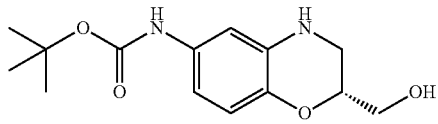 [SMILES: CC(C)(C)OC(=O)Nc1ccc2c(c1)NC[C@H](CO)O2]

The atmosphere above a solution of [(2R)-6-nitro-3,4-dihydro-2H-1,4-benzoxazin-2-yl]methanol (137 g, 652 mmol), palladium on carbon (13.7 g) and di-tert-butyl dicarbonate (157 g, 717 mmol) in methanol (1400 mL) was exchanged with hydrogen. The resulting solution was stirred for twelve hours at room temperature. The mixture was filtered, and the filtrate was concentrated. The crude product was purified by re-crystallization from ether to afford ((R)-2-hydroxymethyl-3,4-dihydro-2H-benzo[1,4]oxazin-6-yl)-carbamic acid tert-butyl ester as an off-white solid. LRMS (ESI) calculated for $C_{14}H_{20}N_2O_4$ 280: Found: 225 $(M-C_4H_8+H)^+$; 281 $(M+H)^+$. $^1H$ NMR (300 MHz, $CDCl_3$): δ 6.92 (s, 1H), 6.71 (d, J=8.7 Hz, 1H), 6.41 (dd, J=8.7, 2.4 Hz, 1H), 6.26 (s, 1H), 4.20-4.21 (m, 1H), 3.76-3.86 (m, 2H), 3.26-3.35 (m, 2H), 1.53 (s, 9H).

Step 4—Synthesis of (R)-tert-butyl (2-((1,3-dioxoisoindolin-2-yl)methyl)-3,4-dihydro-2H-benzo[b][1,4]oxazin-6-yl)carbamate

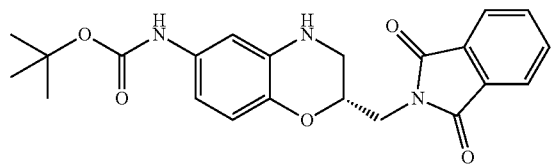 [SMILES: CC(C)(C)OC(=O)Nc1ccc2c(c1)NC[C@H](CN1C(=O)c3ccccc3C1=O)O2]

At 0° C., diisopropyl azodicarboxylate (1.38 mL, 7.12 mmol) was added slowly to a solution of (R)-tert-butyl (2-(hydroxymethyl)-3,4-dihydro-2H-benzo[b][1,4]oxazin-6-yl)carbamate (1.9 g, 6.78 mmol), triphenylphosphine (1.78 g, 6.78 mmol), and phthalimide (1.00 g, 6.78 mmol) in THF (20 mL). The reaction was stirred at room temperature overnight. The mixture was partitioned between ethyl acetate and water. The organic layer was dried ($MgSO_4$) and concentrated. The residue was purified by column chromatography on silica, eluting with 50% ethyl acetate in hexane to afford (R)-tert-butyl (2-((1,3-dioxoisoindolin-2-yl)methyl)-3,4-dihydro-2H-benzo[b][1,4]oxazin-6-yl)carbamate as a yellow solid.

Step 5—Synthesis of (S)-tert-butyl (2-(aminomethyl)-3,4-dihydro-2H-benzo[b][1,4]oxazin-6-yl)carbamate

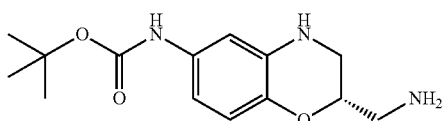

Hydrazine hydrate (2.00 g, 40.0 mmol) was added to a stirred mixture of (R)-tert-butyl (2-((1,3-dioxoisoindolin-2-yl)methyl)-3,4-dihydro-2H-benzo[b][1,4]oxazin-6-yl)carbamate (2.25 g, 5.50 mmol) in ethanol (20 mL). After sixteen hours, the reaction was concentrated and the residue was triturated with dichloromethane. The mixture was filtered and the filtrate was concentrated. The residue was crystallized to obtain (S)-tert-butyl (2-(aminomethyl)-3,4-dihydro-2H-benzo[b][1,4]oxazin-6-yl)carbamate.

Step 6—Synthesis of (R)-tert-butyl (2-(acetamidomethyl)-3,4-dihydro-2H-benzo[b][1,4]oxazin-6-yl)carbamate

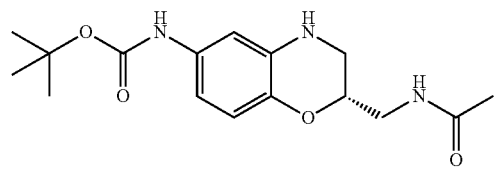 [SMILES: CC(=O)NC[C@H]1CNc2cc(NC(=O)OC(C)(C)C)ccc2O1]

To a stirred solution of (S)-tert-butyl (2-(aminomethyl)-3,4-dihydro-2H-benzo[b][1,4]oxazin-6-yl)carbamate (7.9 g, 28.3 mmol), (benzotriazol-1-yloxy)tris(dimethylamino)phosphonium hexafluorophosphate (13.8 g, 31.1 mmol), and acetic acid (1.6 mL, 28.3 mmol) in THF (141 mL) was added N,N'-diisopropylethylamine (19.8 mL, 113 mmol). After two hours, the mixture was partitioned between isopropanol/chloroform (1:3, v/v) and saturated sodium bicarbonate. The combined organic layers were dried ($MgSO_4$) and concentrated to afford (R)-tert-butyl (2-(acetamidomethyl)-3,4-dihydro-2H-benzo[b][1,4]oxazin-6-yl)carbamate.

Step 7—Synthesis of (S)-tert-butyl (2-(aminomethyl)-4-((4-fluorophenyl)sulfonyl)-3,4-dihydro-2H-benzo[b][1,4]oxazin-6-yl)carbamate

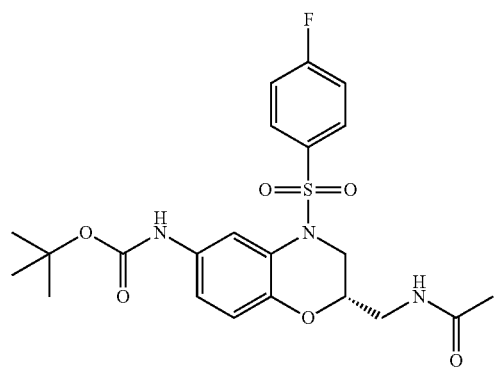 [SMILES: CC(=O)NC[C@H]1CN(S(=O)(=O)c2ccc(F)cc2)c2cc(NC(=O)OC(C)(C)C)ccc2O1]

A solution of (R)-tert-butyl (2-(acetamidomethyl)-3,4-dihydro-2H-benzo[b][1,4]oxazin-6-yl)carbamate (9.09 g, 28.3 mmol), pyridine (141 mL), and 4-fluorobenzene-1-sulfonyl chloride (7.16 g, 36.8 mmol) was sealed and heated at 60° C. for two hours. The crude mixture was partitioned between isopropanol/chloroform (1:3, v/v) and saturated sodium bicarbonate. The combined organic layers were dried ($MgSO_4$) and concentrated. The residue was purified via chromatography over silica gel eluting with a gradient (0-100% ethyl acetate:hexanes) to afford (S)-tert-butyl (2-

(aminomethyl)-4-(4-fluorophenyl)sulfonyl)-3,4-dihydro-2H-benzo[b][1,4]oxazin-6-yl)carbamate as a white foam. LRMS (ESI) calculated for $C_{22}H_{27}FN_3O_6S$ (M+H)⁺: 480. Found: 480. ¹H NMR (600 MHz, DMSO-d6) δ 9.26 (s, 1H), 8.03 (t, 1H, J=6.0 Hz), 7.87 (s, 1H), 7.71 (dd, 2H, J=5.0, 3.5 Hz), 7.38 (t, 2H, J=8.6 Hz), 7.13 (d, 1H, J=7.8 Hz), 6.70 (d, 1H, J=9.0 Hz), 4.22 (d, 1H, J=14 Hz), 3.29 (m, 1H), 3.22 (m, 1H), 3.15 (m, 1H), 3.04 (m, 1H), 1.81 (s, 3H), 1.43 (s, 9H).

Example 2—Synthesis of (S)-tert-butyl (2-(acetamidomethyl)-4-((1-ethyl-3-methyl-1H-pyrazol-4-yl)sulfonyl)-3,4-dihydro-2H-benzo[b][1,4]oxazin-6-yl)carbamate (2)

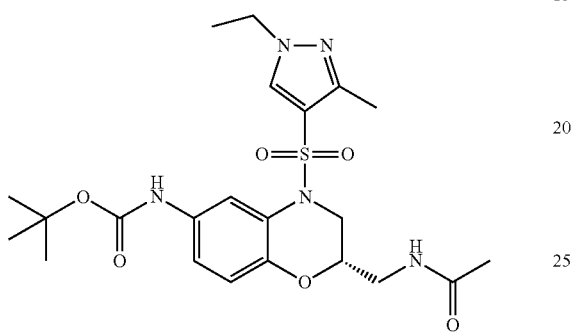

To a solution of (R)-tert-butyl (2-(acetamidomethyl)-3,4-dihydro-2H-benzo[b][1,4]oxazin-6-yl)carbamate (228 mg, 0.71 mmol) in pyridine (1.96 g, 24.7 mmol) at 0° C. was added 1-ethyl-3-methylpyrazole-4-sulfonyl chloride (296 mg, 1.42 mmol). The reaction was heated at 50° C. and stirred overnight. The crude reaction was partitioned between ethyl acetate and 1 N HCl, washed with saturated sodium bicarbonate, brine, dried (MgSO₄), and concentrated. The residue was purified via MPLC on silica gel eluting with ethyl acetate to afford (S)-tert-butyl (2-(acetamidomethyl)-4-((1-ethyl-3-methyl-1H-pyrazol-4-yl)sulfonyl)-3,4-dihydro-2H-benzo[b][1,4]oxazin-6-yl)carbamate as a white solid. ¹H NMR (250 MHz, CDCl₃) δ 7.95 (s, 1H), 7.73 (s, 1H), 7.06 (d, 1H), 6.86 (d, 1H), 6.38 (s, 1H), 5.82 (bt, 1H), 4.16 (m, 1H), 4.06 (q, 2H), 3.84 (m, 1H), 3.53 (m, 1H), 3.42 (m, 1H), 3.24 (dd, 1H), 2.17 (s, 3H), 1.99 (s, 3H), 1.53 (s, 9H), 1.23 (t, 3H).

Example 3—Synthesis of (S)-tert-butyl (2-(acetamidomethyl)-4-((1,5-dimethyl-1H-pyrazol-4-yl)sulfonyl)-3,4-dihydro-2H-benzo[b][1,4]oxazin-6-yl)carbamate (3)

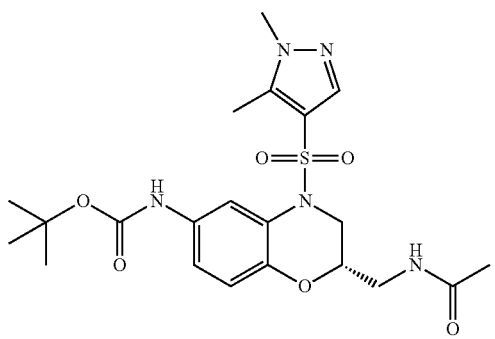 [SMILES: CC(=O)NC[C@H]1CN(S(=O)(=O)c2cnn(C)c2C)c2cc(NC(=O)OC(C)(C)C)ccc2O1]

Using the procedure of Example 2, (R)-tert-butyl (2-(acetamidomethyl)-3,4-dihydro-2H-benzo[b][1,4]oxazin-6-yl)carbamate (114 mg, 0.71 mmol) and 1,5-dimethyl-1H-pyrazole-4-sulfonyl chloride afforded (S)-tert-butyl (2-(acetamidomethyl)-4-(1,5-dimethyl-1H-pyrazol-4-yl)sulfonyl)-3,4-dihydro-2H-benzo[b][1,4]oxazin-6-yl)carbamate as a white solid. ¹H NMR (250 MHz, CDCl₃) δ 7.58 (d, 1H), 7.30 (bs, 1H), 6.77 (d, 1H), 6.41 (s, 1H), 5.81 (t, 1H), 4.19 (dd, 1H), 3.78 (s, 3H), 3.72 (m, 1H), 3.48 (ddd, 1H), 3.37 (ddd, 1H), 3.14 (dd, 1H), 2.27 (s, 3H), 1.98 (s, 3H), 1.47 (s, 9H).

Example 4—Synthesis of (S)-tert-butyl (2-(acetamidomethyl)-4-(imidazo[1,2-a]pyridin-6-ylsulfonyl)-3,4-dihydro-2H-benzo[b][1,4]oxazin-6-yl)carbamate (4)

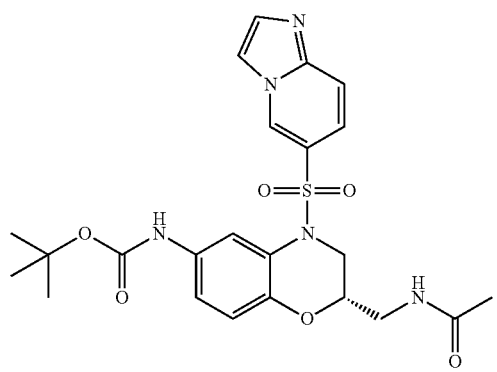 [SMILES: CC(=O)NC[C@H]1CN(S(=O)(=O)c2ccc3nccn3c2)c2cc(NC(=O)OC(C)(C)C)ccc2O1]

The title compound was prepared according to the procedures described below.

Step 1—Synthesis of 6-bromoimidazo[1,2-a]pyridine

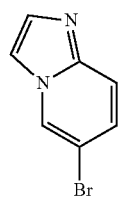

To a solution of 5-bromopyridin-2-amine (2 g, 11.6 mmol) in ethanol (20 mL) was added 2-chloroacetaldehyde (2.00 g, 25.5 mmol) at room temperature and heated to reflux overnight. The reaction was cooled and concentrated and the resulting solid diluted with saturated sodium bicarbonate and extracted twice with ethyl acetate. The combined organic layers were dried over anhydrous sodium sulfate and concentrated to afford 6-bromoimidazo[1,2-a]pyridine as a brown solid.

Step 2—Synthesis of 6-(benzylsulfanyl)imidazo[1,2-a]pyridine

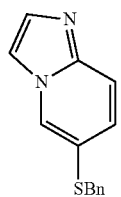

At room temperature, to a solution of 6-bromoimidazo [1,2-a] pyridine (4.35 g, 22.1 mmol) in toluene (50 mL) under nitrogen was added phenylmethanethiol (2.76 g, 22.2 mmol), N, N-diisopropylethylamine (5.73 g, 44.3 mmol), tris(dibenzylideneacetone)-dipalladium(0) (1.02 g, 0.89 mmol), and (9,9-dimethyl-9H-xanthene-4,5-diyl)bis(diphenyl-phosphine) (1.28 g, 2.21 mmol). The resulting solution was stirred for three hours at 110° C. The reaction was cooled and quenched by the addition of water. The resulting solution was extracted with ethyl acetate and the organic layers were combined and dried ($Na_2SO_4$) and concentrated. The residue was purified via MPLC on silica eluting with a gradient of dichloromethane/methanol (100:1-10:1) to afford 6-(benzylsulfanyl)imidazo[1,2-a]pyridine as a brown oil.

Step 3—Synthesis of imidazo[1,2-a]pyridine-6-sulfonyl chloride

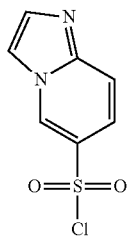

To a solution of 6-(benzylsulfanyl)imidazo[1,2-a]pyridine (4.44 g, 18.5 mmol) in acetic acid/water (3:1) (45 mL) was added N-chlorosuccinimide (7.4 g, 55.4 mmol) at room temperature. The resulting solution was stirred for three hours at room temperature. The resulting mixture was concentrated under vacuum. The resulting solution was diluted with of saturated sodium bicarbonate. The resulting mixture was extracted with ethyl acetate and the organic layers combined and dried over anhydrous sodium sulfate. The residue was purified via MPLC on silica eluting with a gradient of ethyl acetate/petroleum ether (1:10-1:1) to afford imidazo[1,2-a]pyridine-6-sulfonyl chloride as a light yellow solid.

Step 4—Synthesis of tert-butyl N-[(2S)-2-(acetamidomethyl)-4-[imidazo[1,2-a]pyridine-6-sulfonyl]-3,4-dihydro-2H-1,4-benzoxazin-6-yl]carbamate

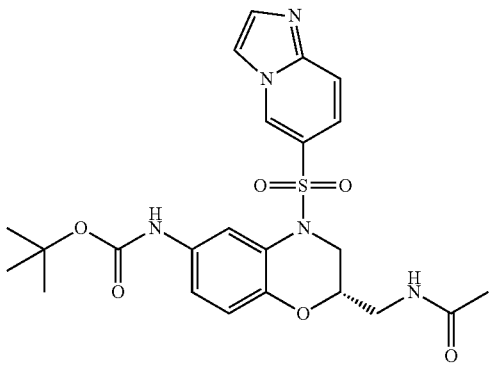 [SMILES: CC(=O)NC[C@H]1CN(S(=O)(=O)c2ccc3nccn3c2)c2cc(NC(=O)OC(C)(C)C)ccc2O1]

To a solution of tert-butyl N-[(2R)-2-(acetamidomethyl)-3,4-dihydro-2H-1,4-benzoxazin-6-yl]carbamate (90 mg, 0.28 mmol) in pyridine (2 mL) was added imidazo[1,2-a]pyridine-6-sulfonyl chloride (180 mg, 3.32 mmol) at room temperature. The resulting solution was stirred for two days at room temperature. The crude product (90 mg) was purified by Prep-HPLC to afford tert-butyl N-[(2S)-2-(acetamidomethyl)-4-[imidazo[1,2-a]pyridine-6-sulfonyl]-3,4-dihydro-2H-1,4-benzoxazin-6-yl]carbamate as a light yellow solid. $^1$H NMR (400 Hz, $CD_3OD$) δ 9.27 (s, 1H), 7.96-7.99 (m, 2H), 7.78 (s, 1H), 7.72 (m, 1H), 7.44-7.47 (m, 1H), 6.96-6.99 (m, 1H), 6.77-6.79 (d, J=8.8 Hz, 1H), 4.44-4.48 (dd, J=14.0 Hz, 1H), 3.85-3.86 (m, 1H), 3.42-3.43 (d, J=5.6 Hz, 2H), 3.28-3.33 (m, 1H), 1.97 (s, 3H), 1.55 (s, 9H); LRMS (ESI) calculated for $C_{23}H_{28}N_5O_6S$ (M+H)$^+$: 502. Found: 502.

Example 5—Preparation of additional (S)-tert-butyl (2-(aminomethyl)-4-((optionally substituted aryl or heteroaryl-sulfonyl)-3,4-dihydro-2H-benzo[b][1,4]oxazin-6-yl)carbamates The compounds in Table 1 below were prepared based on the experimental procedures described in Examples 1-4 and elsewhere in the detailed description, and can be achieved by one of skill in the art in light of the present disclosure.

TABLE 1

| Ex. No. | Structure | Name | Observed m/z |
| --- | --- | --- | --- |
| 5A | 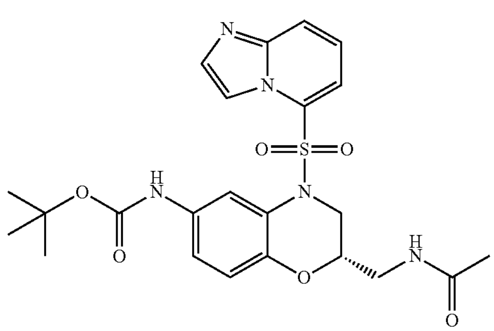 [SMILES: CC(=O)NC[C@H]1CN(S(=O)(=O)c2cccc3nccn23)c2cc(NC(=O)OC(C)(C)C)ccc2O1] | (S)-tert-butyl (2-(acetamidomethyl)-4-(imidazo[1,2-a]pyridin-5-ylsulfonyl)-3,4-dihydro-2H-benzo[b][1,4]oxazin-6-yl)carbamate | 502.4 (M + H)$^+$ |

TABLE 1-continued

| Ex. No. | Structure | Name | Observed m/z |
|---|---|---|---|
| 5B | 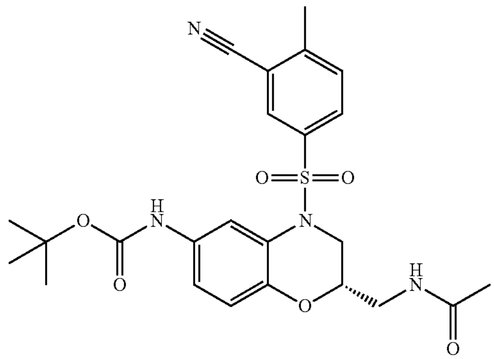 [SMILES: CC(=O)NC[C@H]1CN(S(=O)(=O)c2ccc(C)c(C#N)c2)c2cc(NC(=O)OC(C)(C)C)ccc2O1] | (S)-tert-butyl (2-(acetamidomethyl)-4-((3-cyano-4-methylphenyl)sulfonyl)-3,4-dihydro-2H-benzo[b][1,4]oxazin-6-yl)carbamate | 445.1 (M − tBu + H)+ |
| 5C | 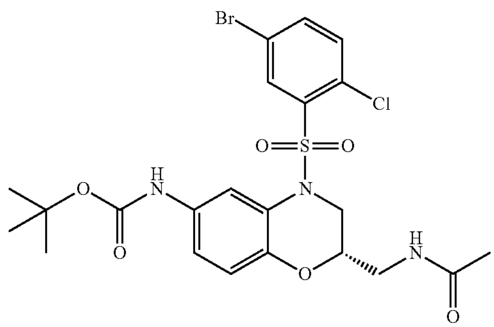 [SMILES: CC(=O)NC[C@H]1CN(S(=O)(=O)c2cc(Br)ccc2Cl)c2cc(NC(=O)OC(C)(C)C)ccc2O1] | (S)-tert-butyl (2-(acetamidomethyl)-4-((5-bromo-2-chlorophenyl)sulfonyl)-3,4-dihydro-2H-benzo[b][1,4]oxazin-6-yl)carbamate | 518.0 M − tBu + H)+ |
| 5D | 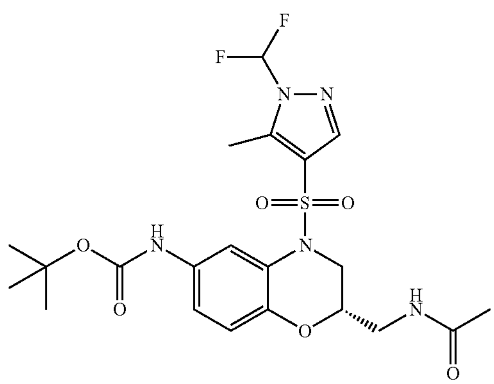 [SMILES: CC(=O)NC[C@H]1CN(S(=O)(=O)c2cnn(C(F)F)c2C)c2cc(NC(=O)OC(C)(C)C)ccc2O1] | (S)-tert-butyl (2-(acetamidomethyl)-4-((1-(difluoromethyl)-5-methyl-1H-pyrazol-4-yl)sulfonyl)-3,4-dihydro-2H-benzo[b][1,4]oxazin-6-yl)carbamate | 514.1 (M − H)− |
| 5E | 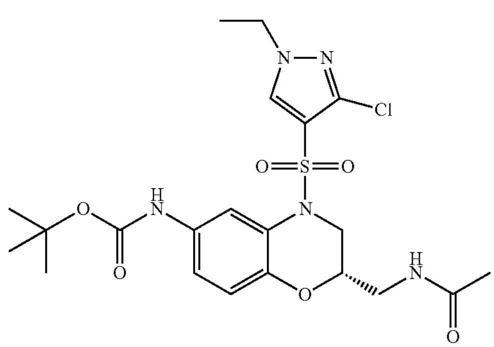 [SMILES: CCn1cc(S(=O)(=O)N2C[C@H](CNC(C)=O)Oc3ccc(NC(=O)OC(C)(C)C)cc32)c(Cl)n1] | (S)-tert-butyl (2-(acetamidomethyl)-4-((3-chloro-1-ethyl-1H-pyrazol-4-yl)sulfonyl)-3,4-dihydro-2H-benzo[b][1,4]oxazin-6-yl)carbamate | 536.01 (M + Na)+ |

TABLE 1-continued

| Ex. No. | Structure | Name | Observed m/z |
|---|---|---|---|
| 5F | 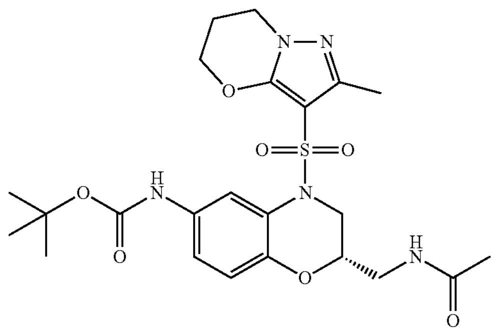 | (S)-tert-butyl (2-(acetamidomethyl)-4-((2-methyl-6,7-dihydro-5H-pyrazolo[5,1-b][1,3]oxazin-3-yl)sulfonyl)-3,4-dihydro-2H-benzo[b][1,4]oxazin-6-yl)carbamate | 522.1 (M + H)+ |
| 5G | 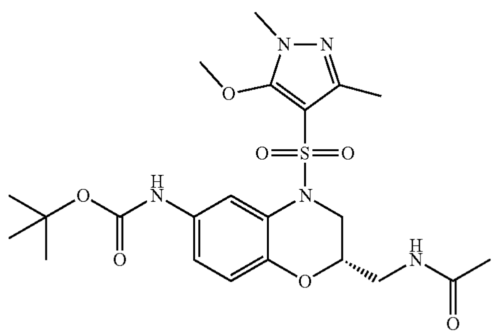 [SMILES: COc1c(S(=O)(=O)N2C[C@H](CNC(C)=O)Oc3ccc(NC(=O)OC(C)(C)C)cc32)c(C)nn1C] | (S)-tert-butyl (2-(acetamidomethyl)-4-((5-methoxy-1,3-dimethyl-1H-pyrazol-4-yl)sulfonyl)-3,4-dihydro-2H-benzo[b][1,4]oxazin-6-yl)carbamate | 510.2 (M + H)+ |
| 5H | 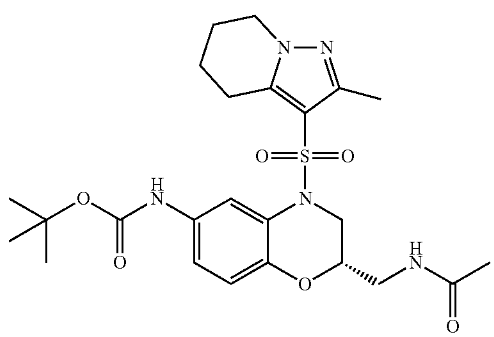 [SMILES: CC(=O)NC[C@H]1CN(S(=O)(=O)c2c(C)nn3c2CCCC3)c2cc(NC(=O)OC(C)(C)C)ccc2O1] | (S)-tert-butyl (2-(acetamidomethyl)-4-((2-methyl-4,5,6,7-tetrahydropyrazolo[1,5-a]pyridin-3-yl)sulfonyl)-3,4-dihydro-2H-benzo[b][1,4]oxazin-6-yl)carbamate | 542.3 (M + Na)+ |
| 5i | 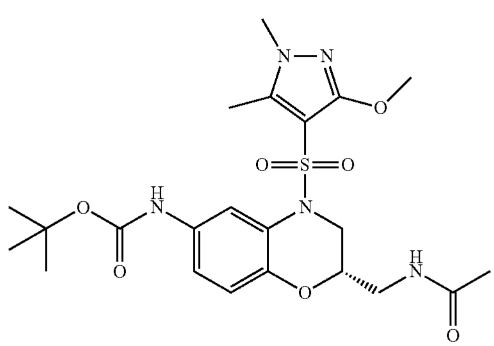 [SMILES: COc1nn(C)c(C)c1S(=O)(=O)N1C[C@H](CNC(C)=O)Oc2ccc(NC(=O)OC(C)(C)C)cc21] | (S)-tert-butyl (2-(acetamidomethyl)-4-((3-methoxy-1,5-dimethyl-1H-pyrazol-4-yl)sulfonyl)-3,4-dihydro-2H-benzo[b][1,4]oxazin-6-yl)carbamate | 532.2 (M + Na)+ |

TABLE 1-continued

| Ex. No. | Structure | Name | Observed m/z |
| --- | --- | --- | --- |
| 5J | 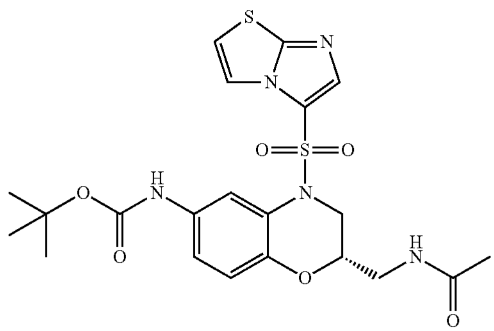 [SMILES: CC(=O)NC[C@H]1CN(S(=O)(=O)c2cnc3sccn23)c2cc(NC(=O)OC(C)(C)C)ccc2O1] | (S)-tert-butyl (2-(acetamidomethyl)-4-(imidazo[2,1-b]thiazol-5-ylsulfonyl)-3,4-dihydro-2H-benzo[b][1,4]oxazin-6-yl)carbamate | 530.1 (M + Na)+ |
| 5K | 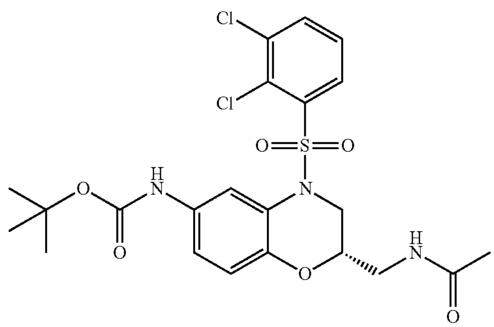 [SMILES: CC(=O)NC[C@H]1CN(S(=O)(=O)c2cccc(Cl)c2Cl)c2cc(NC(=O)OC(C)(C)C)ccc2O1] | (S)-tert-butyl (2-(acetamidomethyl)-4-((2,3-dichlorophenyl)sulfonyl)-3,4-dihydro-2H-benzo[b][1,4]oxazin-6-yl)carbamate | 474.0 (M − tBu + H)+ |
| 5L | 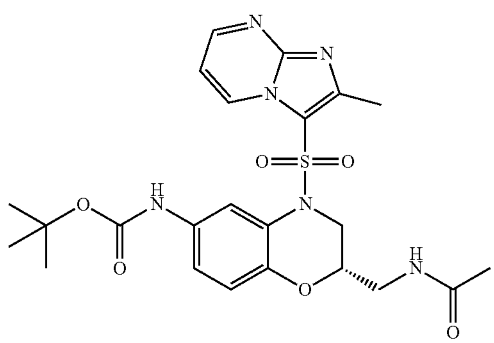 [SMILES: CC(=O)NC[C@H]1CN(S(=O)(=O)c2c(C)nc3ncccn23)c2cc(NC(=O)OC(C)(C)C)ccc2O1] | (S)-tert-butyl (2-(acetamidomethyl)-4-((2-methylimidazo[1,2-c]pyrimidin-3-yl)sulfonyl)-3,4-dihydro-2H-benzo[b][1,4]oxazin-6-yl)carbamate | 517.3 (M + H)+ |
| 5M | 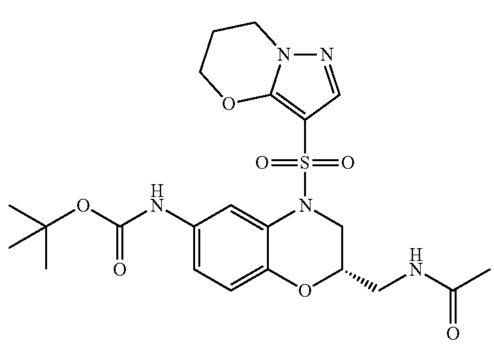 [SMILES: CC(=O)NC[C@H]1CN(S(=O)(=O)c2cnn3c2OCCC3)c2cc(NC(=O)OC(C)(C)C)ccc2O1] | (S)-tert-butyl (2-(acetamidomethyl)-4-((6,7-dihydro-5H-pyrazolo[5,1-b][1,3]oxazin-3-yl)sulfonyl)-3,4-dihydro-2H-benzo[b][1,4]oxazin-6-yl)carbamate | 530.3 (M + Na)+ |

TABLE 1-continued

| Ex. No. | Structure | Name | Observed m/z |
|---|---|---|---|
| 5N | 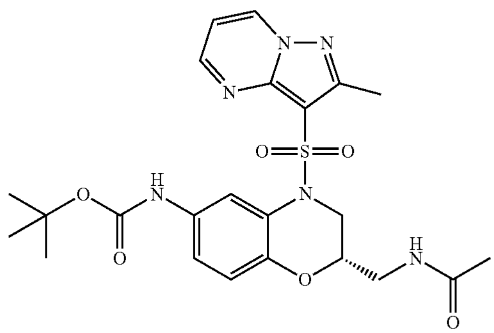 [SMILES: CC(=O)NC[C@H]1CN(S(=O)(=O)c2c(C)nn3cccnc23)c2cc(NC(=O)OC(C)(C)C)ccc2O1] | (S)-tert-butyl (2-(acetamidomethyl)-4-((2-methylpyrazolo[1,5-a]pyrimidin-3-yl)sulfonyl)-3,4-dihydro-2H-benzo[b][1,4]oxazin-6-yl)carbamate | 539.2 (M + Na)+ |
| 5o | 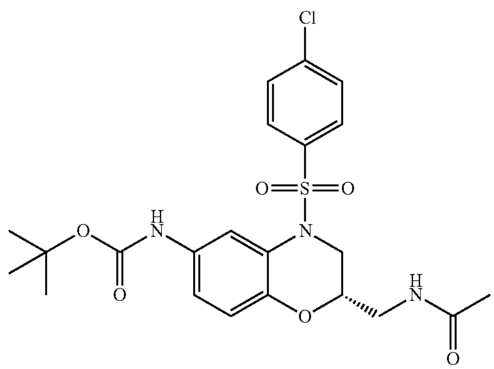 | (S)-tert-butyl (2-(acetamidomethyl)-4-((4-chlorophenyl)sulfonyl)-3,4-dihydro-2H-benzo[b][1,4]oxazin-6-yl)carbamate | 440.0 (M − tBu + H)+ |
| 5P | 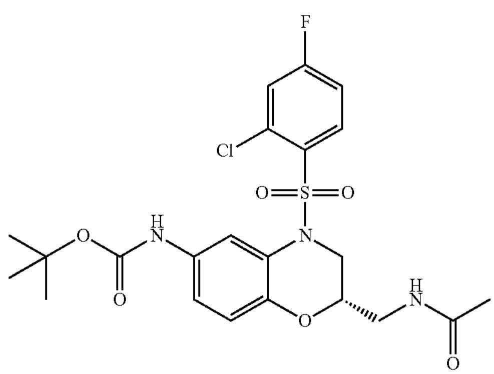 [SMILES: CC(=O)NC[C@H]1CN(S(=O)(=O)c2ccc(F)cc2Cl)c2cc(NC(=O)OC(C)(C)C)ccc2O1] | (S)-tert-butyl (2-(acetamidomethyl)-4-((2-chloro-4-fluorophenyl)sulfonyl)-3,4-dihydro-2H-benzo[b][1,4]oxazin-6-yl)carbamate | 458.0 (M − tBu + H)+ |
| 5Q | 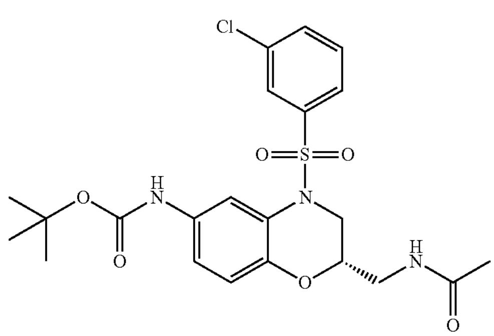 [SMILES: CC(=O)NC[C@H]1CN(S(=O)(=O)c2cccc(Cl)c2)c2cc(NC(=O)OC(C)(C)C)ccc2O1] | (S)-tert-butyl (2-(acetamidomethyl)-4-((3-chlorophenyl)sulfonyl)-3,4-dihydro-2H-benzo[b][1,4]oxazin-6-yl)carbamate | 440.0 (M − tBu + H)+ |

TABLE 1-continued

| Ex. No. | Structure | Name | Observed m/z |
|---|---|---|---|
| 5R | 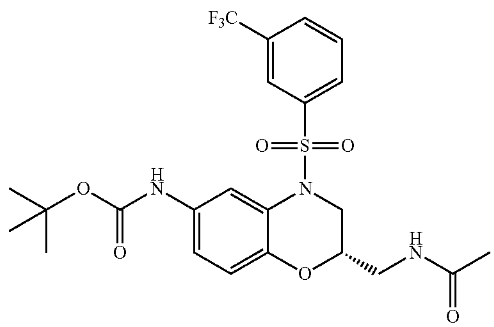 [SMILES: CC(=O)NC[C@H]1CN(S(=O)(=O)c2cccc(C(F)(F)F)c2)c2cc(NC(=O)OC(C)(C)C)ccc2O1] | (S)-tert-butyl (2-(acetamidomethyl)-4-((3-(trifluoromethyl)phenyl)sulfonyl)-3,4-dihydro-2H-(benzo[b][1,4]oxazin-6-yl)carbamate | 552 (M + Na)$^+$ |
| 5S | 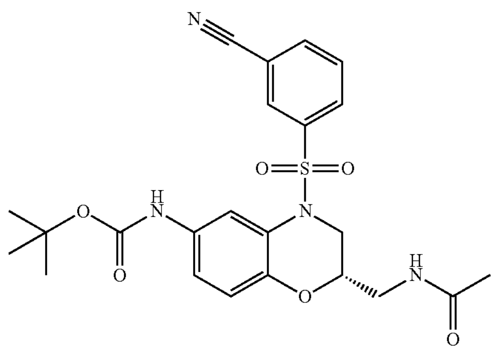 [SMILES: CC(=O)NC[C@H]1CN(S(=O)(=O)c2cccc(C#N)c2)c2cc(NC(=O)OC(C)(C)C)ccc2O1] | (S)-tert-butyl (2-(acetamidomethyl)-4-((3-cyanophenyl)sulfonyl)-3,4-dihydro-2H-benzo[b][1,4]oxazin-6-yl)carbamate | 431.1 (M − tBu + H)$^+$ |
| 5T | 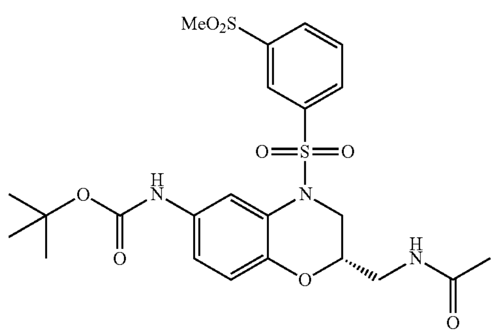 [SMILES: CC(=O)NC[C@H]1CN(S(=O)(=O)c2cccc(S(C)(=O)=O)c2)c2cc(NC(=O)OC(C)(C)C)ccc2O1] | (S)-tert-butyl (2-(acetamidomethyl)-4-((3-(methylsulfonyl)phenyl)sulfonyl)-3,4-dihydro-2H-benzo[b][1,4]oxazin-6-yl)carbamate | 484.0 (M − tBu + H)$^+$ |
| 5U | 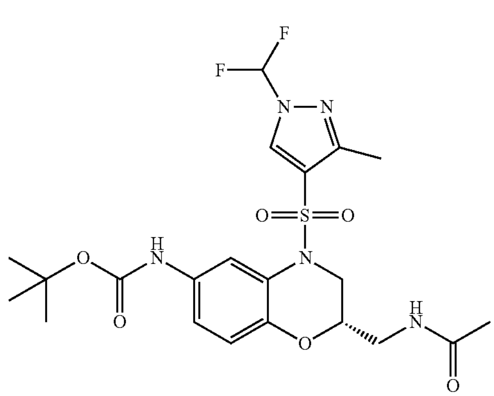 [SMILES: CC(=O)NC[C@H]1CN(S(=O)(=O)c2cn(C(F)F)nc2C)c2cc(NC(=O)OC(C)(C)C)ccc2O1] | (S)-tert-butyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate | 459.0 (M − tBu + H)$^+$ |

| Ex. No. | Structure | Name | Observed m/z |
| --- | --- | --- | --- |
| 5V | 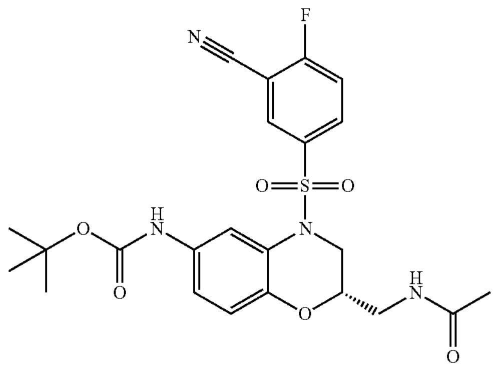 [SMILES: CC(=O)NC[C@H]1CN(S(=O)(=O)c2ccc(F)c(C#N)c2)c2cc(NC(=O)OC(C)(C)C)ccc2O1] | (S)-tert-butyl (2-(acetamidomethyl)-4-((3-cyano-4-fluorophenyl)sulfonyl)-3,4-dihydro-2H-benzo[b][1,4]oxazin-6-yl)carbamate | 449.1 (M − tBu + H)+ |
| 5W | 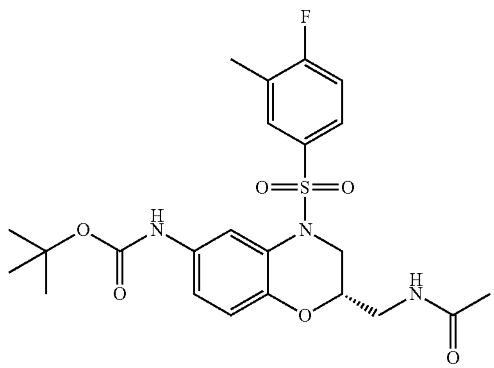 [SMILES: CC(=O)NC[C@H]1CN(S(=O)(=O)c2ccc(F)c(C)c2)c2cc(NC(=O)OC(C)(C)C)ccc2O1] | (S)-tert-butyl (2-(acetamidomethyl)-4-((4-fluoro-3-methylphenyl)sulfonyl)-3,4-dihydro-2H-benzo[b][1,4]oxazin-6-yl)carbamate | 438.1 (M − tBu + H)+ |
| 5X | 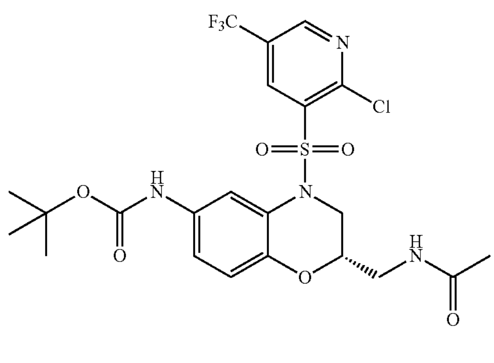 [SMILES: CC(=O)NC[C@H]1CN(S(=O)(=O)c2cc(C(F)(F)F)cnc2Cl)c2cc(NC(=O)OC(C)(C)C)ccc2O1] | (S)-tert-butyl (2-(acetamidomethyl)-4-((2-chloro-5-(trifluoromethyl)pyridin-3-yl)sulfonyl)-3,4-dihydro-2H-benzo[b][1,4]oxazin-6-yl)carbamate | 510 (M − tBu + H)+ |
| 5Y | 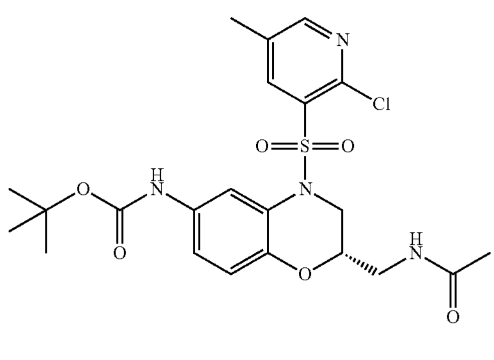 [SMILES: CC(=O)NC[C@H]1CN(S(=O)(=O)c2cc(C)cnc2Cl)c2cc(NC(=O)OC(C)(C)C)ccc2O1] | (S)-tert-butyl (2-(acetamidomethyl)-4-((2-chloro-5-methylpyridin-3-yl)sulfonyl)-3,4-dihydro-2H-benzo[b][1,4]oxazin-6-yl)carbamate | 533 (M + Na)+ |

TABLE 1-continued

| Ex. No. | Structure | Name | Observed m/z |
|---|---|---|---|
| 5Z | 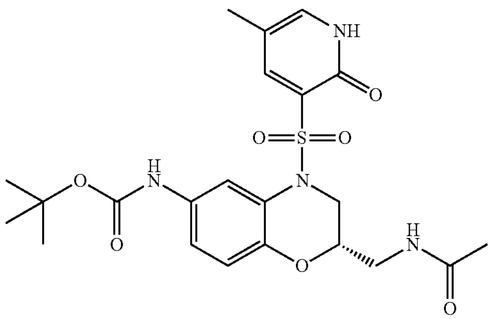 [SMILES: CC(=O)NC[C@H]1CN(S(=O)(=O)c2cc(C)c[nH]c2=O)c2cc(NC(=O)OC(C)(C)C)ccc2O1] | (S)-tert-butyl (2-(acetamidomethyl)-4-((5-methyl-2-oxo-1,2-dihydropyridin-3-yl)sulfonyl)-3,4-dihydro-2H-benzo[b][1,4]oxazin-6-yl)carbamate | 493 (M + H)+ |
| 5AA | 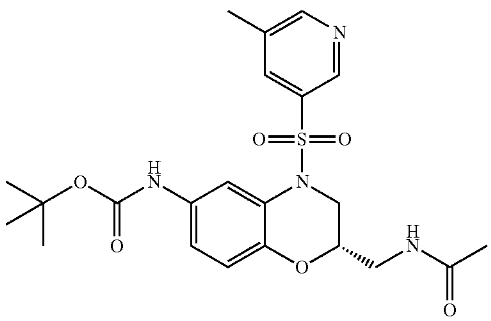 [SMILES: CC(=O)NC[C@H]1CN(S(=O)(=O)c2cncc(C)c2)c2cc(NC(=O)OC(C)(C)C)ccc2O1] | (S)-tert-butyl (2-(acetamidomethyl)-4-((5-methylpyridin-3-yl)sulfonyl)-3,4-dihydro-2H-benzo[b][1,4]oxazin-6-yl)carbamate | 477 (M + H)+ |
| 5AB | 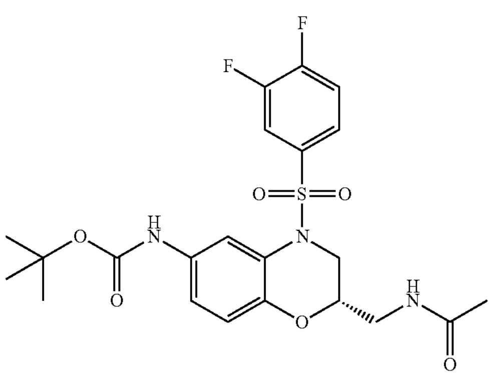 [SMILES: CC(=O)NC[C@H]1CN(S(=O)(=O)c2ccc(F)c(F)c2)c2cc(NC(=O)OC(C)(C)C)ccc2O1] | (S)-tert-butyl (2-(acetamidomethyl)-4-((3,4-difluorophenyl)sulfonyl)-3,4-dihydro-2H-benzo[b][1,4]oxazin-6-yl)carbamate | 442.1 (M − tBu + H)+ |
| 5AC | 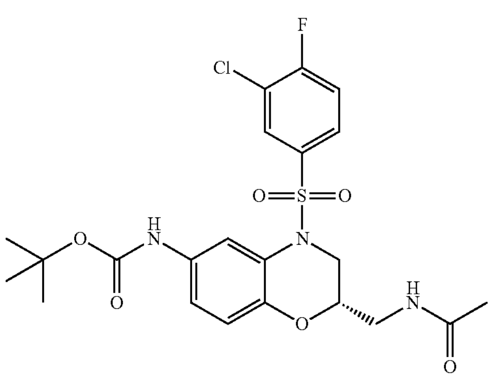 [SMILES: CC(=O)NC[C@H]1CN(S(=O)(=O)c2ccc(F)c(Cl)c2)c2cc(NC(=O)OC(C)(C)C)ccc2O1] | (S)-tert-butyl (2-(acetamidomethyl)-4-((3-chloro-4-fluorophenyl)sulfonyl)-3,4-dihydro-2H-benzo[b][1,4]oxazin-6-yl)carbamate | 458.1 (M − tBu + H)+ |

TABLE 1-continued

| Ex. No. | Structure | Name | Observed m/z |
|---|---|---|---|
| 5AD | 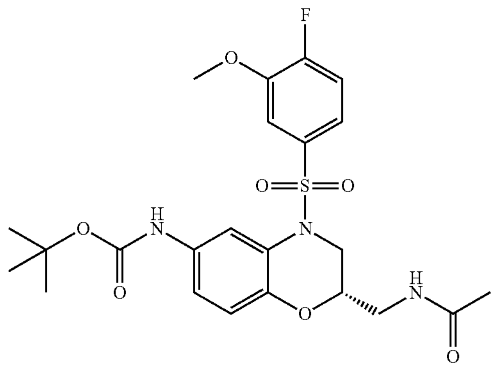 [SMILES: COc1cc(S(=O)(=O)N2C[C@H](CNC(C)=O)Oc3ccc(NC(=O)OC(C)(C)C)cc32)ccc1F] | (S)-tert-butyl (2-(acetamidomethyl)-4-((4-fluoro-3-methoxyphenyl)sulfonyl)-3,4-dihydro-2H-benzo[b][1,4]oxazin-6-yl)carbamate | 454.1 (M − tBu + H)+ |
| 5AE | 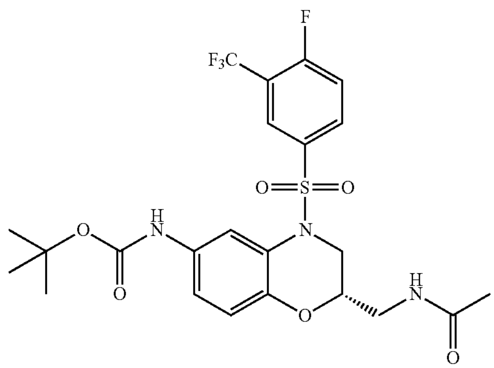 [SMILES: CC(=O)NC[C@H]1CN(S(=O)(=O)c2ccc(F)c(C(F)(F)F)c2)c2cc(NC(=O)OC(C)(C)C)ccc2O1] | (S)-tert-butyl (2-(acetamidomethyl)-4-((4-fluoro-3-(trifluoromethyl)phenyl)sulfonyl)-3,4-dihydro-2H-benzo[b][1,4]oxazin-6-yl)carbamate | 492.0 (M − tBu + H)+ |
| 5AF | 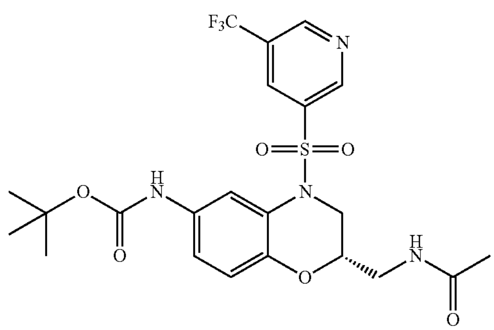 [SMILES: CC(=O)NC[C@H]1CN(S(=O)(=O)c2cncc(C(F)(F)F)c2)c2cc(NC(=O)OC(C)(C)C)ccc2O1] | (S)-tert-butyl (2-(acetamidomethyl)-4-((5-(trifluoromethyl)pyridin-3-yl)sulfonyl)-3,4-dihydro-2H-benzo[b][1,4]oxazin-6-yl)carbamate | 531.3 (M − tBu + H)+ |
| 5AG | 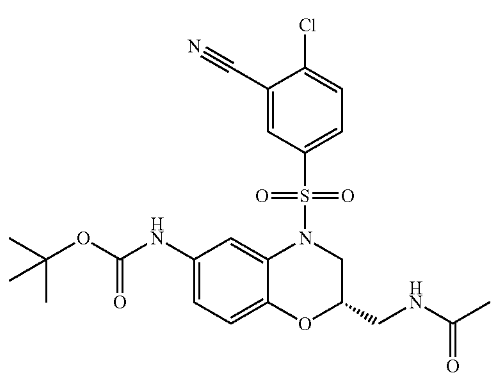 [SMILES: CC(=O)NC[C@H]1CN(S(=O)(=O)c2ccc(Cl)c(C#N)c2)c2cc(NC(=O)OC(C)(C)C)ccc2O1] | (S)-tert-butyl (2-(acetamidomethyl)-4-((4-chloro-3-cyanophenyl)sulfonyl)-3,4-dihydro-2H-benzo[b][1,4]oxazin-6-yl)carbamate | 465.0 (M − tBu + H)+ |

TABLE 1-continued

| Ex. No. | Structure | Name | Observed m/z |
|---|---|---|---|
| 5AH | 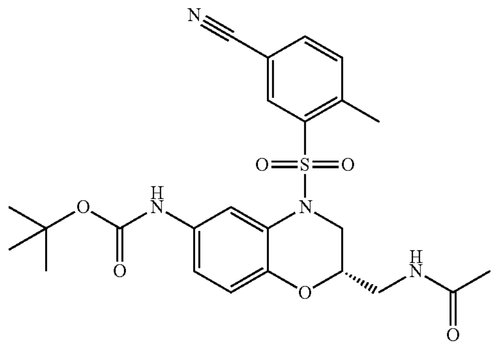 [SMILES: CC(=O)NC[C@H]1CN(S(=O)(=O)c2cc(C#N)ccc2C)c2cc(NC(=O)OC(C)(C)C)ccc2O1] | (S)-tert-butyl (2-(acetamidomethyl)-4-((5-cyano-2-methylphenyl)sulfonyl)-3,4-dihydro-2H-benzo[b][1,4]oxazin-6-yl)carbamate | 445.1 (M − tBu + H)+ |
| 5Ai | 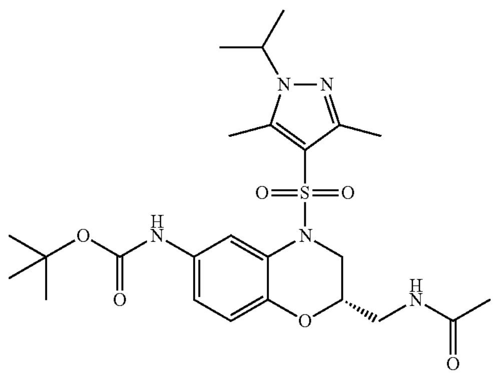 [SMILES: CC(=O)NC[C@H]1CN(S(=O)(=O)c2c(C)nn(C(C)C)c2C)c2cc(NC(=O)OC(C)(C)C)ccc2O1] | (S)-tert-butyl (2-(acetamidomethyl)-4-((1-isopropyl-3,5-dimethyl-1H-pyrazol-4-yl)sulfonyl)-3,4-dihydro-2H-benzo[b][1,4]oxazin-6-yl)carbamate | 466 (M − tBu + H)+ |
| 5AJ | 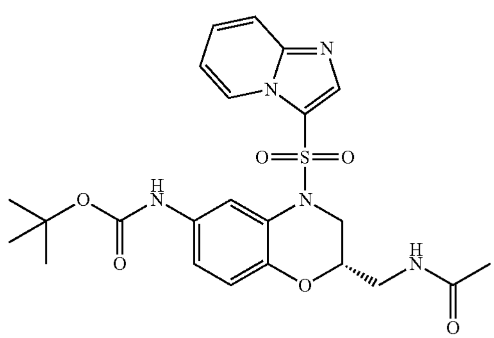 [SMILES: CC(=O)NC[C@H]1CN(S(=O)(=O)c2cnc3ccccn23)c2cc(NC(=O)OC(C)(C)C)ccc2O1] | (S)-tert-butyl (2-(acetamidomethyl)-4-(imidazo[1,2-a]pyridin-3-ylsulfonyl)-3,4-dihydro-2H-benzo[b][1,4]oxazin-6-yl)carbamate | 502 (M + H)+ |
| 5AK | 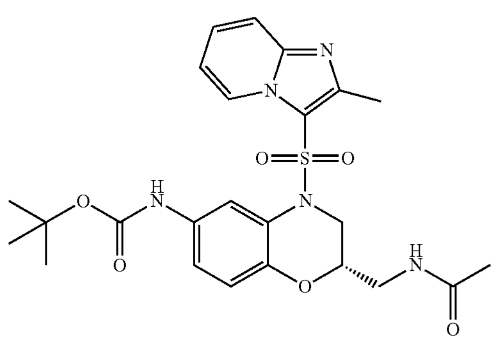 [SMILES: CC(=O)NC[C@H]1CN(S(=O)(=O)c2c(C)nc3ccccn23)c2cc(NC(=O)OC(C)(C)C)ccc2O1] | (S)-tert-butyl (2-(acetamidomethyl)-4-((2-methylimidazo[1,2-a]pyridin-3-yl)sulfonyl)-3,4-dihydro-2H-benzo[b][1,4]oxazin-6-yl)carbamate | 516.1 (M + H)+ |

TABLE 1-continued

| Ex. No. | Structure | Name | Observed m/z |
|---|---|---|---|
| 5AL | 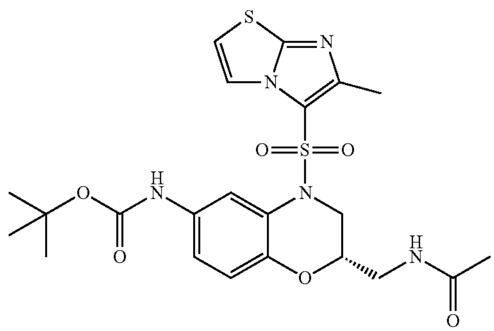 [SMILES: CC(=O)NC[C@H]1CN(S(=O)(=O)c2c(C)nc3sccn23)c2cc(NC(=O)OC(C)(C)C)ccc2O1] | (S)-tert-butyl (2-(acetamidomethyl)-4-((6-methylimidazo[2,1-b]thiazol-5-yl)sulfonyl)-3,4-dihydro-2H-benzo[b][1,4]oxazin-6-yl)carbamate | 522.1 (M + H)+ |
| 5AM | 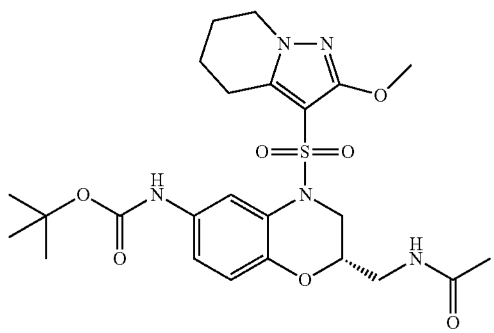 [SMILES: COc1nn2c(c1S(=O)(=O)N1C[C@H](CNC(C)=O)Oc3ccc(NC(=O)OC(C)(C)C)cc31)CCCC2] | (S)-tert-butyl (2-(acetamidomethyl)-4-((2-methoxy-4,5,6,7-tetrahydropyrazolo[1,5-a]pyridin-3-yl)sulfonyl)-3,4-dihydro-2H-benzo[b][1,4]oxazin-6-yl)carbamate | 536.2 (M + H)+ |
| 5AN | 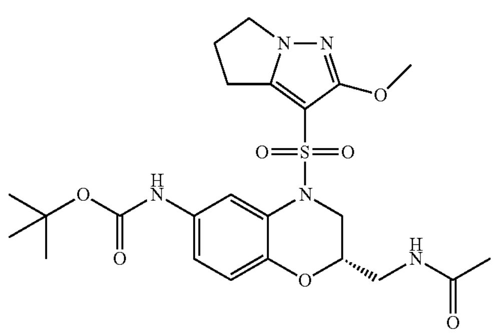 [SMILES: COc1nn2c(c1S(=O)(=O)N1C[C@H](CNC(C)=O)Oc3ccc(NC(=O)OC(C)(C)C)cc31)CCC2] | (S)-tert-butyl (2-(acetamidomethyl)-4-((2-methoxy-5,6-dihydro-4H-pyrrolo[1,2-b]pyrazol-3-yl)sulfonyl)-3,4-dihydro-2H-benzo[b][1,4]oxazin-6-yl)carbamate | 522.3 (M + H)+ |
| 5Ao | 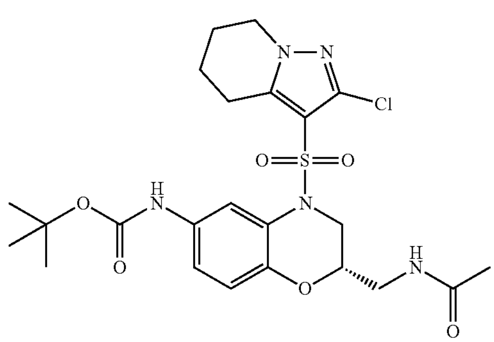 | (S)-tert-butyl (2-(acetamidomethyl)-4-((2-chloro-4,5,6,7-tetrahydropyrazolo[1,5-a]pyridin-3-yl)sulfonyl)-3,4-dihydro-2H-benzo[b][1,4]oxazin-6-yl)carbamate | 540.3 (M + H)+ |

TABLE 1-continued

| Ex. No. | Structure | Name | Observed m/z |
|---|---|---|---|
| 5AP | 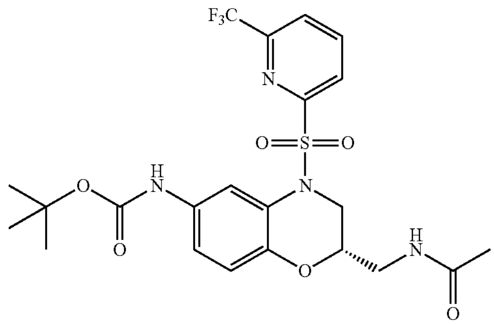 | (S)-tert-butyl (2-(acetamidomethyl)-4-((6-(trifluoromethyl)pyridin-2-yl)sulfonyl)-3,4-dihydro-2H-benzo[b][1,4]oxazin-6-yl)carbamate | 474.8 [M − tBu + H]+ |
| 5AQ | 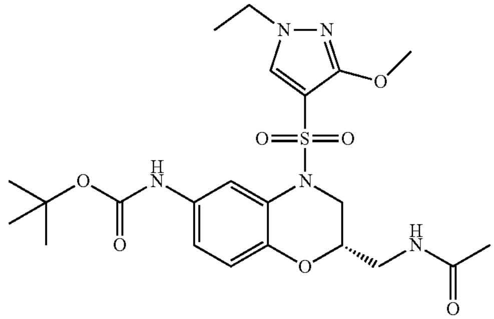 [SMILES: CCn1cc(S(=O)(=O)N2C[C@H](CNC(C)=O)Oc3ccc(NC(=O)OC(C)(C)C)cc32)c(OC)n1] | (S)-tert-butyl (2-(acetamidomethyl)-4-((1-ethyl-3-methoxy-1H-pyrazol-4-yl)sulfonyl)-3,4-dihydro-2H-benzo[b][1,4]oxazin-6-yl)carbamate | 532.1 (M + Na)+ |
| 5AR | 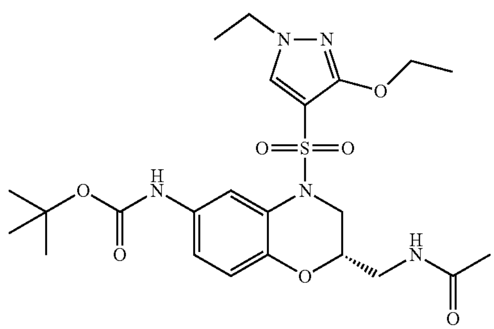 [SMILES: CCOc1nn(CC)cc1S(=O)(=O)N1C[C@H](CNC(C)=O)Oc2ccc(NC(=O)OC(C)(C)C)cc21] | (S)-tert-butyl (2-(acetamidomethyl)-4-((3-ethoxy-1-ethyl-1H-pyrazol-4-yl)sulfonyl)-3,4-dihydro-2H-benzo[b][1,4]oxazin-6-yl)carbamate | 546.1 (M + Na)+ |
| 5AS | 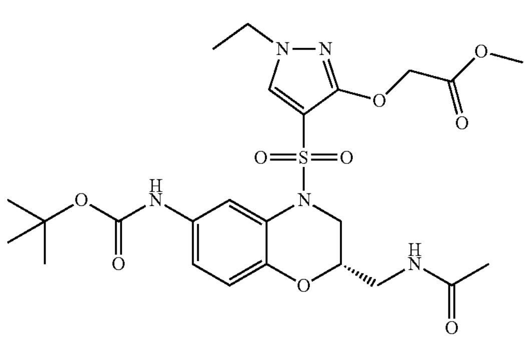 [SMILES: CCn1cc(S(=O)(=O)N2C[C@H](CNC(C)=O)Oc3ccc(NC(=O)OC(C)(C)C)cc32)c(OCC(=O)OC)n1] | (S)-methyl 2-((4-((2-(acetamidomethyl)-6-((tert-butoxycarbonyl)amino)-2H-benzo[b][1,4]oxazin-4(3H)-yl)sulfonyl)-1-ethyl-1H-pyrazol-3-yl)oxy)acetate | 590.1 (M + Na)+ |

TABLE 1-continued

| Ex. No. | Structure | Name | Observed m/z |
|---|---|---|---|
| 5AT | 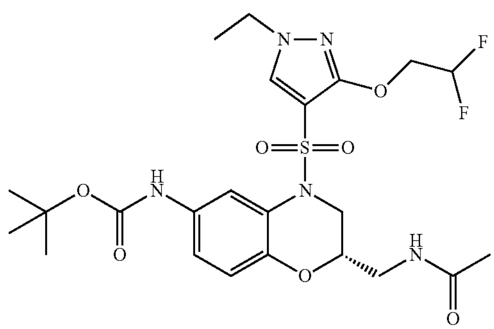 [SMILES: CCn1cc(S(=O)(=O)N2C[C@H](CNC(C)=O)Oc3ccc(NC(=O)OC(C)(C)C)cc32)c(OCC(F)F)n1] | (S)-tert-butyl (2-(acetamidomethyl)-4-((3-(2,2-difluoroethoxy)-1-ethyl-1H-pyrazol-4-yl)sulfonyl)-3,4-dihydro-2H-benzo[b][1,4]oxazin-6-yl)carbamate | 582.1 (M + Na)+ |
| 5AU | 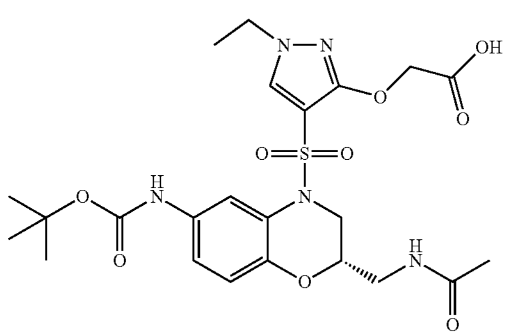 [SMILES: CCn1cc(S(=O)(=O)N2C[C@H](CNC(C)=O)Oc3ccc(NC(=O)OC(C)(C)C)cc32)c(OCC(=O)O)n1] | (S)-2-((4-((2-(acetamidomethyl)-6-((tert-butoxycarbonyl)amino)-2H-benzo[b][1,4]oxazin-4(3H)-yl)sulfonyl)-1-ethyl-1H-pyrazol-3-yl)oxy)acetic acid | 552.3 (M − H)− |
| 5AV | 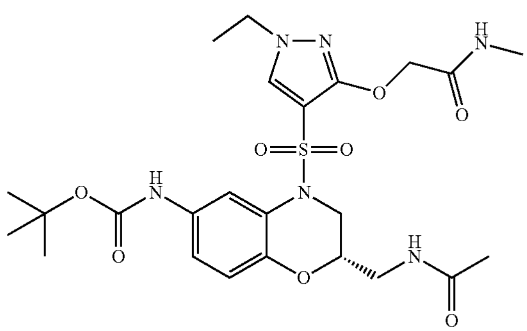 [SMILES: CCn1cc(S(=O)(=O)N2C[C@H](CNC(C)=O)Oc3ccc(NC(=O)OC(C)(C)C)cc32)c(OCC(=O)NC)n1] | (S)-tert-butyl (2-(acetamidomethyl)-4-((1-ethyl-3-(2-(methylamino)-2-oxoethoxy)-1H-pyrazol-4-yl)sulfonyl)-3,4-dihydro-2H-benzo[b][1,4]oxazin-6-yl)carbamate | 589.1 (M + Na)+ |
| 5AW | 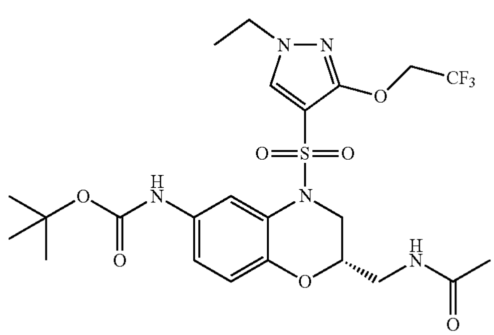 | (S)-tert-butyl (2-(acetamidomethyl)-4-((1-ethyl-3-(2,2,2-trifluoroethoxy)-1H-pyrazol-4-yl)sulfonyl)-3,4-dihydro-2H-benzo[b][1,4]oxazin-6-yl)carbamate | 600.1 (M + Na)+ |

TABLE 1-continued

| Ex. No. | Structure | Name | Observed m/z |
|---|---|---|---|
| 5AY | 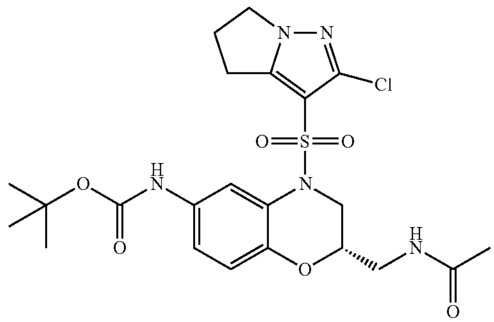 | (S)-tert-butyl (2-(acetamidomethyl)-4-((2-chloro-5,6-dihydro-4H-pyrrolo[1,2-b]pyrazol-3-yl)sulfonyl)-3,4-dihydro-2H-benzo[b][1,4]oxazin-6-yl)carbamate | 526.0 (M + H)+ |
| 5AZ | 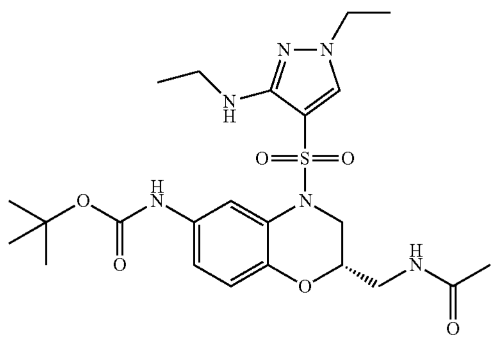 [SMILES: CCNc1nn(CC)cc1S(=O)(=O)N1C[C@H](CNC(C)=O)Oc2ccc(NC(=O)OC(C)(C)C)cc21] | (S)-tert-butyl (2-(acetamidomethyl)-4-((1-ethyl-3-(ethylamino)-1H-pyrazol-4-yl)sulfonyl)-3,4-dihydro-2H-benzo[b][1,4]oxazin-6-yl)carbamate | 523.2 (M + H)+ |
| 5BA | 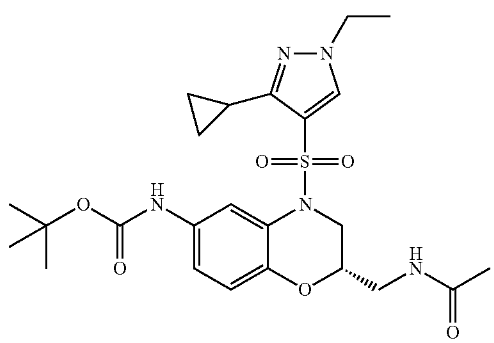 [SMILES: CCn1cc(S(=O)(=O)N2C[C@H](CNC(C)=O)Oc3ccc(NC(=O)OC(C)(C)C)cc32)c(C2CC2)n1] | (S)-tert-butyl (2-(acetamidomethyl)-4-((3-cyclopropyl-1-ethyl-1H-pyrazol-4-yl)sulfonyl)-3,4-dihydro-2H-benzo[b][1,4]oxazin-6-yl)carbamate | 520.2 (M + H)+ |
| 5BB | 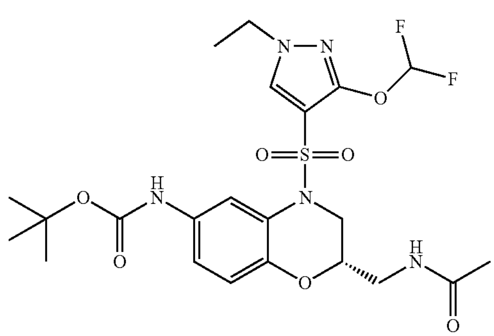 [SMILES: CCn1cc(S(=O)(=O)N2C[C@H](CNC(C)=O)Oc3ccc(NC(=O)OC(C)(C)C)cc32)c(OC(F)F)n1] | (S)-tert-butyl (2-(acetamidomethyl)-4-((3-(difluoromethoxy)-1-ethyl-1H-pyrazol-4-yl)sulfonyl)-3,4-dihydro-2H-benzo[b][1,4]oxazin-6-yl)carbamate | 568.2 (M + Na)+ |

| Ex. No. | Structure | Name | Observed m/z |
|---|---|---|---|
| 5BC | 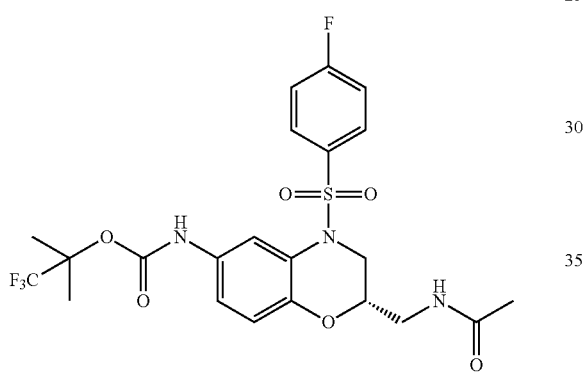 | (S)-tert-butyl (2-(acetamidomethyl)-4-((3-(dimethylamino)-1-ethyl-1H-pyrazol-4-yl)sulfonyl)-3,4-dihydro-2H-benzo[b][1,4]oxazin-6-yl)carbamate | 523.2 (M + H)+ |

Example 6—Synthesis of (S)-1,1,1-trifluoro-2-methylpropan-2-yl (2-(acetamidomethyl)-4-((4-fluorophenyl)sulfonyl)-3,4-dihydro-2H-benzo[b][1,4]oxazin-6-yl)carbamate (6)

The title compound was prepared according to the procedures described below.

Step 1—Synthesis of (S)—N-((6-amino-4-((4-fluorophenyl)sulfonyl)-3,4-dihydro-2H-benzo[b][1,4]oxazin-2-yl)methyl)acetamide hydrochloride

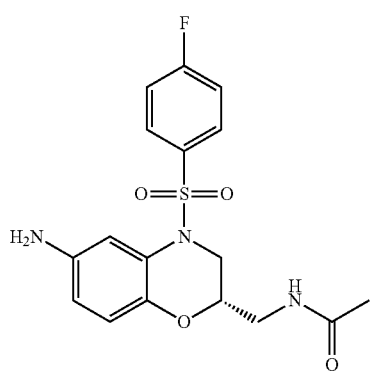 [SMILES: CC(=O)NC[C@H]1CN(S(=O)(=O)c2ccc(F)cc2)c2cc(N)ccc2O1]

A solution of (S)-tert-butyl (2-(aminomethyl)-4-((4-fluorophenyl)sulfonyl)-3,4-dihydro-2H-benzo[b][1,4]oxazin-6-yl)carbamate (5.8 g, 12.10 mmol), in 4M HCl in dioxane (106 mL, 423 mmol) was sealed and heated at 60° C. for three hours. The mixture was concentrated and dried to afford (S)—N-((6-amino-4-((4-fluorophenyl)sulfonyl)-3,4-dihydro-2H-benzo[b][1,4]oxazin-2-yl)methyl)acetamide hydrochloride.

Step 2—Synthesis of (S)-1,1,1-trifluoro-2-methylpropan-2-yl (2-(acetamidomethyl)-4-((4-fluorophenyl)sulfonyl)-3,4-dihydro-2H-benzo[b][1,4]oxazin-6-yl)carbamate

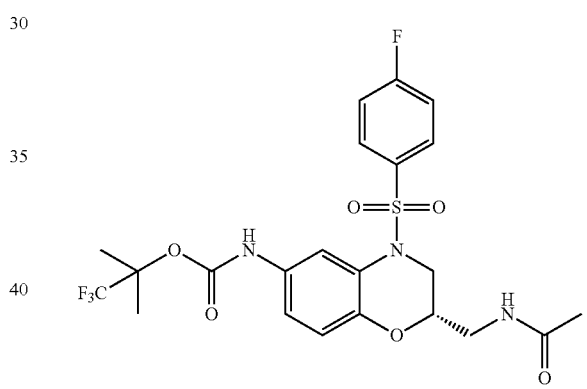

To a solution of (S)—N-((6-amino-4-((4-fluorophenyl)sulfonyl)-3,4-dihydro-2H-benzo[b][1,4]oxazin-2-yl)methyl)acetamide hydrochloride (4.0 g, 9.62 mmol) in dichloromethane (32.1 mL), and triethylamine (8.04 mL, 57.7 mmol) was added 4-nitrophenyl (1,1,1-trifluoro-2-methylpropan-2-yl) carbonate (5.64 g, 19.2 mmol) and 4-N,N-dimethylaminopyridine (0.235 g, 1.92 mmol). The mixture was stirred at room temperature overnight. The reaction was partitioned between isopropanol/chloroform (1:3, v/v) and saturated sodium bicarbonate. The organic layer was washed twice with 1N NaOH, dried (MgSO$_4$) and concentrated. The residue was purified by via chromatography eluting with a gradient (ethyl acetate: Hex 0-100%) to afford (S)-1,1,1-trifluoro-2-methylpropan-2-yl (2-(acetamidomethyl)-4-((4-fluorophenyl)sulfonyl)-3,4-dihydro-2H-benzo[b][1,4]oxazin-6-yl)carbamate as a white solid. LRMS (ESI) calculated for $C_{22}H_{24}F_4N_3O_6S$ (M+H)+: 534. found: 534. $^1$H NMR (600 MHz, DMSO-d6) δ 9.74 (s, 1H), 8.03 (t, 1H, J=6.1 Hz), 7.89 (s, 1H), 7.71 (dd, 2H, J=4.7, 3.4 Hz), 7.39 (t, 2H, J=8.8 Hz), 7.16 (d, 1H, J=8.1 Hz), 6.74 (d, 1H, J=9.0 Hz), 4.23 (d, 1H, J=14.1 Hz), 3.29 (m, 1H), 3.24 (m, 1H), 3.16 (m, 1H), 3.04 (m, 1H), 1.81 (s, 3H), 1.68 (s, 6H).

Example 7—Alternative synthesis of (S)-1,1,1-trifluoro-2-methylpropan-2-yl (2-(acetamidomethyl)-4-((4-fluorophenyl)sulfonyl)-3,4-dihydro-2H-benzo[b][1,4]oxazin-6-yl)carbamate (7)

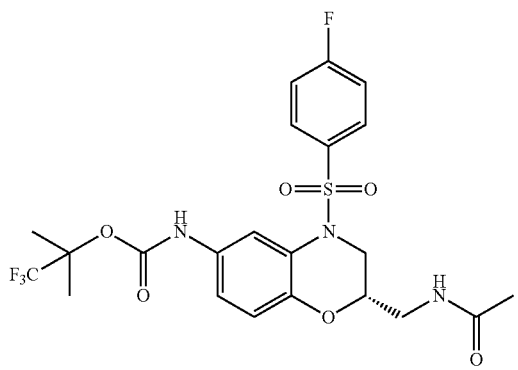 [SMILES: CC(=O)NC[C@H]1CN(S(=O)(=O)c2ccc(F)cc2)c2cc(NC(=O)OC(C)(C)C(F)(F)F)ccc2O1]

The title compound was also prepared according to the procedures described below.

Step 1—Synthesis of (S)-tert-butyl (2-(acetamidomethyl)-4-benzyl-3,4-dihydro-2H-benzo[b][1,4]oxazin-6-yl)carbamate

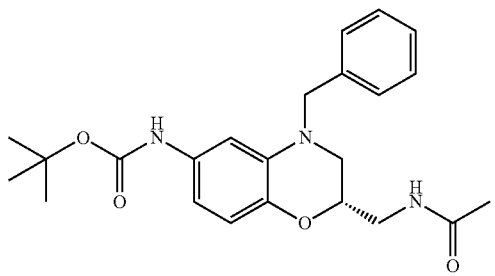 [SMILES: CC(=O)NC[C@H]1CN(Cc2ccccc2)c2cc(NC(=O)OC(C)(C)C)ccc2O1]

To (R)-tert-butyl (2-(acetamidomethyl)-3,4-dihydro-2H-benzo[b][1,4]oxazin-6-yl)carbamate (150 mg, 0.47 mmol), benzaldehyde (0.085 mL, 0.84 mmol), and sodium acetoxyborohydride (198 mg, 0.933 mmol) in dichloroethane (2 mL) at room temperature was added acetic acid (0.053 mL, 0.93 mmol). The mixture was stirred overnight, filtered, and concentrated. The crude product was purified via chromatography on silica gel, eluting with a gradient of ethyl acetate:hexanes (0-100%) to afford (S)-tert-butyl (2-(acetamidomethyl)-4-benzyl-3,4-dihydro-2H-benzo[b][1,4]oxazin-6-yl)carbamate.

Step 2—Synthesis of (S)—N-((6-amino-4-benzyl-3,4-dihydro-2H-benzo[b][1,4]oxazin-2-yl)methyl)acetamide

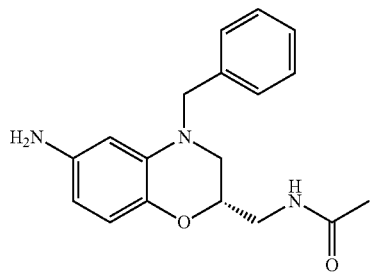 [SMILES: CC(=O)NC[C@H]1CN(Cc2ccccc2)c2cc(N)ccc2O1]

To a solution of (S)-tert-butyl (2-(acetamidomethyl)-4-benzyl-3,4-dihydro-2H-benzo[b][1,4]oxazin-6-yl)carbamate (180 mg, 0.44 mmol) in acetonitrile (5 mL) was added concentrated hydrochloric acid (0.55 mL, 2.2 mmol) and the mixture was stirred for 2.5 hours. The reaction was concentrated to afford (S)—N-((6-amino-4-benzyl-3,4-dihydro-2H-benzo[b][1,4]oxazin-2-yl)methyl)acetamide which was used without further purification.

Step 3—Synthesis of 4-nitrophenyl (1,1,1-trifluoro-2-methylpropan-2-yl) carbonate

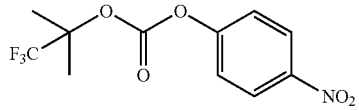 [SMILES: CC(C)(OC(=O)Oc1ccc([N+](=O)[O-])cc1)C(F)(F)F]

To a solution of 1,1,1-trifluoro-2-methylpropan-2-ol (500 mg, 3.90 mmol) in THF (15 mL) was added dropwise n-BuLi (1.60 mL, 4.0 mmol) at −70° C. and the reaction mixture was stirred at −70° C. for three hours. Then a solution of 4-nitrophenyl carbonochloridate (1.18 g, 5.86 mmol) in THF (5 mL) was added to the mixture slowly at −70° C. The reaction mixture was warmed to room temperature and stirred at the same temperature for two hours. The reaction was diluted with ethyl acetate, washed with water, brine, dried ($Na_2SO_4$) and concentrated. The residue was purified by silica gel column chromatography eluting with petroleum ether: ethyl acetate (20:1) to afford 4-nitrophenyl (1,1,1-trifluoro-2-methylpropan-2-yl) carbonate. $^1$H NMR ($CDCl_3$, 400 MHz) δ 8.29 (d, J=8.8 Hz, 2H), 7.39 (d, J=9.2 Hz, 2H), 1.79 (s, 6H). LRMS (ESI) calculated for $C_{11}H_{11}F_3NO_5$ $(M+H)^+$: 294. Found: 294.

Step 4—Synthesis of (S)-1,1,1-trifluoro-2-methylpropan-2-yl (2-(acetamidomethyl)-4-benzyl-3,4-dihydro-2H-benzo[b][1,4]oxazin-6-yl)carbamate

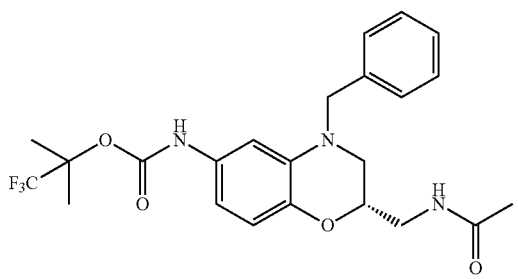 [SMILES: CC(=O)NC[C@H]1CN(Cc2ccccc2)c2cc(NC(=O)OC(C)(C)C(F)(F)F)ccc2O1]

To a solution of (S)—N-((6-amino-4-benzyl-3,4-dihydro-2H-benzo[b][1,4]oxazin-2-yl)methyl)acetamide (130 mg, 0.42 mmol) in dichloromethane (5 mL) and triethyl amine (0.175 mL, 1.25 mmol) at room temperature was added 4-nitrophenyl(1,1,1-trifluoro-2-methylpropan-2-yl)carbonate (184 mg, 0.626 mmol). The mixture was stirred overnight, additional carbonate (100 mg) was added, and stirred for an additional four hours. The mixture was diluted with ethyl acetate, washed with saturated sodium bicarbonate, water, brine, dried ($Na_2SO_4$), and concentrated. The residue was purified via chromatography eluting with a gradient of ethyl acetate:hexanes (0-100%) to afford (S)-1,1,1-trifluoro-2-methylpropan-2-yl (2-(acetamidomethyl)-4-benzyl-3,4-dihydro-2H-benzo[b][1,4]oxazin-6-yl)carbamate.

121

Step 5—Synthesis of (R)-1,1,1-trifluoro-2-methyl-propan-2-yl (2-(acetamidomethyl)-3,4-dihydro-2H-benzo[b][1,4]oxazin-6-yl)carbamate

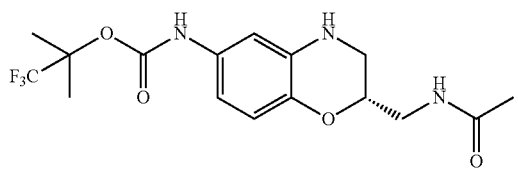 [SMILES: CC(=O)NC[C@H]1CNc2cc(NC(=O)OC(C)(C)C(F)(F)F)ccc2O1]

To a solution of (S)-1,1,1-trifluoro-2-methylpropan-2-yl (2-(acetamidomethyl)-4-benzyl-3,4-dihydro-2H-benzo[b][1,4]oxazin-6-yl)carbamate in methanol purged with nitrogen was added Pd/C (10%) and the atmosphere above the mixture was exchanged with hydrogen three times. The mixture was stirred under one atmosphere hydrogen pressure overnight. The mixture was then filtered through CELITE, and the pad was washed with methanol. The combined filtrate was concentrated to afford (R)-1,1,1-trifluoro-2-methylpropan-2-yl (2-(acetamidomethyl)-3,4-dihydro-2H-benzo[b][1,4]oxazin-6-yl)carbamate as a white solid which was used without further purification.

Step 6—Synthesis of (S)-1,1,1-trifluoro-2-methyl-propan-2-yl (2-(acetamidomethyl)-4-((4-fluorophenyl)sulfonyl)-3,4-dihydro-2H-benzo[b][1,4]oxazin-6-yl)carbamate

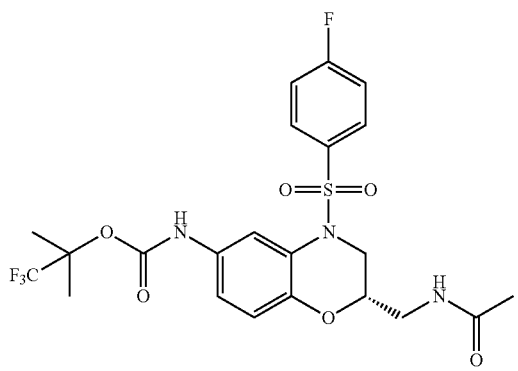

The title compound was prepared via the method used in Part 7 of Example 1 using (R)-1,1,1-trifluoro-2-methylpropan-2-yl (2-(acetamidomethyl)-3,4-dihydro-2H-benzo[b][1,4]oxazin-6-yl)carbamate instead of (R)-tert-butyl (2-(acetamidomethyl)-3,4-dihydro-2H-benzo[b][1,4]oxazin-6-yl)carbamate.

Example 8—Synthesis of (S)-1,1,1-trifluoro-2-methylpropan-2-yl (2-(acetamidomethyl)-4-((1-ethyl-3-hydroxy-1H-pyrazol-4-yl)sulfonyl)-3,4-dihydro-2H-benzo[b][1,4]oxazin-6-yl)carbamate (8)

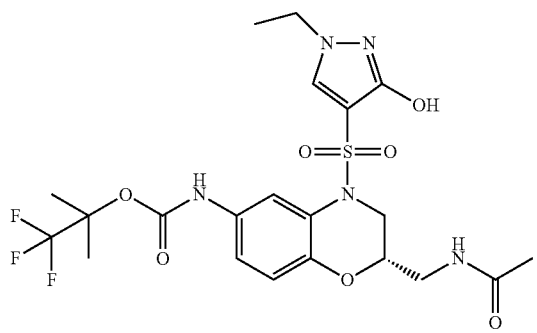 [SMILES: CCn1cc(S(=O)(=O)N2C[C@H](CNC(C)=O)Oc3ccc(NC(=O)OC(C)(C)C(F)(F)F)cc32)c(O)n1]

122

Step 1—Synthesis of 3-(Benzyloxy)-1-ethyl-1H-pyrazole-4-sulfonyl chloride

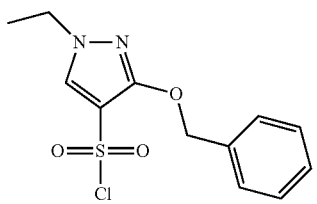 [SMILES: CCn1cc(S(=O)(=O)Cl)c(OCc2ccccc2)n1]

To a suspension of sulfur trioxide dimethylformamide complex (0.49 g, 3.2 mmol) in dichloromethane (10 mL) under nitrogen at 0° C. was added a solution of 3-(benzyloxy)-1-ethyl-1H-pyrazole (0.62 g, 3.1 mmol) in dichloromethane (1 mL). The reaction was allowed to warm to ambient temperature and stirred for 1 hour. The solution was recooled to 0° C., followed by the addition of anhydrous pyridine (0.74 mL, 9.2 mmol) and phosphorus pentachloride (0.7 g, 3.4 mmol) in portions. After 30 minutes the cooling bath was removed and the reaction was stirred at ambient temperature overnight. The reaction was concentrated in the presence of silica. The mixture was purified by column chromatography eluting with a gradient of 10-60% ethyl acetate in hexanes. Pure fractions were combined and concentrated in vacuo to yield the title compound.

Step 2—Synthesis of tert-butyl (S)-(2-(acetamidomethyl)-4-((3-(benzyloxy)-1-ethyl-1H-pyrazol-4-yl)sulfonyl)-3,4-dihydro-2H-benzo[b][1,4]oxazin-6-yl)carbamate

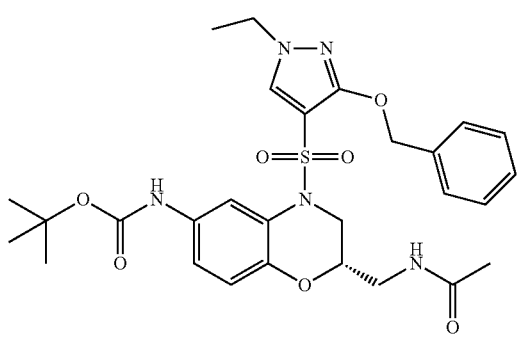 [SMILES: CCn1cc(S(=O)(=O)N2C[C@H](CNC(C)=O)Oc3ccc(NC(=O)OC(C)(C)C)cc32)c(OCc2ccccc2)n1]

In anhydrous pyridine (4 mL) were combined tert-butyl (R)-(2-(acetamidomethyl)-3,4-dihydro-2H-benzo[b][1,4]oxazin-6-yl)carbamate (0.3 g, 0.93 mmol) and 3-(benzyloxy)-1-ethyl-1H-pyrazole-4-sulfonyl chloride (0.31 g, 1.03 mmol) and the solution was stirred at 60° C. overnight. The cooled solution was diluted with ethyl acetate, washed with 10% citric acid, brine, and dried with sodium sulfate. To the suspension was added activated charcoal while the suspension was slurried. The suspension was filtered through CELITE and concentrated in vacuo. The mixture was purified by column chromatography eluting with a gradient of ethyl acetate in hexanes to yield the title compound.

Step 3—Synthesis of 1,1,1-trifluoro-2-methylpropan-2-yl (S)-(2-(acetamidomethyl)-4-((3-(benzyloxy)-1-ethyl-1H-pyrazol-4-yl)sulfonyl)-3,4-dihydro-2H-benzo[b][1,4]oxazin-6-yl)carbamate

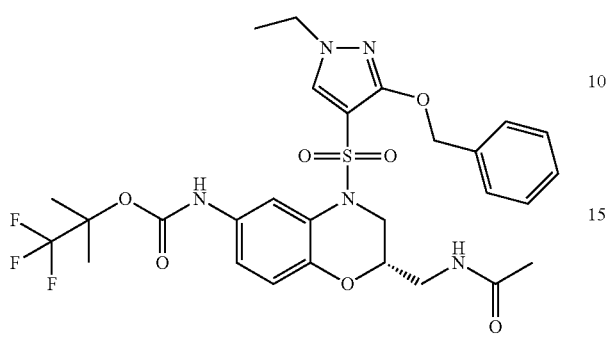

To tert-butyl (S)-(2-(acetamidomethyl)-4-((3-(benzyloxy)-1-ethyl-1H-pyrazol-4-yl)sulfonyl)-3,4-dihydro-2H-benzo[b][1,4]oxazin-6-yl)carbamate (0.37 g, 0.63 mmol) was added 4M hydrogen chloride in 1,4-dioxane (20 mL) and the reaction was stirred at ambient temperature for 1 hour. The resulting suspension was concentrated in vacuo to a solid. This resulting solid was redissolved in N,N-dimethylformamide (5 mL) and combined with (2,2,2-trifluoro-1,1-dimethyl-ethyl) imidazole-1-carboxylate (0.24 g, 1.07 mmol). The reaction was heated at 100° C. in the microwave for 2 hours. The cooled solution was partitioned between ethyl acetate and water, washed with brine, dried with sodium sulfate, filtered and concentrated in the presence of silica. The mixture was purified by column chromatography eluting with a gradient of 70-100% ethyl acetate in hexanes. Pure fractions were combined and concentrated in vacuo to yield the title compound.

Step 4—Synthesis of 1,1,1-trifluoro-2-methylpropan-2-yl (S)-(2-(acetamidomethyl)-4-((1-ethyl-3-hydroxy-1H-pyrazol-4-yl)sulfonyl)-3,4-dihydro-2H-benzo[b][1,4]oxazin-6-yl)carbamate

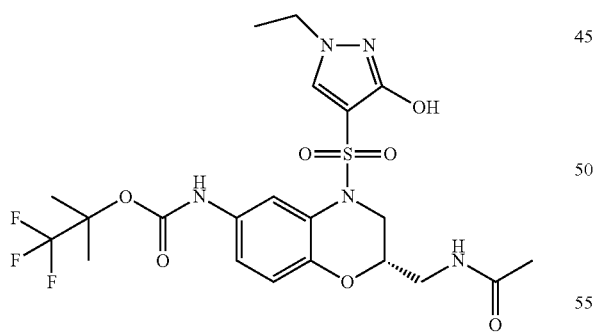

A suspension of the 1,1,1-trifluoro-2-methylpropan-2-yl (S)-(2-(acetamidomethyl)-4-((3-(benzyloxy)-1-ethyl-1H-pyrazol-4-yl)sulfonyl)-3,4-dihydro-2H-benzo[b][1,4]oxazin-6-yl)carbamate (0.13 g, 0.20 mmol) and ammonium formate (0.13 g, 2 mmol) in methanol (5 mL) was first purged under vacuum, then was added 10% palladium on carbon (22 mg) and the reaction was refluxed for 2 hours. The reaction was cooled and filtered through CELITE while washing with methanol. The filtrates were concentrated and partitioned between ethyl acetate and 1M hydrogen chloride. The organics were washed with brine, dried with sodium sulfate, filtered and concentrated in vacuo to yield the title compound. ESI m/z 572.18 (M+Na)+; $^1$H NMR 400 Hz d$_6$-DMSO δ 11.09 (s, 1H), 9.63 (s, 1H), 8.12 (m, 1H), 7.99 (s, 1H), 7.76 (m, 1H), 6.99 (m, 1H), 6.74 (m, 1H), 4.20 (m, 1H), 3.89-3.83 (m, 3H), 3.4 (m, 1H), 3.17 (m, 2H), 1.82 (s, 3H), 1.67 (s, 6H), 1.24 (m, 3H).

Example 9—Synthesis of (S)-1,1,1-trifluoro-2-methylpropan-2-yl (2-(acetamidomethyl)-4-((1-ethyl-3-isopropoxy-1H-pyrazol-4-yl)sulfonyl)-3,4-dihydro-2H-benzo[b][1,4]oxazin-6-yl)carbamate (9)

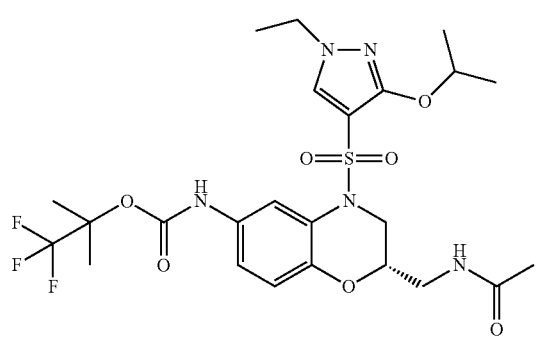 [SMILES: CCn1cc(S(=O)(=O)N2C[C@H](CNC(C)=O)Oc3ccc(NC(=O)OC(C)(C)C(F)(F)F)cc32)c(OC(C)C)n1]

Step 1—Synthesis of 1-Ethyl-3-isopropoxy-1H-pyrazole

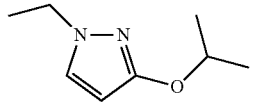

To a solution of 1-ethyl-1,2-dihydro-3H-pyrazol-3-one (1 g, 8.9 mmol) in N,N-dimethylformamide (10 mL) was added potassium carbonate (1.8 g, 13.4 mmol) followed by 2-iodopropane (1.4 mL, 17.8 mmol). The reaction was stirred at ambient temperature overnight. The solution was partitioned between ethyl acetate and water, washed with brine, dried with sodium sulfate, filtered and concentrated in vacuo. The mixture was purified by column chromatography eluting with a gradient of ethyl acetate in hexanes. Pure fractions were combined and concentrated in vacuo to yield the title compound.

Step 2—Synthesis of 1-ethyl-3-isopropoxy-1H-pyrazole-4-sulfonyl chloride

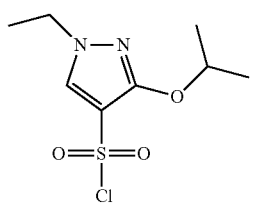

To a suspension of sulfur trioxide dimethylformamide complex (0.63 g, 4.1 mmol) in dichloromethane (10 mL) under nitrogen at 0° C. was added a solution of 1-ethyl-3-isopropoxy-1H-pyrazole (0.6 g, 3.9 mmol) in dichloromethane (5 mL). The reaction was allowed to warm to ambient temperature and stirred for 1 hour. The solution was cooled to 0° C. and treated with 2,6-lutidine (1.4 mL, 11.7 mmol) followed by phosphorus pentachloride (0.89 g, 4.3 mmol) in portions. After 30 minutes the cooling bath was removed and the reaction was stirred at ambient temperature overnight. The reaction was concentrated in the presence of silica. The mixture was purified by column chromatography eluting with a gradient of 10-60% ethyl acetate in hexanes. Pure fractions were combined and concentrated in vacuo to yield the title compound.

Step 3—Synthesis of tert-butyl (S)-(2-(acetamidomethyl)-4-((1-ethyl-3-isopropoxy-1H-pyrazol-4-yl)sulfonyl)-3,4-dihydro-2H-benzo[b][1,4]oxazin-6-yl)carbamate

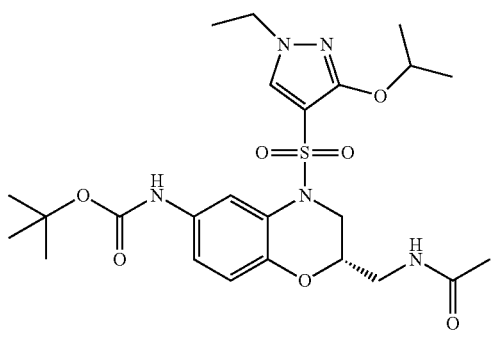 [SMILES: CCn1cc(S(=O)(=O)N2C[C@H](CNC(C)=O)Oc3ccc(NC(=O)OC(C)(C)C)cc32)c(OC(C)C)n1]

In anhydrous pyridine (6 mL) was combined tert-butyl (R)-(2-(acetamidomethyl)-3,4-dihydro-2H-benzo[b][1,4]oxazin-6-yl)carbamate (0.58 g, 1.8 mmol) and 1-ethyl-3-isopropoxy-1H-pyrazole-4-sulfonyl chloride (0.55 g, 2.2 mmol) and the solution was heated at 60° C. for 2 hours. The cooled solution was diluted with ethyl acetate, washed with 10% citric acid, brine, and dried with sodium sulfate. To the suspension was added activated charcoal while the suspension was stirred. The suspension was filtered through CELITE and the filtrate concentrated in vacuo to yield the title compound.

Step 4—Synthesis of 1,1,1-Trifluoro-2-methylpropan-2-yl (S)-(2-(acetamidomethyl)-4-((1-ethyl-3-isopropoxy-1H-pyrazol-4-yl)sulfonyl)-3,4-dihydro-2H-benzo[b][1,4]oxazin-6-yl)carbamate

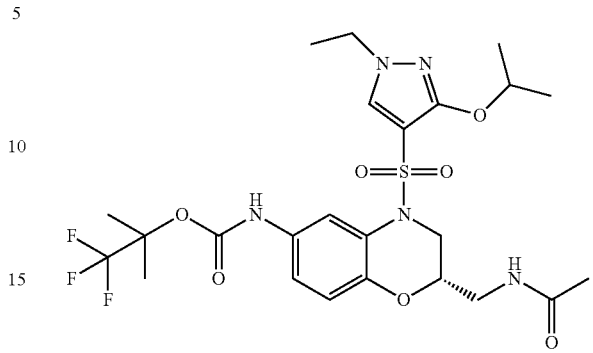

To tert-butyl (S)-(2-(acetamidomethyl)-4-((1-ethyl-3-isopropoxy-1H-pyrazol-4-yl)sulfonyl)-3,4-dihydro-2H-benzo[b][1,4]oxazin-6-yl)carbamate (0.81 g, 1.51 mmol) was added 4M hydrogen chloride in 1,4-dioxane (20 mL) and the reaction was stirred at ambient temperature for 1 hour. The resulting suspension was concentrated in vacuo to a solid. The resulting solid was redissolved in N,N-dimethylformamide (10 mL) and combined with (2,2,2-trifluoro-1,1-dimethylethyl) imidazole-1-carboxylate (0.57 g, 2.56 mmol). The reaction was heated at 100° C. in the microwave for 2 hours. The cooled solution was partitioned between ethyl acetate and water, washed with brine, dried with sodium sulfate, filtered and concentrated in the presence of silica. The residue was purified by column chromatography eluting with a gradient of 70-100% ethyl acetate in hexanes. Pure fractions were combined and concentrated in vacuo to yield the title compound. ESI m/z 614.24 (M+Na)$^+$; $^1$H NMR 400 Hz D$_6$-DMSO δ 9.64 (s, 1H), 8.12 (m, 2H), 7.76 (s, 1H), 7.03 (m, 1H), 6.75 (m, 1H), 4.64 (m, 1H), 4.15 (m, 1H), 3.93 (m, 2H), 3.75 (m, 1H), 3.38 (m, 1H), 3.16 (m, 2H), 1.81 (s, 3H), 1.7 (s, 6H), 1.26 (m, 3H), 1.14 (m, 3H), 1.02 (m, 3H).

Example 10—Preparation of additional (S)-1,1,1-trifluoro-2-methylpropan-2-yl (2-(acetamidomethyl)-4-((-((optionally substituted aryl or heteroaryl)sulfonyl)-3,4-dihydro-2H-benzo[b][1,4]oxazin-6-yl)carbamates The compounds in Table 2 below were prepared based on the experimental procedures described in Examples 7-9 and elsewhere in the detailed description, and can be achieved by one of skill in the art in light of the present disclosure.

TABLE 2

| Ex. No. | Structure | Name | Observed m/z |
|---|---|---|---|
| 10A | 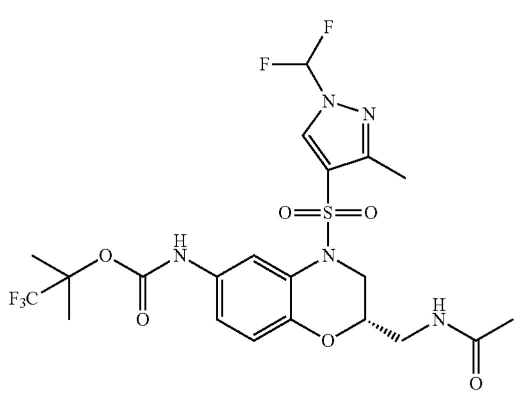 [SMILES: CC(=O)NC[C@H]1CN(S(=O)(=O)c2cn(C(F)F)nc2C)c2cc(NC(=O)OC(C)(C)C(F)(F)F)ccc2O1] | (S)-1,1,1-trifluoro-2-methylpropan-2-yl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate | 570.1 (M + H)$^+$ |

TABLE 2-continued

| Ex. No. | Structure | Name | Observed m/z |
|---|---|---|---|
| 10B | 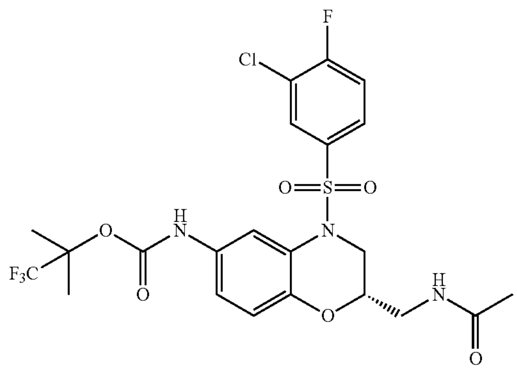 | (S)-1,1,1-trifluoro-2-methylpropan-2-yl (2-(acetamdiomethyl)-4-((3-chloro-4-fluorophenyl)sulfonyl)-3,4-dihydro-2H-benzo[b][1,4]oxazin-6-yl)carbamate | 568.0 (M + H)⁺ |
| 10C | 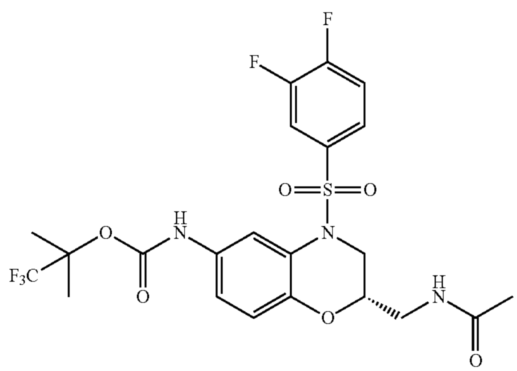 [SMILES: CC(=O)NC[C@H]1CN(S(=O)(=O)c2ccc(F)c(F)c2)c2cc(NC(=O)OC(C)(C)C(F)(F)F)ccc2O1] | (S)-1,1,1-trifluoro-2-methylpropan-2-yl (2-(acetamidomethyl)-4-(3,4-difluorophenyl)sulfonyl)-3,4-dihydro-2H-benzo[b][1,4]oxazin-6-yl)carbamate | 574.0 (M + Na)⁺ |
| 10D | 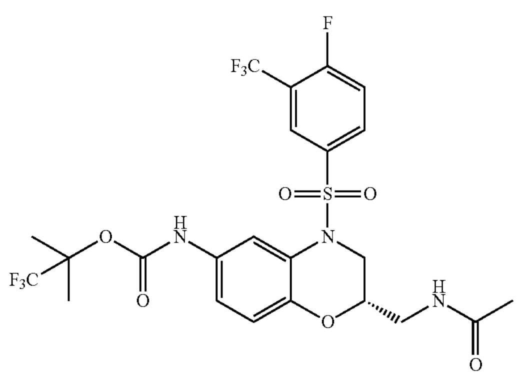 [SMILES: CC(=O)NC[C@H]1CN(S(=O)(=O)c2ccc(F)c(C(F)(F)F)c2)c2cc(NC(=O)OC(C)(C)C(F)(F)F)ccc2O1] | (S)-1,1,1-trifluoro-2-methylpropan-2-yl (2-(acetamidomethyl)-4-((4-fluoro-3-(trifluoromethyl)phenyl)sulfonyl)-3,4-dihydro-2H-benzo[b][1,4]oxazin-6-yl)carbamate | 624.0 (M + Na)⁺ |
| 10E | 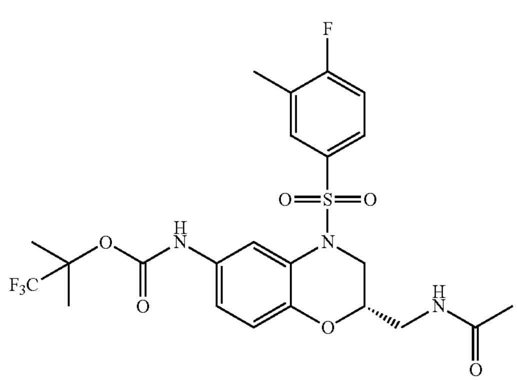 [SMILES: CC(=O)NC[C@H]1CN(S(=O)(=O)c2ccc(F)c(C)c2)c2cc(NC(=O)OC(C)(C)C(F)(F)F)ccc2O1] | (S)-1,1,1-trifluoro-2-methylpropan-2-yl (2-(acetamidomethyl)-4-((4-fluoro-3-methylphenyl)sulfonyl)-3,4-dihydro-2H-benzo[b][1,4]oxazin-6-yl)carbamate | 570.0 (M + Na)⁺ |

TABLE 2-continued

| Ex. No. | Structure | Name | Observed m/z |
|---|---|---|---|
| 10F | 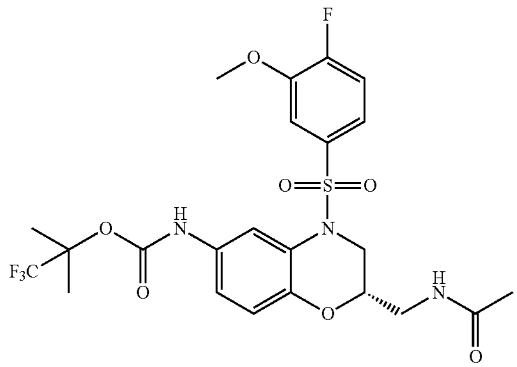 [SMILES: COc1cc(S(=O)(=O)N2C[C@H](CNC(C)=O)Oc3ccc(NC(=O)OC(C)(C)C(F)(F)F)cc32)ccc1F] | (S)-1,1,1-trifluoro-2-methylpropan-2-yl (2-(acetamidomethyl)-4-((4-fluoro-3-methoxyphenyl)sulfonyl)-3,4-dihydro-2H-benzo[b][1,4]oxazin-6-yl)carbamate | 586.0 (M + Na)+ |
| 10G | 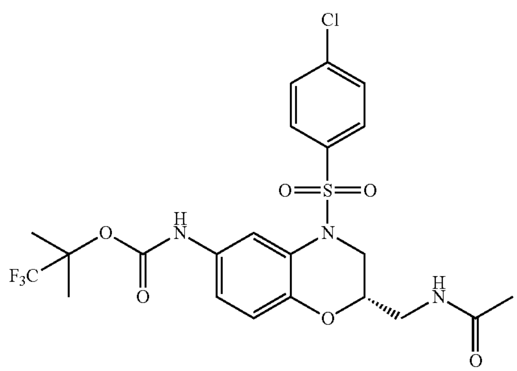 | (S)-1,1,1-trifluoro-2-methylpropan-2-yl (2-(acetamidomethyl)-4-((4-chlorophenyl)sulfonyl)-3,4-dihydro-2H-benzo[b][1,4]oxazin-6-yl)carbamate | 550.0 (M + H)+ |
| 10H | 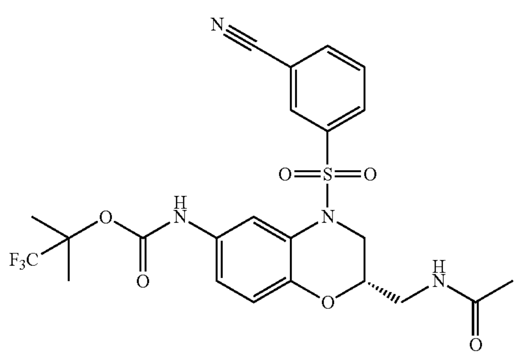 [SMILES: CC(=O)NC[C@H]1CN(S(=O)(=O)c2cccc(C#N)c2)c2cc(NC(=O)OC(C)(C)C(F)(F)F)ccc2O1] | (S)-1,1,1-trifluoro-2-methylpropan-2-yl (2-(acetamidomethyl)-4-((3-cyanophenyl)sulfonyl)-3,4-dihydro-2H-benzo[b][1,4]oxazin-6-yl)carbamate | 541.1 (M + H)+ |
| 10i | 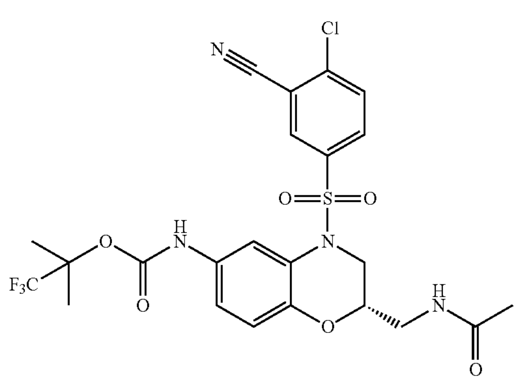 [SMILES: CC(=O)NC[C@H]1CN(S(=O)(=O)c2ccc(Cl)c(C#N)c2)c2cc(NC(=O)OC(C)(C)C(F)(F)F)ccc2O1] | (S)-1,1,1-trifluoro-2-methylpropan-2-yl (2-(acetamidomethyl)-4-((4-chloro-3-cyanophenyl)sulfonyl)-3,4-dihydro-2H-benzo[b][1,4]oxazin-6-yl)carbamate | 575.0 (M + H)+ |

TABLE 2-continued

| Ex. No. | Structure | Name | Observed m/z |
|---|---|---|---|
| 10J | 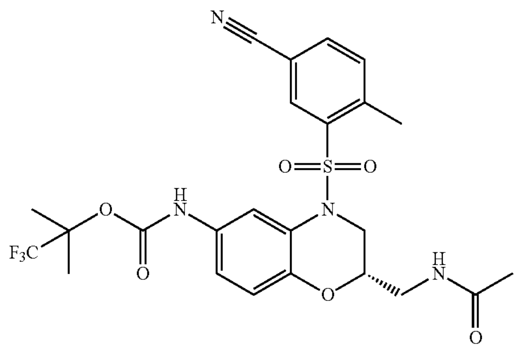 [SMILES: CC(=O)NC[C@H]1CN(S(=O)(=O)c2cc(C#N)ccc2C)c2cc(NC(=O)OC(C)(C)C(F)(F)F)ccc2O1] | (S)-1,1,1-trifluoro-2-methylpropan-2-yl (2-(acetamidomethyl)-4-((5-cyano-2-methylphenyl)sulfonyl)-3,4-dihydro-2H-benzo[b][1,4]oxazin-6-yl)carbamate | 555.2 (M + H)+ |
| 10K | 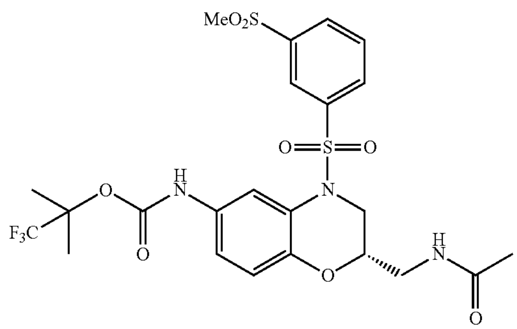 [SMILES: CC(=O)NC[C@H]1CN(S(=O)(=O)c2cccc(S(C)(=O)=O)c2)c2cc(NC(=O)OC(C)(C)C(F)(F)F)ccc2O1] | (S)-1,1,1-trifluoro-2-methylpropan-2-yl (2-(acetamidomethyl)-4-((3-(methylsulfonyl)phenyl)sulfonyl)-3,4-dihydro-2H-benzo[b][1,4]oxazin-6-yl)carbamate | 594.0 (M + H)+ |
| 10L | 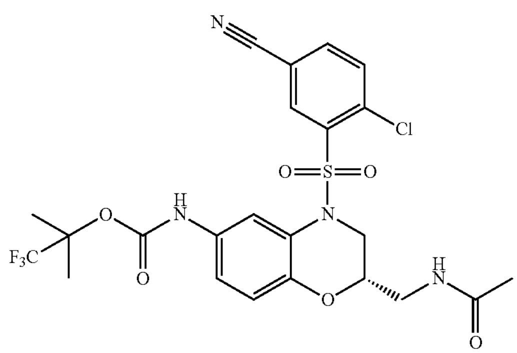 [SMILES: CC(=O)NC[C@H]1CN(S(=O)(=O)c2cc(C#N)ccc2Cl)c2cc(NC(=O)OC(C)(C)C(F)(F)F)ccc2O1] | (S)-1,1,1-trifluoro-2-methylpropan-2-yl (2-(acetamidomethyl)-4-((2-chloro-5-cyanophenyl)sulfonyl)-3,4-dihydro-2H-benzo[b][1,4]oxazin-6-yl)carbamate | 575.0 (M + H)+ |
| 10M | 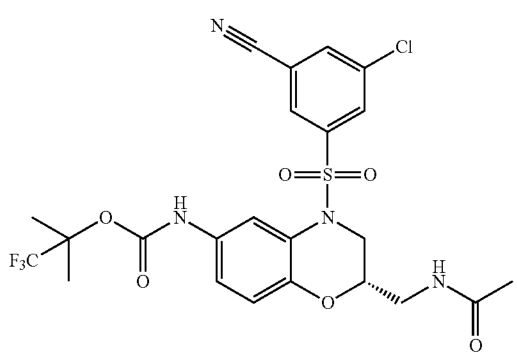 [SMILES: CC(=O)NC[C@H]1CN(S(=O)(=O)c2cc(Cl)cc(C#N)c2)c2cc(NC(=O)OC(C)(C)C(F)(F)F)ccc2O1] | (S)-1,1,1-trifluoro-2-methylpropan-2-yl (2-(acetamidomethyl)-4-((3-chloro-5-cyanophenyl)sulfonyl)-3,4-dihydro-2H-benzo[b][1,4]oxazin-6-yl)carbamate | 575.1 (M + H)+ |

TABLE 2-continued

| Ex. No. | Structure | Name | Observed m/z |
|---|---|---|---|
| 10N | 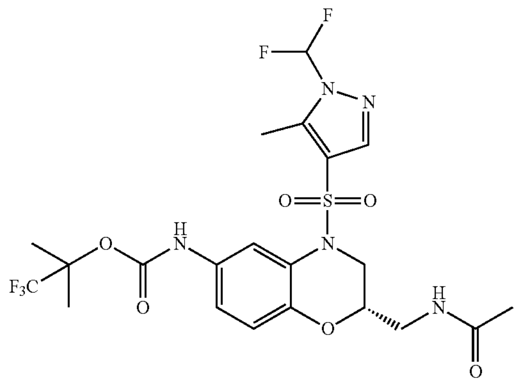 [SMILES: CC(=O)NC[C@H]1CN(S(=O)(=O)c2cnn(C(F)F)c2C)c2cc(NC(=O)OC(C)(C)C(F)(F)F)ccc2O1] | (S)-1,1,1-trifluoro-2-methylpropan-2-yl (2-(acetamidomethyl)-4-((1-(difluoromethyl)-5-methyl-1H-pyrazol-4-yl)sulfonyl)-3,4-dihydro-2H-benzo[b][1,4]oxazin-6-yl)carbamate | 592.02 (M + Na)+ |
| 10o | 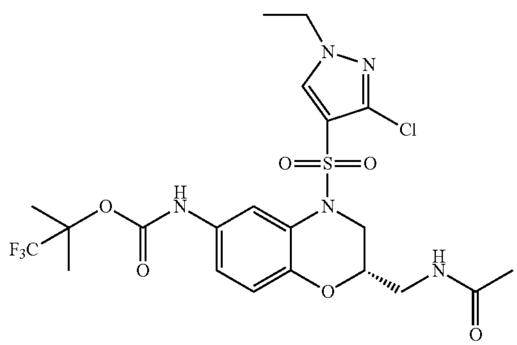 [SMILES: CCn1cc(S(=O)(=O)N2C[C@H](CNC(C)=O)Oc3ccc(NC(=O)OC(C)(C)C(F)(F)F)cc32)c(Cl)n1] | (S)-1,1,1-trifluoro-2-methylpropan-2-yl (2-(acetamidomethyl)-4-((3-chloro-1-ethyl-1H-pyrazol-4-yl)sulfonyl)-3,4-dihydro-2H-benzo[b][1,4]oxazin-6-yl)carbamate | 590.0 (M + Na)+ |
| 10P | 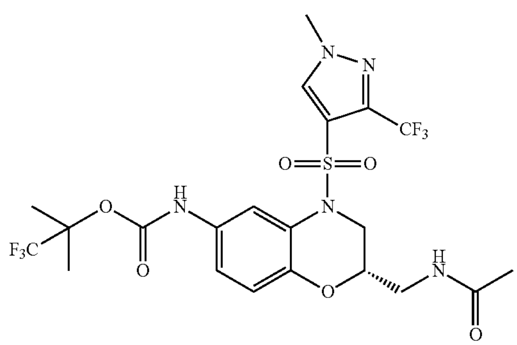 [SMILES: CC(=O)NC[C@H]1CN(S(=O)(=O)c2cn(C)nc2C(F)(F)F)c2cc(NC(=O)OC(C)(C)C(F)(F)F)ccc2O1] | (S)-1,1,1-trifluoro-2-methylpropan-2-yl (2-(acetamidomethyl)-4-((1-methyl-3-(trifluoromethyl)-1H-pyrazol-4-yl)sulfonyl)-3,4-dihydro-2H-benzo[b][1,4]oxazin-6-yl)carbamate | 588 (M + H)+ |
| 10Q | 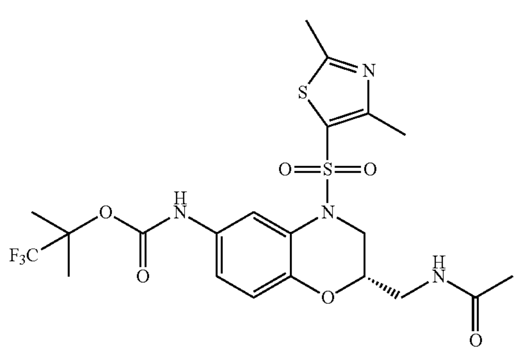 [SMILES: CC(=O)NC[C@H]1CN(S(=O)(=O)c2sc(C)nc2C)c2cc(NC(=O)OC(C)(C)C(F)(F)F)ccc2O1] | (S)-1,1,1-trifluoro-2-methylpropan-2-yl (2-(acetamidomethyl)-4-((2,4-dimethylthiazol-5-yl)sulfonyl)-3,4-dihydro-2H-benzo[b][1,4]oxazin-6-yl)carbamate | 551 (M + H)+ |

TABLE 2-continued

| Ex. No. | Structure | Name | Observed m/z |
|---|---|---|---|
| 10R | 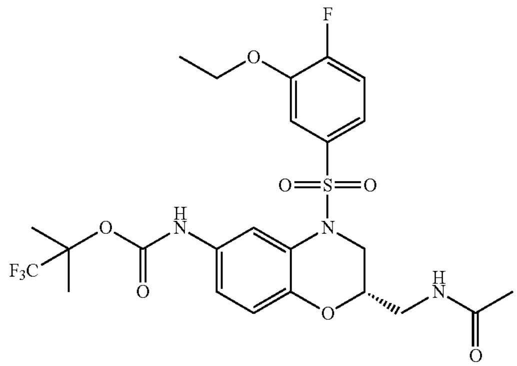 [SMILES: CCOc1cc(S(=O)(=O)N2C[C@H](CNC(C)=O)Oc3ccc(NC(=O)OC(C)(C)C(F)(F)F)cc32)ccc1F] | (S)-1,1,1-trifluoro-2-methylpropan-2-yl (2-(acetamidomethyl)-4-((3-ethoxy-4-fluorophenyl)sulfonyl)-3,4-dihydro-2H-benzo[b][1,4]oxazin-6-yl)carbamate | 600.0 (M + Na)+ |
| 10S | 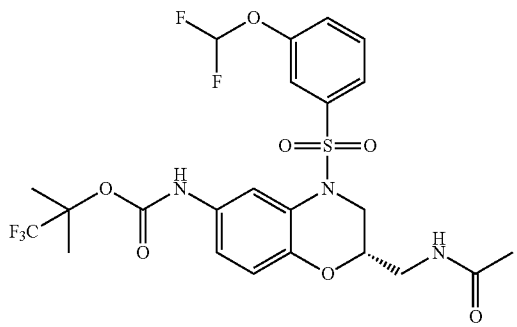 [SMILES: CC(=O)NC[C@H]1CN(S(=O)(=O)c2cccc(OC(F)F)c2)c2cc(NC(=O)OC(C)(C)C(F)(F)F)ccc2O1] | (S)-1,1,1-trifluoro-2-methylpropan-2-yl (2-(acetamidomethyl)-4-((3-(difluoromethoxy)phenyl)sulfonyl)-3,4-dihydro-2H-benzo[b][1,4]oxazin-6-yl)carbamate | 582.0 (M + H)+ |
| 10T | 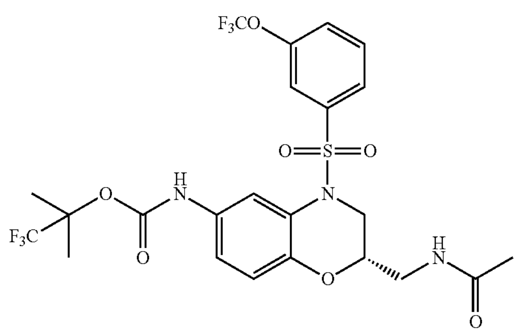 [SMILES: CC(=O)NC[C@H]1CN(S(=O)(=O)c2cccc(OC(F)(F)F)c2)c2cc(NC(=O)OC(C)(C)C(F)(F)F)ccc2O1] | (S)-1,1,1-trifluoro-2-methylpropan-2-yl (2-(acetamidomethyl)-4-((3-(trifluoromethoxy)phenyl)sulfonyl)-3,4-dihydro-2H-benzo[b][1,4]oxazin-6-yl)carbamate | 600.0 (M + H)+ |
| 10U | 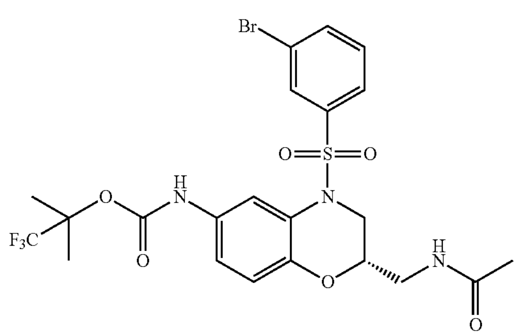 [SMILES: CC(=O)NC[C@H]1CN(S(=O)(=O)c2cccc(Br)c2)c2cc(NC(=O)OC(C)(C)C(F)(F)F)ccc2O1] | (S)-1,1,1-trifluoro-2-methylpropan-2-yl (2-(acetamidomethyl)-4-((3-bromophenyl)sulfonyl)-3,4-dihydro-2H-benzo[b][1,4]oxazin-6-yl)carbamate | 593.9 (M + H)+ |

| Ex. No. | Structure | Name | Observed m/z |
|---|---|---|---|
| 10V | 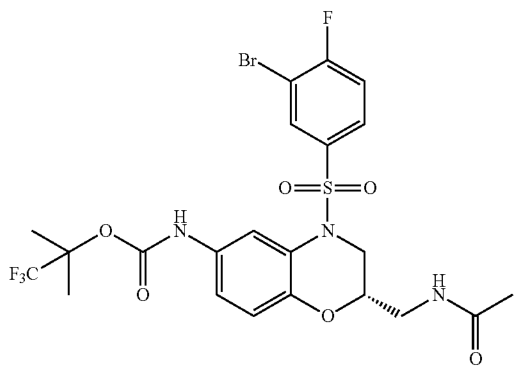 [SMILES: CC(=O)NC[C@H]1CN(S(=O)(=O)c2ccc(F)c(Br)c2)c2cc(NC(=O)OC(C)(C)C(F)(F)F)ccc2O1] | (S)-1,1,1-trifluoro-2-methylpropan-2-yl (2-(acetamidomethyl)-4-((3-bromo-4-fluorophenyl)sulfonyl)-3,4-dihydro-2H-benzo[b][1,4]oxazin-6-yl)carbamate | 613.9 (M + H)+ |
| 10W | 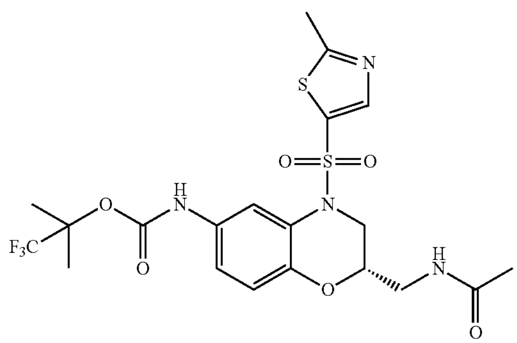 [SMILES: CC(=O)NC[C@H]1CN(S(=O)(=O)c2cnc(C)s2)c2cc(NC(=O)OC(C)(C)C(F)(F)F)ccc2O1] | (S)-1,1,1-trifluoro-2-methylpropan-2-yl (2-(acetamidomethyl)-4-((2-methylthiazol-5-yl)sulfonyl)-3,4-dihydro-2H-benzo[b][1,4]oxazin-6-yl)carbamate | 537 (M + H)+ |
| 10X | 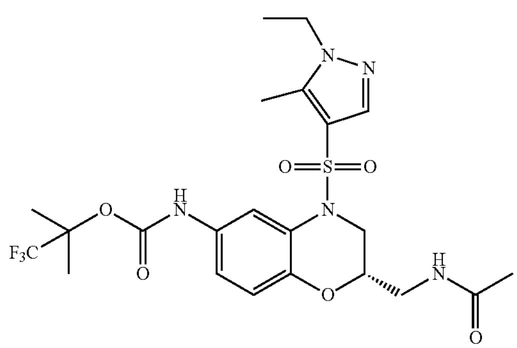 [SMILES: CCn1ncc(S(=O)(=O)N2C[C@H](CNC(C)=O)Oc3ccc(NC(=O)OC(C)(C)C(F)(F)F)cc32)c1C] | (S)-1,1,1-trifluoro-2-methylpropan-2-yl (2-(acetamidomethyl)-4-((1-ethyl-5-methyl-1H-pyrazol-4-yl)sulfonyl)-3,4-dihydro-2H-benzo[b][1,4]oxazin-6-yl)carbamate | 548 (M + H)+ |
| 10Y | 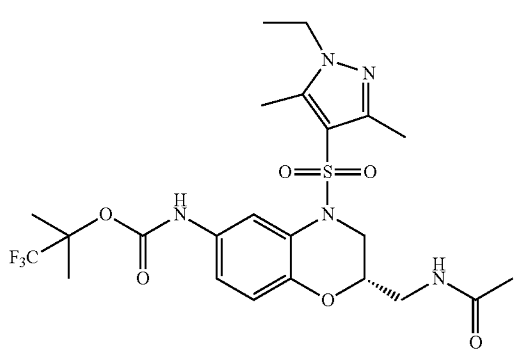 [SMILES: CCn1nc(C)c(S(=O)(=O)N2C[C@H](CNC(C)=O)Oc3ccc(NC(=O)OC(C)(C)C(F)(F)F)cc32)c1C] | (S)-1,1,1-trifluoro-2-methylpropan-2-yl (2-(acetamidomethyl)-4-((1-ethyl-3,5-dimethyl-1H-pyrazol-4-yl)sulfonyl)-3,4-dihydro-2H-benzo[b][1,4]oxazin-6-yl)carbamate | 562 (M + H)+ |

TABLE 2-continued

| Ex. No. | Structure | Name | Observed m/z |
|---|---|---|---|
| 10Z | 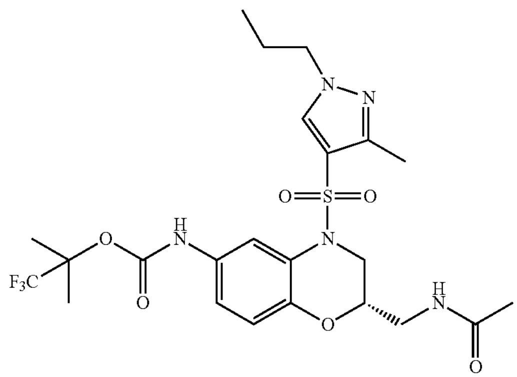 [SMILES: CCCn1cc(S(=O)(=O)N2C[C@H](CNC(C)=O)Oc3ccc(NC(=O)OC(C)(C)C(F)(F)F)cc32)c(C)n1] | (S)-1,1,1-trifluoro-2-methylpropan-2-yl (2-(acetamidomethyl)-4-((3-methyl-1-propyl-1H-pyrazol-4-yl)sulfonyl)-3,4-dihydro-2H-benzo[b][1,4]oxazin-6-yl)carbamate | 562 (M + H)+ |
| 10AA | 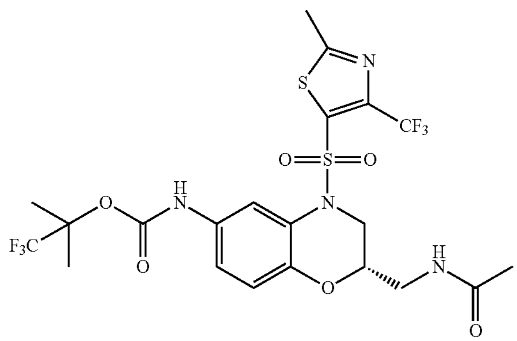 [SMILES: CC(=O)NC[C@H]1CN(S(=O)(=O)c2sc(C)nc2C(F)(F)F)c2cc(NC(=O)OC(C)(C)C(F)(F)F)ccc2O1] | (S)-1,1,1-trifluoro-2-methylpropan-2-yl (2-(acetamidomethyl)-4-((2-methyl-4-(trifluoromethyl)thiazol-5-yl)sulfonyl)-3,4-dihydro-2H-benzo[b][1,4]oxazin-6-yl)carbamate | 605. (M + H)+ |
| 10AB | 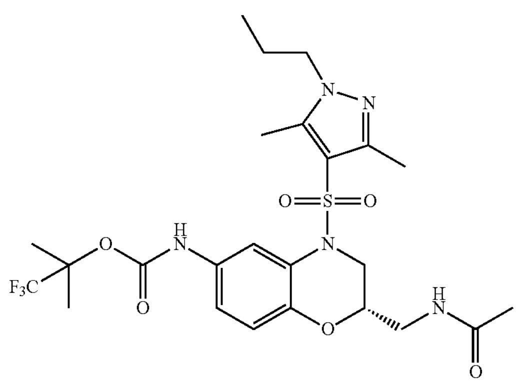 [SMILES: CCCn1nc(C)c(S(=O)(=O)N2C[C@H](CNC(C)=O)Oc3ccc(NC(=O)OC(C)(C)C(F)(F)F)cc32)c1C] | (S)-1,1,1-trifluoro-2-methylpropan-2-yl (2-(acetamidomethyl)-4-((3,5-dimethyl-1-propyl-1H-pyrazol-4-yl)sulfonyl)-3,4-dihydro-2H-benzo[b][1,4]oxazin-6-yl)carbamate | 576 (M + H)+ |
| 10AC | 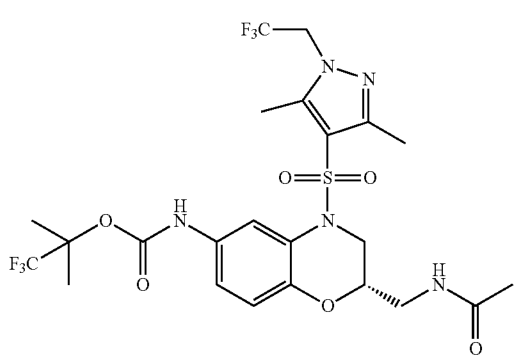 [SMILES: CC(=O)NC[C@H]1CN(S(=O)(=O)c2c(C)nn(CC(F)(F)F)c2C)c2cc(NC(=O)OC(C)(C)C(F)(F)F)ccc2O1] | (S)-1,1,1-trifluoro-2-methylpropan-2-yl (2-(acetamidomethyl)-4-((3,5-dimethyl-1-(2,2,2-trifluoroethyl)-1H-pyrazol-4-yl)sulfonyl)-3,4-dihydro-2H-benzo[b][1,4]oxazin-6-yl)carbamate | 616 (M + H)+ |

TABLE 2-continued

| Ex. No. | Structure | Name | Observed m/z |
|---|---|---|---|
| 10AD | 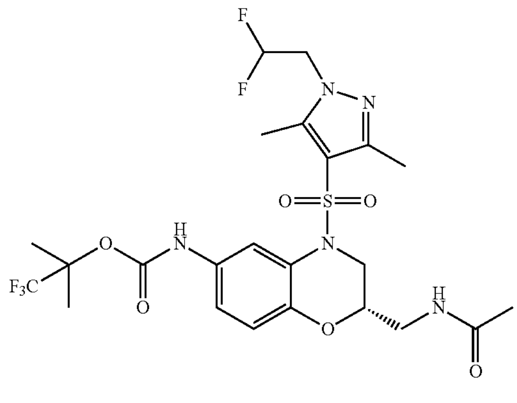 [SMILES: CC(=O)NC[C@H]1CN(S(=O)(=O)c2c(C)nn(CC(F)F)c2C)c2cc(NC(=O)OC(C)(C)C(F)(F)F)ccc2O1] | (S)-1,1,1-trifluoro-2-methylpropan-2-yl (2-(acetamidomethyl)-4-((1-(2,2-difluoroethyl)-3,5-dimethyl-1H-pyrazol-4-yl)sulfonyl)-3,4-dihydro-2H-benzo[b][1,4]oxazin-6-yl)carbamate | 598 (M + H)+ |
| 10AE | 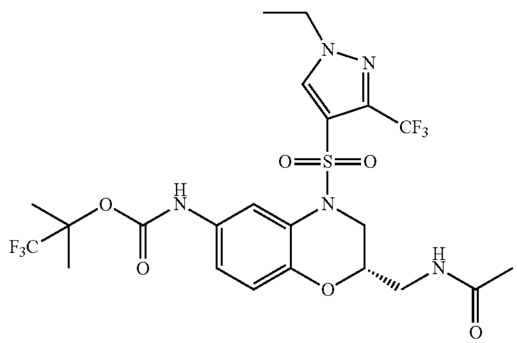 [SMILES: CCn1cc(S(=O)(=O)N2C[C@H](CNC(C)=O)Oc3ccc(NC(=O)OC(C)(C)C(F)(F)F)cc32)c(C(F)(F)F)n1] | (S)-1,1,1-trifluoro-2-methylpropan-2-yl (2-(acetamidomethyl)-4-((1-ethyl-3-(trifluoromethyl)-1H-pyrazol-4-yl)sulfonyl)-3,4-dihydro-2H-benzo[b][1,4]oxazin-6-yl)carbamate | 602 (M + H)+ |
| 10AF | 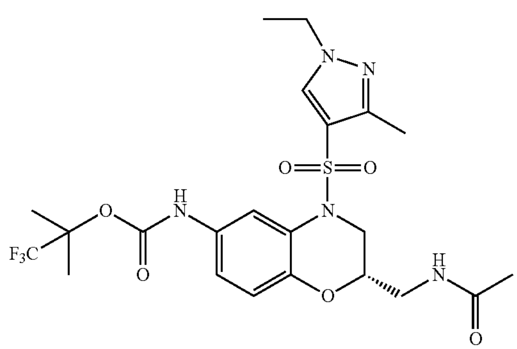 [SMILES: CCn1cc(S(=O)(=O)N2C[C@H](CNC(C)=O)Oc3ccc(NC(=O)OC(C)(C)C(F)(F)F)cc32)c(C)n1] | (S)-1,1,1-trifluoro-2-methylpropan-2-yl (2-(acetamidomethyl)-4-((1-ethyl-3-methyl-1H-pyrazol-4-yl)sulfonyl)-3,4-dihydro-2H-benzo[b][1,4]oxazin-6-yl)carbamate | 548 (M + H)+ |
| 10AG | 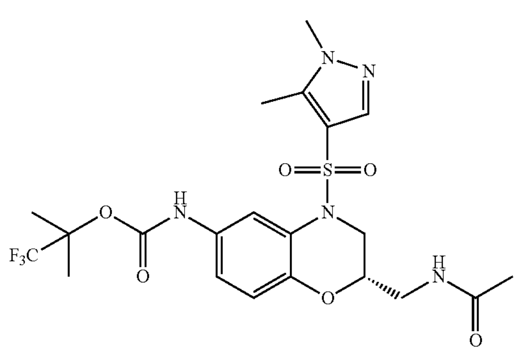 | (S)-1,1,1-trifluoro-2-methylpropan-2-yl (2-(acetamidomethyl)-4-((1,5-dimethyl-1H-pyrazol-4-yl)sulfonyl)-3,4-dihydro-2H-benzo[b][1,4]oxazin-6-yl)carbamate | 543 (M + H)+ |

TABLE 2-continued

| Ex. No. | Structure | Name | Observed m/z |
|---|---|---|---|
| 10AH | 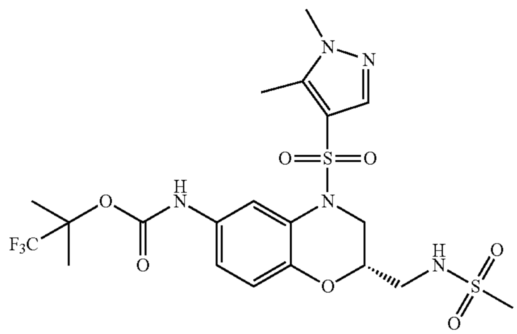 [SMILES: Cc1c(S(=O)(=O)N2C[C@H](CNS(C)(=O)=O)Oc3ccc(NC(=O)OC(C)(C)C(F)(F)F)cc32)cnn1C] | (S)-1,1,1-trifluoro-2-methylpropan-2-yl (4-((1,5-dimethyl-1H-pyrazol-4-yl)sulfonyl)-2-(methylsulfonamidomethyl)-3,4-dihydro-2H-benzo[b][1,4]oxazin-6-yl)carbmate | 570 (M + H)+ |
| 10Ai | 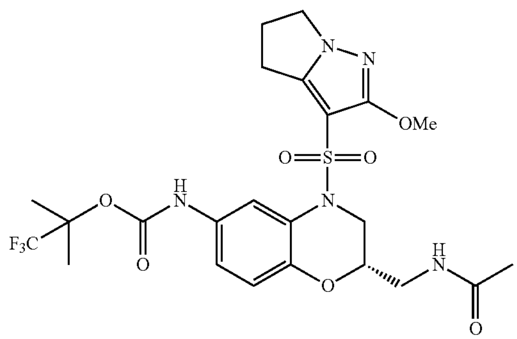 [SMILES: COc1nn2c(c1S(=O)(=O)N1C[C@H](CNC(C)=O)Oc3ccc(NC(=O)OC(C)(C)C(F)(F)F)cc31)CCC2] | (S)-1,1,1-trifluoro-2-methylpropan-2-yl (2-(acetamidomethyl)-4-((2-methoxy-5,6-dihydro-4H-pyrrolo[1,2-b]pyrazol-3-yl)sulfonyl)-3,4-dihydro-2H-benzo[b][1,4]oxazin-6-yl)carbamate | 576.2 (M + H)+ |
| 10AJ | 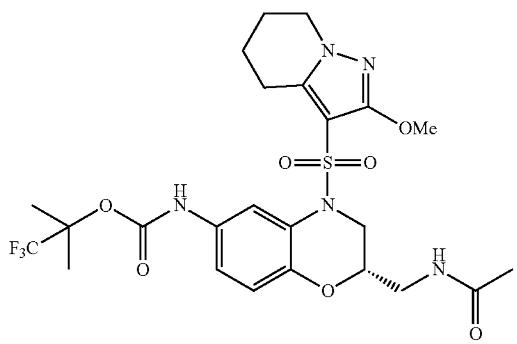 [SMILES: COc1nn2c(c1S(=O)(=O)N1C[C@H](CNC(C)=O)Oc3ccc(NC(=O)OC(C)(C)C(F)(F)F)cc31)CCCC2] | (S)-1,1,1-trifluoro-2-methylpropan-2-yl (2-(acetamidomethyl)-4-((2-methoxy-4,5,6,7-tetrahydropyrazolo[1,5-a]pyridin-3-yl)sulfonyl)-3,4-dihydro-2H-benzo[b][1,4]oxazin-6-yl)carbamate | 590.1 (M + H)+ |
| 10AK | 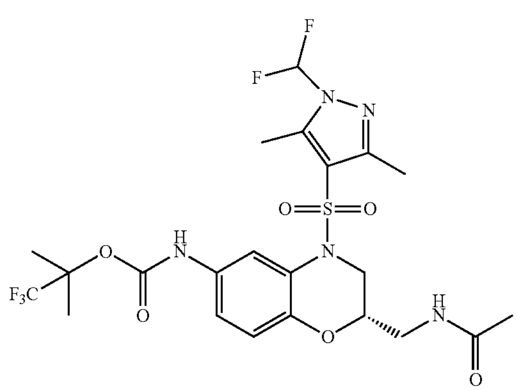 [SMILES: CC(=O)NC[C@H]1CN(S(=O)(=O)c2c(C)nn(C(F)F)c2C)c2cc(NC(=O)OC(C)(C)C(F)(F)F)ccc2O1] | (S)-1,1,1-trifluoro-2-methylpropan-2-yl (2-(acetamidomethyl)-4-((1-(difluoromethyl)-3,5-dimethyl-1H-pyrazol-4-yl)sulfonyl)-3,4-dihydro-2H-benzo[b][1,4]oxazin-6-yl)carbamate | 584 (M + H)+ |

TABLE 2-continued

| Ex. No. | Structure | Name | Observed m/z |
|---|---|---|---|
| 10AL | 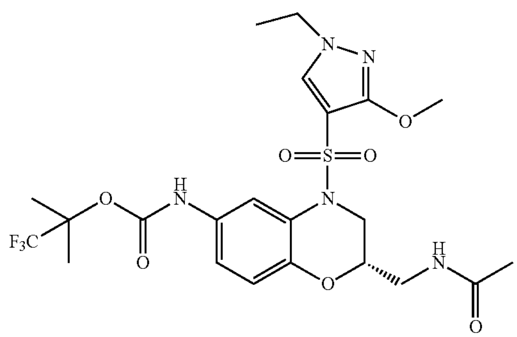 [SMILES: CCn1cc(S(=O)(=O)N2C[C@H](CNC(C)=O)Oc3ccc(NC(=O)OC(C)(C)C(F)(F)F)cc32)c(OC)n1] | (S)-1,1,1-trifluoro-2-methylpropan-2-yl (2-(acetamidomethyl)-4-((1-ethyl-3-methoxy-1H-pyrazol-4-yl)sulfonyl)-3,4-dihydro-2H-benzo[b][1,4]oxazin-6-yl)carbamate | 586.1 (M + Na)+ |
| 10AM | 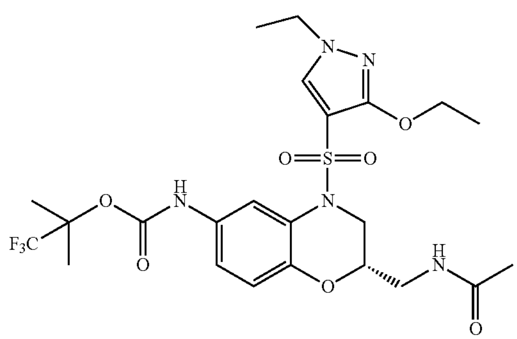 [SMILES: CCOc1nn(CC)cc1S(=O)(=O)N1C[C@H](CNC(C)=O)Oc2ccc(NC(=O)OC(C)(C)C(F)(F)F)cc21] | (S)-1,1,1-trifluoro-2-methylpropan-2-yl (2-(acetamidomethyl)-4-((3-ethoxy-1-ethyl-1H-pyrazol-4-yl)sulfonyl)-3,4-dihydro-2H-benzo[b][1,4]oxazin-6-yl)carbamate | 600.1 (M + Na)+ |
| 10AN | 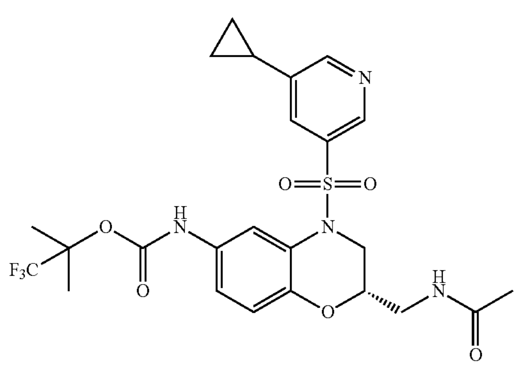 | (S)-1,1,1-trifluoro-2-methylpropan-2-yl (2-(acetamidomethyl)-4-((5-cyclopropylpyridin-3-yl)sulfonyl)-3,4-dihydro-2H-benzo[b][1,4]oxazin-6-yl)carbamate | 557 (M + H)+ |
| 10Ao | 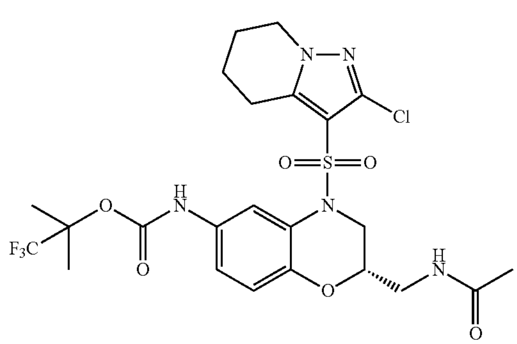 [SMILES: CC(=O)NC[C@H]1CN(S(=O)(=O)c2c(Cl)nn3c2CCCC3)c2cc(NC(=O)OC(C)(C)C(F)(F)F)ccc2O1] | (S)-1,1,1-trifluoro-2-methylpropan-2-yl (2-(acetamidomethyl)-4-((2-chloro-4,5,6,7-tetrahydropyrazolo[1,5-a]pyridin-3-yl)sulfonyl)-3,4-dihydro-2H-benzo[b][1,4]oxazin-6-yl)carbamate | 594.3 (M + H)+ |

TABLE 2-continued

| Ex. No. | Structure | Name | Observed m/z |
|---|---|---|---|
| 10AP | 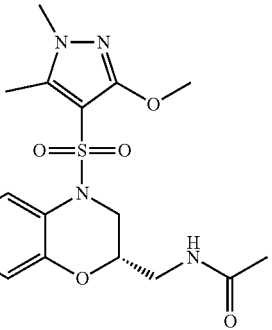 | (S)-1,1,1-trifluoro-2-methylpropan-2-yl (2-(acetamidomethyl)-4-((3-methoxy-1,5-dimethyl-1H-pyrazol-4-yl)sulfonyl)-3,4-dihydro-2H-benzo[b][1,4]oxazin-6-yl)carbamate | 564.3 (M + H)+ |
| 10AQ | 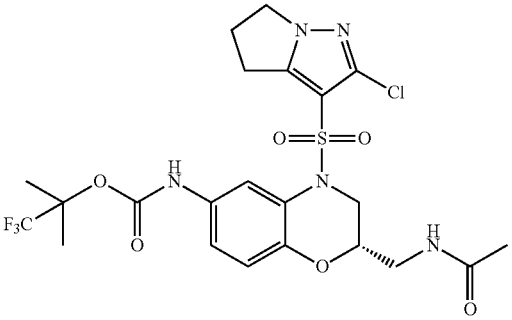 [SMILES: CC(=O)NC[C@H]1CN(S(=O)(=O)c2c(Cl)nn3c2CCC3)c2cc(NC(=O)OC(C)(C)C(F)(F)F)ccc2O1] | (S)-1,1,1-trifluoro-2-methylpropan-2-yl (2-(acetamidomethyl)-4-((2-chloro-5,6-dihydro-4H-pyrrolo[1,2-b]pyrazol-3-yl)sulfonyl)-3,4-dihydro-2H-benzo[b][1,4]oxazin-6-yl)carbamate | 580.1 (M + H)+ |
| 10AR | 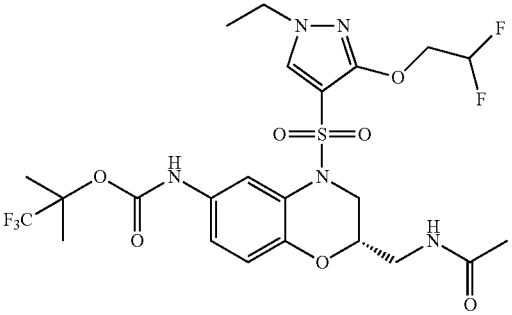 [SMILES: CCn1cc(S(=O)(=O)N2C[C@H](CNC(C)=O)Oc3ccc(NC(=O)OC(C)(C)C(F)(F)F)cc32)c(OCC(F)F)n1] | (S)-1,1,1-trifluoro-2-methylpropan-2-yl (2-(acetamidomethyl)-4-((3-(2,2-difluoroethoxy)-1-ethyl-1H-pyrazol-4-yl)sulfonyl)-3,4-dihydro-2H-benzo[b][1,4]oxazin-6-yl)carbamate | 636.2 (M + Na)+ |
| 10AS | 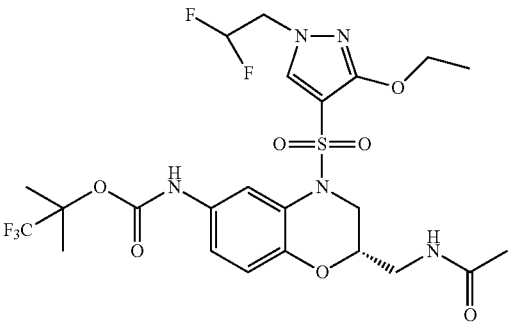 [SMILES: CCOc1nn(CC(F)F)cc1S(=O)(=O)N1C[C@H](CNC(C)=O)Oc2ccc(NC(=O)OC(C)(C)C(F)(F)F)cc21] | (S)-1,1,1-trifluoro-2-methylpropan-2-yl (2-(acetamidomethyl)-4-((1-(2,2-difluoroethyl)-3-ethoxy-1H-pyrazol-4-yl)sulfonyl)-3,4-dihydro-2H-benzo[b][1,4]oxazin-6-yl)carbamate | 636.1 (M + Na)+ |

TABLE 2-continued

| Ex. No. | Structure | Name | Observed m/z |
|---|---|---|---|
| 10AT | 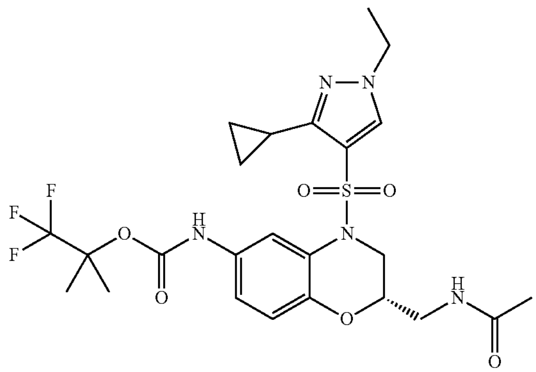 [SMILES: CCn1cc(S(=O)(=O)N2C[C@H](CNC(C)=O)Oc3ccc(NC(=O)OC(C)(C)C(F)(F)F)cc32)c(C2CC2)n1] | (S)-1,1,1-trifluoro-2-methylpropan-2-yl (2-(acetamidomethyl)-4-((3-cyclopropyl-1-ethyl-1H-pyrazol-4-yl)sulfonyl)-3,4-dihydro-2H-benzo[b][1,4]oxazin-6-yl)carbamate | 574.2 (M + H)+ |
| 10AU | 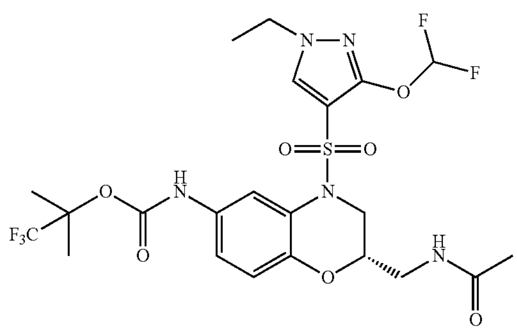 [SMILES: CCn1cc(S(=O)(=O)N2C[C@H](CNC(C)=O)Oc3ccc(NC(=O)OC(C)(C)C(F)(F)F)cc32)c(OC(F)F)n1] | (S)-1,1,1-trifluoro-2-methylpropan-2-yl (2-(acetamidomethyl)-4-((3-(difluoromethoxy)-1-ethyl-1H-pyrazol-4-yl)sulfonyl)-3,4-dihydro-2H-benzo[b][1,4]oxazin-6-yl)carbamate | 600.2 (M + H)+ |
| 10AV | 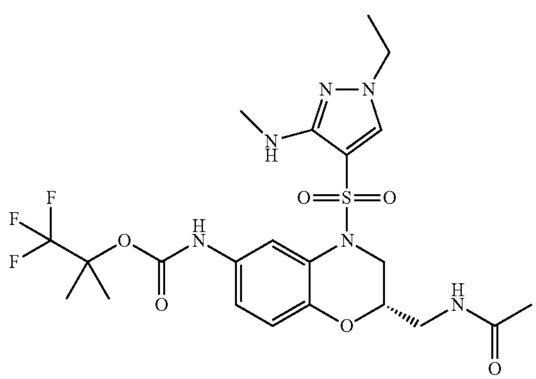 [SMILES: CCn1cc(S(=O)(=O)N2C[C@H](CNC(C)=O)Oc3ccc(NC(=O)OC(C)(C)C(F)(F)F)cc32)c(NC)n1] | (S)-1,1,1-trifluoro-2-methylpropan-2-yl (2-(acetamidomethyl)-4-((1-ethyl-3-(methylamino)-1H-pyrazol-4-yl)sulfonyl)-3,4-dihydro-2H-benzo[b][1,4]oxazin-6-yl)carbamate | 563.2 (M + H)+ |
| 10AW | 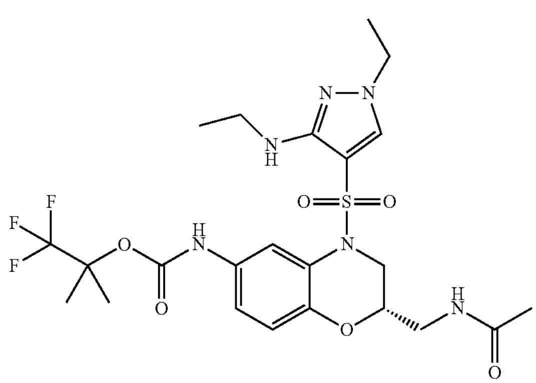 [SMILES: CCNc1nn(CC)cc1S(=O)(=O)N1C[C@H](CNC(C)=O)Oc2ccc(NC(=O)OC(C)(C)C(F)(F)F)cc21] | (S)-1,1,1-trifluoro-2-methylpropan-2-yl (2-(acetamidomethyl)-4-((1-ethyl-3-(ethylamino)-1H-pyrazol-4-yl)sulfonyl)-3,4-dihydro-2H-benzo[b][1,4]oxazin-6-yl)carbamate | 577.2 (M + H)+ |

TABLE 2-continued

| Ex. No. | Structure | Name | Observed m/z |
|---|---|---|---|
| 10AX | 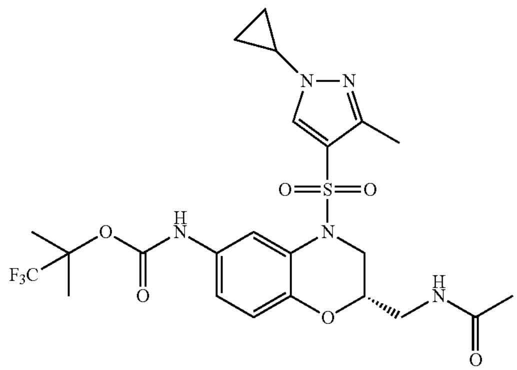 [SMILES: CC(=O)NC[C@H]1CN(S(=O)(=O)c2cn(C3CC3)nc2C)c2cc(NC(=O)OC(C)(C)C(F)(F)F)ccc2O1] | (S)-1,1,1-trifluoro-2-methylpropan-2-yl (2-(acetamidomethyl)-4-((1-cyclopropyl-3-methyl-1H-pyrazol-4-yl)sulfonyl)-3,4-dihydro-2H-benzo[b][1,4]oxazin-6-yl)carbamate | 560 (M + H)+ |
| 10AY | 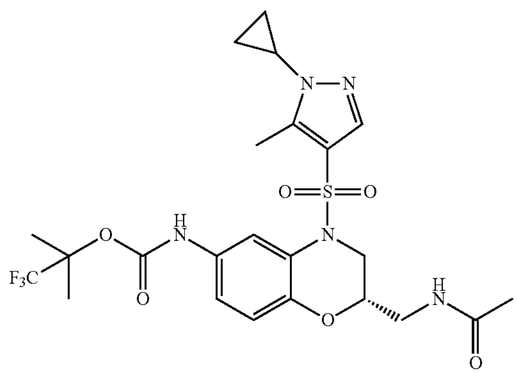 [SMILES: CC(=O)NC[C@H]1CN(S(=O)(=O)c2cnn(C3CC3)c2C)c2cc(NC(=O)OC(C)(C)C(F)(F)F)ccc2O1] | (S)-1,1,1-trifluoro-2-methylpropan-2-yl (2-(acetamidomethyl)-4-((1-cyclopropyl-5-methyl-1H-pyrazol-4-yl)sulfonyl)-3,4-dihydro-2H-benzo[b][1,4]oxazin-6-yl)carbamate | 560 (M + H)+ |
| 10AZ | 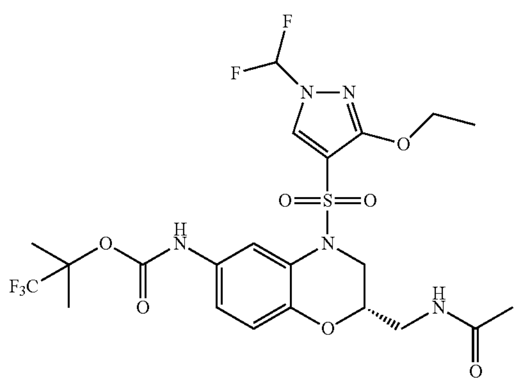 [SMILES: CCOc1nn(C(F)F)cc1S(=O)(=O)N1C[C@H](CNC(C)=O)Oc2ccc(NC(=O)OC(C)(C)C(F)(F)F)cc21] | (S)-1,1,1-trifluoro-2-methylpropan-2-yl (2-(acetamidomethyl)-4-((1-(difluoromethyl)-3-ethoxy-1H-pyrazol-4-yl)sulfonyl)-3,4-dihydro-2H-benzo[b][1,4]oxazin-6-yl)carbamate | 600.4 (M + H)+ |
| 10BA | 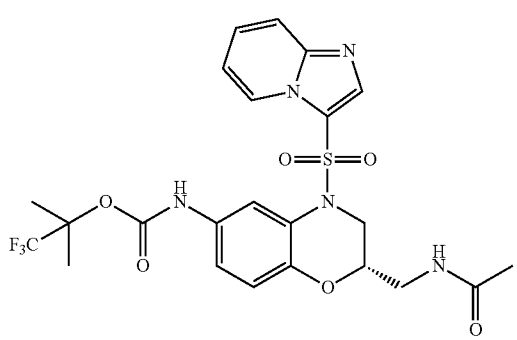 [SMILES: CC(=O)NC[C@H]1CN(S(=O)(=O)c2cnc3ccccn23)c2cc(NC(=O)OC(C)(C)C(F)(F)F)ccc2O1] | (S)-1,1,1-trifluoro-2-methylpropan-2-yl (2-(acetamidomethyl)-4-(imidazo[1,2-a]pyridin-3-ylsulfonyl)-3,4-dihydro-2H-benzo[b][1,4]oxazin-6-yl)carbamate | 556.4 (M + H)+ |

TABLE 2-continued

| Ex. No. | Structure | Name | Observed m/z |
|---|---|---|---|
| 10BB | 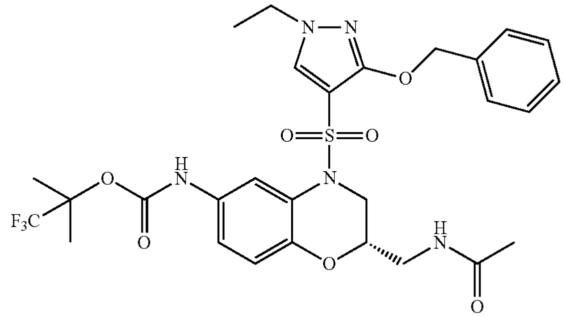 [SMILES: CCn1cc(S(=O)(=O)N2C[C@H](CNC(C)=O)Oc3ccc(NC(=O)OC(C)(C)C(F)(F)F)cc32)c(OCc2ccccc2)n1] | (S)-1,1,1-trifluoro-2-methylpropan-2-yl (2-(acetamidomethyl)-4-((3-(benzyloxy)-1-ethyl-1H-pyrazol-4-yl)sulfonyl)-3,4-dihydro-2H-benzo[b][1,4]oxazin-6-yl)carbamate | 662.3 (M + Na)+ |
| 10BC | 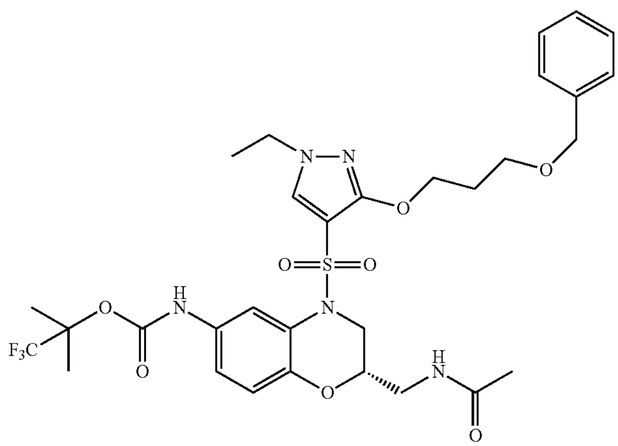 [SMILES: CCn1cc(S(=O)(=O)N2C[C@H](CNC(C)=O)Oc3ccc(NC(=O)OC(C)(C)C(F)(F)F)cc32)c(OCCCOCc2ccccc2)n1] | (S)-1,1,1-trifluoro-2-methylpropan-2-yl (2-(acetamidomethyl)-4-((3-(3-(benzyloxy)propoxy)-1-ethyl-1H-pyrazol-4-yl)sulfonyl)-3,4-dihydro-2H-benzo[b][1,4]oxazin-6-yl)carbamate | 720.3 (M + Na)+ |
| 10BD | 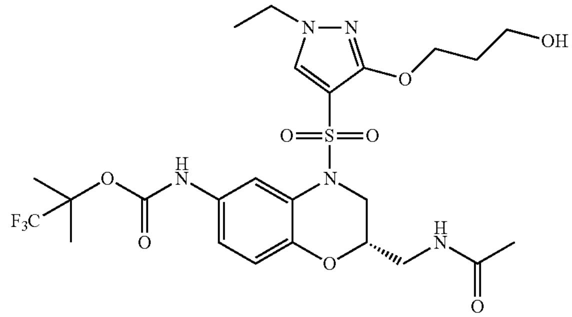 [SMILES: CCn1cc(S(=O)(=O)N2C[C@H](CNC(C)=O)Oc3ccc(NC(=O)OC(C)(C)C(F)(F)F)cc32)c(OCCCO)n1] | (S)-1,1,1-trifluoro-2-methylpropan-2-yl (2-(acetamidomethyl)-4-((1-ethyl-3-(3-hydroxypropoxy)-1H-pyrazol-4-yl)sulfonyl)-3,4-dihydro-2H-benzo[b][1,4]oxazin-6-yl)carbamate | 630.3 (M + Na)+ |
| 10BE | 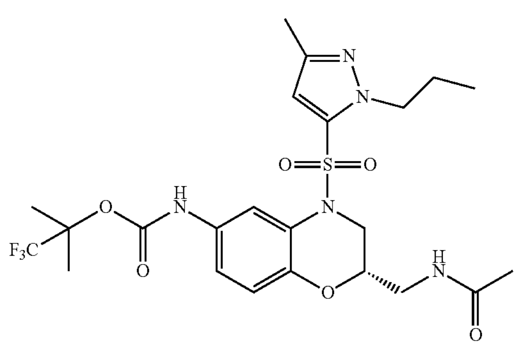 [SMILES: CCCn1nc(C)cc1S(=O)(=O)N1C[C@H](CNC(C)=O)Oc2ccc(NC(=O)OC(C)(C)C(F)(F)F)cc21] | (S)-1,1,1-trifluoro-2-methylpropan-2-yl (2-(acetamidomethyl)-4-((3-methyl-1-propyl-1H-pyrazol-5-yl)sulfonyl)-3,4-dihydro-2H-benzo[b][1,4]oxazin-6-yl)carbamate | 562 (M + H)+ |

TABLE 2-continued

| Ex. No. | Structure | Name | Observed m/z |
|---|---|---|---|
| 10BF | 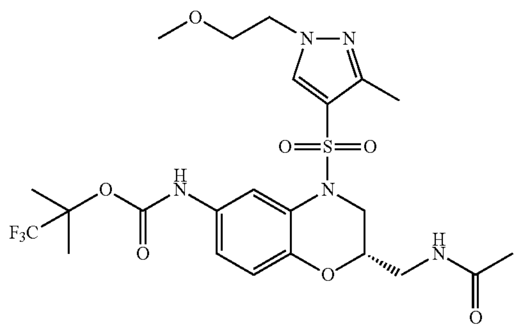 [SMILES: COCCn1cc(S(=O)(=O)N2C[C@H](CNC(C)=O)Oc3ccc(NC(=O)OC(C)(C)C(F)(F)F)cc32)c(C)n1] | (S)-1,1,1-trifluoro-2-methylpropan-2-yl (2-(acetamidomethyl)-4-((1-(2-methoxyethyl)-3-methyl-1H-pyrazol-4-yl)sulfonyl)-3,4-dihydro-2H-benzo[b][1,4]oxazin-6-yl)carbamate | 578 (M + H)+ |
| 10BG | 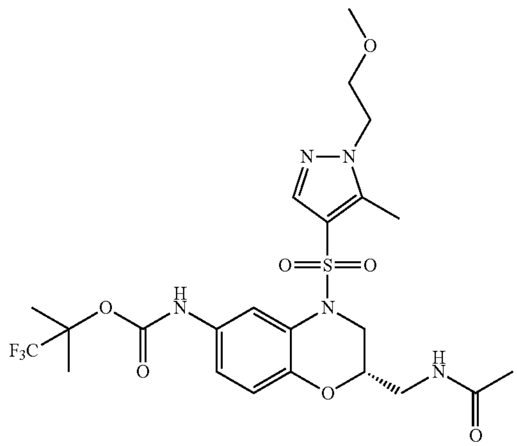 [SMILES: COCCn1ncc(S(=O)(=O)N2C[C@H](CNC(C)=O)Oc3ccc(NC(=O)OC(C)(C)C(F)(F)F)cc32)c1C] | (S)-1,1,1-trifluoro-2-methylpropan-2-yl (2-(acetamidomethyl)-4-((1-(2-methoxyethyl)-5-methyl-1H-pyrazol-4-yl)sulfonyl)-3,4-dihydro-2H-benzo[b][1,4]oxazin-6-yl)carbamate | 578 (M + H)+ |
| 10BH | 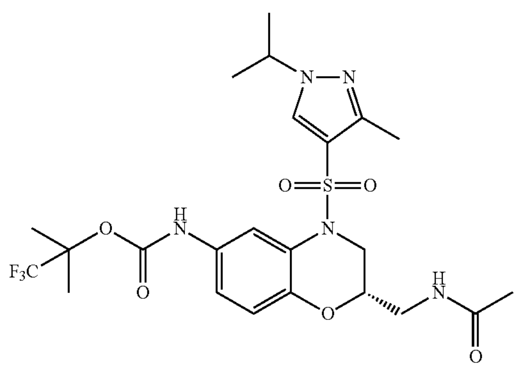 [SMILES: CC(=O)NC[C@H]1CN(S(=O)(=O)c2cn(C(C)C)nc2C)c2cc(NC(=O)OC(C)(C)C(F)(F)F)ccc2O1] | (S)-1,1,1-trifluoro-2-methylpropan-2-yl (2-(acetamidomethyl)-4-((1-isopropyl-3-methyl-1H-pyrazol-4-yl)sulfonyl)-3,4-dihydro-2H-benzo[b][1,4]oxazin-6-yl)carbamate | 562 (M + H)+ |
| 10Bi | 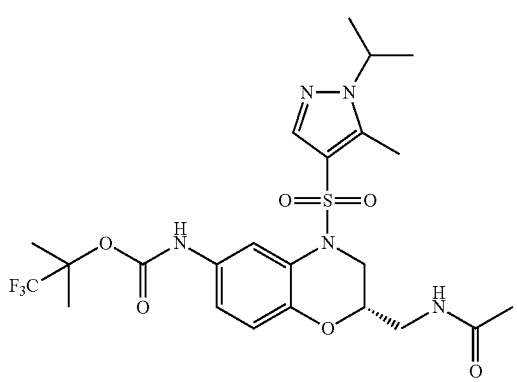 [SMILES: CC(=O)NC[C@H]1CN(S(=O)(=O)c2cnn(C(C)C)c2C)c2cc(NC(=O)OC(C)(C)C(F)(F)F)ccc2O1] | (S)-1,1,1-trifluoro-2-methylpropan-2-yl (2-(acetamidomethyl)-4-((1-isopropyl-5-methyl-1H-pyrazol-4-yl)sulfonyl)-3,4-dihydro-2H-benzo[b][1,4]oxazin-6-yl)carbamate | 562 (M + H)+ |

TABLE 2-continued

| Ex. No. | Structure | Name | Observed m/z |
|---|---|---|---|
| 10BJ | 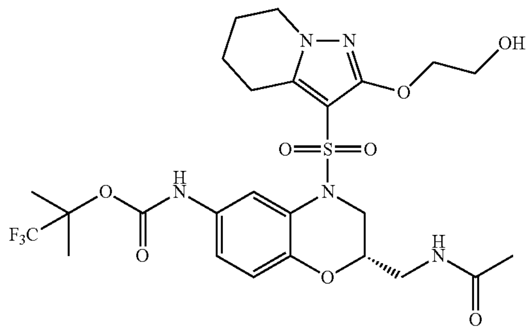 [SMILES: CC(=O)NC[C@H]1CN(S(=O)(=O)c2c(OCCO)nn3c2CCCC3)c2cc(NC(=O)OC(C)(C)C(F)(F)F)ccc2O1] | (S)-1,1,1-trifluoro-2-methylpropan-2-yl (2-(acetamidomethyl)-4-((2-(2-hydroxyethoxy)-4,5,6,7-tetrahydropyrazolo[1,5-a]pyridin-3-yl)sulfonyl)-3,4-dihydro-2H-benzo[b][1,4]oxazin-6-yl)carbamate | 620.4 (M + H)+ |
| 10BK | 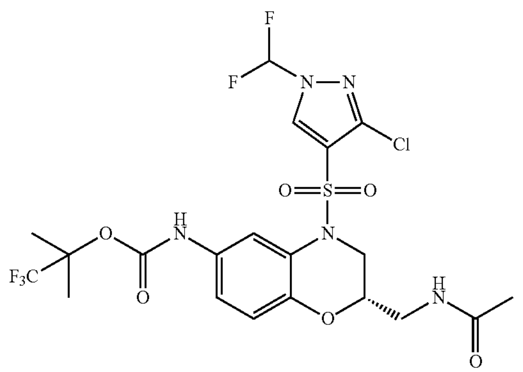 [SMILES: CC(=O)NC[C@H]1CN(S(=O)(=O)c2cn(C(F)F)nc2Cl)c2cc(NC(=O)OC(C)(C)C(F)(F)F)ccc2O1] | (S)-1,1,1-trifluoro-2-methylpropan-2-yl (2-(acetamidomethyl)-4-((3-chloro-1-(difluoromethyl)-1H-pyrazol-4-yl)sulfonyl)-3,4-dihydro-2H-benzo[b][1,4]oxazin-6-yl)carbamate | 606.9 (M + NH4)+ |
| 10BL | 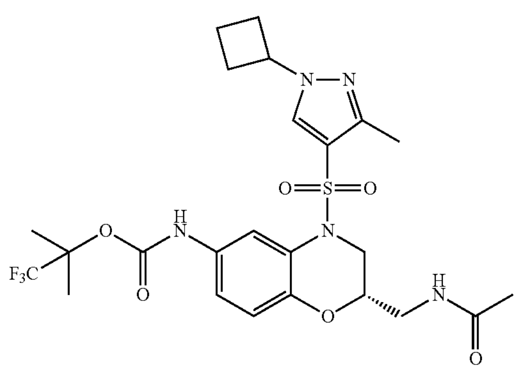 [SMILES: CC(=O)NC[C@H]1CN(S(=O)(=O)c2cn(C3CCC3)nc2C)c2cc(NC(=O)OC(C)(C)C(F)(F)F)ccc2O1] | (S)-1,1,1-trifluoro-2-methylpropan-2-yl (2-(acetamidomethyl)-4-((3-methyl-1-(oxetan-3-yl)-1H-pyrazol-4-yl)sulfonyl)-3,4-dihydro-2H-benzo[b][1,4]oxazin-6-yl)carbamate | 576 (M + H)+ |
| 10BM | 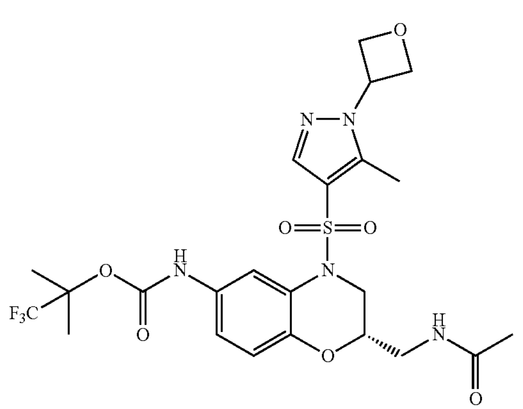 [SMILES: CC(=O)NC[C@H]1CN(S(=O)(=O)c2cnn(C3COC3)c2C)c2cc(NC(=O)OC(C)(C)C(F)(F)F)ccc2O1] | (S)-1,1,1-trifluoro-2-methylpropan-2-yl (2-(acetamidomethyl)-4-((5-methyl-1-(oxetan-3-yl)-1H-pyrazol-4-yl)sulfonyl)-3,4-dihydro-2H-benzo[b][1,4]oxazin-6-yl)carbamate | 576 (M + H)+ |

TABLE 2-continued

| Ex. No. | Structure | Name | Observed m/z |
|---|---|---|---|
| 10BN | 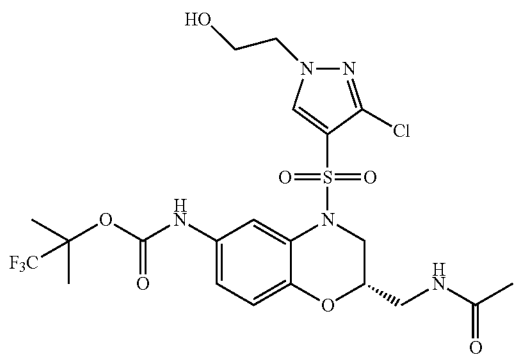 | (S)-1,1,1-trifluoro-2-methylpropan-2-yl (2-(acetamidomethyl)-4-((1-(2-hydroxyethyl)-3-methyl-1H-pyrazol-4-yl)sulfonyl)-3,4-dihydro-2H-benzo[b][1,4]oxazin-6-yl)carbamate | 564 (M + H)+ |
| 10Bo | 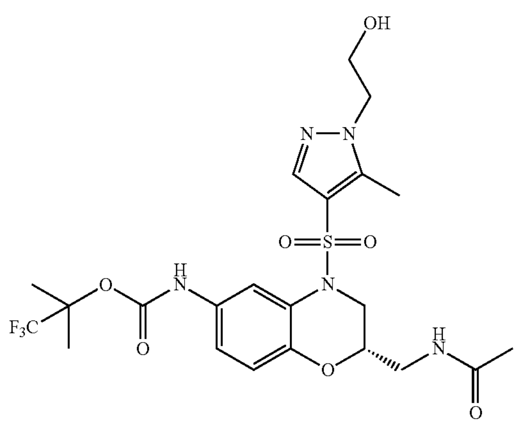 [SMILES: CC(=O)NC[C@H]1CN(S(=O)(=O)c2cnn(CCO)c2C)c2cc(NC(=O)OC(C)(C)C(F)(F)F)ccc2O1] | (S)-1,1,1-trifluoro-2-methylpropan-2-yl (2-(acetamidomethyl)-4-((1-(2-hydroxyethyl)-5-methyl-1H-pyrazol-4-yl)sulfonyl)-3,4-dihydro-2H-benzo[b][1,4]oxazin-6-yl)carbamate | 564 (M + H)+ |
| 10BP | 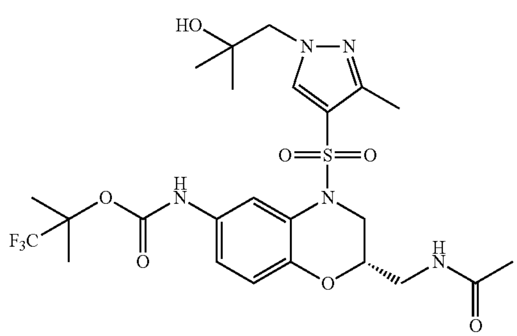 [SMILES: CC(=O)NC[C@H]1CN(S(=O)(=O)c2cn(CC(C)(C)O)nc2C)c2cc(NC(=O)OC(C)(C)C(F)(F)F)ccc2O1] | (S)-1,1,1-trifluoro-2-methylpropan-2-yl (2-(acetamidomethyl)-4-((1-(2-hydroxy-2-methylpropyl)-3-methyl-1H-pyrazol-4-yl)sulfonyl)-3,4-dihydro-2H-benzo[b][1,4]oxazin-6-yl)carbamate | 592 (M + H)+ |
| 10BQ | 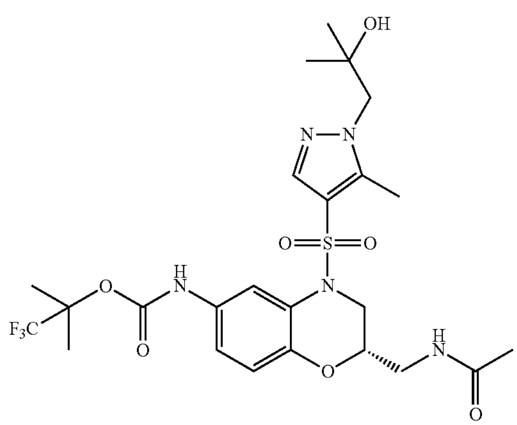 [SMILES: CC(=O)NC[C@H]1CN(S(=O)(=O)c2cnn(CC(C)(C)O)c2C)c2cc(NC(=O)OC(C)(C)C(F)(F)F)ccc2O1] | (S)-1,1,1-trifluoro-2-methylpropan-2-yl (2-(acetamidomethyl)-4-((1-(2-hydroxy-2-methylpropyl)-5-methyl-1H-pyrazol-4-yl)sulfonyl)-3,4-dihydro-2H-benzo[b][1,4]oxazin-6-yl)carbamate | 592 (M + H)+ |

TABLE 2-continued

| Ex. No. | Structure | Name | Observed m/z |
|---|---|---|---|
| 10BR | 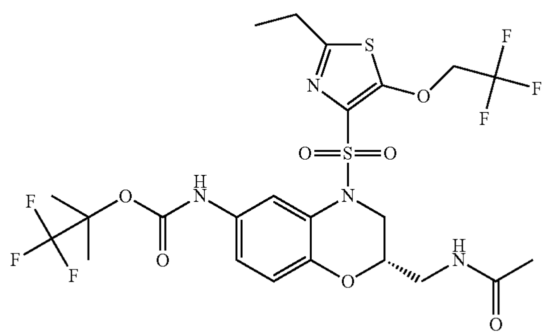 [SMILES: CCc1nc(S(=O)(=O)N2C[C@H](CNC(C)=O)Oc3ccc(NC(=O)OC(C)(C)C(F)(F)F)cc32)c(OCC(F)(F)F)s1] | 2,2,2-trifluoro-1,1-dimethylethyl [(2S)-2-[(acetylamino)methyl]-4-{[2-ethyl-5-(2,2,2-trifluoroethoxy)-1,3-thiazol-4-yl]sulfonyl}-3,4-dihydro-2H-1,4-benzoxazin-6-yl]carbamate | 649 (M + H)+ |
| 10BS | 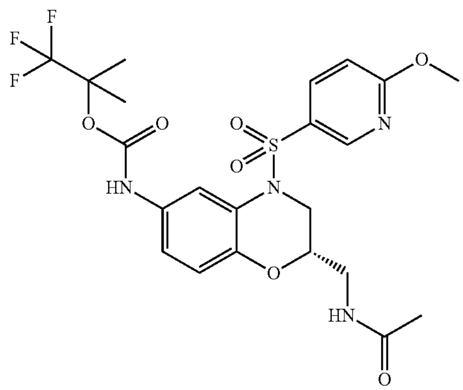 [SMILES: COc1ccc(S(=O)(=O)N2C[C@H](CNC(C)=O)Oc3ccc(NC(=O)OC(C)(C)C(F)(F)F)cc32)cn1] | 2,2,2-trifluoro-1,1-dimethylethyl {(2S)-2-[(acetylamino)methyl]-4-[(6-methoxypyridin-3-yl)sulfonyl]-3,4-dihydro-2H-1,4-benzoxazin-6-yl}carbamate | 547 (M + H)+ |
| 10BT | 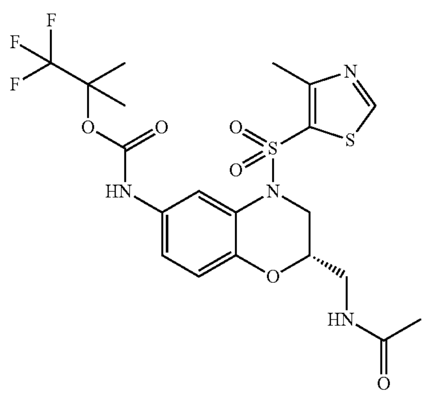 [SMILES: CC(=O)NC[C@H]1CN(S(=O)(=O)c2scnc2C)c2cc(NC(=O)OC(C)(C)C(F)(F)F)ccc2O1] | 2,2,2-trifluoro-1,1-dimethylethyl {(2S)-2-[(acetylamino)methyl]-4-[(4-methyl-1,3-thiazol-5-yl)sulfonyl]-3,4-dihydro-2H-1,4-benzoxazin-6-yl}carbamate | 537 (M + H)+ |
| 10BU | 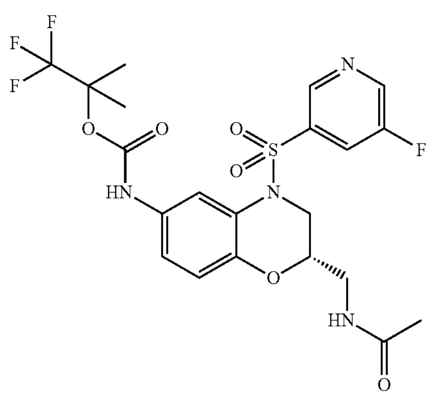 [SMILES: CC(=O)NC[C@H]1CN(S(=O)(=O)c2cncc(F)c2)c2cc(NC(=O)OC(C)(C)C(F)(F)F)ccc2O1] | 2,2,2-trifluoro-1,1-dimethylethyl {(2S)-2-[(acetylamino)methyl]-4-[(5-fluoropyridin-3-yl)suflonyl]-3,4-dihydro-2H-1,4-benzoxazin-6-yl}carbamate | 535 (M + H)+ |

TABLE 2-continued

| Ex. No. | Structure | Name | Observed m/z |
|---|---|---|---|
| 10BV | 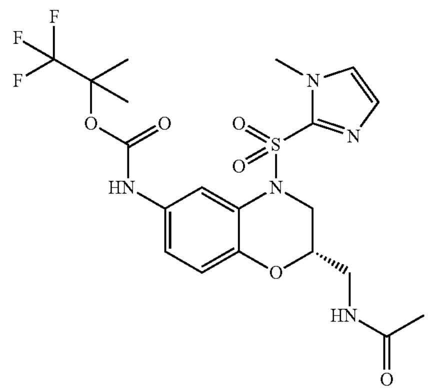 [SMILES: CC(=O)NC[C@H]1CN(S(=O)(=O)c2nccn2C)c2cc(NC(=O)OC(C)(C)C(F)(F)F)ccc2O1] | 2,2,2-trifluoro-1,1-dimethylethyl {(2S)-2-[(acetylamino)methyl]-4-[(1-methyl-1H-imidazol-2-yl)sulfonyl]-3,4-dihydro-2H-1,4-benzoxazin-6-yl}carbamate | 520 (M + H)+ |
| 10BW | 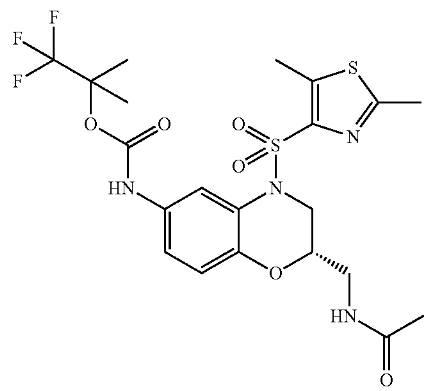 [SMILES: CC(=O)NC[C@H]1CN(S(=O)(=O)c2nc(C)sc2C)c2cc(NC(=O)OC(C)(C)C(F)(F)F)ccc2O1] | 2,2,2-trifluoro-1,1-dimethylethyl {(2S)-2-[(acetylamino)methyl]-4-[(2,5-dimethyl-1,3-thiazol-4-yl)sulfonyl]-3,4-dihydro-2H-1,4-benzoxazin-6-yl}carbamate | 551 (M + H)+ |
| 10BX | 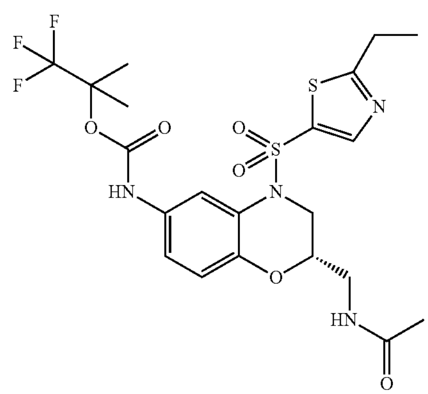 [SMILES: CCc1ncc(S(=O)(=O)N2C[C@H](CNC(C)=O)Oc3ccc(NC(=O)OC(C)(C)C(F)(F)F)cc32)s1] | 2,2,2-trifluoro-1,1-dimethylethyl {(2S)-2-[(acetylamino)methyl]-4-[(2-ethyl-1,3-thiazol-5-yl)sulfonyl]-3,4-dihydro-2H-1,4-benzoxazin-6-yl}carbamate | 551 (M + H)+ |
| 10BY | 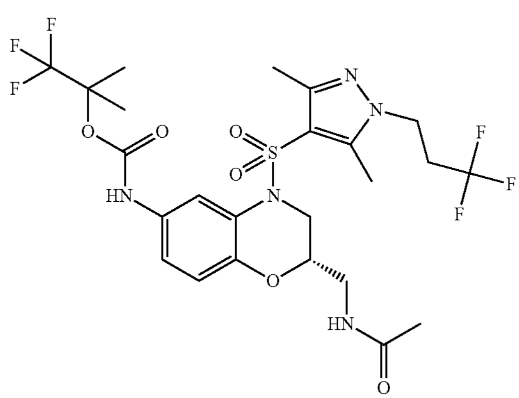 [SMILES: CC(=O)NC[C@H]1CN(S(=O)(=O)c2c(C)nn(CCC(F)(F)F)c2C)c2cc(NC(=O)OC(C)(C)C(F)(F)F)ccc2O1] | 2,2,2-trifluoro-1,1-dimethylethyl [(2S)-2-[(acetylamino)methyl]-4-{[3,5-dimethyl-1-(3,3,3-trifluoropropyl)-1H-pyrazol-4-yl]sulfonyl}-3,4-dihydro-2H-1,4-benzoxazin-6-yl]carbamate | 631 (M + H)+ |

TABLE 2-continued

| Ex. No. | Structure | Name | Observed m/z |
|---|---|---|---|
| 10BZ | 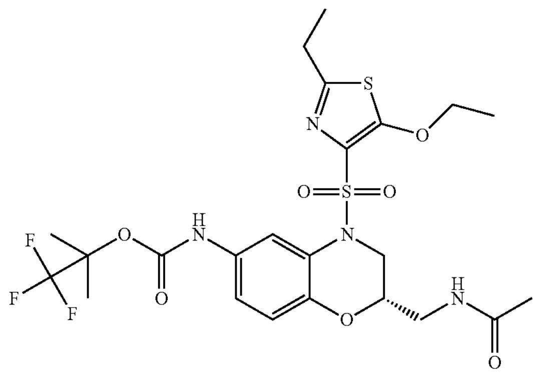 [SMILES: CCOc1sc(CC)nc1S(=O)(=O)N1C[C@H](CNC(C)=O)Oc2ccc(NC(=O)OC(C)(C)C(F)(F)F)cc21] | 2,2,2-trifluoro-1,1-dimethylethyl {(2S)-2-[(acetylamino)methyl]-4-[(5-ethoxy-2-ethyl-1,3-thiazol-4-yl)sulfonyl]-3,4-dihydro-2H-1,4-benzoxazin-6-yl}carbamate | 595 (M + H)+ |
| 10CA | 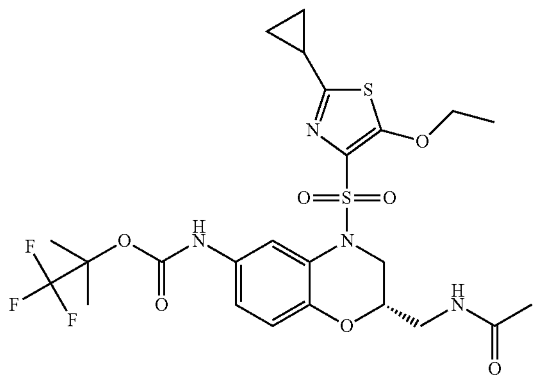 [SMILES: CCOc1sc(C2CC2)nc1S(=O)(=O)N1C[C@H](CNC(C)=O)Oc2ccc(NC(=O)OC(C)(C)C(F)(F)F)cc21] | 2,2,2-trifluoro-1,1-dimethylethyl {(2S)-2-[(acetylamino)methyl]-4-[(2-cyclopropyl-5-ethoxy-1,3-thiazol-4-yl)sulfonyl]-3,4-dihydro-2H-1,4-benzoxazin-6-yl}carbamate | 607 (M + H)+ |
| 10CB | 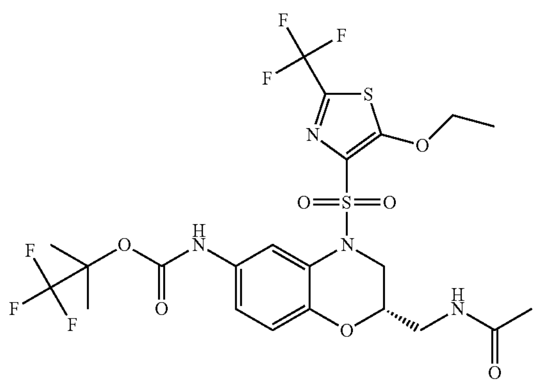 [SMILES: CCOc1sc(C(F)(F)F)nc1S(=O)(=O)N1C[C@H](CNC(C)=O)Oc2ccc(NC(=O)OC(C)(C)C(F)(F)F)cc21] | 2,2,2-trifluoro-1,1-dimethylethyl [(2S)-2-[(acetylamino)methyl]-4-{[5-ethoxy-2-(trifluoromethyl)-1,3-thiazol-4-yl]sulfonyl}-3,4-dihydro-2H-1,4-benzoxazin-6-yl]carbamate | 635 (M + H)+ |
| 10CC | 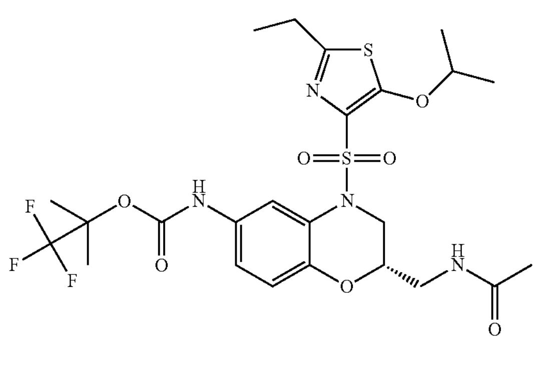 [SMILES: CCc1nc(S(=O)(=O)N2C[C@H](CNC(C)=O)Oc3ccc(NC(=O)OC(C)(C)C(F)(F)F)cc32)c(OC(C)C)s1] | 2,2,2-trifluoro-1,1-dimethylethyl [(2S)-2-[(acetylamino)methyl]-4-{[2-ethyl-5-(1-methylethoxy)-1,3-thiazol-4-yl]sulfonyl}-3,4-dihydro-2H-1,4-benzoxazin-6-yl]carbamate | 609 (M + H)+ |

| Ex. No. | Structure | Name | Observed m/z |
|---|---|---|---|
| 10CD | 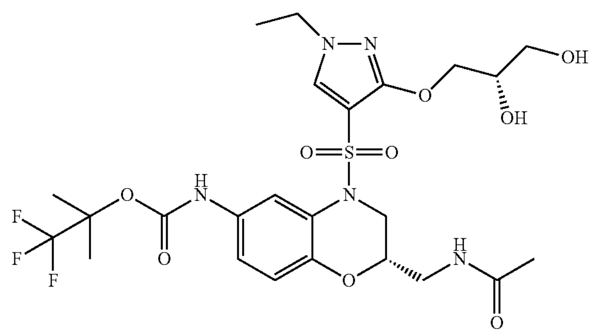 [SMILES: CCn1cc(S(=O)(=O)N2C[C@H](CNC(C)=O)Oc3ccc(NC(=O)OC(C)(C)C(F)(F)F)cc32)c(OC[C@@H](O)CO)n1] | 2,2,2-trifluoro-1,1-dimethylethyl {(2S)-2-[(acetylamino)methyl]-4-[(3-{[(2S)-2,3-dihydroxypropyl]oxy}-1-ethyl-1H-pyrazol-4-yl)sulfonyl]-3,4-dihydro-2H-1,4-benzoxazin-6-yl}carbamate | 624 (M + H)+ |
| 10CE | 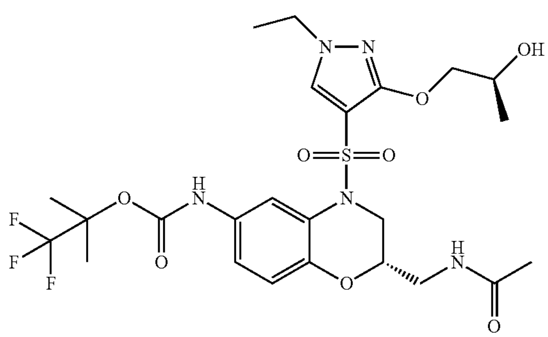 [SMILES: CCn1cc(S(=O)(=O)N2C[C@H](CNC(C)=O)Oc3ccc(NC(=O)OC(C)(C)C(F)(F)F)cc32)c(OC[C@H](C)O)n1] | 2,2,2-trifluoro-1,1-dimethylethyl {(2S)-2-[(acetylamino)methyl]-4-[(1-ethyl-3-{[(2S)-2-hydroxypropyl]oxy}-1H-pyrazol-4-yl)sulfonyl]-3,4-dihydro-2H-1,4-benzoxazin-6-yl}carbamate | 608 (M + H)+ |
| 10CF | 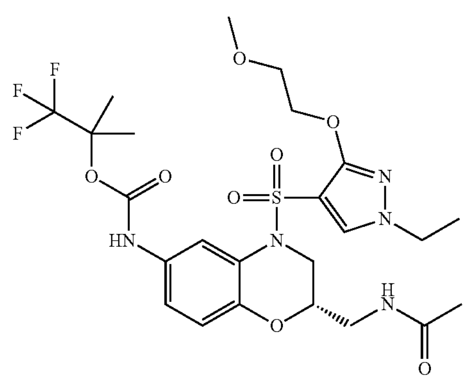 [SMILES: CCn1cc(S(=O)(=O)N2C[C@H](CNC(C)=O)Oc3ccc(NC(=O)OC(C)(C)C(F)(F)F)cc32)c(OCCOC)n1] | 2,2,2-trifluoro-1,1-dimethylethyl [(2S)-2-[(acetylamino)methyl]-4-{[1-ethyl-3-(2-methoxyethoxy)-1H-pyrazol-4-yl]sulfonyl}-3,4-dihydro-2H-1,4-benzoxazin-6-yl]carbamate | 608 (M + H)+ |
| 10CG | 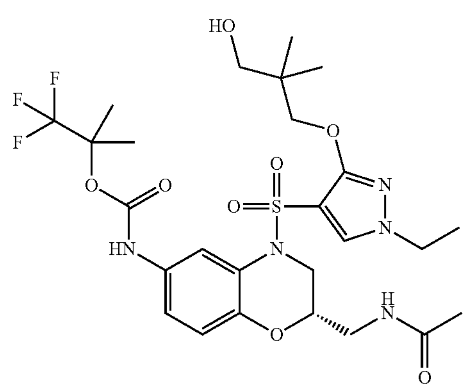 [SMILES: CCn1cc(S(=O)(=O)N2C[C@H](CNC(C)=O)Oc3ccc(NC(=O)OC(C)(C)C(F)(F)F)cc32)c(OCC(C)(C)CO)n1] | 2,2,2-trifluoro-1,1-dimethylethyl [(2S)-2-[(acetylamino)methyl]-4-{[1-ethyl-3-(3-hydroxy-2,2-dimethylpropoxy)-1H-pyrazol-4-yl]sulfonyl}-3,4-dihydro-2H-1,4-benzoxazin-6-yl]carbamate | 636 (M + H)+ |

TABLE 2-continued

| Ex. No. | Structure | Name | Observed m/z |
|---|---|---|---|
| 10CH | 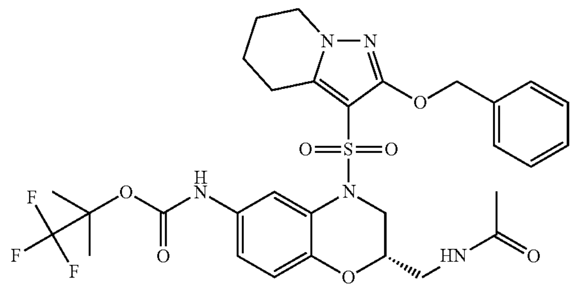 [SMILES: CC(=O)NC[C@H]1CN(S(=O)(=O)c2c(OCc3ccccc3)nn3c2CCCC3)c2cc(NC(=O)OC(C)(C)C(F)(F)F)ccc2O1] | 2,2,2-trifluoro-1,1-dimethylethyl [(2S)-2-[(acetylamino)methyl]-4-{[2-(benzyloxy)-4,5,6,7-tetrahydropyrazolo[1,5-a]pyridin-3-yl]sulfonyl}-3,4-dihydro-2H-1,4-benzoxazin-6-yl]carbamate | 666 (M + H)+ |
| 10Ci | 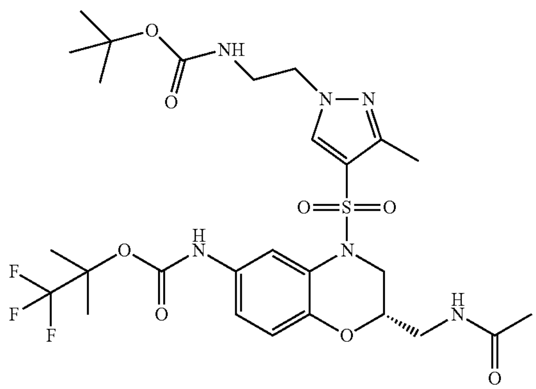 [SMILES: CC(=O)NC[C@H]1CN(S(=O)(=O)c2cn(CCNC(=O)OC(C)(C)C)nc2C)c2cc(NC(=O)OC(C)(C)C(F)(F)F)ccc2O1] | 2,2,2-trifluoro-1,1-dimethylethyl {2-[(acetylamino)methyl]-4-[(1-{2-[(tert-butoxycarbonyl)amino]ethyl}-3-methyl-1H-pyrazol-4-yl)sulfonyl]-3,4-dihydro-2H-1,4-benzoxazin-6-yl}carbamate | 685 (M + Na)+ |
| 10CJ | 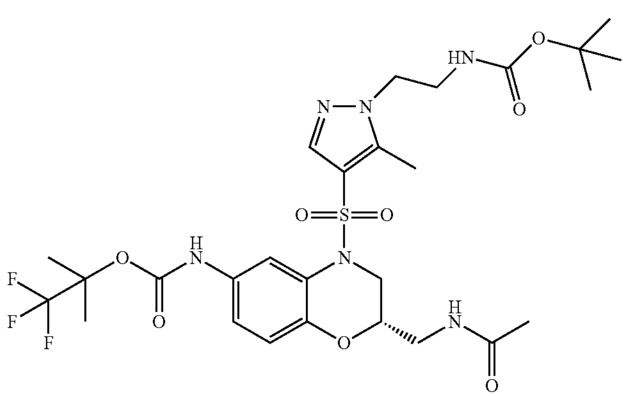 [SMILES: CC(=O)NC[C@H]1CN(S(=O)(=O)c2cnn(CCNC(=O)OC(C)(C)C)c2C)c2cc(NC(=O)OC(C)(C)C(F)(F)F)ccc2O1] | 2,2,2-trifluoro-1,1-dimethylethyl {2S-2-[(acetylamino)methyl]-4-[(1-{2-[(tert-butoxycarbonyl)amino]ethyl}-5-methyl-1H-pyrazol-4-yl)sulfonyl]-3,4-dihydro-2H-1,4-benzoxazin-6-yl}carbamate | 685 (M + Na)+ |
| 10CK | 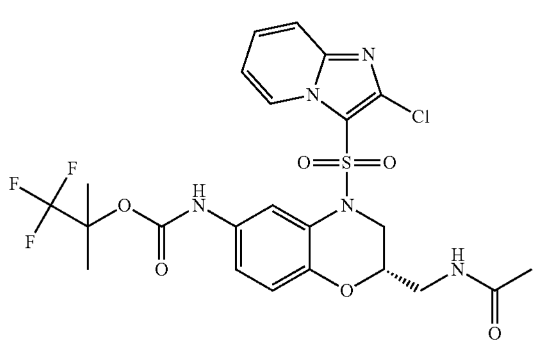 [SMILES: CC(=O)NC[C@H]1CN(S(=O)(=O)c2c(Cl)nc3ccccn23)c2cc(NC(=O)OC(C)(C)C(F)(F)F)ccc2O1] | 2,2,2-trifluoro-1,1-dimethylethyl {(2S)-2-[(acetylamino)methyl]-4-[(2-chloroimidazo[1,2-a]pyridin-3-yl)sulfonyl]-3,4-dihydro-2H-1,4-benzoxazin-6-yl}carbamate | 590 (M + H)+ |

TABLE 2-continued

| Ex. No. | Structure | Name | Observed m/z |
|---|---|---|---|
| 10CL | 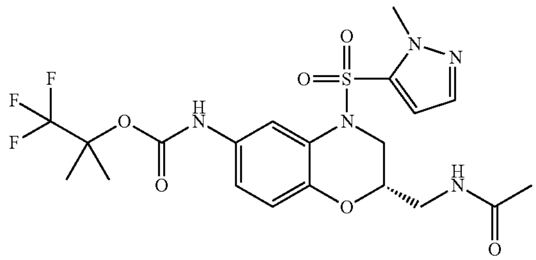 [SMILES: CC(=O)NC[C@H]1CN(S(=O)(=O)c2ccnn2C)c2cc(NC(=O)OC(C)(C)C(F)(F)F)ccc2O1] | 2,2,2-trifluoro-1,1-dimethylethyl {(2S)-2-[(acetylamino)methyl]-4-[(1-methyl-1H-pyrazol-5-yl)sulfonyl]-3,4-dihydro-2H-1,4-benzoxazin-6-yl}carbamate | 520 (M + H)⁺ |
| 10CM | 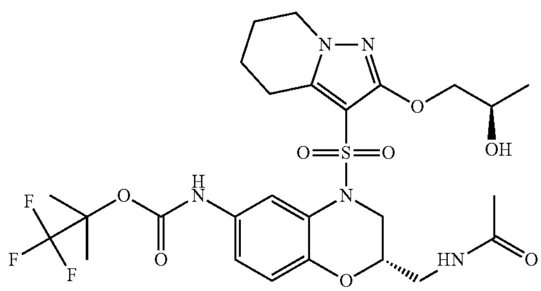 [SMILES: CC(=O)NC[C@H]1CN(S(=O)(=O)c2c(OC[C@@H](C)O)nn3c2CCCC3)c2cc(NC(=O)OC(C)(C)C(F)(F)F)ccc2O1] | 2,2,2-trifluoro-1,1-dimethylethyl {(2S)-2-[(acetylamino)methyl]-4-[(2-{[(2R)-2-hydroxypropyl]oxy}-4,5,6,7-tetrahydropyrazolo[1,5-a]pyridin-3-yl)sulfonyl]-3,4-dihydro-2H-1,4-benzoxazin-6-yl}carbamate | 634 (M + H)⁺ |
| 10CN | 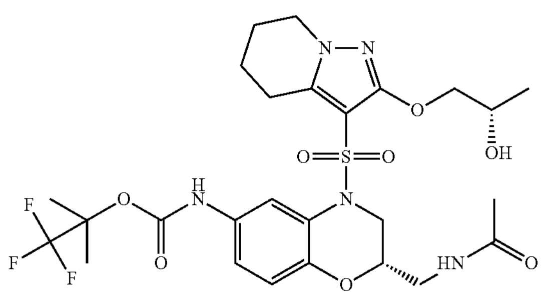 [SMILES: CC(=O)NC[C@H]1CN(S(=O)(=O)c2c(OC[C@H](C)O)nn3c2CCCC3)c2cc(NC(=O)OC(C)(C)C(F)(F)F)ccc2O1] | 2,2,2-trifluoro-1,1-dimethylethyl {(2S)-2-[(acetylamino)methyl]-4-[(2-{[(2S)-2-hydroxypropyl]oxy}-4,5,6,7-tetrahydropyrazolo[1,5-a]pyridin-3-yl)sulfonyl]-3,4-dihydro-2H-1,4-benzoxazin-6-yl}carbamate | 634 (M + H)⁺ |

Example 11—Synthesis of 1,1,1-trifluoro-2-methyl-propan-2-yl (S)-(2-(acetamidomethyl)-4-((1-ethyl-3-(2-hydroxyethoxy)-1H-pyrazol-4-yl)sulfonyl)-3,4-dihydro-2H-benzo[b][1,4]oxazin-6-yl)carbamate (11)

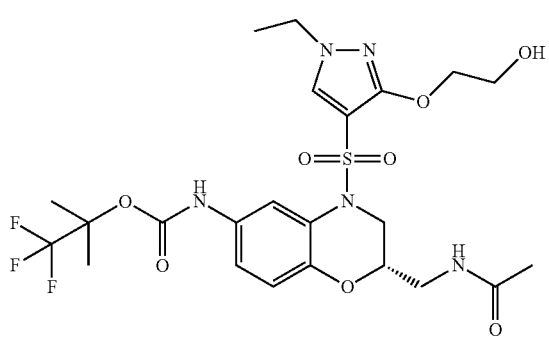 [SMILES: CCn1cc(S(=O)(=O)N2C[C@H](CNC(C)=O)Oc3ccc(NC(=O)OC(C)(C)C(F)(F)F)cc32)c(OCCO)n1]

Step 1—Synthesis of methyl 2-((1-ethyl-1H-pyrazol-3-yl)oxy)acetate

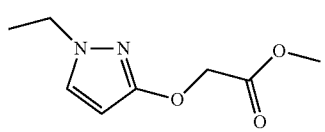

To a solution of 1-ethyl-1,2-dihydro-3H-pyrazol-3-one (13.8 g, 124 mmol) in N,N-dimethylformamide (75 mL) was added potassium carbonate (25.5 g, 185 mmol) followed by methyl bromoacetate (16.3 mL, 172 mmol). The reaction was stirred at ambient temperature overnight. The solution was partitioned between ethyl acetate and water, washed with brine, dried with sodium sulfate, filtered and concentrated in vacuo. The residue was purified by column chromatography eluting with a gradient of ethyl acetate in hexanes. The pure fractions were combined and concentrated in vacuo to yield the title compound.

Step 2—Synthesis of methyl 2-((4-(chlorosulfonyl)-1-ethyl-1H-pyrazol-3-yl)oxy)acetate

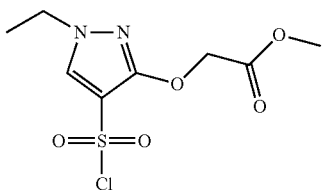 [SMILES: CCn1cc(S(=O)(=O)Cl)c(OCC(=O)OC)n1]

To a suspension of sulfur trioxide dimethylformamide complex (0.42 g, 2.7 mmol) in dichloromethane (10 mL) under nitrogen at 0° C. was added a solution of methyl 2-((1-ethyl-1H-pyrazol-3-yl)oxy)acetate (0.5 g, 2.7 mmol) in dichloromethane (1 mL). The reaction was allowed to warm to ambient temperature and stirred for 1 hour. The solution was recooled to 0° C., and anhydrous pyridine was added (0.65 mL, 8.1 mmol), followed by phosphorus pentachloride (0.62 g, 3 mmol) in portions. After 30 minutes the cooling bath was removed, and the mixture was stirred at ambient temperature overnight. The reaction was concentrated in the presence of silica. The residue was purified by column chromatography eluting with a gradient of 10-60% ethyl acetate in hexanes. The pure fractions were combined and concentrated in vacuo to yield the title compound.

Step 3—Synthesis of methyl (S)-2-((4-((2-(acetamidomethyl)-6-((tert-butoxycarbonyl)amino)-2,3-dihydro-4H-benzo[b][1,4]oxazin-4-yl)sulfonyl)-1-ethyl-1H-pyrazol-3-yl)oxy)acetate

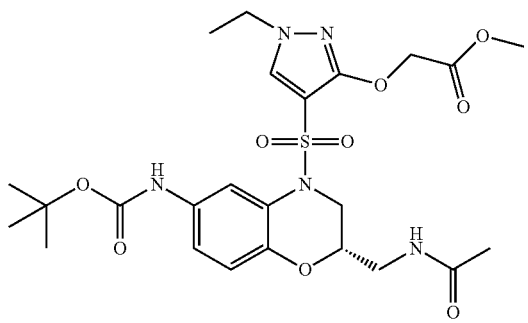 [SMILES: CCn1cc(S(=O)(=O)N2C[C@H](CNC(C)=O)Oc3ccc(NC(=O)OC(C)(C)C)cc32)c(OCC(=O)OC)n1]

In anhydrous pyridine (12 mL) was combined tert-butyl (R)-(2-(acetamidomethyl)-3,4-dihydro-2H-benzo[b][1,4]oxazin-6-yl)carbamate (0.75 g, 2.3 mmol) and methyl 2-((4-(chlorosulfonyl)-1-ethyl-1H-pyrazol-3-yl)oxy)acetate (0.79 g, 2.8 mmol) and the reaction was heated at 70° C. overnight. The cooled solution was diluted with ethyl acetate, washed with 10% citric acid, brine, and dried with sodium sulfate. To the suspension was added activated charcoal while the suspension was stirred. The suspension was filtered through CELITE and the filtrate was concentrated in vacuo. The residue was purified by column chromatography eluting with a gradient of ethyl acetate in hexanes. Pure fractions were combined and concentrated in vacuo to yield the title compound.

Step 4—Synthesis of methyl (S)-2-((4-((2-(acetamidomethyl)-6-((((1,1,1-trifluoro-2-methylpropan-2-yl)oxy)carbonyl)amino)-2,3-dihydro-4H-benzo[b][1,4]oxazin-4-yl)sulfonyl)-1-ethyl-1H-pyrazol-3-yl)oxy)acetate

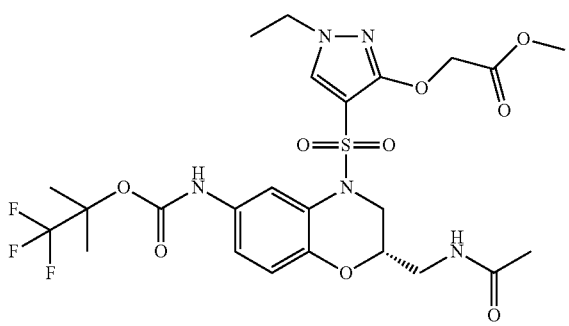 [SMILES: CCn1cc(S(=O)(=O)N2C[C@H](CNC(C)=O)Oc3ccc(NC(=O)OC(C)(C)C(F)(F)F)cc32)c(OCC(=O)OC)n1]

To methyl (S)-2-((4-((2-(acetamidomethyl)-6-((tert-butoxycarbonyl)amino)-2,3-dihydro-4H-benzo[b][1,4]oxazin-4-yl)sulfonyl)-1-ethyl-1H-pyrazol-3-yl)oxy)acetate (0.585 g, 1.03 mmol) was added 4M hydrogen chloride in 1,4-dioxane (30 mL) and the reaction was stirred at ambient temperature for 30 minutes. The resulting suspension was concentrated under vacuum. The resulting solids were redissolved in N,N-dimethylformamide (5 mL), treated with (2,2,2-trifluoro-1,1-dimethyl-ethyl) imidazole-1-carboxylate (0.39 g, 1.75 mmol) and heated in the microwave at 100° C. for 2 hours. The cooled solution was partitioned between ethyl acetate and water, washed with water, brine, dried with sodium sulfate, filtered and concentrated in vacuo. The residue was purified by column chromatography eluting with a gradient of ethyl acetate in hexanes. Pure fractions were combined and concentrated in vacuo to yield the title compound.

Step 5—Synthesis of (S)-2-((4-((2-(acetamidomethyl)-6-((((1,1,1-trifluoro-2-methylpropan-2-yl)oxy)carbonyl)amino)-2,3-dihydro-4H-benzo[b][1,4]oxazin-4-yl)sulfonyl)-1-ethyl-1H-pyrazol-3-yl)oxy)acetic acid

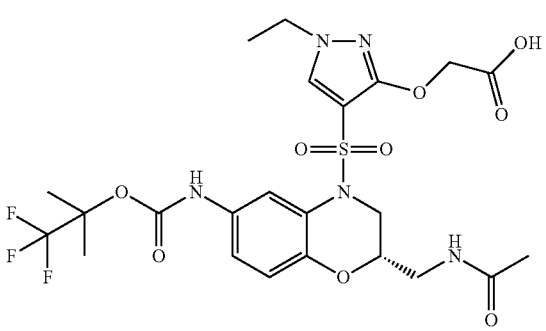 [SMILES: CCn1cc(S(=O)(=O)N2C[C@H](CNC(C)=O)Oc3ccc(NC(=O)OC(C)(C)C(F)(F)F)cc32)c(OCC(=O)O)n1]

To a solution of methyl (S)-2-((4-((2-(acetamidomethyl)-6-((((1,1,1-trifluoro-2-methylpropan-2-yl)oxy)carbonyl)amino)-2,3-dihydro-4H-benzo[b][1,4]oxazin-4-yl)sulfonyl)-1-ethyl-1H-pyrazol-3-yl)oxy)acetate (0.53 g, 0.85 mmol) in tetrahydrofuran (4 mL) and methanol (4 mL) was added 2M sodium hydroxide (1.3 mmol) and the solution was stirred at ambient temperature for 3 hours. The solution was acidified with 1 M hydrogen chloride, extracted with ethyl acetate, washed with brine, dried with sodium sulfate, filtered and concentrated in vacuo to yield the title compound.

Step 6—Synthesis of 1,1,1-trifluoro-2-methylpropan-2-yl (S)-(2-(acetamidomethyl)-4-((1-ethyl-3-(2-hydroxyethoxy)-1H-pyrazol-4-yl)sulfonyl)-3,4-dihydro-2H-benzo[b][1,4]oxazin-6-yl)carbamate

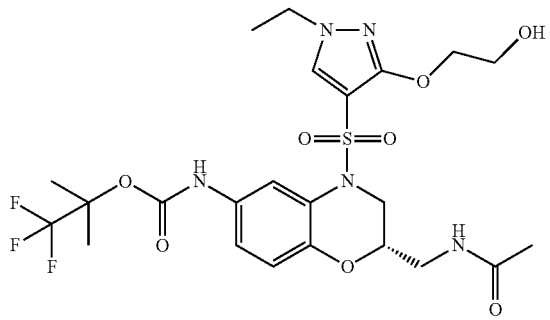 [SMILES: CCn1cc(S(=O)(=O)N2C[C@H](CNC(C)=O)Oc3ccc(NC(=O)OC(C)(C)C(F)(F)F)cc32)c(OCCO)n1]

To a solution of (S)-2-((4-((2-(acetamidomethyl)-6-(((((1,1,1-trifluoro-2-methylpropan-2-yl)oxy)carbonyl)amino)-2,3-dihydro-4H-benzo[b][1,4]oxazin-4-yl)sulfonyl)-1-ethyl-1H-pyrazol-3-yl)oxy)acetic acid (0.44 g, 0.72 mmol) in tetrahydrofuran (5 mL) was added triethylamine (0.14 mL, 1.01 mmol) followed by the slow addition of ethyl chloroformate (76 µL, 0.8 mmol). The mixture was stirred at ambient temperature for 30 minutes, filtered and washed with a small amount of tetrahydrofuran. To the filtrates at 0° C. was slowly added a solution of sodium borohydride (82 mg, 2.2 mmol) in water (0.5 mL). Gas evolution was evident. The reaction was stirred at 0° C. for 20 minutes. The solution was diluted with saturated sodium bicarbonate and brine and extracted with ethyl acetate. The organics were dried with sodium sulfate, filtered and concentrated in vacuo. The residue was purified by column chromatography eluting with a gradient of 70-100% ethyl acetate in hexanes, then switched to 2% methanol in ethyl acetate. The desired fractions were combined and concentrated to yield the title compound. $^1$H NMR 400 Hz $D_6$-DMSO δ 9.63 (s, 1H), 8.12 (m, 2H), 7.76 (s, 1H), 7.00 (m, 1H), 6.75 (m, 1H), 4.64 (m, 1H), 4.21 (m, 1H), 4.08-3.9 (m, 3H), 3.57 (m, 2H), 3.4-3.2 (m, 2H), 1.83 (s, 3H), 1.67 (s, 6H), 1.25 (m, 3H).

Example 12—Preparation of additional 1-alkyl-3-(2-hydroxyethoxy)-1H-pyrazol-4-yl)sulfonyl)-3,4-dihydro-2H-benzo[b][1,4]oxazines The compounds in Table 3 below were prepared based on the experimental procedures described in Examples 7, 8, 9, and 11 and elsewhere in the detailed description, and can be achieved by one of skill in the art in light of the present disclosure.

TABLE 3

| Ex. No. | Structure | Name | Observed m/z |
|---|---|---|---|
| 12A | 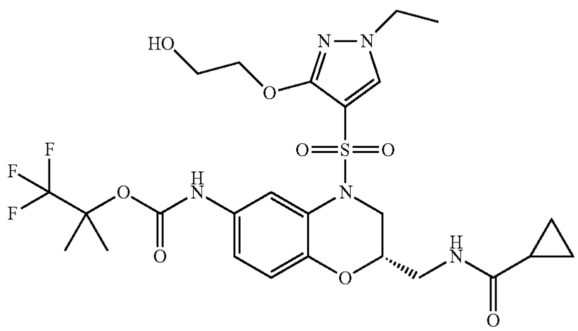 [SMILES: CCn1cc(S(=O)(=O)N2C[C@H](CNC(=O)C3CC3)Oc3ccc(NC(=O)OC(C)(C)C(F)(F)F)cc32)c(OCCO)n1] | (S)-1,1,1-trifluoro-2-methylpropan-2-yl (2-(cyclopropanecarboxamidomethyl)-4-((1-ethyl-3-(2-hydroxyethoxy)-1H-pyrazol-4-yl)sulfonyl)-3,4-dihydro-2H-benzo[b][1,4]oxazin-6-yl)carbamate | 620.2 (M + H)+ |
| 12B | 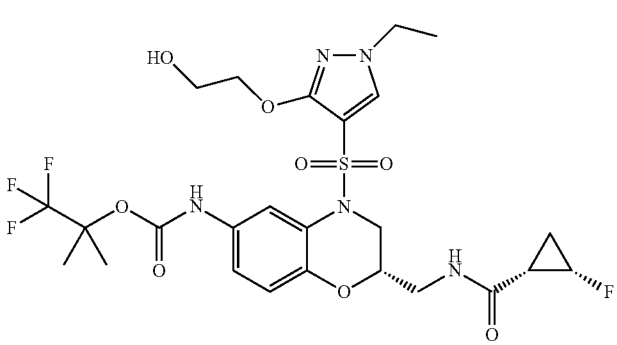 [SMILES: CCn1cc(S(=O)(=O)N2C[C@H](CNC(=O)[C@@H]3C[C@@H]3F)Oc3ccc(NC(=O)OC(C)(C)C(F)(F)F)cc32)c(OCCO)n1] | 1,1,1-trifluoro-2-methylpropan-2-yl ((S)-4-((1-ethyl-3-(2-hydroxyethoxy)-1H-pyrazol-4-yl)sulfonyl)-2-(((1S,2S)-2-fluorocyclopropanecarboxamido)methyl)-3,4-dihydro-2H-benzo[b][1,4]oxazin-6-yl)carbamate | 638.2 (M + H)+ |

| Ex. No. | Structure | Name | Observed m/z |
|---|---|---|---|
| 12C | 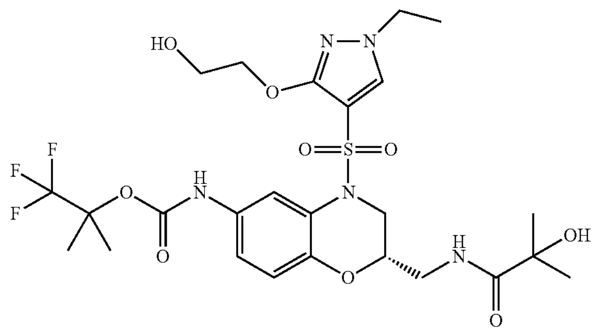 [SMILES: CCn1cc(S(=O)(=O)N2C[C@H](CNC(=O)C(C)(C)O)Oc3ccc(NC(=O)OC(C)(C)C(F)(F)F)cc32)c(OCCO)n1] | (S)-1,1,1-trifluoro-2-methylpropan-2-yl (4-((1-ethyl-3-(2-hydroxyethoxy)-1H-pyrazol-4-yl)sulfonyl)-2-((2-hydroxy-2-methylpropanamido)methyl)-3,4-dihydro-2H-benzo[b][1,4]oxazin-6-yl)carbamate | 638.2 (M + H)+ |
| 12D | 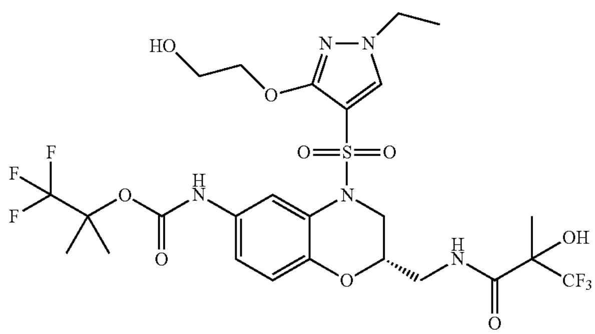 [SMILES: CCn1cc(S(=O)(=O)N2C[C@H](CNC(=O)C(C)(O)C(F)(F)F)Oc3ccc(NC(=O)OC(C)(C)C(F)(F)F)cc32)c(OCCO)n1] | 1,1,1-trifluoro-2-methylpropan-2-yl ((2S)-4-((1-ethyl-3-(2-hydroxyethoxy)-1H-pyrazol-4-yl)sulfonyl)-2-((3,3,3-trifluoro-2-hydroxy-2-methylpropanamido)methyl)-3,4-dihydro-2H-benzo[b][1,4]oxazin-6-yl)carbamate | 714.1 (M + Na)+ |
| 12E | 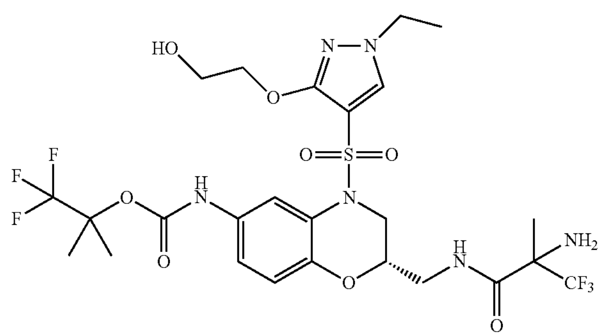 [SMILES: CCn1cc(S(=O)(=O)N2C[C@H](CNC(=O)C(C)(N)C(F)(F)F)Oc3ccc(NC(=O)OC(C)(C)C(F)(F)F)cc32)c(OCCO)n1] | 1,1,1-trifluoro-2-methylpropan-2-yl ((2S)-2-((2-amino-3,3,3-trifluoro-2-methylpropanamido)methyl)-4-((1-ethyl-3-(2-hydroxyethoxy)-1H-pyrazol-4-yl)sulfonyl)-3,4-dihydro-2H-benzo[b][1,4]oxazin-6-yl)carbamate | 691.0 (M + H)+ |
| 12F | 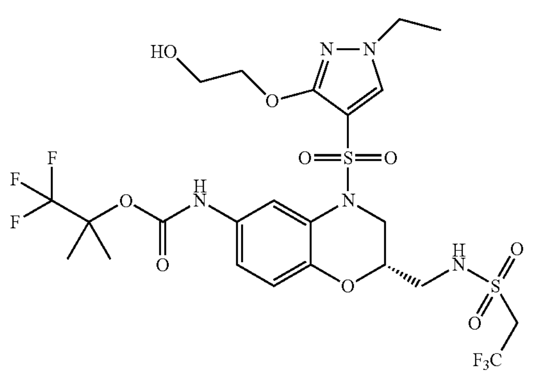 [SMILES: CCn1cc(S(=O)(=O)N2C[C@H](CNS(=O)(=O)CC(F)(F)F)Oc3ccc(NC(=O)OC(C)(C)C(F)(F)F)cc32)c(OCCO)n1] | (S)-1,1,1-trifluoro-2-methylpropan-2-yl (4-((1-ethyl-3-(2-hydroxyethoxy)-1H-pyrazol-4-yl)sulfonyl)-2-((2,2,2-trifluoroethylsulfonamido)methyl)-3,4-dihydro-2H-benzo[b][1,4]oxazin-6-yl)carbamate | 720.0 (M + Na)+ |

TABLE 3-continued

| Ex. No. | Structure | Name | Observed m/z |
|---|---|---|---|
| 12G | 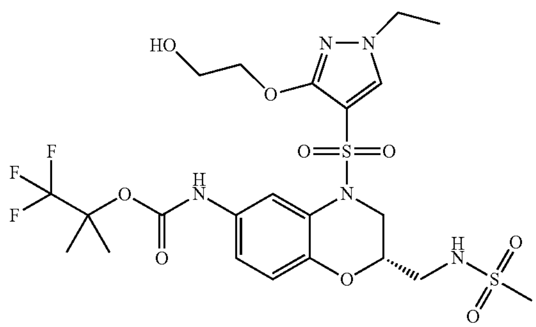 [SMILES: CCn1cc(S(=O)(=O)N2C[C@H](CNS(C)(=O)=O)Oc3ccc(NC(=O)OC(C)(C)C(F)(F)F)cc32)c(OCCO)n1] | (S)-1,1,1-trifluoro-2-methylpropan-2-yl (4-((1-ethyl-3-(2-hydroxyethoxy)-1H-pyrazol-4-yl)sulfonyl)-2-(methylsulfonamidomethyl)-3,4-dihydro-2H-benzo[b][1,4]oxazin-6-yl)carbamate | 630.1 (M + H)+ |
| 12H | 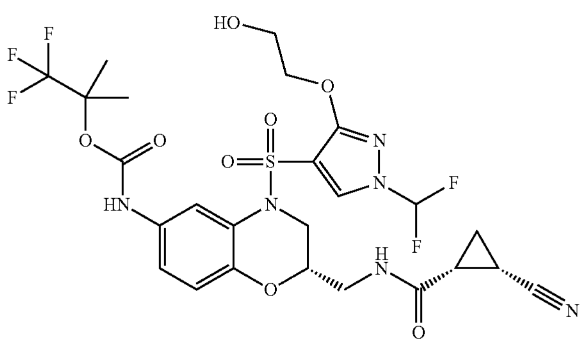 [SMILES: CC(C)(OC(=O)Nc1ccc2c(c1)N(S(=O)(=O)c1cn(C(F)F)nc1OCCO)C[C@H](CNC(=O)[C@@H]1C[C@@H]1C#N)O2)C(F)(F)F] | 2,2,2-trifluoro-1,1-dimethylethyl [(2S)-2-[({[(1R,2S)-2-cyanocyclopropyl]carbonyl}amino)methyl]-4-{[1-(difluoromethyl)-3-(2-hydroxyethoxy)-1H-pyrazol-4-yl]sulfonyl}-3,4-dihydro-2H-1,4-benzoxazin-6-yl]carbamate | 667 (M + H)+ |
| 12i | 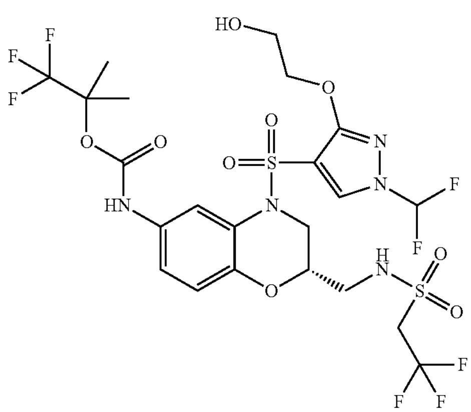 [SMILES: CC(C)(OC(=O)Nc1ccc2c(c1)N(S(=O)(=O)c1cn(C(F)F)nc1OCCO)C[C@H](CNS(=O)(=O)CC(F)(F)F)O2)C(F)(F)F] | 2,2,2-trifluoro-1,1-dimethylethyl [(2S)-4-{[1-(difluoromethyl)-3-(2-hydroxyethoxy)-1H-pyrazol-4-yl]sulfonyl}-2-({[(2,2,2-trifluoroethyl)sulfonyl]amino}methyl)-3,4-dihydro-2H-1,4-benzoxazin-6-yl]carbamate | 742 (M + Na)+ |
| 12J | 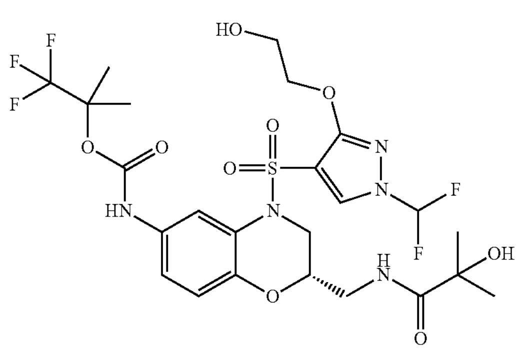 [SMILES: CC(C)(O)C(=O)NC[C@H]1CN(S(=O)(=O)c2cn(C(F)F)nc2OCCO)c2cc(NC(=O)OC(C)(C)C(F)(F)F)ccc2O1] | 2,2,2-trifluoro-1,1-dimethylethyl [(2S)-4-{[1-(difluoromethyl)-3-(2-hydroxyethoxy)-1H-pyrazol-4-yl]sulfonyl}-2-{[(2-hydroxy-2-methylpropanoyl)amino]methyl}-3,4-dihydro-2H-1,4-benzoxazin-6-yl]carbamate | 660 (M + H)+ |

TABLE 3-continued

| Ex. No. | Structure | Name | Observed m/z |
|---|---|---|---|
| 12K | 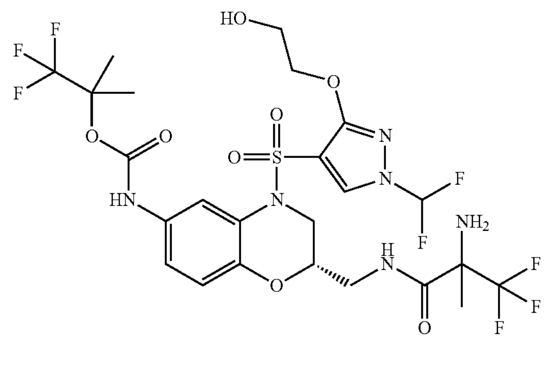 [SMILES: CC(C)(OC(=O)Nc1ccc2c(c1)N(S(=O)(=O)c1cn(C(F)F)nc1OCCO)C[C@H](CNC(=O)C(C)(N)C(F)(F)F)O2)C(F)(F)F] | 2,2,2-trifluoro-1,1-dimethylethyl [(2S)-2-{[(2S and 2R-amino-3,3,3-trifluoro-2-methylpropanoyl)amino]methyl}-4-{[1-(difluoromethyl)-3-(2-hydroxyethoxy)-1H-pyrazol-4-yl]sulfonyl}-3,4-dihydro-2H-1,4-benzoxazin-6-yl]carbamate | 713 (M + H)+ |
| 12L | 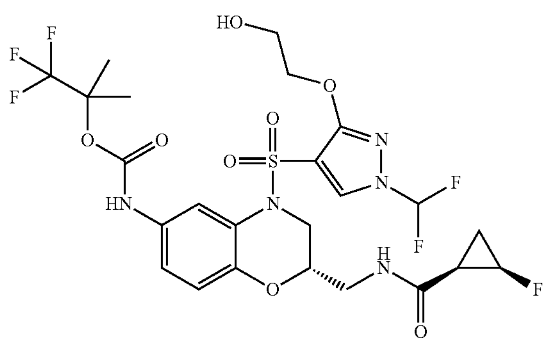 [SMILES: CC(C)(OC(=O)Nc1ccc2c(c1)N(S(=O)(=O)c1cn(C(F)F)nc1OCCO)C[C@H](CNC(=O)[C@H]1C[C@H]1F)O2)C(F)(F)F] | 2,2,2-trifluoro-1,1-dimethylethyl {(2S)-4-{[1-(difluoromethyl)-3-(2-hydroxyethoxy)-1H-pyrazol-4-yl]sulfonyl}-2-[({[(1R,2R)-2-fluorocyclopropyl]carbonyl}amino)methyl]-3,4-dihydro-2H-1,4-benzoxazin-6-yl}carbamate | 660 (M + H)+ |
| 12M | 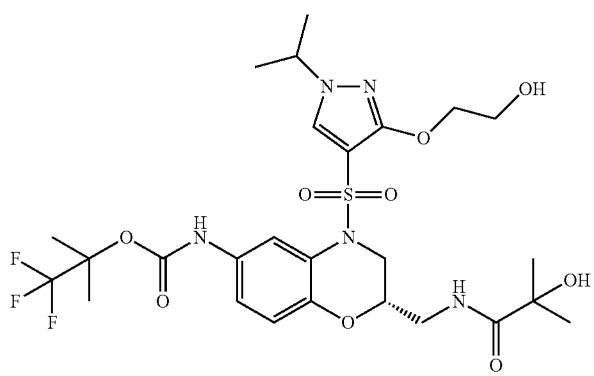 [SMILES: CC(C)n1cc(S(=O)(=O)N2C[C@H](CNC(=O)C(C)(C)O)Oc3ccc(NC(=O)OC(C)(C)C(F)(F)F)cc32)c(OCCO)n1] | 2,2,2-trifluoro-1,1-dimethylethyl [(2S)-4-{[3-(2-hydroxyethoxy)-1-(1-methylethyl)-1H-pyrazol-4-yl]sulfonyl}-2-{[(2-hydroxy-2-methylpropanoyl)amino]methyl}-3,4-dihydro-2H-1,4-benzoxazin-6-yl]carbamate | 674 (M + Na)+ |
| 12N | 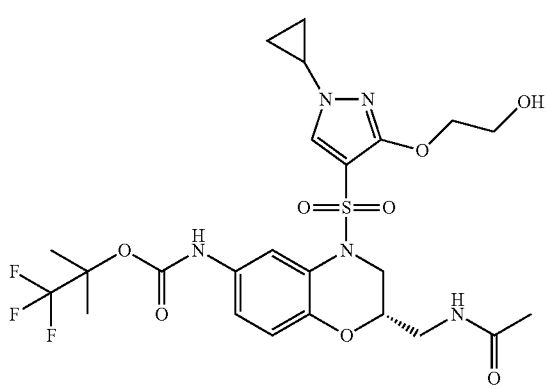 [SMILES: CC(=O)NC[C@H]1CN(S(=O)(=O)c2cn(C3CC3)nc2OCCO)c2cc(NC(=O)OC(C)(C)C(F)(F)F)ccc2O1] | 2,2,2-trifluoro-1,1-dimethylethyl [(2S)-2-[(acetylamino)methyl]-4-{[1-cyclopropyl-3-(2-hydroxyethoxy)-1H-pyrazol-4-yl]sulfonyl}-3,4-dihydro-2H-1,4-benzoxazin-6-yl]carbamate | 628 (M + Na)+ |

TABLE 3-continued

| Ex. No. | Structure | Name | Observed m/z |
|---|---|---|---|
| 12o | 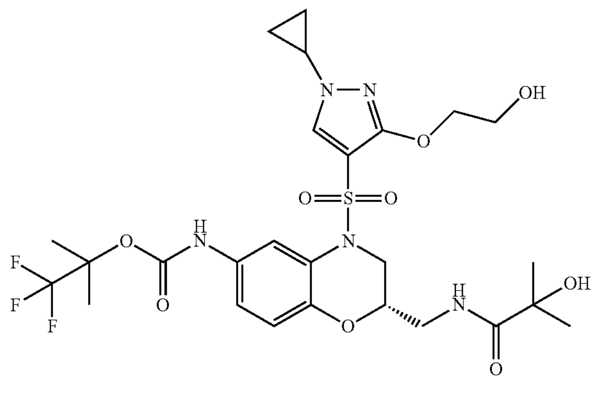 [SMILES: CC(C)(O)C(=O)NC[C@H]1CN(S(=O)(=O)c2cn(C3CC3)nc2OCCO)c2cc(NC(=O)OC(C)(C)C(F)(F)F)ccc2O1] | 2,2,2-trifluoro-1,1-dimethylethyl [(2S)-4-{[1-cyclopropyl-3-(2-hydroxyethoxy)-1H-pyrazol-4-yl]sulfonyl}-2-{[(2-hydroxy-2-methylpropanoyl)amino]methyl}-3,4-dihydro-2H-1,4-benzoxazin-6-yl]carbamate | 672 (M + Na)+ |
| 12P | 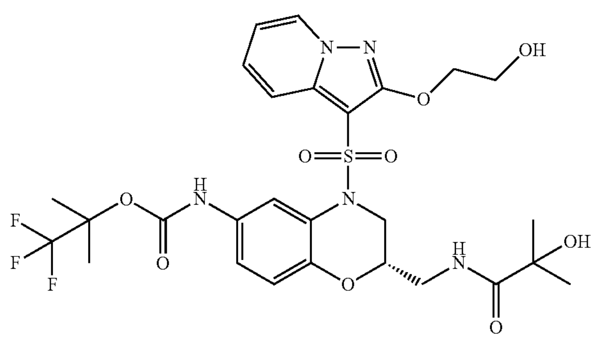 [SMILES: CC(C)(O)C(=O)NC[C@H]1CN(S(=O)(=O)c2c(OCCO)nn3ccccc23)c2cc(NC(=O)OC(C)(C)C(F)(F)F)ccc2O1] | 2,2,2-trifluoro-1,1-dimethylethyl [(2S)-4-{[2-(2-hydroxyethoxy)pyrazolo[1,5-a]pyridin-3-yl]sulfonyl}-2-{[(2-hydroxy-2-methylpropanoyl)amino]methyl}-3,4-dihydro-2H-1,4-benzoxazin-6-yl]carbamate | 682 (M + Na)+ |
| 12Q | 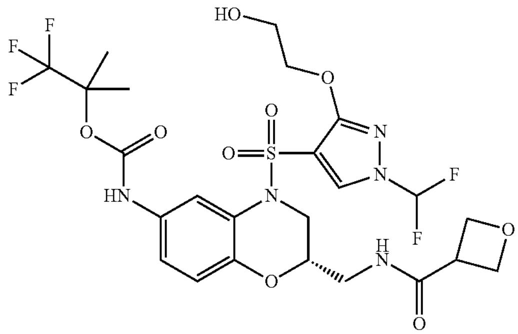 | 2,2,2-trifluoro-1,1-dimethylethyl [(2S)-4-{[1-ethyl-3-(2-hydroxyethoxy)-1H-pyrazol-4-yl]sulfonyl}-2-{[(oxetan-3-ylcarbonyl)amino]methyl}-3,4-dihydro-2H-1,4-benzoxazin-6-yl]carbamate | 636 (M + H)+ |
| 12R | 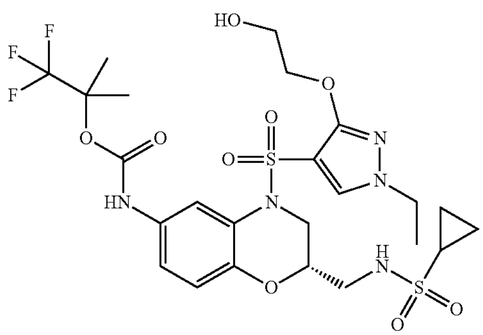 [SMILES: CCn1cc(S(=O)(=O)N2C[C@H](CNS(=O)(=O)C3CC3)Oc3ccc(NC(=O)OC(C)(C)C(F)(F)F)cc32)c(OCCO)n1] | 2,2,2-trifluoro-1,1-dimethylethyl [(2S)-2-{[(cyclopropylsulfonyl)amino]methyl}-4-{[1-ethyl-3-(2-hydroxyethoxy)-1H-pyrazol-4-yl]sulfonyl}-3,4-dihydro-2H-1,4-benzoxazin-6-yl]carbamate | 656 (M + H)+ |

TABLE 3-continued

| Ex. No. | Structure | Name | Observed m/z |
| --- | --- | --- | --- |
| 12S | 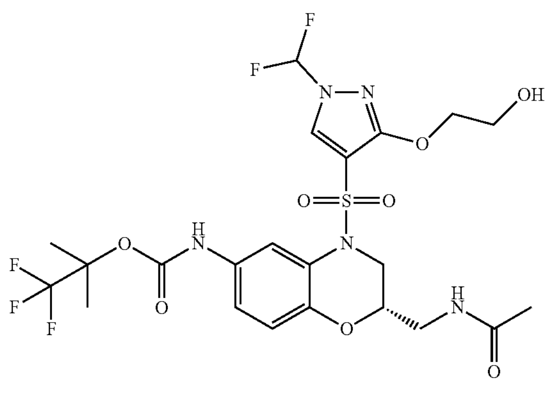 [SMILES: CC(=O)NC[C@H]1CN(S(=O)(=O)c2cn(C(F)F)nc2OCCO)c2cc(NC(=O)OC(C)(C)C(F)(F)F)ccc2O1] | 2,2,2-trifluoro-1,1-dimethylethyl [(2S)-2-[(acetylamino)methyl]-4-{[1-(difluoromethyl)-3-(2-hydroxyethoxy)-1H-pyrazol-4-yl]sulfonyl}-3,4-dihydro-2H-1,4-benzoxazin-6-yl]carbamate | 616 (M + H)+ |
| 12T | 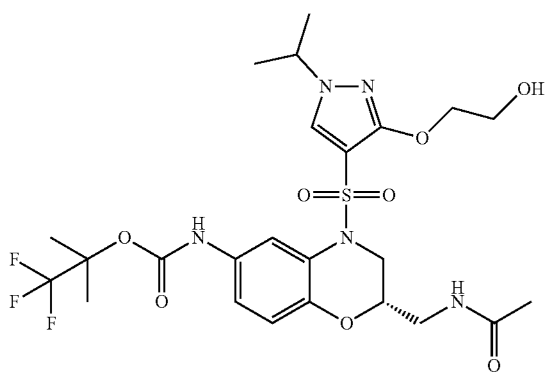 [SMILES: CC(=O)NC[C@H]1CN(S(=O)(=O)c2cn(C(C)C)nc2OCCO)c2cc(NC(=O)OC(C)(C)C(F)(F)F)ccc2O1] | 2,2,2-trifluoro-1,1-dimethylethyl [(2S)-2-[(acetylamino)methyl]-4-{[3-(2-hydroxyethoxy)-1-(1-methylethyl)-1H-pyrazol-4-yl]sulfonyl}-3,4-dihydro-2H-1,4-benzoxazin-6-yl]carbamate | 608 (M + H)+ |
| 12U | 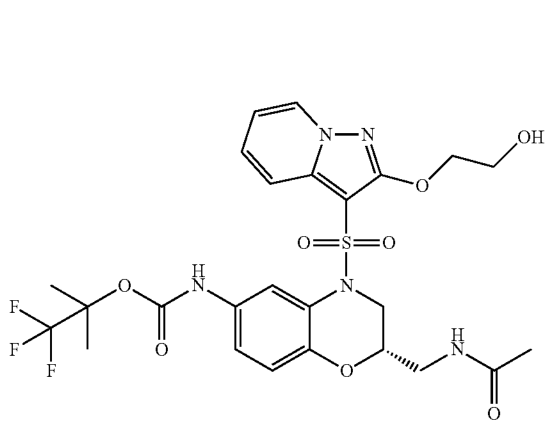 [SMILES: CC(=O)NC[C@H]1CN(S(=O)(=O)c2c(OCCO)nn3ccccc23)c2cc(NC(=O)OC(C)(C)C(F)(F)F)ccc2O1] | 2,2,2-trifluoro-1,1-dimethylethyl [(2S)-2-[(acetylamino)methyl]-4-{2-(2-hydroxyethoxy)pyrazolo[1,5-a]pyridin-3-yl]sulfonyl}-3,4-dihydro-2H-1,4-benzoxazin-6-yl]carbamte | 616 (M + H)+ |

Example 13—Synthesis of (S)-1,1,1-trifluoro-2-methylpropan-2-yl (2-(acetamidomethyl)-4-((3-cyclopropyl-4-fluorophenyl)sulfonyl)-3,4-dihydro-2H-benzo[b][1,4]oxazin-6-yl)carbamate (13)

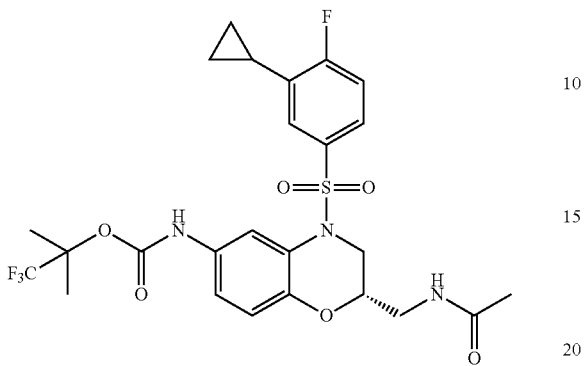

A mixture of (S)-1,1,1-trifluoro-2-methylpropan-2-yl (2-(acetamidomethyl)-4-((3-bromo-4-fluorophenyl)sulfonyl)-3,4-dihydro-2H-benzo[b][1,4]oxazin-6-yl)carbamate (60 mg, 0.098 mmol), cyclopropylboronic acid (0.196 mmol), bis(triphenylphosphine)palladium (II) dichloride (0.0098 mmol), potassium phosphate tribasic (0.294 mmol) and toluene (1 mL) was degassed under argon, sealed and heated at 100° C. overnight. The reaction was cooled and partitioned between saturated sodium bicarbonate and ethyl acetate. The organic layer was dried (MgSO$_4$) and concentrated. The residue was purified by flash chromatography (10-100% ethyl acetate:hexanes), followed by reverse phase purification. The starting material by-product was finally removed by SFC purification (Chiralcel OJ-H column; 21×250 mm dimensions) using 15% CO$_2$ modifier) to afford the title compound as a white solid. LRMS (ESI) calculated for C$_{25}$H$_{28}$F$_4$N$_3$O$_6$S (M+H)$^+$: 574. Found: 574.0; $^1$H NMR (600 MHz, DMSO-d6) δ 9.75 (s, 1H), 8.04 (m, 1H), 7.97 (s, 1H), 7.50 (m, 1H), 7.32 (t, 1H, J=9.2 Hz), 7.15 (d, 1H, J=5.9 Hz), 7.09 (d, 1H, J=8.8 Hz), 6.73 (d, 1H, J=9 Hz), 4.26 (d, 1H, J=14 Hz), 3.30 (m, 2H), 3.14 (m, 1H), 3.08 (m, 1H), 1.99 (m, 1H), 1.81 (s, 3H), 1.69 (s, 6H), 0.94 (m, 2H), 0.83 (m, 2H).

Example 14—Synthesis of (S)-1,1,1-trifluoro-2-methylpropan-2-yl (2-(acetamidomethyl)-4-((3-cyclopropylphenyl)sulfonyl)-3,4-dihydro-2H-benzo[b][1,4]oxazin-6-yl)carbamate (14)

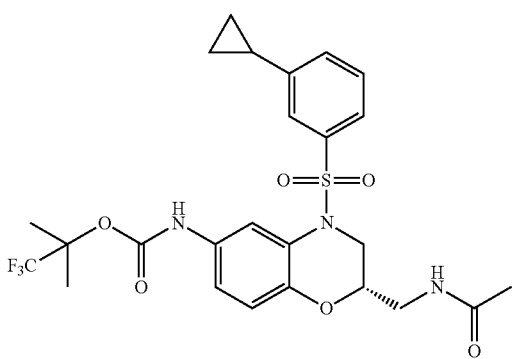 [SMILES: CC(=O)NC[C@H]1CN(S(=O)(=O)c2cccc(C3CC3)c2)c2cc(NC(=O)OC(C)(C)C(F)(F)F)ccc2O1]

The procedure described in Example 13 was used to prepare the title compound. LRMS (ESI) calculated for C$_{25}$H$_{29}$F$_4$N$_3$O$_6$S (M+H)$^+$: 556. Found 556.

Example 15—Synthesis of 1,1,1-trifluoro-2-methylpropan-2-yl ((R)-2-((R)-1-acetamidoethyl)-4-((3-chloro-4-fluorophenyl)sulfonyl)-3,4-dihydro-2H-benzo[b][1,4]oxazin-6-yl)carbamate and 1,1,1-trifluoro-2-methylpropan-2-yl ((R)-2-((S)-1-acetamidoethyl)-4-((3-chloro-4-fluorophenyl)sulfonyl)-3,4-dihydro-2H-benzo[b][1,4]oxazin-6-yl)carbamate (15A and 15B)

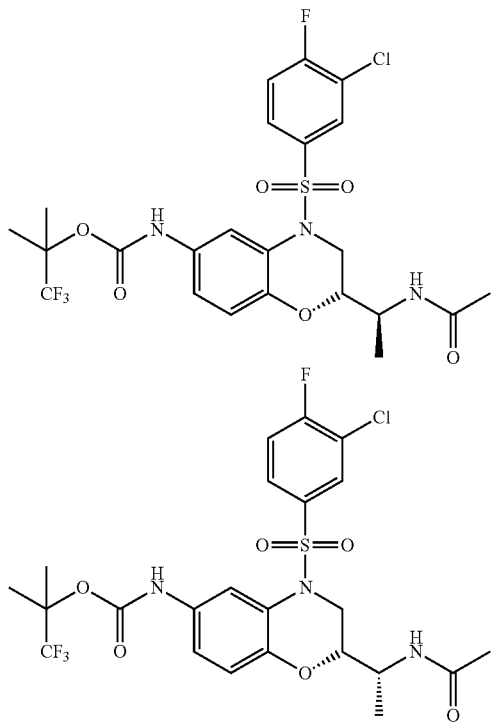

Step 1—Synthesis of (R)-tert-butyl (4-benzyl-2-(hydroxymethyl)-3,4-dihydro-2H-benzo[b][1,4]oxazin-6-yl)carbamate

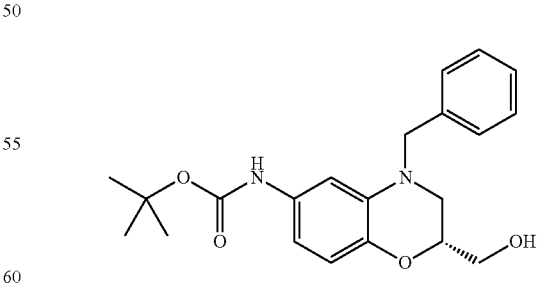

A solution of (R)-tert-butyl (2-(hydroxymethyl)-3,4-dihydro-2H-benzo[b][1,4]oxazin-6-yl)carbamate (5.4494 g, 19.44 mmol) in DMF (26 mL) was charged with potassium carbonate (5.61 g, 40.6 mmol) and benzyl bromide (2.6 mL, 21.86 mmol) and stirred at room temperature for 23 hours. The reaction was quenched with brine and extracted three times with methyl tert-butyl ether. The organics were washed with water followed by brine, dried over $Na_2SO_4$, filtered and concentrated in vacuo. The crude mixture was purified by flash chromatography (0-100% EtOAc/Hex) to provide (R)-tert-butyl (4-benzyl-2-(hydroxymethyl)-3,4-dihydro-2H-benzo[b][1,4]oxazin-6-yl)carbamate. LRMS (ESI) calculated for $C_{21}H_{27}N_2O_4$ (M+H)+: 371. Found: 371.

Step 2—Synthesis of (R)-4-benzyl-6-((tert-butoxycarbonyl)amino)-3,4-dihydro-2H-benzo[b][1,4]oxazine-2-carboxylic acid

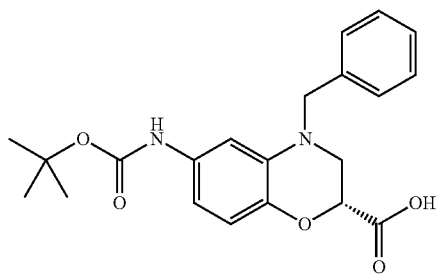 [SMILES: CC(C)(C)OC(=O)Nc1ccc2c(c1)N(Cc1ccccc1)C[C@H](C(=O)O)O2]

To (R)-tert-butyl (4-benzyl-2-(hydroxymethyl)-3,4-dihydro-2H-benzo[b][1,4]oxazin-6-yl)carbamate (4.561 g, 12.31 mmol) and dichloromethane (41 mL), cooled in an ice bath to an internal temperature of 3° C., was added TPAP (454 mg, 1.292 mmol), and the resulting mixture was treated portionwise with 4-methylmorpholine 4-oxide (14.50 g, 124 mmol) while maintaining the internal temperature below 7° C. Upon completion of the addition, the cold bath was removed and stirring continued at ambient temperature. After 30 minutes, the reaction was poured onto silica gel and purified by flash chromatography (0-20% MeOH/DCM) to provide (R)-4-benzyl-6-((tert-butoxycarbonyl)amino)-3,4-dihydro-2H-benzo[b][1,4]oxazine-2-carboxylic acid as a black solid, which was taken forward without further purification. LRMS (ESI) calculated for $C_{21}H_{25}N_2O_5$ (M+H)+: 384.5. Found: 385.

Step 3—Synthesis of (R)-tert-butyl (4-benzyl-2-(methoxy(methyl)carbamoyl)-3,4-dihydro-2H-benzo[b][1,4]oxazin-6-yl)carbamate

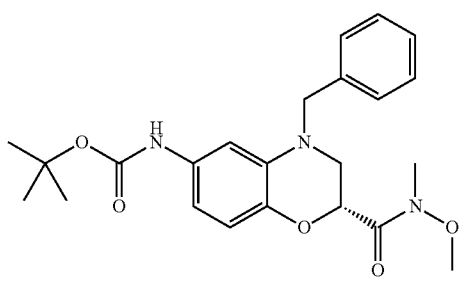 [SMILES: CON(C)C(=O)[C@H]1CN(Cc2ccccc2)c2cc(NC(=O)OC(C)(C)C)ccc2O1]

A solution of (R)-4-benzyl-6-((tert-butoxycarbonyl)amino)-3,4-dihydro-2H-benzo[b][1,4]oxazine-2-carboxylic acid (3.68 g, 5.36 mmol) in DMF (12 mL) was cooled to 0° C. internal temperature, and then was added EDC (2.07 g, 10.82 mmol), N,O-dimethylhydroxylamine hydrochloride (1.05 g, 10.77 mmol), HOBT (211, 1.38 mmol) and DIPEA (6.6 mL, 37.8 mmol), and the reaction was stirred at room temperature for 40 hours. Water was added and the mixture was extracted three times with methyl tert-butyl ether. The organics were washed with brine, dried over $Na_2SO_4$, filtered and concentrated in vacuo. The residue was purified by flash chromatography (25-100% EtOAc/Hex) to provide (R)-tert-butyl (4-benzyl-2-(methoxy(methyl)carbamoyl)-3,4-dihydro-2H-benzo[b][1,4]oxazin-6-yl)carbamate. LRMS (ESI) calculated for $C_{23}H_{30}N_3O_5$ (M+H)+: 427.5. Found: 428.

Step 4—Synthesis of (R)-tert-butyl (2-acetyl-4-benzyl-3,4-dihydro-2H-benzo[b][1,4]oxazin-6-yl)carbamate

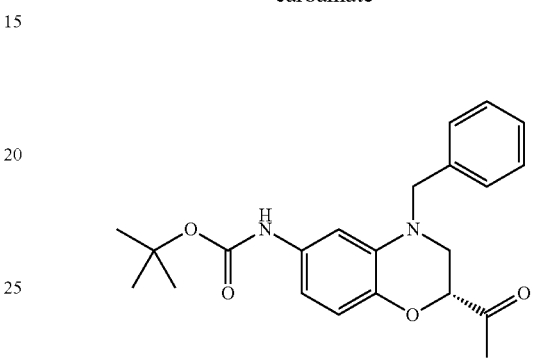

A solution of (R)-tert-butyl (4-benzyl-2-(methoxy(methyl)carbamoyl)-3,4-dihydro-2H-benzo[b][1,4]oxazin-6-yl)carbamate (1.68 g, 3.93 mmol) in THF (10 mL) was cooled to −78° C., then was added methylmagnesium bromide (6.5 mL, 19.5 mmol) and the reaction was stirred for 45 minutes. The reaction was quenched with saturated aqueous $NaHCO_3$ and the mixture was extracted three times with ethyl acetate. The combined organic layers were washed with brine, dried over $Na_2SO_4$, filtered and concentrated in vacuo. The residue was purified by flash chromatography (0-50% EtOAc/Hex) to provide (R)-tert-butyl (2-acetyl-4-benzyl-3,4-dihydro-2H-benzo[b][1,4]oxazin-6-yl)carbamate. LRMS (ESI) calculated for $C_{22}H_{27}N_2O_4$ (M+H)+: 382.5. Found: 383.

Step 5—Synthesis of tert-butyl ((R)-2-((R)-1-aminoethyl)-4-benzyl-3,4-dihydro-2H-benzo[b][1,4]oxazin-6-yl)carbamate and tert-butyl ((R)-2-((S)-1-aminoethyl)-4-benzyl-3,4-dihydro-2H-benzo[b][1,4]oxazin-6-yl)carbamate

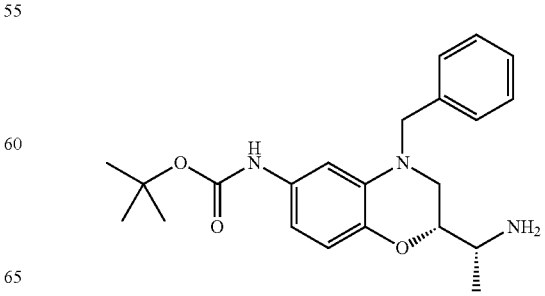

-continued

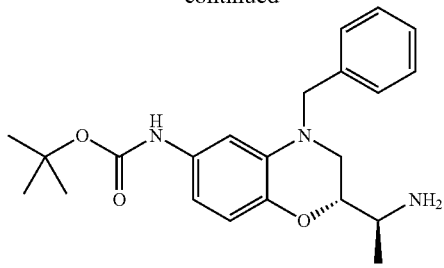

A suspension of (R)-tert-butyl (2-acetyl-4-benzyl-3,4-dihydro-2H-benzo[b][1,4]oxazin-6-yl)carbamate (1.02 g, 2.67 mmol) in methanol (15 mL) was charged with ammonium acetate (2.24 g, 29.1 mmol), followed by sodium cyanoborohydride (0.34 g, 5.41 mmol), and the reaction was stirred at ambient temperature for 3 hours. The reaction was quenched with saturated aqueous NaHCO3 and extracted with ethyl acetate. The organic layer was washed with brine, dried over Na$_2$SO$_4$, filtered, concentrated in vacuo and purified by flash chromatography (0-20% MeOH/DCM). The mixture of diastereomers was purified by SFC as follows:

Column & Dimensions: Chiralcel, OD-H, 21×250 (mm); Outlet Pressure (bar): 100; UV wavelength (nm): 220; Flow rate (mL/min): 70; Modifier: Methanol; % modifier in CO2: 40; Sample amount (mg): 935; Diluent: Methanol:ACN (1:1); Diluent volume (mL): 18; Injection volume (mL): 1.00.

Each separated isomer was then purified via flash chromatography (0-100% EtOAc/Hex followed by 0-20% MeOH/DCM) to provide tert-butyl ((R)-2-((R)-1-aminoethyl)-4-benzyl-3,4-dihydro-2H-benzo[b][1,4]oxazin-6-yl)carbamate and tert-butyl ((R)-2-((S)-1-aminoethyl)-4-benzyl-3,4-dihydro-2H-benzo[b][1,4]oxazin-6-yl)carbamate. LRMS (ESI) calculated for C$_{22}$H$_{30}$N$_3$O$_4$ (M+H)$^+$: 383.5. Found: 384.

Step 6—Synthesis of tert-butyl ((R)-2-((R)-1-acetamidoethyl)-4-benzyl-3,4-dihydro-2H-benzo[b][1,4]oxazin-6-yl)carbamate

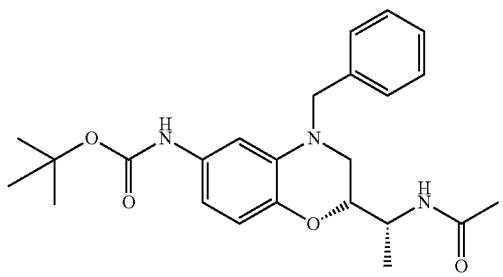

To tert-butyl ((R)-2-((R)-1-aminoethyl)-4-benzyl-3,4-dihydro-2H-benzo[b][1,4]oxazin-6-yl)carbamate (50 mg, 0.13 mmol), BOP (63.4 mg, 0.143 mmol), acetic acid (7.46 µL, 0.130 mmol), and THF (1304 µL). DIEA (91 µL, 0.52 mmol) was added last and the reaction was allowed to stir at room temperature for 2.5 hours. The mixture was washed with ethyl acetate and saturated NaHCO$_3$, followed by brine. The combined organics were dried over magnesium sulfate, filtered, and concentrated in vacuo. LRMS (ESI) calculated for C$_{20}$H$_{23}$N$_3$O$_4$ (M+H)$^+$: 369.4. Found: 369.

Step 7—Synthesis of tert-butyl ((R)-2-((R)-1-acetamidoethyl)-3,4-dihydro-2H-benzo[b][1,4]oxazin-6-yl)carbamate

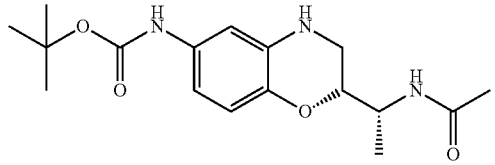

A mixture of tert-butyl ((R)-2-((R)-1-acetamidoethyl)-4-benzyl-3,4-dihydro-2H-benzo[b][1,4]oxazin-6-yl)carbamate (65.9 mg, 0.155 mmol) and MeOH (1549 µL) was purged with nitrogen for 5 minutes. Pd/C (16 mg, 0.015 mmol) was added and the flask was purged for an additional 5 minutes. The reaction was placed under one atmosphere of hydrogen (balloon) and the reaction was stirred for 19 hours at room temperature. The crude mixture was then filtered through over CELITE, while rinsing with methanol. The combined organics were concentrated in vacuo. The material was carried on to the next step without further purification. LRMS (ESI) calculated for C$_{17}$H$_{25}$N$_3$O$_4$ (M+H)$^+$: 335.5. Found: 336.

Step 8—Synthesis of tert-butyl ((R)-2-((R)-1-acetamidoethyl)-4-((3-chloro-4-fluorophenyl)sulfonyl)-3,4-dihydro-2H-benzo[b][1,4]oxazin-6-yl)carbamate

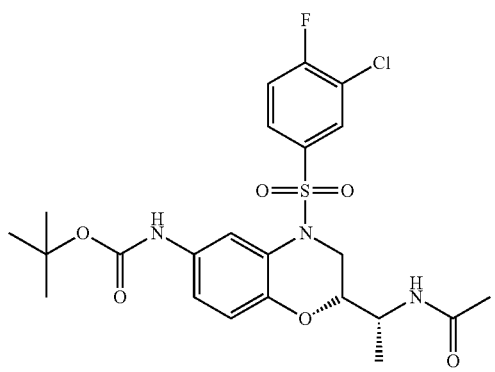

A mixture of tert-butyl ((R)-2-((R)-1-acetamidoethyl)-3,4-dihydro-2H-benzo[b][1,4]oxazin-6-yl)carbamate (51.9 mg, 0.155 mmol), 3-chloro-4-fluorobenzene-1-sulfonyl chloride (70.9 mg, 0.309 mmol), and pyridine (1547 µL) was heated at 60° C. for 2 hours. The mixture was washed with ethyl acetate and saturated NaHCO$_3$, followed by brine. The combined organics were dried over magnesium sulfate, filtered, and concentrated in vacuo. The residue was carried on to the next step without further purification. LRMS (ESI) calculated for C$_{19}$H$_{19}$ClFN$_3$O$_6$S (M-tBu+H)$^+$: 471.9. Found: 472.

Step 9—Synthesis of N—((R)-1-((R)-6-amino-4-((3-chloro-4-fluorophenyl)sulfonyl)-3,4-dihydro-2H-benzo[b][1,4]oxazin-2-yl)ethyl)acetamide

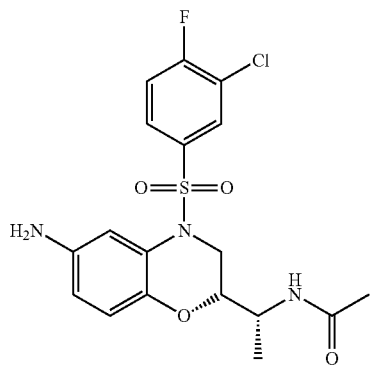

A mixture of tert-butyl ((R)-2-((R)-1-acetamidoethyl)-4-((3-chloro-4-fluorophenyl)sulfonyl)-3,4-dihydro-2H-benzo[b][1,4]oxazin-6-yl)carbamate (82 mg, 0.155 mmol), HCl (777 µL, 3.11 mmol), and THF (1553 µL) was heated at 50° C. for 18 hours. The mixture was concentrated in vacuo. The residue was carried on to the next step without further purification. LRMS (ESI) calculated for $C_{18}H_{20}ClFN_3O_4S$ (M+H)$^+$: 427.9. Found: 428.

Step 10—Synthesis of 1,1,1-trifluoro-2-methylpropan-2-yl ((R)-2-((R)-1-acetamidoethyl)-4-((3-chloro-4-fluorophenyl)sulfonyl)-3,4-dihydro-2H-benzo[b][1,4]oxazin-6-yl)carbamate

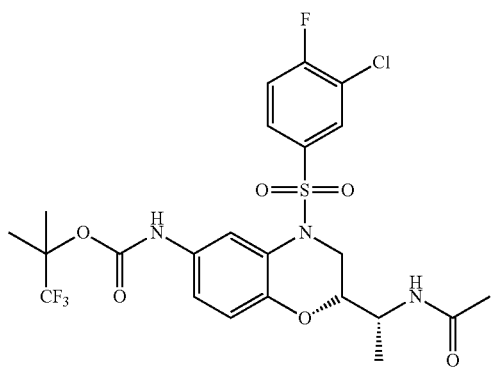

A mixture of N—((R)-1-((R)-6-amino-4-((3-chloro-4-fluorophenyl)sulfonyl)-3,4-dihydro-2H-benzo[b][1,4]oxazin-2-yl)ethyl)acetamide (66.5 mg, 0.155 mmol), 1,1,1-trifluoro-2-methylpropan-2-yl 1H-imidazole-1-carboxylate (58.7 mg, 0.264 mmol), and DMF (1554 µL) was heated at 100° C. for 2 hours. The mixture was washed with ethyl acetate and saturated NaHCO$_3$, followed by brine. The combined organics were dried over magnesium sulfate, filtered, and concentrated in vacuo. The residue was dissolved in DMSO (1.5 mL), filtered, and purified by reverse-phase HPLC (MeCN:H$_2$O, TFA buffer). LRMS (ESI) calculated for $C_{23}H_{25}ClF_4N_3O_6S$ (M+H)$^+$: 582. Found: 582. $^1$H NMR: (300 MHz, CDCl$_3$): δ 9.77 (1H, s), 8.00 (1H, d, J=6.22 Hz), 7.92 (2H, d, J=7.77 Hz), 7.71 (1H, m), 7.65 (1H, t, J=8.54 Hz), 7.16 (1H, d, J=8.54), 6.82 (1H, d, J=9.32), 4.29 (1H, d, J=14.36 Hz), 4.12 (1H, t, J=6.85 Hz), 3.66 (1H, t, J=6.16 Hz), 3.23 (1H, m), 1.83 (3H, s), 1.73 (6H, s), 1.06 (3H, d, J=7.51 Hz).

The anti-diastereomer 1,1,1-trifluoro-2-methylpropan-2-yl ((R)-2-((S)-1-acetamidoethyl)-4-((3-chloro-4-fluorophenyl)sulfonyl)-3,4-dihydro-2H-benzo[b][1,4]oxazin-6-yl)carbamate was prepared from tert-butyl ((R)-2-((R)-1-aminoethyl)-4-benzyl-3,4-dihydro-2H-benzo[b][1,4]oxazin-6-yl)carbamate using the same synthetic route outlined above. LRMS (ESI) calculated for $C_{23}H_{25}ClF_4N_3O_6S$ (M+H)$^+$: 582. Found: 582. $^1$H NMR: (300 MHz, CDCl$_3$): δ 9.78 (1H, s), 8.04 (1H, d, J=6.78 Hz), 7.98 (1H, d, J=8.29 Hz), 7.88 (1H, s), 7.78 (1H, m), 7.66 (1H, t, J=9.05 Hz), 7.12 (1H, d, J=9.80 Hz), 6.81 (1H, d, J=9.79 Hz), 4.29 (1H, d, J=13.49 Hz), 4.12 (1H, t, J=6.75 Hz), 3.66 (1H, t, J=4.49 Hz), 3.29 (1H, m), 1.84 (3H, s), 1.71 (6H, s), 1.08 (3H, s).

Example 16

The compounds in Table 4 below were prepared based on the experimental procedures described in Examples 6 and 15, and can be achieved by one of skill in the art in light of the present disclosure.

TABLE 4

| Ex. No. | Structure | Name | Observed m/z |
|---|---|---|---|
| 16A | 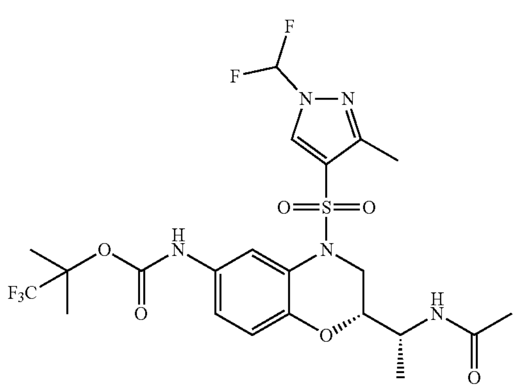 [SMILES: CC(=O)N[C@H](C)[C@H]1CN(S(=O)(=O)c2cn(C(F)F)nc2C)c2cc(NC(=O)OC(C)(C)C(F)(F)F)ccc2O1] | 1,1,1-trifluoro-2-methylpropan-2-yl ((R)-2-((R or S)-1-acetamidoethyl)-4-((1-(difluoromethyl)-3-methyl-1H-pyrazol-4-yl)sulfonyl)-3,4-dihydro-2H-benzo[b][1,4]oxazin-6-yl)carbamate | 584 (M + H)$^+$ |

TABLE 4-continued

| Ex. No. | Structure | Name | Observed m/z |
|---|---|---|---|
| 16B | 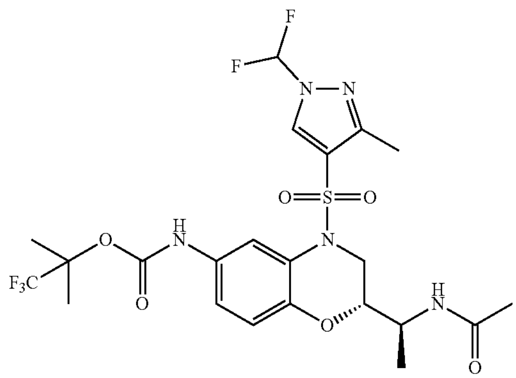 [SMILES: CC(=O)N[C@@H](C)[C@H]1CN(S(=O)(=O)c2cn(C(F)F)nc2C)c2cc(NC(=O)OC(C)(C)C(F)(F)F)ccc2O1] | 1,1,1-trifluoro-2-methylpropan-2-yl ((R)-2-((S or R)-1-acetamidoethyl)-4-((1-(difluoromethyl)-3-methyl-1H-pyrazol-4-yl)sulfonyl)-3,4-dihydro-2H-benzo[b][1,4]oxazin-6-yl)carbamate | 584 (M + H)+ |
| 16C | 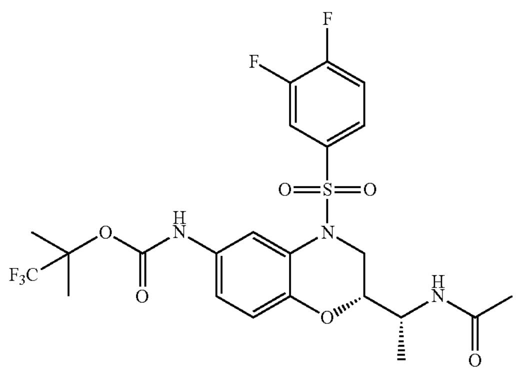 [SMILES: CC(=O)N[C@H](C)[C@H]1CN(S(=O)(=O)c2ccc(F)c(F)c2)c2cc(NC(=O)OC(C)(C)C(F)(F)F)ccc2O1] | 1,1,1-trifluoro-2-methylpropan-2-yl ((R)-2-((R or S)-1-acetamidoethyl)-4-((3,4-difluorophenyl)sulfonyl)-3,4-dihydro-2H-benzo[b][1,4]oxazin-6-yl)carbamate | 566 (M + H)+ |
| 16D | 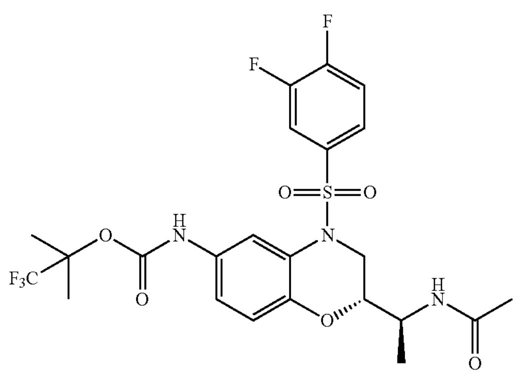 [SMILES: CC(=O)N[C@@H](C)[C@H]1CN(S(=O)(=O)c2ccc(F)c(F)c2)c2cc(NC(=O)OC(C)(C)C(F)(F)F)ccc2O1] | 1,1,1-trifluoro-2-methylpropan-2-yl ((R)-2-((S or R)-1-acetamidoethyl)-4-((3,4-difluorophenyl)sulfonyl)-3,4-dihydro-2H-benzo[b][1,4]oxazin-6-yl)carbamate | 566 (M + H)+ |
| 16E | 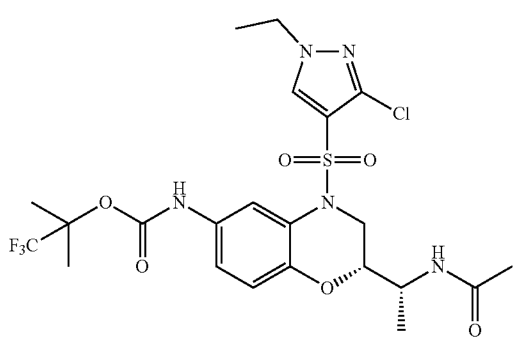 [SMILES: CCn1cc(S(=O)(=O)N2C[C@H]([C@@H](C)NC(C)=O)Oc3ccc(NC(=O)OC(C)(C)C(F)(F)F)cc32)c(Cl)n1] | 1,1,1-trifluoro-2-methylpropan-2-yl ((R)-2-((R or S)-1-acetamidoethyl)-4-((3-chloro-1-ethyl-1H-pyrazol-4-yl)sulfonyl)-3,4-dihydro-2H-benzo[b][1,4]oxazin-6-yl)carbamate | 583 (M + H)+ |

TABLE 4-continued

| Ex. No. | Structure | Name | Observed m/z |
|---|---|---|---|
| 16F | 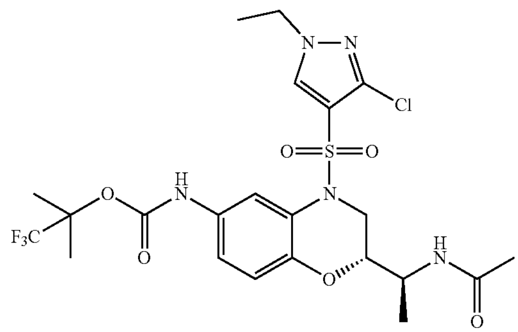 [SMILES: CCn1cc(S(=O)(=O)N2C[C@H]([C@H](C)NC(C)=O)Oc3ccc(NC(=O)OC(C)(C)C(F)(F)F)cc32)c(Cl)n1] | 1,1,1-trifluoro-2-methylpropan-2-yl ((R)-2-((S or R)-1-acetamidoethyl)-4-((3-chloro-1-ethyl-1H-pyrazol-4-yl)sulfonyl)-3,4-dihydro-2H-benzo[b][1,4]oxazin-6-yl)carbamate | 584 (M + H)+ |
| 16G | 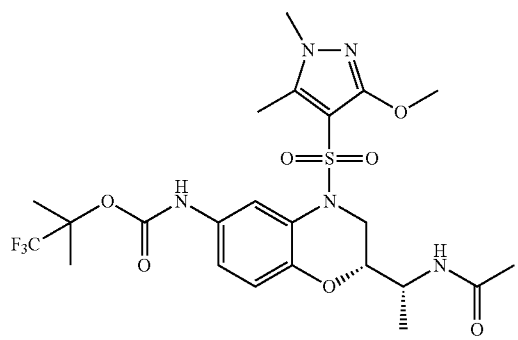 [SMILES: COc1nn(C)c(C)c1S(=O)(=O)N1C[C@H]([C@@H](C)NC(C)=O)Oc2ccc(NC(=O)OC(C)(C)C(F)(F)F)cc21] | 1,1,1-trifluoro-2-methylpropan-2-yl ((R)-2-((R or S)-1-acetamidoethyl)-4-((3-methoxy-1,5-dimethyl-1H-pyrazol-4-yl)sulfonyl)-3,4-dihydro-2H-benzo[b][1,4]oxazin-6-yl)carbamate | 578 (M + H)+ |
| 16H | 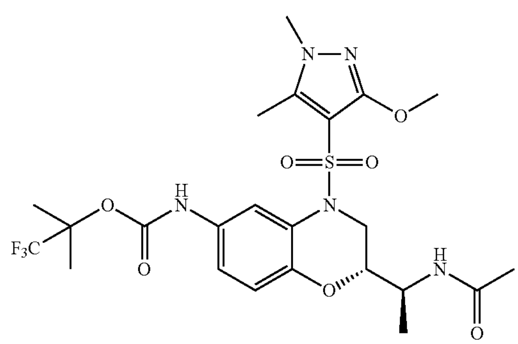 [SMILES: COc1nn(C)c(C)c1S(=O)(=O)N1C[C@H]([C@H](C)NC(C)=O)Oc2ccc(NC(=O)OC(C)(C)C(F)(F)F)cc21] | 1,1,1-trifluoro-2-methylpropan-2-yl ((R)-2-((S)-1-acetamidoethyl)-4-((3-methoxy-1,5-dimethyl-1H-pyrazol-4-yl)sulfonyl)-3,4-dihydro-2H-benzo[b][1,4]oxazin-6-yl)carbamate | 578 (M + H)+ |
| 16i | 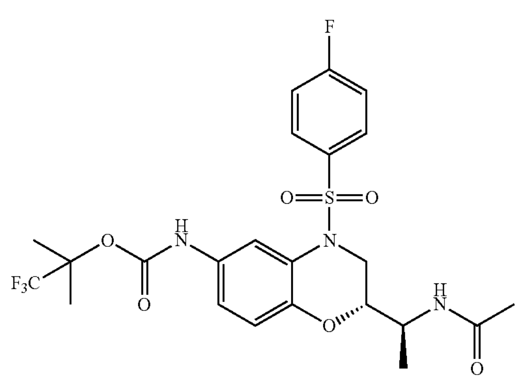 [SMILES: CC(=O)N[C@@H](C)[C@H]1CN(S(=O)(=O)c2ccc(F)cc2)c2cc(NC(=O)OC(C)(C)C(F)(F)F)ccc2O1] | 1,1,1-trifluoro-2-mehtylpropan-2-yl ((R or S)-2-((S or R)-1-acetamidoethyl)-4-((4-fluorophenyl)sulfonyl)-3,4-dihydro-2H-benzo[b][1,4]oxazin-6-yl)carbamate | 548 (M + H)+ |

TABLE 4-continued

| Ex. No. | Structure | Name | Observed m/z |
|---|---|---|---|
| 16J | 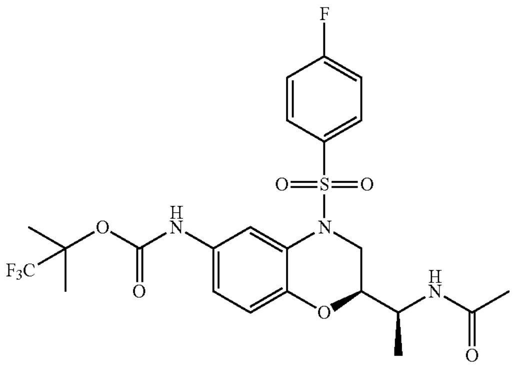 [SMILES: CC(=O)N[C@@H](C)[C@@H]1CN(S(=O)(=O)c2ccc(F)cc2)c2cc(NC(=O)OC(C)(C)C(F)(F)F)ccc2O1] | 1,1,1-trifluoro-2-methylpropan-2-yl ((S or R)-2-((S or R)-1-acetamidoethyl)-4-((4-fluorophenyl)sulfonyl)-3,4-dihydro-2H-benzo[b][1,4]oxazin-6-yl)carbamte | 548 (M + H)+ |
| 16K | 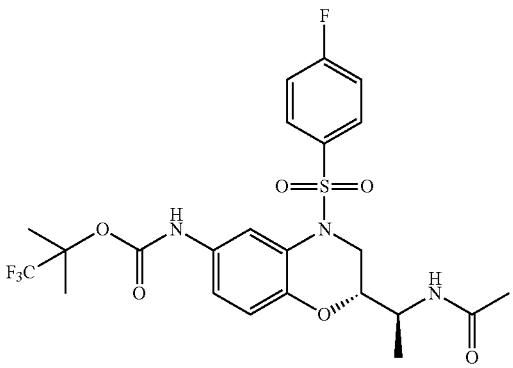 [SMILES: CC(=O)N[C@@H](C)[C@H]1CN(S(=O)(=O)c2ccc(F)cc2)c2cc(NC(=O)OC(C)(C)C(F)(F)F)ccc2O1] | 1,1,1-trifluoro-2-methylpropan-2-yl ((R or S)-2-((S or R)-1-acetamidoethyl)-4-((4-fluorophenyl)sulfonyl)-3,4-dihydro-2H-benzo[b][1,4]oxazin-6-yl)carbamate | 548 (M + H)+ |
| 16L | 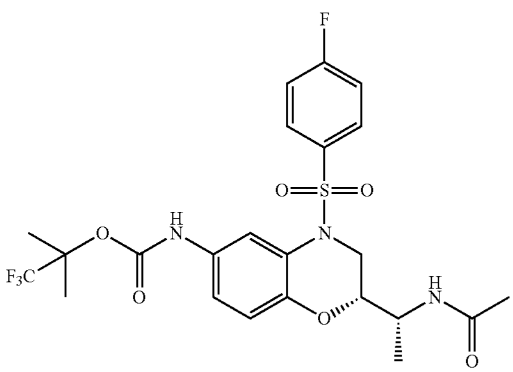 [SMILES: CC(=O)N[C@H](C)[C@H]1CN(S(=O)(=O)c2ccc(F)cc2)c2cc(NC(=O)OC(C)(C)C(F)(F)F)ccc2O1] | 1,1,1-trifluoro-2-methylpropan-2-yl ((R or S)-2-((R or S)-1-acetamidoethyl)-4-((4-fluorophenyl)sulfonyl)-3,4-dihydro-2H-benzo[b][1,4]oxazin-6-yl)carbamate | 548 (M + H)+ |
| 16M | 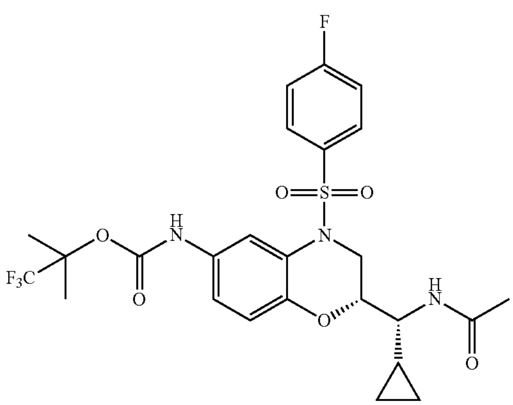 [SMILES: CC(=O)N[C@H](C1CC1)[C@H]1CN(S(=O)(=O)c2ccc(F)cc2)c2cc(NC(=O)OC(C)(C)C(F)(F)F)ccc2O1] | 1,1,1-trifluoro-2-methylpropan-2-yl ((R)-2-((R or S)-acetamido(cyclopropyl)methyl)-4-((4-fluorophenyl)sulfonyl)-3,4-dihydro-2H-benzo[b][1,4]oxazin-6-yl)carbamate | 574 (M + H)+ |

TABLE 4-continued

| Ex. No. | Structure | Name | Observed m/z |
|---|---|---|---|
| 16N | 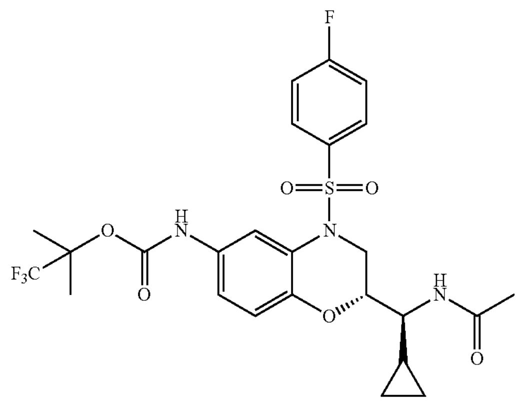 [SMILES: CC(=O)N[C@@H](C1CC1)[C@H]1CN(S(=O)(=O)c2ccc(F)cc2)c2cc(NC(=O)OC(C)(C)C(F)(F)F)ccc2O1] | 1,1,1-trifluoro-2-methylpropan-2-yl ((R)-2-((S or R)-acetamido(cyclopropyl)methyl)-4-((4-fluorophenyl)sulfonyl)-3,4-dihydro-2H-benzo[b][1,4]oxazin-6-yl)carbamate | 574 (M + H)+ |
| 16o | 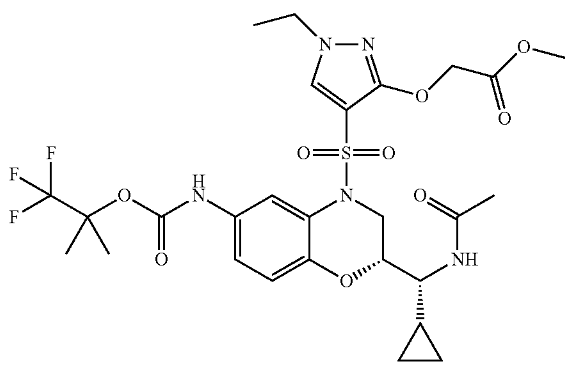 [SMILES: CCn1cc(S(=O)(=O)N2C[C@H]([C@H](NC(C)=O)C3CC3)Oc3ccc(NC(=O)OC(C)(C)C(F)(F)F)cc32)c(OCC(=O)OC)n1] | methyl 2-((4-(((R)-2-((R or S)-acetamido(cyclopropyl)methyl)-6-((((1,1,1-trifluoro-2-methylpropan-2-yl)oxy)carbonyl)amino)-2H-benzo[b][1,4]oxazin-4(3H)-yl)sulfonyl)-1-ethyl-1H-pyrazol-3-yl)oxy)acetate | 662 (M + H)+ |
| 16P | 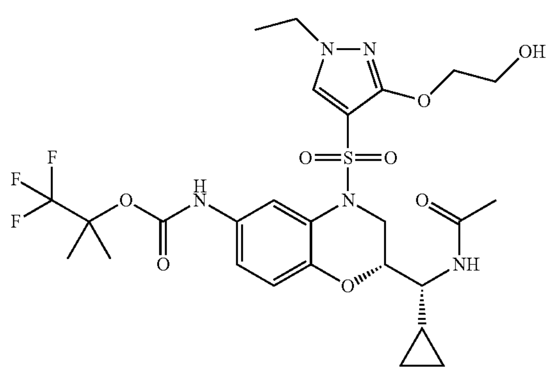 [SMILES: CCn1cc(S(=O)(=O)N2C[C@H]([C@H](NC(C)=O)C3CC3)Oc3ccc(NC(=O)OC(C)(C)C(F)(F)F)cc32)c(OCCO)n1] | 1,1,1-trifluoro-2-methylpropan-2-yl ((R)-2-((R or S)-acetamido(cyclopropyl)methyl)-4-((1-ethyl-3-(2-hydroxyethoxy)-1H-pyrazol-4-yl)sulfonyl)-3,4-dihydro-2H-benzo[b][1,4]oxazin-6-yl)carbamate | 634 (M + H)+ |
| 16Q | 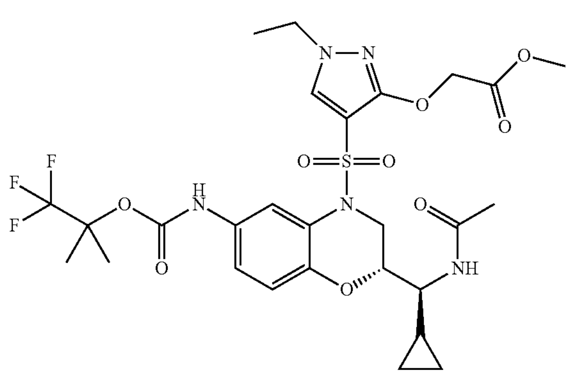 [SMILES: CCn1cc(S(=O)(=O)N2C[C@H]([C@@H](NC(C)=O)C3CC3)Oc3ccc(NC(=O)OC(C)(C)C(F)(F)F)cc32)c(OCC(=O)OC)n1] | methyl 2-((4-(((R)-2-((R or S)-acetamido(cyclopropyl)methyl)-6-((((1,1,1-trifluoro-2-methylpropan-2-yl)oxy)carbonyl)amino)-2H-benzo[b][1,4]oxazin-4(3H)-yl)sulfonyl)-1-ethyl-1H-pyrazol-3-yl)oxy)acetate | 662 (M + H)+ |

TABLE 4-continued

| Ex. No. | Structure | Name | Observed m/z |
|---|---|---|---|
| 16R | 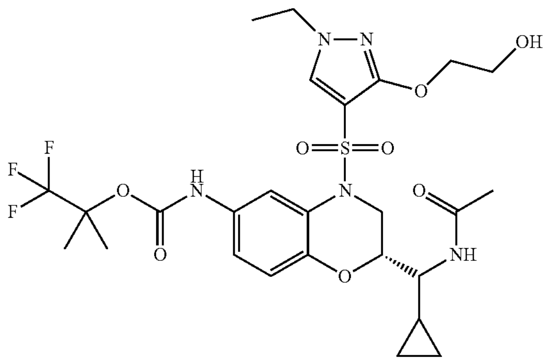 [SMILES: CCn1cc(S(=O)(=O)N2C[C@H](C(NC(C)=O)C3CC3)Oc3ccc(NC(=O)OC(C)(C)C(F)(F)F)cc32)c(OCCO)n1] | 1,1,1-trifluoro-2-methylpropan-2-yl ((R)-2-((R or S)-acetamido(cyclopropyl)methyl)-4-((1-ethyl-3-(2-hydroxyethoxy)-1H-pyrazol-4-yl)sulfonyl)-3,4-dihydro-2H-benzo[b][1,4]oxazin-6-yl)carbamate | 634 (M + H)+ |
| 16S | 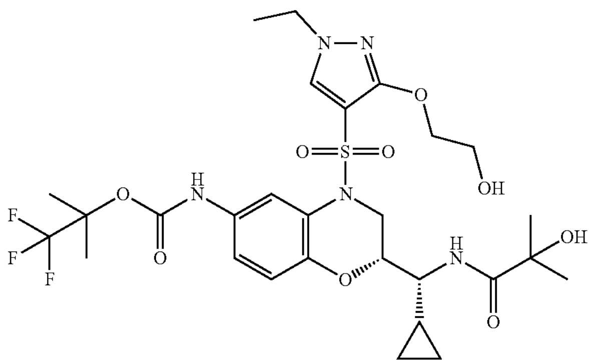 [SMILES: CCn1cc(S(=O)(=O)N2C[C@H]([C@H](NC(=O)C(C)(C)O)C3CC3)Oc3ccc(NC(=O)OC(C)(C)C(F)(F)F)cc32)c(OCCO)n1] | 1,1,1-trifluoro-2-methylpropan-2-yl ((R)-2-((R or S)-cyclopropyl(2-hydroxy-2-methylpropanamido)methyl)-4-((1-ethyl-3-(2-hydroxyethoxy)-1H-pyrazol-4-yl)sulfonyl)-3,4-dihydro-2H-benzo[b][1,4]oxazin-6-yl)carbamate | 678 (M + H)+ |
| 16T | 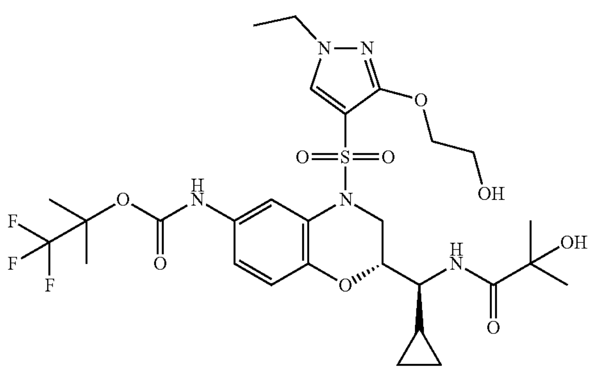 [SMILES: CCn1cc(S(=O)(=O)N2C[C@H]([C@@H](NC(=O)C(C)(C)O)C3CC3)Oc3ccc(NC(=O)OC(C)(C)C(F)(F)F)cc32)c(OCCO)n1] | 1,1,1-trifluoro-2-methylpropan-2-yl ((R)-2-((R or S)-cyclopropyl(2-hydroxy-2-methylpropanamido)methyl)-4-((1-ethyl-3-(2-hydroxyethoxy)-1H-pyrazol-4-yl)sulfonyl)-3,4-dihydro-2H-benzo[b][1,4]oxazin-6-yl)carbamate | 678 (M + H)+ |
| 16U | 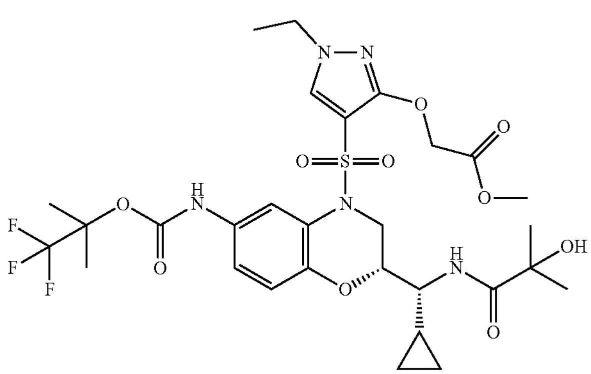 [SMILES: CCn1cc(S(=O)(=O)N2C[C@H]([C@H](NC(=O)C(C)(C)O)C3CC3)Oc3ccc(NC(=O)OC(C)(C)C(F)(F)F)cc32)c(OCC(=O)OC)n1] | methyl 2-((4-(((R)-2-((R or S)-cyclopropyl(2-hydroxy-2-methylpropanamido)methyl)-6-((((1,1,1-trifluoro-2-methylpropan-2-yl)oxy)carbonyl)amino)-2H-benzo[b][1,4]oxazin-4(3H)-yl)sulfonyl)-1-ethyl-1H-pyrazol-3-yl)oxy)acetate | 706 (M + H)+ |

TABLE 4-continued

| Ex. No. | Structure | Name | Observed m/z |
|---|---|---|---|
| 16V | 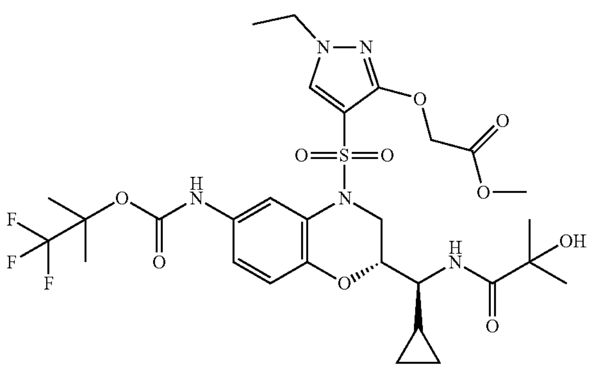 [SMILES: CCn1cc(S(=O)(=O)N2C[C@H]([C@@H](NC(=O)C(C)(C)O)C3CC3)Oc3ccc(NC(=O)OC(C)(C)C(F)(F)F)cc32)c(OCC(=O)OC)n1] | methyl 2-((4-(((R)-2-((R or S)-cyclopropyl(2-hydroxy-2-methylpropanamido)methyl)-6-(((,1,1-trifluoro-2-methylpropan-2-yl)oxy)carbonyl)amino)-2H-benzo[b][1,4]oxazin-4(3H)-yl)sulfonyl)-1-ethyl-1H-pyrazol-3-yloxy)acetate | 706 (M + H)+ |
| 16W | 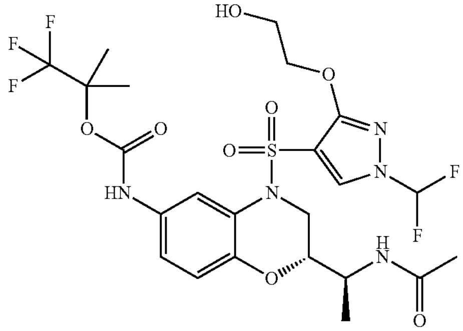 [SMILES: CC(=O)N[C@@H](C)[C@H]1CN(S(=O)(=O)c2cn(C(F)F)nc2OCCO)c2cc(NC(=O)OC(C)(C)C(F)(F)F)ccc2O1] | 2,2,2-trifluoro-1,1-dimethylethyl [(2R)-2-[(1S or 1R)-1-(acetylamino)ethyl]-4-{[1-(difluoromethyl)-3-(2-hydroxyethoxy)-1H-pyrazol-4-yl]sulfonyl}-3,4-dihydro-2H-1,4-benzoxazin-6-yl]carbamate | 630 (M + H)+ |
| 16X | 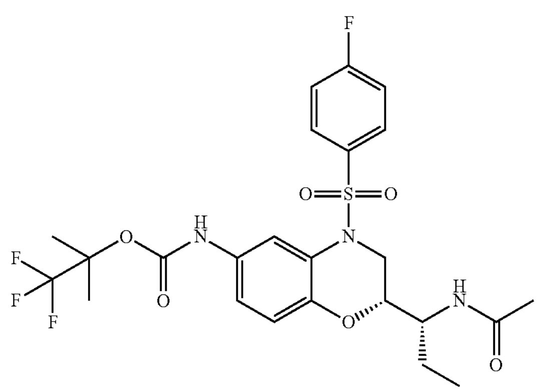 [SMILES: CC[C@@H](NC(C)=O)[C@H]1CN(S(=O)(=O)c2ccc(F)cc2)c2cc(NC(=O)OC(C)(C)C(F)(F)F)ccc2O1] | 1,1,1-trifluoro-2-methylpropan-2-yl ((R)-2-((R or S)-1-acetamidopropyl)-4-((4-fluorophenyl)sulfonyl)-3,4-dihydro-2H-benzo[b][1,4]oxazin-6-yl)carbamate | 562 (M + H)+ |
| 16Y | 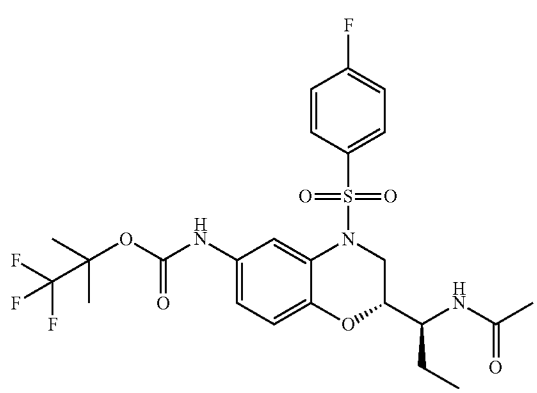 [SMILES: CC[C@H](NC(C)=O)[C@H]1CN(S(=O)(=O)c2ccc(F)cc2)c2cc(NC(=O)OC(C)(C)C(F)(F)F)ccc2O1] | 1,1,1-trifluoro-2-methylpropan-2-yl ((R)-2-((R or S)-1-acetamidopropyl)-4-((4-fluorophenyl)sulfonyl)-3,4-dihydro-2H-benzo[b][1,4]oxazin-6-yl)carbamate | 562 (M + H)+ |

TABLE 4-continued

| Ex. No. | Structure | Name | Observed m/z |
|---|---|---|---|
| 16Z | 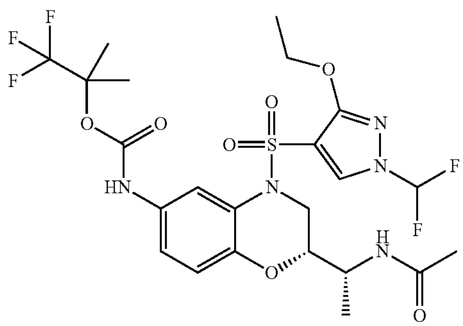 [SMILES: CCOc1nn(C(F)F)cc1S(=O)(=O)N1C[C@H]([C@@H](C)NC(C)=O)Oc2ccc(NC(=O)OC(C)(C)C(F)(F)F)cc21] | 2,2,2-trifluoro-1,1-dimethylethyl [(2R)-2-[(1R or S)-1-(acetylamino)ethyl]-4-{[1-(difluoromethyl)-3-ethoxy-1H-pyrazol-4-yl]sulfonyl}-3,4-dihydro-2H-1,4-benzoxazin-6-yl]carbamate | 614 (M + H)+ |
| 16AA | 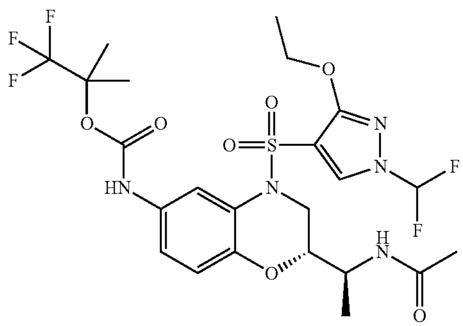 [SMILES: CCOc1nn(C(F)F)cc1S(=O)(=O)N1C[C@H]([C@H](C)NC(C)=O)Oc2ccc(NC(=O)OC(C)(C)C(F)(F)F)cc21] | 2,2,2-trifluoro-1,1-dimethylethyl [(2R)-2-[(1R or S)-1-(acetylamino)ethyl]-4-{[1-(difluoromethyl)-3-ethoxy-1H-pyrazol-4-yl]sulfonyl}-3,4-dihydro-2H-1,4-benzoxazin-6-yl]carbamate | 614 (M + H)+ |
| 16AB | 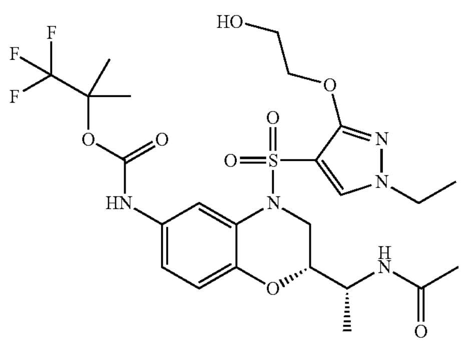 [SMILES: CCn1cc(S(=O)(=O)N2C[C@H]([C@@H](C)NC(C)=O)Oc3ccc(NC(=O)OC(C)(C)C(F)(F)F)cc32)c(OCCO)n1] | 2,2,2-trifluoro-1,1-dimethylethyl [(2R)-2-[(1R or S)-1-(acetylamino)ethyl]-4-{[1-ethyl-3-(2-hydroxyethoxy)-1H-pyrazol-4-yl]sulfonyl}-3,4-dihydro-2H-1,4-benzoxazin-6-yl]carbamate | 608 (M + H)+ |
| 16AC | 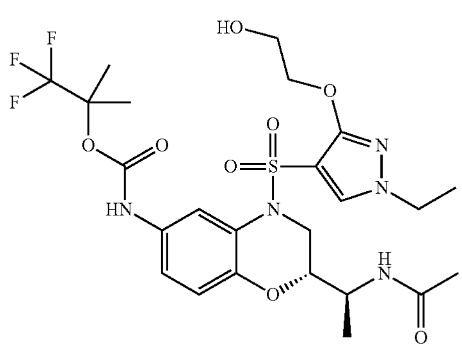 [SMILES: CCn1cc(S(=O)(=O)N2C[C@H]([C@H](C)NC(C)=O)Oc3ccc(NC(=O)OC(C)(C)C(F)(F)F)cc32)c(OCCO)n1] | 2,2,2-trifluoro-1,1-dimethylethyl [(2R)-2-[(1R or S)-1-(acetylamino)ethyl]-4-{[1-ethyl-3-(2-hydroxyethoxy)-1H-pyrazol-4-yl]sulfonyl}-3,4-dihydro-2H-1,4-benzoxazin-6-yl]carbamate | 608 (M + H)+ |

Example 17—Synthesis of (R)-tert-butyl (2-(2-acet-amidopropan-2-yl)-4-((4-fluorophenyl)sulfonyl)-3,4-dihydro-2H-benzo[b][1,4]oxazin-6-yl)carbamate (17)

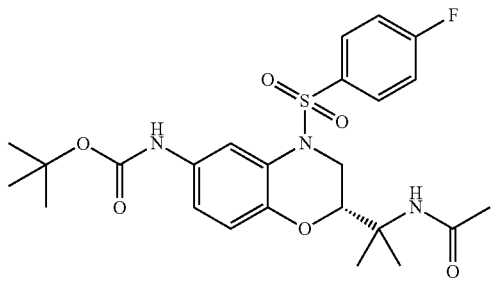 [SMILES: CC(=O)NC(C)(C)[C@H]1CN(S(=O)(=O)c2ccc(F)cc2)c2cc(NC(=O)OC(C)(C)C)ccc2O1]

The title compound was prepared according to the procedures described below.

Step 1—Synthesis of ethyl 4-((4-fluorophenyl)sulfonyl)-6-nitro-3,4-dihydro-2H-benzo[b][1,4]oxazine-2-carboxylate

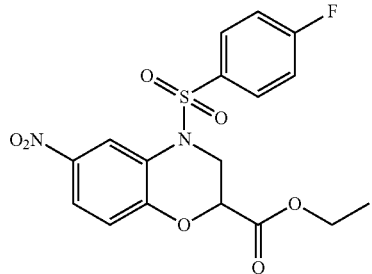 [SMILES: CCOC(=O)C1CN(S(=O)(=O)c2ccc(F)cc2)c2cc([N+](=O)[O-])ccc2O1]

A mixture of ethyl 6-nitro-3,4-dihydro-2H-benzo[b][1,4]oxazine-2-carboxylate (4.5 g, 17.9 mmol), 4-fluorobenzene-1-sulfonyl chloride (4.52 g, 23.3 mmol) and pyridine (7.07 g, 89.5 mmol) in THF (100 mL) was heated at 60° C. for fifteen hours. The reaction mixture was concentrated, and the residue was partitioned between dichloromethane (100 mL) and water (100 mL). The aqueous layer was extracted with dichloromethane (100 mL×2), and the combined organic layers were washed with brine (100 mL), dried (Na$_2$SO$_4$), and concentrated. The residue was purified by column chromatography on silica gel eluting with petroleum ether: ethyl acetate (5:1) to afford ethyl 4-(4-fluorophenyl)sulfonyl)-6-nitro-3,4-dihydro-2H-benzo[b][1,4]oxazine-2-carboxylate as a yellow solid. LRMS (ESI) calculated for C$_{17}$H$_{16}$FN$_2$O$_7$S (M+H)$^+$: 411. Found: 411.

Step 2—Synthesis of ethyl 6-((tert-butoxycarbonyl)amino)-4-((4-fluorophenyl)sulfonyl)-3,4-dihydro-2H-benzo[b][1,4]oxazine-2-carboxylate

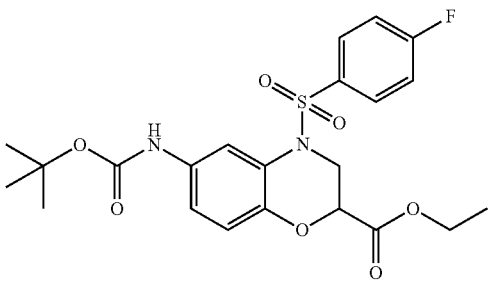 [SMILES: CCOC(=O)C1CN(S(=O)(=O)c2ccc(F)cc2)c2cc(NC(=O)OC(C)(C)C)ccc2O1]

To a solution of ethyl 4-((4-fluorophenyl)sulfonyl)-6-nitro-3,4-dihydro-2H-benzo[b][1,4]oxazine-2-carboxylate (5.0 g, 12.2 mmol) and di-tert-butyl dicarbonate (2.92 g, 13.4 mmol) in ethanol (100 mL) was added Pd/C (1.0 g, 10% wt) under argon. The suspension was degassed under vacuo and purged with hydrogen three times. The mixture was stirred under the pressure of 40 psi hydrogen at 30° C. for four hours. The suspension was filtered through a pad of CELITE and the filter cake was washed with ethanol (20 mL). The combined filtrates were concentrated to dryness to give ethyl 6-((tert-butoxycarbonyl)amino)-4-((4-fluorophenyl)sulfonyl)-3,4-dihydro-2H-benzo[b][1,4]oxazine-2-carboxylate as a yellow solid. LRMS (ESI) calculated for C$_{22}$H$_{26}$FN$_2$O$_7$S (M+H)$^+$: 481. Found: 481.

Step 3—Synthesis of (R)-tert-butyl (4-((4-fluorophenyl)sulfonyl)-2-(2-hydroxypropan-2-yl)-3,4-dihydro-2H-benzo[b][1,4]oxazin-6-yl)carbamate and (S)-tert-butyl (4-((4-fluorophenyl) sulfonyl)-2-(2-hydroxypropan-2-yl)-3,4-dihydro-2H-benzo[b][1,4]oxazin-6-yl)carbamate

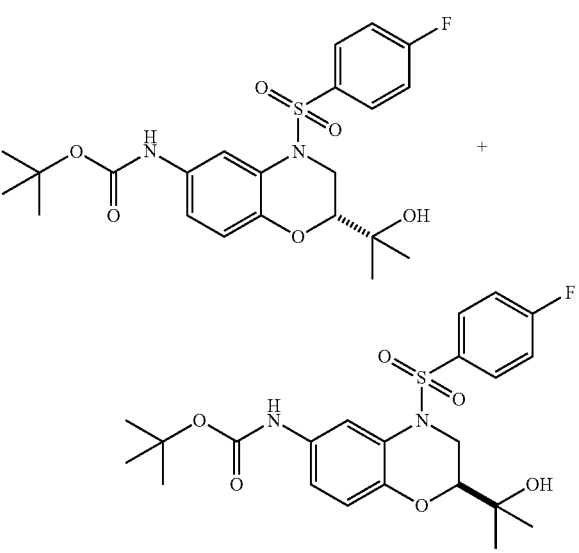

To a stirred solution of ethyl 6-((tert-butoxycarbonyl)amino)-4-((4-fluorophenyl)sulfonyl)-3,4-dihydro-2H-benzo[b][1,4]oxazine-2-carboxylate (5.5 g, 11.5 mmol) in anhydrous THF (70 mL) was added a 3M solution of methyl magnesium bromide (38.3 mL, 115 mmol) in ethyl ether at −78° C., and the resultant mixture was warmed to 25° C. and stirred for an additional hour. The reaction mixture was poured into saturated ammonium chloride (500 mL), and extracted with dichloromethane (500 mL×2). The combined organic layers were dried (Na$_2$SO$_4$), and concentrated. The crude product was purified by column chromatography on silica gel eluting with petroleum ether:ethyl acetate (3:1) to afford a racemic mixture of the title compounds as a white solid, which was chirally separated by SFC (Instrument: Thar SFC 350; Column: AD 300 mm*50 mm, 10 um; Mobile phase: A: Supercritical CO$_2$, B: MeOH (0.1% NH$_3$.H$_2$O), A: B=65:35 at 240 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford the two isomers.

(R)-tert-butyl (4-((4-fluorophenyl)sulfonyl)-2-(2-hydroxypropan-2-yl)-3,4-dihydro-2H-benzo[b][1,4]oxazin-6-yl)carbamate. $^1$H NMR (400 MHz, CDCl$_3$) δ 7.62-7.75 (m, 3H), 7.32 (br. s., 1H), 7.15 (t, J=8.4 Hz, 2H), 6.81 (d, J=9.2 Hz, 1H), 6.44 (br. s., 1H), 4.38 (dd, J=2.0, 14.4 Hz, 1H), 3.19 (dd, J=10.4, 14.4 Hz, 1H), 3.03 (dd, J=1.6, 10.4 Hz, 1H), 1.53 (s, 9H), 1.20 (d, J=12.4 Hz, 6H). LRMS (ESI) calculated for C$_{22}$H$_{28}$FN$_2$O$_6$S (M+H)$^+$: 467. Found: 467.

(S)-tert-butyl (4-((4-fluorophenyl)sulfonyl)-2-(2-hydroxypropan-2-yl)-3,4-dihydro-2H-benzo[b][1,4]oxazin-6-yl)carbamate. $^1$H NMR (400 MHz, CDCl$_3$) δ 7.65-7.74 (m, 3H), 7.33 (br. s, 1H), 7.15 (t, J=8.4 Hz, 2H), 6.81 (d, J=8.4 Hz, 1H), 6.44 (br. s, 1H), 4.38 (dd, J=2.0, 14.0 Hz, 1H), 3.19 (dd, J=10.4, 14.0 Hz, 1H), 3.03 (dd, J=1.6, 10.4 Hz, 1H), 1.53 (s, 9H), 1.20 (d, J=12.4 Hz, 6H). LRMS (ESI) calculated for C$_{22}$H$_{28}$FN$_2$O$_6$S (M+H)$^+$: 467. Found: 467.

Step 4—Synthesis of (R)—N-(2-(6-amino-4-((4-fluorophenyl)sulfonyl)-3,4-dihydro-2H-benzo[b][1,4]oxazin-2-yl)propan-2-yl)acetamide

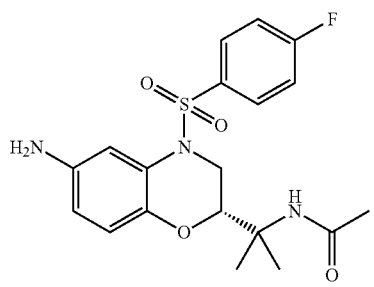 [SMILES: CC(=O)NC(C)(C)[C@H]1CN(S(=O)(=O)c2ccc(F)cc2)c2cc(N)ccc2O1]

To a stirred solution of (R)-tert-butyl (4-((4-fluorophenyl)sulfonyl)-2-(2-hydroxypropan-2-yl)-3,4-dihydro-2H-benzo[b][1,4]oxazin-6-yl)carbamate (300 mg, 0.64 mmol) in acetonitrile (3 mL) was added concentrated sulfuric acid (3 mL) dropwise at 0° C., and the resultant mixture was stirred at 15° C. for fifteen hours. The reaction mixture was poured into ice water (30 mL), and the aqueous solution was adjusted to pH 8 with solid sodium carbonate, and extracted with dichloromethane (30 mL×2). The combined organic layers were dried (Na$_2$SO$_4$) and concentrated. The residue was purified by column chromatography on silica gel (petroleum ether: ethyl acetate=2:1) to give (R)—N-(2-(6-amino-4-((4-fluorophenyl)sulfonyl)-3,4-dihydro-2H-benzo[b][1,4]oxazin-2-yl)propan-2-yl)acetamide as a yellow solid. LRMS (ESI) calculated for C$_{19}$H$_{23}$FN$_3$O$_4$S (M+H)$^+$: 408. Found: 408.

Step 5—Synthesis of (R)-tert-butyl (2-(2-acetamidopropan-2-yl)-4-((4-fluorophenyl)sulfonyl)-3,4-dihydro-2H-benzo[b][1,4]oxazin-6-yl)carbamate

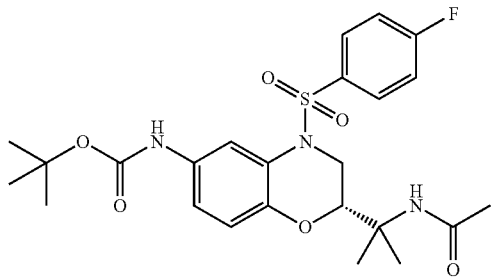 [SMILES: CC(=O)NC(C)(C)[C@H]1CN(S(=O)(=O)c2ccc(F)cc2)c2cc(NC(=O)OC(C)(C)C)ccc2O1]

A mixture of (R)—N-(2-(6-amino-4-((4-fluorophenyl)sulfonyl)-3,4-dihydro-2H-benzo[b][1,4]oxazin-2-yl)propan-2-yl)acetamide (100 mg, 0.25 mmol), triethyl amine (51 mg, 0.50 mmol) and di-tert-butyl dicarbonate (65 mg, 0.30 mmol) in dichloromethane (3 mL) was stirred at 15° C. for two days. The reaction mixture was concentrated, and the residue was partitioned between dichloromethane (20 mL) and water (20 mL). The aqueous layer was extracted with dichloromethane (20 mL×2), and the combined organic layers were dried (Na$_2$SO$_4$) and concentrated. The residue was purified by prep-HPLC (46-76% acetonitrile+0.75% trifluoroacetic acid in water) to give (R)-tert-butyl (2-(2-acetamidopropan-2-yl)-4-((4-fluorophenyl)sulfonyl)-3,4-dihydro-2H-benzo[b][1,4]oxazin-6-yl)carbamate as a white solid. $^1$H NMR (400 MHz, CDCl$_3$) δ 7.77-7.64 (m, 3H), 7.16 (t, J=8.4 Hz, 2H), 6.78 (d, J=9.0 Hz, 1H), 5.59 (s, 1H), 4.41 (dd, J=1.8, 14.4 Hz, 1H), 3.71 (d, J=8.8 Hz, 1H), 3.10 (dd, J=10.4, 14.4 Hz, 1H), 2.02 (s, 3H), 1.54 (s, 9H), 1.35 (d, J=4.0 Hz, 6H). LRMS (ESI) calculated for C$_{24}$H$_{31}$FN$_3$O$_6$S (M+H)$^+$: 508. Found: 508.

Example 18—Synthesis of (S)-tert-butyl (2-(2-acetamidopropan-2-yl)-4-((4-fluorophenyl)sulfonyl)-3,4-dihydro-2H-benzo[b][1,4]oxazin-6-yl)carbamate (18)

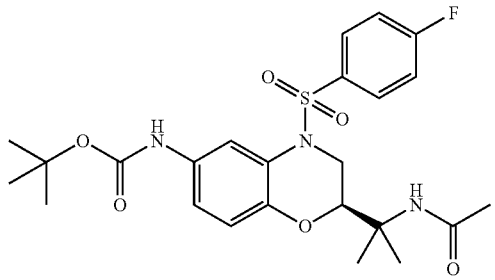 [SMILES: CC(=O)NC(C)(C)[C@@H]1CN(S(=O)(=O)c2ccc(F)cc2)c2cc(NC(=O)OC(C)(C)C)ccc2O1]

The title compound was prepared via the same method as in Example 17 but with the enantiomer of the starting material in Example 17.

Example 19—Preparation of (S)-1,1,1-trifluoro-2-methylpropan-2-yl (2-(2-(substituted amine)-propan-2-yl)-4-((-((optionally substituted aryl or heteroaryl)sulfonyl)-3,4-dihydro-2H-benzo[b][1,4]oxazin-6-yl)carbamates The compounds in Table 5 below were prepared based on the experimental procedures described in Examples 17 and 18 and elsewhere in the detailed description, and can be achieved by one of skill in the art in light of the present disclosure.

TABLE 5

| Ex. No. | Structure | Name | Observed m/z |
|---|---|---|---|
| 19A | 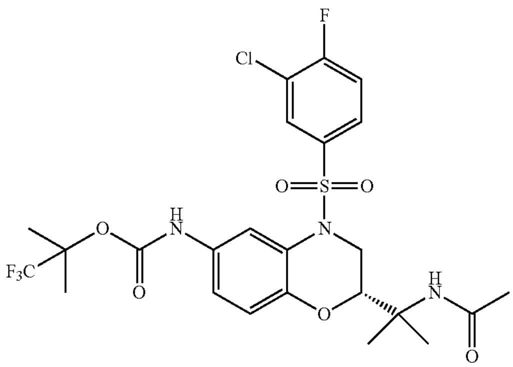 [SMILES: CC(=O)NC(C)(C)[C@H]1CN(S(=O)(=O)c2ccc(F)c(Cl)c2)c2cc(NC(=O)OC(C)(C)C(F)(F)F)ccc2O1] | (R)-1,1,1-trifluoro-2-methylpropan-2-yl (2-(2-acetamidopropan-2-yl)-4-((3-chloro-4-fluorophenyl)sulfonyl)-3,4-dihydro-2H-benzo[b][1,4]oxazin-6-yl)carbamate | 596 (M + H)+ |
| 19B | 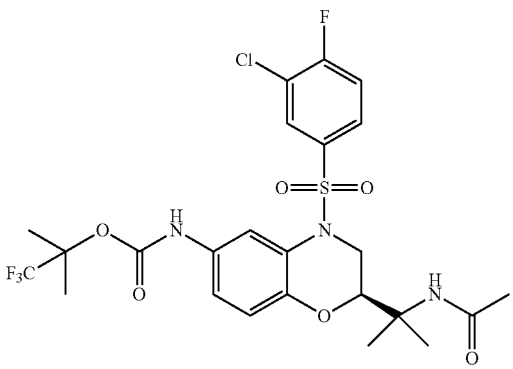 [SMILES: CC(=O)NC(C)(C)[C@@H]1CN(S(=O)(=O)c2ccc(F)c(Cl)c2)c2cc(NC(=O)OC(C)(C)C(F)(F)F)ccc2O1] | (S)-1,1,1-trifluoro-2-methylpropan-2-yl (2-(2-acetamidopropan-2-yl)-4-((3-chloro-4-fluorophenyl)sulfonyl)-3,4-dihydro-2H-benzo[b][1,4]oxazin-6-yl)carbamate | 596 (M + H)+ |
| 19C | 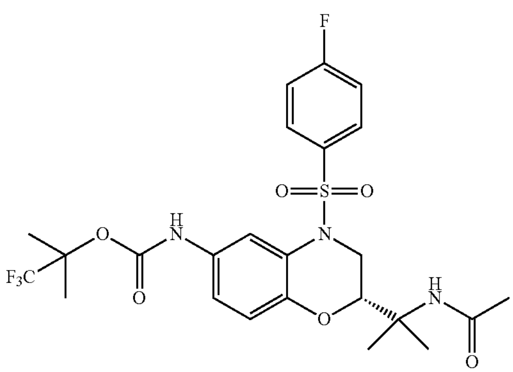 [SMILES: CC(=O)NC(C)(C)[C@H]1CN(S(=O)(=O)c2ccc(F)cc2)c2cc(NC(=O)OC(C)(C)C(F)(F)F)ccc2O1] | (R)-1,1,1-trifluoro-2-methylpropan-2-yl (2-(2-acetamidopropan-2-yl)-4-((4-fluorophenyl)sulfonyl)-3,4-dihydro-2H-benzo[b][1,4]oxazin-6-yl)carbamate | 562 (M + H)+ |
| 19D | 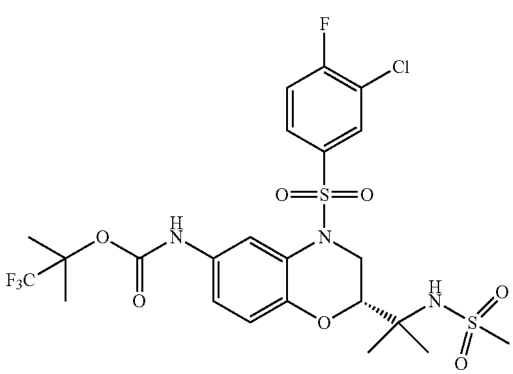 [SMILES: CC(C)(NS(C)(=O)=O)[C@H]1CN(S(=O)(=O)c2ccc(F)c(Cl)c2)c2cc(NC(=O)OC(C)(C)C(F)(F)F)ccc2O1] | (R)-1,1,1-trifluoro-2-methylpropan-2-yl (4-((3-chloro-4-fluorophenyl)sulfonyl)-2-(2-(methylsulfonamido)propan-2-yl)-3,4-dihydro-2H-benzo[b][1,4]oxazin-6-yl)carbamate | 654 (M + Na)+ |

TABLE 5-continued

| Ex. No. | Structure | Name | Observed m/z |
|---|---|---|---|
| 19E | 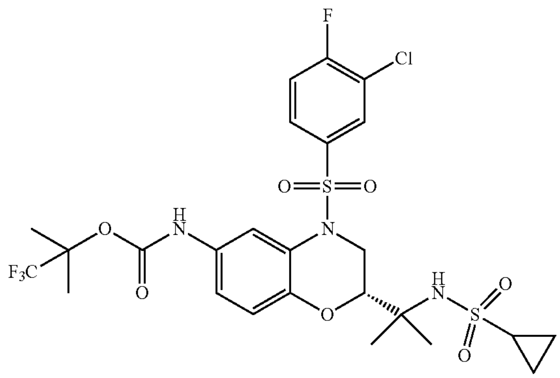 [SMILES: CC(C)(NS(=O)(=O)C1CC1)[C@H]1CN(S(=O)(=O)c2ccc(F)c(Cl)c2)c2cc(NC(=O)OC(C)(C)C(F)(F)F)ccc2O1] | (R)-1,1,1-trifluoro-2-methylpropan-2-yl (4-((3-chloro-4-fluorophenyl)sulfonyl)-2-(2-(cyclopropanesulfonamido)propan-2-yl)-3,4-dihydro-2H-benzo[b][1,4]oxazin-6-yl)carbamate | 680 (M + Na)+ |
| 19F | 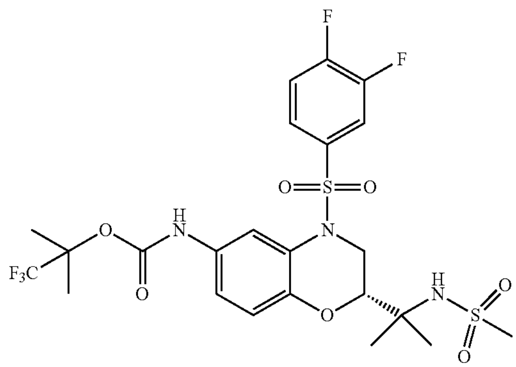 [SMILES: CC(C)(NS(C)(=O)=O)[C@H]1CN(S(=O)(=O)c2ccc(F)c(F)c2)c2cc(NC(=O)OC(C)(C)C(F)(F)F)ccc2O1] | (R)-1,1,1-trifluoro-2-methylpropan-2-yl (4-((3,4-difluorophenyl)sulfonyl)-2-(2-(methylsulfonamido)propan-2-yl)-3,4-dihydro-2H-benzo[b][1,4]oxazin-6-yl)carbamate | 638 (M + Na)+ |
| 19G | 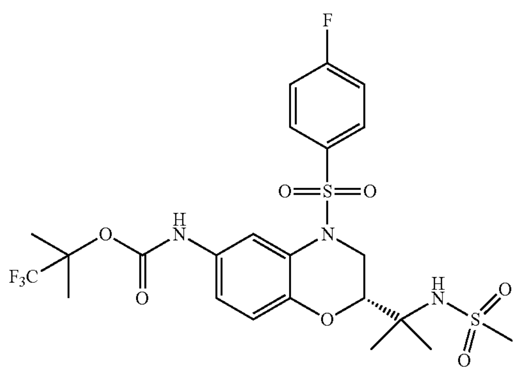 [SMILES: CC(C)(NS(C)(=O)=O)[C@H]1CN(S(=O)(=O)c2ccc(F)cc2)c2cc(NC(=O)OC(C)(C)C(F)(F)F)ccc2O1] | (R)-1,1,1-trifluoro-2-methylpropan-2-yl (4-((4-fluorophenyl)sulfonyl)-2-(2-(methylsulfonamido)propan-2-yl)-3,4-dihydro-2H-benzo[b][1,4]oxazin-6-yl)carbamate | 598 (M + H)+ |
| 19H | 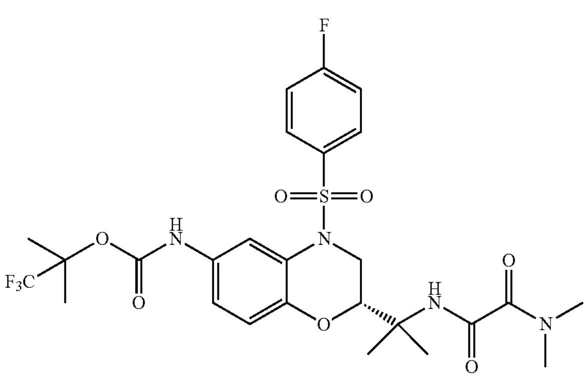 [SMILES: CN(C)C(=O)C(=O)NC(C)(C)[C@H]1CN(S(=O)(=O)c2ccc(F)cc2)c2cc(NC(=O)OC(C)(C)C(F)(F)F)ccc2O1] | (R)-1,1,1-trifluoro-2-methylpropan-2-yl (2-(2-(2-(dimethylamino)-2-oxoacetamido)propan-2-yl)-4-((4-fluorophenyl)sulfonyl)-3,4-dihydro-2H-benzo[b][1,4]oxazin-6-yl)carbamate | 619 (M + H)+ |

TABLE 5-continued

| Ex. No. | Structure | Name | Observed m/z |
|---|---|---|---|
| 19i | 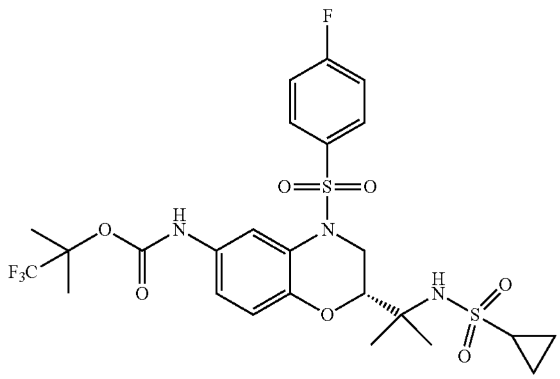 [SMILES: CC(C)(NS(=O)(=O)C1CC1)[C@H]1CN(S(=O)(=O)c2ccc(F)cc2)c2cc(NC(=O)OC(C)(C)C(F)(F)F)ccc2O1] | (R)-1,1,1-trifluoro-2-methylpropan-2-yl (2-(2-(cyclopropanesulfonamido)propan-2-yl)-4-((4-fluorophenyl)sulfonyl)-3,4-dihydro-2H-benzo[b][1,4]oxazin-6-yl)carbamate | 646 (M + Na)+ |
| 19J | 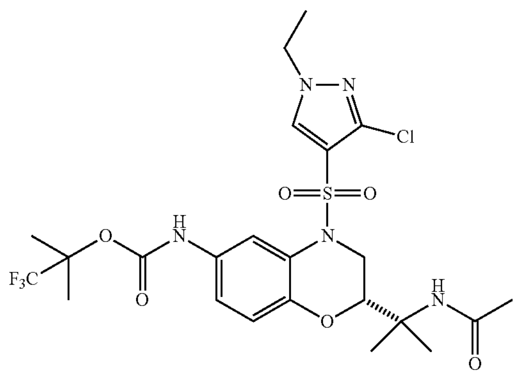 [SMILES: CCn1cc(S(=O)(=O)N2C[C@H](C(C)(C)NC(C)=O)Oc3ccc(NC(=O)OC(C)(C)C(F)(F)F)cc32)c(Cl)n1] | (R or S)-1,1,1-trifluoro-2-methylpropan-2-yl (2-(2-acetamidopropan-2-yl)-4-((3-chloro-1-ethyl-1H-pyrazol-4-yl)sulfonyl)-3,4-dihydro-2H-benzo[b][1,4]oxazin-6-yl)carbamate | 596 (M + H)+ |
| 19K | 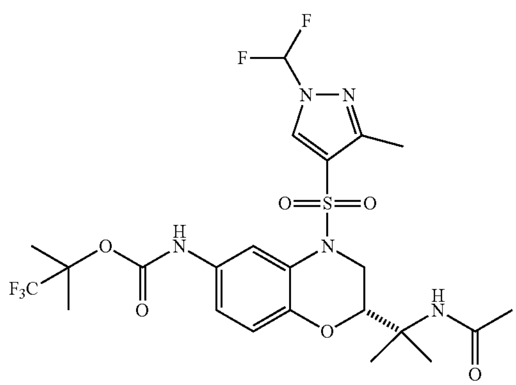 [SMILES: CC(=O)NC(C)(C)[C@H]1CN(S(=O)(=O)c2cn(C(F)F)nc2C)c2cc(NC(=O)OC(C)(C)C(F)(F)F)ccc2O1] | (R or S)-1,1,1-trifluoro-2-methylpropan-2-yl (2-(2-acetamidopropan-2-yl)-4-((1-(difluoromethyl)-3-methyl-1H-pyrazol-4-yl)sulfonyl)-3,4-dihydro-2H-benzo[b][1,4]oxazin-6-yl)carbamate | 598 (M + H)+ |
| 19L | 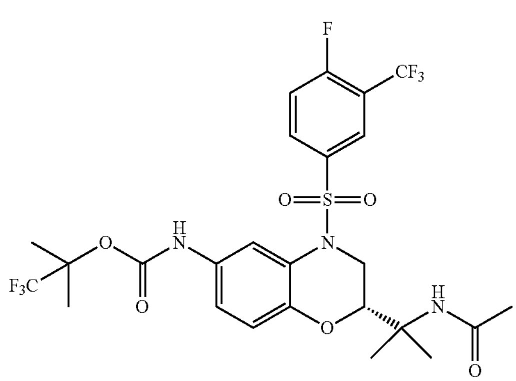 [SMILES: CC(=O)NC(C)(C)[C@H]1CN(S(=O)(=O)c2ccc(F)c(C(F)(F)F)c2)c2cc(NC(=O)OC(C)(C)C(F)(F)F)ccc2O1] | (R or S)-1,1,1-trifluoro-2-methylpropan-2-yl (2-(2-acetamidopropan-2-yl)-4-((4-fluoro-3-(trifluoromethyl)phenyl)sulfonyl)-3,4-dihydro-2H-benzo[b][1,4]oxazin-6-yl)carbamate | 630 (M + H)+ |

TABLE 5-continued

| Ex. No. | Structure | Name | Observed m/z |
|---|---|---|---|
| 19M | 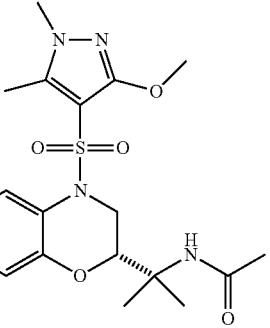 | (R or S)-1,1,1-trifluoro-2-methylpropan-2-yl (2-(2-acetamidopropan-2-yl)-4-((3-methoxy-1,5-dimethyl-1H-pyrazol-4-yl)sulfonyl)-3,4-dihydro-2H-benzo[b][1,4]oxazin-6-yl)carbamate | 592 (M + H)+ |
| 19N | 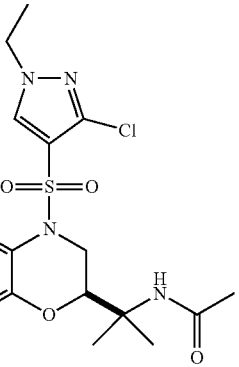 | (R or S)-1,1,1-trifluoro-2-methylpropan-2-yl (2-(2-acetamidopropan-2-yl)-4-((3-chloro-1-ethyl-1H-pyrazol-4-yl)sulfonyl)-3,4-dihydro-2H-benzo[b][1,4]oxazin-6-yl)carbamate | 597 (M + H)+ |
| 19o | 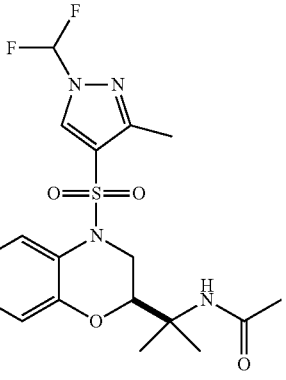 | (R or S)-1,1,1-trifluoro-2-methylpropan-2-yl (2-(2-acetamidopropan-2-yl)-4-((1-(difluoromethyl)-3-methyl-1H-pyrazol-4-yl)sulfonyl)-3,4-dihydro-2H-benzo[b][1,4]oxazin-6-yl)carbamate | 598 (M + H)+ |
| 19P | 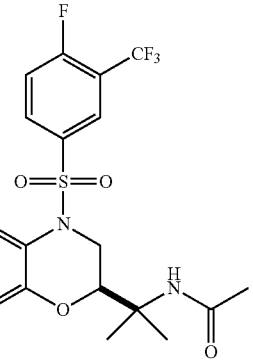 | (R or S)-1,1,1-trifluoro-2-methylpropan-2-yl (2-(2-acetamidopropan-2-yl)-4-((4-fluoro-3-(trifluoromethyl)phenyl)sulfonyl)-3,4-dihydro-2H-benzo[b][1,4]oxazin-6-yl)carbamate | 630 (M + H)+ |

TABLE 5-continued

| Ex. No. | Structure | Name | Observed m/z |
|---|---|---|---|
| 19Q | 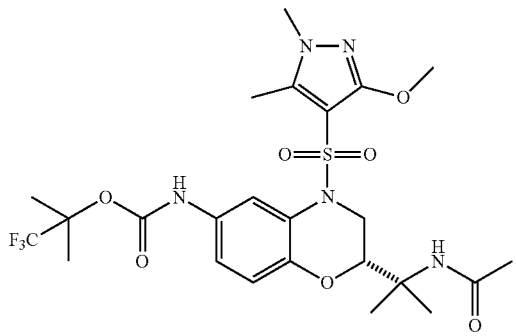 [SMILES: COc1nn(C)c(C)c1S(=O)(=O)N1C[C@H](C(C)(C)NC(C)=O)Oc2ccc(NC(=O)OC(C)(C)C(F)(F)F)cc21] | (R or S)-1,1,1-trifluoro-2-methylpropan-2-yl (2-(2-acetamidopropan-2-yl)-4-((3-methoxy-1,5-dimethyl-1H-pyrazol-4-yl)sulfonyl)-3,4-dihydro-2H-benzo[b][1,4]oxazin-6-yl)carbamate | 592 (M + H)+ |

Example 20—Synthesis of 1,1,1-trifluoro-2-methylbutan-2-yl ((S)-2-(acetamidomethyl)-4-((4-fluorophenyl)sulfonyl)-3,4-dihydro-2H-benzo[b][1,4]oxazin-6-yl)carbamate (20)

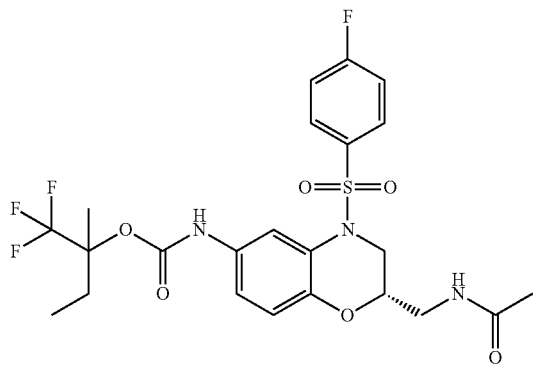 [SMILES: CCC(C)(OC(=O)Nc1ccc2c(c1)N(S(=O)(=O)c1ccc(F)cc1)C[C@H](CNC(C)=O)O2)C(F)(F)F]

A solution of (S)—N-((6-amino-4-((4-fluorophenyl)sulfonyl)-3,4-dihydro-2H-benzo[b][1,4]oxazin-2-yl)methyl)acetamide hydrochloride (30 mg, 0.072 mmol), 1,1'-carbonyldiimidazole (46.8 mg, 0.289 mmol), 4-N,N-dimethylaminopyridine (17.63 mg, 0.144 mmol), and acetonitrile (1 mL) was heated at 80° C. for eight hours. 1,1,1-Trifluoro-2-methylbutan-2-ol (102 mg, 0.721 mmol) was added and the mixture was heated at 110° C. for another twelve hours. The reaction was diluted with DMSO (1 mL) and purified by mass-triggered reverse phase HPLC, eluting with a 1% trifluoroacetic acid buffered water/acetonitrile gradient over a Waters X-Bridge C-18 column, to afford 1,1,1-trifluoro-2-methylbutan-2-yl ((S)-2-(acetamidomethyl)-4-((4-fluorophenyl)sulfonyl)-3,4-dihydro-2H-benzo[b][1,4]oxazin-6-yl)carbamate. LRMS ESI calculated for $C_{23}H_{23}F_6N_3O_6S$ (M+H):+ 548. Found: 548. $^1$H NMR (600 MHz, DMSO-d6) δ 0.94 (3H, t, J=7.51 Hz), 1.65 (3H, s), 1.81 (3H, s), 2.06 (1H, s), 2.08 (1H, s), 2.96 (1H, d, J=0.56 Hz), 3.06 (1H, d, J=5.75 Hz), 3.17 (1H, dd, J=13.97, 0.08 Hz), 3.24 (1H, dd, J=6.58, 3.88 Hz), 4.23 (1H, d, J=14.2 Hz), 6.76 (1H, s), 7.16 (1H, s), 7.39 (2H, t, J=8.62 Hz), 7.71 (2H, dd, J=8.52, 4.93 Hz), 7.88 (1H, s), 8.05 (1H, s), 9.76 (1H, s).

Example 21—Preparation of additional tertiary carbamates of (S)—N-((6-amino-4-((4-fluorophenyl)sulfonyl)-3,4-dihydro-2H-benzo[b][1,4]oxazin-2-yl)methyl)acetamide The compounds in Table 6 below were prepared based on the experimental procedures described in Examples 7, 14, 15, and 20 and elsewhere in the detailed description, and can be achieved by one of skill in the art in light of the present disclosure.

TABLE 6

| Ex. No. | Structure | Name | Observed m/z |
|---|---|---|---|
| 21A | 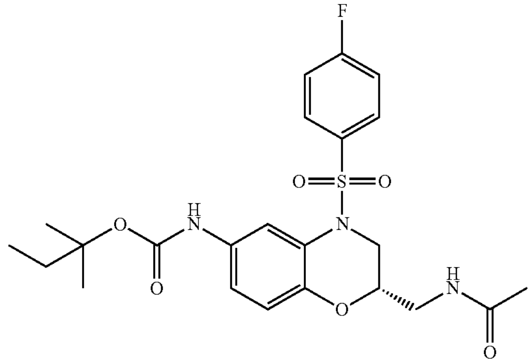 [SMILES: CCC(C)(C)OC(=O)Nc1ccc2c(c1)N(S(=O)(=O)c1ccc(F)cc1)C[C@H](CNC(C)=O)O2] | (S)-tert-pentyl (2-(acetamidomethyl)-4-((4-fluorophenyl)sulfonyl)-3,4-dihydro-2H-benzo[b][1,4]oxazin-6-yl)carbamate | 494.4 (M + H)+ |

TABLE 6-continued

| Ex. No. | Structure | Name | Observed m/z |
|---|---|---|---|
| 21B | 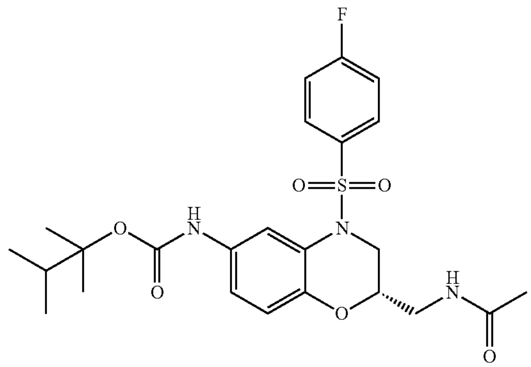 [SMILES: CC(=O)NC[C@H]1CN(S(=O)(=O)c2ccc(F)cc2)c2cc(NC(=O)OC(C)(C)C(C)C)ccc2O1] | (S)-2,3-dimethylbutan-2-yl (2-(acetamidomethyl)-4-((4-fluorophenyl)sulfonyl)-3,4-dihydro-2H-benzo[b][1,4]oxazin-6-yl)carbamate | 530.1 (M + Na)+ |
| 21C | 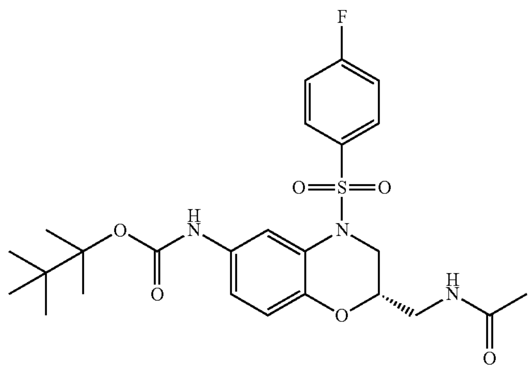 [SMILES: CC(=O)NC[C@H]1CN(S(=O)(=O)c2ccc(F)cc2)c2cc(NC(=O)OC(C)(C)C(C)(C)C)ccc2O1] | (S)-2,3,3-trimethylbutan-2-yl (2-(acetamidomethyl)-4-((4-fluorophenyl)sulfonyl)-3,4-dihydro-2H-benzo[b][1,4]oxazin-6-yl)carbamate | 544.1 (M + Na)+ |
| 21D | 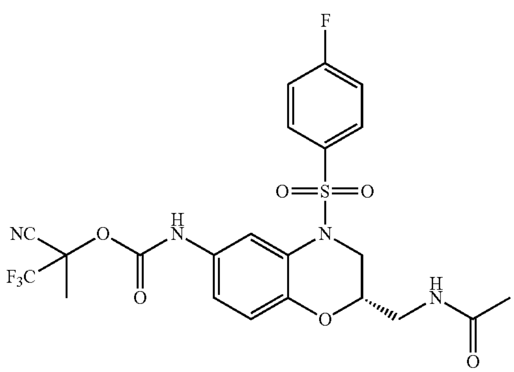 [SMILES: CC(=O)NC[C@H]1CN(S(=O)(=O)c2ccc(F)cc2)c2cc(NC(=O)OC(C)(C#N)C(F)(F)F)ccc2O1] | 2-cyano-1,1,1-trifluoropropan-2-yl ((S)-2-(acetamidomethyl)-4-((4-fluorophenyl)sulfonyl)-3,4-dihydro-2H-benzo[b][1,4]oxazin-6-yl)carbamate | 545 (M + H)+ |
| 21E | 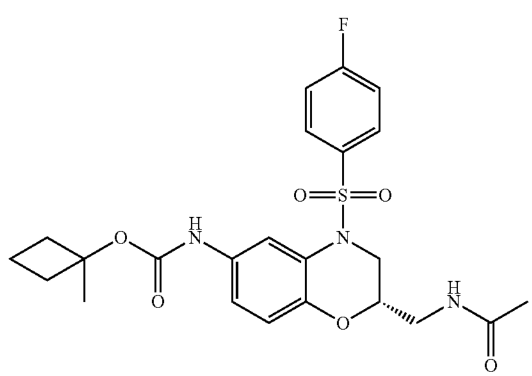 [SMILES: CC(=O)NC[C@H]1CN(S(=O)(=O)c2ccc(F)cc2)c2cc(NC(=O)OC3(C)CCC3)ccc2O1] | (S)-1-methylcyclobutyl (2-(acetamidomethyl)-4-((4-fluorophenyl)sulfonyl)-3,4-dihydro-2H-benzo[b][1,4]oxazin-6-yl)carbamate | 492.3 (M + H)+ |

TABLE 6-continued

| Ex. No. | Structure | Name | Observed m/z |
|---|---|---|---|
| 21F | 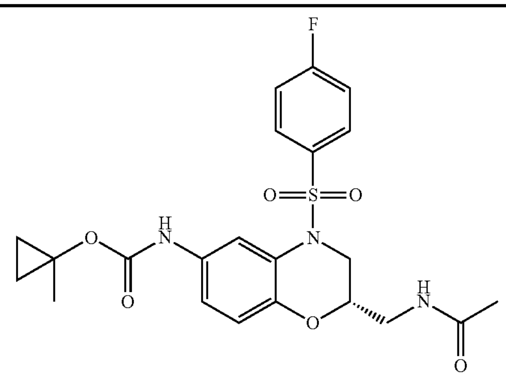 | (S)-1-methylcyclopropyl (2-(acetamidomethyl)-4-((4-fluorophenyl)sulfonyl)-3,4-dihydro-2H-benzo[b][1,4]oxazin-6-yl)carbamate | 478.3 (M + H)+ |
| 21G | 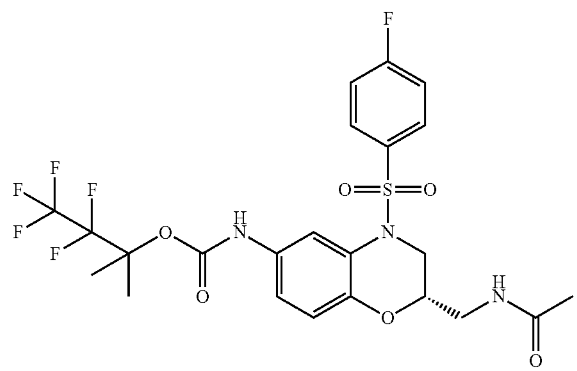 [SMILES: CC(=O)NC[C@H]1CN(S(=O)(=O)c2ccc(F)cc2)c2cc(NC(=O)OC(C)(C)C(F)(F)C(F)(F)F)ccc2O1] | (S)-3,3,4,4,4-pentafluoro-2-methylbutan-2-yl (2-(acetamidomethyl)-4-((4-fluorophenyl)sulfonyl)-3,4-dihydro-2H-benzo[b][1,4]oxazin-6-yl)carbamate | 584 (M + H)+ |

Example 22—Synthesis of (S)-2,2,3,3,3-pentafluoropropyl (2-(acetamidomethyl)-4-((4-fluorophenyl)sulfonyl)-3,4-dihydro-2H-benzo[b][1,4]oxazin-6-yl)carbamate (22)

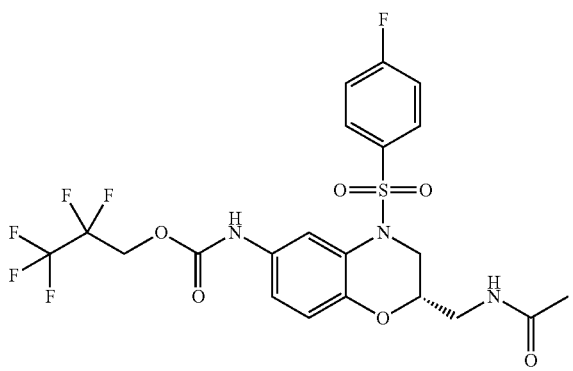 [SMILES: CC(=O)NC[C@H]1CN(S(=O)(=O)c2ccc(F)cc2)c2cc(NC(=O)OCC(F)(F)C(F)(F)F)ccc2O1]

A solution of (S)—N-((6-amino-4-((4-fluorophenyl)sulfonyl)-3,4-dihydro-2H-benzo[b][1,4]oxazin-2-yl)methyl) acetamide hydrochloride (30 mg, 0.072 mmol), 1,1'-carbonyldiimidazole (46.8 mg, 0.289 mmol), 4-N,N-dimethylaminopyridine (17.63 mg, 0.144 mmol), and acetonitrile (1 mL) was heated at 80° C. for eight hours. 2,2,3,3,3-Pentafluoropropan-1-ol (118 mg, 0.721 mmol) was added and the mixture was heated at 110° C. for another twelve hours. The reaction was then diluted with DMSO (1 mL) and purified by mass-triggered reverse phase HPLC, eluting with a 1% trifluoroacetic acid buffered water/acetonitrile gradient over a Waters X-Bridge C-18 column, to afford (S)-2,2,3,3,3-pentafluoropropyl (2-(acetamidomethyl)-4-((4-fluorophenyl)sulfonyl)-3,4-dihydro-2H-benzo[b][1,4]oxazin-6-yl)carbamate. LRMS ESI calculated $C_{21}H_{19}F_6N_3O_6S$ (M+H):+ 556. Found: 556. $^1$H NMR (600 MHz, DMSO-d6) δ 1.82 (3H, s), 3.09-3.17 (4H, m), 4.25 (1H, dd, J=14.23, 2.03 Hz), 4.85 (2H, td, J=14.06, 5.16 Hz), 6.78 (1H, d, J=8.87 Hz), 7.15 (1H, d, J=8.82 Hz), 7.39 (2H, t, J=8.65 Hz), 7.71 (2H, dd, J=8.56, 4.99 Hz), 7.95 (1H, s), 8.04 (1H, t, J=5.82 Hz), 10.06 (1H, s).

Example 23—Preparation of Additional $CF_3$ Ethyl and Substituted $CF_2$ Ethyl Carbamate Analogs The compounds in Table 7 below were prepared based on the experimental procedures described in Examples 1-8 and 22 and elsewhere in the detailed description, and can be achieved by one of skill in the art in light of the present disclosure.

TABLE 7

| Ex. No. | Structure | Name | Observed m/z |
|---|---|---|---|
| 23A | 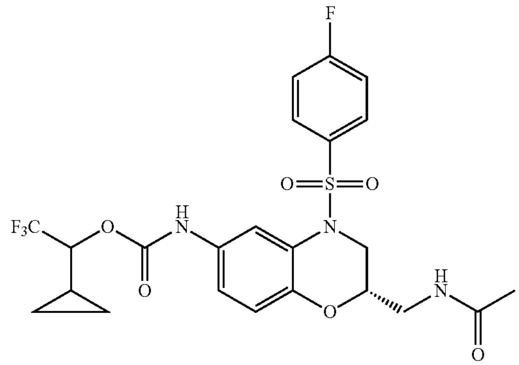 [SMILES: CC(=O)NC[C@H]1CN(S(=O)(=O)c2ccc(F)cc2)c2cc(NC(=O)OC(C3CC3)C(F)(F)F)ccc2O1] | 1-cyclopropyl-2,2,2-trifluoroethyl ((S)-2-(acetamidomethyl)-4-((4-fluorophenyl)sulfonyl)-3,4-dihydro-2H-benzo[b][1,4]oxazin-6-yl)carbamate | 546.1 (M + H)+ |
| 23B | 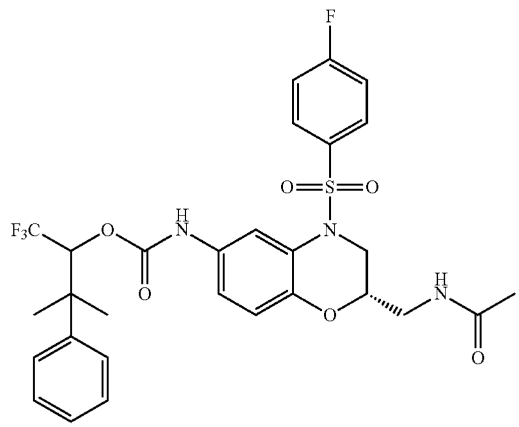 [SMILES: CC(=O)NC[C@H]1CN(S(=O)(=O)c2ccc(F)cc2)c2cc(NC(=O)OC(C(F)(F)F)C(C)(C)c3ccccc3)ccc2O1] | 1,1,1-trifluoro-3-methyl-3-phenylbutan-2-yl ((S)-2-(acetamidomethyl)-4-((4-fluorophenyl)sulfonyl)-3,4-dihydro-2H-benzo[b][1,4]oxazin-6-yl)carbamate | 624 (M + H)+ |
| 23C | 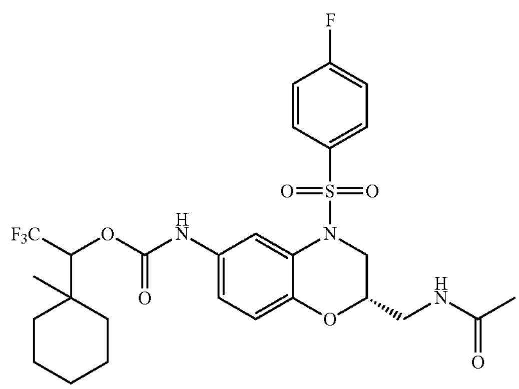 [SMILES: CC(=O)NC[C@H]1CN(S(=O)(=O)c2ccc(F)cc2)c2cc(NC(=O)OC(C(F)(F)F)C3(C)CCCCC3)ccc2O1] | 2,2,2-trifluoro-1-(1-methylcyclohexyl)ethyl ((S)-2-(acetamidomethyl)-4-((4-fluorophenyl)sulfonyl)-3,4-dihydro-2H-benzo[b][1,4]oxazin-6-yl)carbamate | 602.0 (M + H)+ |
| 23D | 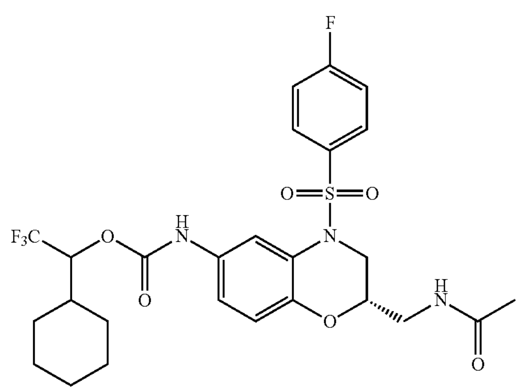 [SMILES: CC(=O)NC[C@H]1CN(S(=O)(=O)c2ccc(F)cc2)c2cc(NC(=O)OC(C3CCCCC3)C(F)(F)F)ccc2O1] | 1-cyclohexyl-2,2,2-trifluoroethyl ((S)-2-(acetamidomethyl)-4-((4-fluorophenyl)sulfonyl)-3,4-dihydro-2H-benzo[b][1,4]oxazin-6-yl)carbamate | 588.3 (M + H)+ |

TABLE 7-continued

| Ex. No. | Structure | Name | Observed m/z |
|---|---|---|---|
| 23E | 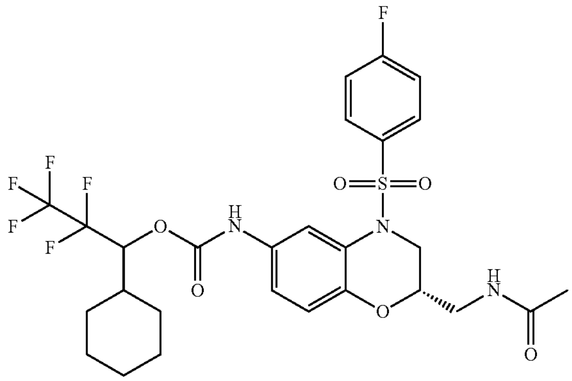 [SMILES: CC(=O)NC[C@H]1CN(S(=O)(=O)c2ccc(F)cc2)c2cc(NC(=O)OC(C3CCCCC3)C(F)(F)C(F)(F)F)ccc2O1] | 1-cyclohexyl-2,2,3,3,3-pentafluoropropyl ((S)-2-(acetamidomethyl)-4-((4-fluorophenyl)sulfonyl)-3,4-dihydro-2H-benzo[b][1,4]oxazin-6-yl)carbamate | 638 (M + H)+ |
| 23F | 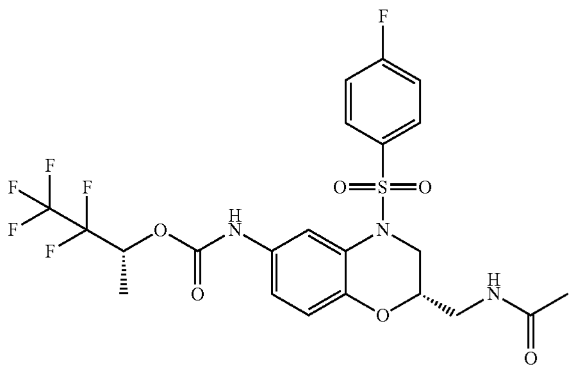 [SMILES: CC(=O)NC[C@H]1CN(S(=O)(=O)c2ccc(F)cc2)c2cc(NC(=O)O[C@H](C)C(F)(F)C(F)(F)F)ccc2O1] | (R)-3,3,4,4,4-pentafluorobutan-2-yl ((S)-2-(acetamidomethyl)-4-((4-fluorophenyl)sulfonyl)-3,4-dihydro-2H-benzo[b][1,4]oxazin-6-yl)carbamate | 570 (M + H)+ |
| 23G | 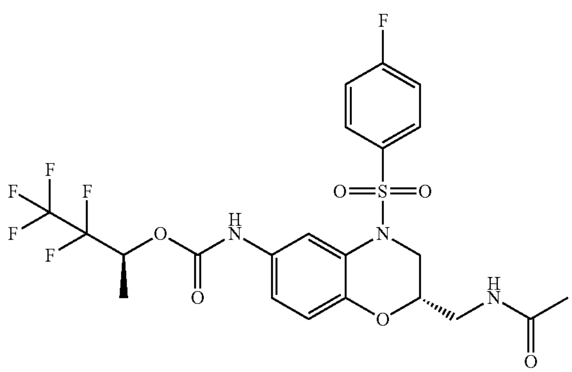 [SMILES: CC(=O)NC[C@H]1CN(S(=O)(=O)c2ccc(F)cc2)c2cc(NC(=O)O[C@@H](C)C(F)(F)C(F)(F)F)ccc2O1] | (S)-3,3,4,4,4-pentafluorobutan-2-yl ((S)-2-(acetamidomethyl)-4-((4-fluorophenyl)sulfonyl)-3,4-dihydro-2H-benzo[b][1,4]oxazin-6-yl)carbamate | 570 (M + H)+ |
| 23H | 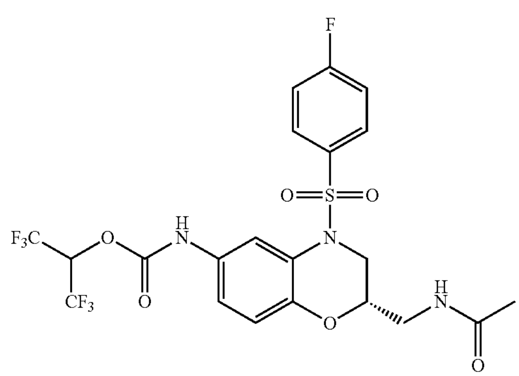 [SMILES: CC(=O)NC[C@H]1CN(S(=O)(=O)c2ccc(F)cc2)c2cc(NC(=O)OC(C(F)(F)F)C(F)(F)F)ccc2O1] | (S)-1,1,1,3,3,3-hexafluoropropan-2-yl (2-(acetamidomethyl)-4-((4-fluorophenyl)sulfonyl)-3,4-dihydro-2H-benzo[b][1,4]oxazin-6-yl)carbamate | 574 (M + H)+ |

TABLE 7-continued

| Ex. No. | Structure | Name | Observed m/z |
|---|---|---|---|
| 23i | 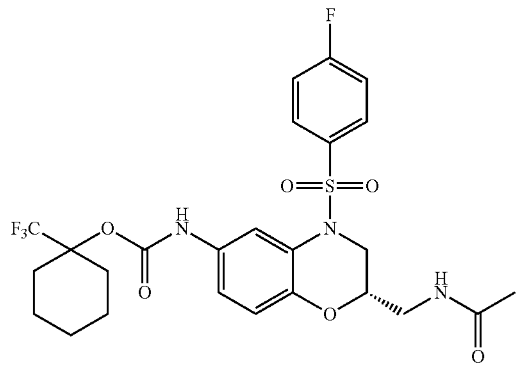 [SMILES: CC(=O)NC[C@H]1CN(S(=O)(=O)c2ccc(F)cc2)c2cc(NC(=O)OC3(C(F)(F)F)CCCCC3)ccc2O1] | (S)-1-(trifluoromethyl)cyclohexyl (2-(acetamidomethyl)-4-((4-fluorophenyl)sulfonyl)-3,4-dihydro-2H-benzo[b][1,4]oxazin-6-yl)carbamate | 574 (M + H)+ |
| 23J | 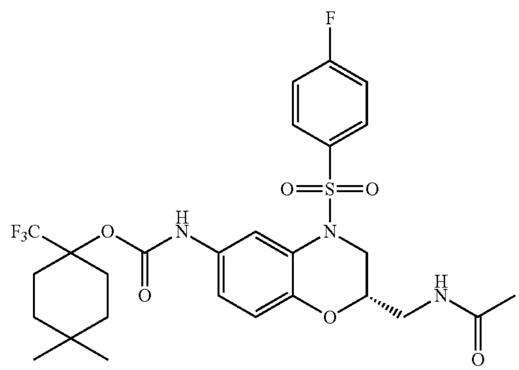 [SMILES: CC(=O)NC[C@H]1CN(S(=O)(=O)c2ccc(F)cc2)c2cc(NC(=O)OC3(C(F)(F)F)CCC(C)(C)CC3)ccc2O1] | (S)-4,4-dimethyl-1-(trifluoromethyl)cyclohexyl (2-(acetamidomethyl)-4-((4-fluorophenyl)sulfonyl)-3,4-dihydro-2H-benzo[b][1,4]oxazin-6-yl)carbamate | 602 (M + H)+ |
| 23K | 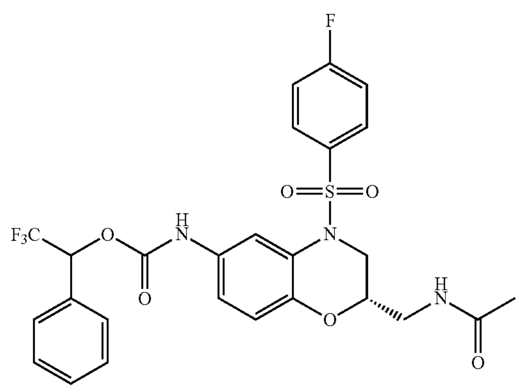 [SMILES: CC(=O)NC[C@H]1CN(S(=O)(=O)c2ccc(F)cc2)c2cc(NC(=O)OC(c3ccccc3)C(F)(F)F)ccc2O1] | 2,2,2-trifluoro-1-phenylethyl ((S)-2-(acetamidomethyl)-4-((4-fluorophenyl)sulfonyl)-3,4-dihydro-2H-benzo[b][1,4]oxazin-6-yl)carbamate | 582 (M + H)+ |
| 23L | 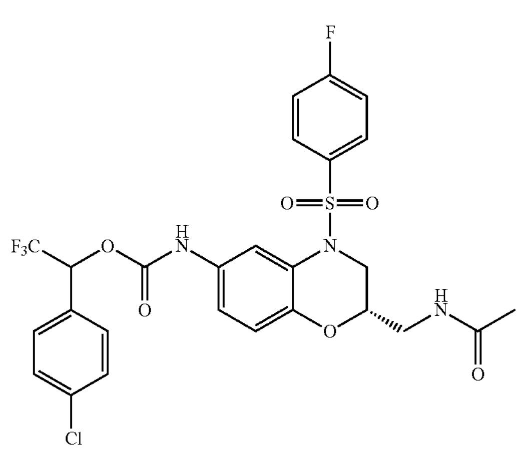 [SMILES: CC(=O)NC[C@H]1CN(S(=O)(=O)c2ccc(F)cc2)c2cc(NC(=O)OC(c3ccc(Cl)cc3)C(F)(F)F)ccc2O1] | 1-(4-chlorophenyl)-2,2,2-trifluoroethyl ((S)-2-(acetamidomethyl)-4-((4-fluorophenyl)sulfonyl)-3,4-dihydro-2H-benzo[b][1,4]oxazin-6-yl)carbamate | 616 (M + H)+ |

TABLE 7-continued

| Ex. No. | Structure | Name | Observed m/z |
|---|---|---|---|
| 23M | 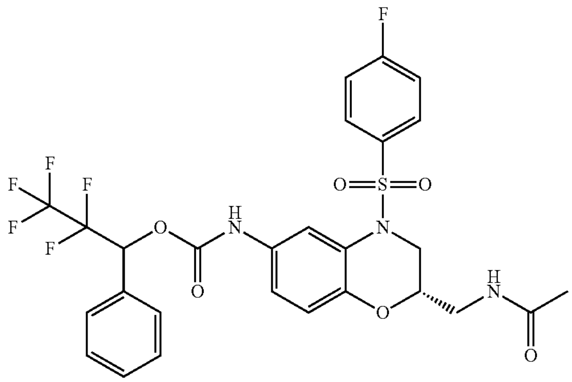 [SMILES: CC(=O)NC[C@H]1CN(S(=O)(=O)c2ccc(F)cc2)c2cc(NC(=O)OC(c3ccccc3)C(F)(F)C(F)(F)F)ccc2O1] | 2,2,3,3,3-pentafluoro-1-phenylpropyl ((S)-2-(acetamidomethyl)-4-((4-fluorophenyl)sulfonyl)-3,4-dihydro-2H-benzo[b][1,4]oxazin-6-yl)carbamate | 632 (M + H)+ |
| 23N | 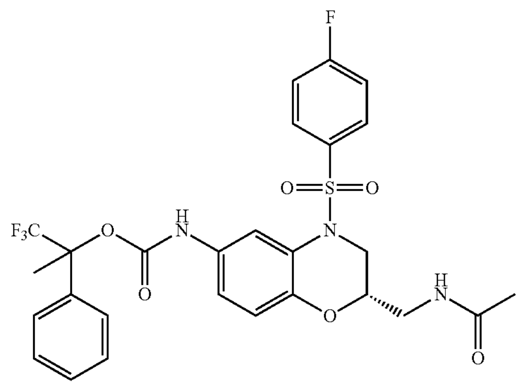 [SMILES: CC(=O)NC[C@H]1CN(S(=O)(=O)c2ccc(F)cc2)c2cc(NC(=O)OC(C)(c3ccccc3)C(F)(F)F)ccc2O1] | 1,1,1-trifluoro-2-phenylpropan-2-yl ((S)-2-(acetamidomethyl)-4-((4-fluorophenyl)sulfonyl)-3,4-dihydro-2H-benzo[b][1,4]oxazin-6-yl)carbamate | 596.3 (M + H)+ |
| 23o | 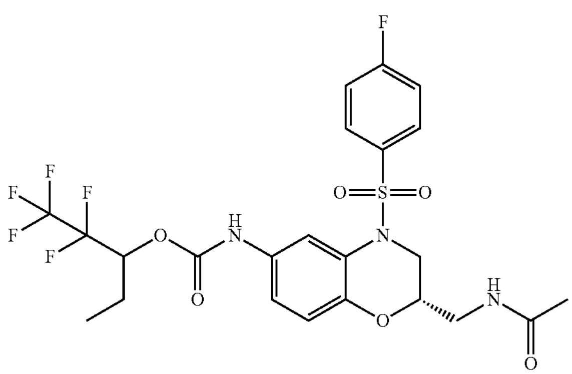 [SMILES: CCC(OC(=O)Nc1ccc2c(c1)N(S(=O)(=O)c1ccc(F)cc1)C[C@H](CNC(C)=O)O2)C(F)(F)C(F)(F)F] | 1,1,1,2,2-pentafluoropentan-3-yl ((S)-2-(acetamidomethyl)-4-((4-fluorophenyl)sulfonyl)-3,4-dihydro-2H-benzo[b][1,4]oxazin-6-yl)carbamate | 584 (M + H)+ |
| 23P | 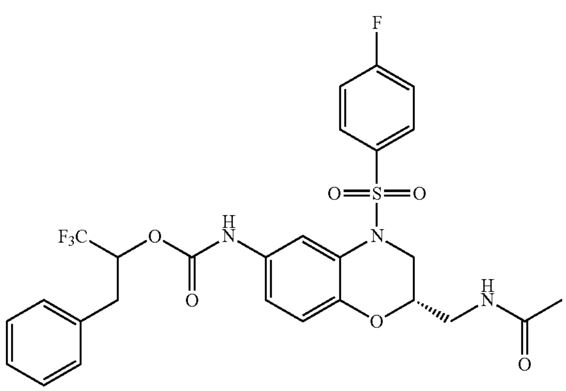 [SMILES: CC(=O)NC[C@H]1CN(S(=O)(=O)c2ccc(F)cc2)c2cc(NC(=O)OC(Cc3ccccc3)C(F)(F)F)ccc2O1] | 1,1,1-trifluoro-3-phenylpropan-2-yl ((S)-2-(acetamidomethyl)-4-((4-fluorophenyl)sulfonyl)-3,4-dihydro-2H-benzo[b][1,4]oxazin-6-yl)carbamate | 596 (M + H)+ |

TABLE 7-continued

| Ex. No. | Structure | Name | Observed m/z |
|---|---|---|---|
| 23Q | 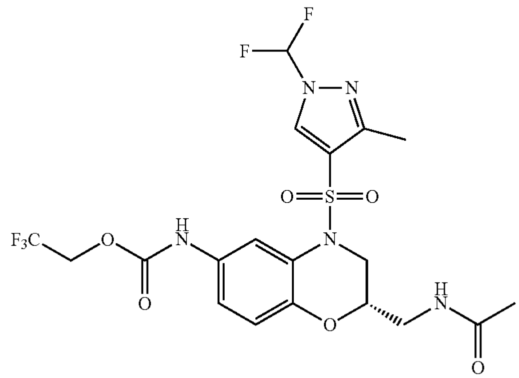 [SMILES: CC(=O)NC[C@H]1CN(S(=O)(=O)c2cn(C(F)F)nc2C)c2cc(NC(=O)OCC(F)(F)F)ccc2O1] | (S)-2,2,2-trifluoroethyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate | 542 (M + H)+ |

Example 24—Synthesis of (S)-(1-(trifluoromethyl)cyclopropyl)methyl (2-(acetamidomethyl)-4-((4-fluorophenyl)sulfonyl)-3,4-dihydro-2H-benzo[b][1,4]oxazin-6-yl)carbamate (24)

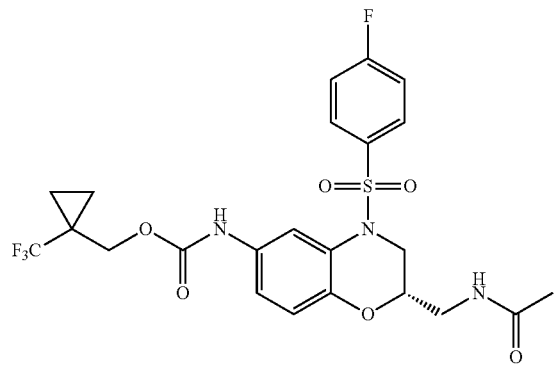 [SMILES: CC(=O)NC[C@H]1CN(S(=O)(=O)c2ccc(F)cc2)c2cc(NC(=O)OCC3(C(F)(F)F)CC3)ccc2O1]

A solution of (S)—N-((6-amino-4-((4-fluorophenyl)sulfonyl)-3,4-dihydro-2H-benzo[b][1,4]oxazin-2-yl)methyl)acetamide hydrochloride (30 mg, 0.072 mmol), carbonyldiimidazole (46.8 mg, 0.289 mmol), and N,N-dimethylpyridin-4-amine (1.50 mg, 0.012 mmol) in acetonitrile (500 μL) was sealed and heated at 80° C. After twenty-two hours, a solution of (1-(trifluoromethyl)cyclopropyl)methanol (152 mg, 1.08 mmol) in acetonitrile (500 μl) was added to the reaction. The mixture was heated at 80° C. for forty five minutes. The mixture was cooled, and concentrated. The residue was dissolved in DMSO (1 mL), filtered, and purified via reverse-phase HPLC (MeCN:water, trifluoroacetic acid buffer) to afford (S)-(1-(trifluoromethyl)cyclopropyl)methyl (2-(acetamidomethyl)-4-((4-fluorophenyl)sulfonyl)-3,4-dihydro-2H-benzo[b][1,4]oxazin-6-yl)carbamate. LRMS (ESI) calculated for $C_{23}H_{23}F_4N_3O_6S$ (M+H)+: 546. Found: 546. $^1$H NMR (600 MHz, DMSO-d6) δ 9.71 (s, 1H), 8.06 (1H, t, J=5.5 Hz), 7.96 (s, 1H), 7.73 (1H, dd, J=8.7 Hz, 3.8 Hz), 7.41 (2H, t, J=10.2 Hz), 7.16 (1H, d, J=9.3 Hz), 6.76 (1H, d, J=9.2 Hz), 4.24 (m, 3H), 3.26 (m, 2H), 3.18 (m, 1H), 3.08 (m, 1H), 1.83 (s, 3H), 1.03 (m, 4H).

Example 25—Preparation of additional carbamates of 1-(trifluoromethyl)cyclopropylalcohol with aminobenzoxazines The compounds in Table 8 below were prepared based on the experimental procedure described in Example 24 and elsewhere in the detailed description, and can be achieved by one of skill in the art in light of the present disclosure.

TABLE 8

| Ex. No. | Structure | Name | Observed m/z |
|---|---|---|---|
| 25A | 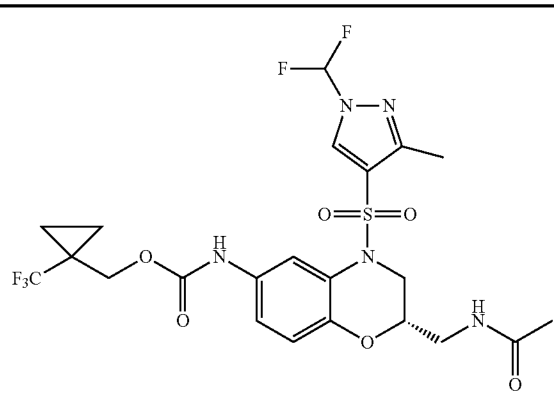 | (S)-(1-(trifluoromethyl)cyclopropyl)methyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate | 582.2 (M + H)+ |

TABLE 8-continued

| Ex. No. | Structure | Name | Observed m/z |
|---|---|---|---|
| 25B | 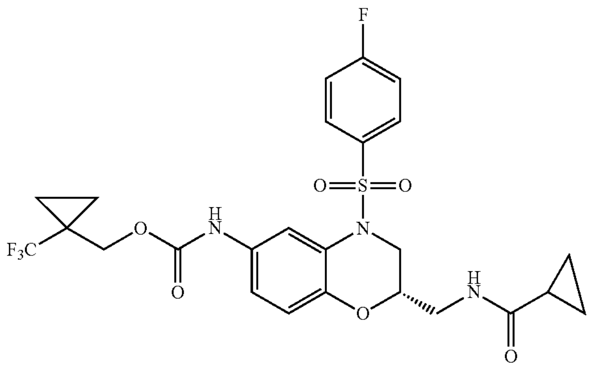 [SMILES: O=C(Nc1ccc2c(c1)N(S(=O)(=O)c1ccc(F)cc1)C[C@H](CNC(=O)C1CC1)O2)OCC1(C(F)(F)F)CC1] | (S)-(1-(trifluoromethyl)cyclopropyl)methyl (2-(cyclopropanecarboxamidomethyl)-4-((4-fluorophenyl)sulfonyl)-3,4-dihydro-2H-benzo[b][1,4]oxazin-6-yl)carbamate | 572 (M + H)+ |
| 25C | 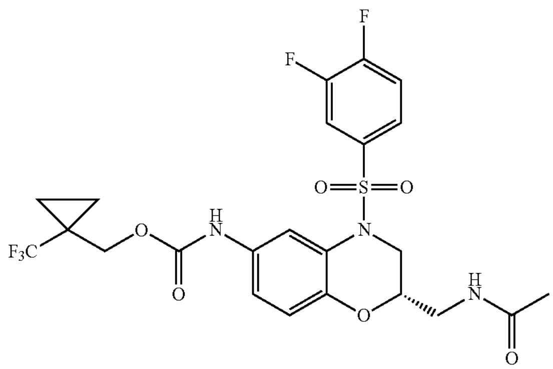 [SMILES: CC(=O)NC[C@H]1CN(S(=O)(=O)c2ccc(F)c(F)c2)c2cc(NC(=O)OCC3(C(F)(F)F)CC3)ccc2O1] | (S)-(1-(trifluoromethyl)cyclopropyl)methyl (2-(acetamidomethyl)-4-((3,4-difluorophenyl)sulfonyl)-3,4-dihydro-2H-benzo[b][1,4]oxazin-6-yl)carbamate | 564.0 (M + H)+ |
| 25D | 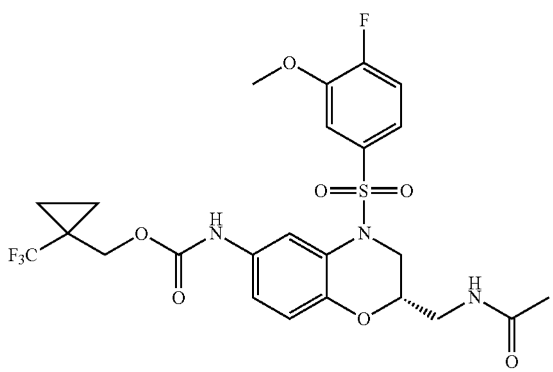 [SMILES: COc1cc(S(=O)(=O)N2C[C@H](CNC(C)=O)Oc3ccc(NC(=O)OCC4(C(F)(F)F)CC4)cc32)ccc1F] | (S)-(1-(trifluoromethyl)cyclopropyl)methyl (2-(acetamidomethyl)-4-((4-fluoro-3-methoxyphenyl)sulfonyl)-3,4-dihydro-2H-benzo[b][1,4]oxazin-6-yl)carbamate | 576.0 (M + H)+ |
| 25E | 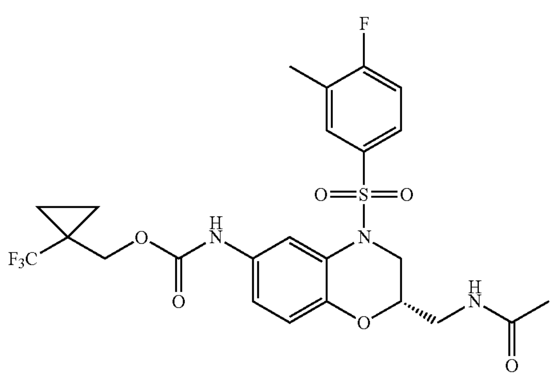 [SMILES: CC(=O)NC[C@H]1CN(S(=O)(=O)c2ccc(F)c(C)c2)c2cc(NC(=O)OCC3(C(F)(F)F)CC3)ccc2O1] | (S)-(1-(trifluoromethyl)cyclopropyl)methyl (2-(acetamidomethyl)-4-((4-fluoro-3-methylphenyl)sulfonyl)-3,4-dihydro-2H-benzo[b][1,4]oxazin-6-yl)carbamate | 560.0 (M + H)+ |

TABLE 8-continued

| Ex. No. | Structure | Name | Observed m/z |
|---|---|---|---|
| 25F | 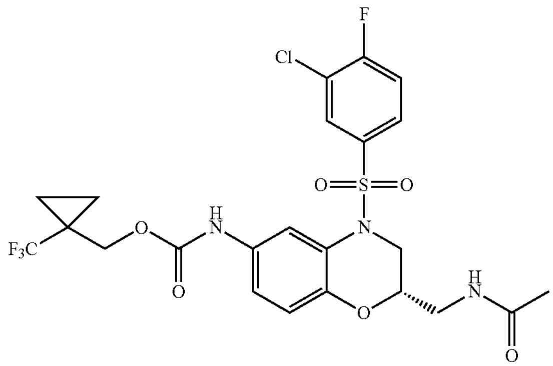 [SMILES: CC(=O)NC[C@H]1CN(S(=O)(=O)c2ccc(F)c(Cl)c2)c2cc(NC(=O)OCC3(C(F)(F)F)CC3)ccc2O1] | (S)-(1-(trifluoromethyl)cyclopropyl)methyl (2-(acetamidomethyl)-4-((3-chloro-4-fluorophenyl)sulfonyl)-3,4-dihydro-2H-benzo[b][1,4]oxazin-6-yl)carbamate | 580.0 (M + H)+ |

Example 26—Synthesis of (S)-4,4-difluorocyclohexyl (2-(acetamidomethyl)-4-((4-fluorophenyl)sulfonyl)-3,4-dihydro-2H-benzo[b][1,4]oxazin-6-yl) carbamate (26)

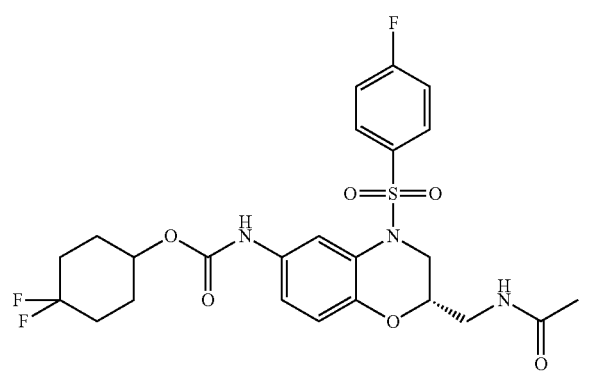 [SMILES: CC(=O)NC[C@H]1CN(S(=O)(=O)c2ccc(F)cc2)c2cc(NC(=O)OC3CCC(F)(F)CC3)ccc2O1]

A solution of (S)—N-((6-amino-4-((4-fluorophenyl)sulfonyl)-3,4-dihydro-2H-benzo[b][1,4]oxazin-2-yl)methyl) acetamide hydrochloride (30 mg, 0.072 mmol), 1,1'-carbonyldiimidazole (46.8 mg, 0.289 mmol), 4-N,N-dimethylaminopyridine (17.63 mg, 0.144 mmol), and acetonitrile (1 mL) was heated at 80° C. for eight hours. 4,4-Difluorocyclohexanol (98 mg, 0.721 mmol) was added and the mixture was heated at 110° C. for another twelve hours. The reaction was then diluted with DMSO (1.0 mL) and purified by mass-triggered reverse phase HPLC, eluting with a 1% trifluoroacetic acid buffered water/acetonitrile gradient over a Waters X-Bridge C-18 column, to afford (S)-4,4-difluorocyclohexyl (2-(acetamidomethyl)-4-((4-fluorophenyl)sulfonyl)-3,4-dihydro-2H-benzo[b][1,4]oxazin-6-yl)carbamate. LRMS ESI calculated for $C_{24}H_{26}F_3N_3O_6S$ (M+H):+ 542. Found: 542. $^1$H NMR (600 MHz, DMSO-d6) δ 1.74-1.71 (4H, m), 1.81-1.78 (4H, m), 1.99 (3H, s), 2.96 (2H, m), 3.06 (1H, dt, J=13.71, 5.55 Hz), 3.16 (1H, dd, J=14.25, 9.91 Hz), 4.24 (1H, dt, J=14.17, 1.95 Hz), 4.83 (1H, dt, J=7.25, 4.19 Hz), 6.74 (1H, d, J=8.87 Hz), 7.13 (1H, s), 7.39 (2H, dd, J=8.65, 8.63 Hz), 7.71 (2H, dd, J=8.52, 4.98 Hz), 7.92 (1H, s), 8.04 (1H, t, J=5.86 Hz), 9.57 (1H, s).

Example 27—Preparation of Additional Carbamates Prepared from Cycloalkyl Alcohols and Amino-Benzoxazines The compounds in Table 9 below were prepared based on the experimental procedures described in Example 26 and elsewhere in the detailed description using the appropriate cyclic alcohol, and can be achieved by one of skill in the art in light of the present disclosure.

TABLE 9

| Ex. No. | Structure | Name | Observed m/z |
|---|---|---|---|
| 27A | 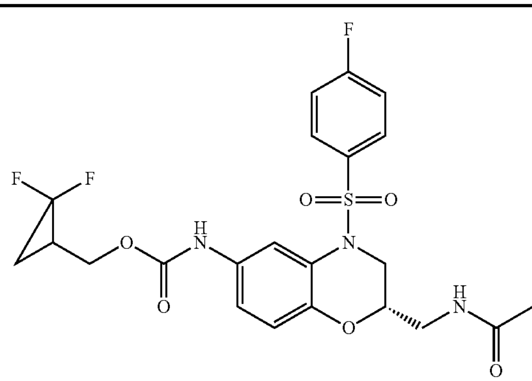 | (2,2-difluorocyclopropyl)methyl ((S)-2-(acetamidomethyl)-4-((4-fluorophenyl)sulfonyl)-3,4-dihydro-2H-benzo[b][1,4]oxazin-6-yl)carbamate | 514 (M + H)+ |

TABLE 9-continued

| Ex. No. | Structure | Name | Observed m/z |
|---|---|---|---|
| 27B | 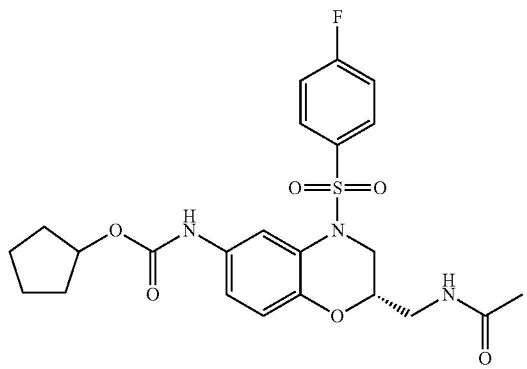 [SMILES: CC(=O)NC[C@H]1CN(S(=O)(=O)c2ccc(F)cc2)c2cc(NC(=O)OC3CCCC3)ccc2O1] | (S)-cyclopentyl (2-(acetamidomethyl)-4-((4-fluorophenyl)sulfonyl)-3,4-dihydro-2H-benzo[b][1,4]oxazin-6-yl)carbamate | 492.3 (M + H)+ |
| 27C | 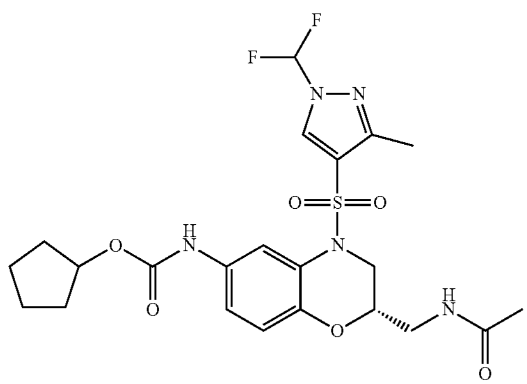 [SMILES: CC(=O)NC[C@H]1CN(S(=O)(=O)c2cn(C(F)F)nc2C)c2cc(NC(=O)OC3CCCC3)ccc2O1] | (S)-cyclopentyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate | 528 (M + H)+ |
| 27D | 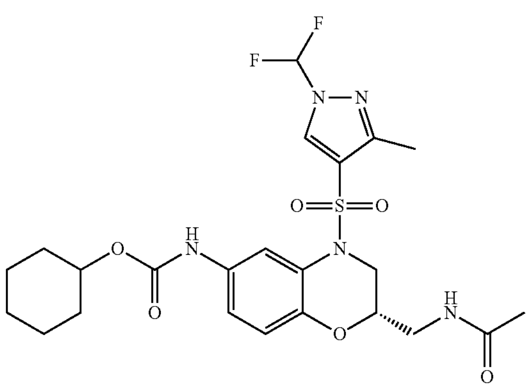 [SMILES: CC(=O)NC[C@H]1CN(S(=O)(=O)c2cn(C(F)F)nc2C)c2cc(NC(=O)OC3CCCCC3)ccc2O1] | (S)-cyclohexyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate | 542 (M + H)+ |
| 27E | 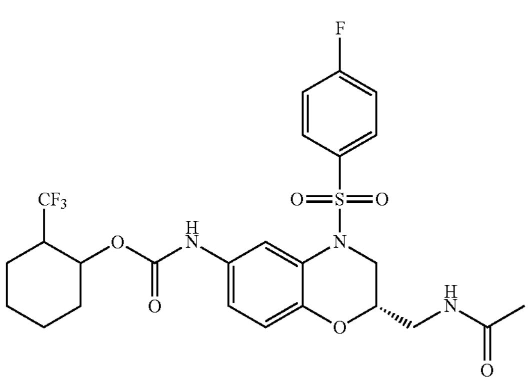 [SMILES: CC(=O)NC[C@H]1CN(S(=O)(=O)c2ccc(F)cc2)c2cc(NC(=O)OC3CCCCC3C(F)(F)F)ccc2O1] | 2-(trifluoromethyl)cyclohexyl ((S)-2-(acetamidomethyl)-4-((4-fluorophenyl)sulfonyl)-3,4-dihydro-2H-benzo[b][1,4]oxazin-6-yl)carbamate | 574 (M + H)+ |

TABLE 9-continued

| Ex. No. | Structure | Name | Observed m/z |
|---|---|---|---|
| 27F | 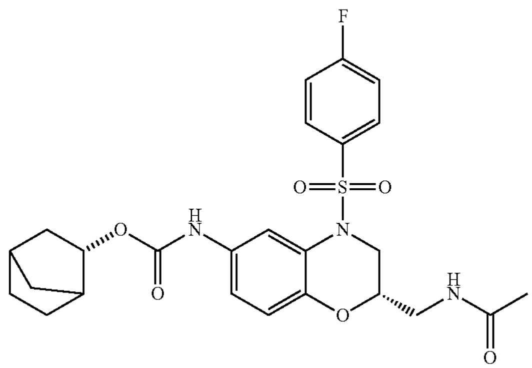 | (2S)-bicyclo[2.2.1]heptan-2-yl ((S)-2-(acetamidomethyl)-4-((4-fluorophenyl)sulfonyl)-3,4-dihydro-2H-benzo[b][1,4]oxazin-6-yl)carbamate | 518.2 (M + H)+ |
| 27G | 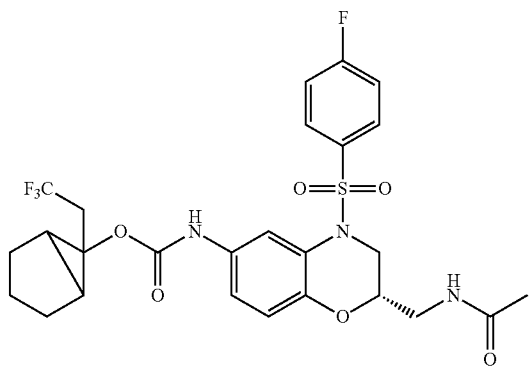 [SMILES: CC(=O)NC[C@H]1CN(S(=O)(=O)c2ccc(F)cc2)c2cc(NC(=O)OC3(CC(F)(F)F)C4CCCC43)ccc2O1] | 6-(2,2,2-trifluoroethyl)bicyclo[3.1.0]hexan-6-yl ((S)-2-(acetamidomethyl)-4-((4-fluorophenyl)sulfonyl)-3,4-dihydro-2H-benzo[b][1,4]oxazin-6-yl)carbamate | 586 (M + H)+ |
| 27H | 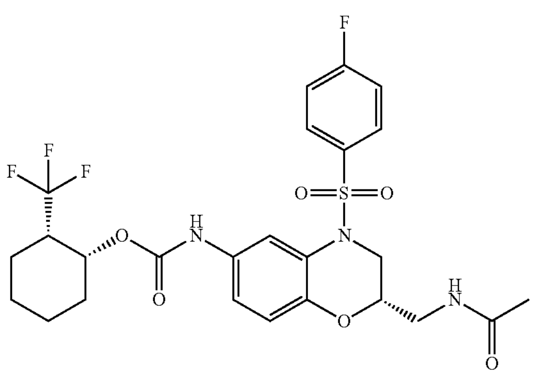 [SMILES: CC(=O)NC[C@H]1CN(S(=O)(=O)c2ccc(F)cc2)c2cc(NC(=O)O[C@@H]3CCCC[C@@H]3C(F)(F)F)ccc2O1] | (1R,2S)-2-(trifluoromethyl)cyclohexyl ((S)-2-(acetamidomethyl)-4-((4-fluorophenyl)sulfonyl)-3,4-dihydro-2H-benzo[b][1,4]oxazin-6-yl)carbamate | 574 (M + H)+ |
| 27i | 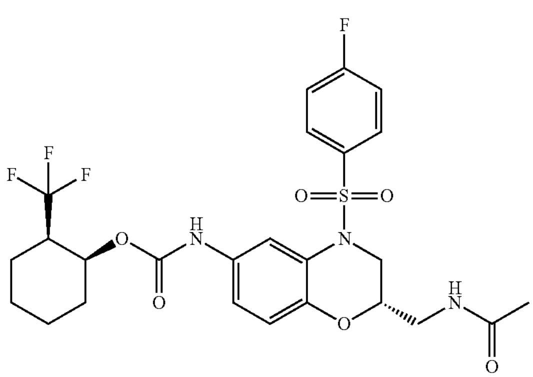 [SMILES: CC(=O)NC[C@H]1CN(S(=O)(=O)c2ccc(F)cc2)c2cc(NC(=O)O[C@H]3CCCC[C@H]3C(F)(F)F)ccc2O1] | (1S,2R)-2-(trifluoromethyl)cyclohexyl ((S)-2-(acetamidomethyl)-4-((4-fluorophenyl)sulfonyl)-3,4-dihydro-2H-benzo[b][1,4]oxazin-6-yl)carbamate | 574 (M + H)+ |

Example 28—Synthesis of 3,3-dimethylbutan-2-yl ((S)-2-(acetamidomethyl)-4-((4-fluorophenyl)sulfonyl)-3,4-dihydro-2H-benzo[b][1,4]oxazin-6-yl)carbamate (28)

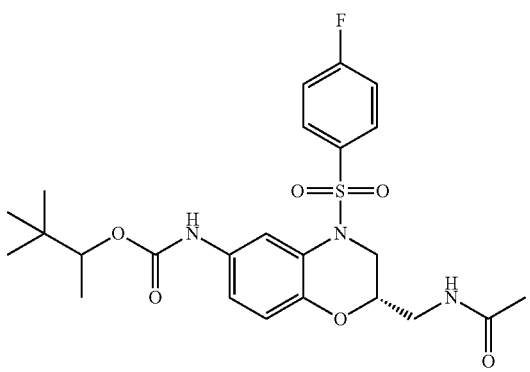

A solution of (S)—N-((6-amino-4-((4-fluorophenyl)sulfonyl)-3,4-dihydro-2H-benzo[b][1,4]oxazin-2-yl)methyl)acetamide, hydrochloride (30 mg, 0.072 mmol), 1,1'-carbonyldiimidazole (46.8 mg, 0.289 mmol), and 4-N,N-dimethylaminopyridine (1.498 mg, 0.012 mmol) in acetonitrile (500 µL) was heated at 80° C. After 22 hours, a solution of 3,3-dimethylbutan-2-ol (111 mg, 1.082 mmol) in acetonitrile (500 µL) was added and the reaction was stirred at 80° C. After 2.5 hours, mixture was concentrated under reduced pressure, dissolved in DMSO (1 mL), filtered, and purified by reverse phase chromatography to afford the title compound. LRMS (ESI) calculated for $C_{24}H_{31}FN_3O_6S$ (M+H): 508. Found: 508. $^1$H NMR (300 MHz, CDCl$_3$) δ 9.45 (1H, s), 8.06 (1H, m), 7.93 (1H, s), 7.28 (2H, m), 7.41 (2H, t, J=9.49 Hz), 7.21 (1H, m), 6.75 (1H, d, J=8.69 Hz), 4.54 (1H, m), 4.25 (1H, d, J=15.76 Hz), 3.25 (1H, m), 3.22 (1H, m), 3.17 (1H, m), 3.08 (1H, m), 1.83 (3H, s), 1.25 (3H, d, J=6.36 Hz), 0.91 (9H, s).

Example 29—Preparation of additional 3,3-dimethylbutan-2-yl or 1,1,1-trifluoropropan-2-yl carbamates The compounds in Table 10 below were prepared based on the experimental procedures described in Examples 28 and elsewhere in the detailed description using the appropriate cyclic alcohol, and can be achieved by one of skill in the art in light of the present disclosure.

TABLE 10

| Ex. No. | Structure | Name | Observed m/z |
|---|---|---|---|
| 29A | 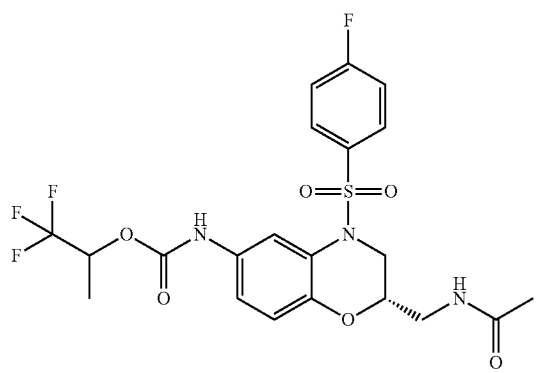 [SMILES: CC(=O)NC[C@H]1CN(S(=O)(=O)c2ccc(F)cc2)c2cc(NC(=O)OC(C)C(F)(F)F)ccc2O1] | 1,1,1-trifluoropropan-2-yl ((S)-2-(acetamidomethyl)-4-((4-fluorophenyl)sulfonyl)-3,4-dihydro-2H-benzo[b][1,4]oxazin-6-yl)carbamate | 520.1 (M + H)$^+$ |
| 29B | 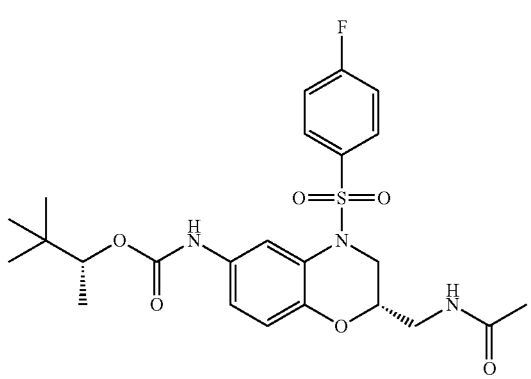 [SMILES: CC(=O)NC[C@H]1CN(S(=O)(=O)c2ccc(F)cc2)c2cc(NC(=O)O[C@H](C)C(C)(C)C)ccc2O1] | (R)-3,3-dimethylbutan-2-yl ((S)-2-(acetamidomethyl)-4-((4-fluorophenyl)sulfonyl)-3,4-dihydro-2H-benzo[b][1,4]oxazin-6-yl)carbamate | 508.2 (M + H)$^+$ |

TABLE 10-continued

| Ex. No. | Structure | Name | Observed m/z |
|---|---|---|---|
| 29C | 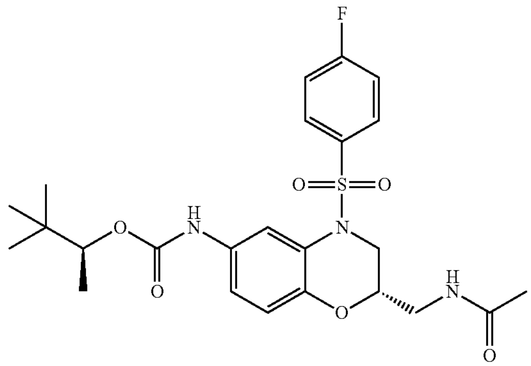 | (S)-3,3-dimethylbutan-2-yl ((S)-2-(acetamidomethyl)-4-((4-fluorophenyl)sulfonyl)-3,4-dihydro-2H-benzo[b][1,4]oxazin-6-yl)carbamate | 508.2 (M + H)+ |
| 29D | 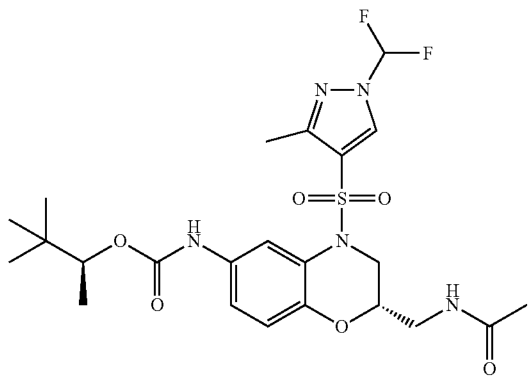 [SMILES: CC(=O)NC[C@H]1CN(S(=O)(=O)c2cn(C(F)F)nc2C)c2cc(NC(=O)O[C@@H](C)C(C)(C)C)ccc2O1] | (S)-3,3-dimethylbutan-2-yl ((S)-2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate | 544.2 (M + H)+ |
| 29E | 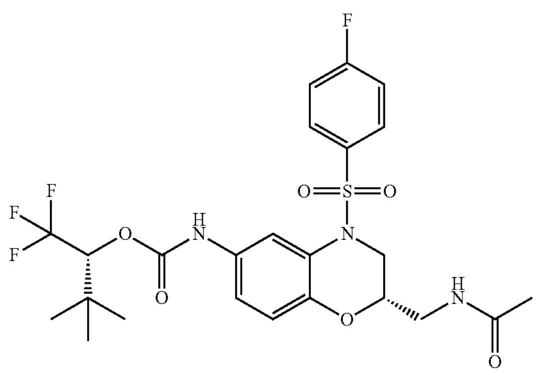 [SMILES: CC(=O)NC[C@H]1CN(S(=O)(=O)c2ccc(F)cc2)c2cc(NC(=O)O[C@H](C(C)(C)C)C(F)(F)F)ccc2O1] | (R)-1,1,1-trifluoro-3,3-dimethylbutan-2-yl ((S)-2-(acetamidomethyl)-4-((4-fluorophenyl)sulfonyl)-3,4-dihydro-2H-benzo[b][1,4]oxazin-6-yl)carbamate | 562.2 (M + H)+ |
| 29F | 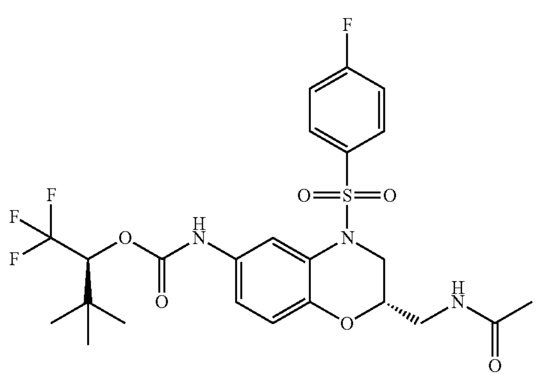 [SMILES: CC(=O)NC[C@H]1CN(S(=O)(=O)c2ccc(F)cc2)c2cc(NC(=O)O[C@@H](C(C)(C)C)C(F)(F)F)ccc2O1] | (S)-1,1,1-trifluoro-3,3-dimethylbutan-2-yl ((S)-2-(acetamidomethyl)-4-((4-fluorophenyl)sulfonyl)-3,4-dihydro-2H-benzo[b][1,4]oxazin-6-yl)carbamate | 562.2 (M + H)+ |

TABLE 10-continued

| Ex. No. | Structure | Name | Observed m/z |
|---|---|---|---|
| 29G | 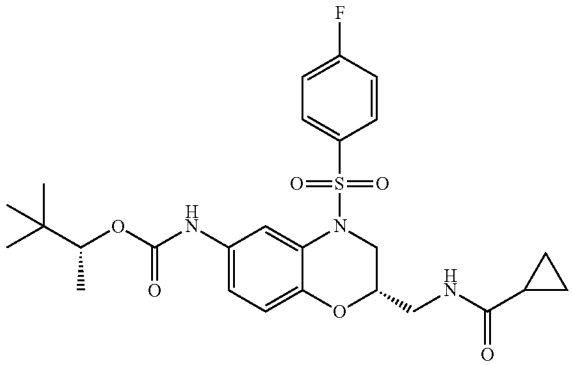 [SMILES: C[C@@H](OC(=O)Nc1ccc2c(c1)N(S(=O)(=O)c1ccc(F)cc1)C[C@H](CNC(=O)C1CC1)O2)C(C)(C)C] | (R)-3,3-dimethylbutan-2-yl ((S)-2-(cyclopropanecarboxamidomethyl)-4-((4-fluorophenyl)sulfonyl)-3,4-dihydro-2H-benzo[b][1,4]oxazin-6-yl)carbamate | 534.2 (M + H)+ |
| 29H | 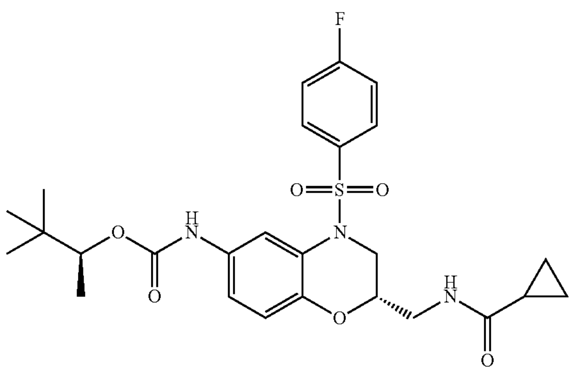 [SMILES: C[C@H](OC(=O)Nc1ccc2c(c1)N(S(=O)(=O)c1ccc(F)cc1)C[C@H](CNC(=O)C1CC1)O2)C(C)(C)C] | (S)-3,3-dimethylbutan-2-yl ((S)-2-(cyclopropanecarboxamidomethyl)-4-((4-fluorophenyl)sulfonyl)-3,4-dihydro-2H-benzo[b][1,4]oxazin-6-yl)carbamate | 534.2 (M + H)+ |
| 29i | 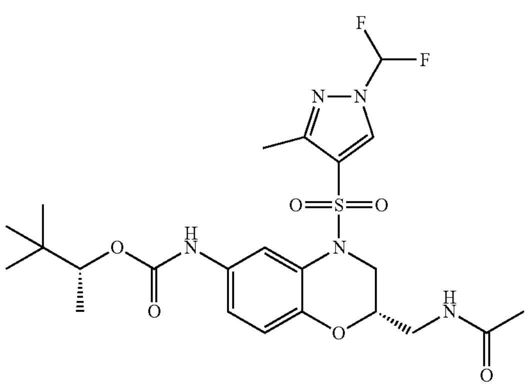 [SMILES: CC(=O)NC[C@H]1CN(S(=O)(=O)c2cn(C(F)F)nc2C)c2cc(NC(=O)O[C@H](C)C(C)(C)C)ccc2O1] | (R)-3,3-dimethylbutan-2-yl ((S)-2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate | 544.2 (M + H)+ |

Example 30—Additional Carbamates Prepared from Aminobenzoxazines

The compounds in Table 11 below were prepared based on the experimental procedures described in Examples 28 and elsewhere in the detailed description, and can be achieved by one of skill in the art in light of the present disclosure.

TABLE 11

| Ex. No. | Structure | Name | Observed m/z |
|---|---|---|---|
| 30A | 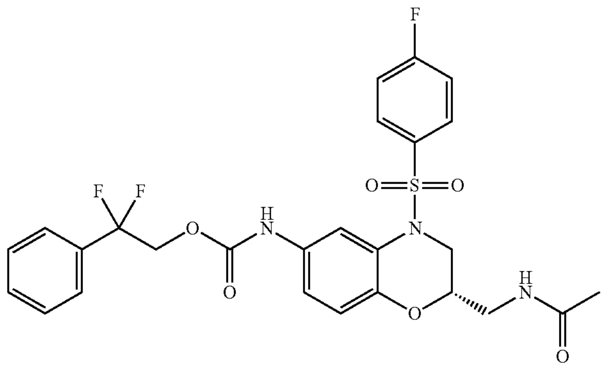 [SMILES: CC(=O)NC[C@H]1CN(S(=O)(=O)c2ccc(F)cc2)c2cc(NC(=O)OCC(F)(F)c3ccccc3)ccc2O1] | (S)-2,2-difluoro-2-phenylethyl (2-(acetamidomethyl)-4-((4-fluorophenyl)sulfonyl)-3,4-dihydro-2H-benzo[b][1,4]oxazin-6-yl)carbamate | 564 (M + H)+ |
| 30B | 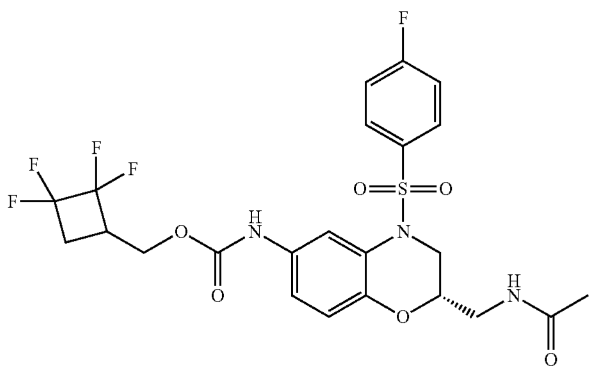 [SMILES: CC(=O)NC[C@H]1CN(S(=O)(=O)c2ccc(F)cc2)c2cc(NC(=O)OCC3CC(F)(F)C3(F)F)ccc2O1] | (2,2,3,3-tetrafluorocyclobutyl)methyl ((S)-2-(acetamidomethyl)-4-((4-fluorophenyl)sulfonyl)-3,4-dihydro-2H-benzo[b][1,4]oxazin-6-yl)carbamate | 564 (M + H)+ |
| 30C | 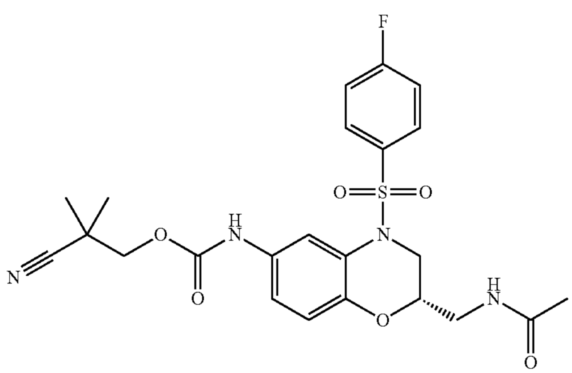 [SMILES: CC(=O)NC[C@H]1CN(S(=O)(=O)c2ccc(F)cc2)c2cc(NC(=O)OCC(C)(C)C#N)ccc2O1] | (S)-2-cyano-2-methylpropyl (2-(acetamidomethyl)-4-((4-fluorophenyl)sulfonyl)-3,4-dihydro-2H-benzo[b][1,4]oxazin-6-yl)carbamate | 505.1 (M + H)+ |
| 30D | 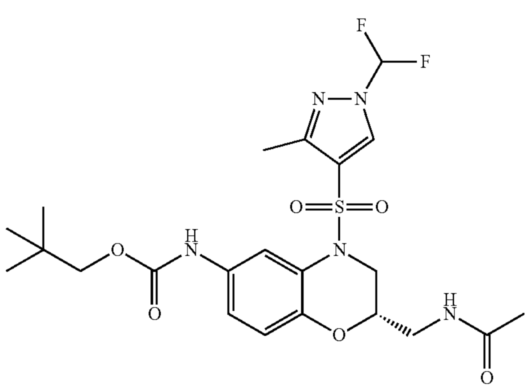 [SMILES: CC(=O)NC[C@H]1CN(S(=O)(=O)c2cn(C(F)F)nc2C)c2cc(NC(=O)OCC(C)(C)C)ccc2O1] | (S)-4-((2-(acetamidomethyl)-6-(((neopentyloxy)carbonyl)amino)-2H-benzo[b][1,4]oxazin-4(3H)-yl)sulfonyl)-1-(difluoromethyl)-3-methyl-1H-pyrazole | 530.2 (M + H)+ |

TABLE 11-continued

| Ex. No. | Structure | Name | Observed m/z |
|---|---|---|---|
| 30E | 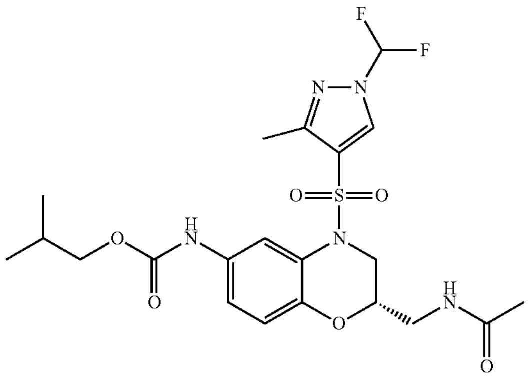 [SMILES: CC(=O)NC[C@H]1CN(S(=O)(=O)c2cn(C(F)F)nc2C)c2cc(NC(=O)OCC(C)C)ccc2O1] | (S)-isobutyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate | 516 (M + H)+ |
| 30F | 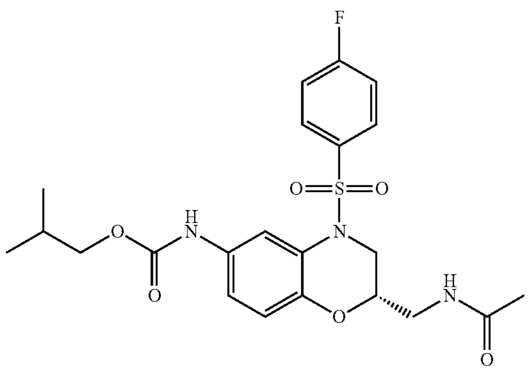 [SMILES: CC(=O)NC[C@H]1CN(S(=O)(=O)c2ccc(F)cc2)c2cc(NC(=O)OCC(C)C)ccc2O1] | (S)-isobutyl (2-(acetamidomethyl)-4-((4-fluorophenyl)sulfonyl)-3,4-dihydro-2H-benzo[b][1,4]oxazin-6-yl)carbamate | 480.3 (M + H)+ |
| 30G | 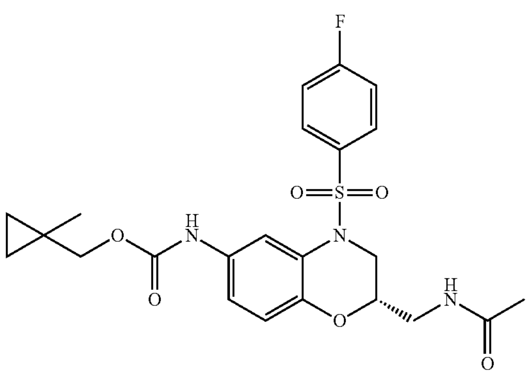 [SMILES: CC(=O)NC[C@H]1CN(S(=O)(=O)c2ccc(F)cc2)c2cc(NC(=O)OCC3(C)CC3)ccc2O1] | (S)-(1-methylcyclopropyl)methyl (2-(acetamidomethyl)-4-((4-fluorophenyl)sulfonyl)-3,4-dihydro-2H-benzo[b][1,4]oxazin-6-yl)carbamate | 492.3 (M + H)+ |
| 30H | 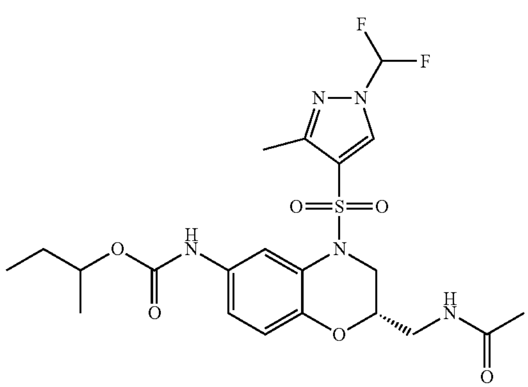 [SMILES: CCC(C)OC(=O)Nc1ccc2c(c1)N(S(=O)(=O)c1cn(C(F)F)nc1C)C[C@H](CNC(C)=O)O2] | sec-butyl ((S)-2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate | 516 (M + H)+ |

TABLE 11-continued

| Ex. No. | Structure | Name | Observed m/z |
|---|---|---|---|
| 30i | 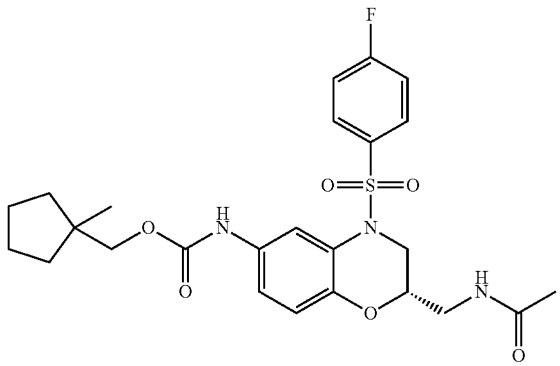 [SMILES: CC(=O)NC[C@H]1CN(S(=O)(=O)c2ccc(F)cc2)c2cc(NC(=O)OCC3(C)CCCC3)ccc2O1] | (S)-(1-methylcyclopentyl)methyl (2-(acetamidomethyl)-4-((4-fluorophenyl)sulfonyl)-3,4-dihydro-2H-benzo[b][1,4]oxazin-6-yl)carbamate | 520.2 (M + H)+ |
| 30J | 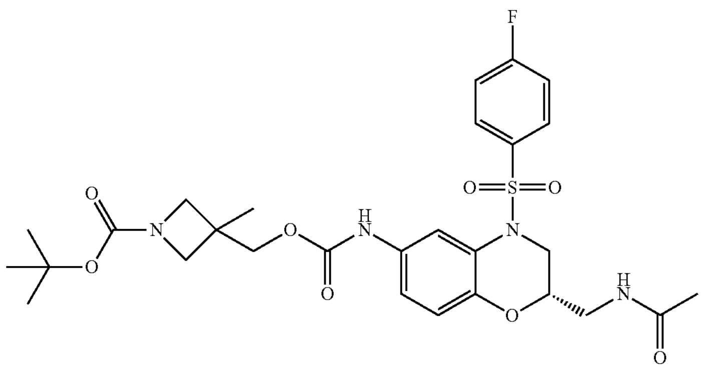 [SMILES: CC(=O)NC[C@H]1CN(S(=O)(=O)c2ccc(F)cc2)c2cc(NC(=O)OCC3(C)CN(C(=O)OC(C)(C)C)C3)ccc2O1] | (S)-tert-butyl 3-((((2-(acetamidomethyl)-4-((4-fluorophenyl)sulfonyl)-3,4-dihydro-2H-benzo[b][1,4]oxazin-6-yl)carbamoyl)oxy)methyl)-3-methylazetidine-1-carboxylate | 607.2 (M + H)+ |
| 30K | 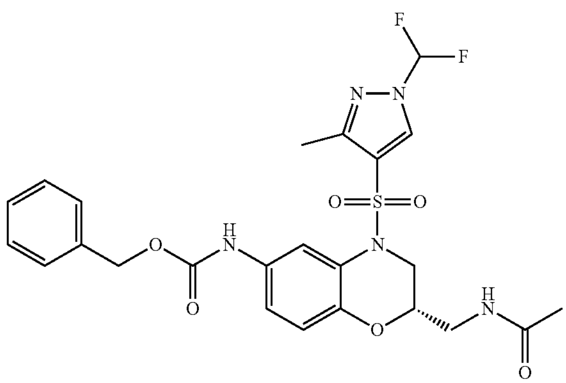 [SMILES: CC(=O)NC[C@H]1CN(S(=O)(=O)c2cn(C(F)F)nc2C)c2cc(NC(=O)OCc3ccccc3)ccc2O1] | (S)-benzyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate | 550 (M + H)+ |
| 30L | 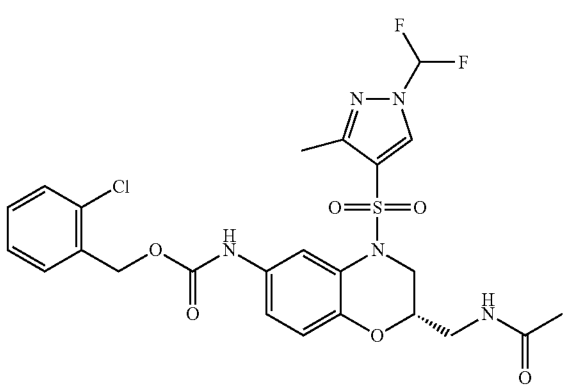 [SMILES: CC(=O)NC[C@H]1CN(S(=O)(=O)c2cn(C(F)F)nc2C)c2cc(NC(=O)OCc3ccccc3Cl)ccc2O1] | (S)-2-chlorobenzyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate | 584 (M + H)+ |

TABLE 11-continued

| Ex. No. | Structure | Name | Observed m/z |
|---|---|---|---|
| 30M | 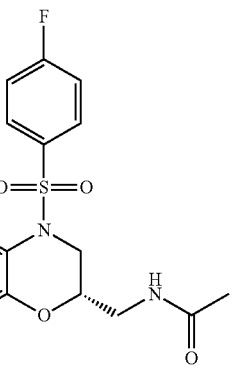 | (S)-2,2-difluoro-3,3-dimethylpentyl (2-(acetamidomethyl)-4-((4-fluorophenyl)sulfonyl)-3,4-dihydro-2H-benzo[b][1,4]oxazin-6-yl)carbamate | 558.2 (M + H)+ |
| 30N | 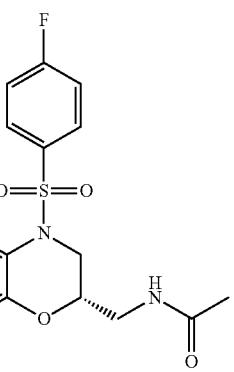 | (S)-2,2-difluoro-3,3-dimethylpent-4-en-1-yl (2-(acetamidomethyl)-4-((4-fluorophenyl)sulfonyl)-3,4-dihydro-2H-benzo[b][1,4]oxazin-6-yl)carbamate | 556.1 (M + H)+ |
| 30o | 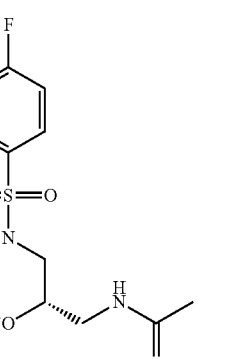 | (2,2-difluoro-1-phenylcyclopropyl)methyl ((S)-2-(acetamidomethyl)-4-((4-fluorophenyl)sulfonyl)-3,4-dihydro-2H-benzo[b][1,4]oxazin-6-yl)carbamate | 590 (M + H)+ |
| 30P | 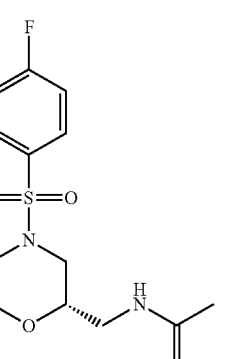 | (S)-3,3,3-trifluoropropyl (2-(acetamidomethyl)-4-((4-fluorophenyl)sulfonyl)-3,4-dihydro-2H-benzo[b][1,4]oxazin-6-yl)carbamate | 520 (M + H)+ |

TABLE 11-continued

| Ex. No. | Structure | Name | Observed m/z |
|---|---|---|---|
| 30Q | 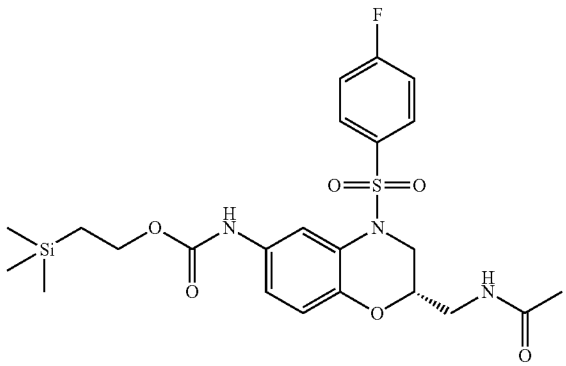 [SMILES: CC(=O)NC[C@H]1CN(S(=O)(=O)c2ccc(F)cc2)c2cc(NC(=O)OCC[Si](C)(C)C)ccc2O1] | (S)-2-(trimethylsilyl)ethyl (2-(acetamidomethyl)-4-((4-fluorophenyl)sulfonyl)-3,4-dihydro-2H-benzo[b][1,4]oxazin-6-yl)carbamate | 524.1 (M + H)+ |
| 30R | 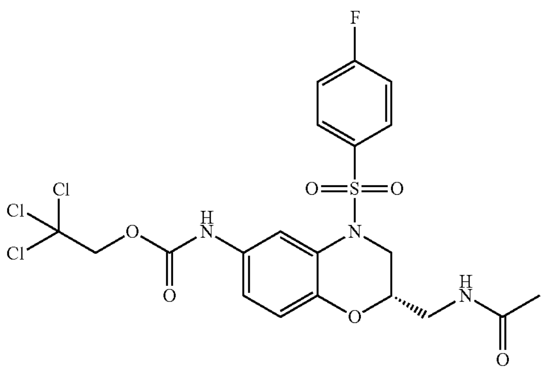 [SMILES: CC(=O)NC[C@H]1CN(S(=O)(=O)c2ccc(F)cc2)c2cc(NC(=O)OCC(Cl)(Cl)Cl)ccc2O1] | (S)-2,2,2-trichloroethyl (2-(acetamidomethyl)-4-((4-fluorophenyl)sulfonyl)-3,4-dihydro-2H-benzo[b][1,4]oxazin-6-yl)carbamate | 553.9 (M + H)+ |
| 30S | 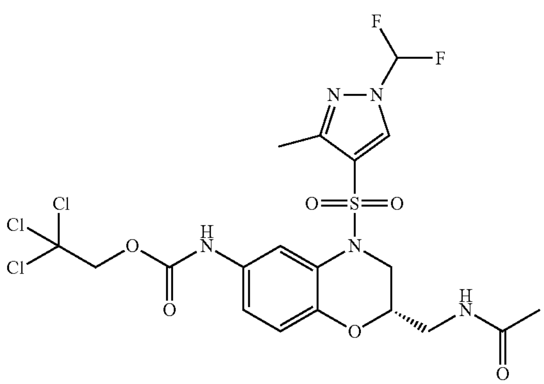 [SMILES: CC(=O)NC[C@H]1CN(S(=O)(=O)c2cn(C(F)F)nc2C)c2cc(NC(=O)OCC(Cl)(Cl)Cl)ccc2O1] | (S)-2,2,2-trichloroethyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate | 591.0 (M + H)+ |
| 30T | 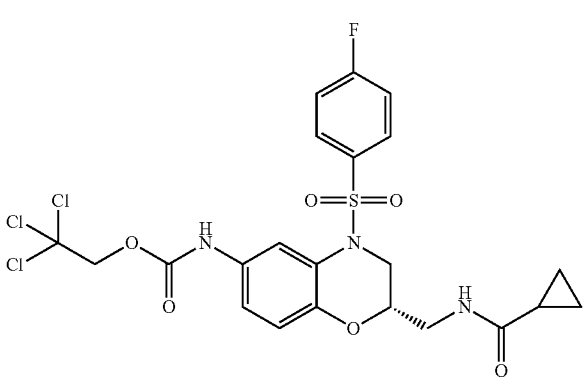 [SMILES: O=C(Nc1ccc2c(c1)N(S(=O)(=O)c1ccc(F)cc1)C[C@H](CNC(=O)C1CC1)O2)OCC(Cl)(Cl)Cl] | (S)-2,2,2-trichloroethyl (2-(cyclopropanecarboxamidomethyl)-4-((4-fluorophenyl)sulfonyl)-3,4-dihydro-2H-benzo[b][1,4]oxazin-6-yl)carbamate | 604.0 (M + Na)+ |

TABLE 11-continued

| Ex. No. | Structure | Name | Observed m/z |
|---|---|---|---|
| 30U | 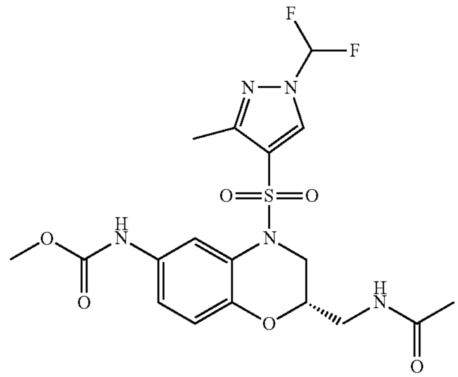 [SMILES: COC(=O)Nc1ccc2c(c1)N(S(=O)(=O)c1cn(C(F)F)nc1C)C[C@H](CNC(C)=O)O2] | (S)-methyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate | 474 (M + H)+ |
| 30V | 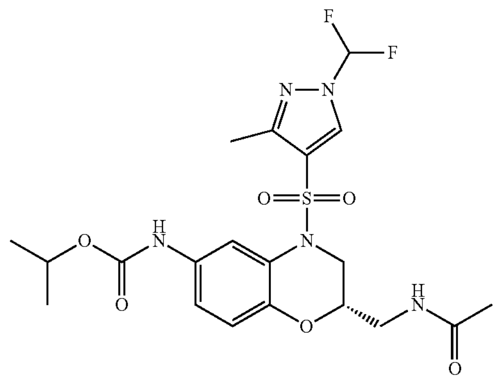 [SMILES: CC(=O)NC[C@H]1CN(S(=O)(=O)c2cn(C(F)F)nc2C)c2cc(NC(=O)OC(C)C)ccc2O1] | (S)-isopropyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate | 502 (M + H)+ |
| 30W | 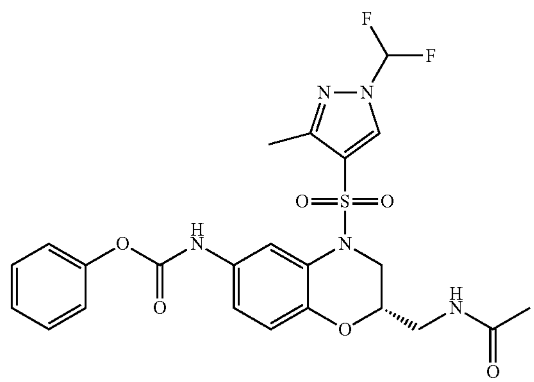 [SMILES: CC(=O)NC[C@H]1CN(S(=O)(=O)c2cn(C(F)F)nc2C)c2cc(NC(=O)Oc3ccccc3)ccc2O1] | (S)-phenyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate | 536 (M + H)+ |
| 30X | 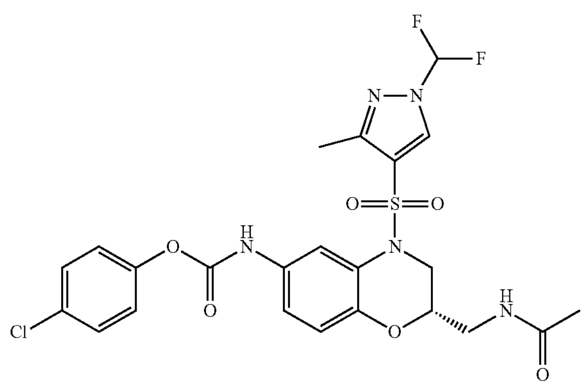 [SMILES: CC(=O)NC[C@H]1CN(S(=O)(=O)c2cn(C(F)F)nc2C)c2cc(NC(=O)Oc3ccc(Cl)cc3)ccc2O1] | (S)-4-chlorophenyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate | 570 (M + H)+ |

TABLE 11-continued

| Ex. No. | Structure | Name | Observed m/z |
|---|---|---|---|
| 30Y | 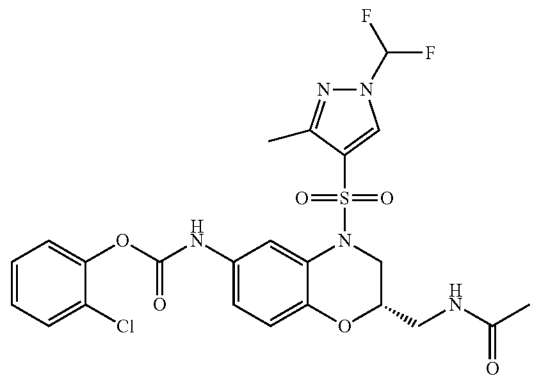 [SMILES: CC(=O)NC[C@H]1CN(S(=O)(=O)c2cn(C(F)F)nc2C)c2cc(NC(=O)Oc3ccccc3Cl)ccc2O1] | (S)-2-chlorophenyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate | 570 (M + H)+ |
| 30Z | 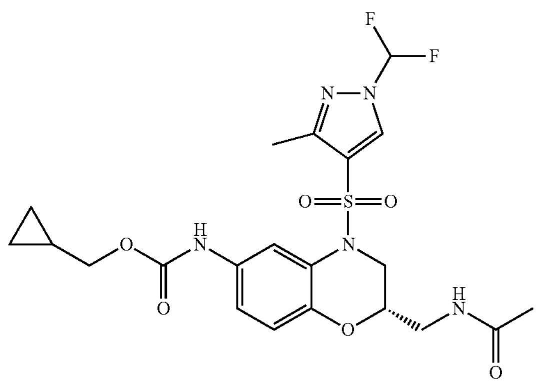 [SMILES: CC(=O)NC[C@H]1CN(S(=O)(=O)c2cn(C(F)F)nc2C)c2cc(NC(=O)OCC3CC3)ccc2O1] | (S)-cyclopropylmethyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate | 514 (M + H)+ |
| 30AA | 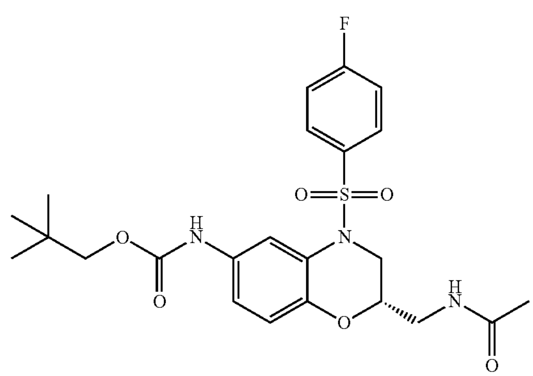 [SMILES: CC(=O)NC[C@H]1CN(S(=O)(=O)c2ccc(F)cc2)c2cc(NC(=O)OCC(C)(C)C)ccc2O1] | (S)-neopentyl (2-(acetamidomethyl)-4-((4-fluorophenyl)sulfonyl)-3,4-dihydro-2H-benzo[b][1,4]oxazin-6-yl)carbamate | 494 (M + H)+ |
| 30AB | 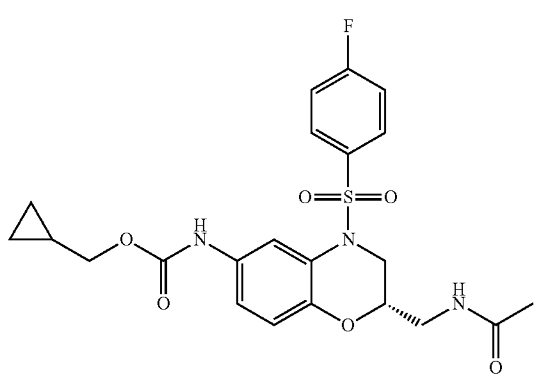 [SMILES: CC(=O)NC[C@H]1CN(S(=O)(=O)c2ccc(F)cc2)c2cc(NC(=O)OCC3CC3)ccc2O1] | (S)-cyclopropylmethyl (2-(acetamidomethyl)-4-((4-fluorophenyl)sulfonyl)-3,4-dihydro-2H-benzo[b][1,4]oxazin-6-yl)carbamate | 478.1 (M + H)+ |

TABLE 11-continued

| Ex. No. | Structure | Name | Observed m/z |
|---|---|---|---|
| 30AC | 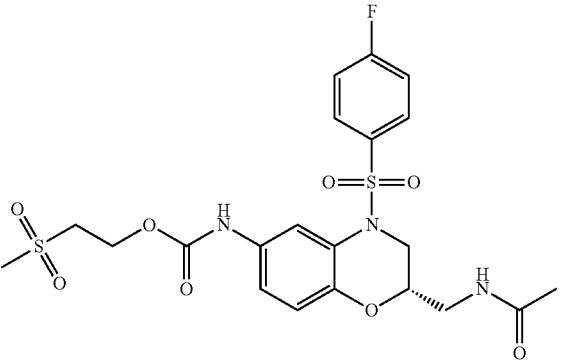 [SMILES: CC(=O)NC[C@H]1CN(S(=O)(=O)c2ccc(F)cc2)c2cc(NC(=O)OCCS(C)(=O)=O)ccc2O1] | (S)-2-(methylsulfonyl)ethyl (2-(acetamidomethyl)-4-((4-fluorophenyl)sulfonyl)-3,4-dihydro-2H-benzo[b][1,4]oxazin-6-yl)carbamate | 530.0 (M + H)$^+$ |
| 30AD | 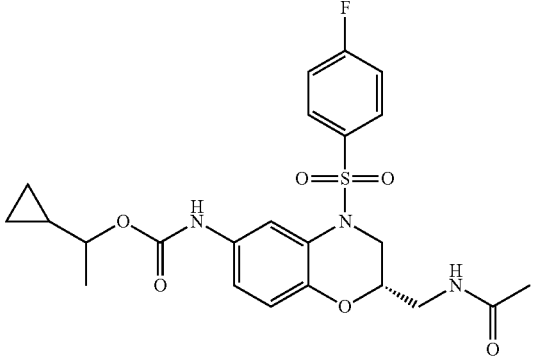 [SMILES: CC(=O)NC[C@H]1CN(S(=O)(=O)c2ccc(F)cc2)c2cc(NC(=O)OC(C)C3CC3)ccc2O1] | 1-cyclopropylethyl ((S)-2-(acetamidomethyl)-4-((4-fluorophenyl)sulfonyl)-3,4-dihydro-2H-benzo[b][1,4]oxazin-6-yl)carbamate | 492.1 (M + H)$^+$ |
| 30AE | 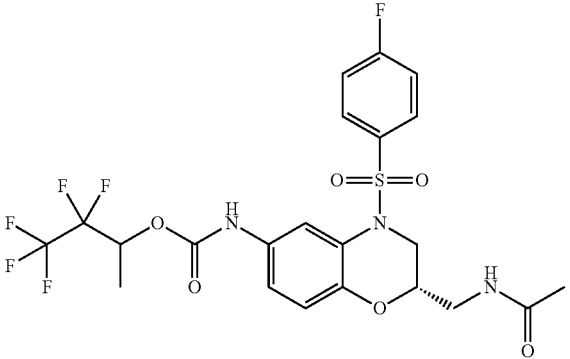 [SMILES: CC(=O)NC[C@H]1CN(S(=O)(=O)c2ccc(F)cc2)c2cc(NC(=O)OC(C)C(F)(F)C(F)(F)F)ccc2O1] | 3,3,4,4,4-pentafluorobutan-2-yl ((S)-2-(acetamidomethyl)-4-((4-fluorophenyl)sulfonyl)-3,4-dihydro-2H-benzo[b][1,4]oxazin-6-yl)carbamate | 570 (M + H)$^+$ |

Example 31—Synthesis of (S)-1,1,1-trifluoro-2-methylpropan-2-yl (2-((1-fluorocyclopropanecarboxamido)methyl)-4-((4-fluorophenyl)sulfonyl)-3,4-dihydro-2H-benzo[b][1,4]oxazin-6-yl)carbamate (31)

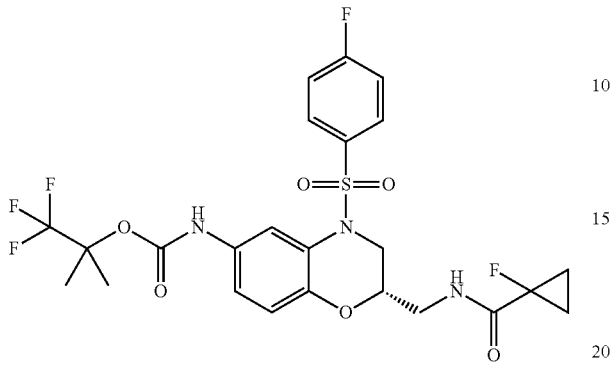

The title compound was prepared according to the procedures described below.

Part I—Synthesis of (S)-tert-butyl (2-(((benzyloxy)carbonyl)aminomethyl)-3,4-dihydro-2H-benzo[b][1,4]oxazin-6-yl)carbamate

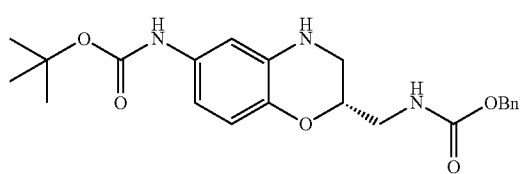 [SMILES: CC(C)(C)OC(=O)Nc1ccc2c(c1)NC[C@H](CNC(=O)OCc1ccccc1)O2]

To (S)-tert-butyl (2-(aminomethyl)-3,4-dihydro-2H-benzo[b][1,4]oxazin-6-yl)carbamate (2.5 g, 8.95 mmol), N,N'-diisopropylethylamine (3.91 mL, 22.37 mmol), and dichloromethane (44.7 mL) was added dropwise benzyl chloroformate (1.28 mL, 8.95 mmol) over five minutes at 0° C. The mixture was warmed to room temperature and stirred for four hours. The mixture was diluted in saturated sodium bicarbonate and extracted with isopropanol/chloroform (1:3 v/v). The combined organic layers were washed with brine, dried (MgSO$_4$) and concentrated to afford (S)-tert-butyl (2-(((benzyloxy)carbonyl)aminomethyl)-3,4-dihydro-2H-benzo[b][1,4]oxazin-6-yl)carbamate.

Part II—Synthesis of (S)-tert-butyl (2-(((benzyloxy)carbonyl)aminomethyl)-4-((4-fluorophenyl)sulfonyl)-3,4-dihydro-2H-benzo[b][1,4]oxazin-6-yl)carbamate

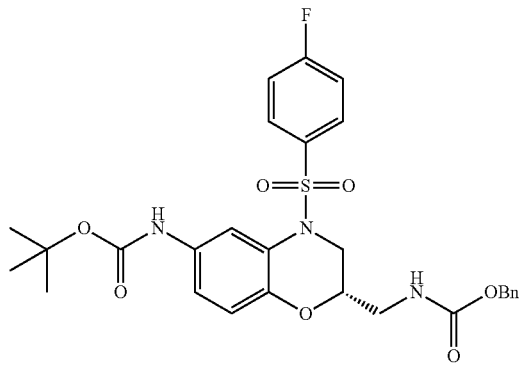 [SMILES: CC(C)(C)OC(=O)Nc1ccc2c(c1)N(S(=O)(=O)c1ccc(F)cc1)C[C@H](CNC(=O)OCc1ccccc1)O2]

A mixture of (S)-tert-butyl (2-(((benzyloxy)carbonyl)aminomethyl)-3,4-dihydro-2H-benzo[b][1,4]oxazin-6-yl)carbamate (7.4 g, 17.90 mmol), pyridine (89 mL), and 4-fluorobenzene-1-sulfonyl chloride (6.97 g, 35.8 mmol) was heated at 60° C. for two hours. The mixture was partitioned between isopropanol chloroform and saturated sodium bicarbonate. The organic layer was washed with brine, dried (MgSO$_4$) and concentrated to afford (S)-tert-butyl (2-(((benzyloxy)carbonyl)aminomethyl)-4-((4-fluorophenyl)sulfonyl)-3,4-dihydro-2H-benzo[b][1,4]oxazin-6-yl)carbamate

Part III—Synthesis of (S)-benzyl ((6-amino-4-((4-fluorophenyl)sulfonyl)-3,4-dihydro-2H-benzo[b][1,4]oxazin-2-yl)methyl)carbamate

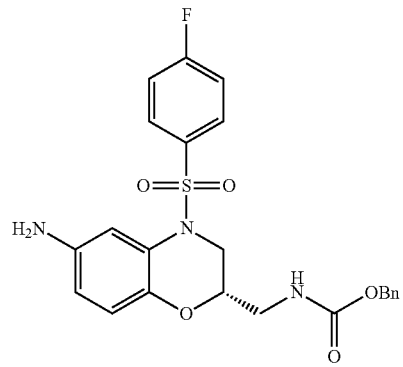 [SMILES: Nc1ccc2c(c1)N(S(=O)(=O)c1ccc(F)cc1)C[C@H](CNC(=O)OCc1ccccc1)O2]

A mixture of (S)-tert-butyl (2-(((benzyloxy)carbonyl)aminomethyl)-4-((4-fluorophenyl)sulfonyl)-3,4-dihydro-2H-benzo[b][1,4]oxazin-6-yl)carbamate (10 g, 17.49 mmol) and 4M HCl in p-dioxane (109 mL, 437 mmol) was stirred at room temperature for 30 minutes and concentrated to afford (S)-benzyl ((6-amino-4-((4-fluorophenyl)sulfonyl)-3,4-dihydro-2H-benzo[b][1,4]oxazin-2-yl)methyl)carbamate.

Part IV—Synthesis of (S)-1,1,1-trifluoro-2-methylpropan-2-yl (2-(((benzyloxy)carbonyl)aminomethyl)-4-((4-fluorophenyl)sulfonyl)-3,4-dihydro-2H-benzo[b][1,4]oxazin-6-yl)carbamate

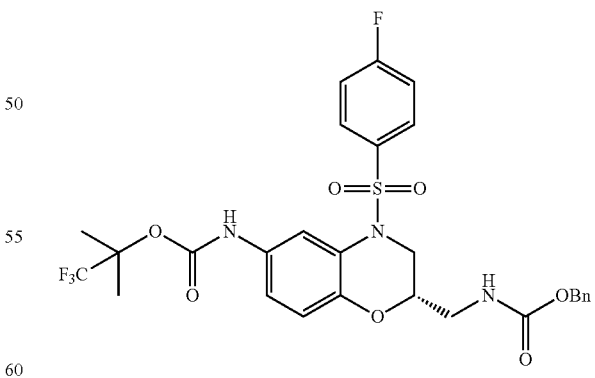

To (S)-benzyl ((6-amino-4-((4-fluorophenyl)sulfonyl)-3,4-dihydro-2H-benzo[b][1,4]oxazin-2-yl)methyl)carbamate (4.00 g, 7.87 mmol), dichloromethane (39.4 mL), and triethyl amine (6.59 mL, 47.2 mmol) was added 4-nitrophenyl (1,1,1-trifluoro-2-methylpropan-2-yl) carbonate (5.77 g, 19.69 mmol) and 4-N,N-dimethylaminopyridine (0.192 g, 1.575 mmol). The mixture was stirred at room temperature overnight and poured into saturated sodium bicarbonate. The mixture was extracted with isopropanol/chloroform. The combined organic layers were washed with 1N NaOH, dried (MgSO$_4$) and concentrated. The residue was purified via chromatography eluting with a gradient of (0-100% ethyl acetate/hexanes) to afford (S)-1,1,1-trifluoro-2-methylpropan-2-yl (2-(((benzyloxy)carbonyl)aminomethyl)-4-((4-fluorophenyl)sulfonyl)-3,4-dihydro-2H-benzo[b][1,4]oxazin-6-yl)carbamate.

Part V—Synthesis of (S)-1,1,1-trifluoro-2-methylpropan-2-yl (2-(aminomethyl)-4-((4-fluorophenyl)sulfonyl)-3,4-dihydro-2H-benzo[b][1,4]oxazin-6-yl) carbamate

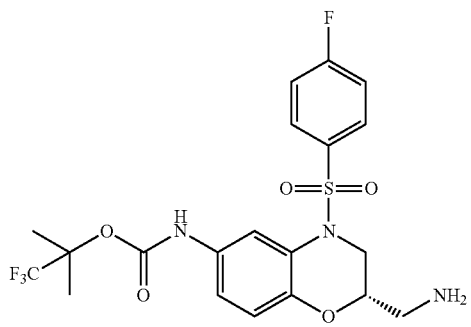 [SMILES: CC(C)(OC(=O)Nc1ccc2c(c1)N(S(=O)(=O)c1ccc(F)cc1)C[C@H](CN)O2)C(F)(F)F]

A solution of (S)-1,1,1-trifluoro-2-methylpropan-2-yl (2-(((benzyloxy)carbonyl)aminomethyl)-4-((4-fluorophenyl)sulfonyl)-3,4-dihydro-2H-benzo[b][1,4]oxazin-6-yl)carbamate (750 mg, 1.20 mmol) and methanol (12 mL) was purged with nitrogen. Palladium 10% on carbon (76 mg, 0.072 mmol) was added. The atmosphere was exchanged with hydrogen at one atmosphere and stirred for four hours. The mixture was filtered through CELITE. The filtrate was concentrated to afford (S)-1,1,1-trifluoro-2-methylpropan-2-yl (2-(aminomethyl)-4-((4-fluorophenyl)sulfonyl)-3,4-dihydro-2H-benzo[b][1,4]oxazin-6-yl)carbamate as a white solid. $^1$H NMR: (300 MHz, CDCl$_3$): δ 9.81 (1H, s), 8.00 (2H, s), 7.92 (1H, s), 7.84 (2H, m), 7.46 (2H, m), 7.22 (1H, d, J=9.7 Hz), 6.80 (1H, d, J=8.24 Hz), 4.41 (1H, dd, J=11.79 Hz, 2.66 Hz), 3.72 (1H, m), 3.34 (1H, m), 3.20 (1H, m), 2.96 (1H, m), 1.70 (6H, s). LRMS (ESI) calculated for C$_{20}$H$_{21}$F$_4$N$_3$O$_5$S (M+H)$^+$: 492. Found 492.1.

Part VI—Synthesis of (S)-1,1,1-trifluoro-2-methylpropan-2-yl (2-((1-fluorocyclopropanecarboxamido) methyl)-4-((4-fluorophenyl)sulfonyl)-3,4-dihydro-2H-benzo[b][1,4]oxazin-6-yl)carbamate A solution of (S)-1,1,1-trifluoro-2-methylpropan-2-yl (2-(aminomethyl)-4-((4-fluorophenyl)sulfonyl)-3,4-dihydro-2H-benzo[b][1,4]oxazin-6-yl)carbamate (26 mg, 0.053 mmol), 1-fluorocyclopropanecarboxylic acid (7.0 mg, 0.058 mmol), (benzotriazol-1-yloxy)tris(dimethylamino)phosphonium hexafluorophosphate (25.7 mg, 0.058 mmol), N,N'-diisopropylethylamine (0.028 mL, 0.159 mmol), and THF (1 mL) was stirred at room temperature overnight. The reaction was then diluted with DMSO (1 mL) and purified by mass-triggered reverse phase HPLC, eluting with a 1% trifluoroacetic acid buffered water/acetonitrile gradient over a Waters X-Bridge C-18 column, to afford (S)-1,1,1-trifluoro-2-methylpropan-2-yl (2-((1-fluorocyclopropanecarboxamido)methyl)-4-((4-fluorophenyl)sulfonyl)-3,4-dihydro-2H-benzo[b][1,4]oxazin-6-yl)carbamate. MS ESI calculated C$_{24}$H$_{24}$F$_5$N$_3$O$_6$S (M+H):$^+$ 578. Found: 578. $^1$H NMR (600 MHz, DMSO-d6) δ 1.17-1.14 (2H, m), 1.36-1.24 (2H, m), 1.67 (6H, d, J=3.38 Hz), 2.47 (2H, d, J=2.06 Hz), 3.19-3.18 (2H, m), 4.27 (1H, dd, J=14.44, 2.17 Hz), 6.76 (1H, d, J=8.90 Hz), 7.16 (1H, d, J=8.74 Hz), 7.38 (2H, t, J=8.64 Hz), 7.69 (2H, dd, J=8.59, 4.99 Hz), 7.89 (1H, s), 8.60 (1H, t, J=5.95 Hz), 9.75 (1H, s).

Example 32—Additional Amides of Lower Alkyl Carboxylic Acids and Cyclopropylcarboxylic Acids with Amino-Benzoxazines The compounds in Table 12 below were prepared based on the experimental procedures described in Example 31 and elsewhere in the detailed description, and can be achieved by one of skill in the art in light of the present disclosure.

TABLE 12

| Ex. No. | Structure | Name | Observed m/z |
|---|---|---|---|
| 32A | 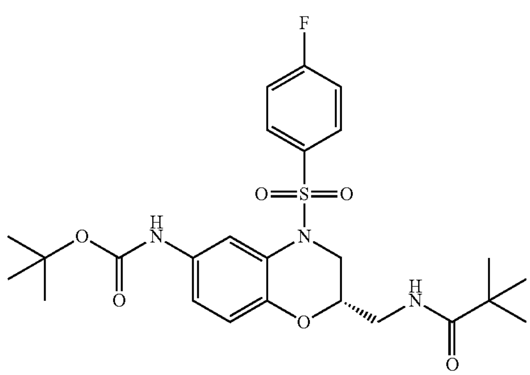 [SMILES: CC(C)(C)OC(=O)Nc1ccc2c(c1)N(S(=O)(=O)c1ccc(F)cc1)C[C@H](CNC(=O)C(C)(C)C)O2] | (S)-tert-butyl (4-((4-fluorophenyl)sulfonyl)-2-(pivalamidomethyl)-3,4-dihydro-2H-benzo[b][1,4]oxazin-6-yl)carbamate | 466.1 (M − tBu + H)$^+$ |

TABLE 12-continued

| Ex. No. | Structure | Name | Observed m/z |
|---|---|---|---|
| 32B | 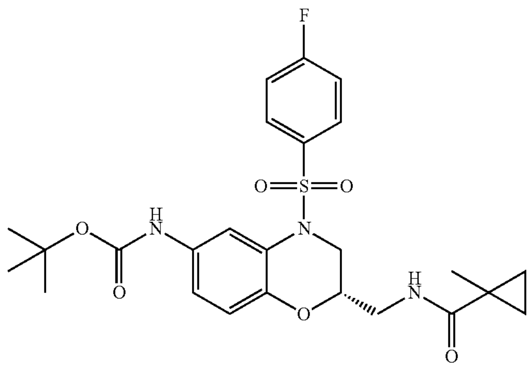 [SMILES: CC(C)(C)OC(=O)Nc1ccc2c(c1)N(S(=O)(=O)c1ccc(F)cc1)C[C@H](CNC(=O)C1(C)CC1)O2] | (S)-tert-butyl (4-((4-fluorophenyl)sulfonyl)-2-((1-methylcyclopropanecarboxamido)methyl)-3,4-dihydro-2H-benzo[b][1,4]oxazin-6-yl)carbamate | 464.1 (M − tBu + H)+ |
| 32C | 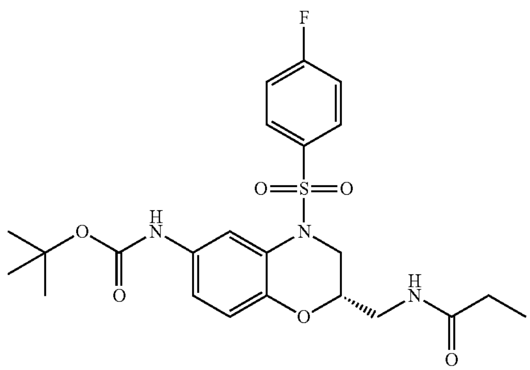 [SMILES: CCC(=O)NC[C@H]1CN(S(=O)(=O)c2ccc(F)cc2)c2cc(NC(=O)OC(C)(C)C)ccc2O1] | (S)-tert-butyl (4-((4-fluorophenyl)sulfonyl)-2-(propionamidomethyl)-3,4-dihydro-2H-benzo[b][1,4]oxazin-6-yl)carbamate | 438.1 (M − tBu + H)+ |
| 32D | 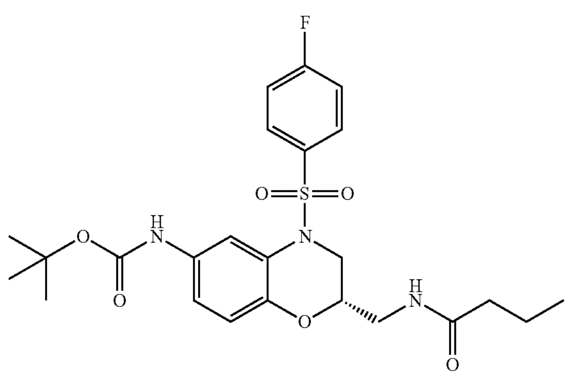 [SMILES: CCCC(=O)NC[C@H]1CN(S(=O)(=O)c2ccc(F)cc2)c2cc(NC(=O)OC(C)(C)C)ccc2O1] | (S)-tert-butyl (2-(butyramidomethyl)-4-((4-fluorophenyl)sulfonyl)-3,4-dihydro-2H-benzo[b][1,4]oxazin-6-yl)carbamate | 452.0 (M − tBu + H)+ |
| 32E | 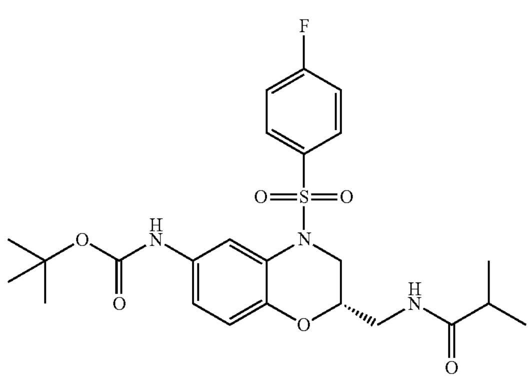 [SMILES: CC(C)C(=O)NC[C@H]1CN(S(=O)(=O)c2ccc(F)cc2)c2cc(NC(=O)OC(C)(C)C)ccc2O1] | (S)-tert-butyl (4-((4-fluorophenyl)sulfonyl)-2-(isobutyramidomethyl)-3,4-dihydro-2H-benzo[b][1,4]oxazin-6-yl)carbamate | 452.1 (M − tBu + H)+ |

TABLE 12-continued

| Ex. No. | Structure | Name | Observed m/z |
|---|---|---|---|
| 32F | 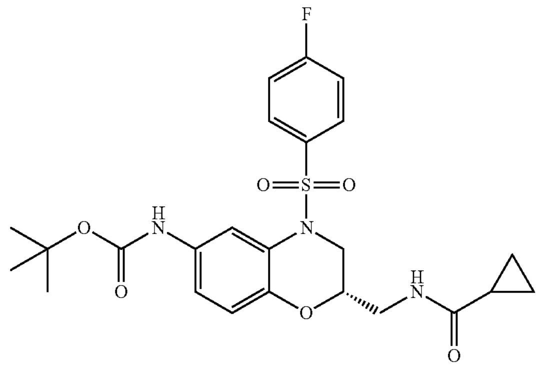 [SMILES: CC(C)(C)OC(=O)Nc1ccc2c(c1)N(S(=O)(=O)c1ccc(F)cc1)C[C@H](CNC(=O)C1CC1)O2] | (S)-tert-butyl (2-(cyclopropanecarboxamidomethyl)-4-((4-fluorophenyl)sulfonyl)-3,4-dihydro-2H-benzo[b][1,4]oxazin-6-yl)carbamate | 450.1 (M − tBu + H)+ |
| 32G | 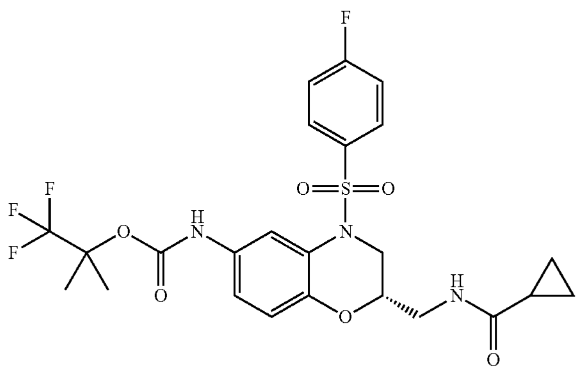 [SMILES: CC(C)(OC(=O)Nc1ccc2c(c1)N(S(=O)(=O)c1ccc(F)cc1)C[C@H](CNC(=O)C1CC1)O2)C(F)(F)F] | (S)-1,1,1-trifluoro-2-methylpropan-2-yl (2-(cyclopropanecarboxamidomethyl)-4-((4-fluorophenyl)sulfonyl)-3,4-dihydro-2H-benzo[b][1,4]oxazin-6-yl)carbamate | 560.1 (M + H)+ |
| 32H | 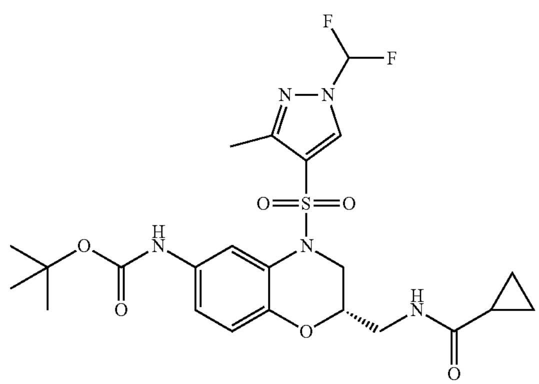 [SMILES: Cc1nn(C(F)F)cc1S(=O)(=O)N1C[C@H](CNC(=O)C2CC2)Oc2ccc(NC(=O)OC(C)(C)C)cc21] | (S)-tert-butyl (2-(cyclopropanecarboxamidomethyl)-4-((1-(difluoromethyl)-3-methyl-1H-pyrazol-4-yl)sulfonyl)-3,4-dihydro-2H-benzo[b][1,4]oxazin-6-yl)carbamate | 542.2 (M + H)+ |
| 32i | 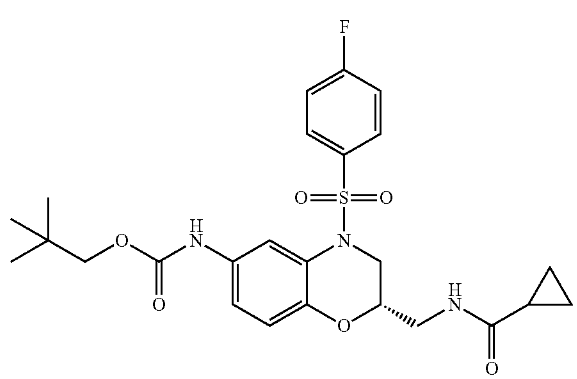 [SMILES: CC(C)(C)COC(=O)Nc1ccc2c(c1)N(S(=O)(=O)c1ccc(F)cc1)C[C@H](CNC(=O)C1CC1)O2] | (S)-neopentyl (2-(cyclopropanecarboxamidomethyl)-4-((4-fluorophenyl)sulfonyl)-3,4-dihydro-2H-benzo[b][1,4]oxazin-6-yl)carbamate | 520.2 (M + H)+ |

TABLE 12-continued

| Ex. No. | Structure | Name | Observed m/z |
|---|---|---|---|
| 32J | 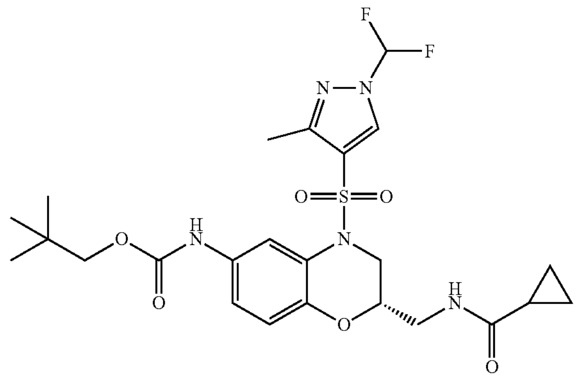 [SMILES: Cc1nn(C(F)F)cc1S(=O)(=O)N1C[C@H](CNC(=O)C2CC2)Oc2ccc(NC(=O)OCC(C)(C)C)cc21] | (S)-neopentyl (2-(cyclopropanecarboxamidomethyl)-4-((1-(difluoromethyl)-3-methyl-1H-pyrazol-4-yl)sulfonyl)-3,4-dihydro-2H-benzo[b][1,4]oxazin-6-yl)carbamate | 556.2 (M + H)+ |
| 32K | 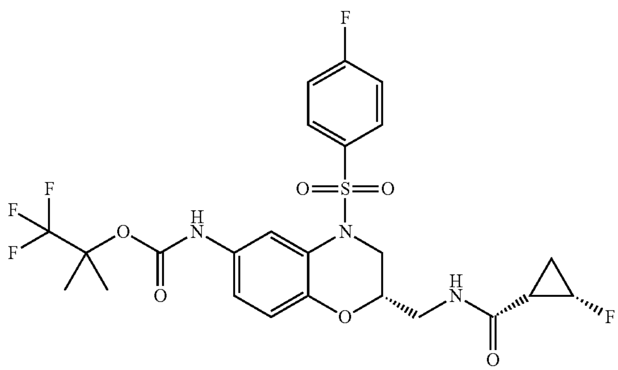 | 1,1,1-trifluoro-2-methylpropan-2-yl ((S)-2-((((1S,2S)-2-fluorocyclopropanecarboxamido)methyl)-4-((4-fluorophenyl)sulfonyl)-3,4-dihydro-2H-benzo[b][1,4]oxazin-6-yl)carbamate | 578 (M + H)+ |
| 32L | 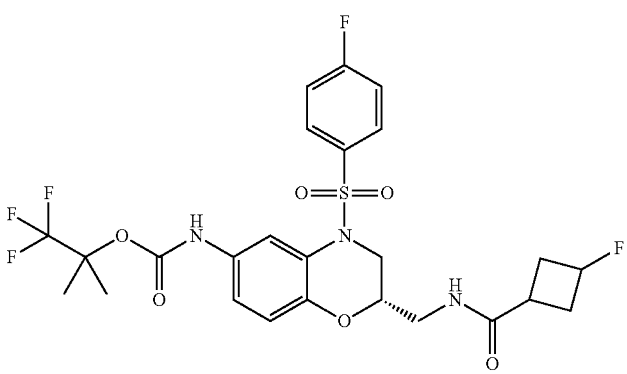 [SMILES: CC(C)(OC(=O)Nc1ccc2c(c1)N(S(=O)(=O)c1ccc(F)cc1)C[C@H](CNC(=O)C1CC(F)C1)O2)C(F)(F)F] | (S)-1,1,1-trifluoro-2-methylpropan-2-yl (2-((3-fluorocyclobutanecarboxamido)methyl)-4-((4-fluorophenyl)sulfonyl)-3,4-dihydro-2H-benzo[b][1,4]oxazin-6-yl)carbamate | 592 (M + H)+ |
| 32M | 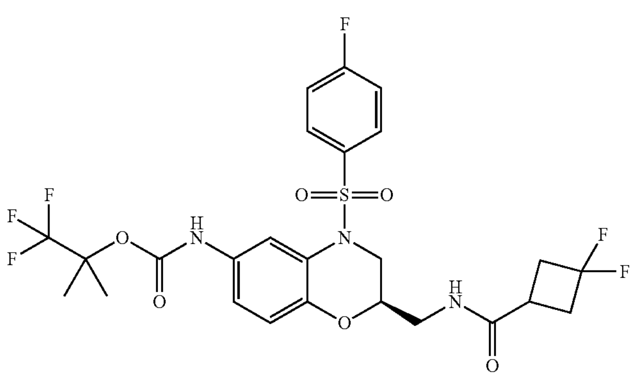 [SMILES: CC(C)(OC(=O)Nc1ccc2c(c1)N(S(=O)(=O)c1ccc(F)cc1)C[C@@H](CNC(=O)C1CC(F)(F)C1)O2)C(F)(F)F] | (S)-1,1,1-trifluoro-2-methylpropan-2-yl (2-((3,3-difluorocyclobutanecarboxamido)methyl)-4-((4-fluorophenyl)sulfonyl)-3,4-dihydro-2H-benzo[b][1,4]oxazin-6-yl)carbamate | 610 (M + H)+ |

TABLE 12-continued

| Ex. No. | Structure | Name | Observed m/z |
|---|---|---|---|
| 32N | 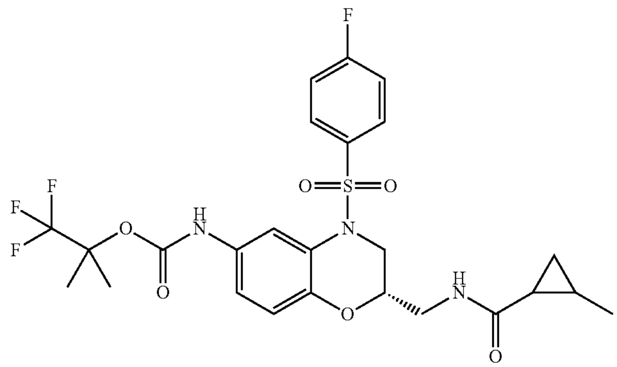 [SMILES: CC1CC1C(=O)NC[C@H]1CN(S(=O)(=O)c2ccc(F)cc2)c2cc(NC(=O)OC(C)(C)C(F)(F)F)ccc2O1] | 1,1,1-trifluoro-2-methylpropan-2-yl ((2S)-4-((4-fluorophenyl)sulfonyl)-2-((2-methylcyclopropanecarboxamido)methyl)-3,4-dihydro-2H-benzo[b][1,4]oxazin-6-yl)carbamate | 574 (M + H)+ |
| 32o | 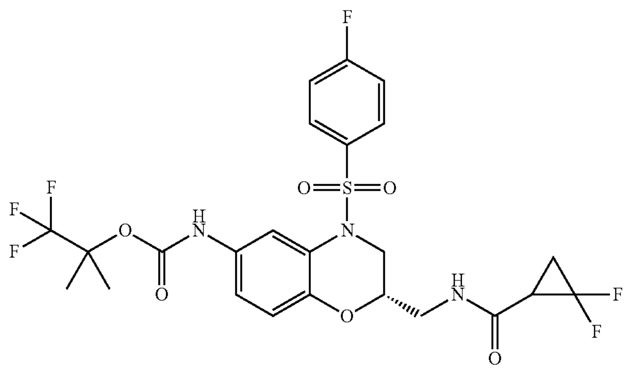 [SMILES: CC(C)(OC(=O)Nc1ccc2c(c1)N(S(=O)(=O)c1ccc(F)cc1)C[C@H](CNC(=O)C1CC1(F)F)O2)C(F)(F)F] | 1,1,1-trifluoro-2-methylpropan-2-yl ((2S)-2-((2,2-difluorocyclopropanecarboxamido)methyl)-4-((4-fluorophenyl)sulfonyl)-3,4-dihydro-2H-benzo[b][1,4]oxazin-6-yl)carbamate | 596 (M + H)+ |
| 32P | 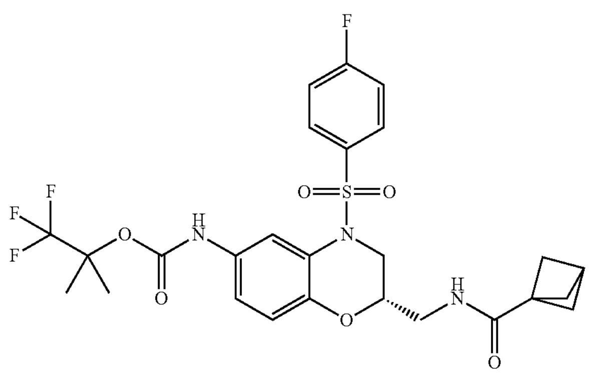 [SMILES: CC(C)(OC(=O)Nc1ccc2c(c1)N(S(=O)(=O)c1ccc(F)cc1)C[C@H](CNC(=O)C13CC(C1)C3)O2)C(F)(F)F] | (S)-1,1,1-trifluoro-2-methylpropan-2-yl (2-((bicyclo[1.1.1]pentane-1-carboxamido)methyl)-4-((4-fluorophenyl)sulfonyl)-3,4-dihydro-2H-benzo[b][1,4]oxazin-6-yl)carbamate | 586 (M + H)+ |
| 32Q | 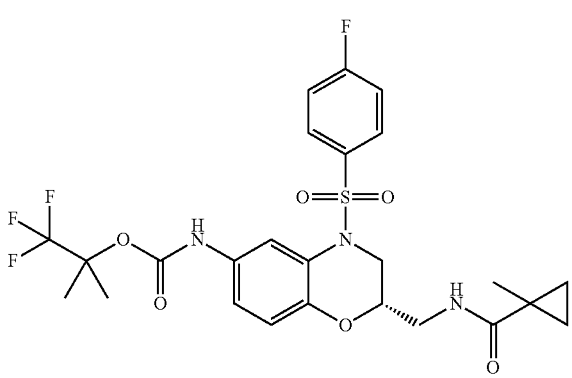 [SMILES: CC1(C(=O)NC[C@H]2CN(S(=O)(=O)c3ccc(F)cc3)c3cc(NC(=O)OC(C)(C)C(F)(F)F)ccc3O2)CC1] | (S)-1,1,1-trifluoro-2-methylpropan-2-yl (4-((4-fluorophenyl)sulfonyl)-2-((1-methylcyclopropanecarboxamido)methyl)-3,4-dihydro-2H-benzo[b][1,4]oxazin-6-yl)carbamate | 574 (M + H)+ |

TABLE 12-continued

| Ex. No. | Structure | Name | Observed m/z |
|---|---|---|---|
| 32R | 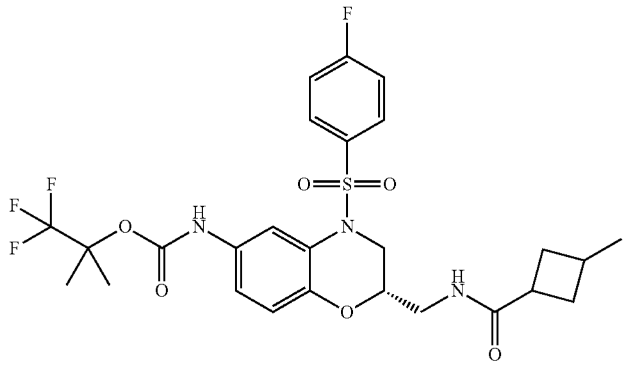 [SMILES: CC1CC(C(=O)NC[C@H]2CN(S(=O)(=O)c3ccc(F)cc3)c3cc(NC(=O)OC(C)(C)C(F)(F)F)ccc3O2)C1] | (S)-1,1,1-trifluoro-2-methylpropan-2-yl (4-((4-fluorophenyl)sulfonyl)-2-((3-methylcyclobutanecarboxamido)methyl)-3,4-dihydro-2H-benzo[b][1,4]oxazin-6-yl)carbamate | 588 (M + H)+ |
| 32S | 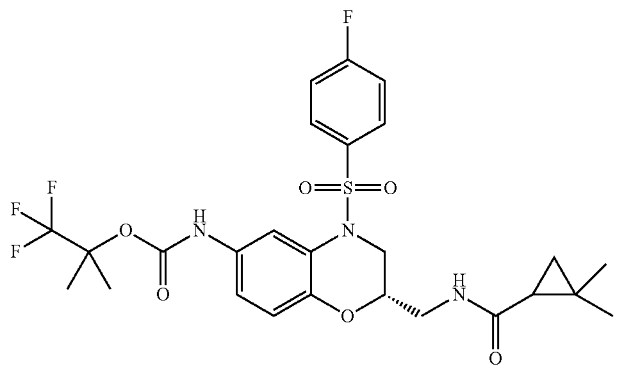 [SMILES: CC1(C)CC1C(=O)NC[C@H]1CN(S(=O)(=O)c2ccc(F)cc2)c2cc(NC(=O)OC(C)(C)C(F)(F)F)ccc2O1] | 1,1,1-trifluoro-2-methylpropan-2-yl ((2S)-2-((2,2-dimethylcyclopropanecarboxamido)methyl)-4-((4-fluorophenyl)sulfonyl)-3,4-dihydro-2H-benzo[b][1,4]oxazin-6-yl)carbamate | 588 (M + H)+ |
| 32T | 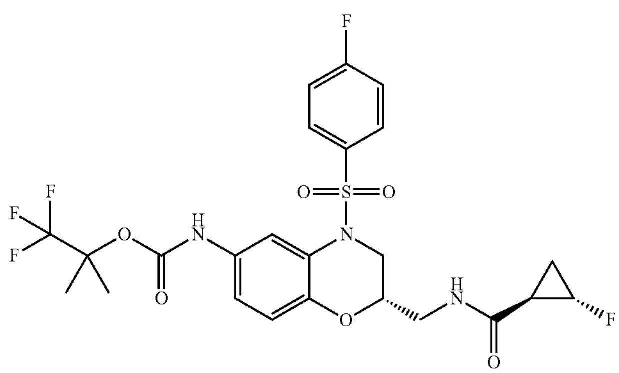 [SMILES: CC(C)(OC(=O)Nc1ccc2c(c1)N(S(=O)(=O)c1ccc(F)cc1)C[C@H](CNC(=O)[C@H]1C[C@@H]1F)O2)C(F)(F)F] | 1,1,1-trifluoro-2-methylpropan-2-yl ((S)-2-(((1R,2S)-2-fluorocyclopropanecarboxamido)methyl)-4-((4-fluorophenyl)sulfonyl)-3,4-dihydro-2H-benzo[b][1,4]oxazin-6-yl)carbamate | 578 (M + H)+ |
| 32U | 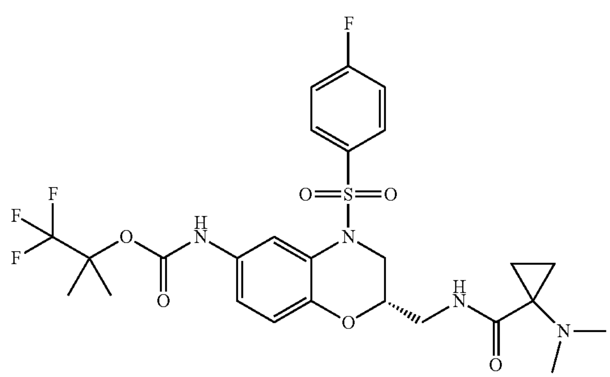 [SMILES: CN(C)C1(C(=O)NC[C@H]2CN(S(=O)(=O)c3ccc(F)cc3)c3cc(NC(=O)OC(C)(C)C(F)(F)F)ccc3O2)CC1] | (S)-1,1,1-trifluoro-2-methylpropan-2-yl (2-((1-(dimethylamino)cyclopropanecarboxamido)methyl)-4-((4-fluorophenyl)sulfonyl)-3,4-dihydro-2H-benzo[b][1,4]oxazin-6-yl)carbamate | 603 (M + H)+ |

TABLE 12-continued

| Ex. No. | Structure | Name | Observed m/z |
|---|---|---|---|
| 32V | 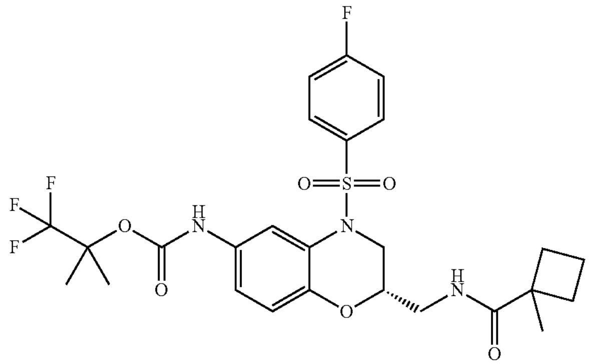 [SMILES: CC1(C(=O)NC[C@H]2CN(S(=O)(=O)c3ccc(F)cc3)c3cc(NC(=O)OC(C)(C)C(F)(F)F)ccc3O2)CCC1] | (S)-1,1,1-trifluoro-2-methylpropan-2-yl (4-((4-fluorophenyl)sulfonyl)-2-((1-methylcyclobutanecarboxamido)methyl)-3,4-dihydro-2H-benzo[b][1,4]oxazin-6-yl)carbamate | 588 (M + H)+ |

Example 33—Synthesis of (S)-1,1,1-trifluoro-2-methylpropan-2-yl (2-((2-amino-2-methylpropanamido)methyl)-4-((4-fluorophenyl)sulfonyl)-3,4-dihydro-2H-benzo[b][1,4]oxazin-6-yl)carbamate (33)

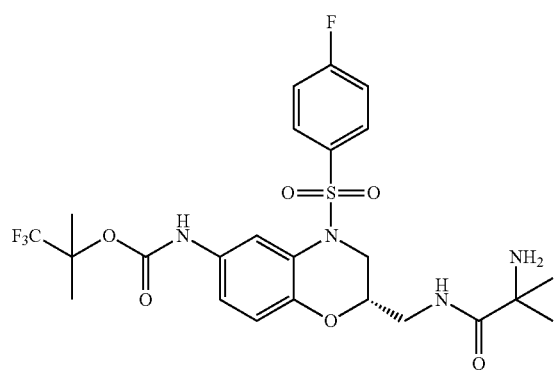 [SMILES: CC(C)(N)C(=O)NC[C@H]1CN(S(=O)(=O)c2ccc(F)cc2)c2cc(NC(=O)OC(C)(C)C(F)(F)F)ccc2O1]

To a solution of (S)-1,1,1-trifluoro-2-methylpropan-2-yl (2-(aminomethyl)-4-((4-fluorophenyl)sulfonyl)-3,4-dihydro-2H-benzo[b][1,4]oxazin-6-yl)carbamate (50 mg, 0.102 mmol), (benzotriazol-1-yloxy)tris(dimethylamino)phosphonium hexafluorophosphate (49.5 mg, 0.112 mmol), 2-amino-2-methylpropanoic acid (10.49 mg, 0.102 mmol), and THF (1017 µL) was added N,N'-diisopropylethylamine (71.1 µl, 0.407 mmol) and the mixture was stirred at room temperature. After nineteen hours, the mixture was partitioned between ethyl acetate and saturated NaHCO$_3$. The organic layer was washed with brine, dried (MgSO$_4$) and concentrated. The residue was dissolved in DMSO (1.5 mL), filtered, and purified by reverse phase chromatography to afford (S)-1,1,1-trifluoro-2-methylpropan-2-yl (2-((2-amino-2-methylpropanamido)methyl)-4-((4-fluorophenyl)sulfonyl)-3,4-dihydro-2H-benzo[b][1,4]oxazin-6-yl)carbamate. LRMS (ESI) calculated for C$_{24}$H$_{29}$F$_4$N$_4$O$_6$S (M+H)+: 577. Found: 577. $^1$H NMR (300 MHz, CDCl$_3$) δ 9.78 (1H, s), 8.48 (1H, m), 8.15 (2H, s), 7.89 (1H, s), 7.77 (2H, m), 7.44 (2H, m), 7.18 (1H, d, J=9.26 Hz), 6.76 (1H, dd, J=2.58 Hz, 6.69 Hz), 4.28 (1H, d, 13.33 Hz), 3.22 (4H, m), 1.69 (6H, s), 1.44 (6H, s).

Example 34—Additional Amides of Carboxylic Acids with Amino-Benzoxazines

The compounds in Table 13 below were prepared based on the experimental procedures described in Example 33 and elsewhere in the detailed description, and can be achieved by one of skill in the art in light of the present disclosure. The appropriate carboxylic acid was coupled with an amine prepared via procedures within Example 9.

TABLE 13

| Ex. No. | Structure | Name | Observed m/z |
|---|---|---|---|
| 34A | 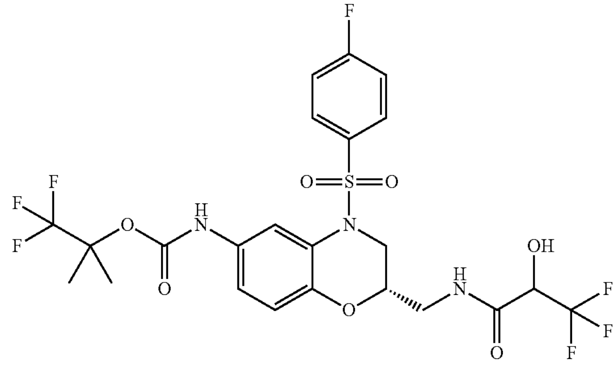 [SMILES: CC(C)(OC(=O)Nc1ccc2c(c1)N(S(=O)(=O)c1ccc(F)cc1)C[C@H](CNC(=O)C(O)C(F)(F)F)O2)C(F)(F)F] | 1,1,1-trifluoro-2-methylpropan-2-yl ((2S)-4-((4-fluorophenyl)sulfonyl)-2-((3,3,3-trifluoro-2-hydroxypropanamido)methyl)-3,4-dihydro-2H-benzo[b][1,4]oxazin-6-yl)carbamate | 618.1 (M + H)+ |

TABLE 13-continued

| Ex. No. | Structure | Name | Observed m/z |
|---|---|---|---|
| 34B | 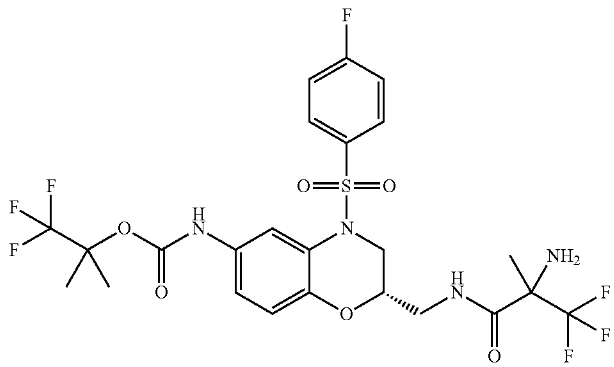 [SMILES: CC(C)(OC(=O)Nc1ccc2c(c1)N(S(=O)(=O)c1ccc(F)cc1)C[C@H](CNC(=O)C(C)(N)C(F)(F)F)O2)C(F)(F)F] | 1,1,1-trifluoro-2-methylpropan-2-yl ((2S)-2-((2-amino-3,3,3-trifluoro-2-methylpropanamido)methyl)-4-((4-fluorophenyl)sulfonyl)-3,4-dihydro-2H-benzo[b][1,4]oxazin-6-yl)carbamate | 631.2 (M + H)+ |
| 34C | 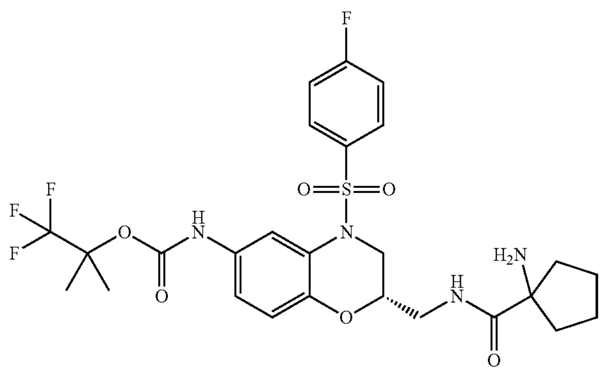 [SMILES: CC(C)(OC(=O)Nc1ccc2c(c1)N(S(=O)(=O)c1ccc(F)cc1)C[C@H](CNC(=O)C1(N)CCCC1)O2)C(F)(F)F] | (S)-1,1,1-trifluoro-2-methylpropan-2-yl (2-((1-aminocyclopentane-carboxamido)methyl)-4-((4-fluorophenyl)sulfonyl)-3,4-dihydro-2H-benzo[b][1,4]oxazin-6-yl)carbamate | 603.2 (M + H)+ |
| 34D | 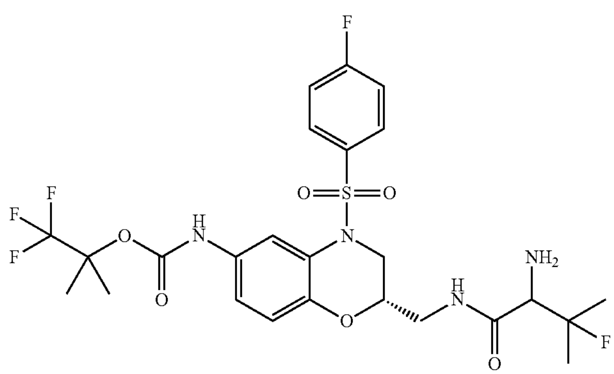 [SMILES: CC(C)(F)C(N)C(=O)NC[C@H]1CN(S(=O)(=O)c2ccc(F)cc2)c2cc(NC(=O)OC(C)(C)C(F)(F)F)ccc2O1] | 1,1,1-trifluoro-2-methylpropan-2-yl ((2S)-2-((2-amino-3-fluoro-3-methylbutanamido)methyl)-4-((4-fluorophenyl)sulfonyl)-3,4-dihydro-2H-benzo[b][1,4]oxazin-6-yl)carbamate | 609.2 (M + H)+ |
| 34E | 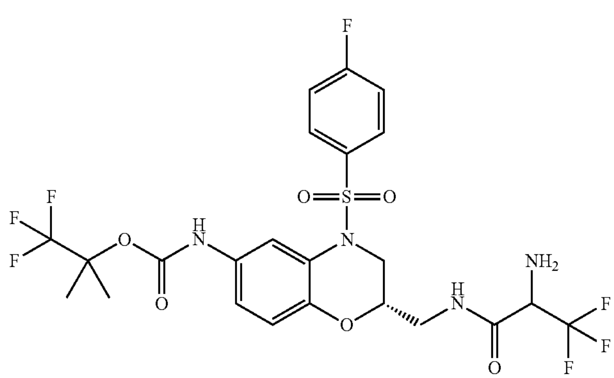 [SMILES: CC(C)(OC(=O)Nc1ccc2c(c1)N(S(=O)(=O)c1ccc(F)cc1)C[C@H](CNC(=O)C(N)C(F)(F)F)O2)C(F)(F)F] | 1,1,1-trifluoro-2-methylpropan-2-yl ((2S)-2-((2-amino-3,3,3-trifluoropropanamido)methyl)-4-((4-fluorophenyl)sulfonyl)-3,4-dihydro-2H-benzo[b][1,4]oxazin-6-yl)carbamate | 617.2 (M + H)+ |

TABLE 13-continued

| Ex. No. | Structure | Name | Observed m/z |
|---|---|---|---|
| 34F | 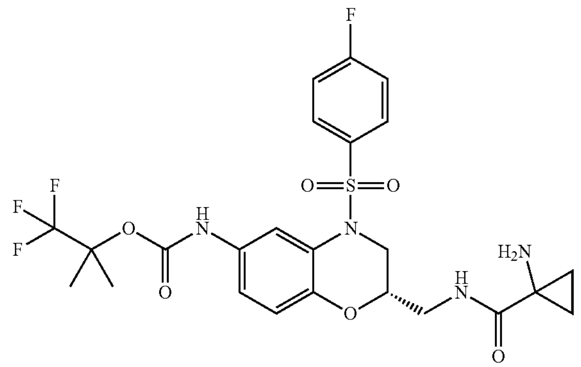 [SMILES: CC(C)(OC(=O)Nc1ccc2c(c1)N(S(=O)(=O)c1ccc(F)cc1)C[C@H](CNC(=O)C1(N)CC1)O2)C(F)(F)F] | (S)-1,1,1-trifluoro-2-methylpropan-2-yl (2-((1-aminocyclopropane-carboxamido)methyl)-4-((4-fluorophenyl)sulfonyl)-3,4-dihydro-2H-benzo[b][1,4]oxazin-6-yl)carbamate | 575.2 (M + H)+ |
| 34G | 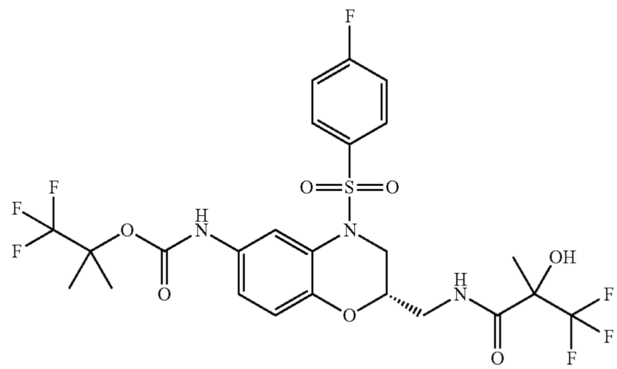 [SMILES: CC(C)(OC(=O)Nc1ccc2c(c1)N(S(=O)(=O)c1ccc(F)cc1)C[C@H](CNC(=O)C(C)(O)C(F)(F)F)O2)C(F)(F)F] | 1,1,1-trifluoro-2-methylpropan-2-yl ((2S)-4-((4-fluorophenyl)sulfonyl)-2-((3,3,3-trifluoro-2-hydroxy-2-methylpropanamido)methyl)-3,4-dihydro-2H-benzo[b][1,4]oxazin-6-yl)carbamate | 632.1 (M + H)+ |
| 34H | 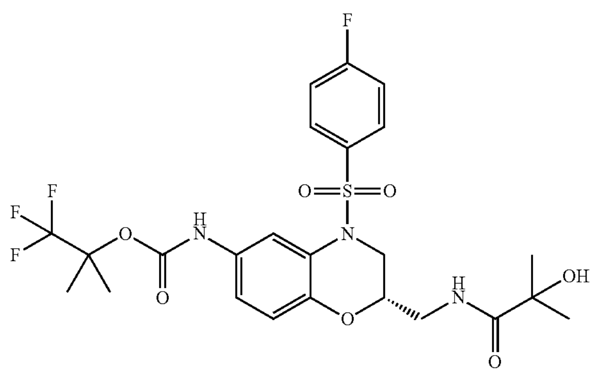 [SMILES: CC(C)(O)C(=O)NC[C@H]1CN(S(=O)(=O)c2ccc(F)cc2)c2cc(NC(=O)OC(C)(C)C(F)(F)F)ccc2O1] | (S)-1,1,1-trifluoro-2-methylpropan-2-yl (4-((4-fluorophenyl)sulfonyl)-2-((2-hydroxy-2-methylpropanamido)methyl)-3,4-dihydro-2H-benzo[b][1,4]oxazin-6-yl)carbamate | 578.1 (M + H)+ |
| 34i | 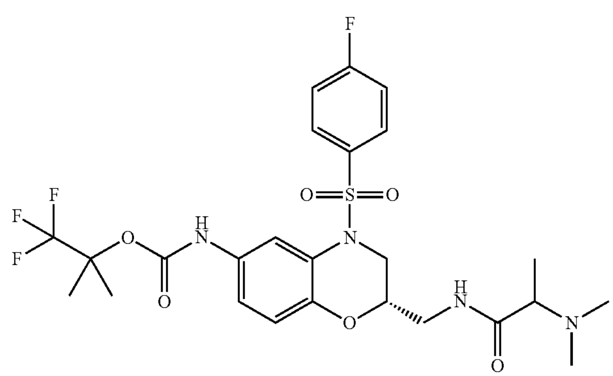 [SMILES: CC(C(=O)NC[C@H]1CN(S(=O)(=O)c2ccc(F)cc2)c2cc(NC(=O)OC(C)(C)C(F)(F)F)ccc2O1)N(C)C] | 1,1,1-trifluoro-2-methylpropan-2-yl ((2S)-2-((2-(dimethylamino)propanamido)methyl)-4-((4-fluorophenyl)sulfonyl)-3,4-dihydro-2H-benzo[b][1,4]oxazin-6-yl)carbamate | 591.2 (M + H)+ |

TABLE 13-continued

| Ex. No. | Structure | Name | Observed m/z |
|---|---|---|---|
| 34J | 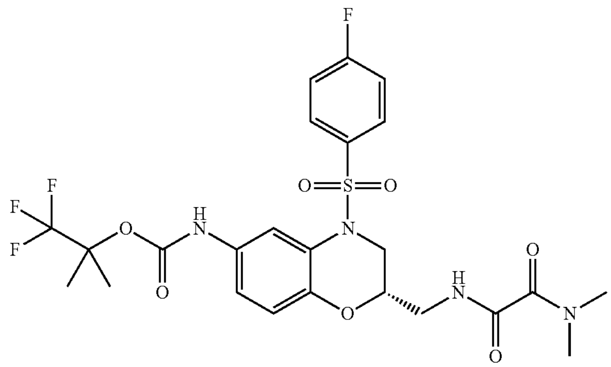 [SMILES: CN(C)C(=O)C(=O)NC[C@H]1CN(S(=O)(=O)c2ccc(F)cc2)c2cc(NC(=O)OC(C)(C)C(F)(F)F)ccc2O1] | (S)-1,1,1-trifluoro-2-methylpropan-2-yl (2-((2-(dimethylamino)-2-oxoacetamido)methyl)-4-((4-fluorophenyl)sulfonyl)-3,4-dihydro-2H-benzo[b][1,4]oxazin-6-yl)carbamate | 591.2 (M + H)+ |
| 34K | 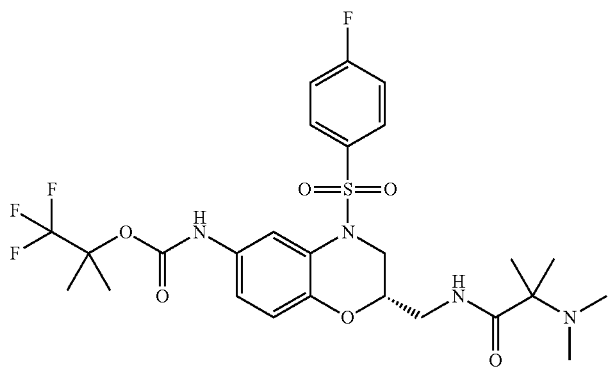 [SMILES: CN(C)C(C)(C)C(=O)NC[C@H]1CN(S(=O)(=O)c2ccc(F)cc2)c2cc(NC(=O)OC(C)(C)C(F)(F)F)ccc2O1] | (S)-1,1,1-trifluoro-2-methylpropan-2-yl (2-((2-(dimethylamino)-2-methylpropanamido)methyl)-4-((4-fluorophenyl)sulfonyl)-3,4-dihydro-2H-benzo[b][1,4]oxazin-6-yl)carbamate | 605.1 (M + H)+ |
| 34L | 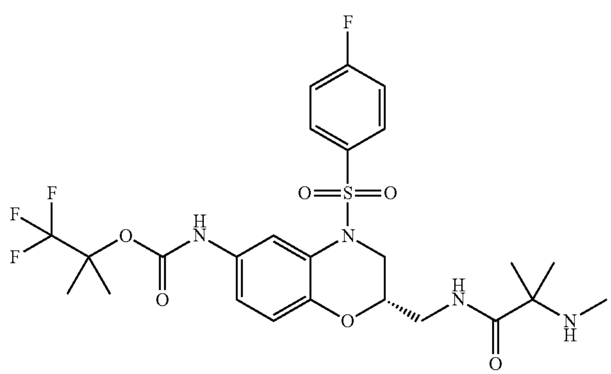 [SMILES: CNC(C)(C)C(=O)NC[C@H]1CN(S(=O)(=O)c2ccc(F)cc2)c2cc(NC(=O)OC(C)(C)C(F)(F)F)ccc2O1] | (S)-1,1,1-trifluoro-2-methylpropan-2-yl (4-((4-fluorophenyl)sulfonyl)-2-((2-methyl-2-(methylamino)propanamido)methyl)-3,4-dihydro-2H-benzo[b][1,4]oxazin-6-yl)carbamate | 591.1 (M + H)+ |
| 34M | 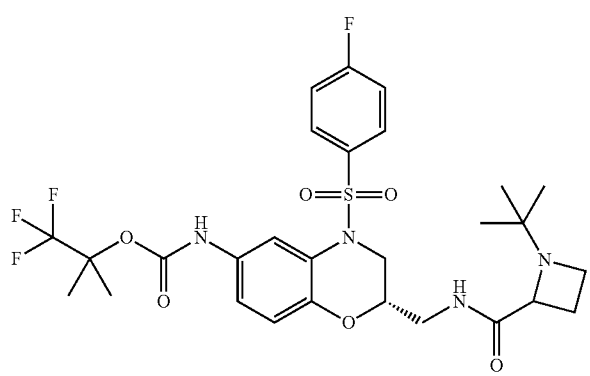 [SMILES: CC(C)(C)N1CCC1C(=O)NC[C@H]1CN(S(=O)(=O)c2ccc(F)cc2)c2cc(NC(=O)OC(C)(C)C(F)(F)F)ccc2O1] | 1,1,1-trifluoro-2-methylpropan-2-yl ((2S)-2-((1-(tert-butyl)azetidine-2-carboxamido)methyl)-4-((4-fluorophenyl)sulfonyl)-3,4-dihydro-2H-benzo[b][1,4]oxazin-6-yl)carbamate | 631 (M + H)+ |

TABLE 13-continued

| Ex. No. | Structure | Name | Observed m/z |
|---|---|---|---|
| 34N | 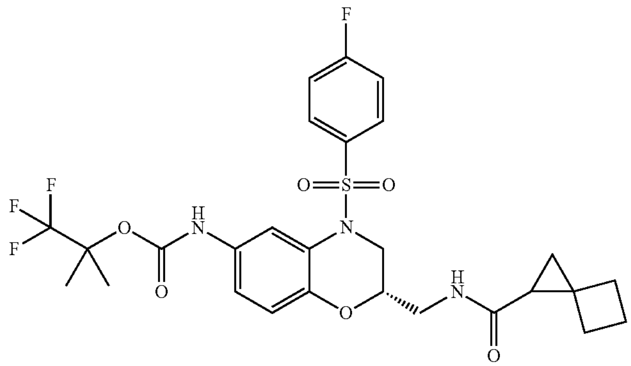 [SMILES: CC(C)(OC(=O)Nc1ccc2c(c1)N(S(=O)(=O)c1ccc(F)cc1)C[C@H](CNC(=O)C1CC13CCC3)O2)C(F)(F)F] | 1,1,1-trifluoro-2-methylpropan-2-yl ((2S)-4-((4-fluorophenyl)sulfonyl)-2-((spiro[2.3]hexane-1-carboxamido)methyl)-3,4-dihydro-2H-benzo[b][1,4]oxazin-6-yl)carbamate | 600 (M + H)+ |
| 34o | 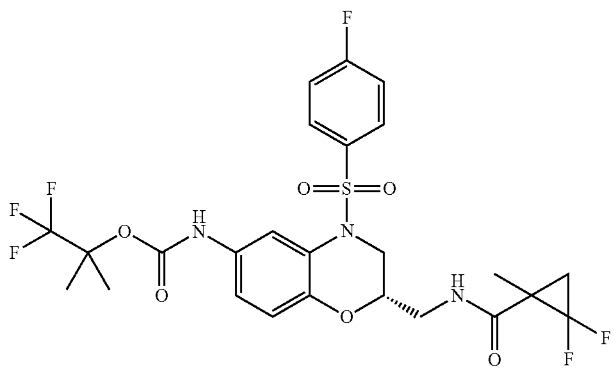 [SMILES: CC(C)(OC(=O)Nc1ccc2c(c1)N(S(=O)(=O)c1ccc(F)cc1)C[C@H](CNC(=O)C1(C)CC1(F)F)O2)C(F)(F)F] | 1,1,1-trifluoro-2-methylpropan-2-yl ((2S)-2-((2,2-difluoro-1-methylcyclopropane-carboxamido)methyl)-4-((4-fluorophenyl)sulfonyl)-3,4-dihydro-2H-benzo[b][1,4]oxazin-6-yl)carbamate | 610 (M + H)+ |
| 34P | 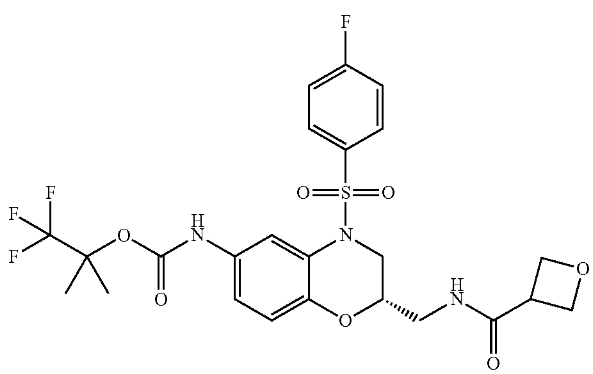 [SMILES: CC(C)(OC(=O)Nc1ccc2c(c1)N(S(=O)(=O)c1ccc(F)cc1)C[C@H](CNC(=O)C1COC1)O2)C(F)(F)F] | (S)-1,1,1-trifluoro-2-methylpropan-2-yl (4-((4-fluorophenyl)sulfonyl)-2-((oxetane-3-carboxamido)methyl)-3,4-dihydro-2H-benzo[b][1,4]oxazin-6-yl)carbamate | 576 (M + H)+ |
| 34Q | 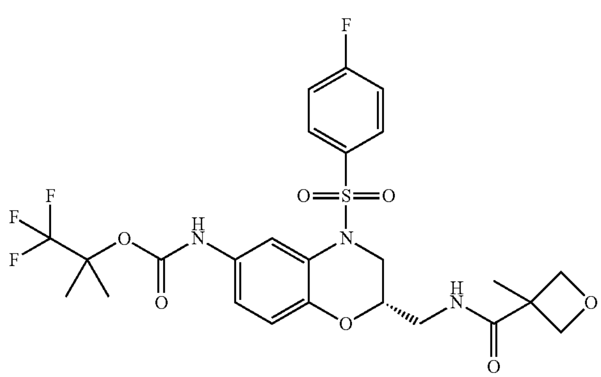 [SMILES: CC1(C(=O)NC[C@H]2CN(S(=O)(=O)c3ccc(F)cc3)c3cc(NC(=O)OC(C)(C)C(F)(F)F)ccc3O2)COC1] | (S)-1,1,1-trifluoro-2-methylpropan-2-yl (4-((4-fluorophenyl)sulfonyl)-2-((3-methyloxetane-3-carboxamido)methyl)-3,4-dihydro-2H-benzo[b][1,4]oxazin-6-yl)carbamate | 590 (M + H)+ |

TABLE 13-continued

| Ex. No. | Structure | Name | Observed m/z |
|---|---|---|---|
| 34R | 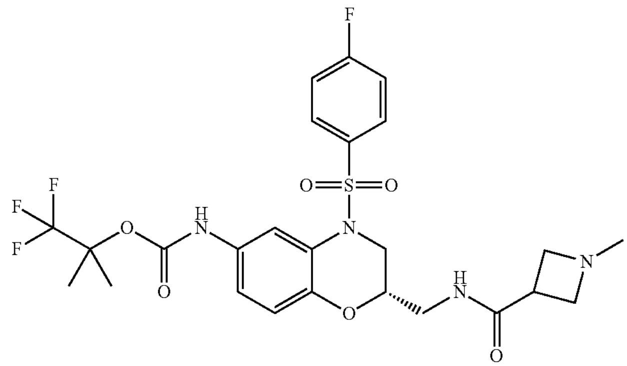 [SMILES: CN1CC(C(=O)NC[C@H]2CN(S(=O)(=O)c3ccc(F)cc3)c3cc(NC(=O)OC(C)(C)C(F)(F)F)ccc3O2)C1] | (S)-1,1,1-trifluoro-2-methylpropan-2-yl (4-((4-fluorophenyl)sulfonyl)-2-((1-methylazetidine-3-carboxamido)methyl)-3,4-dihydro-2H-benzo[b][1,4]oxazin-6-yl)carbamate | 589 (M + H)+ |
| 34S | 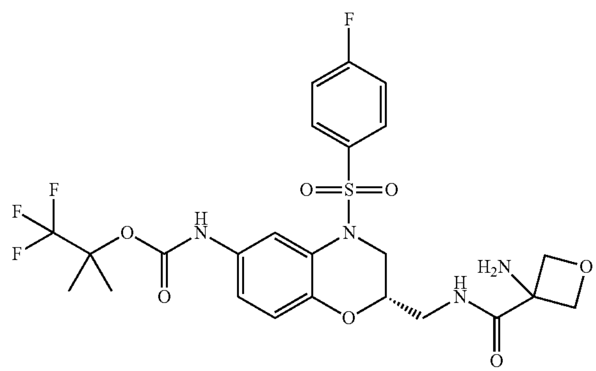 [SMILES: CC(C)(OC(=O)Nc1ccc2c(c1)N(S(=O)(=O)c1ccc(F)cc1)C[C@H](CNC(=O)C1(N)COC1)O2)C(F)(F)F] | (S)-1,1,1-trifluoro-2-methylpropan-2-yl (2-((3-aminooxetane-3-carboxamido)methyl)-4-((4-fluorophenyl)sulfonyl)-3,4-dihydro-2H-benzo[b][1,4]oxazin-6-yl)carbamate | 591 (M + H)+ |
| 34T | 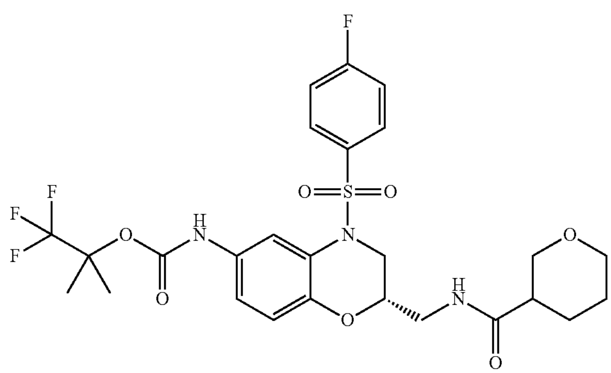 [SMILES: CC(C)(OC(=O)Nc1ccc2c(c1)N(S(=O)(=O)c1ccc(F)cc1)C[C@H](CNC(=O)C1CCCOC1)O2)C(F)(F)F] | 1,1,1-trifluoro-2-methylpropan-2-yl ((2S)-4-((4-fluorophenyl)sulfonyl)-2-((tetrahydro-2H-pyran-3-carboxamido)methyl)-3,4-dihydro-2H-benzo[b][1,4]oxazin-6-yl)carbamate | 604 (M + H)+ |
| 34U | 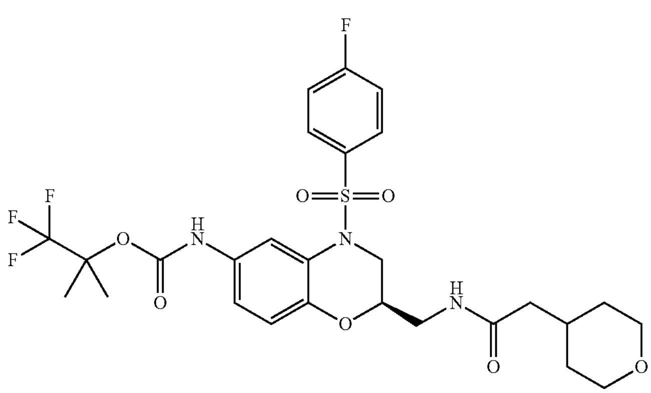 [SMILES: CC(C)(OC(=O)Nc1ccc2c(c1)N(S(=O)(=O)c1ccc(F)cc1)C[C@@H](CNC(=O)CC1CCOCC1)O2)C(F)(F)F] | (S)-1,1,1-trifluoro-2-methylpropan-2-yl (4-((4-fluorophenyl)sulfonyl)-2-((2-(tetrahydro-2H-pyran-4-yl)acetamido)methyl)-3,4-dihydro-2H-benzo[b][1,4]oxazin-6-yl)carbamate | 618 (M + H)+ |

TABLE 13-continued

| Ex. No. | Structure | Name | Observed m/z |
|---|---|---|---|
| 34V | 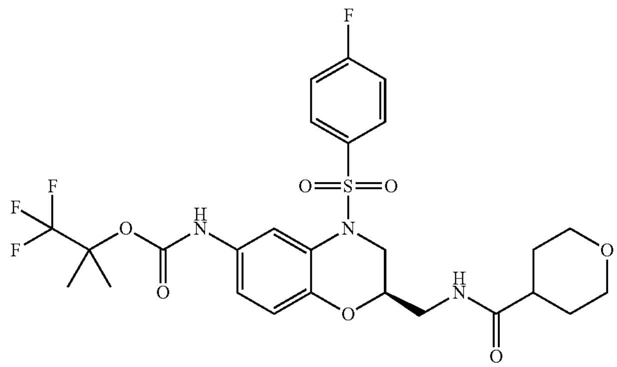 [SMILES: CC(C)(OC(=O)Nc1ccc2c(c1)N(S(=O)(=O)c1ccc(F)cc1)C[C@@H](CNC(=O)C1CCOCC1)O2)C(F)(F)F] | (S)-1,1,1-trifluoro-2-methylpropan-2-yl (4-((4-fluorophenyl)sulfonyl)-2-((tetrahydro-2H-pyran-4-carboxamido)methyl)-3,4-dihydro-2H-benzo[b][1,4]oxazin-6-yl)carbamate | 604 (M + H)+ |
| 34W | 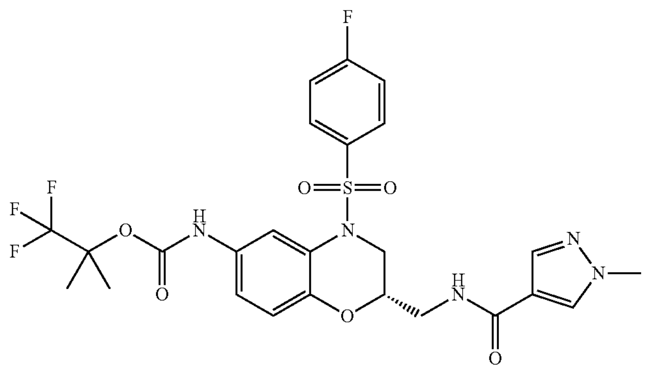 [SMILES: Cn1cc(C(=O)NC[C@H]2CN(S(=O)(=O)c3ccc(F)cc3)c3cc(NC(=O)OC(C)(C)C(F)(F)F)ccc3O2)cn1] | (S)-1,1,1-trifluoro-2-methylpropan-2-yl (4-((4-fluorophenyl)sulfonyl)-2-((1-methyl-1H-pyrazole-4-carboxamido)methyl)-3,4-dihydro-2H-benzo[b][1,4]oxazin-6-yl)carbamate | 600 (M + H)+ |
| 34X | 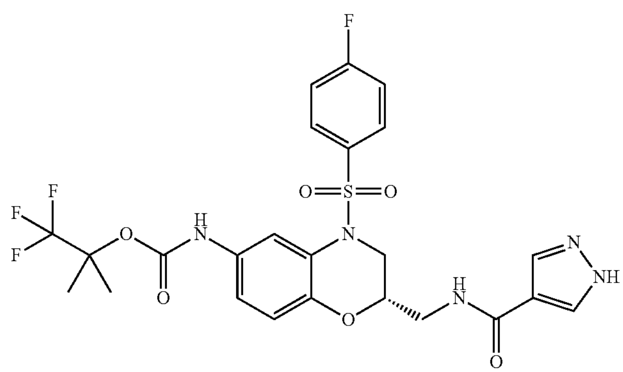 [SMILES: CC(C)(OC(=O)Nc1ccc2c(c1)N(S(=O)(=O)c1ccc(F)cc1)C[C@H](CNC(=O)c1cn[nH]c1)O2)C(F)(F)F] | (S)-1,1,1-trifluoro-2-methylpropan-2-yl (2-((1H-pyrazole-4-carboxamido)methyl)-4-((4-fluorophenyl)sulfonyl)-3,4-dihydro-2H-benzo[b][1,4]oxazin-6-yl)carbamate | 586 (M + H)+ |
| 34Y | 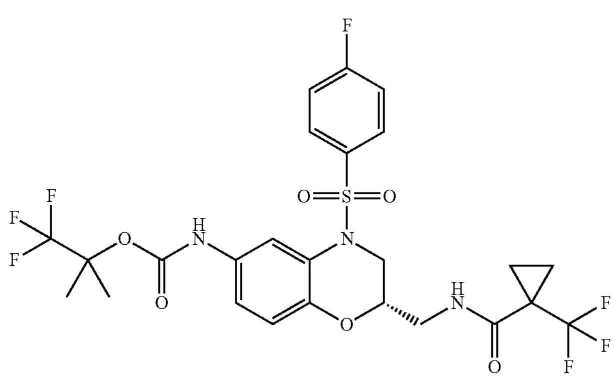 [SMILES: CC(C)(OC(=O)Nc1ccc2c(c1)N(S(=O)(=O)c1ccc(F)cc1)C[C@H](CNC(=O)C1(C(F)(F)F)CC1)O2)C(F)(F)F] | (S)-1,1,1-trifluoro-2-methylpropan-2-yl (4-((4-fluorophenyl)sulfonyl)-2-((1-(trifluoromethyl)cyclopropanecarboxamido)methyl)-3,4-dihydro-2H-benzo[b][1,4]oxazin-6-yl)carbamate | 628 (M + H)+ |

TABLE 13-continued

| Ex. No. | Structure | Name | Observed m/z |
|---|---|---|---|
| 34Z | 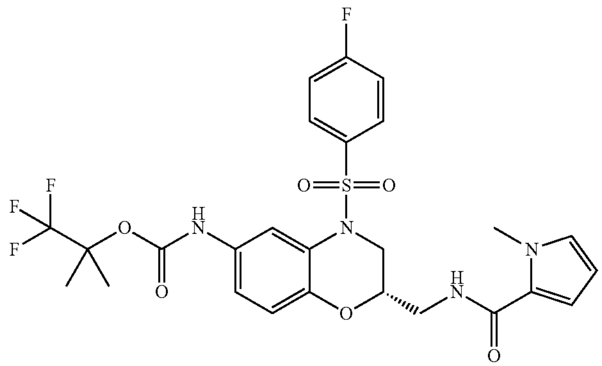 [SMILES: Cn1cccc1C(=O)NC[C@H]1CN(S(=O)(=O)c2ccc(F)cc2)c2cc(NC(=O)OC(C)(C)C(F)(F)F)ccc2O1] | (S)-1,1,1-trifluoro-2-methylpropan-2-yl (4-((4-fluorophenyl)sulfonyl)-2-((1-methyl-1H-pyrrole-2-carboxamido)methyl)-3,4-dihydro-2H-benzo[b][1,4]oxazin-6-yl)carbamate | 599 (M + H)+ |
| 34AA | 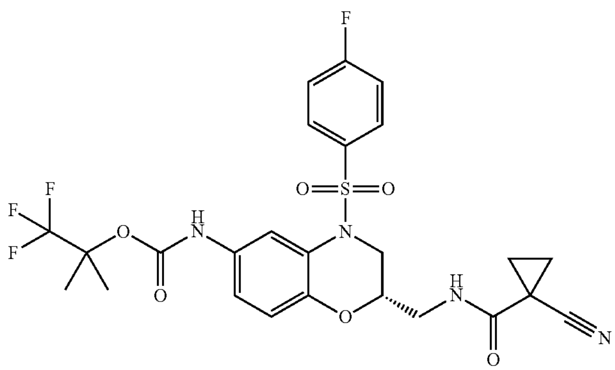 [SMILES: CC(C)(OC(=O)Nc1ccc2c(c1)N(S(=O)(=O)c1ccc(F)cc1)C[C@H](CNC(=O)C1(C#N)CC1)O2)C(F)(F)F] | (S)-1,1,1-trifluoro-2-methylpropan-2-yl (2-((1-cyanocyclopropane-carboxamido)methyl)-4-((4-fluorophenyl)sulfonyl)-3,4-dihydro-2H-benzo[b][1,4]oxazin-6-yl)carbamate | 585 (M + H)+ |
| 34AB | 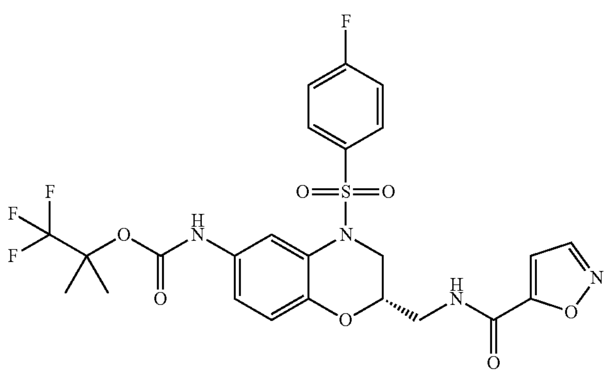 [SMILES: CC(C)(OC(=O)Nc1ccc2c(c1)N(S(=O)(=O)c1ccc(F)cc1)C[C@H](CNC(=O)c1ccno1)O2)C(F)(F)F] | (S)-5-(((4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)carbamoyl)isoxazole | 587 (M + H)+ |
| 34AC | 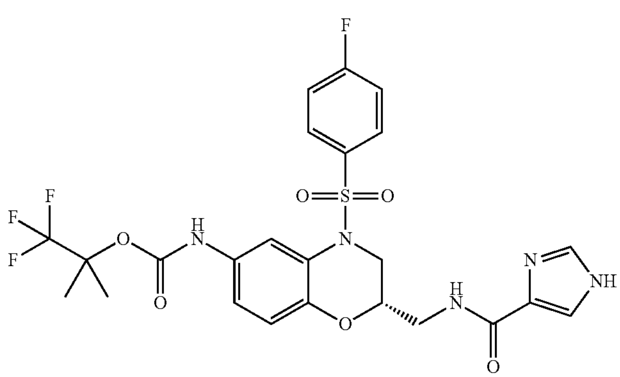 [SMILES: CC(C)(OC(=O)Nc1ccc2c(c1)N(S(=O)(=O)c1ccc(F)cc1)C[C@H](CNC(=O)c1c[nH]cn1)O2)C(F)(F)F] | (S)-4-(((4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)carbamoyl)-1H-imidazole | 586 (M + H)+ |

TABLE 13-continued

| Ex. No. | Structure | Name | Observed m/z |
|---|---|---|---|
| 34AD | 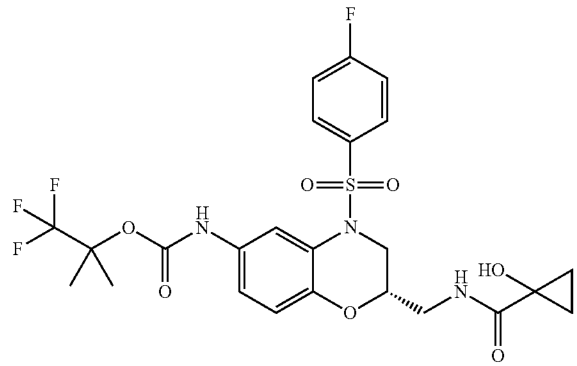 [SMILES: CC(C)(OC(=O)Nc1ccc2c(c1)N(S(=O)(=O)c1ccc(F)cc1)C[C@H](CNC(=O)C1(O)CC1)O2)C(F)(F)F] | (S)-1,1,1-trifluoro-2-methylpropan-2-yl (4-((4-fluorophenyl)sulfonyl)-2-((1-hydroxycyclopropane-carboxamido)methyl)-3,4-dihydro-2H-benzo[b][1,4]oxazin-6-yl)carbamate | 576 (M + H)+ |
| 34AE | 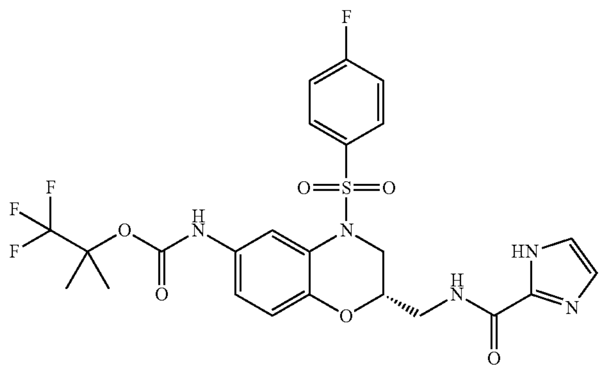 [SMILES: CC(C)(OC(=O)Nc1ccc2c(c1)N(S(=O)(=O)c1ccc(F)cc1)C[C@H](CNC(=O)c1ncc[nH]1)O2)C(F)(F)F] | (S)-2-(((4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)carbamoyl)-1H-imidazole | 586 (M + H)+ |
| 34AF | 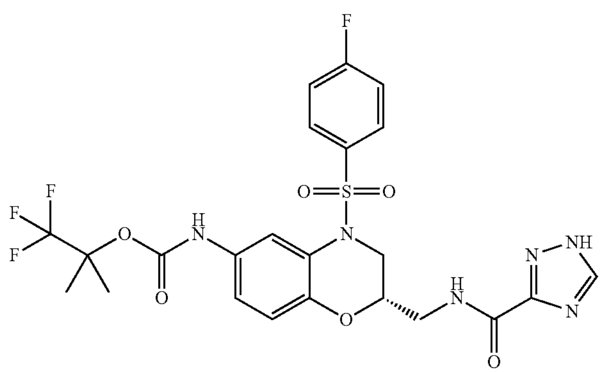 [SMILES: CC(C)(OC(=O)Nc1ccc2c(c1)N(S(=O)(=O)c1ccc(F)cc1)C[C@H](CNC(=O)c1nc[nH]n1)O2)C(F)(F)F] | (S)-3-(((4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)carbamoyl)-1H-1,2,4-triazole | 587 (M + H)+ |
| 34AG | 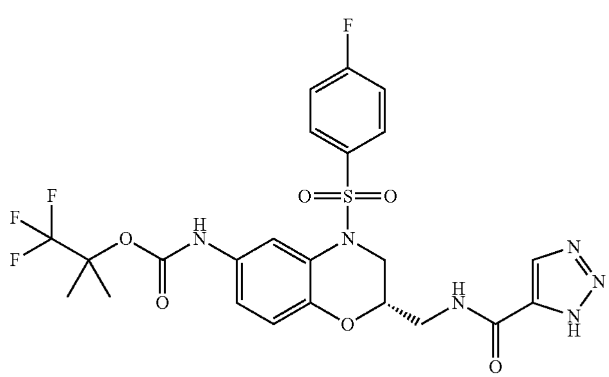 [SMILES: CC(C)(OC(=O)Nc1ccc2c(c1)N(S(=O)(=O)c1ccc(F)cc1)C[C@H](CNC(=O)c1cnn[nH]1)O2)C(F)(F)F] | (S)-5-(((4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)carbamoyl)-1H-1,2,3-triazole | 587 (M + H)+ |

TABLE 13-continued

| Ex. No. | Structure | Name | Observed m/z |
|---|---|---|---|
| 34AH | 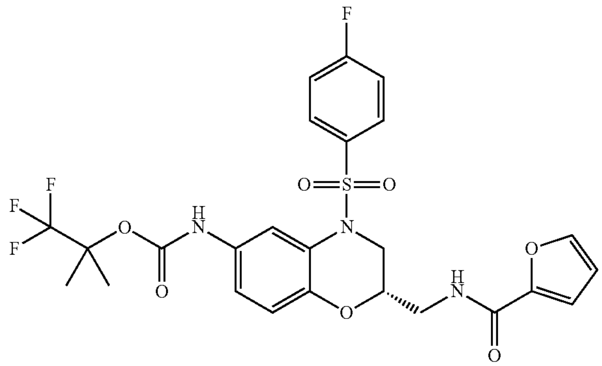 [SMILES: CC(C)(OC(=O)Nc1ccc2c(c1)N(S(=O)(=O)c1ccc(F)cc1)C[C@H](CNC(=O)c1ccco1)O2)C(F)(F)F] | (S)-1,1,1-trifluoro-2-methylpropan-2-yl (4-((4-fluorophenyl)sulfonyl)-2-((furan-2-carboxamido)methyl)-3,4-dihydro-2H-benzo[b][1,4]oxazin-6-yl)carbamate | 586 (M + H)+ |
| 34Ai | 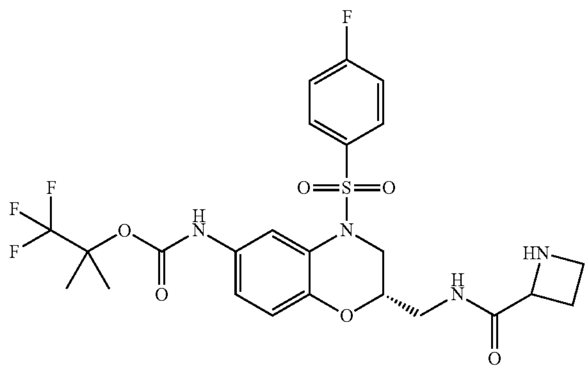 [SMILES: CC(C)(OC(=O)Nc1ccc2c(c1)N(S(=O)(=O)c1ccc(F)cc1)C[C@H](CNC(=O)C1CCN1)O2)C(F)(F)F] | 2-(((((S)-4-((4-fluorophenyl)sulfonyl)-6-(((((1,1,1-trifluoro-2-methylpropan-2-yl)oxy)carbonyl)amino)-3,4-dihydro-2H-benzo[b][1,4]oxazin-2-yl)methyl)carbamoyl)azetidine | 575 (M + H)+ |
| 34AJ | 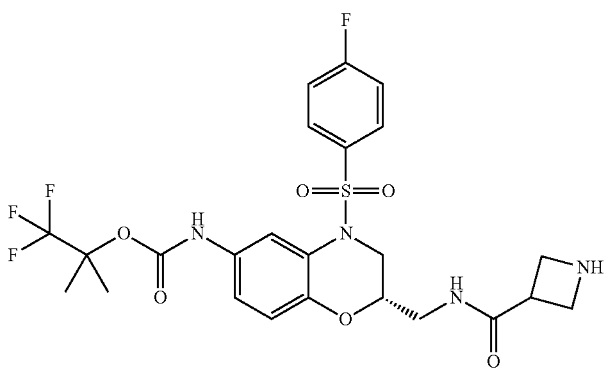 [SMILES: CC(C)(OC(=O)Nc1ccc2c(c1)N(S(=O)(=O)c1ccc(F)cc1)C[C@H](CNC(=O)C1CNC1)O2)C(F)(F)F] | (S)-3-(((4-((4-fluorophenyl)sulfonyl)-6-(((((1,1,1-trifluoro-2-methylpropan-2-yl)oxy)carbonyl)amino)-3,4-dihydro-2H-benzo[b][1,4]oxazin-2-yl)methyl)carbamoyl)azetidine | 575 (M + H)+ |
| 34AK | 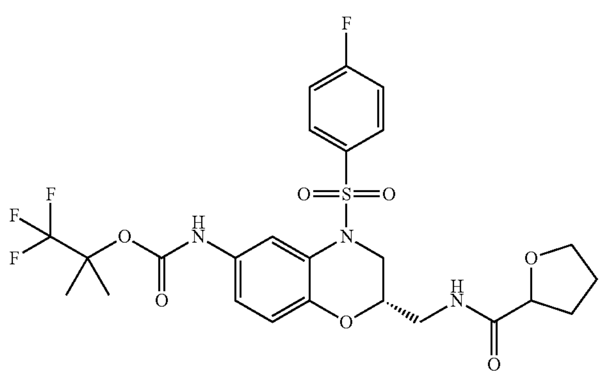 [SMILES: CC(C)(OC(=O)Nc1ccc2c(c1)N(S(=O)(=O)c1ccc(F)cc1)C[C@H](CNC(=O)C1CCCO1)O2)C(F)(F)F] | 1,1,1-trifluoro-2-methylpropan-2-yl ((2S)-4-((4-fluorophenyl)sulfonyl)-2-((tetrahydrofuran-2-carboxamido)methyl)-3,4-dihydro-2H-benzo[b][1,4]oxazin-6-yl)carbamate | 590 (M + H)+ |

TABLE 13-continued

| Ex. No. | Structure | Name | Observed m/z |
|---|---|---|---|
| 34AL | 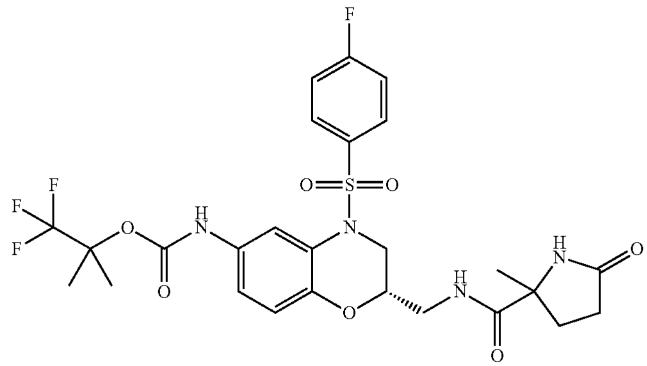 [SMILES: CC1(C(=O)NC[C@H]2CN(S(=O)(=O)c3ccc(F)cc3)c3cc(NC(=O)OC(C)(C)C(F)(F)F)ccc3O2)CCC(=O)N1] | 1,1,1-trifluoro-2-methylpropan-2-yl ((2S)-4-((4-fluorophenyl)sulfonyl)-2-((2-methyl-5-oxopyrrolidine-2-carboxamido)methyl)-3,4-dihydro-2H-benzo[b][1,4]oxazin-6-yl)carbamate | 617 (M + H)+ |
| 34AM | 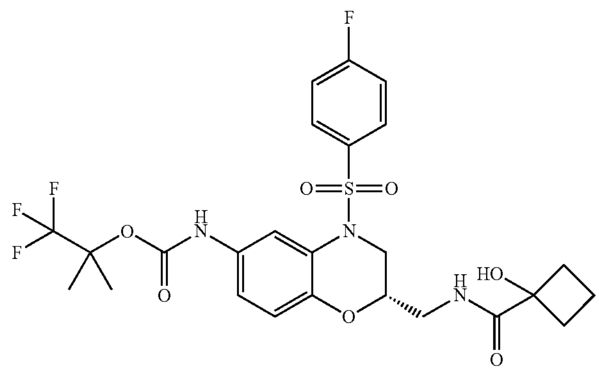 [SMILES: CC(C)(OC(=O)Nc1ccc2c(c1)N(S(=O)(=O)c1ccc(F)cc1)C[C@H](CNC(=O)C1(O)CCC1)O2)C(F)(F)F] | (S)-1,1,1-trifluoro-2-methylpropan-2-yl (4-((4-fluorophenyl)sulfonyl)-2-((1-hydroxycyclobutane-carboxamido)methyl)-3,4-dihydro-2H-benzo[b][1,4]oxazin-6-yl)carbamate | 590 (M + H)+ |
| 34AN | 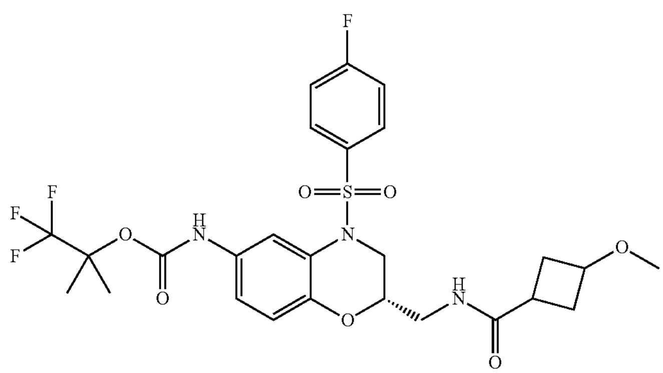 [SMILES: COC1CC(C(=O)NC[C@H]2CN(S(=O)(=O)c3ccc(F)cc3)c3cc(NC(=O)OC(C)(C)C(F)(F)F)ccc3O2)C1] | (S)-1,1,1-trifluoro-2-methylpropan-2-yl (4-((4-fluorophenyl)sulfonyl)-2-((3-methoxycyclobutane-carboxamido)methyl)-3,4-dihydro-2H-benzo[b][1,4]oxazin-6-yl)carbamate | 604 (M + H)+ |
| 34Ao | 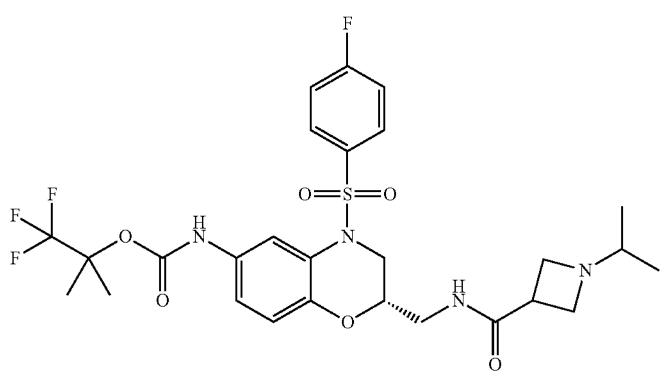 [SMILES: CC(C)N1CC(C(=O)NC[C@H]2CN(S(=O)(=O)c3ccc(F)cc3)c3cc(NC(=O)OC(C)(C)C(F)(F)F)ccc3O2)C1] | (S)-1,1,1-trifluoro-2-methylpropan-2-yl (4-((4-fluorophenyl)sulfonyl)-2-((1-isopropylazetidine-3-carboxamido)methyl)-3,4-dihydro-2H-benzo[b][1,4]oxazin-6-yl)carbamate | 617 (M + H)+ |

TABLE 13-continued

| Ex. No. | Structure | Name | Observed m/z |
|---|---|---|---|
| 34AP | 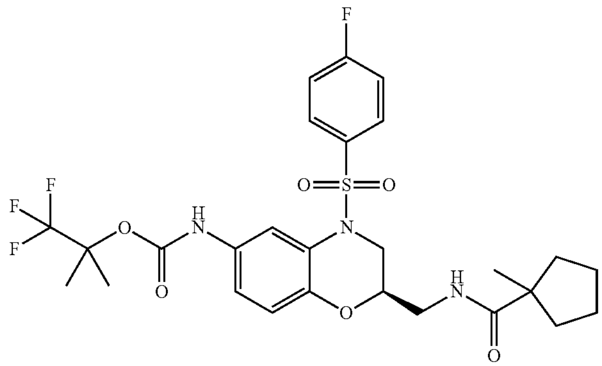 [SMILES: CC1(C(=O)NC[C@@H]2CN(S(=O)(=O)c3ccc(F)cc3)c3cc(NC(=O)OC(C)(C)C(F)(F)F)ccc3O2)CCCC1] | (S)-1,1,1-trifluoro-2-methylpropan-2-yl (4-((4-fluorophenyl)sulfonyl)-2-((1-methylcyclopentane-carboxamido)methyl)-3,4-dihydro-2H-benzo[b][1,4]oxazin-6-yl)carbamate | 602 (M + H)+ |
| 34AQ | 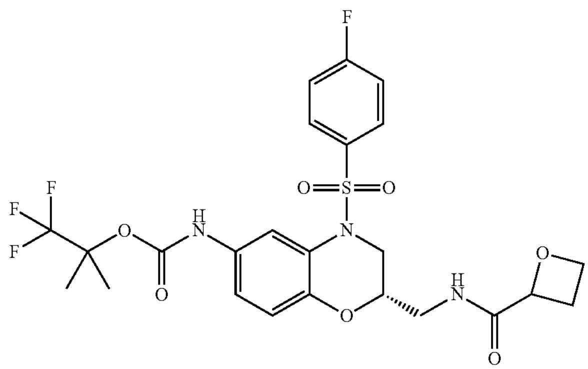 [SMILES: CC(C)(OC(=O)Nc1ccc2c(c1)N(S(=O)(=O)c1ccc(F)cc1)C[C@H](CNC(=O)C1CCO1)O2)C(F)(F)F] | 1,1,1-trifluoro-2-methylpropan-2-yl ((2S)-4-((4-fluorophenyl)sulfonyl)-2-((oxetane-2-carboxamido)methyl)-3,4-dihydro-2H-benzo[b][1,4]oxazin-6-yl)carbamate | 576 (M + H)+ |
| 34AR | 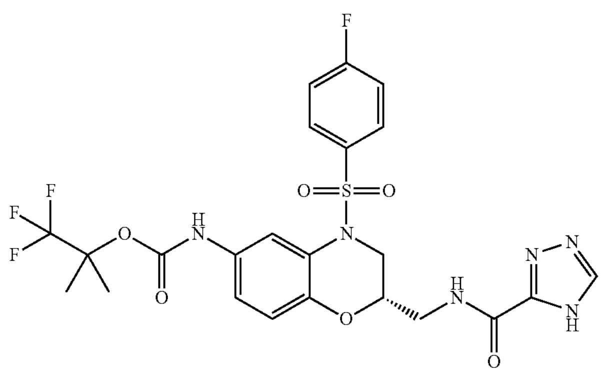 [SMILES: CC(C)(OC(=O)Nc1ccc2c(c1)N(S(=O)(=O)c1ccc(F)cc1)C[C@H](CNC(=O)c1nnc[nH]1)O2)C(F)(F)F] | (S)-1,1,1-trifluoro-2-methylpropan-2-yl (2-((4H-1,2,4-triazole-3-carboxamido)methyl)-4-((4-fluorophenyl)sulfonyl)-3,4-dihydro-2H-benzo[b][1,4]oxazin-6-yl)carbamate | 587 (M + H)+ |
| 34AS | 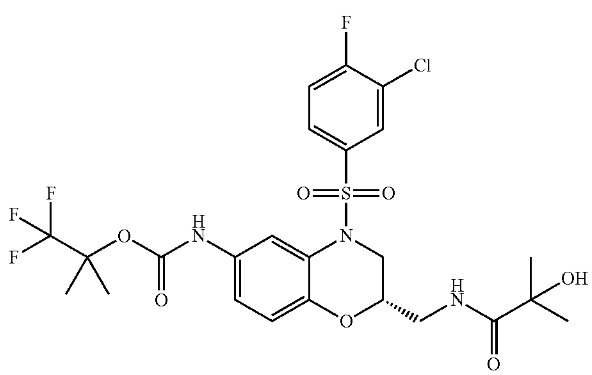 [SMILES: CC(C)(O)C(=O)NC[C@H]1CN(S(=O)(=O)c2ccc(F)c(Cl)c2)c2cc(NC(=O)OC(C)(C)C(F)(F)F)ccc2O1] | (S)-1,1,1-trifluoro-2-methylpropan-2-yl (4-((3-chloro-4-fluorophenyl)sulfonyl)-2-((2-hydroxy-2-methylpropanamido)methyl)-3,4-dihydro-2H-benzo[b][1,4]oxazin-6-yl)carbamate | 612.2 (M + H)+ |

TABLE 13-continued

| Ex. No. | Structure | Name | Observed m/z |
|---|---|---|---|
| 34AT | 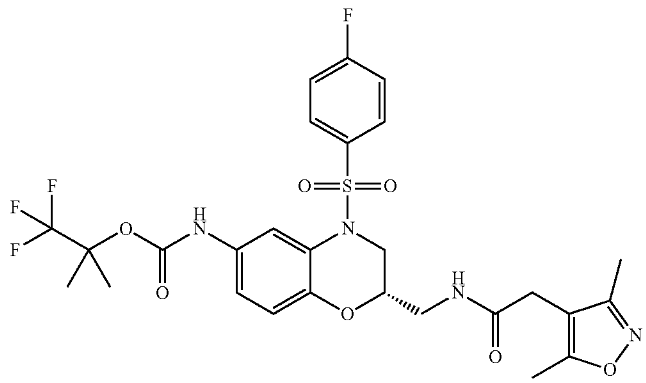 [SMILES: Cc1noc(C)c1CC(=O)NC[C@H]1CN(S(=O)(=O)c2ccc(F)cc2)c2cc(NC(=O)OC(C)(C)C(F)(F)F)ccc2O1] | (S)-1,1,1-trifluoro-2-methylpropan-2-yl (2-((2-(3,5-dimethylisoxazol-4-yl)acetamido)methyl)-4-((4-fluorophenyl)sulfonyl)-3,4-dihydro-2H-benzo[b][1,4]oxazin-6-yl)carbamate | 629 (M + H)+ |
| 34AU | 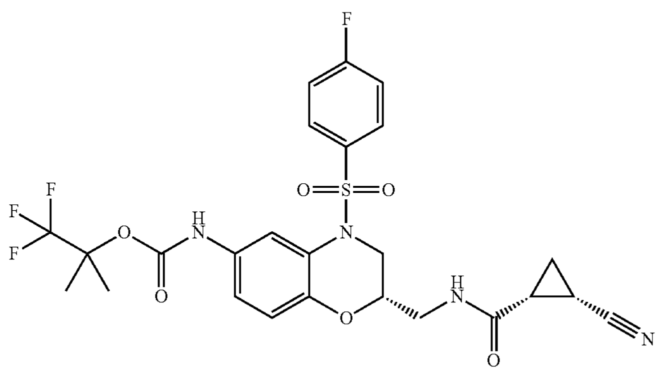 [SMILES: CC(C)(OC(=O)Nc1ccc2c(c1)N(S(=O)(=O)c1ccc(F)cc1)C[C@H](CNC(=O)[C@@H]1C[C@@H]1C#N)O2)C(F)(F)F] | 1,1,1-trifluoro-2-methylpropan-2-yl ((S)-2-(((1R,2S)-2-cyanocyclopropane-carboxamido)methyl)-4-((4-fluorophenyl)sulfonyl)-3,4-dihydro-2H-benzo[b][1,4]oxazin-6-yl)carbamate | 585 (M + H)+ |
| 34AV | 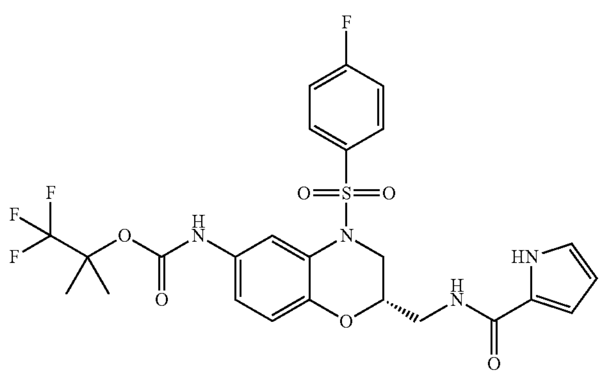 | (S)-1,1,1-trifluoro-2-methylpropan-2-yl (2-((1H-pyrrole-2-carboxamido)methyl)-4-((4-fluorophenyl)sulfonyl)-3,4-dihydro-2H-benzo[b][1,4]oxazin-6-yl)carbamate | 585 (M + H)+ |
| 34AW | 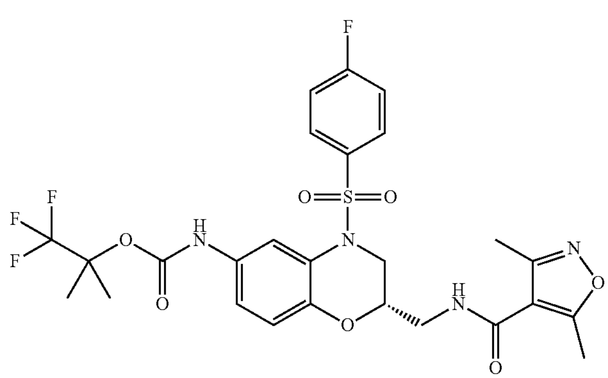 [SMILES: Cc1noc(C)c1C(=O)NC[C@H]1CN(S(=O)(=O)c2ccc(F)cc2)c2cc(NC(=O)OC(C)(C)C(F)(F)F)ccc2O1] | (S)-1,1,1-trifluoro-2-methylpropan-2-yl (2-((3,5-dimethylisoxazole-4-carboxamido)methyl)-4-((4-fluorophenyl)sulfonyl)-3,4-dihydro-2H-benzo[b][1,4]oxazin-6-yl)carbamate | 615 (M + H)+ |

TABLE 13-continued

| Ex. No. | Structure | Name | Observed m/z |
|---|---|---|---|
| 34AX | 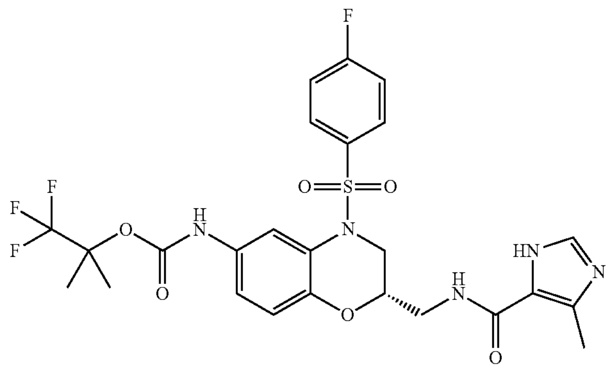 [SMILES: Cc1nc[nH]c1C(=O)NC[C@H]1CN(S(=O)(=O)c2ccc(F)cc2)c2cc(NC(=O)OC(C)(C)C(F)(F)F)ccc2O1] | (S)-1,1,1-trifluoro-2-methylpropan-2-yl (4-((4-fluorophenyl)sulfonyl)-2-((4-methyl-1H-imidazole-5-carboxamido)methyl)-3,4-dihydro-2H-benzo[b][1,4]oxazin-6-yl)carbamate | 600 (M + H)+ |
| 34AY | 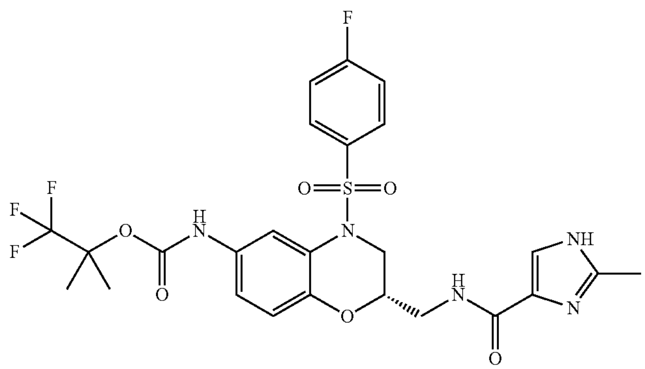 [SMILES: Cc1nc(C(=O)NC[C@H]2CN(S(=O)(=O)c3ccc(F)cc3)c3cc(NC(=O)OC(C)(C)C(F)(F)F)ccc3O2)c[nH]1] | (S)-1,1,1-trifluoro-2-methylpropan-2-yl (4-((4-fluorophenyl)sulfonyl)-2-((2-methyl-1H-imidazole-4-carboxamido)methyl)-3,4-dihydro-2H-benzo[b][1,4]oxazin-6-yl)carbamate | 600 (M + H)+ |
| 34AZ | 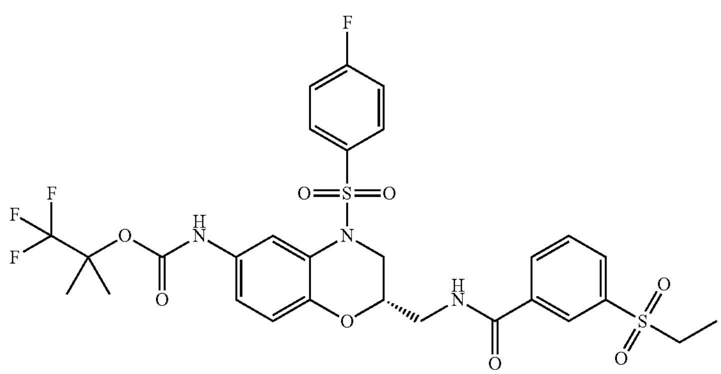 [SMILES: CCS(=O)(=O)c1cccc(C(=O)NC[C@H]2CN(S(=O)(=O)c3ccc(F)cc3)c3cc(NC(=O)OC(C)(C)C(F)(F)F)ccc3O2)c1] | (S)-1,1,1-trifluoro-2-methylpropan-2-yl (2-((3-(ethylsulfonyl)benzamido)methyl)-4-((4-fluorophenyl)sulfonyl)-3,4-dihydro-2H-benzo[b][1,4]oxazin-6-yl)carbamate | 688 (M + H)+ |
| 34BA | 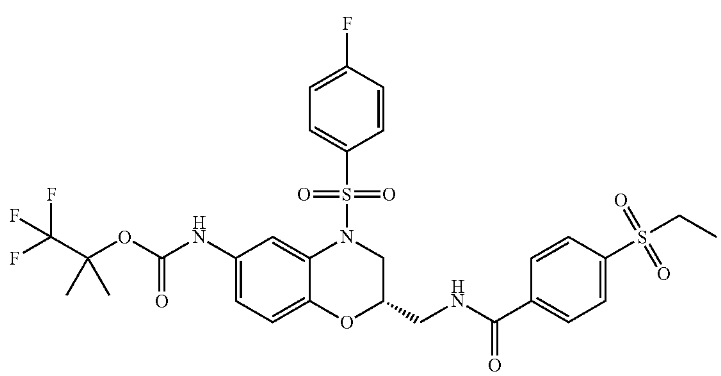 [SMILES: CCS(=O)(=O)c1ccc(C(=O)NC[C@H]2CN(S(=O)(=O)c3ccc(F)cc3)c3cc(NC(=O)OC(C)(C)C(F)(F)F)ccc3O2)cc1] | (S)-1,1,1-trifluoro-2-methylpropan-2-yl (2-((4-(ethylsulfonyl)benzamido)methyl)-4-((4-fluorophenyl)sulfonyl)-3,4-dihydro-2H-benzo[b][1,4]oxazin-6-yl)carbamate | 688 (M + H)+ |

TABLE 13-continued

| Ex. No. | Structure | Name | Observed m/z |
|---|---|---|---|
| 34BB | 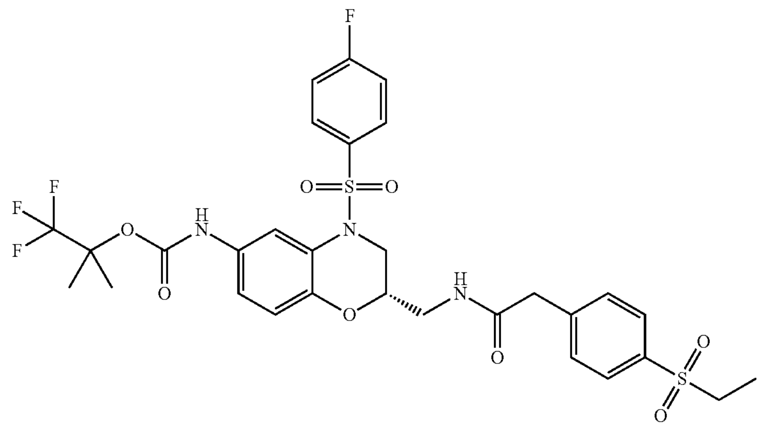 [SMILES: CCS(=O)(=O)c1ccc(CC(=O)NC[C@H]2CN(S(=O)(=O)c3ccc(F)cc3)c3cc(NC(=O)OC(C)(C)C(F)(F)F)ccc3O2)cc1] | (S)-1,1,1-trifluoro-2-methylpropan-2-yl (2-((2-(4-(ethylsulfonyl)phenyl)acetamido)methyl)-4-((4-fluorophenyl)sulfonyl)-3,4-dihydro-2H-benzo[b][1,4]oxazin-6-yl)carbamate | 702 (M + H)+ |
| 34BC | 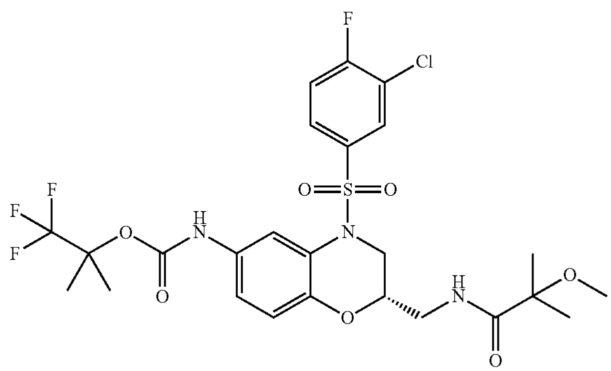 [SMILES: COC(C)(C)C(=O)NC[C@H]1CN(S(=O)(=O)c2ccc(F)c(Cl)c2)c2cc(NC(=O)OC(C)(C)C(F)(F)F)ccc2O1] | (S)-1,1,1-trifluoro-2-methylpropan-2-yl (4-((3-chloro-4-fluorophenyl)sulfonyl)-2-((2-methoxy-2-methylpropanamido)methyl)-3,4-dihydro-2H-benzo[b][1,4]oxazin-6-yl)carbamate | 626 (M + H)+ |
| 34BD | 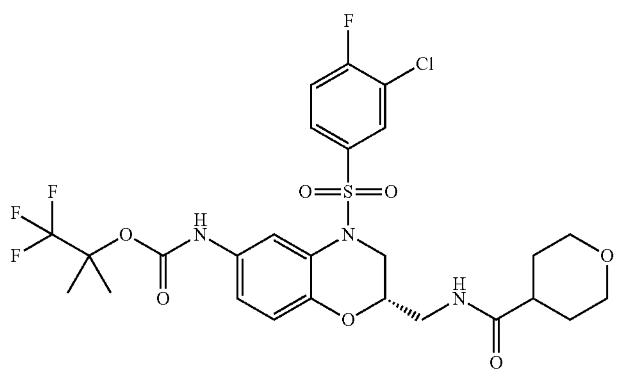 [SMILES: CC(C)(OC(=O)Nc1ccc2c(c1)N(S(=O)(=O)c1ccc(F)c(Cl)c1)C[C@H](CNC(=O)C1CCOCC1)O2)C(F)(F)F] | (S)-1,1,1-trifluoro-2-methylpropan-2-yl (4-((3-chloro-4-fluorophenyl)sulfonyl)-2-((tetrahydro-2H-pyran-4-carboxamido)methyl)-3,4-dihydro-2H-benzo[b][1,4]oxazin-6-yl)carbamate | 638.1 (M + H)+ |
| 34BE | 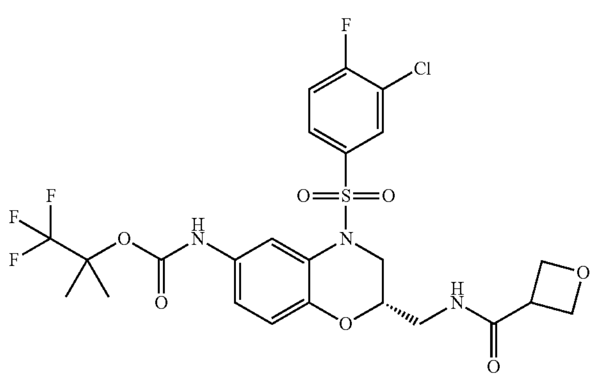 [SMILES: CC(C)(OC(=O)Nc1ccc2c(c1)N(S(=O)(=O)c1ccc(F)c(Cl)c1)C[C@H](CNC(=O)C1COC1)O2)C(F)(F)F] | (S)-1,1,1-trifluoro-2-methylpropan-2-yl (4-((3-chloro-4-fluorophenyl)sulfonyl)-2-((oxetane-3-carboxamido)methyl)-3,4-dihydro-2H-benzo[b][1,4]oxazin-6-yl)carbamate | 632.0 (M + Na)+ |

TABLE 13-continued

| Ex. No. | Structure | Name | Observed m/z |
|---|---|---|---|
| 34BF | 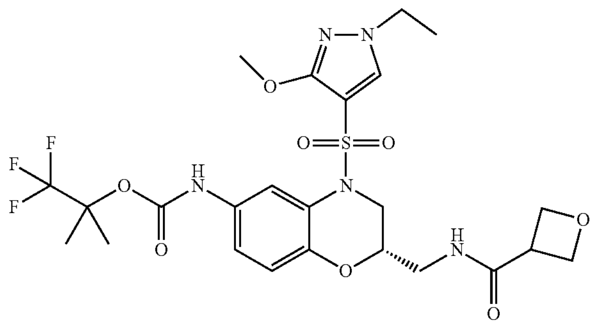 [SMILES: CCn1cc(S(=O)(=O)N2C[C@H](CNC(=O)C3COC3)Oc3ccc(NC(=O)OC(C)(C)C(F)(F)F)cc32)c(OC)n1] | (S)-1,1,1-trifluoro-2-methylpropan-2-yl (4-((1-ethyl-3-methoxy-1H-pyrazol-4-yl)sulfonyl)-2-((oxetane-3-carboxamido)methyl)-3,4-dihydro-2H-benzo[b][1,4]oxazin-6-yl)carbamate | 628.1 (M + Na)+ |
| 34BG | 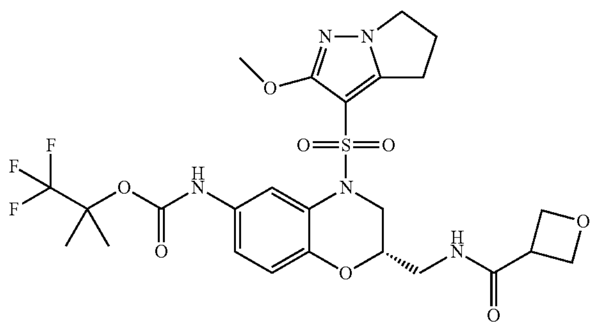 [SMILES: COc1nn2c(c1S(=O)(=O)N1C[C@H](CNC(=O)C3COC3)Oc3ccc(NC(=O)OC(C)(C)C(F)(F)F)cc31)CCC2] | (S)-1,1,1-trifluoro-2-methylpropan-2-yl (4-((2-methoxy-5,6-dihydro-4H-pyrrolo[1,2-b]pyrazol-3-yl)sulfonyl)-2-((oxetane-3-carboxamido)methyl)-3,4-dihydro-2H-benzo[b][1,4]oxazin-6-yl)carbamate | 618.2 (M + H)+ |
| 34BH | 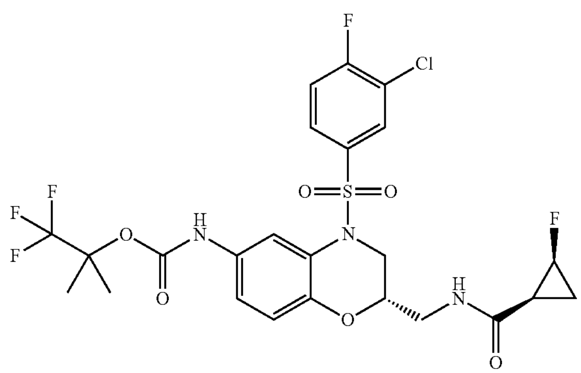 [SMILES: CC(C)(OC(=O)Nc1ccc2c(c1)N(S(=O)(=O)c1ccc(F)c(Cl)c1)C[C@H](CNC(=O)[C@@H]1C[C@@H]1F)O2)C(F)(F)F] | 1,1,1-trifluoro-2-methylpropan-2-yl ((S)-4-((3-chloro-4-fluorophenyl)sulfonyl)-2-((((1S,2S)-2-fluorocyclopropanecarboxamido)methyl)-3,4-dihydro-2H-benzo[b][1,4]oxazin-6-yl)carbamate | 612 (M + H)+ |
| 34Bi | 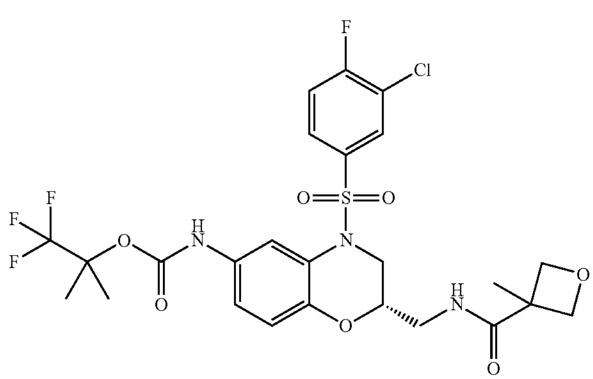 [SMILES: CC1(C(=O)NC[C@H]2CN(S(=O)(=O)c3ccc(F)c(Cl)c3)c3cc(NC(=O)OC(C)(C)C(F)(F)F)ccc3O2)COC1] | (S)-1,1,1-trifluoro-2-methylpropan-2-yl (4-((3-chloro-4-fluorophenyl)sulfonyl)-2-((3-methyloxetane-3-carboxamido)methyl)-3,4-dihydro-2H-benzo[b][1,4]oxazin-6-yl)carbamate | 624 (M + H)+ |

TABLE 13-continued

| Ex. No. | Structure | Name | Observed m/z |
|---|---|---|---|
| 34BJ | 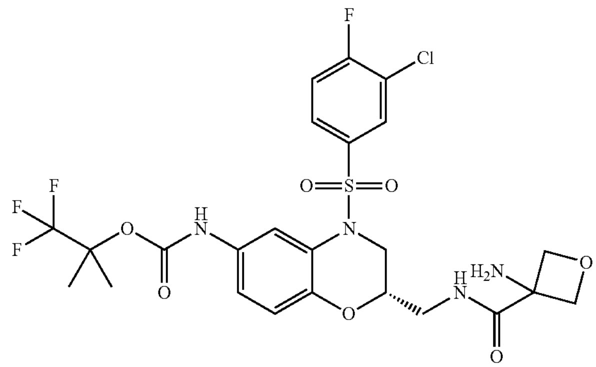 [SMILES: CC(C)(OC(=O)Nc1ccc2c(c1)N(S(=O)(=O)c1ccc(F)c(Cl)c1)C[C@H](CNC(=O)C1(N)COC1)O2)C(F)(F)F] | (S)-1,1,1-trifluoro-2-methylpropan-2-yl (2-((3-aminooxetane-3-carboxamido)methyl)-4-((3-chloro-4-fluorophenyl)sulfonyl)-3,4-dihydro-2H-benzo[b][1,4]oxazin-6-yl)carbamate | 625 (M + H)+ |
| 34BK | 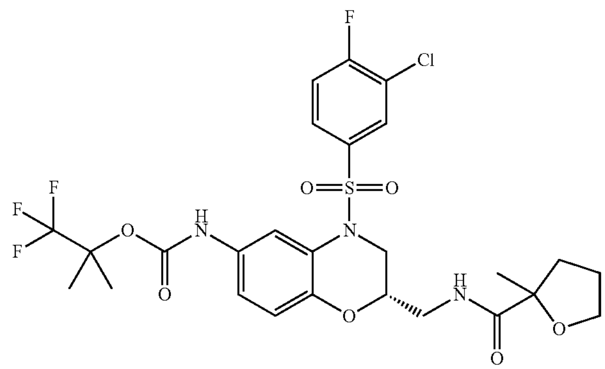 [SMILES: CC1(C(=O)NC[C@H]2CN(S(=O)(=O)c3ccc(F)c(Cl)c3)c3cc(NC(=O)OC(C)(C)C(F)(F)F)ccc3O2)CCCO1] | 1,1,1-trifluoro-2-methylpropan-2-yl ((2S)-4-((3-chloro-4-fluorophenyl)sulfonyl)-2-((2-methyltetrahydrofuran-2-carboxamido)methyl)-3,4-dihydro-2H-benzo[b][1,4]oxazin-6-yl)carbamate | 638 (M + H)+ |
| 34BL | 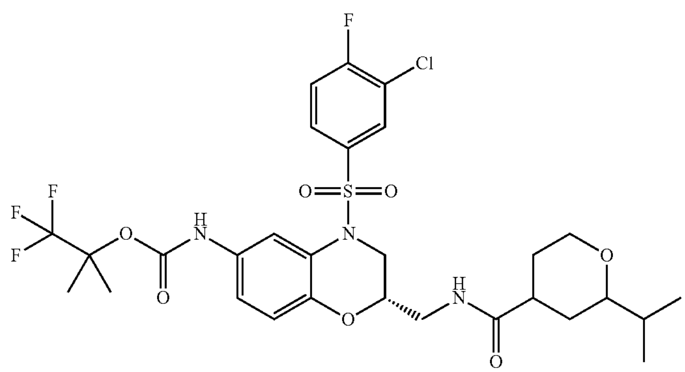 [SMILES: CC(C)C1CC(C(=O)NC[C@H]2CN(S(=O)(=O)c3ccc(F)c(Cl)c3)c3cc(NC(=O)OC(C)(C)C(F)(F)F)ccc3O2)CCO1] | 1,1,1-trifluoro-2-methylpropan-2-yl ((2S)-4-((3-chloro-4-fluorophenyl)sulfonyl)-2-((2-isopropyltetrahydro-2H-pyran-4-carboxamido)methyl)-3,4-dihydro-2H-benzo[b][1,4]oxazin-6-yl)carbamate | 680 (M + H)+ |
| 34BM | 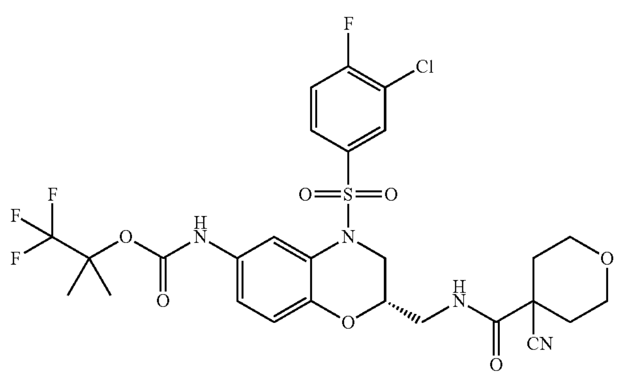 [SMILES: CC(C)(OC(=O)Nc1ccc2c(c1)N(S(=O)(=O)c1ccc(F)c(Cl)c1)C[C@H](CNC(=O)C1(C#N)CCOCC1)O2)C(F)(F)F] | (S)-1,1,1-trifluoro-2-methylpropan-2-yl (4-((3-chloro-4-fluorophenyl)sulfonyl)-2-((4-cyanotetrahydro-2H-pyran-4-carboxamido)methyl)-3,4-dihydro-2H-benzo[b][1,4]oxazin-6-yl)carbamate | 663 (M + H)+ |

TABLE 13-continued

| Ex. No. | Structure | Name | Observed m/z |
|---|---|---|---|
| 34BN | 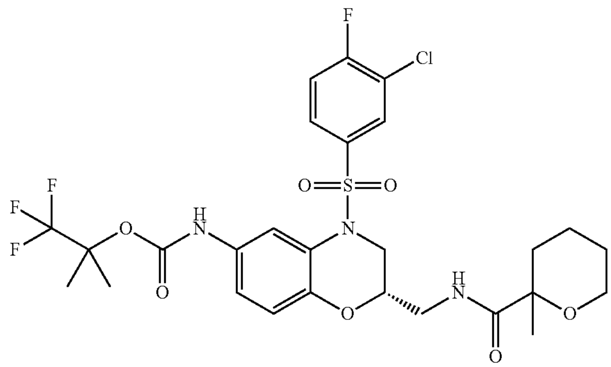 [SMILES: CC1(C(=O)NC[C@H]2CN(S(=O)(=O)c3ccc(F)c(Cl)c3)c3cc(NC(=O)OC(C)(C)C(F)(F)F)ccc3O2)CCCCO1] | 1,1,1-trifluoro-2-methylpropan-2-yl ((2S)-4-((3-chloro-4-fluorophenyl)sulfonyl)-2-((2-methyltetrahydro-2H-pyran-2-carboxamido)methyl)-3,4-dihydro-2H-benzo[b][1,4]oxazin-6-yl)carbamate | 652 (M + H)+ |
| 34Bo | 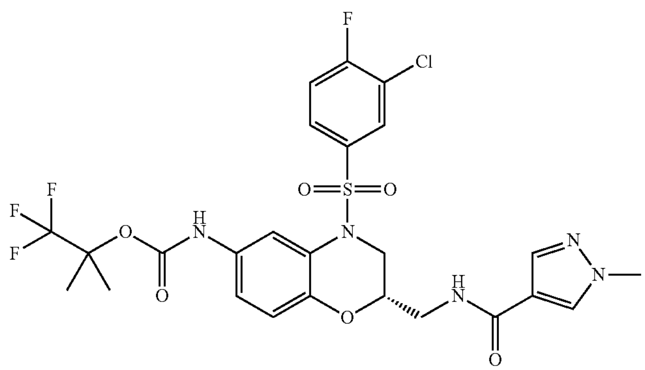 [SMILES: Cn1cc(C(=O)NC[C@H]2CN(S(=O)(=O)c3ccc(F)c(Cl)c3)c3cc(NC(=O)OC(C)(C)C(F)(F)F)ccc3O2)cn1] | (S)-1,1,1-trifluoro-2-methylpropan-2-yl (4-((3-chloro-4-fluorophenyl)sulfonyl)-2-((1-methyl-1H-pyrazole-4-carboxamido)methyl)-3,4-dihydro-2H-benzo[b][1,4]oxazin-6-yl)carbamate | 634 (M + H)+ |
| 34BP | 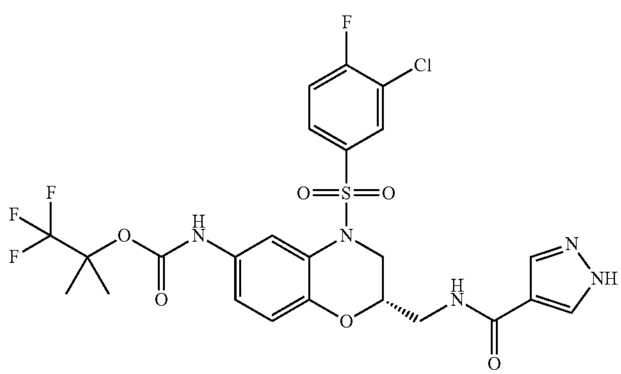 [SMILES: CC(C)(OC(=O)Nc1ccc2c(c1)N(S(=O)(=O)c1ccc(F)c(Cl)c1)C[C@H](CNC(=O)c1cn[nH]c1)O2)C(F)(F)F] | (S)-1,1,1-trifluoro-2-methylpropan-2-yl (2-((1H-pyrazole-4-carboxamido)methyl)-4-((3-chloro-4-fluorophenyl)sulfonyl)-3,4-dihydro-2H-benzo[b][1,4]oxazin-6-yl)carbamate | 620 (M + H)+ |
| 34BQ | 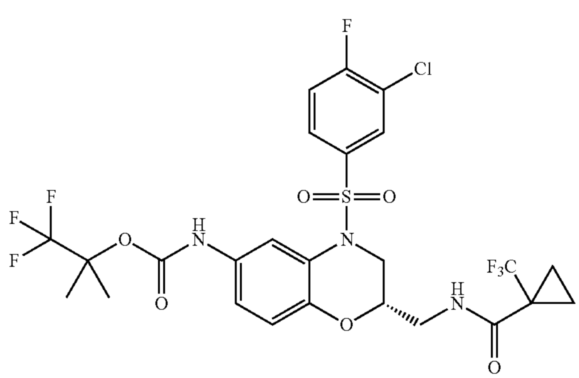 [SMILES: CC(C)(OC(=O)Nc1ccc2c(c1)N(S(=O)(=O)c1ccc(F)c(Cl)c1)C[C@H](CNC(=O)C1(C(F)(F)F)CC1)O2)C(F)(F)F] | (S)-1,1,1-trifluoro-2-methylpropan-2-yl (4-((3-chloro-4-fluorophenyl)sulfonyl)-2-((1-(trifluoromethyl)cyclopropanecarboxamido)methyl)-3,4-dihydro-2H-benzo[b][1,4]oxazin-6-yl)carbamate | 662 (M + H)+ |

TABLE 13-continued

| Ex. No. | Structure | Name | Observed m/z |
|---|---|---|---|
| 34BR | 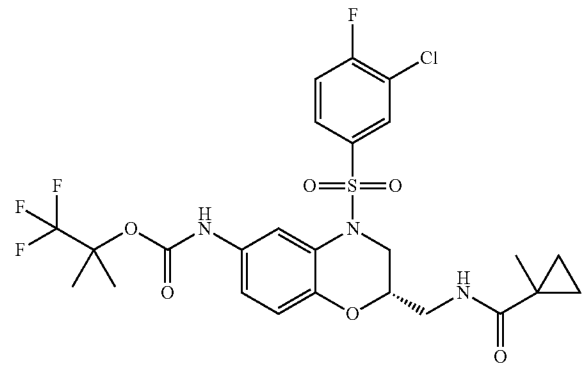 [SMILES: CC1(C(=O)NC[C@H]2CN(S(=O)(=O)c3ccc(F)c(Cl)c3)c3cc(NC(=O)OC(C)(C)C(F)(F)F)ccc3O2)CC1] | (S)-1,1,1-trifluoro-2-methylpropan-2-yl (4-((3-chloro-4-fluorophenyl)sulfonyl)-2-((1-methylcyclopropane-carboxamido)methyl)-3,4-dihydro-2H-benzo[b][1,4]oxazin-6-yl)carbamate | 608 (M + H)+ |
| 34BS | 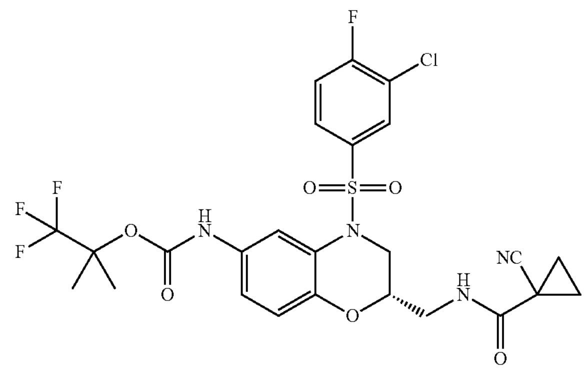 [SMILES: CC(C)(OC(=O)Nc1ccc2c(c1)N(S(=O)(=O)c1ccc(F)c(Cl)c1)C[C@H](CNC(=O)C1(C#N)CC1)O2)C(F)(F)F] | (S)-1,1,1-trifluoro-2-methylpropan-2-yl (4-((3-chloro-4-fluorophenyl)sulfonyl)-2-((1-cyanocyclopropane-carboxamido)methyl)-3,4-dihydro-2H-benzo[b][1,4]oxazin-6-yl)carbamate | 619 (M + H)+ |
| 34BT | 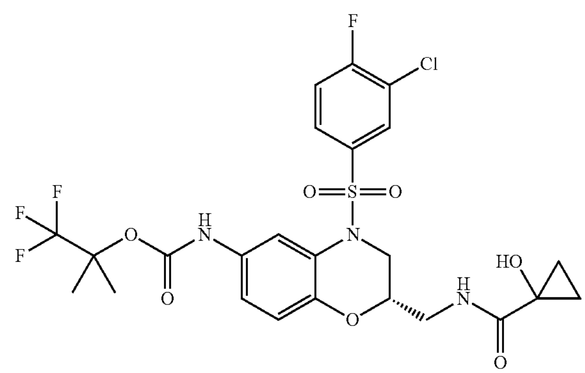 | (S)-1,1,1-trifluoro-2-methylpropan-2-yl (4-((3-chloro-4-fluorophenyl)sulfonyl)-2-((1-hydroxycyclopropane-carboxamido)methyl)-3,4-dihydro-2H-benzo[b][1,4]oxazin-6-yl)carbamate | 610 (M + H)+ |
| 34BU | 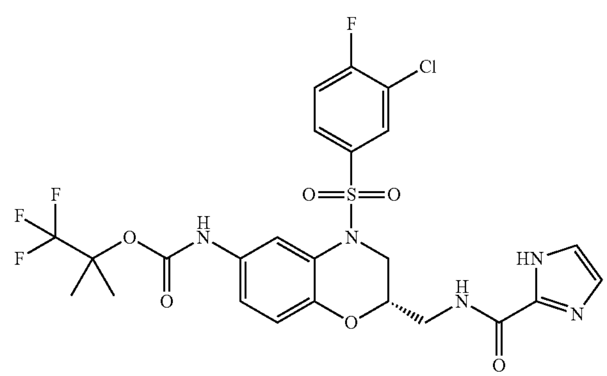 [SMILES: CC(C)(OC(=O)Nc1ccc2c(c1)N(S(=O)(=O)c1ccc(F)c(Cl)c1)C[C@H](CNC(=O)c1ncc[nH]1)O2)C(F)(F)F] | (S)-1,1,1-trifluoro-2-methylpropan-2-yl (2-((1H-imidazole-2-carboxamido)methyl)-4-((3-chloro-4-fluorophenyl)sulfonyl)-3,4-dihydro-2H-benzo[b][1,4]oxazin-6-yl)carbamate | 620 (M + H)+ |

TABLE 13-continued

| Ex. No. | Structure | Name | Observed m/z |
|---|---|---|---|
| 34BV | 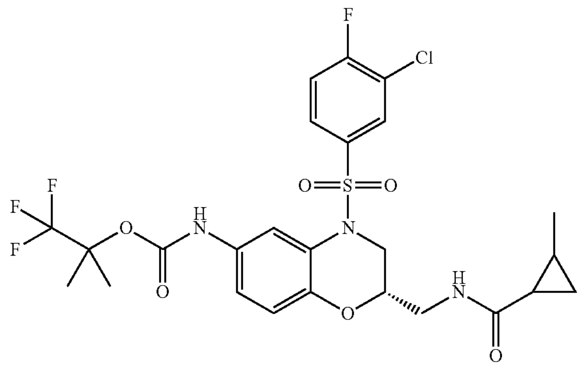 [SMILES: CC1CC1C(=O)NC[C@H]1CN(S(=O)(=O)c2ccc(F)c(Cl)c2)c2cc(NC(=O)OC(C)(C)C(F)(F)F)ccc2O1] | 1,1,1-trifluoro-2-methylpropan-2-yl ((2S)-4-((3-chloro-4-fluorophenyl)sulfonyl)-2-((2-methylcyclopropane-carboxamido)methyl)-3,4-dihydro-2H-benzo[b][1,4]oxazin-6-yl)carbamate | 608 (M + H)+ |
| 34BW | 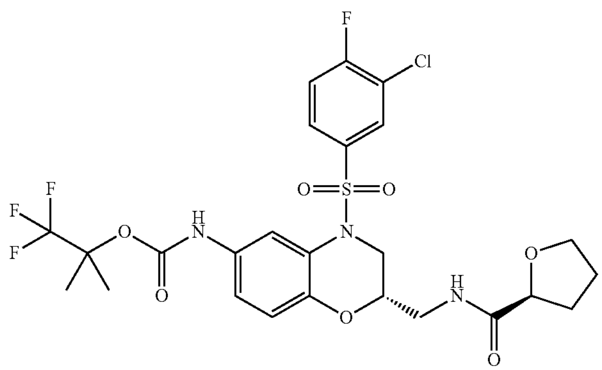 [SMILES: CC(C)(OC(=O)Nc1ccc2c(c1)N(S(=O)(=O)c1ccc(F)c(Cl)c1)C[C@H](CNC(=O)[C@@H]1CCCO1)O2)C(F)(F)F] | 1,1,1-trifluoro-2-methylpropan-2-yl ((S)-4-((3-chloro-4-fluorophenyl)sulfonyl)-2-(((S)-tetrahydrofuran-2-carboxamido)methyl)-3,4-dihydro-2H-benzo[b][1,4]oxazin-6-yl)carbamate | 624 (M + H)+ |
| 34BX | 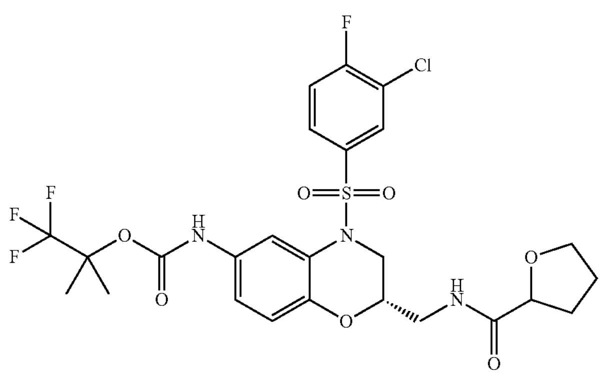 [SMILES: CC(C)(OC(=O)Nc1ccc2c(c1)N(S(=O)(=O)c1ccc(F)c(Cl)c1)C[C@H](CNC(=O)C1CCCO1)O2)C(F)(F)F] | 1,1,1-trifluoro-2-methylpropan-2-yl ((2S)-4-((3-chloro-4-fluorophenyl)sulfonyl)-2-((tetrahydrofuran-2-carboxamido)methyl)-3,4-dihydro-2H-benzo[b][1,4]oxazin-6-yl)carbamate | 624 (M + H)+ |
| 34BY | 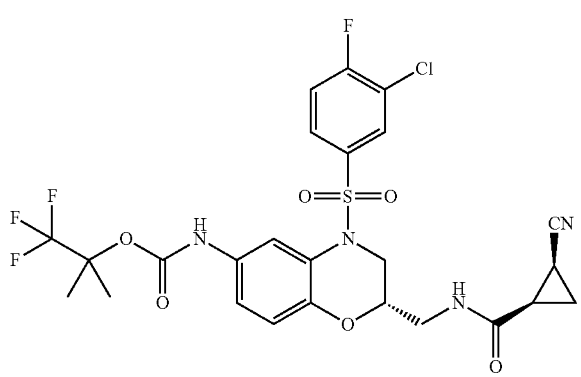 [SMILES: CC(C)(OC(=O)Nc1ccc2c(c1)N(S(=O)(=O)c1ccc(F)c(Cl)c1)C[C@H](CNC(=O)[C@@H]1C[C@@H]1C#N)O2)C(F)(F)F] | 1,1,1-trifluoro-2-methylpropan-2-yl ((S)-4-((3-chloro-4-fluorophenyl)sulfonyl)-2-(((1R,2S)-2-cyanocyclopropane-carboxamido)methyl)-3,4-dihydro-2H-benzo[b][1,4]oxazin-6-yl)carbamate | 619 (M + H)+ |

TABLE 13-continued

| Ex. No. | Structure | Name | Observed m/z |
|---|---|---|---|
| 34BZ | 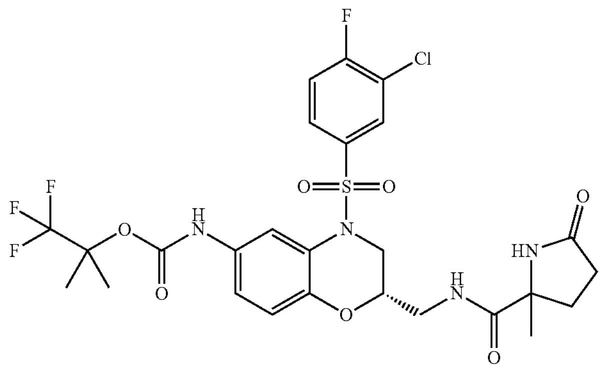 [SMILES: CC1(C(=O)NC[C@H]2CN(S(=O)(=O)c3ccc(F)c(Cl)c3)c3cc(NC(=O)OC(C)(C)C(F)(F)F)ccc3O2)CCC(=O)N1] | 1,1,1-trifluoro-2-methylpropan-2-yl ((2S)-4-((3-chloro-4-fluorophenyl)sulfonyl)-2-((2-methyl-5-oxopyrrolidine-2-carboxamido)methyl)-3,4-dihydro-2H-benzo[b][1,4]oxazin-6-yl)carbamate | 651 (M + H)+ |
| 34CA | 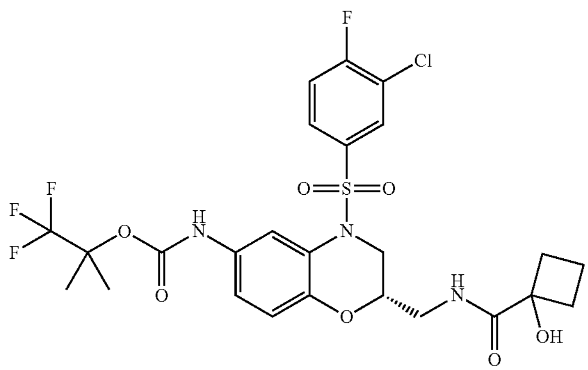 [SMILES: CC(C)(OC(=O)Nc1ccc2c(c1)N(S(=O)(=O)c1ccc(F)c(Cl)c1)C[C@H](CNC(=O)C1(O)CCC1)O2)C(F)(F)F] | (S)-1,1,1-trifluoro-2-methylpropan-2-yl (4-((3-chloro-4-fluorophenyl)sulfonyl)-2-((1-hydroxycyclobutane-carboxamido)methyl)-3,4-dihydro-2H-benzo[b][1,4]oxazin-6-yl)carbamate | 624 (M + H)+ |
| 34CB | 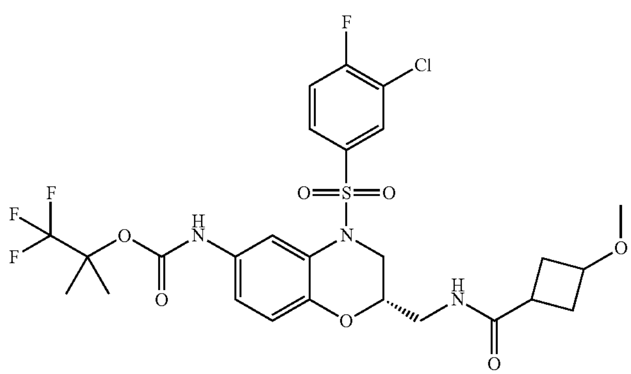 [SMILES: COC1CC(C(=O)NC[C@H]2CN(S(=O)(=O)c3ccc(F)c(Cl)c3)c3cc(NC(=O)OC(C)(C)C(F)(F)F)ccc3O2)C1] | (S)-1,1,1-trifluoro-2-methylpropan-2-yl (4-((3-chloro-4-fluorophenyl)sulfonyl)-2-((3-methoxycyclobutane-carboxamido)methyl)-3,4-dihydro-2H-benzo[b][1,4]oxazin-6-yl)carbamate | 638 (M + H)+ |
| 34CC | 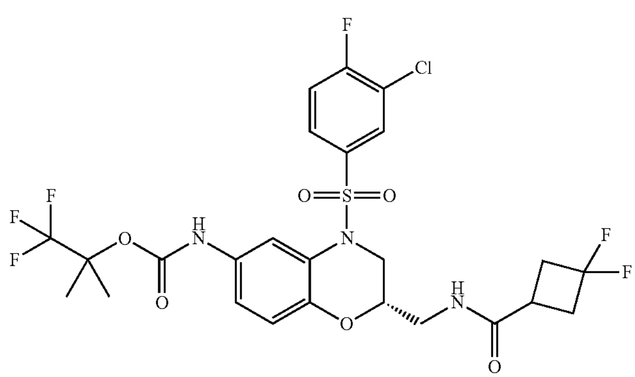 [SMILES: CC(C)(OC(=O)Nc1ccc2c(c1)N(S(=O)(=O)c1ccc(F)c(Cl)c1)C[C@H](CNC(=O)C1CC(F)(F)C1)O2)C(F)(F)F] | (S)-1,1,1-trifluoro-2-methylpropan-2-yl (4-((3-chloro-4-fluorophenyl)sulfonyl)-2-((3,3-difluorocyclobutane-carboxamido)methyl)-3,4-dihydro-2H-benzo[b][1,4]oxazin-6-yl)carbamate | 644 (M + H)+ |

TABLE 13-continued

| Ex. No. | Structure | Name | Observed m/z |
|---|---|---|---|
| 34CD | 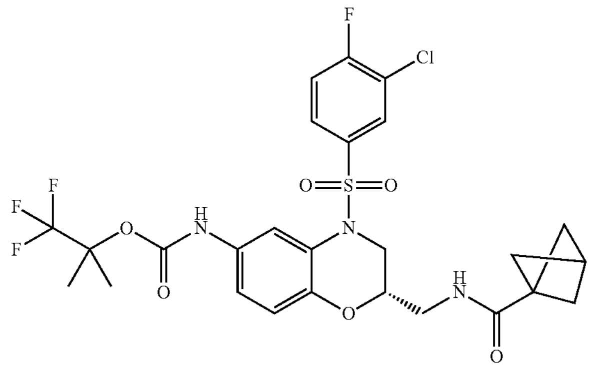 [SMILES: CC(C)(OC(=O)Nc1ccc2c(c1)N(S(=O)(=O)c1ccc(F)c(Cl)c1)C[C@H](CNC(=O)C13CC(C1)C3)O2)C(F)(F)F] | (S)-1,1,1-trifluoro-2-methylpropan-2-yl (2-((bicyclo[1.1.1]pentane-1-carboxamido)methyl)-4-((3-chloro-4-fluorophenyl)sulfonyl)-3,4-dihydro-2H-benzo[b][1,4]oxazin-6-yl)carbamate | 620 (M + H)+ |
| 34CE | 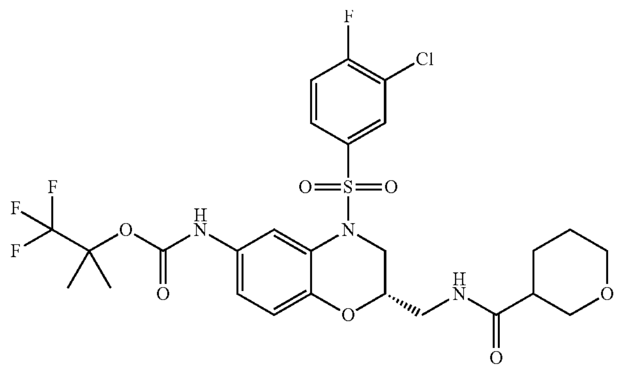 [SMILES: CC(C)(OC(=O)Nc1ccc2c(c1)N(S(=O)(=O)c1ccc(F)c(Cl)c1)C[C@H](CNC(=O)C1CCCOC1)O2)C(F)(F)F] | 1,1,1-trifluoro-2-methylpropan-2-yl ((2S)-4-((3-chloro-4-fluorophenyl)sulfonyl)-2-((tetrahydro-2H-pyran-3-carboxamido)methyl)-3,4-dihydro-2H-benzo[b][1,4]oxazin-6-yl)carbamate | 638 (M + H)+ |
| 34CF | 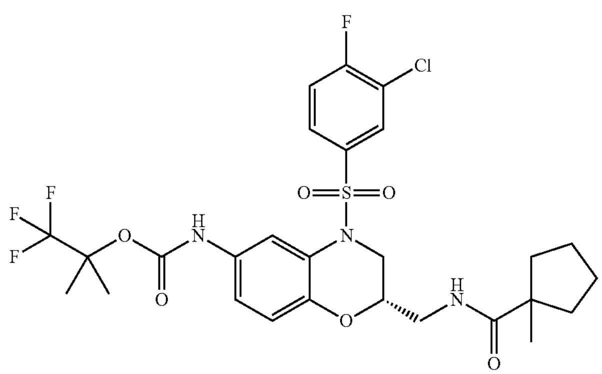 [SMILES: CC1(C(=O)NC[C@H]2CN(S(=O)(=O)c3ccc(F)c(Cl)c3)c3cc(NC(=O)OC(C)(C)C(F)(F)F)ccc3O2)CCCC1] | (S)-1,1,1-trifluoro-2-methylpropan-2-yl (4-((3-chloro-4-fluorophenyl)sulfonyl)-2-((1-methylcyclopentane-carboxamido)methyl)-3,4-dihydro-2H-benzo[b][1,4]oxazin-6-yl)carbamate | 636 (M + H)+ |
| 34CG | 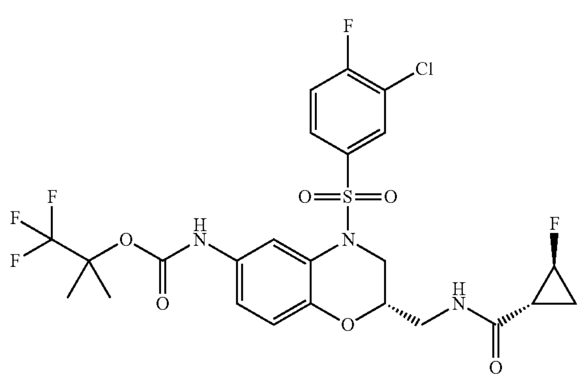 [SMILES: CC(C)(OC(=O)Nc1ccc2c(c1)N(S(=O)(=O)c1ccc(F)c(Cl)c1)C[C@H](CNC(=O)[C@H]1C[C@@H]1F)O2)C(F)(F)F] | 1,1,1-trifluoro-2-methylpropan-2-yl ((S)-4-((3-chloro-4-fluorophenyl)sulfonyl)-2-(((1R,2S)-2-fluorocyclopropane-carboxamido)methyl)-3,4-dihydro-2H-benzo[b][1,4]oxazin-6-yl)carbamate | 612 (M + H)+ |

TABLE 13-continued

| Ex. No. | Structure | Name | Observed m/z |
|---|---|---|---|
| 34CH | 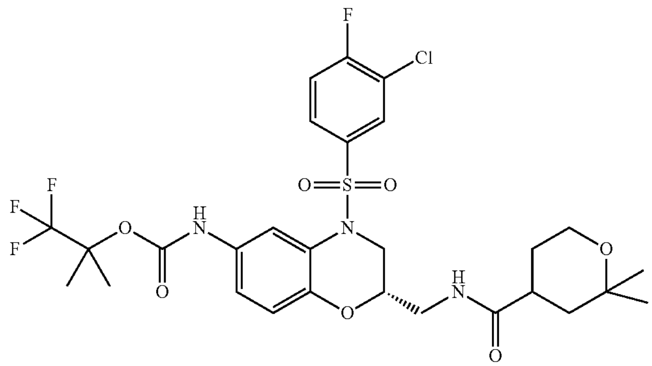 [SMILES: CC1(C)CC(C(=O)NC[C@H]2CN(S(=O)(=O)c3ccc(F)c(Cl)c3)c3cc(NC(=O)OC(C)(C)C(F)(F)F)ccc3O2)CCO1] | 1,1,1-trifluoro-2-methylpropan-2-yl ((2S)-4-((3-chloro-4-fluorophenyl)sulfonyl)-2-((2,2-dimethyltetrahydro-2H-pyran-4-carboxamido)methyl)-3,4-dihydro-2H-benzo[b][1,4]oxazin-6-yl)carbamate | 667 (M + H)+ |
| 34Ci | 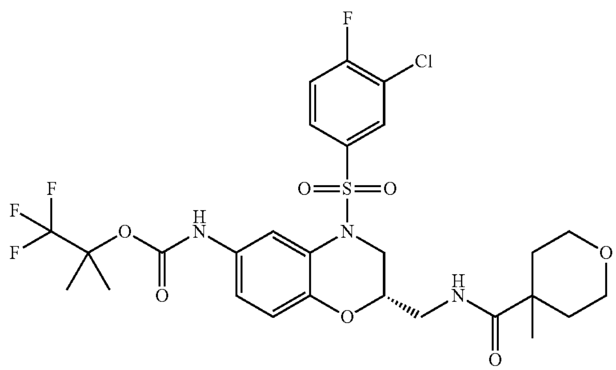 [SMILES: CC1(C(=O)NC[C@H]2CN(S(=O)(=O)c3ccc(F)c(Cl)c3)c3cc(NC(=O)OC(C)(C)C(F)(F)F)ccc3O2)CCOCC1] | (S)-1,1,1-trifluoro-2-methylpropan-2-yl (4-((3-chloro-4-fluorophenyl)sulfonyl)-2-((4-methyltetrahydro-2H-pyran-4-carboxamido)methyl)-3,4-dihydro-2H-benzo[b][1,4]oxazin-6-yl)carbamate | 652 (M + H)+ |
| 34CJ | 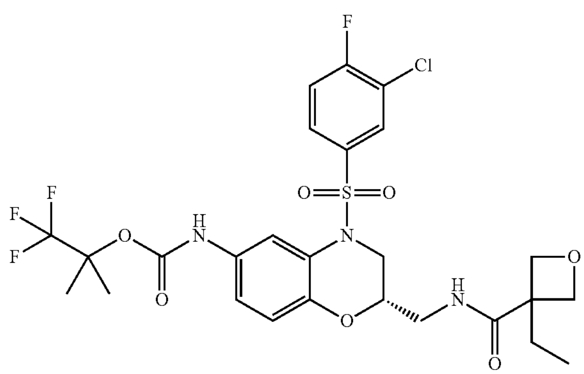 [SMILES: CCC1(C(=O)NC[C@H]2CN(S(=O)(=O)c3ccc(F)c(Cl)c3)c3cc(NC(=O)OC(C)(C)C(F)(F)F)ccc3O2)COC1] | (S)-1,1,1-trifluoro-2-methylpropan-2-yl (4-((3-chloro-4-fluorophenyl)sulfonyl)-2-((3-ethyloxetane-3-carboxamido)methyl)-3,4-dihydro-2H-benzo[b][1,4]oxazin-6-yl)carbamate | 638 (M + H)+ |
| 34CK | 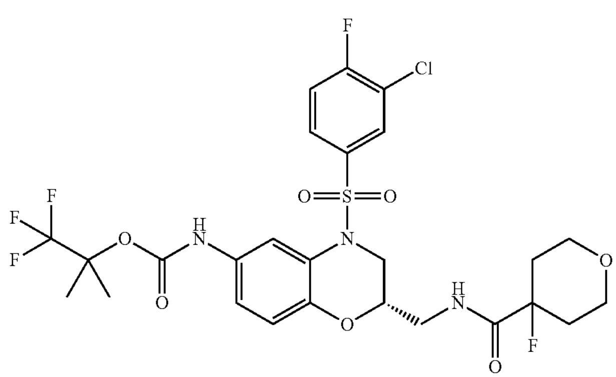 | (S)-1,1,1-trifluoro-2-methylpropan-2-yl (4-((3-chloro-4-fluorophenyl)sulfonyl)-2-((4-fluorotetrahydro-2H-pyran-4-carboxamido)methyl)-3,4-dihydro-2H-benzo[b][1,4]oxazin-6-yl)carbamate | 656 (M + H)+ |

TABLE 13-continued

| Ex. No. | Structure | Name | Observed m/z |
|---|---|---|---|
| 34CL | 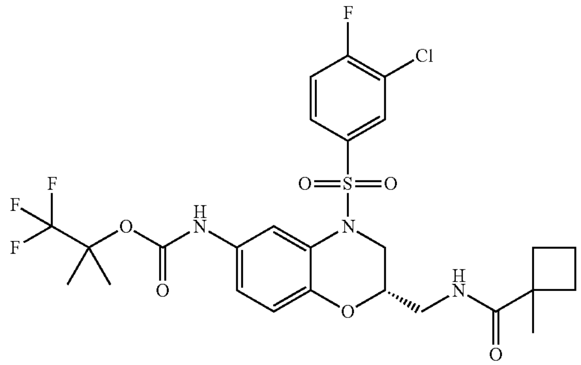 [SMILES: CC1(C(=O)NC[C@H]2CN(S(=O)(=O)c3ccc(F)c(Cl)c3)c3cc(NC(=O)OC(C)(C)C(F)(F)F)ccc3O2)CCC1] | (S)-1,1,1-trifluoro-2-methylpropan-2-yl (4-((3-chloro-4-fluorophenyl)sulfonyl)-2-((1-methylcyclobutane-carboxamido)methyl)-3,4-dihydro-2H-benzo[b][1,4]oxazin-6-yl)carbamate | 622 (M + H)+ |
| 34CM | 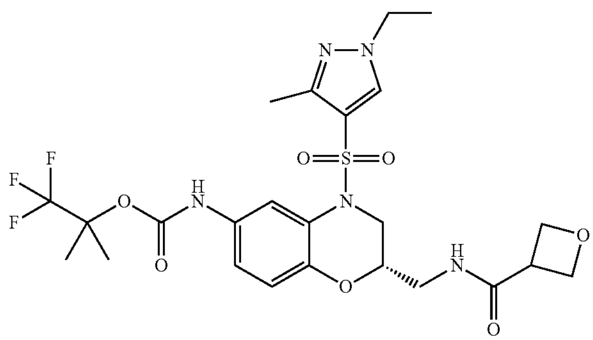 [SMILES: CCn1cc(S(=O)(=O)N2C[C@H](CNC(=O)C3COC3)Oc3ccc(NC(=O)OC(C)(C)C(F)(F)F)cc32)c(C)n1] | (S)-1,1,1-trifluoro-2-methylpropan-2-yl (4-((1-ethyl-3-methyl-1H-pyrazol-4-yl)sulfonyl)-2-((oxetane-3-carboxamido)methyl)-3,4-dihydro-2H-benzo[b][1,4]oxazin-6-yl)carbamate | 590.2 (M + H)+ |
| 34CN | 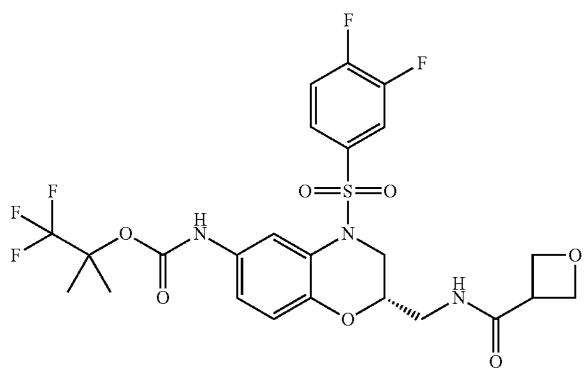 [SMILES: CC(C)(OC(=O)Nc1ccc2c(c1)N(S(=O)(=O)c1ccc(F)c(F)c1)C[C@H](CNC(=O)C1COC1)O2)C(F)(F)F] | (S)-1,1,1-trifluoro-2-methylpropan-2-yl (4-((3,4-difluorophenyl)sulfonyl)-2-((oxetane-3-carboxamido)methyl)-3,4-dihydro-2H-benzo[b][1,4]oxazin-6-yl)carbamate | 594.1 (M + H)+ |
| 34Co | 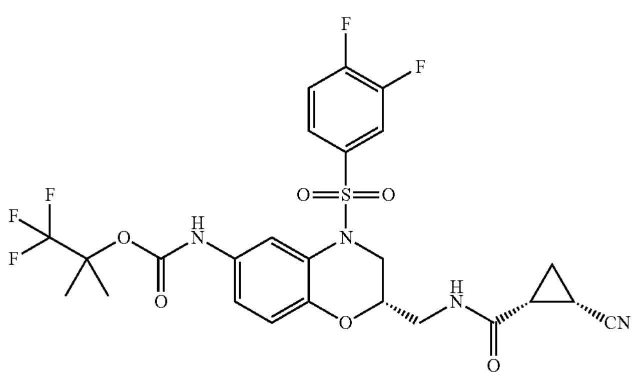 [SMILES: CC(C)(OC(=O)Nc1ccc2c(c1)N(S(=O)(=O)c1ccc(F)c(F)c1)C[C@H](CNC(=O)[C@@H]1C[C@@H]1C#N)O2)C(F)(F)F] | 1,1,1-trifluoro-2-methylpropan-2-yl ((S)-2-(((1R,2S)-2-cyanocyclopropane-carboxamido)methyl)-4-((3,4-difluorophenyl)sulfonyl)-3,4-dihydro-2H-benzo[b][1,4]oxazin-6-yl)carbamate | 603.1 (M + H)+ |

TABLE 13-continued

| Ex. No. | Structure | Name | Observed m/z |
|---|---|---|---|
| 34CP | 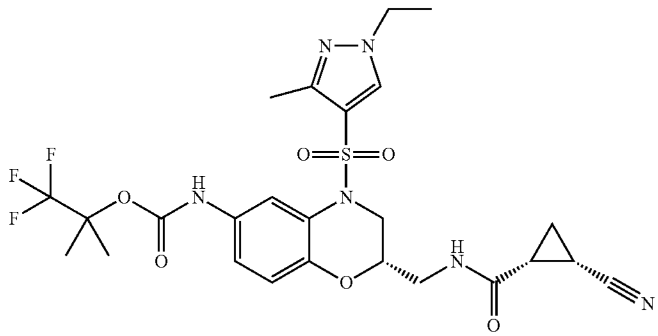 [SMILES: CCn1cc(S(=O)(=O)N2C[C@H](CNC(=O)[C@@H]3C[C@@H]3C#N)Oc3ccc(NC(=O)OC(C)(C)C(F)(F)F)cc32)c(C)n1] | 1,1,1-trifluoro-2-methylpropan-2-yl ((S)-2-(((1R,2S)-2-cyanocyclopropane-carboxamido)methyl)-4-((1-ethyl-3-methyl-1H-pyrazol-4-yl)sulfonyl)-3,4-dihydro-2H-benzo[b][1,4]oxazin-6-yl)carbamate | 599.1 (M + H)+ |
| 34CQ | 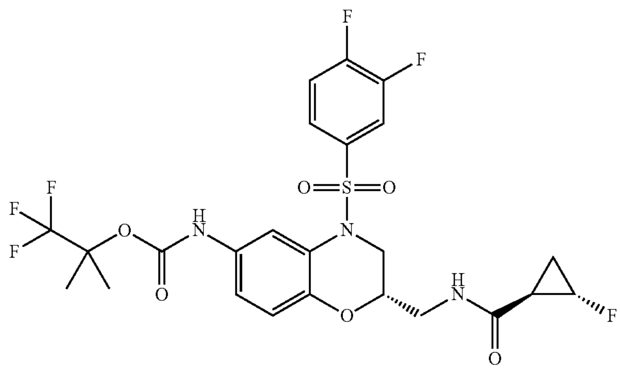 [SMILES: CC(C)(OC(=O)Nc1ccc2c(c1)N(S(=O)(=O)c1ccc(F)c(F)c1)C[C@H](CNC(=O)[C@H]1C[C@@H]1F)O2)C(F)(F)F] | 1,1,1-trifluoro-2-methylpropan-2-yl ((S)-4-((3,4-difluorophenyl)sulfonyl)-2-(((1R,2S)-2-fluorocyclopropane-carboxamido)methyl)-3,4-dihydro-2H-benzo[b][1,4]oxazin-6-yl)carbamate | 596 (M + H)+ |
| 34CR | 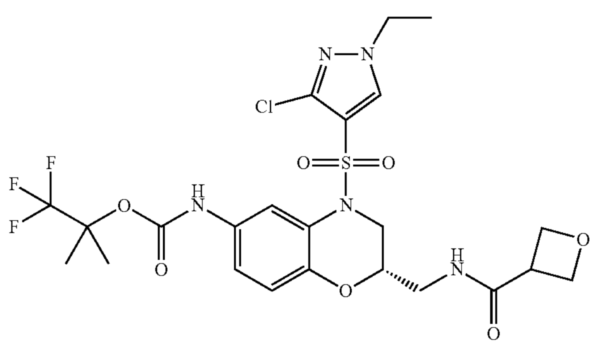 | (S)-1,1,1-trifluoro-2-methylpropan-2-yl (4-((3-chloro-1-ethyl-1H-pyrazol-4-yl)sulfonyl)-2-((oxetane-3-carboxamido)methyl)-3,4-dihydro-2H-benzo[b][1,4]oxazin-6-yl)carbamate | 610.1 (M + H)+ |
| 34CS | 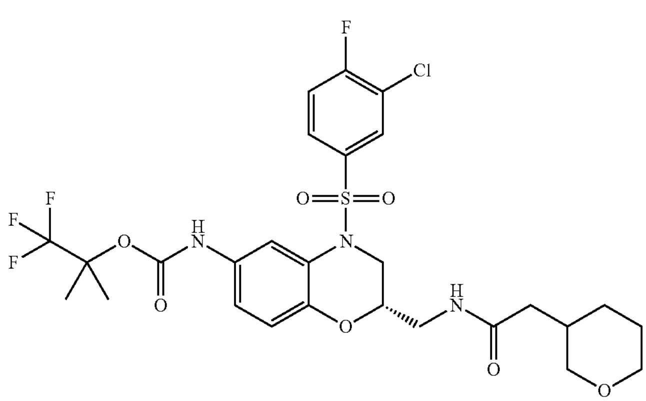 [SMILES: CC(C)(OC(=O)Nc1ccc2c(c1)N(S(=O)(=O)c1ccc(F)c(Cl)c1)C[C@H](CNC(=O)CC1CCCOC1)O2)C(F)(F)F] | 1,1,1-trifluoro-2-methylpropan-2-yl ((2S)-4-((3-chloro-4-fluorophenyl)sulfonyl)-2-((2-(tetrahydro-2H-pyran-3-yl)acetamido)methyl)-3,4-dihydro-2H-benzo[b][1,4]oxazin-6-yl)carbamate | 652 (M + H)+ |

TABLE 13-continued

| Ex. No. | Structure | Name | Observed m/z |
|---|---|---|---|
| 34CT | 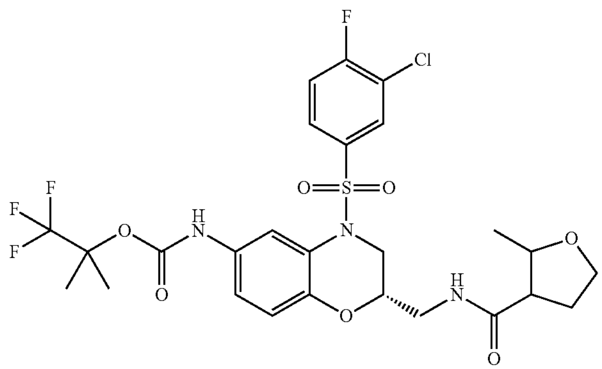 [SMILES: CC1OCCC1C(=O)NC[C@H]1CN(S(=O)(=O)c2ccc(F)c(Cl)c2)c2cc(NC(=O)OC(C)(C)C(F)(F)F)ccc2O1] | 1,1,1-trifluoro-2-methylpropan-2-yl ((2S)-4-((3-chloro-4-fluorophenyl)sulfonyl)-2-((2-methyltetrahydrofuran-3-carboxamido)methyl)-3,4-dihydro-2H-benzo[b][1,4]oxazin-6-yl)carbamate | 638 (M + H)+ |
| 34CU | 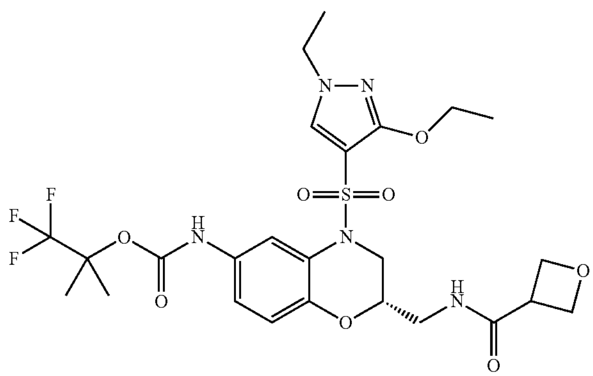 [SMILES: CCOc1nn(CC)cc1S(=O)(=O)N1C[C@H](CNC(=O)C2COC2)Oc2ccc(NC(=O)OC(C)(C)C(F)(F)F)cc21] | (S)-1,1,1-trifluoro-2-methylpropan-2-yl (4-((3-ethoxy-1-ethyl-1H-pyrazol-4-yl)sulfonyl)-2-((oxetane-3-carboxamido)methyl)-3,4-dihydro-2H-benzo[b][1,4]oxazin-6-yl)carbamate | 642.1 (M + Na)+ |
| 34CV | 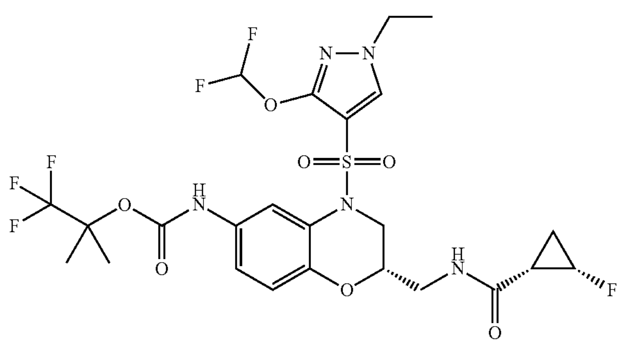 [SMILES: CCn1cc(S(=O)(=O)N2C[C@H](CNC(=O)[C@@H]3C[C@@H]3F)Oc3ccc(NC(=O)OC(C)(C)C(F)(F)F)cc32)c(OC(F)F)n1] | 1,1,1-trifluoro-2-methylpropan-2-yl ((S)-4-((3-(difluoromethoxy)-1-ethyl-1H-pyrazol-4-yl)sulfonyl)-2-((((1S,2S)-2-fluorocyclopropane-carboxamido)methyl)-3,4-dihydro-2H-benzo[b][1,4]oxazin-6-yl)carbamate | 644.1 (M + H)+ |
| 34CW | 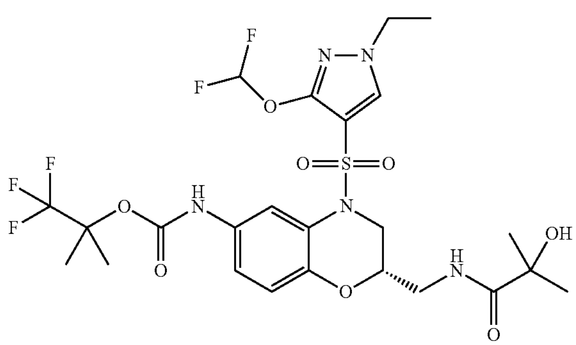 [SMILES: CCn1cc(S(=O)(=O)N2C[C@H](CNC(=O)C(C)(C)O)Oc3ccc(NC(=O)OC(C)(C)C(F)(F)F)cc32)c(OC(F)F)n1] | (S)-1,1,1-trifluoro-2-methylpropan-2-yl (4-((3-(difluoromethoxy)-1-ethyl-1H-pyrazol-4-yl)sulfonyl)-2-((2-hydroxy-2-methylpropanamido)methyl)-3,4-dihydro-2H-benzo[b][1,4]oxazin-6-yl)carbamate | 644.1 (M + H)+ |

TABLE 13-continued

| Ex. No. | Structure | Name | Observed m/z |
|---|---|---|---|
| 34CX | 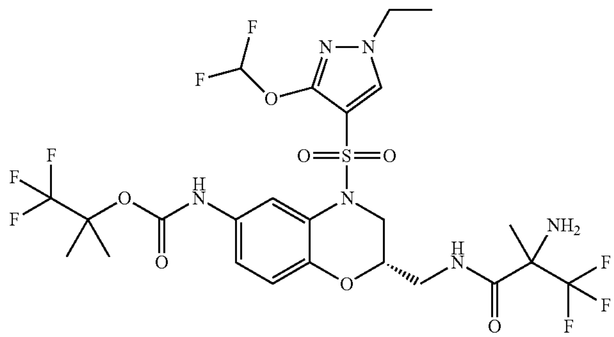 [SMILES: CCn1cc(S(=O)(=O)N2C[C@H](CNC(=O)C(C)(N)C(F)(F)F)Oc3ccc(NC(=O)OC(C)(C)C(F)(F)F)cc32)c(OC(F)F)n1] | 1,1,1-trifluoro-2-methylpropan-2-yl ((2S)-2-((2-amino-3,3,3-trifluoro-2-methylpropanamido)methyl)-4-((3-(difluoromethoxy)-1-ethyl-1H-pyrazol-4-yl)sulfonyl)-3,4-dihydro-2H-benzo[b][1,4]oxazin-6-yl)carbamate | 697.1 (M + H)+ |
| 34CY | 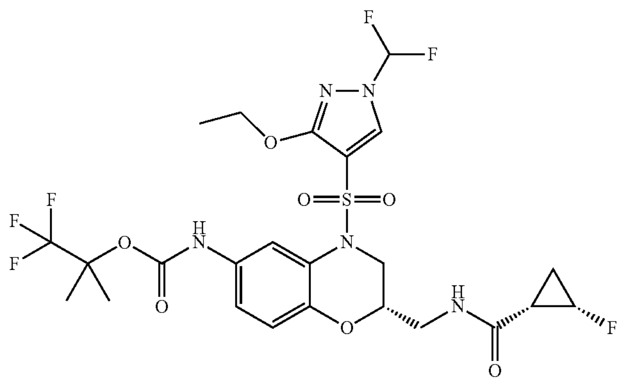 [SMILES: CCOc1nn(C(F)F)cc1S(=O)(=O)N1C[C@H](CNC(=O)[C@@H]2C[C@@H]2F)Oc2ccc(NC(=O)OC(C)(C)C(F)(F)F)cc21] | 1,1,1-trifluoro-2-methylpropan-2-yl ((S)-4-((1-(difluoromethyl)-3-ethoxy-1H-pyrazol-4-yl)sulfonyl)-2-((((1S,2S)-2-fluorocyclopropane-carboxamido)methyl)-3,4-dihydro-2H-benzo[b][1,4]oxazin-6-yl)carbamate | 644.1 (M + H)+ |
| 34CZ | 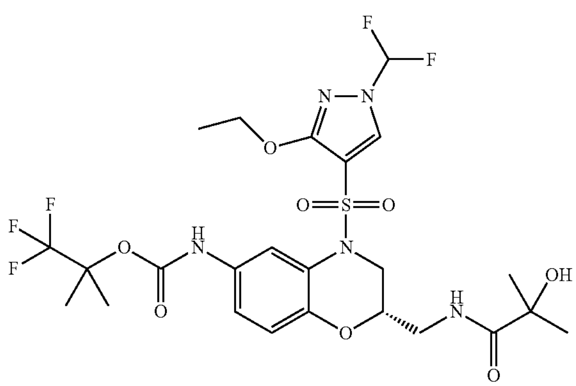 [SMILES: CCOc1nn(C(F)F)cc1S(=O)(=O)N1C[C@H](CNC(=O)C(C)(C)O)Oc2ccc(NC(=O)OC(C)(C)C(F)(F)F)cc21] | (S)-1,1,1-trifluoro-2-methylpropan-2-yl (4-((1-(difluoromethyl)-3-ethoxy-1H-pyrazol-4-yl)sulfonyl)-2-((2-hydroxy-2-methylpropanamido)methyl)-3,4-dihydro-2H-benzo[b][1,4]oxazin-6-yl)carbamate | 644.1 (M + H)+ |
| 34DA | 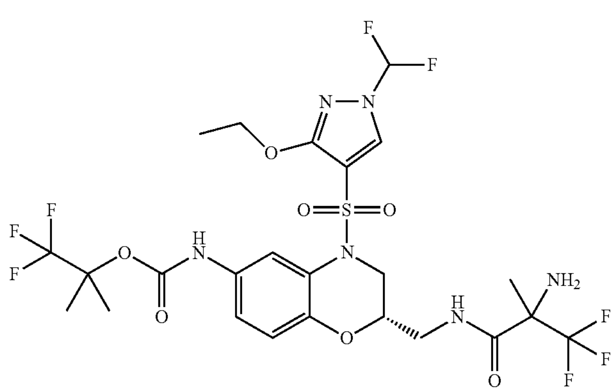 [SMILES: CCOc1nn(C(F)F)cc1S(=O)(=O)N1C[C@H](CNC(=O)C(C)(N)C(F)(F)F)Oc2ccc(NC(=O)OC(C)(C)C(F)(F)F)cc21] | 1,1,1-trifluoro-2-methylpropan-2-yl ((2S)-2-((2-amino-3,3,3-trifluoro-2-methylpropanamido)methyl)-4-((1-(difluoromethyl)-3-ethoxy-1H-pyrazol-4-yl)sulfonyl)-3,4-dihydro-2H-benzo[b][1,4]oxazin-6-yl)carbamate | 697.1 (M + H)+ |

TABLE 13-continued

| Ex. No. | Structure | Name | Observed m/z |
|---|---|---|---|
| 34DB | 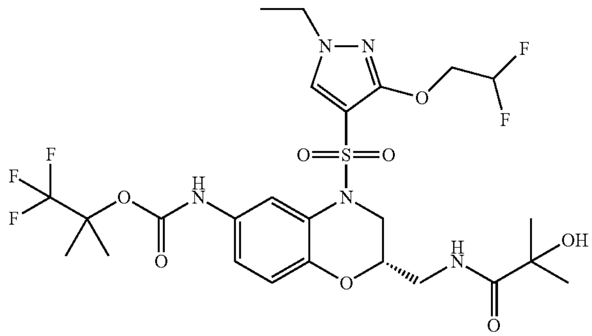 [SMILES: CCn1cc(S(=O)(=O)N2C[C@H](CNC(=O)C(C)(C)O)Oc3ccc(NC(=O)OC(C)(C)C(F)(F)F)cc32)c(OCC(F)F)n1] | (S)-1,1,1-trifluoro-2-methylpropan-2-yl (4-((3-(2,2-difluoroethoxy)-1-ethyl-1H-pyrazol-4-yl)sulfonyl)-2-((2-hydroxy-2-methylpropanamido)methyl)-3,4-dihydro-2H-benzo[b][1,4]oxazin-6-yl)carbamate | 658 (M + H)+ |
| 34DC | 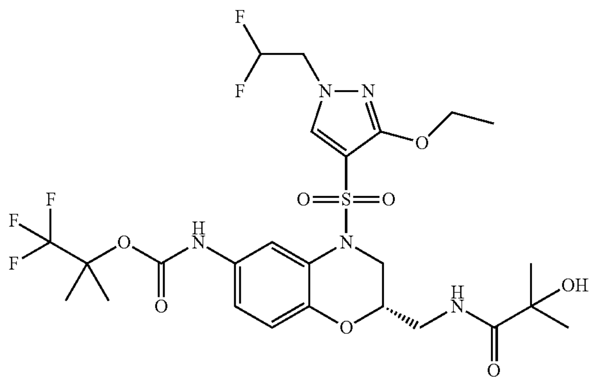 [SMILES: CCOc1nn(CC(F)F)cc1S(=O)(=O)N1C[C@H](CNC(=O)C(C)(C)O)Oc2ccc(NC(=O)OC(C)(C)C(F)(F)F)cc21] | (S)-1,1,1-trifluoro-2-methylpropan-2-yl (4-((1-(2,2-difluoroethyl)-3-ethoxy-1H-pyrazol-4-yl)sulfonyl)-2-((2-hydroxy-2-methylpropanamido)methyl)-3,4-dihydro-2H-benzo[b][1,4]oxazin-6-yl)carbamate | 658 (M + H)+ |
| 34DD | 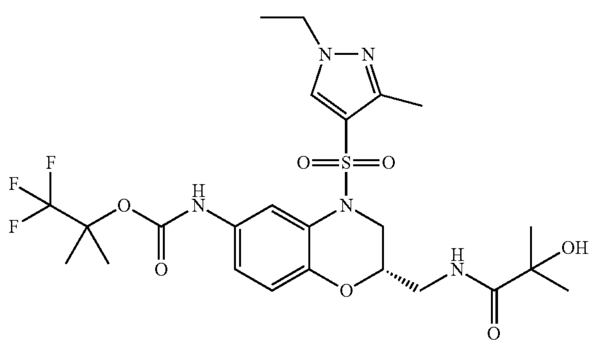 [SMILES: CCn1cc(S(=O)(=O)N2C[C@H](CNC(=O)C(C)(C)O)Oc3ccc(NC(=O)OC(C)(C)C(F)(F)F)cc32)c(C)n1] | (S)-1,1,1-trifluoro-2-methylpropan-2-yl (4-((1-ethyl-3-methyl-1H-pyrazol-4-yl)sulfonyl)-2-((2-hydroxy-2-methylpropanamido)methyl)-3,4-dihydro-2H-benzo[b][1,4]oxazin-6-yl)carbamate | 592 (M + H)+ |
| 34DE | 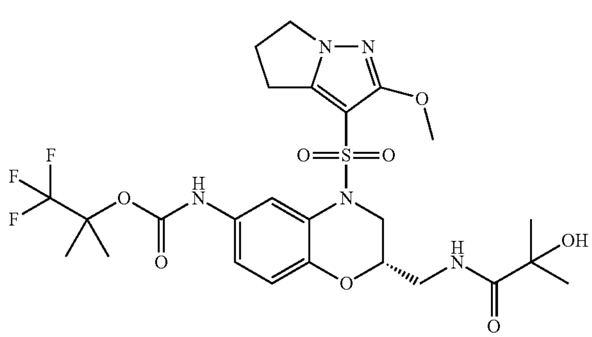 [SMILES: COc1nn2c(c1S(=O)(=O)N1C[C@H](CNC(=O)C(C)(C)O)Oc3ccc(NC(=O)OC(C)(C)C(F)(F)F)cc31)CCC2] | (S)-1,1,1-trifluoro-2-methylpropan-2-yl (2-((2-hydroxy-2-methylpropanamido)methyl)-4-((2-methoxy-5,6-dihydro-4H-pyrrolo[1,2-b]pyrazol-3-yl)sulfonyl)-3,4-dihydro-2H-benzo[b][1,4]oxazin-6-yl)carbamate | 620 (M + H)+ |

TABLE 13-continued

| Ex. No. | Structure | Name | Observed m/z |
|---|---|---|---|
| 34DF | 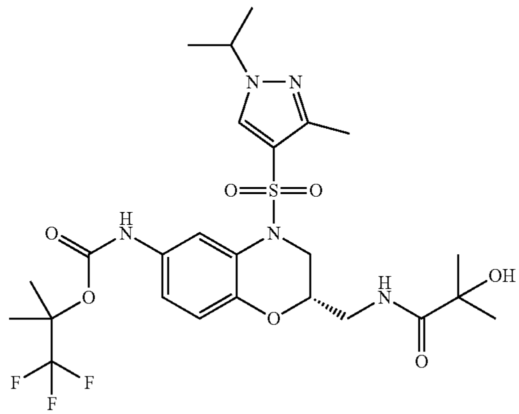 [SMILES: Cc1nn(C(C)C)cc1S(=O)(=O)N1C[C@H](CNC(=O)C(C)(C)O)Oc2ccc(NC(=O)OC(C)(C)C(F)(F)F)cc21] | (S)-1,1,1-trifluoro-2-methylpropan-2-yl (2-((2-hydroxy-2-methylpropanamido)methyl)-4-((1-isopropyl-3-methyl-1H-pyrazol-4-yl)sulfonyl)-3,4-dihydro-2H-benzo[b][1,4]oxazin-6-yl)carbamate | 606 (M + H)+ |
| 34DG | 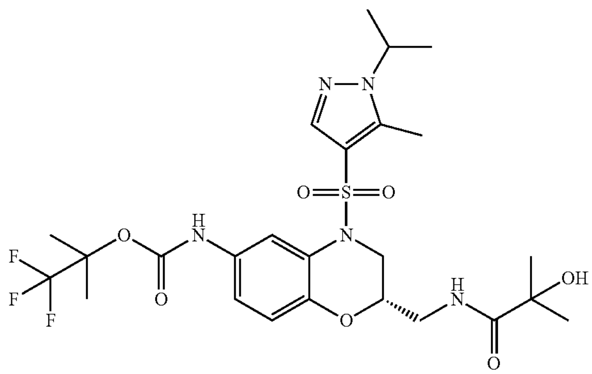 [SMILES: Cc1c(S(=O)(=O)N2C[C@H](CNC(=O)C(C)(C)O)Oc3ccc(NC(=O)OC(C)(C)C(F)(F)F)cc32)cnn1C(C)C] | (S)-1,1,1-trifluoro-2-methylpropan-2-yl (2-((2-hydroxy-2-methylpropanamido)methyl)-4-((1-isopropyl-5-methyl-1H-pyrazol-4-yl)sulfonyl)-3,4-dihydro-2H-benzo[b][1,4]oxazin-6-yl)carbamate | 606 (M + H)+ |
| 34DH | 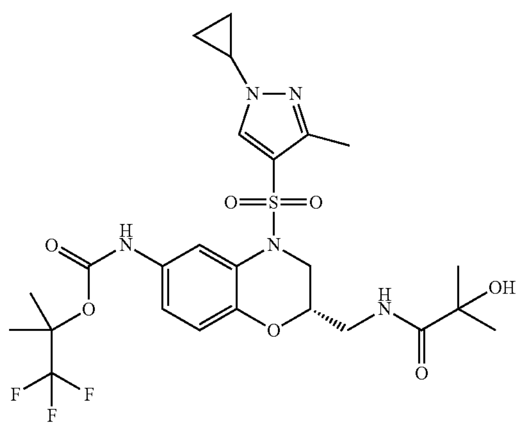 [SMILES: Cc1nn(C2CC2)cc1S(=O)(=O)N1C[C@H](CNC(=O)C(C)(C)O)Oc2ccc(NC(=O)OC(C)(C)C(F)(F)F)cc21] | (S)-1,1,1-trifluoro-2-methylpropan-2-yl (4-((1-cyclopropyl-3-methyl-1H-pyrazol-4-yl)sulfonyl)-2-((2-hydroxy-2-methylpropanamido)methyl)-3,4-dihydro-2H-benzo[b][1,4]oxazin-6-yl)carbamate | 604 (M + H)+ |
| 34Di | 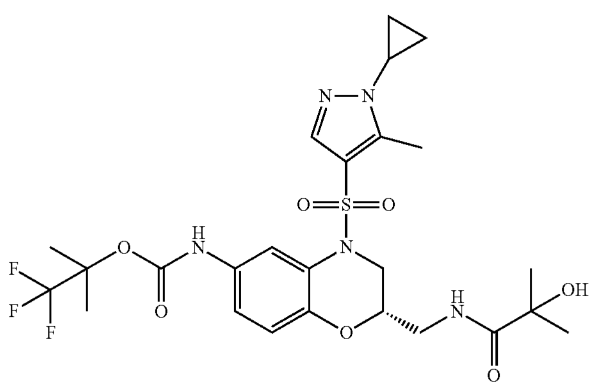 [SMILES: Cc1c(S(=O)(=O)N2C[C@H](CNC(=O)C(C)(C)O)Oc3ccc(NC(=O)OC(C)(C)C(F)(F)F)cc32)cnn1C1CC1] | (S)-1,1,1-trifluoro-2-methylpropan-2-yl (4-((1-cyclopropyl-5-methyl-1H-pyrazol-4-yl)sulfonyl)-2-((2-hydroxy-2-methylpropanamido)methyl)-3,4-dihydro-2H-benzo[b][1,4]oxazin-6-yl)carbamate | 604 (M + H)+ |

TABLE 13-continued

| Ex. No. | Structure | Name | Observed m/z |
|---|---|---|---|
| 34DJ | 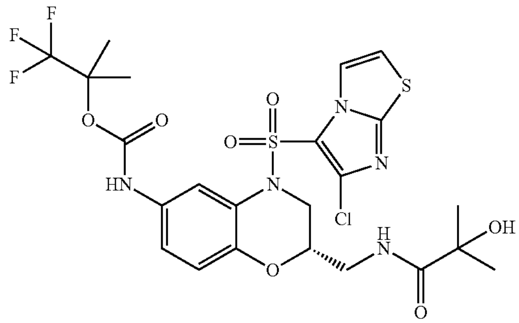 [SMILES: CC(C)(O)C(=O)NC[C@H]1CN(S(=O)(=O)c2c(Cl)nc3sccn23)c2cc(NC(=O)OC(C)(C)C(F)(F)F)ccc2O1] | 2,2,2-trifluoro-1,1-dimethylethyl [(2S)-4-[(6-chloroimidazo[2,1-b][1,3]thiazol-5-yl)sulfonyl]-2-{[(2-hydroxy-2-methylpropanoyl)amino]methyl}-3,4-dihydro-2H-1,4-benzoxazin-6-yl]carbamate | 640 (M + H)+ |
| 34DK | 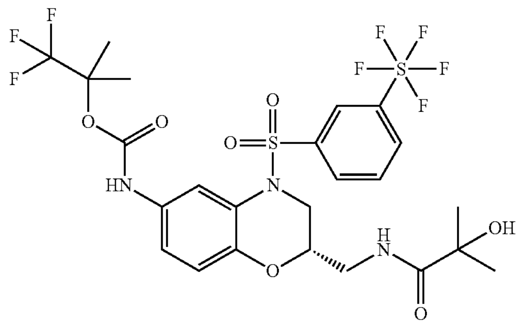 [SMILES: CC(C)(O)C(=O)NC[C@H]1CN(S(=O)(=O)c2cccc(S(F)(F)(F)(F)F)c2)c2cc(NC(=O)OC(C)(C)C(F)(F)F)ccc2O1] | 2,2,2-trifluoro-1,1-dimethylethyl [(2S)-2-{[(2-hydroxy-2-methylpropanoyl)amino]methyl}-4-{[3-(pentafluoro-lambda~6~-sulfanyl)phenyl]sulfonyl}-3,4-dihydro-2H-1,4-benzoxazin-6-yl]carbamate | 686 (M + H)+ |
| 34DL | 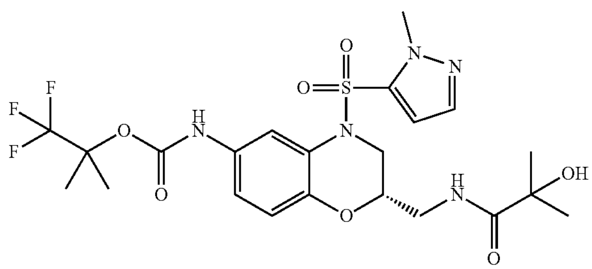 [SMILES: Cn1nccc1S(=O)(=O)N1C[C@H](CNC(=O)C(C)(C)O)Oc2ccc(NC(=O)OC(C)(C)C(F)(F)F)cc21] | 2,2,2-trifluoro-1,1-dimethylethyl {(2S)-2-{[(2-hydroxy-2-methylpropanoyl)amino]methyl}-4-[(1-methyl-1H-pyrazol-5-yl)sulfonyl]-3,4-dihydro-2H-1,4-benzoxazin-6-yl}carbamate | 564 (M + H)+ |
| 34DM | 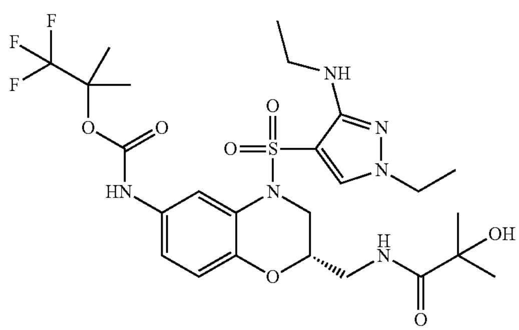 [SMILES: CCNc1nn(CC)cc1S(=O)(=O)N1C[C@H](CNC(=O)C(C)(C)O)Oc2ccc(NC(=O)OC(C)(C)C(F)(F)F)cc21] | 2,2,2-trifluoro-1,1-dimethylethyl [(2S)-4-{[1-ethyl-3-(ethylamino)-1H-pyrazol-4-yl]sulfonyl}-2-{[(2-hydroxy-2-methylpropanoyl)amino]methyl}-3,4-dihydro-2H-1,4-benzoxazin-6-yl]carbamate | 621 (M + H)+ |
| 34DN | 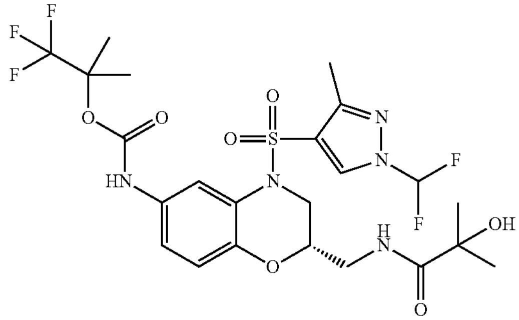 [SMILES: Cc1nn(C(F)F)cc1S(=O)(=O)N1C[C@H](CNC(=O)C(C)(C)O)Oc2ccc(NC(=O)OC(C)(C)C(F)(F)F)cc21] | 2,2,2-trifluoro-1,1-dimethylethyl [(2S)-4-{[1-(difluoromethyl)-3-methyl-1H-pyrazol-4-yl]sulfonyl}-2-{[(2-hydroxy-2-methylpropanoyl)amino]methyl}-3,4-dihydro-2H-1,4-benzoxazin-6-yl]carbamate | 614 (M + H)+ |

Example 35—Synthesis of (S)-1,1,1-trifluoro-2-methylpropan-2-yl (2-(cyclopropanesulfonamidomethyl)-4-((4-fluorophenyl)sulfonyl)-3,4-dihydro-2H-benzo[b][1,4]oxazin-6-yl)carbamate (35)

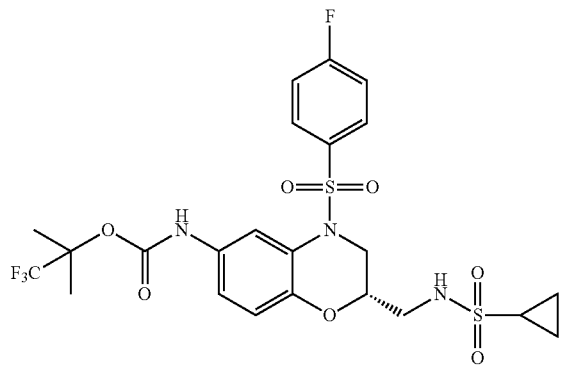 [SMILES: CC(C)(OC(=O)Nc1ccc2c(c1)N(S(=O)(=O)c1ccc(F)cc1)C[C@H](CNS(=O)(=O)C1CC1)O2)C(F)(F)F]

The title compound was prepared according to the procedures described below.

Part I—Synthesis of (R)-tert-butyl (2-(cyclopropanesulfonamidomethyl)-3,4-dihydro-2H-benzo[b][1,4]oxazin-6-yl)carbamate

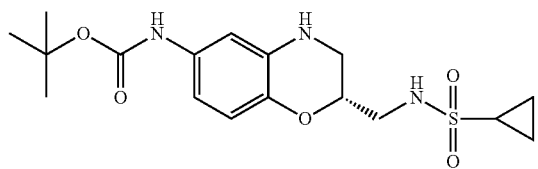 [SMILES: CC(C)(C)OC(=O)Nc1ccc2c(c1)NC[C@H](CNS(=O)(=O)C1CC1)O2]

To a stirred mixture of (S)-tert-butyl (2-(aminomethyl)-3,4-dihydro-2H-benzo[b][1,4]oxazin-6-yl)carbamate (200 mg, 0.716 mmol), cyclopropanesulfonyl chloride (77 µL, 0.716 mmol), and dichloromethane (3580 µL) was added DIEA (188 µL, 1.074 mmol). After 21 hours, the reaction was heated at 40° C. for three additional hours. The mixture was partitioned between ethyl acetate and saturated sodium bicarbonate. The organic layer was washed with brine, dried (MgSO$_4$) and concentrated to afford (R)-tert-butyl (2-(cyclopropanesulfonamidomethyl)-3,4-dihydro-2H-benzo[b][1,4]oxazin-6-yl)carbamate. LRMS (ESI) calculated for C$_{17}$H$_{26}$N$_3$O$_5$S (M+H)$^+$: 384. Found: 384.

Part II—Synthesis of (S)-tert-butyl (2-(cyclopropanesulfonamidomethyl)-4-((4-fluorophenyl)sulfonyl)-3,4-dihydro-2H-benzo[b][1,4]oxazin-6-yl)carbamate

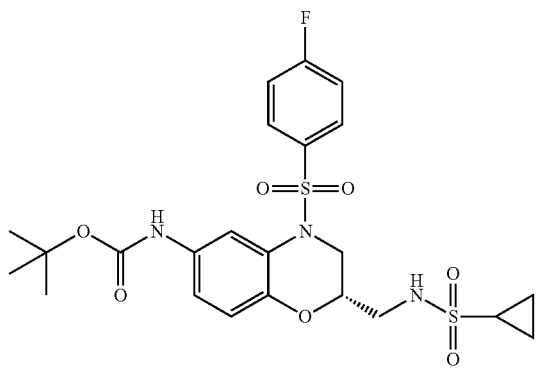 [SMILES: CC(C)(C)OC(=O)Nc1ccc2c(c1)N(S(=O)(=O)c1ccc(F)cc1)C[C@H](CNS(=O)(=O)C1CC1)O2]

A mixture of (R)-tert-butyl (2-(cyclopropanesulfonamidomethyl)-3,4-dihydro-2H-benzo[b][1,4]oxazin-6-yl)carbamate (275 mg, 0.717 mmol), 4-fluorobenzene-1-sulfonyl chloride (419 mg, 2.151 mmol), and pyridine (6 mL) was heated at 60° C. overnight. The mixture was partitioned between ethyl acetate and saturated sodium bicarbonate. The organic layer was washed with brine, dried (MgSO$_4$) and concentrated to afford (S)-tert-butyl (2-(cyclopropanesulfonamidomethyl)-4-((4-fluorophenyl)sulfonyl)-3,4-dihydro-2H-benzo[b][1,4]oxazin-6-yl)carbamate. LRMS (ESI) calculated for C$_{19}$H$_{21}$FN$_3$O$_7$S$_2$ (M-tBu+H)$^+$: 486. Found: 486.

Part III—Synthesis of (S)-2-(cyclopropanesulfonamidomethyl)-4-((4-fluorophenyl)sulfonyl)-3,4-dihydro-2H-benzo[b][1,4]oxazin-6-aminium chloride

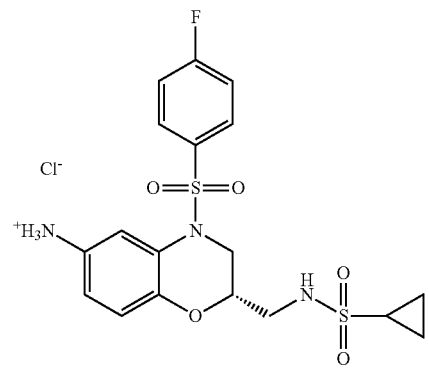

A mixture of (S)-tert-butyl (2-(cyclopropanesulfonamidomethyl)-4-((4-fluorophenyl)sulfonyl)-3,4-dihydro-2H-benzo[b][1,4]oxazin-6-yl)carbamate (388 mg, 0.716 mmol), THF (7164 µL), and 4 M HCl in p-dioxane (2686 µL, 10.75 mmol) was heated at 60° C. for three hours. The crude was concentrated under reduced pressure to obtain the title compound which was used without further purification. LRMS (ESI) calculated for C$_{18}$H$_{21}$FN$_3$O$_5$S$_2$ (M+H)$^+$: 442. Found: 442.

Part IV—Synthesis of (S)-1,1,1-trifluoro-2-methylpropan-2-yl (2-(cyclopropanesulfonamidomethyl)-4-((4-fluorophenyl)sulfonyl)-3,4-dihydro-2H-benzo[b][1,4]oxazin-6-yl)carbamate

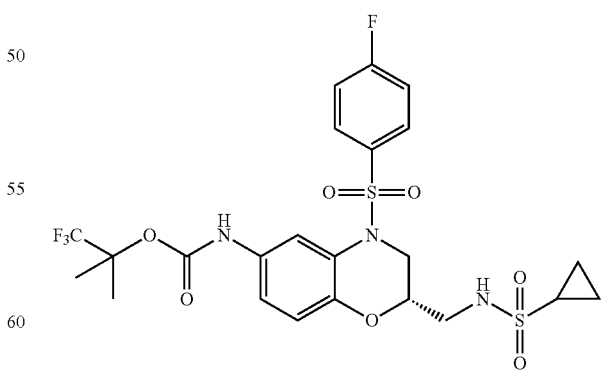

To a mixture of (S)—N-((6-amino-4-((4-fluorophenyl)sulfonyl)-3,4-dihydro-2H-benzo[b][1,4]oxazin-2-yl)methyl)cyclopropanesulfonamide (150 mg, 0.340 mmol), dichloromethane (2265 µL), and triethyl amine (142 µL, 1.019 mmol) was added 4-nitrophenyl (1,1,1-trifluoro-2-methylpropan-2-yl) carbonate (149 mg, 0.510 mmol) and the mixture was stirred at room temperature. After sixteen hours 4-N,N-dimethylaminopyridine (8.30 mg, 0.068 mmol) was added and stirring resumed at room temperature for six hours. The mixture was partitioned between ethyl acetate and saturated sodium bicarbonate. The organic layer was washed with brine, dried (MgSO$_4$) and concentrated. The residue was purified via MPLC eluting with a gradient of 100% hexanes to 100% ethyl acetate to afford the title compound. LRMS (ESI) calculated for $C_{23}H_{26}F_4N_3O_7S_2$ (M+H)$^+$: 596. Found: 596. $^1$H NMR: (300 MHz, CDCl$_3$): δ 9.77 (1H, s), 7.91 (1H, s), 7.78 (2H, m), 7.41 (3H, m), 7.17 (1H, d, J=8.8 Hz), 6.77 (1H, d, J=9.54 Hz), 4.38 (1H, m), 3.44 (1H, m), 3.24 (1H, m), 3.18 (2H, m), 2.56 (1H, m), 1.70 (6H, m), 0.90 (4H, m).

Example 36—Additional 2-cyclopropanesulfamidomethyl benzoxazines

The compounds in Table 14 below were prepared based on the experimental procedures described in Example 35 and elsewhere in the detailed description, and can be achieved by one of skill in the art in light of the present disclosure.

TABLE 14

| Ex. No. | Structure | Name | Observed m/z |
|---|---|---|---|
| 36A | 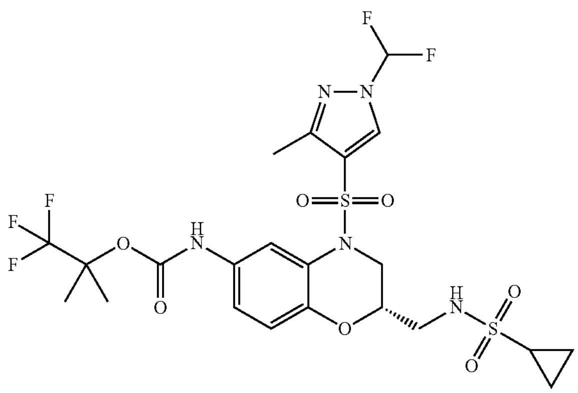 [SMILES: Cc1nn(C(F)F)cc1S(=O)(=O)N1C[C@H](CNS(=O)(=O)C2CC2)Oc2ccc(NC(=O)OC(C)(C)C(F)(F)F)cc21] | (S)-4-((2-(cyclopropanesulfonamidomethyl)-6-((((1,1,1-trifluoro-2-methylpropan-2-yl)oxy)carbonyl)amino)-2H-benzo[b][1,4]oxazin-4(3H)-yl)sulfonyl)-1-(difluoromethyl)-3-methyl-1H-pyrazole | 633.0 (M + H)$^+$ |
| 36B | 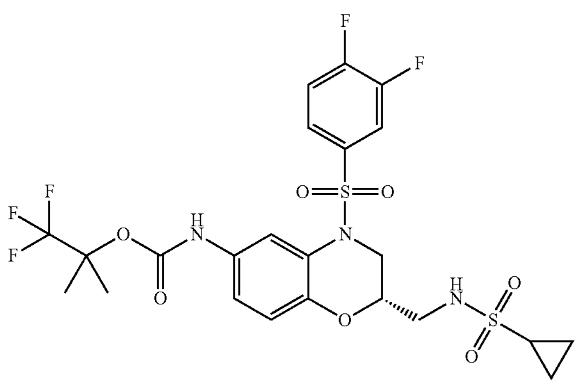 [SMILES: CC(C)(OC(=O)Nc1ccc2c(c1)N(S(=O)(=O)c1ccc(F)c(F)c1)C[C@H](CNS(=O)(=O)C1CC1)O2)C(F)(F)F] | (S)-1,1,1-trifluoro-2-methylpropan-2-yl (2-(cyclopropanesulfonamidomethyl)-4-((3,4-difluorophenyl)sulfonyl)-3,4-dihydro-2H-benzo[b][1,4]oxazin-6-yl)carbamate | 614.2 (M + H)$^+$ |
| 36C | 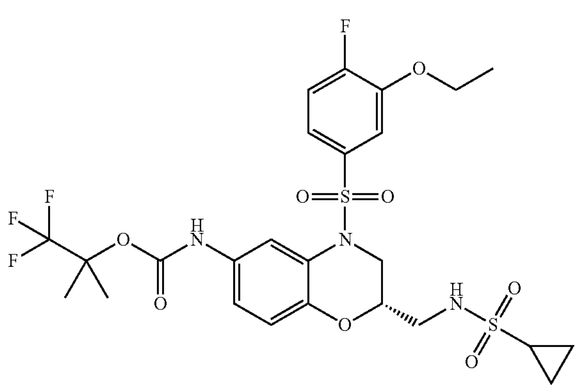 [SMILES: CCOc1cc(S(=O)(=O)N2C[C@H](CNS(=O)(=O)C3CC3)Oc3ccc(NC(=O)OC(C)(C)C(F)(F)F)cc32)ccc1F] | (S)-1,1,1-trifluoro-2-methylpropan-2-yl (2-(cyclopropanesulfonamidomethyl)-4-((3-ethoxy-4-fluorophenyl)sulfonyl)-3,4-dihydro-2H-benzo[b][1,4]oxazin-6-yl)carbamate | 640.0 (M + H)$^+$ |

TABLE 14-continued

| Ex. No. | Structure | Name | Observed m/z |
|---|---|---|---|
| 36D | 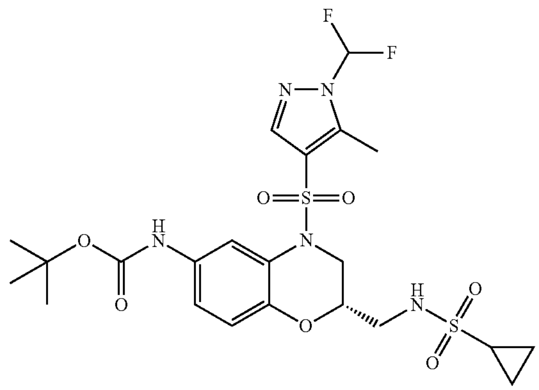 [SMILES: Cc1c(S(=O)(=O)N2C[C@H](CNS(=O)(=O)C3CC3)Oc3ccc(NC(=O)OC(C)(C)C)cc32)cnn1C(F)F] | (S)-tert-buty[ (2-(cyclopropanesulfonamidomethyl)-4-((1-(difluoromethyl)-5-methyl-1H-pyrazol-4-yl)sulfonyl)-3,4-dihydro-2H-benzo[b][1,4]oxazin-6-yl)carbamate | 576.02 (M − H)⁻ |
| 36E | 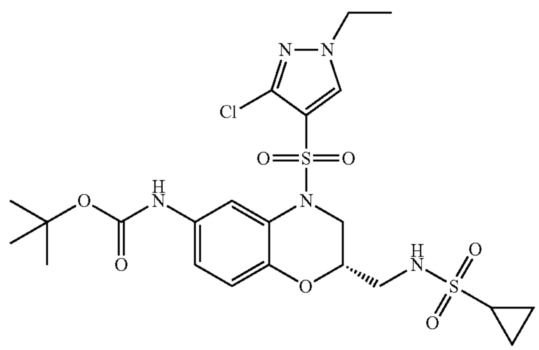 [SMILES: CCn1cc(S(=O)(=O)N2C[C@H](CNS(=O)(=O)C3CC3)Oc3ccc(NC(=O)OC(C)(C)C)cc32)c(Cl)n1] | (S)-4-((6-((tert-butoxycarbonyl)amino)-2-(cyclopropanesulfonamidomethyl)-2H-benzo[b][1,4]oxazin-4(3H)-yl)sulfonyl)-3-chloro-1-ethyl-1H-pyrazole | 598.01 (M + Na)⁺ |
| 36F | 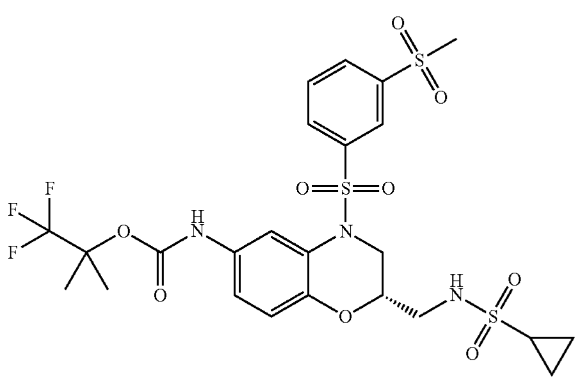 [SMILES: CC(C)(OC(=O)Nc1ccc2c(c1)N(S(=O)(=O)c1cccc(S(C)(=O)=O)c1)C[C@H](CNS(=O)(=O)C1CC1)O2)C(F)(F)F] | (S)-1,1,1-trifluoro-2-methylpropan-2-yl (2-(cyclopropanesulfonamidomethyl)-4-((3-(methylsulfonyl)phenyl)sulfonyl)-3,4-dihydro-2H-benzo[b][1,4]oxazin-6-yl)carbamate | 683.0 (M + NH₄)⁺ |
| 36G | 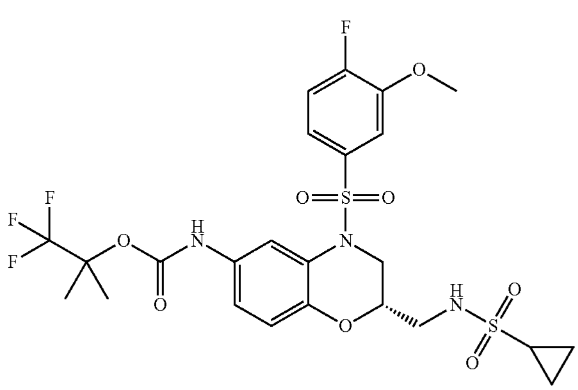 [SMILES: COc1cc(S(=O)(=O)N2C[C@H](CNS(=O)(=O)C3CC3)Oc3ccc(NC(=O)OC(C)(C)C(F)(F)F)cc32)ccc1F] | (S)-1,1,1-trifluoro-2-methylpropan-2-yl (2-(cyclopropanesulfonamidomethyl)-4-((4-fluoro-3-methoxyphenyl)sulfonyl)-3,4-dihydro-2H-benzo[b][1,4]oxazin-6-yl)carbamate | 643.0 (M + NH4)⁺ |

TABLE 14-continued

| Ex. No. | Structure | Name | Observed m/z |
|---|---|---|---|
| 36H | 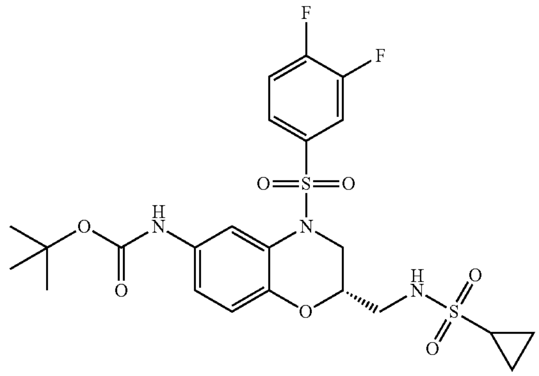 [SMILES: CC(C)(C)OC(=O)Nc1ccc2c(c1)N(S(=O)(=O)c1ccc(F)c(F)c1)C[C@H](CNS(=O)(=O)C1CC1)O2] | (S)-tert-butyl (2-(cyclopropanesulfonamidomethyl)-4-((3,4-difluorophenyl)sulfonyl)-3,4-dihydro-2H-benzo[b][1,4]oxazin-6-yl)carbamate | 504.0 (M + H − tBu)+ |
| 36i | 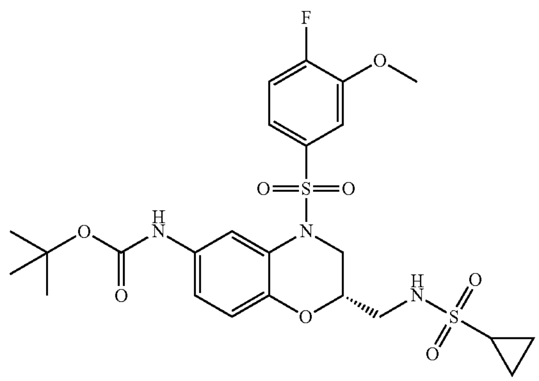 [SMILES: COc1cc(S(=O)(=O)N2C[C@H](CNS(=O)(=O)C3CC3)Oc3ccc(NC(=O)OC(C)(C)C)cc32)ccc1F] | (S)-tert-butyl (2-(cyclopropanesulfonamidomethyl)-4-((4-fluoro-3-methoxyphenyl)sulfonyl)-3,4-dihydro-2H-benzo[b][1,4]oxazin-6-yl)carbamate | 589.2 (M + NH$_4$)+ |
| 36J | 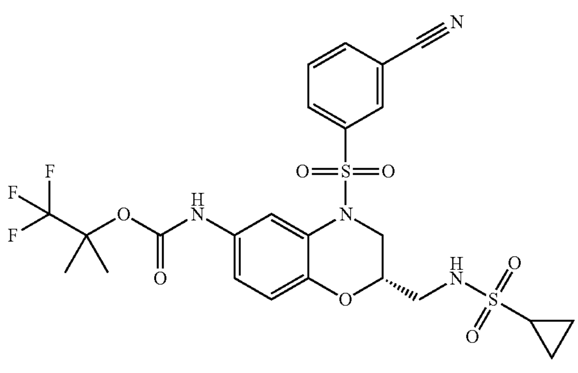 [SMILES: CC(C)(OC(=O)Nc1ccc2c(c1)N(S(=O)(=O)c1cccc(C#N)c1)C[C@H](CNS(=O)(=O)C1CC1)O2)C(F)(F)F] | (S)-1,1,1-trifluoro-2-methylpropan-2-yl (4-((3-cyanophenyl)sulfonyl)-2-(cyclopropanesulfonamidomethyl)-3,4-dihydro-2H-benzo[b][1,4]oxazin-6-yl)carbamate | 620.2 (M + NH$_4$)+ |
| 36K | 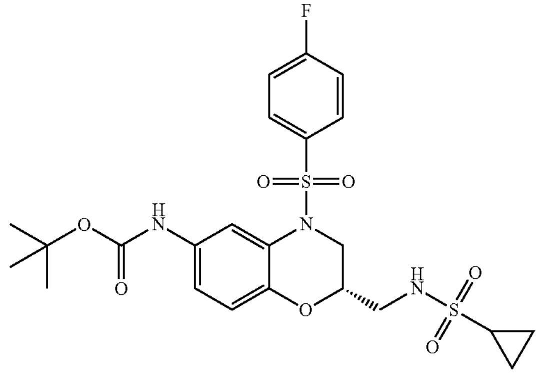 [SMILES: CC(C)(C)OC(=O)Nc1ccc2c(c1)N(S(=O)(=O)c1ccc(F)cc1)C[C@H](CNS(=O)(=O)C1CC1)O2] | (S)-tert-butyl (2-(cyclopropanesulfonamidomethyl)-4-((4-fluorophenyl)sulfonyl)-3,4-dihydro-2H-benzo[b][1,4]oxazin-6-yl)carbamate | 486.1 (M − tBu + H)+ |

TABLE 14-continued

| Ex. No. | Structure | Name | Observed m/z |
|---|---|---|---|
| 36L | 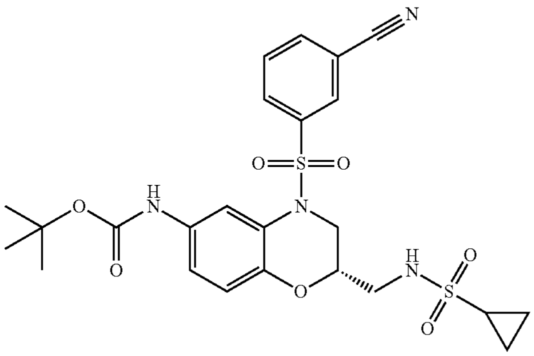 [SMILES: CC(C)(C)OC(=O)Nc1ccc2c(c1)N(S(=O)(=O)c1cccc(C#N)c1)C[C@H](CNS(=O)(=O)C1CC1)O2] | (S)-tert-butyl (4-((3-cyanophenyl)sulfonyl)-2-(cyclopropanesulfonamidomethyl)-3,4-dihydro-2H-benzo[b][1,4]oxazin-6-yl)carbamate | 493.2 (M + H − tBu)+ |
| 36M | 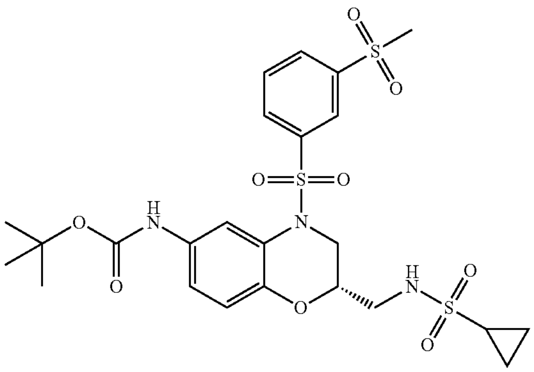 [SMILES: CC(C)(C)OC(=O)Nc1ccc2c(c1)N(S(=O)(=O)c1cccc(S(C)(=O)=O)c1)C[C@H](CNS(=O)(=O)C1CC1)O2] | (S)-tert-butyl (2-(cyclopropanesulfonamidomethyl)-4-((3-(methylsulfonyl)phenyl)sulfonyl)-3,4-dihydro-2H-benzo[b][1,4]oxazin-6-yl)carbamate | 546.0 (M + H − tBu)+ |
| 36N | 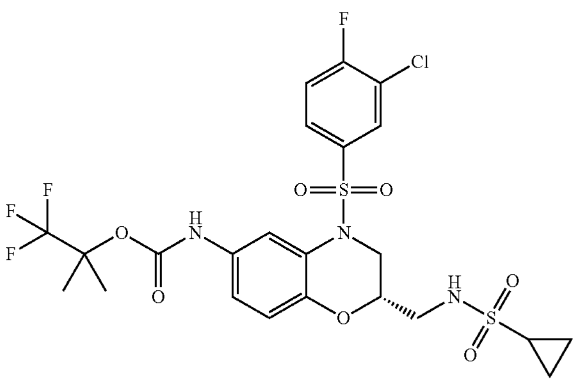 | (S)-1,1,1-trifluoro-2-methylpropan-2-yl (4-((3-chloro-4-fluorophenyl)sulfonyl)-2-(cyclopropanesulfonamidomethyl)-3,4-dihydro-2H-benzo[b][1,4]oxazin-6-yl)carbamate | 631.2 (M + H)+ |
| 36o | 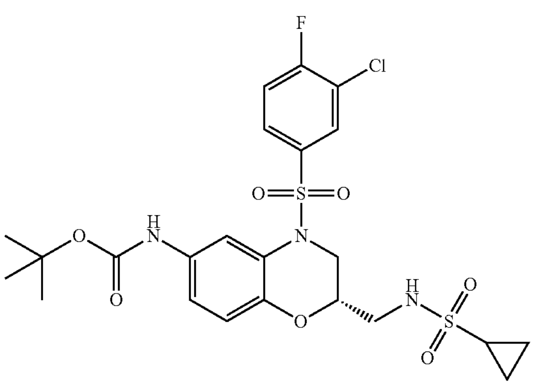 [SMILES: CC(C)(C)OC(=O)Nc1ccc2c(c1)N(S(=O)(=O)c1ccc(F)c(Cl)c1)C[C@H](CNS(=O)(=O)C1CC1)O2] | (S)-tert-butyl (4-((3-chloro-4-fluorophenyl)sulfonyl)-2-(cyclopropanesulfonamidomethyl)-3,4-dihydro-2H-benzo[b][1,4]oxazin-6-yl)carbamate | 520.0 (M + H − tBu)+ |

TABLE 14-continued

| Ex. No. | Structure | Name | Observed m/z |
|---|---|---|---|
| 36P | 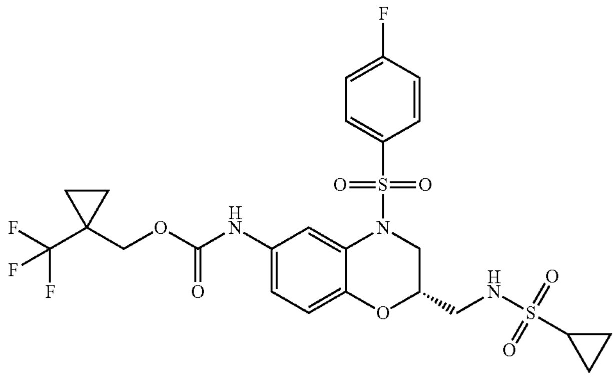 [SMILES: O=C(Nc1ccc2c(c1)N(S(=O)(=O)c1ccc(F)cc1)C[C@H](CNS(=O)(=O)C1CC1)O2)OCC1(C(F)(F)F)CC1] | (S)-(1-(trifluoromethyl)cyclopropyl)methyl (2-(cyclopropanesulfonamidomethyl)-4-((4-fluorophenyl)sulfonyl)-3,4-dihydro-2H-benzo[b][1,4]oxazin-6-yl)carbamate | 608.2 (M + H)+ |
| 36Q | 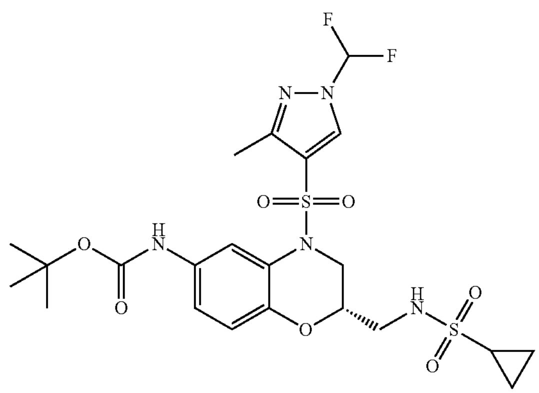 [SMILES: Cc1nn(C(F)F)cc1S(=O)(=O)N1C[C@H](CNS(=O)(=O)C2CC2)Oc2ccc(NC(=O)OC(C)(C)C)cc21] | (S)-4-((6-((tert-butoxycarbonyl)amino)-2-(cyclopropanesulfonamidomethyl)-2H-benzo[b][1,4]oxazin-4(3H)-yl)sulfonyl)-1-(difluoromethyl)-3-methyl-1H-pyrazole | 595.3 (M + NH$_4$)+ |
| 36R | 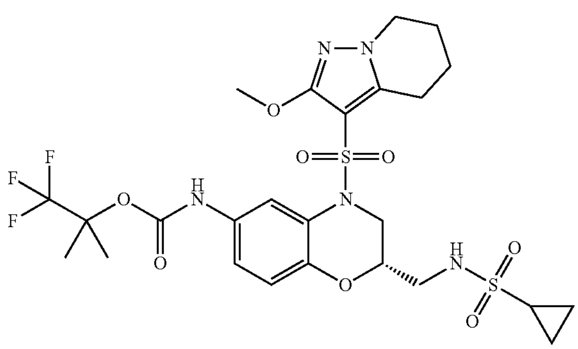 [SMILES: COc1nn2c(c1S(=O)(=O)N1C[C@H](CNS(=O)(=O)C3CC3)Oc3ccc(NC(=O)OC(C)(C)C(F)(F)F)cc31)CCCC2] | 3-(((S)-2-(cyclopropanesulfonamidomethyl)-6-((((1,1,1-trifluoro-2-methylpropan-2-yl)oxy)carbonyl)amino)-2H-benzo[b][1,4]oxazin-4(3H)-yl)sulfonyl)-2-methoxy-5,6,7,8-tetrahydro-4H-pyrazolo[1,5-a]pyridine | 652.2 (M + H)+ |
| 36S | 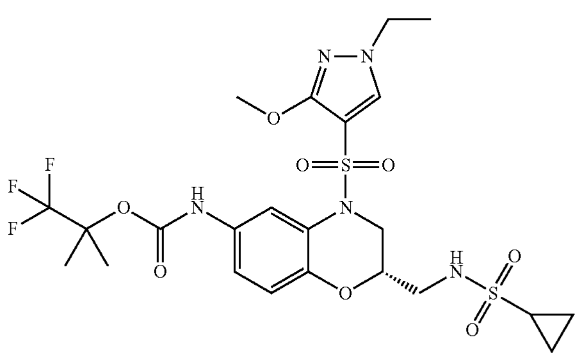 [SMILES: CCn1cc(S(=O)(=O)N2C[C@H](CNS(=O)(=O)C3CC3)Oc3ccc(NC(=O)OC(C)(C)C(F)(F)F)cc32)c(OC)n1] | 4-(((S)-2-(cyclopropanesulfonamidomethyl)-6-((((1,1,1-trifluoro-2-methylpropan-2-yl)oxy)carbonyl)amino)-2H-benzo[b][1,4]oxazin-4(3H)-yl)sulfonyl)-1-ethyl-3-methoxy-1H-pyrazole | 626.1 (M + H)+ |

TABLE 14-continued

| Ex. No. | Structure | Name | Observed m/z |
|---|---|---|---|
| 36T | 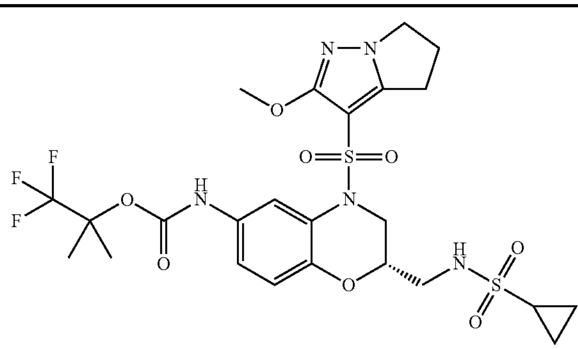 | 3-(((S)-2-(cyclopropanesulfonamidomethyl)-6-(((((1,1,1-trifluoro-2-methylpropan-2-yl)oxy)carbonyl)amino)-2H-benzo[b][1,4]oxazin-4(3H)-yl)sulfonyl)-2-methoxy-4,5,6,7-tetrahydropyrrolo[1,2-b]pyrazole | 660.1 (M + Na)+ |
| 36U | 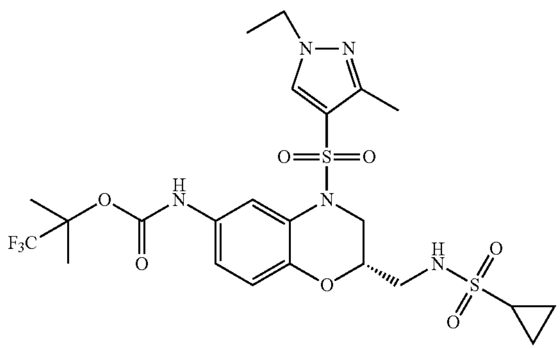 [SMILES: CCn1cc(S(=O)(=O)N2C[C@H](CNS(=O)(=O)C3CC3)Oc3ccc(NC(=O)OC(C)(C)C(F)(F)F)cc32)c(C)n1] | (S)-1,1,1-trifluoro-2-methylpropan-2-yl (2-(cyclopropanesulfonamidomethyl)-4-((1-ethyl-3-methyl-1H-pyrazol-4-yl)sulfonyl)-3,4-dihydro-2H-benzo[b][1,4]oxazin-6-yl)carbamate | 610 (M + H)+ |
| 36V | 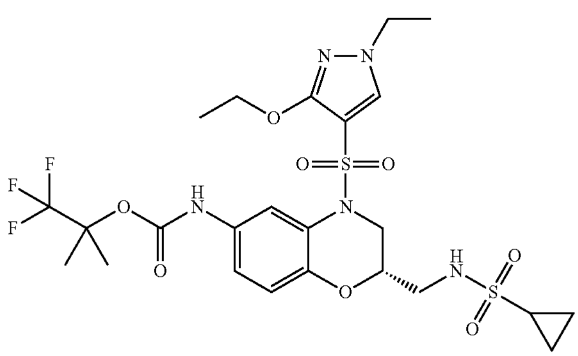 [SMILES: CCOc1nn(CC)cc1S(=O)(=O)N1C[C@H](CNS(=O)(=O)C2CC2)Oc2ccc(NC(=O)OC(C)(C)C(F)(F)F)cc21] | (S)-4-((2-(cyclopropanesulfonamidomethyl)-6-(((((1,1,1-trifluoro-2-methylpropan-2-yl)oxy)carbonyl)amino)-2H-benzo[b][1,4]oxazin-4(3H)-yl)sulfonyl)-3-ethoxy-1-ethyl-1H-pyrazole | 640.1 (M + H)+ |
| 36W | 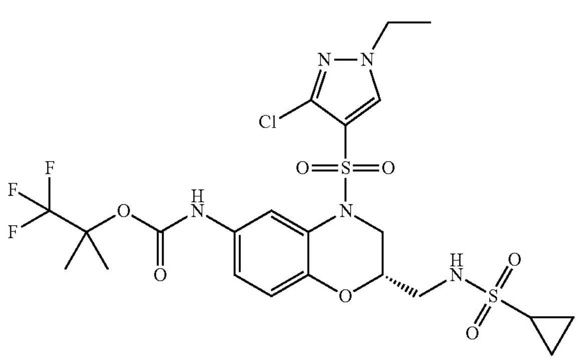 [SMILES: CCn1cc(S(=O)(=O)N2C[C@H](CNS(=O)(=O)C3CC3)Oc3ccc(NC(=O)OC(C)(C)C(F)(F)F)cc32)c(Cl)n1] | (S)-3-chloro-4-((2-(cyclopropanesulfonamidomethyl)-6-(((((1,1,1-trifluoro-2-methylpropan-2-yl)oxy)carbonyl)amino)-2H-benzo[b][1,4]oxazin-4(3H)-yl)sulfonyl)-1-ethyl-1H-pyrazole | 630.1 (M + H)+ |

TABLE 14-continued

| Ex. No. | Structure | Name | Observed m/z |
|---|---|---|---|
| 36X | 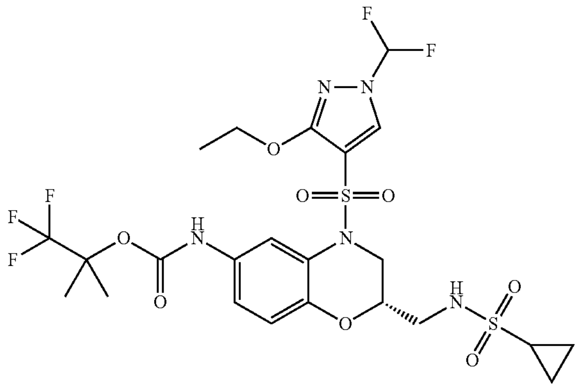 [SMILES: CCOc1nn(C(F)F)cc1S(=O)(=O)N1C[C@H](CNS(=O)(=O)C2CC2)Oc2ccc(NC(=O)OC(C)(C)C(F)(F)F)cc21] | (S)-4-((2-(cyclopropanesulfonamidomethyl)-6-((((1,1,1-trifluoro-2-methylpropan-2-yl)oxy)carbonyl)amino)-2H-benzo[b][1,4]oxazin-4(3H)-yl)sulfonyl)-1-(difluoromethyl)-3-ethoxy-1H-pyrazole | 662.1 (M + H)+ |
| 36Y | 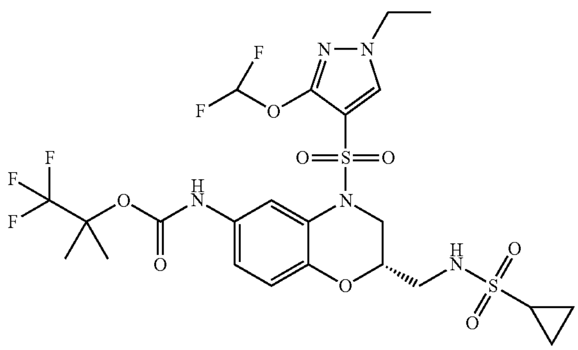 [SMILES: CCn1cc(S(=O)(=O)N2C[C@H](CNS(=O)(=O)C3CC3)Oc3ccc(NC(=O)OC(C)(C)C(F)(F)F)cc32)c(OC(F)F)n1] | (S)-4-((2-(cyclopropanesulfonamidomethyl)-6-((((1,1,1-trifluoro-2-methylpropan-2-yl)oxy)carbonyl)amino)-2H-benzo[b][1,4]oxazin-4(3H)-yl)sulfonyl)-3-(difluoromethoxy)-1-ethyl-1H-pyrazole | 662.0 (M + H)+ |
| 36Z | 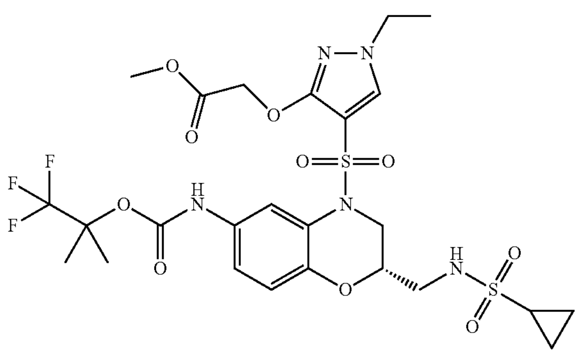 [SMILES: CCn1cc(S(=O)(=O)N2C[C@H](CNS(=O)(=O)C3CC3)Oc3ccc(NC(=O)OC(C)(C)C(F)(F)F)cc32)c(OCC(=O)OC)n1] | (S)-4-((2-(cyclopropanesulfonamidomethyl)-6-((((1,1,1-trifluoro-2-methylpropan-2-yl)oxy)carbonyl)amino)-2H-benzo[b][1,4]oxazin-4(3H)-yl)sulfonyl)-1-ethyl-3-(2-methoxy-2-oxoethoxy)-1H-pyrazole | 684.0 (M + H)+ |
| 36AA | 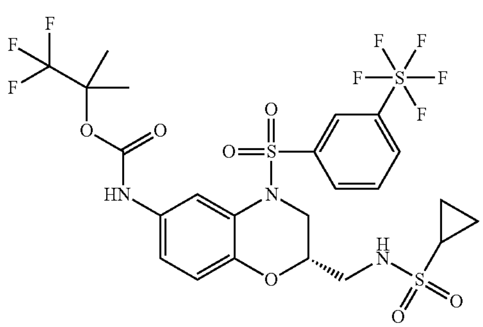 [SMILES: CC(C)(OC(=O)Nc1ccc2c(c1)N(S(=O)(=O)c1cccc(S(F)(F)(F)(F)F)c1)C[C@H](CNS(=O)(=O)C1CC1)O2)C(F)(F)F] | 2,2,2-trifluoro-1,1-dimethylethyl [(2S)-2-{[(cyclopropylsulfonyl)amino]methyl}-4-{[3-(pentafluoro-lambda~6~-sulfanyl)phenyl]sulfonyl}-3,4-dihydro-2H-1,4-benzoxazin-6-yl]carbamate | 704 (M + H)+ |

Example 37—Preparation of Methylsulfonamides of Aminobenzoxazines

The compounds in Table 15 below were prepared based on the experimental procedures described in Example 35 and elsewhere in the detailed description, and can be achieved by one of skill in the art in light of the present disclosure.

TABLE 15

| Ex. No. | Structure | Name | Observed m/z |
|---|---|---|---|
| 37A | 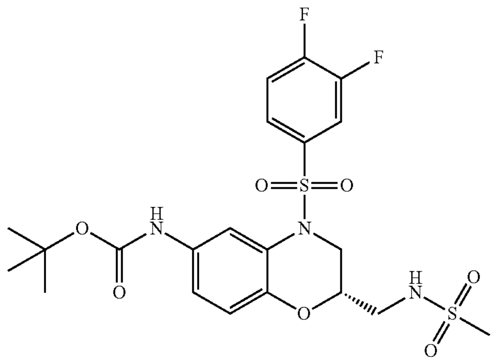 [SMILES: CC(C)(C)OC(=O)Nc1ccc2c(c1)N(S(=O)(=O)c1ccc(F)c(F)c1)C[C@H](CNS(C)(=O)=O)O2] | (S)-tert-butyl (4-((3,4-difluorophenyl)sulfonyl)-2-(methylsulfonamidomethyl)-3,4-dihydro-2H-benzo[b][1,4]oxazin-6-yl)carbamate | 479.0 (M − tBu + H)+ |
| 37B | 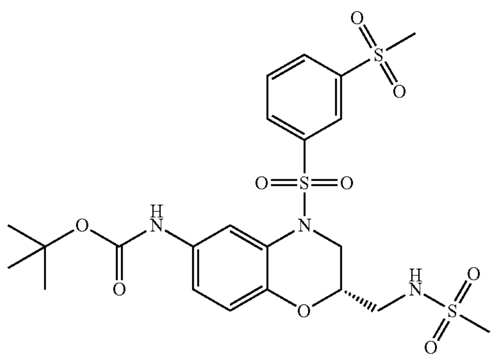 [SMILES: CC(C)(C)OC(=O)Nc1ccc2c(c1)N(S(=O)(=O)c1cccc(S(C)(=O)=O)c1)C[C@H](CNS(C)(=O)=O)O2] | (S)-tert-butyl (2-(methylsulfonamidomethyl)-4-((3-(methylsulfonyl)phenyl)sulfonyl)-3,4-dihydro-2H-benzo[b][1,4]oxazin-6-yl)carbamate | 520.0 (M + H − tBu)+ |
| 37C | 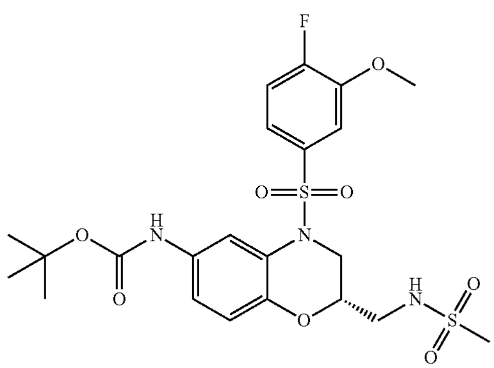 | (S)-tert-butyl (4-((4-fluoro-3-methoxyphenyl)sulfonyl)-2-(methylsulfonamidomethyl)-3,4-dihydro-2H-benzo[b][1,4]oxazin-6-yl)carbamate | 490.0 (M + H − tBu)+ |
| 37D | 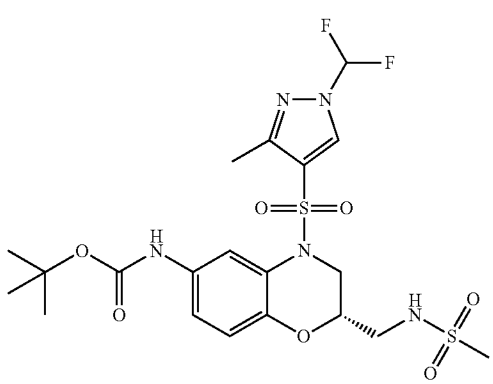 [SMILES: Cc1nn(C(F)F)cc1S(=O)(=O)N1C[C@H](CNS(C)(=O)=O)Oc2ccc(NC(=O)OC(C)(C)C)cc21] | (S)-4-((6-((tert-butoxycarbonyl)amino)-2-(methylsulfonamidomethyl)-2H-benzo[b][1,4]oxazin-4(3H)-yl)sulfonyl)-1-(difluoromethyl)-3-methyl-1H-pyrazole | 496.0 (M + H − tBu)+ |

TABLE 15-continued

| Ex. No. | Structure | Name | Observed m/z |
|---|---|---|---|
| 37E | 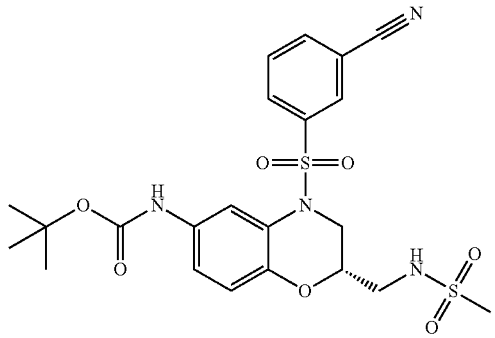 [SMILES: CC(C)(C)OC(=O)Nc1ccc2c(c1)N(S(=O)(=O)c1cccc(C#N)c1)C[C@H](CNS(C)(=O)=O)O2] | (S)-tert-butyl (4-((3-cyanophenyl)sulfonyl)-2-(methylsulfonamidomethyl)-3,4-dihydro-2H-benzo[b][1,4]oxazin-6-yl)carbamate | 467.0 (M + H − tBu)+ |
| 37F | 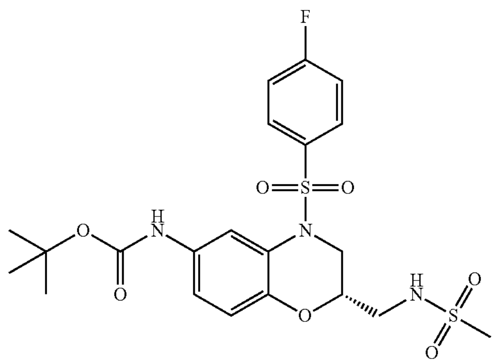 [SMILES: CC(C)(C)OC(=O)Nc1ccc2c(c1)N(S(=O)(=O)c1ccc(F)cc1)C[C@H](CNS(C)(=O)=O)O2] | (S)-tert-butyl (4-((4-fluorophenyl)sulfonyl)-2-(methylsulfonamidomethyl)-3,4-dihydro-2H-benzo[b][1,4]oxazin-6-yl)carbamate | 460.0 (M − tBu + H)+ |
| 37G | 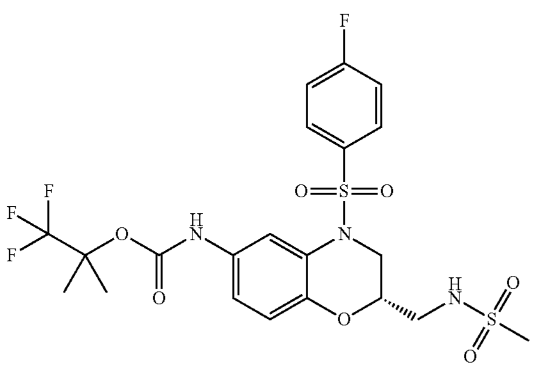 [SMILES: CC(C)(OC(=O)Nc1ccc2c(c1)N(S(=O)(=O)c1ccc(F)cc1)C[C@H](CNS(C)(=O)=O)O2)C(F)(F)F] | (S)-1,1,1-trifluoro-2-methylpropan-2-yl (4-((4-fluorophenyl)sulfonyl)-2-(methylsulfonamidomethyl)-3,4-dihydro-2H-benzo[b][1,4]oxazin-6-yl)carbamate | 570.1 (M + H)+ |
| 37H | 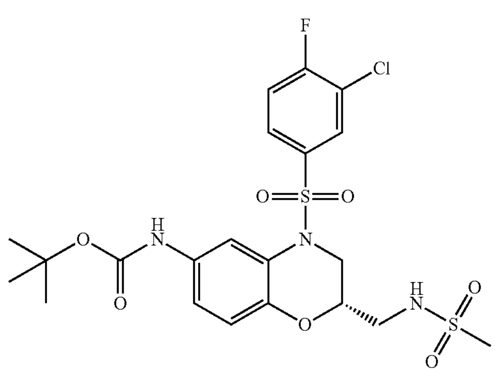 [SMILES: CC(C)(C)OC(=O)Nc1ccc2c(c1)N(S(=O)(=O)c1ccc(F)c(Cl)c1)C[C@H](CNS(C)(=O)=O)O2] | (S)-tert-butyl (4-((3-chloro-4-fluorophenyl)sulfonyl)-2-(methylsulfonamidomethyl)-3,4-dihydro-2H-benzo[b][1,4]oxazin-6-yl)carbamate | 551.0 (M + H)+ |

TABLE 15-continued

| Ex. No. | Structure | Name | Observed m/z |
|---|---|---|---|
| 37i | 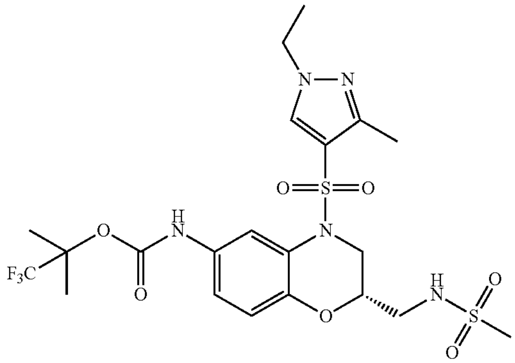 [SMILES: CCn1cc(S(=O)(=O)N2C[C@H](CNS(C)(=O)=O)Oc3ccc(NC(=O)OC(C)(C)C(F)(F)F)cc32)c(C)n1] | (S)-1,1,1-trifluoro-2-methylpropan-2-yl (4-((1-ethyl-3-methyl-1H-pyrazol-4-yl)sulfonyl)-2-(methylsulfonamidomethyl)-3,4-dihydro-2H-benzo[b][1,4]oxazin-6-yl)carbamate | 584 (M + H)+ |
| 37J | 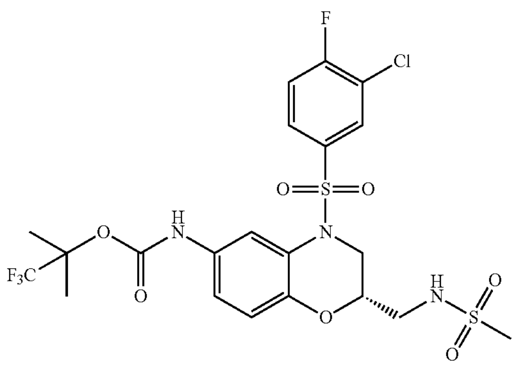 [SMILES: CC(C)(OC(=O)Nc1ccc2c(c1)N(S(=O)(=O)c1ccc(F)c(Cl)c1)C[C@H](CNS(C)(=O)=O)O2)C(F)(F)F] | (S)-1,1,1-trifluoro-2-methylpropan-2-yl (4-((3-chloro-4-fluorophenyl)sulfonyl)-2-(methylsulfonamidomethyl)-3,4-dihydro-2H-benzo[b][1,4]oxazin-6-yl)carbamate | 604 (M + H)+ |

Example 38—Additional Sulfonamides of Aminobenzoxazines

The compounds in Table 16 below were prepared based on the experimental procedures described in Example 35 and elsewhere in the detailed description utilizing the appropriate sulfonyl halide in place of cyclopropane sulfonyl halide, and can be achieved by one of skill in the art in light of the present disclosure.

TABLE 16

| Ex. No. | Structure | Name | Observed m/z |
|---|---|---|---|
| 38A | 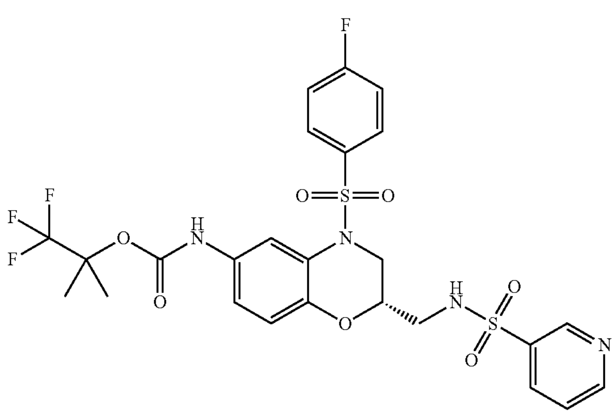 [SMILES: CC(C)(OC(=O)Nc1ccc2c(c1)N(S(=O)(=O)c1ccc(F)cc1)C[C@H](CNS(=O)(=O)c1cccnc1)O2)C(F)(F)F] | (S)-1,1,1-trifluoro-2-methylpropan-2-yl (4-((4-fluorophenyl)sulfonyl)-2-((pyridine-3-sulfonamido)methyl)-3,4-dihydro-2H-benzo[b][1,4]oxazin-6-yl)carbamate | 633.2 (M + H)+ |

TABLE 16-continued

| Ex. No. | Structure | Name | Observed m/z |
|---|---|---|---|
| 38B | 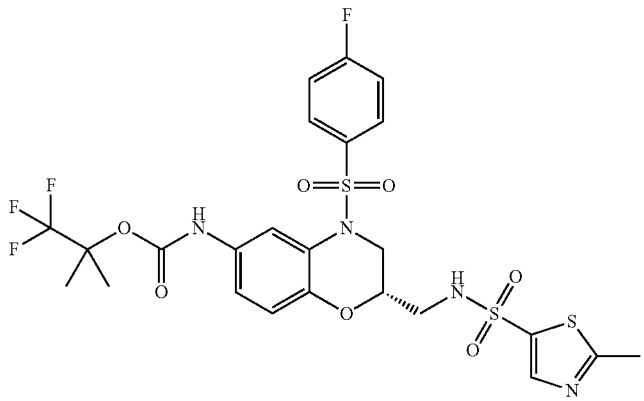 | (S)-5-(N-(4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)sulfamoyl)-2-methylthiazole | 596.0 (M + H)+ |
| 38C | 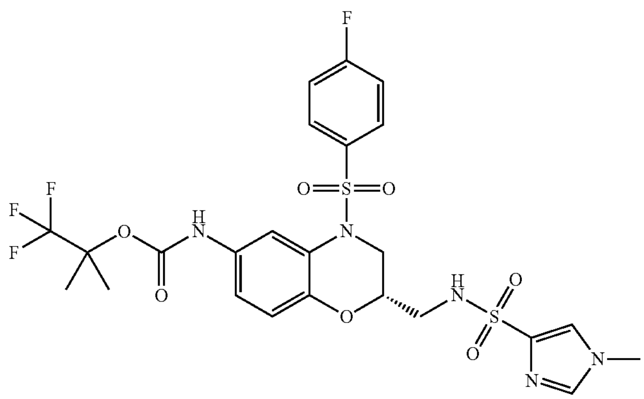 [SMILES: Cn1cnc(S(=O)(=O)NC[C@H]2CN(S(=O)(=O)c3ccc(F)cc3)c3cc(NC(=O)OC(C)(C)C(F)(F)F)ccc3O2)c1] | (S)-1,1,1-trifluoro-2-methylpropan-2-yl (4-((4-fluorophenyl)sulfonyl)-2-((1-methyl-1H-imidazole-4-sulfonamido)methyl)-3,4-dihydro-2H-benzo[b][1,4]oxazin-6-yl)carbamate | 636.2 (M + H)+ |
| 38D | 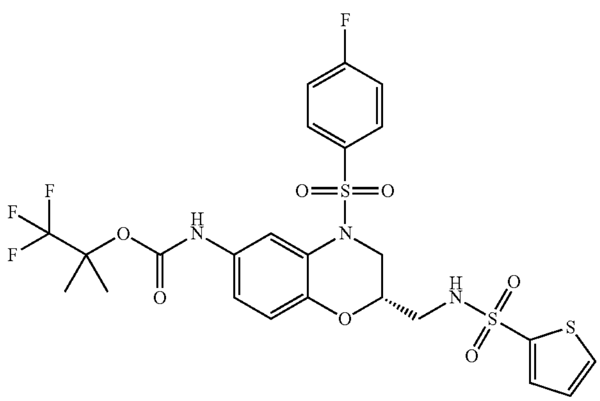 [SMILES: CC(C)(OC(=O)Nc1ccc2c(c1)N(S(=O)(=O)c1ccc(F)cc1)C[C@H](CNS(=O)(=O)c1cccs1)O2)C(F)(F)F] | (S)-1,1,1-trifluoro-2-methylpropan-2-yl (4-((4-fluorophenyl)sulfonyl)-2-((thiophene-2-sulfonamido)methyl)-3,4-dihydro-2H-benzo[b][1,4]oxazin-6-yl)carbamate | 638.2 (M + H)+ |
| 38E | 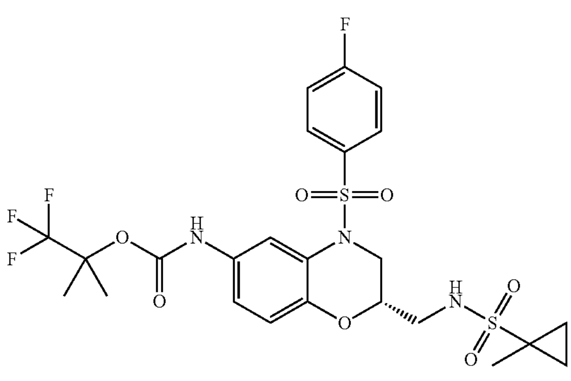 [SMILES: CC(C)(OC(=O)Nc1ccc2c(c1)N(S(=O)(=O)c1ccc(F)cc1)C[C@H](CNS(=O)(=O)C1(C)CC1)O2)C(F)(F)F] | (S)-1,1,1-trifluoro-2-methylpropan-2-yl (4-((4-fluorophenyl)sulfonyl)-2-((1-methylcyclopropanesulfonamido)methyl)-3,4-dihydro-2H-benzo[b][1,4]oxazin-6-yl)carbamate | 610.1 (M + H)+ |

TABLE 16-continued

| Ex. No. | Structure | Name | Observed m/z |
| --- | --- | --- | --- |
| 38F | 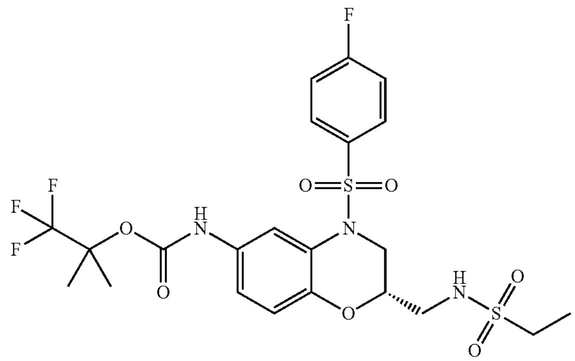 [SMILES: CCS(=O)(=O)NC[C@H]1CN(S(=O)(=O)c2ccc(F)cc2)c2cc(NC(=O)OC(C)(C)C(F)(F)F)ccc2O1] | (S)-1,1,1-trifluoro-2-methylpropan-2-yl (2-(ethylsulfonamidomethyl)-4-((4-fluorophenyl)sulfonyl)-3,4-dihydro-2H-benzo[b][1,4]oxazin-6-yl)carbamate | 584.2 (M + H)+ |
| 38G | 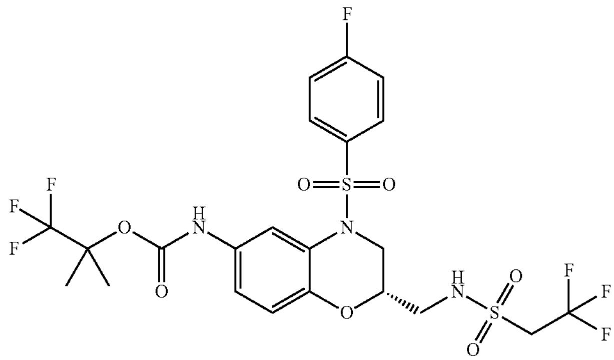 [SMILES: CC(C)(OC(=O)Nc1ccc2c(c1)N(S(=O)(=O)c1ccc(F)cc1)C[C@H](CNS(=O)(=O)CC(F)(F)F)O2)C(F)(F)F] | (S)-1,1,1-trifluoro-2-methylpropan-2-yl (4-((4-fluorophenyl)sulfonyl)-2-(((2,2,2-trifluoroethylsulfonamido)methyl)-3,4-dihydro-2H-benzo[b][1,4]oxazin-6-yl)carbamate | 638.0 (M + H)+ |
| 38H | 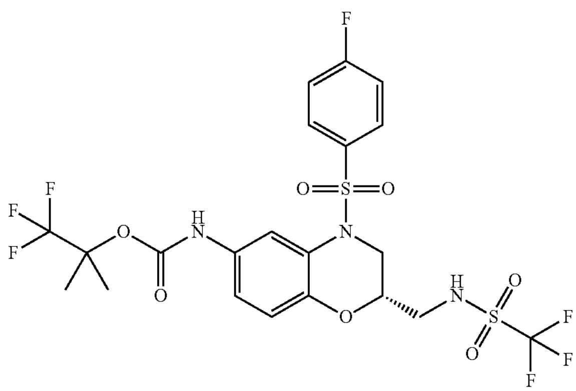 [SMILES: CC(C)(OC(=O)Nc1ccc2c(c1)N(S(=O)(=O)c1ccc(F)cc1)C[C@H](CNS(=O)(=O)C(F)(F)F)O2)C(F)(F)F] | (S)-1,1,1-trifluoro-2-methylpropan-2-yl (4-((4-fluorophenyl)sulfonyl)-2-((trifluoromethylsulfonamido)methyl)-3,4-dihydro-2H-benzo[b][1,4]oxazin-6-yl)carbamate | 624.1 (M + H)+ |
| 38i | 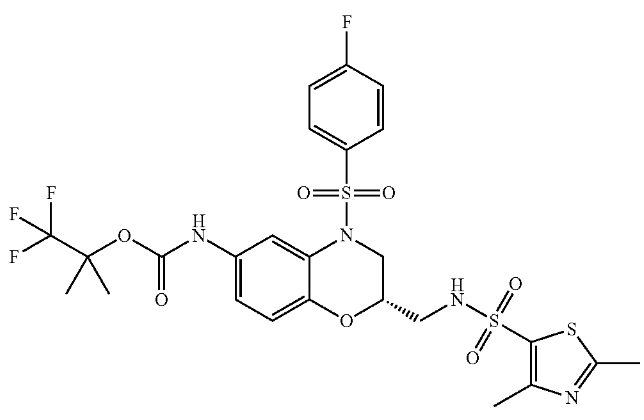 [SMILES: Cc1nc(C)c(S(=O)(=O)NC[C@H]2CN(S(=O)(=O)c3ccc(F)cc3)c3cc(NC(=O)OC(C)(C)C(F)(F)F)ccc3O2)s1] | (S)-5-(N-(4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)sulfamoyl)-2,4-dimethylthiazole | 667 (M + H)+ |

TABLE 16-continued

| Ex. No. | Structure | Name | Observed m/z |
|---|---|---|---|
| 38J | 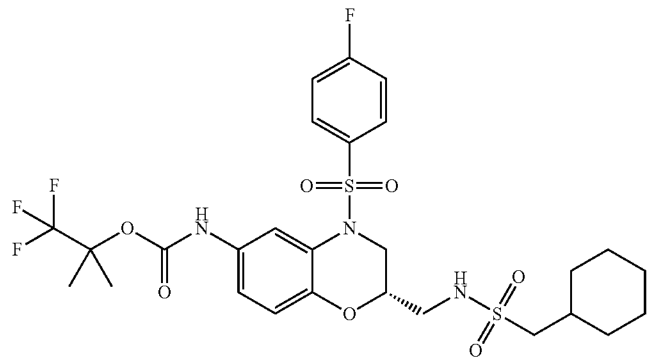 | (S)-1,1,1-trifluoro-2-methylpropan-2-yl (2-((cyclohexylmethylsulfonamido)methyl)-4-((4-fluorophenyl)sulfonyl)-3,4-dihydro-2H-benzo[b][1,4]oxazin-6-yl)carbamate | 652 (M + H)+ |
| 38K | 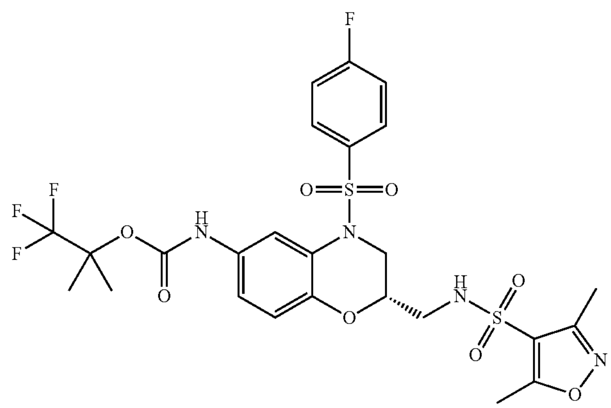 [SMILES: Cc1noc(C)c1S(=O)(=O)NC[C@H]1CN(S(=O)(=O)c2ccc(F)cc2)c2cc(NC(=O)OC(C)(C)C(F)(F)F)ccc2O1] | (S)-4-(N-(4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)sulfamoyl)-3,5-dimethylisoxazole | 651 (M + H)+ |
| 38L | 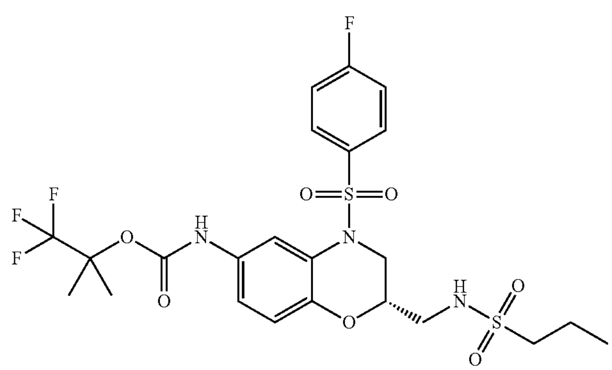 [SMILES: CCCS(=O)(=O)NC[C@H]1CN(S(=O)(=O)c2ccc(F)cc2)c2cc(NC(=O)OC(C)(C)C(F)(F)F)ccc2O1] | (S)-1,1,1-trifluoro-2-methylpropan-2-yl (4-((4-fluorophenyl)sulfonyl)-2-(propylsulfonamidomethyl)-3,4-dihydro-2H-benzo[b][1,4]oxazin-6-yl)carbamate | 598 (M + H)+ |
| 38M | 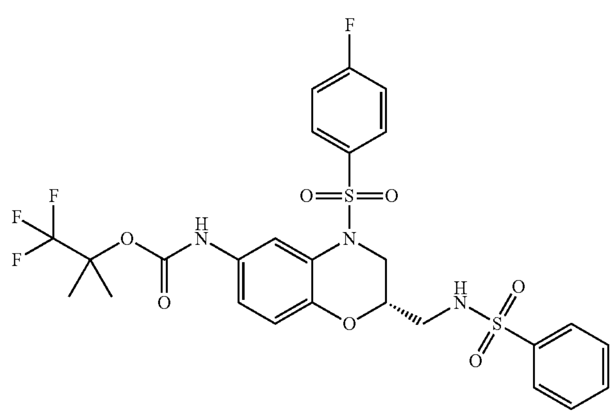 [SMILES: CC(C)(OC(=O)Nc1ccc2c(c1)N(S(=O)(=O)c1ccc(F)cc1)C[C@H](CNS(=O)(=O)c1ccccc1)O2)C(F)(F)F] | (S)-1,1,1-trifluoro-2-methylpropan-2-yl (4-((4-fluorophenyl)sulfonyl)-2-(phenylsulfonamidomethyl)-3,4-dihydro-2H-benzo[b][1,4]oxazin-6-yl)carbamate | 632 (M + H)+ |

TABLE 16-continued

| Ex. No. | Structure | Name | Observed m/z |
|---|---|---|---|
| 38N | 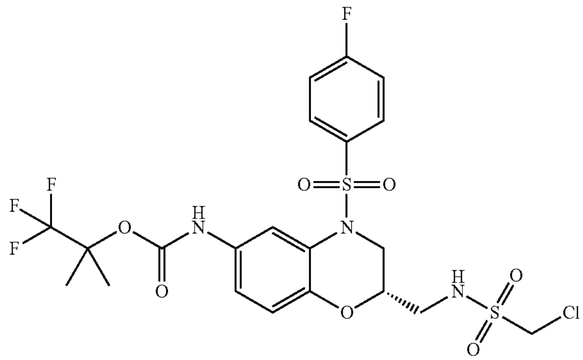 [SMILES: CC(C)(OC(=O)Nc1ccc2c(c1)N(S(=O)(=O)c1ccc(F)cc1)C[C@H](CNS(=O)(=O)CCl)O2)C(F)(F)F] | (S)-1,1,1-trifluoro-2-methylpropan-2-yl (2-((chloromethylsulfonamido)methyl)-4-((4-fluorophenyl)sulfonyl)-3,4-dihydro-2H-benzo[b][1,4]oxazin-6-yl)carbamate | 604 (M + H)+ |
| 38o | 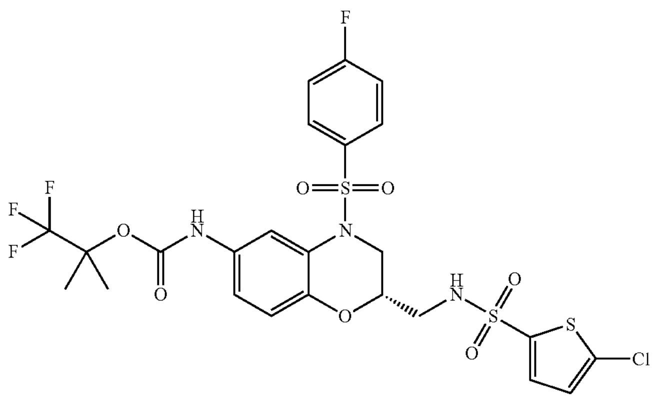 [SMILES: CC(C)(OC(=O)Nc1ccc2c(c1)N(S(=O)(=O)c1ccc(F)cc1)C[C@H](CNS(=O)(=O)c1ccc(Cl)s1)O2)C(F)(F)F] | (S)-1,1,1-trifluoro-2-methylpropan-2-yl (2-((5-chlorothiophene-2-sulfonamido)methyl)-4-((4-fluorophenyl)sulfonyl)-3,4-dihydro-2H-benzo[b][1,4]oxazin-6-yl)carbamate | 672 (M + H)+ |
| 38P | 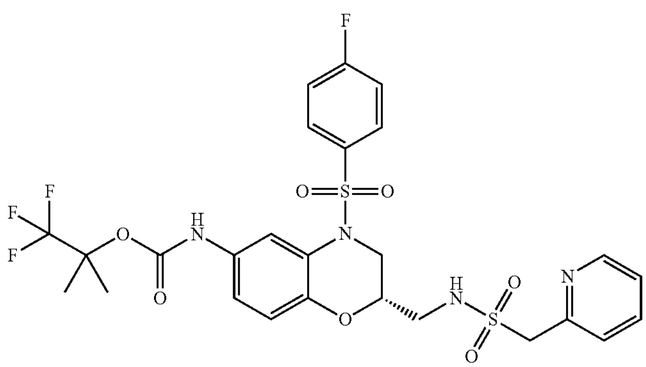 [SMILES: CC(C)(OC(=O)Nc1ccc2c(c1)N(S(=O)(=O)c1ccc(F)cc1)C[C@H](CNS(=O)(=O)Cc1ccccn1)O2)C(F)(F)F] | (S)-2-((N-(4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)sulfamoyl)methyl)pyridine | 647 (M + H)+ |
| 38Q | 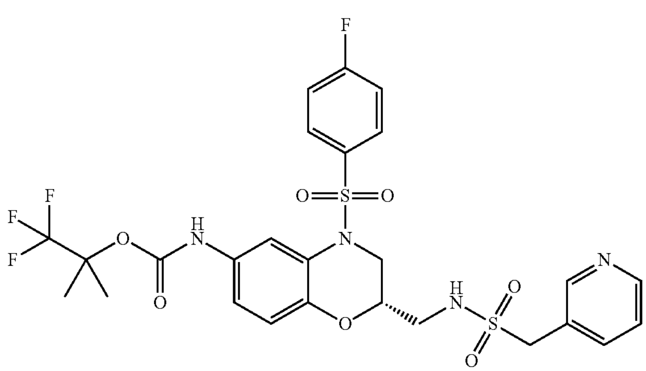 [SMILES: CC(C)(OC(=O)Nc1ccc2c(c1)N(S(=O)(=O)c1ccc(F)cc1)C[C@H](CNS(=O)(=O)Cc1cccnc1)O2)C(F)(F)F] | (S)-3-((N-(4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)sulfamoyl)methyl)pyridine | 647 (M + H)+ |

TABLE 16-continued

| Ex. No. | Structure | Name | Observed m/z |
|---|---|---|---|
| 38R | 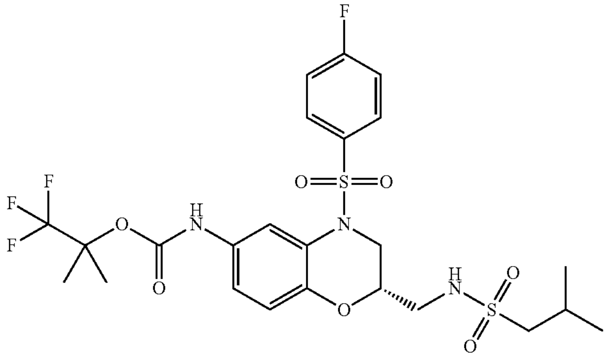 [SMILES: CC(C)CS(=O)(=O)NC[C@H]1CN(S(=O)(=O)c2ccc(F)cc2)c2cc(NC(=O)OC(C)(C)C(F)(F)F)ccc2O1] | (S)-1,1,1-trifluoro-2-methylpropan-2-yl (4-((4-fluorophenyl)sulfonyl)-2-((2-methylpropylsulfonamido)methyl)-3,4-dihydro-2H-benzo[b][1,4]oxazin-6-yl)carbamate | 612 (M + H)+ |
| 38S | 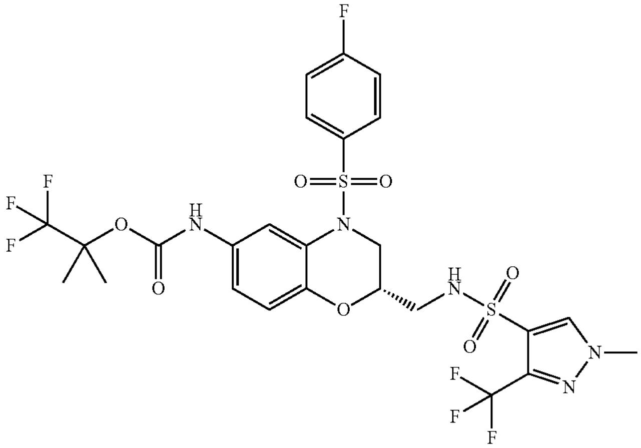 [SMILES: Cn1cc(S(=O)(=O)NC[C@H]2CN(S(=O)(=O)c3ccc(F)cc3)c3cc(NC(=O)OC(C)(C)C(F)(F)F)ccc3O2)c(C(F)(F)F)n1] | (S)-4-(N-(4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)sulfamoyl)-1-methyl-3-(trifluoromethyl)-1H-pyrazole | 704 (M + H)+ |
| 38T | 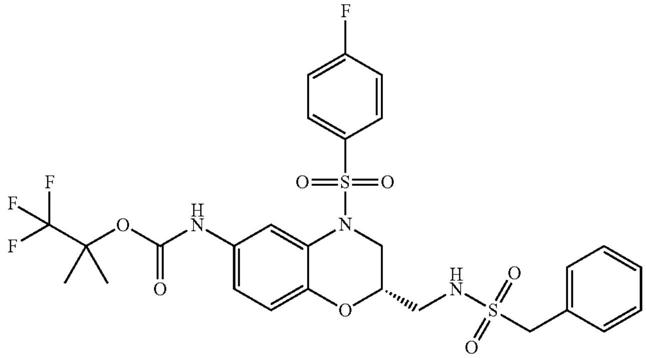 [SMILES: CC(C)(OC(=O)Nc1ccc2c(c1)N(S(=O)(=O)c1ccc(F)cc1)C[C@H](CNS(=O)(=O)Cc1ccccc1)O2)C(F)(F)F] | (S)-1,1,1-trifluoro-2-methylpropan-2-yl (4-((4-fluorophenyl)sulfonyl)-2-((phenylmethylsulfonamido)methyl)-3,4-dihydro-2H-benzo[b][1,4]oxazin-6-yl)carbamate | 646 (M + H)+ |
| 38U | 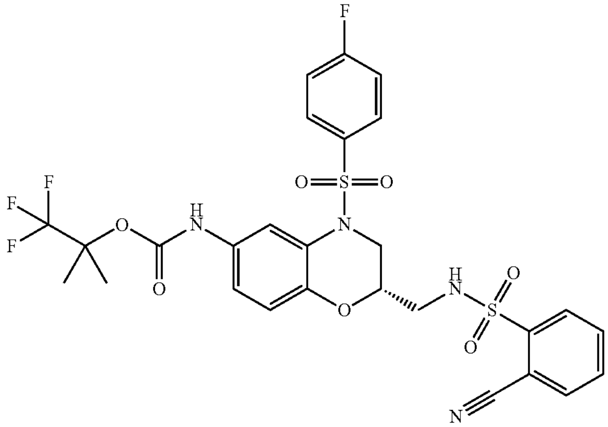 [SMILES: CC(C)(OC(=O)Nc1ccc2c(c1)N(S(=O)(=O)c1ccc(F)cc1)C[C@H](CNS(=O)(=O)c1ccccc1C#N)O2)C(F)(F)F] | (S)-1,1,1-trifluoro-2-methylpropan-2-yl (2-((2-cyanophenylsulfonamido)methyl)-4-((4-fluorophenyl)sulfonyl)-3,4-dihydro-2H-benzo[b][1,4]oxazin-6-yl)carbamate | 657 (M + H)+ |

TABLE 16-continued

| Ex. No. | Structure | Name | Observed m/z |
|---|---|---|---|
| 38V | 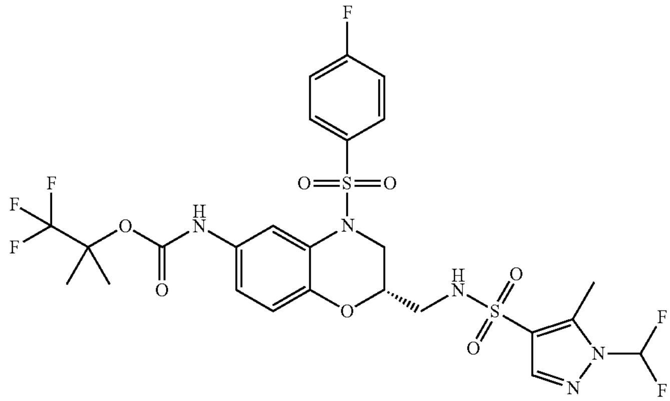 [SMILES: Cc1c(S(=O)(=O)NC[C@H]2CN(S(=O)(=O)c3ccc(F)cc3)c3cc(NC(=O)OC(C)(C)C(F)(F)F)ccc3O2)cnn1C(F)F] | (S)-1-(difluoromethyl)-4-(N-((4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)sulfamoyl)-5-methyl-1H-pyrazole | 686 (M + H)+ |
| 38W | 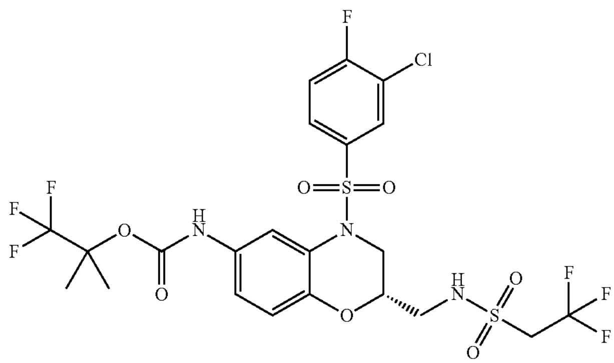 [SMILES: CC(C)(OC(=O)Nc1ccc2c(c1)N(S(=O)(=O)c1ccc(F)c(Cl)c1)C[C@H](CNS(=O)(=O)CC(F)(F)F)O2)C(F)(F)F] | (S)-1,1,1-trifluoro-2-methylpropan-2-yl (4-((3-chloro-4-fluorophenyl)sulfonyl)-2-((2,2,2-trifluoroethylsulfonamido)methyl)-3,4-dihydro-2H-benzo[b][1,4]oxazin-6-yl)carbamate | 672.0 (M + H)+ |
| 38X | 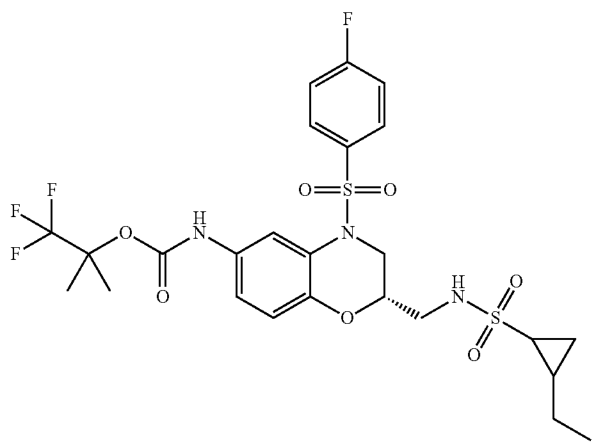 [SMILES: CCC1CC1S(=O)(=O)NC[C@H]1CN(S(=O)(=O)c2ccc(F)cc2)c2cc(NC(=O)OC(C)(C)C(F)(F)F)ccc2O1] | 1,1,1-trifluoro-2-methylpropan-2-yl ((2S)-2-((2-ethylcyclopropanesulfonamido)methyl)-4-((4-fluorophenyl)sulfonyl)-3,4-dihydro-2H-benzo[b][1,4]oxazin-6-yl)carbamate | 624 (M + H)+ |
| 38Y | 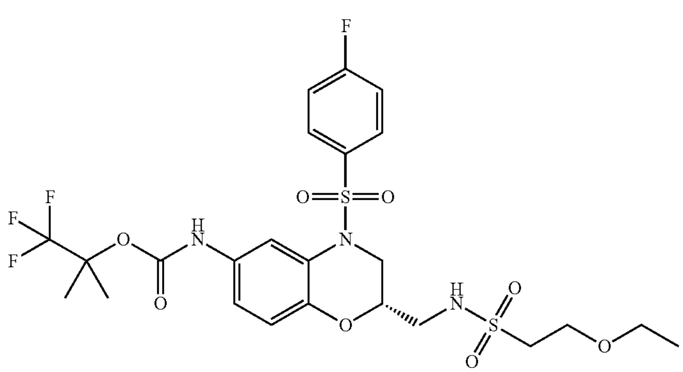 [SMILES: CCOCCS(=O)(=O)NC[C@H]1CN(S(=O)(=O)c2ccc(F)cc2)c2cc(NC(=O)OC(C)(C)C(F)(F)F)ccc2O1] | (S)-1,1,1-trifluoro-2-methylpropan-2-yl (2-((2-ethoxyethylsulfonamido)methyl)-4-((4-fluorophenyl)sulfonyl)-3,4-dihydro-2H-benzo[b][1,4]oxazin-6-yl)carbamate | 628 (M + H)+ |

TABLE 16-continued

| Ex. No. | Structure | Name | Observed m/z |
|---|---|---|---|
| 38Z | 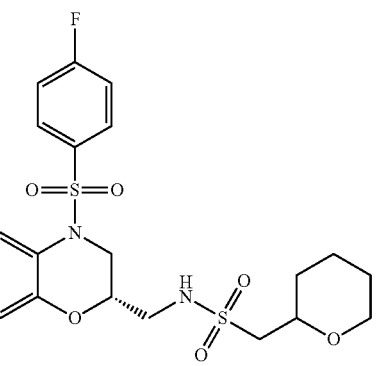 | 1,1,1-trifluoro-2-methylpropan-2-yl ((2S)-4-((4-fluorophenyl)sulfonyl)-2-(((tetrahydro-2H-pyran-2-yl)methylsulfonamido)methyl)-3,4-dihydro-2H-benzo[b][1,4]oxazin-6-yl)carbamate | 654 (M + H)⁺ |
| 38AA | 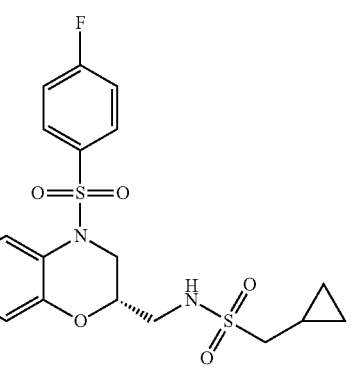 | (S)-1,1,1-trifluoro-2-methylpropan-2-yl (2-((cyclopropylmethylsulfonamido)methyl)-4-((4-fluorophenyl)sulfonyl)-3,4-dihydro-2H-benzo[b][1,4]oxazin-6-yl)carbamate | 610 (M + H)⁺ |
| 38AB | 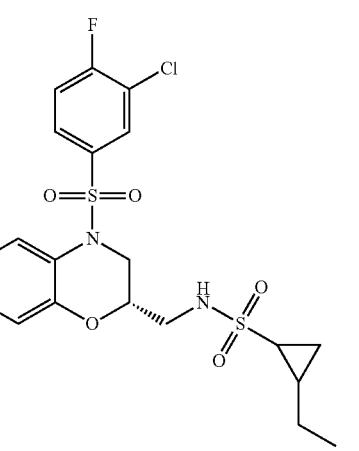 | 1,1,1-trifluoro-2-methylpropan-2-yl ((2S)-4-((3-chloro-4-fluorophenyl)sulfonyl)-2-((2-ethylcyclopropanesulfonamido)methyl)-3,4-dihydro-2H-benzo[b][1,4]oxazin-6-yl)carbamate | 658 (M + H)⁺ |
| 38AC | 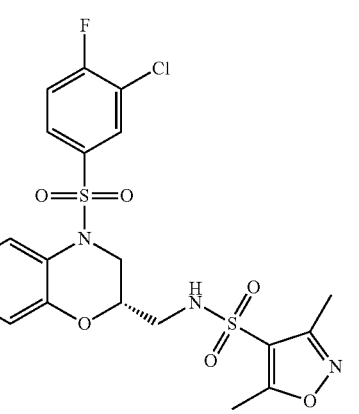 | (S)-4-(N-((4-((3-chloro-4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)sulfamoyl)-3,5-dimethylisoxazole | 685 (M + H)⁺ |

TABLE 16-continued

| Ex. No. | Structure | Name | Observed m/z |
|---|---|---|---|
| 38AD | 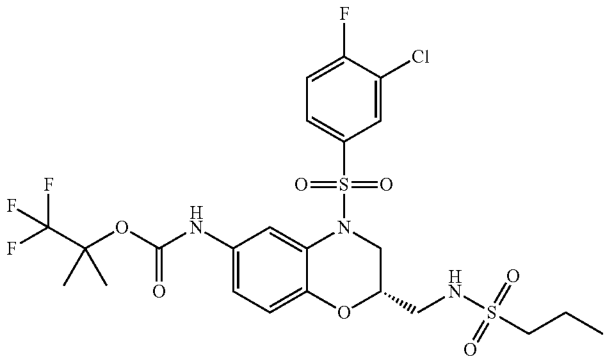 [SMILES: CCCS(=O)(=O)NC[C@H]1CN(S(=O)(=O)c2ccc(F)c(Cl)c2)c2cc(NC(=O)OC(C)(C)C(F)(F)F)ccc2O1] | (S)-1,1,1-trifluoro-2-methylpropan-2-yl (4-((3-chloro-4-fluorophenyl)sulfonyl)-2-(propylsulfonamidomethyl)-3,4-dihydro-2H-benzo[b][1,4]oxazin-6-yl)carbamate | 632 (M + H)+ |
| 38AE | 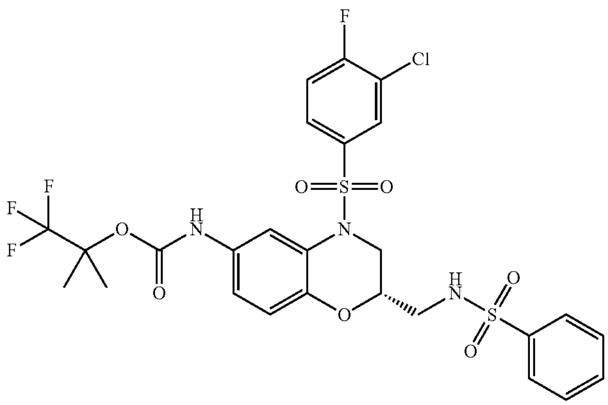 [SMILES: CC(C)(OC(=O)Nc1ccc2c(c1)N(S(=O)(=O)c1ccc(F)c(Cl)c1)C[C@H](CNS(=O)(=O)c1ccccc1)O2)C(F)(F)F] | (S)-1,1,1-trifluoro-2-methylpropan-2-yl (4-((3-chloro-4-fluorophenyl)sulfonyl)-2-(phenylsulfonamidomethyl)-3,4-dihydro-2H-benzo[b][1,4]oxazin-6-yl)carbamate | 666 (M + H)+ |
| 38AF | 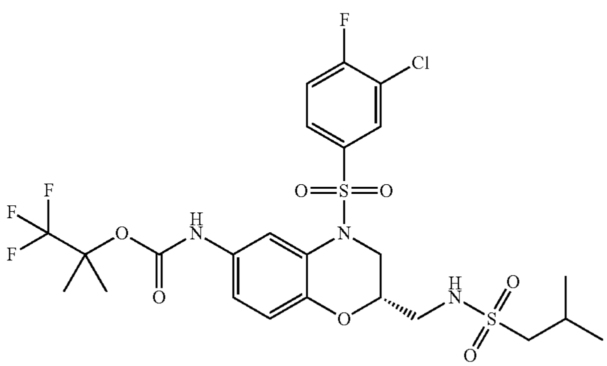 [SMILES: CC(C)CS(=O)(=O)NC[C@H]1CN(S(=O)(=O)c2ccc(F)c(Cl)c2)c2cc(NC(=O)OC(C)(C)C(F)(F)F)ccc2O1] | (S)-1,1,1-trifluoro-2-methylpropan-2-yl (4-((3-chloro-4-fluorophenyl)sulfonyl)-2-((2-methylpropylsulfonamido)methyl)-3,4-dihydro-2H-benzo[b][1,4]oxazin-6-yl)carbamate | 646 (M + H)+ |
| 38AG | 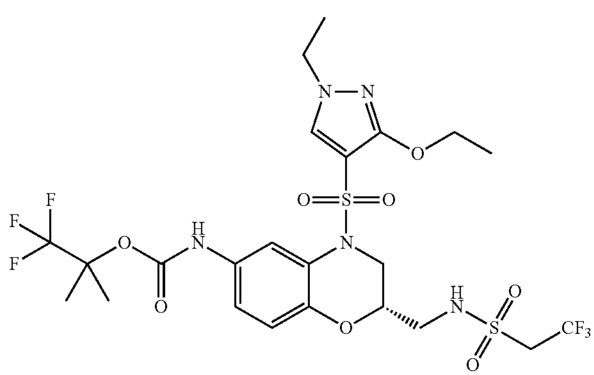 [SMILES: CCOc1nn(CC)cc1S(=O)(=O)N1C[C@H](CNS(=O)(=O)CC(F)(F)F)Oc2ccc(NC(=O)OC(C)(C)C(F)(F)F)cc21] | (S)-1,1,1-trifluoro-2-methylpropan-2-yl (4-((3-ethoxy-1-ethyl-1H-pyrazol-4-yl)sulfonyl)-2-((2,2,2-trifluoroethylsulfonamido)methyl)-3,4-dihydro-2H-benzo[b][1,4]oxazin-6-yl)carbamate | 682.1 (M + H)+ |

Example 39—Synthesis of (S)-1,1,1-trifluoro-2-methylpropan-2-yl (4-((4-fluorophenyl)sulfonyl)-2-((N-methylmethylsulfonamido)methyl)-3,4-dihydro-2H-benzo[b][1,4]oxazin-6-yl)carbamate (39)

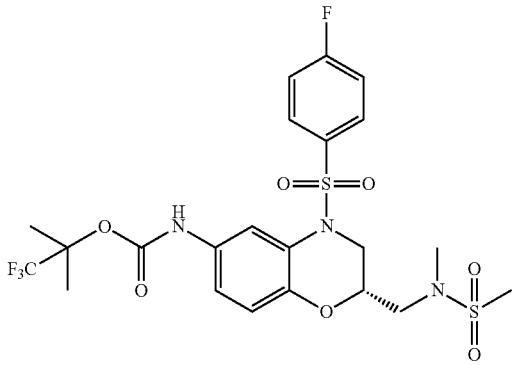 [SMILES: CN(C[C@H]1CN(S(=O)(=O)c2ccc(F)cc2)c2cc(NC(=O)OC(C)(C)C(F)(F)F)ccc2O1)S(C)(=O)=O]

The title compound was prepared according to the procedures described below.

Part I—Synthesis of (R)-tert-butyl (2-((N-methylmethylsulfonamido)methyl)-3,4-dihydro-2H-benzo[b][1,4]oxazin-6-yl)carbamate

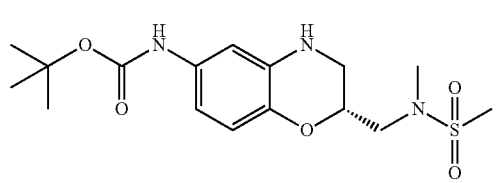 [SMILES: CN(C[C@H]1CNc2cc(NC(=O)OC(C)(C)C)ccc2O1)S(C)(=O)=O]

To a solution of (R)-tert-butyl (2-(hydroxymethyl)-3,4-dihydro-2H-benzo[b][1,4]oxazin-6-yl)carbamate (200 mg, 0.713 mmol), triphenylphosphine (187 mg, 0.713 mmol), N-methylmethanesulfonamide (65.2 μL, 0.713 mmol), in toluene (4760 μL) was added diisopropylazodicarboxylate (146 μL, 0.749 mmol) dropwise. The reaction was stirred for eighteen hours at 50° C. The reaction was diluted with ethyl acetate and washed with saturated NaHCO$_3$, followed by brine. The combined organic layers were dried (MgSO$_4$) and concentrated. The residue was purified via chromatography eluting with a gradient of 100% hexanes to 100% ethyl acetate to afford (R)-tert-butyl (2-((N-methylmethylsulfonamido)methyl)-3,4-dihydro-2H-benzo[b][1,4]oxazin-6-yl)carbamate. LRMS (ESI) calculated for C$_{12}$H$_{17}$N$_3$O$_5$S (M-tBu+H)$^+$: 316. Found: 316.

Part II—Synthesis of (S)-tert-butyl (4-((4-fluorophenyl)sulfonyl)-2-((N-methylmethylsulfonamido)methyl)-3,4-dihydro-2H-benzo[b][1,4]oxazin-6-yl)carbamate

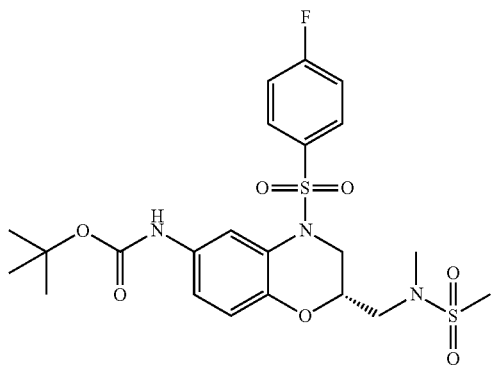 [SMILES: CN(C[C@H]1CN(S(=O)(=O)c2ccc(F)cc2)c2cc(NC(=O)OC(C)(C)C)ccc2O1)S(C)(=O)=O]

A mixture of (R)-tert-butyl (2-((N-methylmethylsulfonamido)methyl)-3,4-dihydro-2H-benzo[b][1,4]oxazin-6-yl)carbamate (79.6 mg, 0.214 mmol), 4-fluorobenzene-1-sulfonyl chloride (83 mg, 0.429 mmol), and pyridine (2143 μL) was heated at 60° C. for 1.5 hours. The mixture was diluted with ethyl acetate and washed with saturated NaHCO$_3$, followed by brine. The combined organics were dried (MgSO$_4$), filtered, and concentrated to afford (S)-tert-butyl (4-((4-fluorophenyl)sulfonyl)-2-((N-methylmethylsulfonamido)methyl)-3,4-dihydro-2H-benzo[b][1,4]oxazin-6-yl)carbamate. LRMS (ESI) calculated for C$_{18}$H$_{20}$FN$_3$O$_7$S$_2$ (M-tBu+H)$^+$: 474. Found: 474.

Part III—Synthesis of (S)—N-((6-amino-4-((4-fluorophenyl)sulfonyl)-3,4-dihydro-2H-benzo[b][1,4]oxazin-2-yl)methyl)-N-methylmethanesulfonamide

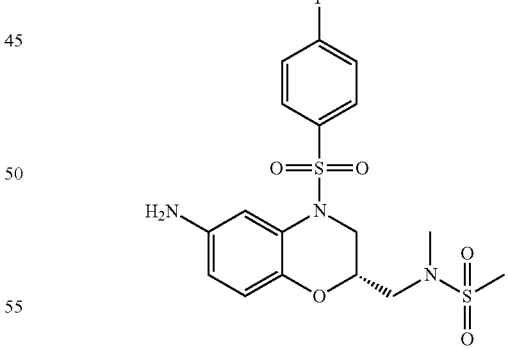

A mixture of (S)-tert-butyl (4-((4-fluorophenyl)sulfonyl)-2-((N-methylmethylsulfonamido)methyl)-3,4-dihydro-2H-benzo[b][1,4]oxazin-6-yl)carbamate (99.9 mg, 0.189 mmol), THF (1886 μL), and 4 M HCl (943 μL, 3.77 mmol) in p-dioxane was heated at 60° C. for 3.5 hours. The mixture was concentrated to afford (S)—N-((6-amino-4-((4-fluorophenyl)sulfonyl)-3,4-dihydro-2H-benzo[b][1,4]oxazin-2-yl)methyl)-N-methylmethanesulfonamide. LRMS (ESI) calculated for C$_{17}$H$_{20}$FN$_3$O$_5$S$_2$ (M+H)$^+$: 430. Found: 430.

Part IV—Synthesis of (S)-1,1,1-trifluoro-2-methyl-propan-2-yl (4-((4-fluorophenyl)sulfonyl)-2-((N-methylmethylsulfonamido)methyl)-3,4-dihydro-2H-benzo[b][1,4]oxazin-6-yl)carbamate

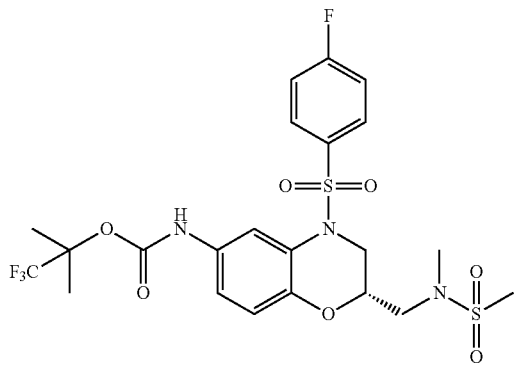 [SMILES: CN(C[C@H]1CN(S(=O)(=O)c2ccc(F)cc2)c2cc(NC(=O)OC(C)(C)C(F)(F)F)ccc2O1)S(C)(=O)=O]

A solution of (S)—N-((6-amino-4-((4-fluorophenyl)sulfonyl)-3,4-dihydro-2H-benzo[b][1,4]oxazin-2-yl)methyl)-N-methylmethanesulfonamide hydrochloride (88 mg, 0.189 mmol) and 1,1,1-trifluoro-2-methylpropan-2-yl 1H-imidazole-1-carboxylate (71.3 mg, 0.321 mmol) in DMF (1890 µL) was heated at 100° C. for two hours. The reaction was cooled and partitioned between ether and water, then reextracted with ether. The combined organic layers were washed with 1N HCl, followed by saturated aqueous sodium bicarbonate, dried (MgSO$_4$) and concentrated. The residue was dissolved in DMSO (2 mL), filtered, and purified by reverse-phase HPLC (MeCN:water, trifluoroacetic acid buffer) to afford (S)-1,1,1-trifluoro-2-methylpropan-2-yl (4-(4-fluorophenyl)sulfonyl)-2-((N-methylmethylsulfonamido)methyl)-3,4-dihydro-2H-benzo[b][1,4]oxazin-6-yl)carbamate. LRMS (ESI) calculated for $C_{22}H_{25}F_4N_3O_7S_2$ (M+H)$^+$: 584. Found: 584. $^1$H NMR (500 MHz, DMSO-d6) δ 9.79 (s, 1H), 7.91 (s, 1H), 7.77 (m, 2H), 7.43 (t, 2H, J=8.81 Hz), 7.19 (d, 1H, J=9.83 Hz), 6.79 (d, 1H, J=8.67 Hz), 4.27 (dd, 1H, J=2.3, 14.3 Hz), 3.58 (m, 1H), 3.29 (m, 1H), 3.25 (m, 2H), 2.89 (s, 3H), 2.76 (s, 3H), 1.69 (s, 6H).

Example 40—Synthesis of (S)-1,1,1-trifluoro-2-methylpropan-2-yl (2-((1,1-dioxidoisothiazolidin-2-yl)methyl)-4-((4-fluorophenyl)sulfonyl)-3,4-dihydro-2H-benzo[b][1,4]oxazin-6-yl)carbamate (40)

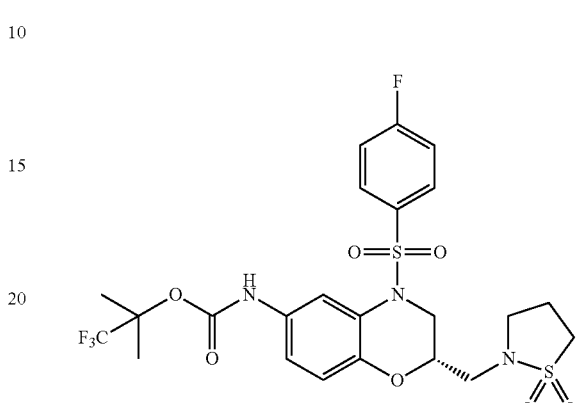

The title compound was prepared via the method of Example 39, using the appropriate sulfonamide in the Mitsunobu reaction. LRMS (ESI) calculated for $C_{23}H_{26}F_4N_3O_7S_2$ (M+H)$^+$ 596. Found: 596. $^1$H NMR: (300 MHz, CDCl$_3$): δ 9.78 (1H, s), 7.90 (1H, s), 7.80 (2H, m), 7.42 (2H, t, J=8.27), 7.18 (1H, d, J=9.77), 6.77 (1H, d, J=9.77), 4.32 (1H, d, J=15.27), 3.29 (2H, m), 3.20 (6H, m), 2.21 (2H, m), 1.70 (6H, s).

Example 41—Preparation of additional 2-(N-methylmethylsulfonamido)methyl benzoxazines The compound in Table 17 below was prepared based on the experimental procedures described in Example 39 and elsewhere in the detailed description, and can be achieved by one of skill in the art in light of the present disclosure.

TABLE 17

| Ex. No. | Structure | Name | Observed m/z |
|---|---|---|---|
| 41A | (structure shown) | (S)-1,1,1-trifluoro-2-methylpropan-2-yl (4-((3-chloro-4-fluorophenyl)sulfonyl)-2-((N-methylmethylsulfonamido)methyl)-3,4-dihydro-2H-benzo[b][1,4]oxazin-6-yl)carbamate | 618 (M + Na)$^+$ |

Example 42—Synthesis of Synthesis of (S)-tert-butyl (2-(acetamidomethyl)-4-((4-(trifluoromethyl)piperidin-1-yl)sulfonyl)-3,4-dihydro-2H-benzo[b][1,4]oxazin-6-yl)carbamate (42)

Part II—Synthesis of (S)-tert-butyl (2-(acetamidomethyl)-4-((4-(trifluoromethyl)piperidin-1-yl)sulfonyl)-3,4-dihydro-2H-benzo[b][1,4]oxazin-6-yl)carbamate

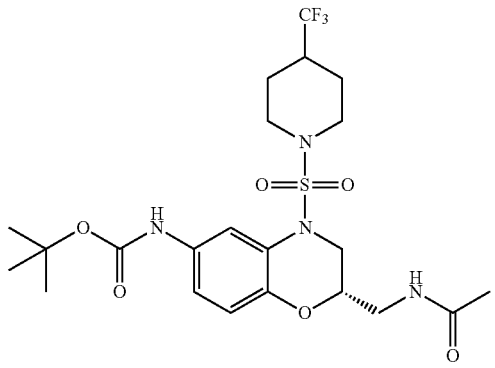 [SMILES: CC(=O)NC[C@H]1CN(S(=O)(=O)N2CCC(C(F)(F)F)CC2)c2cc(NC(=O)OC(C)(C)C)ccc2O1]

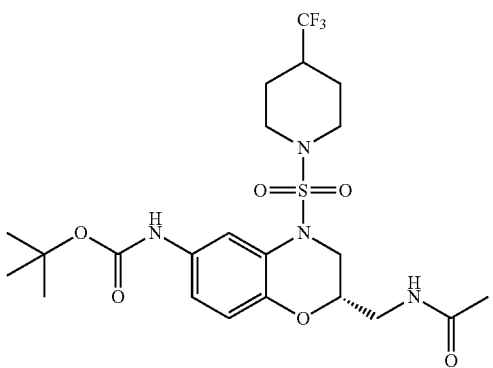 [SMILES: CC(=O)NC[C@H]1CN(S(=O)(=O)N2CCC(C(F)(F)F)CC2)c2cc(NC(=O)OC(C)(C)C)ccc2O1]

The title compound was prepared according to the procedures described below.

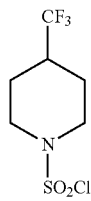

Part I—Synthesis of 4-(trifluoromethyl)piperidine-1-sulfonyl chloride

A solution of 4-(trifluoromethyl)piperidine hydrochloride (50 mg, 0.264 mmol) in dichloromethane (0.5 mL) and N,N'-diisopropylethylamine (0.069 mL, 0.396 mmol) was stirred at room temperature for five minutes. The reaction was cooled down to −30° C. (dry ice/acetonitrile) and sulfuryl chloride (0.043 mL, 0.527 mmol) was added. The mixture was stirred at this temperature for one hour, then warmed to room temperature and stirred overnight. The reaction mixture was diluted with ethyl acetate, washed with 1N HCl and brine, then dried (MgSO$_4$) and concentrated to afford 4-(trifluoromethyl)piperidine-1-sulfonyl chloride which was used without further purification.

To a stirred solution of (R)-tert-butyl (2-(acetamidomethyl)-3,4-dihydro-2H-benzo[b][1,4]oxazin-6-yl)carbamate in THF (5 mL) and pyridine (0.5 mL, 6.18 mmol) was added 4-(trifluoromethyl)piperidine-1-sulfonyl chloride and the mixture was heated at 60° C. overnight. The reaction mixture was cooled, diluted with ethyl acetate, washed with saturated sodium bicarbonate, brine, dried (MgSO$_4$) and concentrated. The residue was purified via HPLC purification eluting with a gradient of water/acetonitrile with trifluoroacetic acid to afford the title compound as a yellow solid. LRMS (ESI) calculated for $C_{22}H_{31}F_3N_4O_6S$ (M+H)$^+$: 537, Found: 481 (M-tBu+H)$^+$ and 559 (M+Na)$^+$. $^1$H NMR (600 MHz, DMSO-d6) δ 9.21 (s, 1H), 8.13 (t, J=5.7, 1H), 7.77 (s, 1H), 6.99 (d, J=8.7, 1H), 6.76 (d, J=8.8, 1H), 4.11-3.94 (m, 2H), 3.74-3.58 (m, 2H), 3.45-3.09 (m, 2H), 2.84 (t, J=12.2, 2H), 1.82-1.78 (m, 5H), 1.56-1.26 (m, 2H), 1.40 (s, 9H).

Example 43—Preparation of additional 4-sulfamides of benzoxazines

The compounds in Table 18 below were prepared based on the experimental procedures described in Example 42 and elsewhere in the detailed description using the appropriate sulfamoyl halide, and can be achieved by one of skill in the art in light of the present disclosure.

TABLE 18

| Ex. No. | Structure | Name | Observed m/z |
|---|---|---|---|
| 43A | (structure shown) | tert-butyl ((2S)-2-(acetamidomethyl)-4-((3-(trifluoromethyl)pyrrolidin-1-yl)sulfonyl)-3,4-dihydro-2H-benzo[b][1,4]oxazin-6-yl)carbamate | 467.0 (M − tBu + H)$^+$ |

TABLE 18-continued

| Ex. No. | Structure | Name | Observed m/z |
|---|---|---|---|
| 43B | 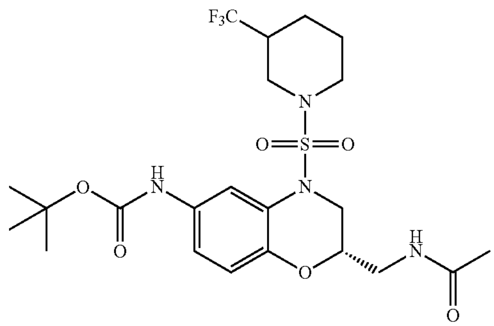 [SMILES: CC(=O)NC[C@H]1CN(S(=O)(=O)N2CCCC(C(F)(F)F)C2)c2cc(NC(=O)OC(C)(C)C)ccc2O1] | tert-butyl ((2S)-2-(acetamidomethyl)-4-((3-(trifluoromethyl)piperidin-1-yl)sulfonyl)-3,4-dihydro-2H-benzo[b][1,4]oxazin-6-yl)carbamate | 481.0 (M − tBu + H)+ |
| 43C | 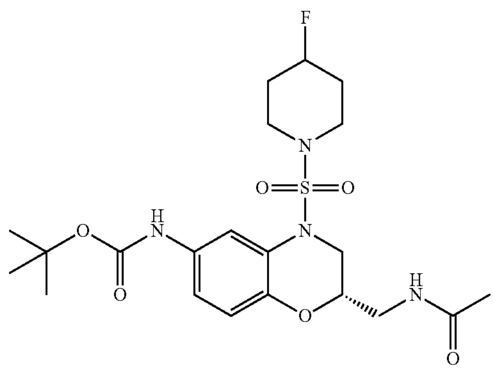 [SMILES: CC(=O)NC[C@H]1CN(S(=O)(=O)N2CCC(F)CC2)c2cc(NC(=O)OC(C)(C)C)ccc2O1] | (S)-tert-butyl (2-(acetamidomethyl)-4-((4-fluoropiperidin-1-yl)sulfonyl)-3,4-dihydro-2H-benzo[b][1,4]oxazin-6-yl)carbamate | 509.0 (M + Na)+ |

Example 44—(S)-tert-butyl (2-(acetamidomethyl)-8-fluoro-4-((4-fluorophenyl)sulfonyl)-3,4-dihydro-2H-benzo[b][1,4]oxazin-6-yl)carbamate (44)

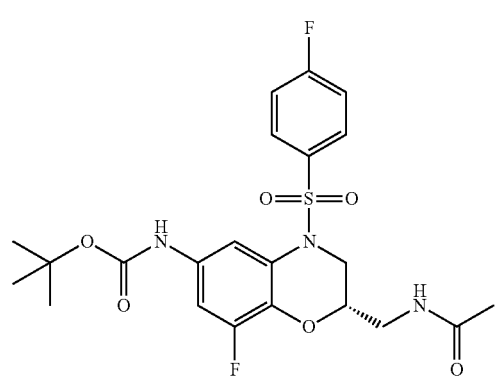 [SMILES: CC(=O)NC[C@H]1CN(S(=O)(=O)c2ccc(F)cc2)c2cc(NC(=O)OC(C)(C)C)cc(F)c2O1]

The title compound was prepared according to the procedures described below.

Part I—Synthesis of (R)-(6-bromo-8-fluoro-3,4-dihydro-2H-benzo[b][1,4]oxazin-2-yl)methanol

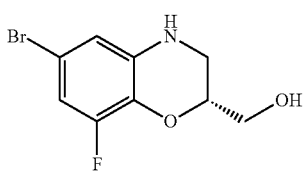 [SMILES: OC[C@H]1CNc2cc(Br)cc(F)c2O1]

A solution of 2-amino-4-bromo-6-fluorophenol (2.5 g, 12.1 mmol) and (2S)-2-(chloromethyl)oxirane (2.1 mL, 26.7 mmol) in ethanol/water (25/0.25 mL) was stirred for twelve hours at 60° C. The resulting mixture was concentrated and dissolved in ethanol (25 mL) and potassium carbonate (5 g, 36 mmol) was added. The mixture was refluxed for two hours. The solids were filtered through CELITE and the filtrate was concentrated. The residue was dissolved in ethyl acetate, washed with water, brine, dried (Na$_2$SO$_4$) and concentrated in the presence of silica. Purification by column chromatography, eluting with a gradient of 20-80% ethyl acetate in hexanes, afforded (R)-(6-bromo-8-fluoro-3,4-dihydro-2H-benzo[b][1,4]oxazin-2-yl)methanol.

Part II—Synthesis of (R)-2-((6-bromo-8-fluoro-3,4-dihydro-2H-benzo[b][1,4]oxazin-2-yl)methyl)isoindoline-1,3-dione

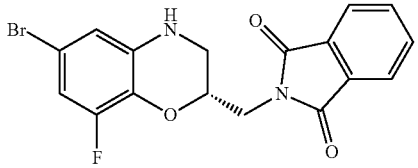 [SMILES: O=C1c2ccccc2C(=O)N1C[C@H]1CNc2cc(Br)cc(F)c2O1]

To a solution of (R)-(6-bromo-8-fluoro-3,4-dihydro-2H-benzo[b][1,4]oxazin-2-yl)methanol (1.27 g, 4.8 mmol) in anhydrous tetrahydrofuran (15 mL) under a nitrogen atmosphere at 0° C. was added triphenylphosphine (1.4 g, 5.3 mmol) and phthalimide (0.78 g, 5.3 mmol) followed by the dropwise addition of diisopropyl azodicarboxylate (1.1 mL, 5.8 mmol). The solution was allowed to slowly warm to ambient temperature and then stirred overnight. The concentrated reaction was purified by column chromatography eluting with a gradient of ethyl acetate in hexanes. The major UV active fraction was combined and concentrated. The residue was triturated with ethyl acetate/hexanes (2:1), and the resulting solid filtered to afford (R)-2-((6-bromo-8-fluoro-3,4-dihydro-2H-benzo[b][1,4]oxazin-2-yl)methyl)isoindoline-1,3-dione.

Part III—Synthesis of (S)-2-((6-bromo-8-fluoro-4-((4-fluorophenyl)sulfonyl)-3,4-dihydro-2H-benzo[b][1,4]oxazin-2-yl)methyl)isoindoline-1,3-dione

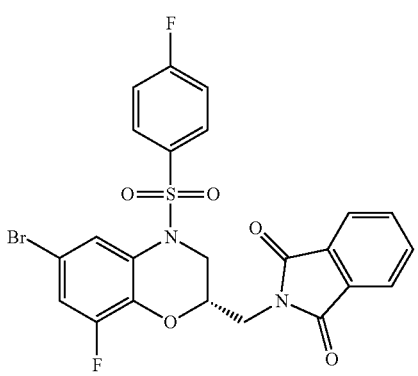 [SMILES: O=C1c2ccccc2C(=O)N1C[C@H]1CN(S(=O)(=O)c2ccc(F)cc2)c2cc(Br)cc(F)c2O1]

To a solution of (R)-2-((6-bromo-8-fluoro-2H-benzo[b][1,4]oxazin-2-yl)methyl)isoindoline-1,3-dione (0.74 g, 1.89 mmol) in anhydrous pyridine (8 mL) was added the 4-fluorophenylsulfonyl chloride (0.44 g, 2.3 mmol) and shaken at 50° C. overnight. To the resulting suspension was added water (10 mL) and the suspension was slurried for 20 minutes. The solids were filtered off, washed with water and dried to yield (S)-2-((6-bromo-8-fluoro-4-((4-fluorophenyl)sulfonyl)-3,4-dihydro-2H-benzo[b][1,4]oxazin-2-yl)methyl)isoindoline-1,3-dione.

Part IV—Synthesis of (S)-tert-butyl (2-((1,3-dioxoisoindolin-2-yl)methyl)-8-fluoro-4-((4-fluorophenyl)sulfonyl)-3,4-dihydro-2H-benzo[b][1,4]oxazin-6-yl)carbamate

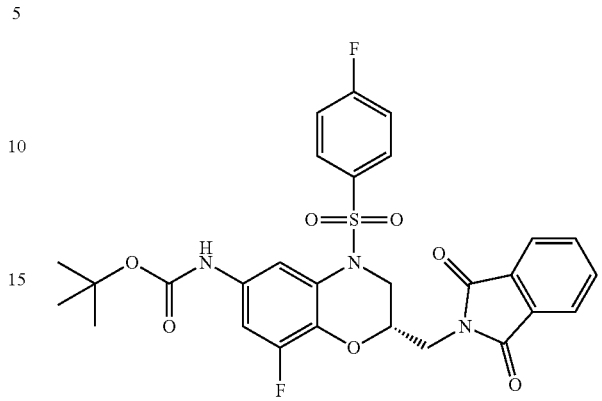

To a suspension of (S)-2-((6-bromo-8-fluoro-4-((4-fluorophenyl)sulfonyl)-3,4-dihydro-2H-benzo[b][1,4]oxazin-2-yl)methyl)isoindoline-1,3-dione (0.97 g, 1.77 mmol) in toluene (10 mL) was added potassium phosphate tribasic (1.1 g, 5.3 mmol), water (3 mL), 2-dicyclohexylphosphino-2',4',6'-triisopropylbiphenyl (0.08 g, 0.18 mmol), tert-butyl carbamate (0.62 g, 5.3 mmol) followed by the addition of tris(dibenzylideneacetone)dipalladium(0) (0.16 g, 0.18 mmol). The reaction was heated at 105° C. overnight. Once the reaction was cooled, methanol was added (10 mL) along with CELITE. The reaction was stirred as a slurry for 10 minutes, then filtered through CELITE. The crude product was purified by column chromatography eluting with a gradient of 5-50% ethyl acetate in hexanes to afford (S)-tert-butyl (2-((1,3-dioxoisoindolin-2-yl)methyl)-8-fluoro-4-((4-fluorophenyl)sulfonyl)-3,4-dihydro-2H-benzo[b][1,4]oxazin-6-yl)carbamate.

The title compound was prepared utilizing the procedure within Example 7. $^1$H NMR (400 Hz, DMSO-d6) δ 9.46 (s, 1H), 8.07 (m, 1H), 7.76 (m, 2H), 7.65 (m, 1H), 7.42 (m, 2H), 7.22 (m, 1H), 4.28 (m, 1H), 3.4-3.23 (m, 2H), 3.09 (m, 2H), 1.82 (s, 3H), 1.44 (s, 9H).

Example 45—(S)-1,1,1-trifluoro-2-methylpropan-2-yl (2-(acetamidomethyl)-8-fluoro-4-((4-fluorophenyl)sulfonyl)-3,4-dihydro-2H-benzo[b][1,4]oxazin-6-yl)carbamate (45)

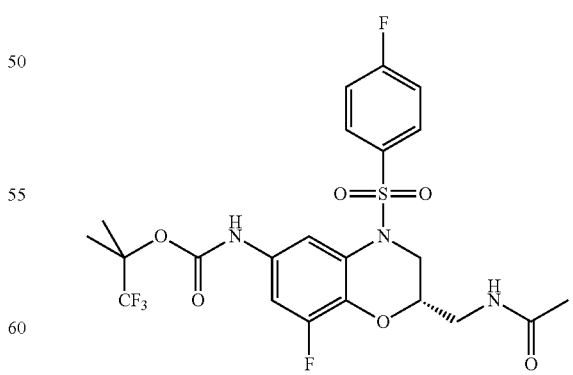

The title compound was prepared utilizing the procedure within examples 7 and 44. $^1$H NMR (400 Hz, DMSO-d6) δ 9.94 (s, 1H), 8.07 (m, 1H), 7.76 (m, 2H), 7.69 (m, 1H), 7.42 (m, 2H), 7.22 (m, 1H), 4.28 (m, 1H), 3.4-3.23 (m, 2H), 3.12-3.04 (m, 2H), 1.82 (s, 3H), 1.68 (s, 6H).

Example 46—Preparation of additional 8-fluorobenzoxazines

The compounds in Table 21 below were prepared based on the experimental procedures described in Examples 44 and 45 and elsewhere in the detailed description, and can be achieved by one of skill in the art in light of the present disclosure.

TABLE 19

| Ex. No. | Structure | Name | Observed m/z |
|---|---|---|---|
| 46A | 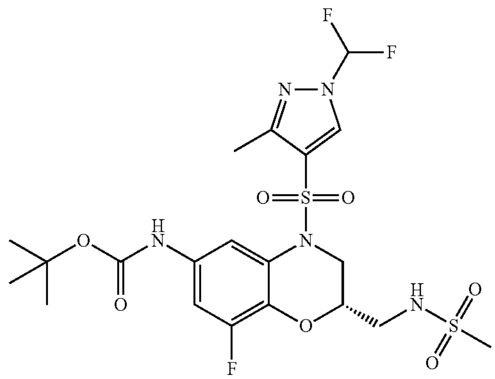 [SMILES: Cc1nn(C(F)F)cc1S(=O)(=O)N1C[C@H](CNS(C)(=O)=O)Oc2c(F)cc(NC(=O)OC(C)(C)C)cc21] | (S)-4-((6-((tert-butoxycarbonyl)amino)-8-fluoro-2-(methylsulfonamidomethyl)-2H-benzo[b][1,4]oxazin-4(3H)-yl)sulfonyl)-1-(difluoromethyl)-3-methyl-1H-pyrazole | 592 (M + Na)+ |
| 46B | 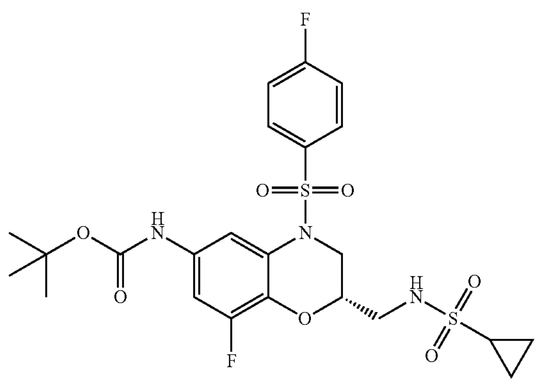 [SMILES: CC(C)(C)OC(=O)Nc1cc(F)c2c(c1)N(S(=O)(=O)c1ccc(F)cc1)C[C@H](CNS(=O)(=O)C1CC1)O2] | (S)-tert-butyl (2-(cyclopropanesulfonamidomethyl)-8-fluoro-4-((4-fluorophenyl)sulfonyl)-3,4-dihydro-2H-benzo[b][1,4]oxazin-6-yl)carbamate | 560 (M + H)+ |
| 46C | 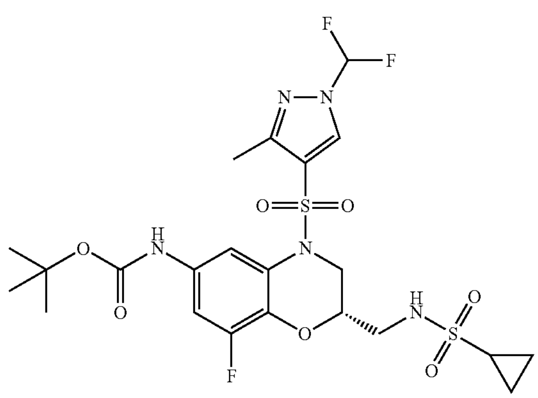 [SMILES: Cc1nn(C(F)F)cc1S(=O)(=O)N1C[C@H](CNS(=O)(=O)C2CC2)Oc2c(F)cc(NC(=O)OC(C)(C)C)cc21] | (S)-tert-butyl (2-(cyclopropanesulfonamidomethyl)-4-((1-(difluoromethyl)-3-methyl-1H-pyrazol-4-yl)sulfonyl)-8-fluoro-3,4-dihydro-2H-benzo[b][1,4]oxazin-6-yl)carbamate | 618 (M + Na)+ |

TABLE 19-continued

| Ex. No. | Structure | Name | Observed m/z |
|---|---|---|---|
| 46D | 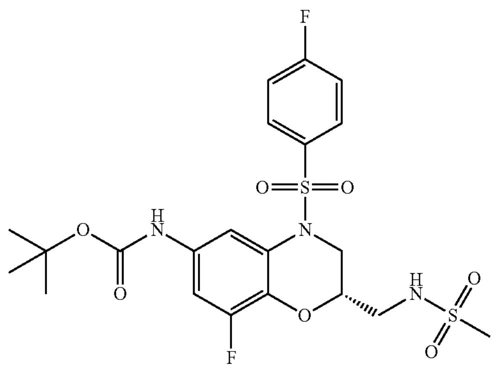 [SMILES: CC(C)(C)OC(=O)Nc1cc(F)c2c(c1)N(S(=O)(=O)c1ccc(F)cc1)C[C@H](CNS(C)(=O)=O)O2] | (S)-tert-butyl (8-fluoro-4-((4-fluorophenyl)sulfonyl)-2-(methylsulfonamidomethyl)-3,4-dihydro-2H-benzo[b][1,4]oxazin-6-yl)carbamate | 555.9 (M + Na)+ |
| 46E | 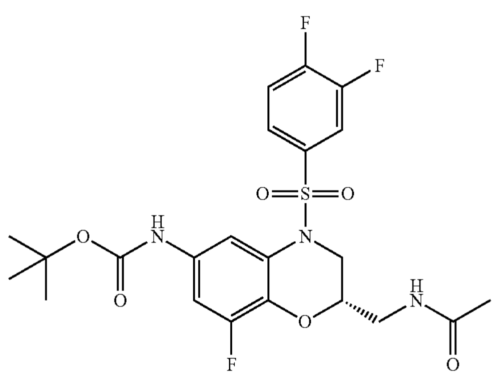 [SMILES: CC(=O)NC[C@H]1CN(S(=O)(=O)c2ccc(F)c(F)c2)c2cc(NC(=O)OC(C)(C)C)cc(F)c2O1] | (S)-tert-butyl (2-(acetamidomethyl)-4-((3,4-difluorophenyl)sulfonyl)-8-fluoro-3,4-dihydro-2H-benzo[b][1,4]oxazin-6-yl)carbamate | 538 (M + Na)+ |
| 46F | 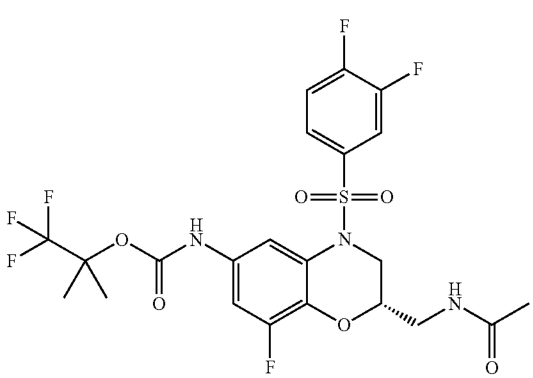 [SMILES: CC(=O)NC[C@H]1CN(S(=O)(=O)c2ccc(F)c(F)c2)c2cc(NC(=O)OC(C)(C)C(F)(F)F)cc(F)c2O1] | (S)-1,1,1-trifluoro-2-methylpropan-2-yl (2-(acetamidomethyl)-4-((3,4-difluorophenyl)sulfonyl)-8-fluoro-3,4-dihydro-2H-benzo[b][1,4]oxazin-6-yl)carbamate | 589.1 (M + Na)+ |

Example 47—Synthesis of (S)-1,1,1-trifluoro-2-methylpropan-2-yl (2-(acetamidomethyl)-8-chloro-4-((4-fluorophenyl)sulfonyl)-3,4-dihydro-2H-benzo[b][1,4]oxazin-6-yl)carbamate (47)

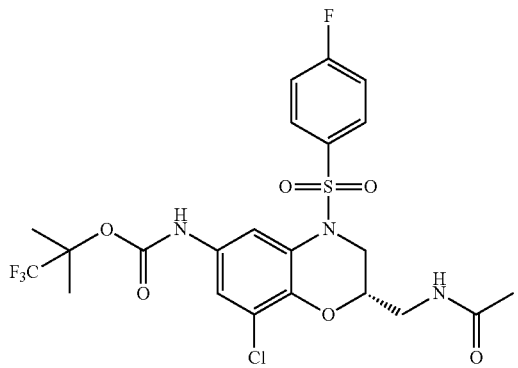 [SMILES: CC(=O)NC[C@H]1CN(S(=O)(=O)c2ccc(F)cc2)c2cc(NC(=O)OC(C)(C)C(F)(F)F)cc(Cl)c2O1]

The title compound was prepared according to the procedures described below.

Part I—Synthesis of (R)-(8-chloro-6-nitro-3,4-dihydro-2H-benzo[b][1,4]oxazin-2-yl)methanol

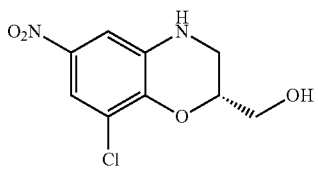 [SMILES: O=[N+]([O-])c1cc(Cl)c2c(c1)NC[C@H](CO)O2]

A solution of 2-amino-6-chloro-4-nitrophenol (6.5 g, 34.5 mmol) and (2S)-2-(chloromethyl)oxirane (5.9 mL, 76 mmol) in ethanol/water (25/0.25 mL) was stirred at 60° C. for three days. The reaction was concentrated and dissolved in ethanol (50 mL), followed by the addition of potassium carbonate (14.3 g, 103 mmol). After refluxing the reaction for six hours, the solids were filtered off through CELITE and the filtrate was concentrated. The residue was dissolved in ethyl acetate and washed with 1M hydrogen chloride, water, brine, dried ($Na_2SO_4$) and concentrated in the presence of silica. Purification by column chromatography eluting with a gradient of methanol in dichloromethane afforded (R)-(8-chloro-6-nitro-3,4-dihydro-2H-benzo[b][1,4]oxazin-2-yl)methanol.

Part II—Synthesis of (R)-2-((8-chloro-6-nitro-3,4-dihydro-2H-benzo[b][1,4]oxazin-2-yl)methyl)isoindoline-1,3-dione

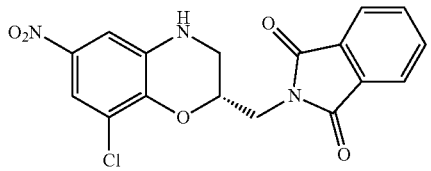 [SMILES: O=C1c2ccccc2C(=O)N1C[C@H]1CNc2cc([N+](=O)[O-])cc(Cl)c2O1]

To a solution of (R)-(8-chloro-6-nitro-3,4-dihydro-2H-benzo[b][1,4]oxazin-2-yl)methanol (1.82 g, 7.44 mmol) in anhydrous THF (24 mL) at 0° C. was added triphenyl phosphine (2.15 mmol, 8.18 mmol) followed by the dropwise addition of diisopropyl-diazodicarboxylate (1.76 mL, 8.93 mmol). The reaction was allowed to slowly warm to room temperature, then stirred for three hours and concentrated onto silica. Purification by column chromatography eluting with a gradient of ethyl acetate in hexanes afforded (R)-2-((8-chloro-6-nitro-3,4-dihydro-2H-benzo[b][1,4]oxazin-2-yl)methyl)isoindoline-1,3-dione.

Part III—Synthesis of (S)-2-((8-chloro-4-((4-fluorophenyl)sulfonyl)-6-nitro-3,4-dihydro-2H-benzo[b][1,4]oxazin-2-yl)methyl)isoindoline-1,3-dione

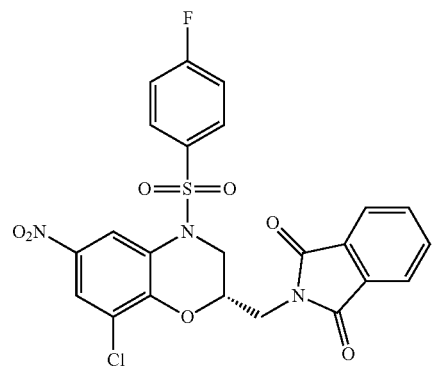

To (R)-2-((8-chloro-6-nitro-3,4-dihydro-2H-benzo[b][1,4]oxazin-2-yl)methyl)isoindoline-1,3-dione (0.51 g, 1.4 mmol) in anhydrous pyridine (10 mL) under a nitrogen atmosphere was added 4-fluorophenylsulfonyl chloride (0.37 g, 1.9 mmol) and the reaction was stirred at 80° C. overnight. The reaction was cooled, diluted with ethyl acetate, washed with 1M hydrogen chloride, water, brine, dried ($Na_2SO_4$) and concentrated. Purification by column chromatography eluting with a gradient of methanol in dichloromethane afforded (S)-2-((8-chloro-4-((4-fluorophenyl)sulfonyl)-6-nitro-3,4-dihydro-2H-benzo[b][1,4]oxazin-2-yl)methyl)isoindoline-1,3-dione.

Part IV—Synthesis of (S)-2-((6-amino-8-chloro-4-((4-fluorophenyl)sulfonyl)-3,4-dihydro-2H-benzo[b][1,4]oxazin-2-yl)methyl)isoindoline-1,3-dione

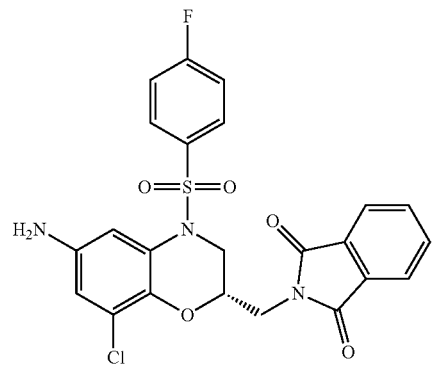 [SMILES: O=C1c2ccccc2C(=O)N1C[C@H]1CN(S(=O)(=O)c2ccc(F)cc2)c2cc([N+](=O)[O-])cc(Cl)c2O1]

To (S)-2-((8-chloro-4-((4-fluorophenyl)sulfonyl)-6-nitro-3,4-dihydro-2H-benzo[b][1,4]oxazin-2-yl)methyl)isoindoline-1,3-dione (1.5 g, 2.8 mmol) in 2-propanol (25 mL) and water (2.5 mL) was added ammonium chloride (0.3 g, 5.6 mmol) and powdered iron (0.47 g, 8.5 mmol) and the reaction was heated at 70° C. for four hours. The reaction was cooled, diluted with ethyl acetate, then filtered through CELITE, washing with more ethyl acetate. The filtrates were washed with saturated ammonium chloride, brine, dried ($Na_2SO_4$) and concentrated under vacuum to afford (S)-2-

((6-amino-8-chloro-4-((4-fluorophenyl)sulfonyl)-3,4-dihydro-2H-benzo[b][1,4]oxazin-2-yl)methyl)isoindoline-1,3-dione.

Part V—Synthesis of (S)-1,1,1-trifluoro-2-methylpropan-2-yl (8-chloro-2-((1,3-dioxoisoindolin-2-yl)methyl)-4-((4-fluorophenyl)sulfonyl)-3,4-dihydro-2H-benzo[b][1,4]oxazin-6-yl)carbamate

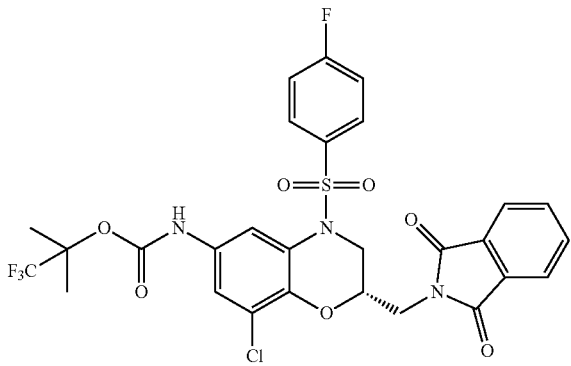 [SMILES: CC(C)(OC(=O)Nc1cc(Cl)c2c(c1)N(S(=O)(=O)c1ccc(F)cc1)C[C@H](CN1C(=O)c3ccccc3C1=O)O2)C(F)(F)F]

To a solution of (S)-2-((6-amino-8-chloro-4-((4-fluorophenyl)sulfonyl)-3,4-dihydro-2H-benzo[b][1,4]oxazin-2-yl)methyl)isoindoline-1,3-dione (1.0 g, 2 mmol) in tetrahydrofuran (10 mL) was added triethylamine (1.1 mL, 8 mmol), 4-nitrophenyl (1,1,1-trifluoro-2-methylpropan-2-yl) carbonate (1.2 g, 4 mmol), and 4-dimethylaminopyridine (0.49 g, 4 mmol). The reaction was stirred at ambient temperature overnight. The solution was diluted with methyl tert-butyl ether, washed four times with 2M sodium hydroxide, then brine, dried ($Na_2SO_4$) and concentrated in the presence of silica. Purification by column chromatography eluting with a gradient of 5-40% ethyl acetate in hexanes yielded the title compound.

The title compound was completed based on the experimental procedures described in example 7 and 44. $^1$H NMR (400 Hz, DMSO-d6) δ 9.93 (s, 1H), 8.05 (m, 1H), 7.83 (m, 1H), 7.75 (m, 2H), 7.45-7.40 (m, 3H), 4.28 (m, 1H), 3.4-3.23 (m, 3H), 3.06 (m, 1H), 1.83 (s, 3H), 1.68 (s, 6H).

Example 48—Synthesis of (S)-1,1,1-trifluoro-2-methylpropan-2-yl (8-chloro-4-((4-fluorophenyl)sulfonyl)-2-(methylsulfonamidomethyl)-3,4-dihydro-2H-benzo[b][1,4]oxazin-6-yl)carbamate (48)

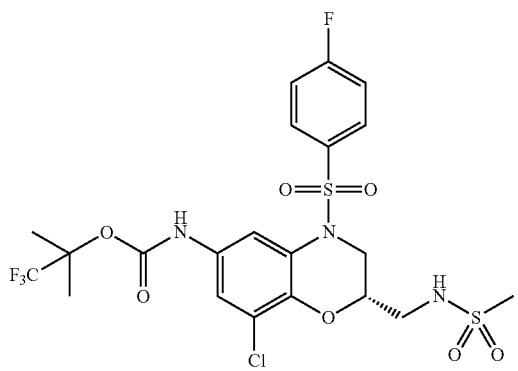 [SMILES: CC(C)(OC(=O)Nc1cc(Cl)c2c(c1)N(S(=O)(=O)c1ccc(F)cc1)C[C@H](CNS(C)(=O)=O)O2)C(F)(F)F]

The title compound was prepared according to the procedures described below.

Part I—Synthesis of (S)-1,1,1-trifluoro-2-methylpropan-2-yl (2-(aminomethyl)-8-chloro-4-((4-fluorophenyl)sulfonyl)-3,4-dihydro-2H-benzo[b][1,4]oxazin-6-yl)carbamate

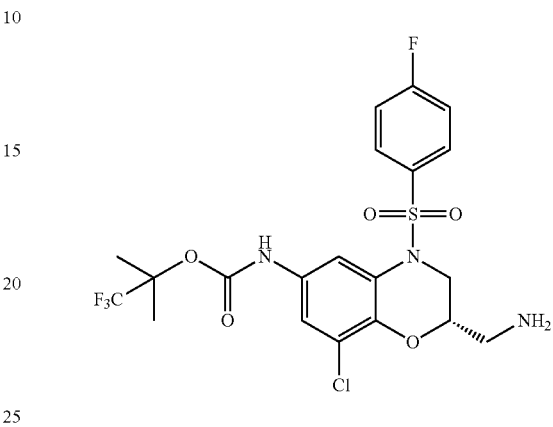

To (S)-1,1,1-trifluoro-2-methylpropan-2-yl (8-chloro-2-((1,3-dioxoisoindolin-2-yl)methyl)-4-((4-fluorophenyl)sulfonyl)-3,4-dihydro-2H-benzo[b][1,4]oxazin-6-yl)carbamate (0.49 g, 0.75 mmol) in ethanol (5 mL) was added hydrazine (0.23 mL, 7.5 mmol) and the solution was heated at 70° C. for 2 hours. The solution was cooled and then filtered to yield the title compound.

Part II—Synthesis of (S)-1,1,1-trifluoro-2-methylpropan-2-yl (8-chloro-4-((4-fluorophenyl)sulfonyl)-2-(methylsulfonamidomethyl)-3,4-dihydro-2H-benzo[b][1,4]oxazin-6-yl)carbamate

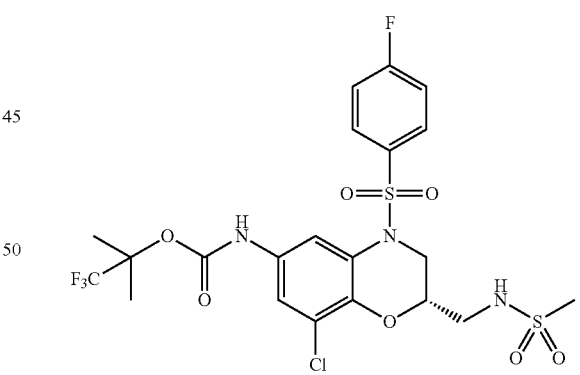

To a solution of (S)-1,1,1-trifluoro-2-methylpropan-2-yl (2-(aminomethyl)-8-chloro-4-((4-fluorophenyl)sulfonyl)-3,4-dihydro-2H-benzo[b][1,4]oxazin-6-yl)carbamate (69 mg, 0.13 mmol) in dichloromethane (1 mL) and tetrahydrofuran (1 mL) was added N,N-diisopropylethylamine (46 μL, 0.26 mmol) and methanesulfonic anhydride (34 mg, 0.2 mmol). The reaction was shaken at ambient temperature overnight. The evaporated residue was purified by column chromatography eluting with a gradient of 20-80% ethyl acetate in hexanes. The purified fractions were combined and concentrated to yield the title compound. $^1$H NMR (400 Hz, DMSO-d6) δ 9.94 (s, 1H), 7.83-7.78 (m, 3H), 7.44-7.35 (m, 4H), 4.38 (m, 1H), 3.52 (m, 1H), 3.3-3.15 (m, 3H), 2.92 (s, 3H), 1.68 (s, 6H).

Example 49—Synthesis of (R,S or S,R) tert-butyl (cis-2-(acetamidomethyl)-4-((4-fluorophenyl)sulfonyl)-3-methyl-3,4-dihydro-2H-benzo[b][1,4]oxazin-6-yl)carbamate (49A and 49B)

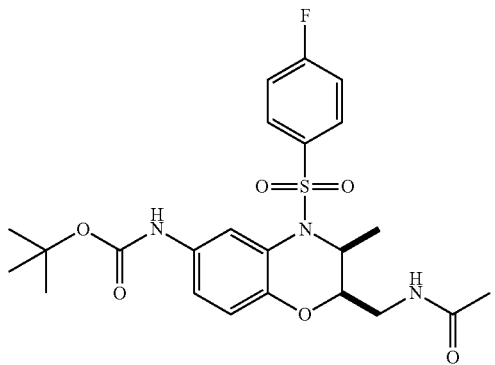 [SMILES: CC(=O)NC[C@H]1Oc2ccc(NC(=O)OC(C)(C)C)cc2N(S(=O)(=O)c2ccc(F)cc2)[C@H]1C]

The title compound was prepared according to the procedures described below.

Part I—Synthesis of ethyl 3-methyl-6-nitro-2H-benzo[b][1,4]oxazine-2-carboxylate

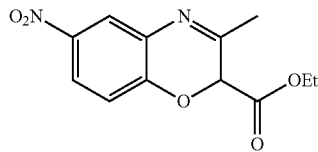 [SMILES: CCOC(=O)C1Oc2ccc([N+](=O)[O-])cc2N=C1C]

A mixture of 2-amino-4-nitrophenol (50 g, 320 mmol) and potassium carbonate (90 g, 625 mmol) in acetone (600 mL) was stirred for 10 minutes at room temperature. Ethyl 2-chloro-3-oxobutanoate (53 g, 320 mmol) was added into the reaction mixture and solution was stirred for two hours at 80° C. The reaction mixture was diluted with water and extracted with ethyl acetate. The combined organic layers were washed with brine, dried (Na$_2$SO$_4$) and concentrated to afford ethyl 3-methyl-6-nitro-2H-benzo[b][1,4]oxazine-2-carboxylate. LRMS (ESI) calculated for C$_{12}$H$_{13}$N$_2$O$_5$ (M+H)$^+$: 265. Found: 265.

Part II—Synthesis of cis- and trans-3-methyl-6-nitro-3,4-dihydro-2H-benzo[b][1,4]oxazin-2-yl methanol

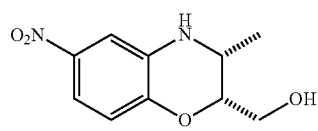

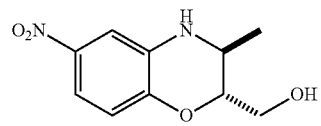

To a solution of compound ethyl 3-methyl-6-nitro-2H-benzo[b][1,4]oxazine-2-carboxylate (80 g, 302 mmol) in EtOH (900 mL) was added NaBH$_4$ (34 g, 905 mmol) in portions at 40° C., then the mixture was stirred at this temperature for 3 hours. When LCMS showed the reaction was completed, the reaction was quenched with water (200 mL) and extracted with EtOAc (1000 mL*3). The combined organic layers were washed with brine, dried over anhydrous Na$_2$SO$_4$. After filtration and concentration, the residue was purified by column chromatography (PE/EtOAc=5/1 to 1/1) to afford the desired product as a mixture of 4 diastereomers. The mixture was further purified with chiral SFC (Instrument: Thar SFC 200; Column: AD 300 mm*50 mm, 10 um; Mobile phase: A: Supercritical CO$_2$, B: MeOH (0.1% NH$_3$.H$_2$O), A:B=60:40 at 200 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to give four isomers: Isomer 1, trans; Isomer 2, cis; Isomer 3, trans; Isomer 4, cis. LRMS (ESI) calculated for C$_{10}$H$_{13}$N$_2$O$_4$ (M+H)$^+$: 225. Found: 225.

Part III—Synthesis of tert-butyl (cis-2-(hydroxymethyl)-3-methyl-3,4-dihydro-2H-benzo[b][1,4]oxazin-6-yl)carbamate

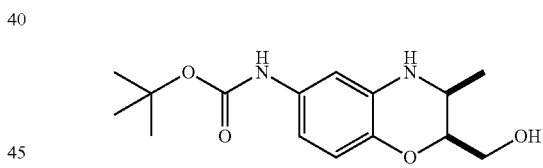

Isomer 2 (Example 64, Part II) cis-3-methyl-6-nitro-3,4-dihydro-2H-benzo[b][1,4]oxazin-2-yl methanol (60 mg, 0.26 mmol), palladium on carbon (50 mg) and Boc$_2$O (87 mg, 0.4 mmol) in EtOAc (6 mL) was stirred for 5 hours under H$_2$ atmosphere at room temperature. The reaction was monitored by TLC (PE/EtOAc=1/1). The solid was filtered off and the filtrate was diluted with 20 mL of DCM, washed with water, brine, dried and concentrated to afford the crude product. The residue was purified by prep-TLC (PE/EtOAc=1/1) to give tert-butyl (trans-2-(hydroxymethyl)-3-methyl-3,4-dihydro-2H-benzo[b][1,4]oxazin-6-yl)carbamate. $^1$H-NMR (CDCl$_3$, 400 MHz) δ 6.80 (br. s., 1H), 6.64 (d, J=8.4 Hz, 1H), 6.34 (dd, J=2.0, 8.0 Hz, 1H), 6.25 (br. s., 1H), 3.78~3.87 (m, 1H), 3.68~3.76 (m, 1H), 3.62~3.68 (m, 1H), 3.33 (m, J=6.4 Hz, 1H), 1.43 (s, 9H), 1.12 (d, J=5.6 Hz, 3H). LRMS (ESI) calculated for C$_{15}$H$_{23}$N$_2$O$_4$ (M+H)$^+$: 295. Found: 295.

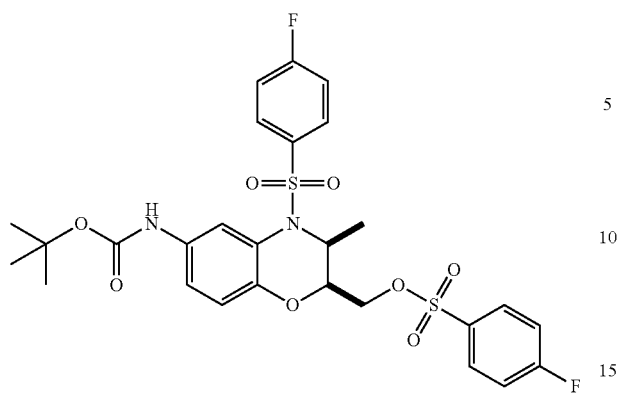

Part IV—Synthesis of (cis-6-((tert-butoxycarbonyl)amino)-4-((4-fluorophenyl)sulfonyl)-3-methyl-3,4-dihydro-2H-benzo[b][1,4]oxazin-2-yl)methyl 4-fluorobenzenesulfonate To a solution of compound tert-butyl (cis-2-(hydroxymethyl)-3-methyl-3,4-dihydro-2H-benzo[b][1,4]oxazin-6-yl)carbamate (60 mg, 0.2 mmol) in pyridine (0.2 mL, 2 mmol) was added 4-fluorobenzene-1-sulfonyl chloride (194 mg, 1 mmol) in one portion. Then the reaction was stirred at 50° C. for 6 hours. The reaction mixture was diluted with 20 mL of EtOAc, washed with 3 mL of 1 M HCl, brine, dried and concentrated to afford the crude product. The residue was purified by prep-TLC (PE/EtOAc=1/1) to afford (cis-6-((tert-butoxycarbonyl)amino)-4-((4-fluorophenyl)sulfonyl)-3-methyl-3,4-dihydro-2H-benzo[b][1,4]oxazin-2-yl)methyl 4-fluorobenzenesulfonate. $^1$H-NMR (CDCl$_3$, 400 MHz) δ 7.87 (dd, J=5.2, 8.4 Hz, 2H), 7.74~7.82 (m, 2H), 7.67 (br s, 1H), 7.06~7.16 (m, 4H), 6.79 (dd, J=2.4, 9.2 Hz, 1H), 6.59 (d, J=9.2 Hz, 1H), 6.34 (br s, 1H), 4.58 (dd, J=2.4, 6.4 Hz, 1H), 4.17 (dt, J=2.4, 5.6 Hz, 1H), 4.05 (q, J=7.2 Hz, 1H), 3.77~3.90 (m, 2H), 1.44 (s, 9H), 1.16 (d, J=6.65 Hz, 3H). LRMS (ESI) calculated for C$_{27}$H$_{29}$F$_3$N$_2$O$_4$S$_2$ (M+H)$^+$: 611. Found: 611.

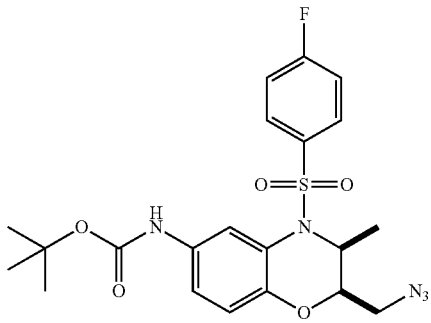 [SMILES: C[C@H]1[C@@H](CN=[N+]=[N-])Oc2ccc(NC(=O)OC(C)(C)C)cc2N1S(=O)(=O)c1ccc(F)cc1]

Part V—Synthesis of tert-butyl (cis-2-(azidomethyl)-4-((4-fluorophenyl)sulfonyl)-3-methyl-3,4-dihydro-2H-benzo[b][1,4]oxazin-6-yl)carbamate To a suspension of (cis-6-((tert-butoxycarbonyl)amino)-4-((4-fluorophenyl)sulfonyl)-3-methyl-3,4-dihydro-2H-benzo[b][1,4]oxazin-2-yl)methyl 4-fluorobenzenesulfonate (60 mg, 0.1 mmol) in dry DMF (5 mL) was added NaN$_3$ (30 mg, 0.4 mmol) at room temperature. Then the mixture was heated at 100° C. for 4 hours. The reaction mixture was quenched with saturated aq. NaHCO$_3$ (5 mL), extracted three times with DCM (20 mL each), and the combined organic layers were washed with brine, dried and concentrated to afford the desired crude product, which was used for the next step without further purification.

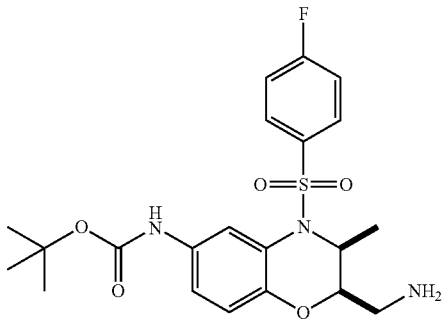 [SMILES: C[C@H]1[C@@H](CN)Oc2ccc(NC(=O)OC(C)(C)C)cc2N1S(=O)(=O)c1ccc(F)cc1]

Part VI—Synthesis of cis-butyl (trans-2-(aminomethyl)-4-((4-fluorophenyl)sulfonyl)-3-methyl-3,4-dihydro-2H-benzo[b][1,4]oxazin-6-yl)carbamate To a solution of tert-butyl (cis-2-(azidomethyl)-4-((4-fluorophenyl)sulfonyl)-3-methyl-3,4-dihydro-2H-benzo[b][1,4]oxazin-6-yl)carbamate (40 mg, 0.08 mmol) in 5 mL of EtOAc was added 30 mg of Pd/C at room temperature under hydrogen atmosphere. The mixture was stirred at room temperature for 4 hours. After filtration by suction on CELITE pad, the filtrate was concentrated to afford the desired crude product, which was used for the next step without further purification.

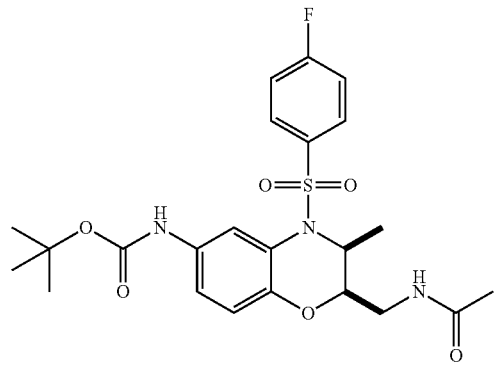 [SMILES: CC(=O)NC[C@H]1Oc2ccc(NC(=O)OC(C)(C)C)cc2N(S(=O)(=O)c2ccc(F)cc2)[C@H]1C]

Part VII—Synthesis of (S,R or R,S) tert-butyl (cis-2-(acetamidomethyl)-4-((4-fluorophenyl)sulfonyl)-3-methyl-3,4-dihydro-2H-benzo[b][1,4]oxazin-6-yl)carbamate To a solution of tert-butyl (cis-2-(aminomethyl)-4-((4-fluorophenyl)sulfonyl)-3-methyl-3,4-dihydro-2H-benzo[b][1,4]oxazin-6-yl)carbamate (30 mg, 0.07 mmol) and acetic anhydride (20 mg, 0.14 mmol) in DCM (5 mL) was added TEA (20 mg, 0.2 mmol) at room temperature, and the resulting mixture was stirred at room temperature for 6 hours. The reaction mixture was diluted with water (5 mL) and extracted three times with dichloromethane (20 mL each). The combined organic layers were concentrated and the residue was purified by column chromatography (PE:EtOAc=1:1) to afford tert-butyl (cis-2-(acetamidomethyl)-4-((4-fluorophenyl)sulfonyl)-3-methyl-3,4-dihydro-2H-benzo[b][1,4]oxazin-6-yl)carbamate. $^1$H-NMR (CDCl$_3$, 400 MHz) δ 7.91 (dd, J=5.2, 8.4 Hz, 1H), 7.59 (br. s., 1H), 7.15

(t, J=8.4 Hz, 2H), 6.84 (dd, J=2.0, 8.8 Hz, 1H), 6.73 (d, J=9.2 Hz, 1H), 6.32 (br. s., 1H), 5.90 (br. s., 1H), 4.47 (dd, J=2.4, 6.4 Hz, 1H), 4.07-4.13 (m, 1H), 3.17-3.36 (m, 2H), 1.94 (s, 3H), 1.44 (s, 8H), 1.12 (d, J=6.4 Hz, 3H). LRMS (ESI) calculated for $C_{23}H_{29}FN_3O_6S$ (M+H)$^+$: 494. Found: 494.

The other enantiomeric cis-isomer (S,R or R,S) of 1,1,1-trifluoro-2-methylpropan-2-yl (cis-2-(acetamidomethyl)-4-((4-fluorophenyl)sulfonyl)-3-methyl-3,4-dihydro-2H-benzo[b][1,4]oxazin-6-yl)carbamate was prepared from Isomer 4 using the same procedures exemplified above.

Example 50—Synthesis of both (S,R) and (R,S) 1,1,1-trifluoro-2-methylpropan-2-yl (cis-2-(acetamidomethyl)-4-((4-fluorophenyl)sulfonyl)-3-methyl-3,4-dihydro-2H-benzo[b][1,4]oxazin-6-yl)carbamate (50A and 50B)

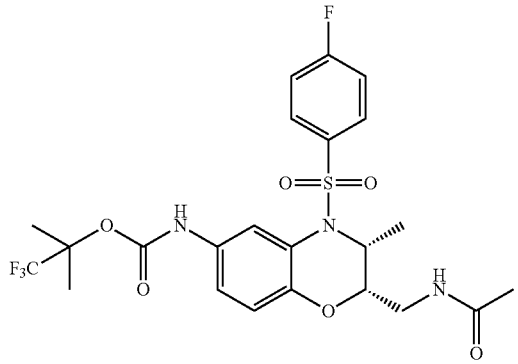

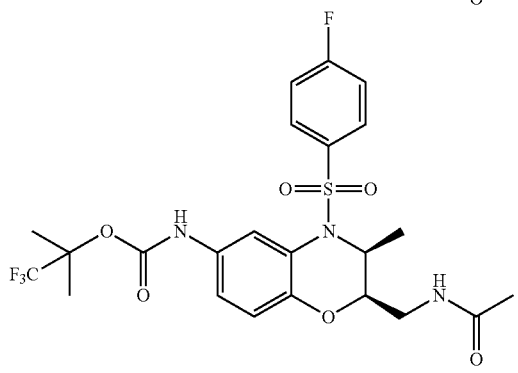

The title compound was prepared according to the procedures described below.

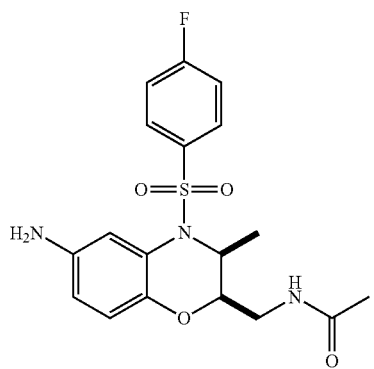 [SMILES: CC(=O)NC[C@H]1Oc2ccc(N)cc2N(S(=O)(=O)c2ccc(F)cc2)[C@H]1C]

Part I—Synthesis of (N-((cis-6-amino-4-((4-fluorophenyl)sulfonyl)-3-methyl-3,4-dihydro-2H-benzo[b][1,4]oxazin-2-yl)methyl)acetamide To a solution of tert-butyl (cis-2-(acetamidomethyl)-4-((4-fluorophenyl)sulfonyl)-3-methyl-3,4-dihydro-2H-benzo[b][1,4]oxazin-6-yl)carbamate (20 mg, 0.04 mmol) in dichloromethane (3 mL) was added TFA (1 mL), and the resulting mixture was stirred at room temperature for 4 hours. The reaction mixture was diluted with aq. NaHCO$_3$ and extracted with dichloromethane. The organic layer was washed with water, brine, dried and concentrated to afford the desired crude product.

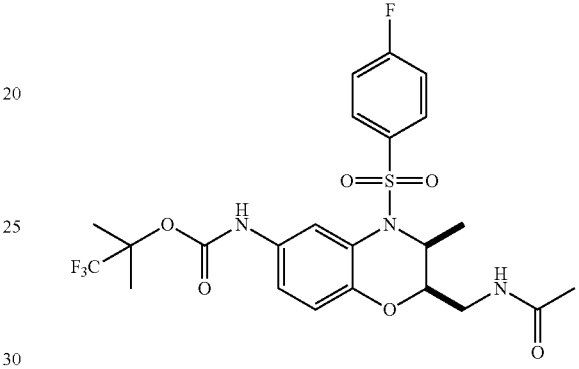

Part II—Synthesis of (R,S or S,R)-1,1,1-trifluoro-2-methylpropan-2-yl (cis-2-(acetamidomethyl)-4-((4-fluorophenyl)sulfonyl)-3-methyl-3,4-dihydro-2H-benzo[b][1,4]oxazin-6-yl)carbamate To a mixture of 4-nitrophenyl (1,1,1-trifluoro-2-methylpropan-2-yl) carbonate (40 mg, 0.046 mmol) and N-((cis-6-amino-4-((4-fluorophenyl)sulfonyl)-3-methyl-3,4-dihydro-2H-benzo[b][1,4]oxazin-2-yl)methyl)acetamide (15 mg, 0.04 mmol) was added DIPEA (0.2 mL) at room temperature. The resulting mixture was stirred at 100° C. for 3 hours. The reaction mixture was cooled to room temperature, diluted with EtOAc (20 mL), washed with saturated aq. NaHCO$_3$, followed by brine, and then 1 N NaOH. The combined organic layers were dried and concentrated to afford the crude product. The residue was purified by prep-TLC (PE:EtOAc=1:1) to afford 1,1,1-trifluoro-2-methylpropan-2-yl (cis-2-(acetamidomethyl)-4-((4-fluorophenyl)sulfonyl)-3-methyl-3,4-dihydro-2H-benzo[b][1,4]oxazin-6-yl)carbamate. $^1$H-NMR (CDCl$_3$, 400 MHz) δ 7.98 (dd, J=5.2, 8.0 Hz, 2H), 7.68 (br. s., 1H), 7.19~7.26 (m, 2H), 6.87~6.94 (m, 1H), 6.81~6.87 (m, 1H), 6.57 (br. s., 1H), 5.96 (br. s., 1H), 4.55 (d, J=4.8 Hz, 1H), 4.17~4.24 (m, 1H), 3.23~3.44 (m, 2H), 2.02 (s, 3H), 1.75 (d, J=2.8 Hz, 6H), 1.19 (d, J=6.4 Hz, 3H). LRMS (ESI) calculated for $C_{23}H_{26}F_4N_3O_6S$ (M+H)$^+$: 548. Found: 548.

The other enantiomeric cis-isomer (S,R or R,S) of 1,1,1-trifluoro-2-methylpropan-2-yl (cis-2-(acetamidomethyl)-4-((4-fluorophenyl)sulfonyl)-3-methyl-3,4-dihydro-2H-benzo[b][1,4]oxazin-6-yl)carbamate was prepared using the same procedures shown above.

Example 51—Synthesis of both (S,S) and (R,R)-tert-butyl-2-(acetamidomethyl)-4-(4-fluorophenylsulfonyl)-3-methyl-3,4-dihydro-2H-benzo[b][1,4]oxazin-6-ylcarbamate (51A and 51B)

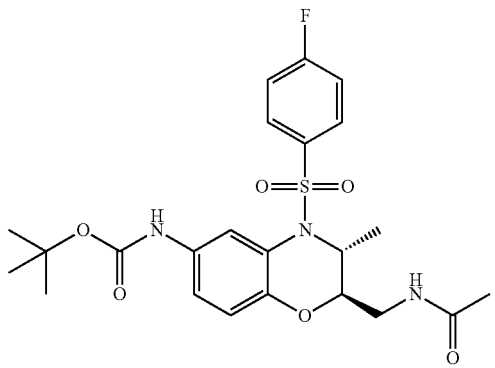

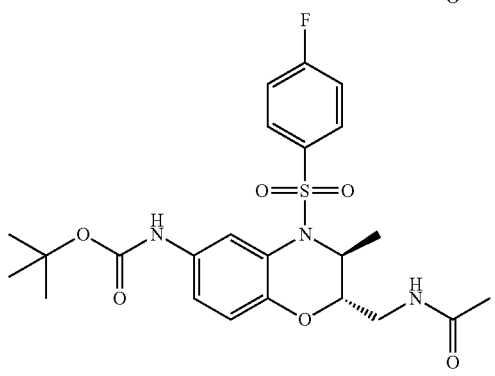

Starting from Isomers 1 and 3 isolated in Example 49, the two trans-enantiomers (S,S and R,R) of cis-tert-butyl-2-(acetamidomethyl)-4-(4-fluorophenylsulfonyl)-3-methyl-3,4-dihydro-2H-benzo[b][1,4]oxazin-6-ylcarbamate were prepared using the same procedures shown in Example 49 and 50. $^1$H NMR (400 MHz, DMSO-$d_6$): δ 9.32 (br s, 1H), 8.10 (t, J=5.6 Hz, 1H), 7.98 (br s, 1H), 7.67 (dd, J=9.2, 5.2 Hz, 2H), 7.41 (t, J=8.8 Hz, 2H), 7.17 (d, J=8.0 Hz, 1H), 6.77 (d, J=9.2 Hz, 1H), 4.38~4.50 (m, 1H), 3.15~3.24 (m, 1H), 3.00~3.13 (m, 2H), 1.87 (s, 3H), 1.48 (s, 9H), 1.00 (d, J=6.4 Hz, 3H). LCMS ESI calculated for $C_{23}H_{29}FN_3O_6S$ (M+H)$^+$: 494. found 494.

Example 52—Preparation of additional carbamates of 3-alkyl-3,4-dihydro-2H-benzo[b][1,4]oxazines The compounds in Table 20 below were prepared based on the experimental procedures described in Examples 49-51 and elsewhere in the detailed description, and can be achieved by one of skill in the art in light of the present disclosure.

TABLE 20

| Ex. No. | Structure | Name | Observed m/z |
|---|---|---|---|
| 52A | 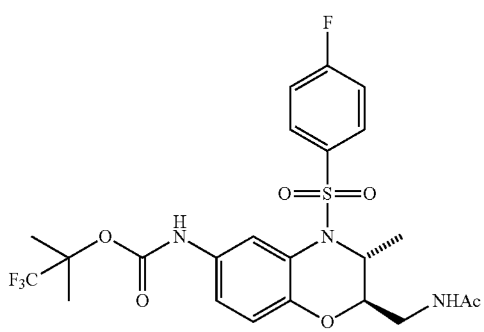 [SMILES: CC(=O)NC[C@H]1Oc2ccc(NC(=O)OC(C)(C)C(F)(F)F)cc2N(S(=O)(=O)c2ccc(F)cc2)[C@@H]1C] | 1,1,1-trifluoro-2-methylpropan-2-yl ((2S,3S or 2R,3R)-2-(acetamidomethyl)-4-((4-fluorophenyl)sulfonyl)-3-methyl-3,4-dihydro-2H-benzo[b][1,4]oxazin-6-yl)carbamate | 548 (M + H)$^+$ |
| 52B | 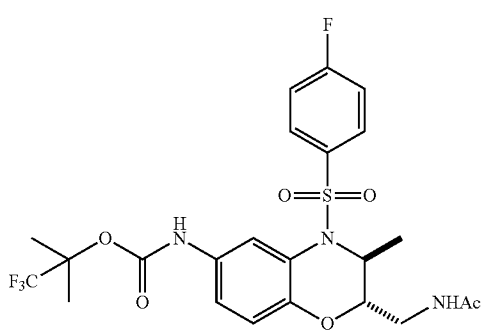 [SMILES: CC(=O)NC[C@@H]1Oc2ccc(NC(=O)OC(C)(C)C(F)(F)F)cc2N(S(=O)(=O)c2ccc(F)cc2)[C@H]1C] | 1,1,1-trifluoro-2-methylpropan-2-yl ((2S,3S or 2R,3R)-2-(acetamidomethyl)-4-((4-fluorophenyl)sulfonyl)-3-methyl-3,4-dihydro-2H-benzo[b][1,4]oxazin-6-yl)carbamate | 548 (M + H)$^+$ |

TABLE 20-continued

| Ex. No. | Structure | Name | Observed m/z |
|---|---|---|---|
| 52C | 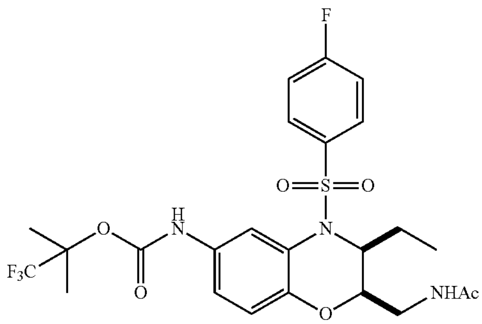 [SMILES: CC[C@H]1[C@@H](CNC(C)=O)Oc2ccc(NC(=O)OC(C)(C)C(F)(F)F)cc2N1S(=O)(=O)c1ccc(F)cc1] | 1,1,1-trifluoro-2-methylpropan-2-yl ((2R,3S or 2S,3R)-2-(acetamidomethyl)-3-ethyl-4-((4-fluorophenyl)sulfonyl)-3,4-dihydro-2H-benzo[b][1,4]oxazin-6-yl)carbamate | 562 (M + H)+ |
| 52D | 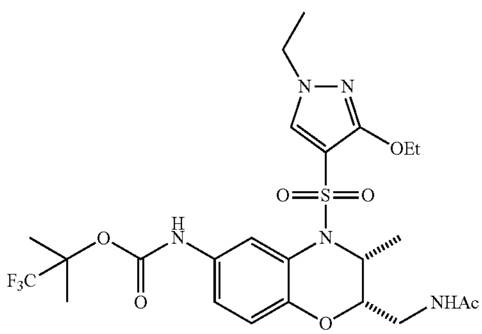 [SMILES: CCOc1nn(CC)cc1S(=O)(=O)N1c2cc(NC(=O)OC(C)(C)C(F)(F)F)ccc2O[C@@H](CNC(C)=O)[C@H]1C] | 1,1,1-trifluoro-2-methylpropan-2-yl ((2S,3R or 2R,3S)-2-(acetamidomethyl)-4-((3-ethoxy-1-ethyl-1H-pyrazol-4-yl)sulfonyl)-3-methyl-3,4-dihydro-2H-benzo[b][1,4]oxazin-6-yl)carbamate | 592 (M + H)+ |
| 52E | 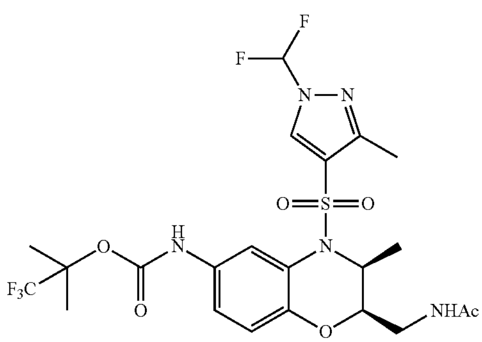 [SMILES: CC(=O)NC[C@H]1Oc2ccc(NC(=O)OC(C)(C)C(F)(F)F)cc2N(S(=O)(=O)c2cn(C(F)F)nc2C)[C@H]1C] | 1,1,1-trifluoro-2-methylpropan-2-yl ((2R,3S or 2S,3R)-2-(acetamidomethyl)-4-((1-(difluoromethyl)-3-methyl-1H-pyrazol-4-yl)sulfonyl)-3-methyl-3,4-dihydro-2H-benzo[b][1,4]oxazin-6-yl)carbamate | 584 (M + H)+ |
| 52F | 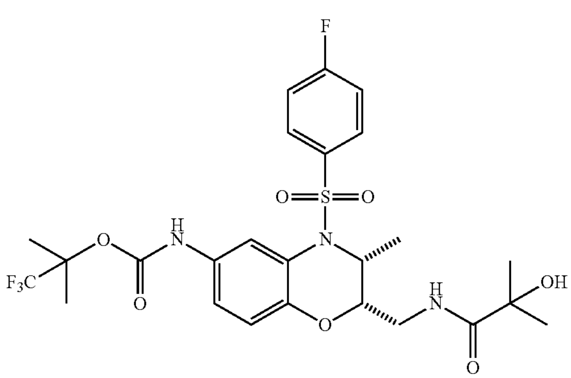 [SMILES: C[C@@H]1[C@H](CNC(=O)C(C)(C)O)Oc2ccc(NC(=O)OC(C)(C)C(F)(F)F)cc2N1S(=O)(=O)c1ccc(F)cc1] | 1,1,1-trifluoro-2-methylpropan-2-yl ((2S,3R or 2R,3S)-4-((4-fluorophenyl)sulfonyl)-2-((2-hydroxy-2-methylpropanamido)methyl)-3-methyl-3,4-dihydro-2H-benzo[b][1,4]oxazin-6-yl)carbamate | 592 (M + H)+ |

TABLE 20-continued

| Ex. No. | Structure | Name | Observed m/z |
|---|---|---|---|
| 52G | 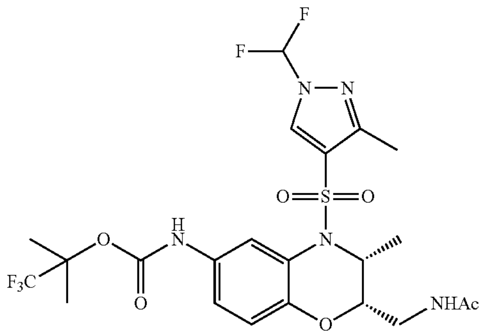 [SMILES: CC(=O)NC[C@@H]1Oc2ccc(NC(=O)OC(C)(C)C(F)(F)F)cc2N(S(=O)(=O)c2cn(C(F)F)nc2C)[C@@H]1C] | 1,1,1-trifluoro-2-methylpropan-2-yl ((2S,3R)-2-(acetamidomethyl)-4-((1-(difluoromethyl)-3-methyl-1H-pyrazol-4-yl)sulfonyl)-3-methyl-3,4-dihydro-2H-benzo[b][1,4]oxazin-6-yl)carbamate | 584 (M + H)+ |
| 52H | 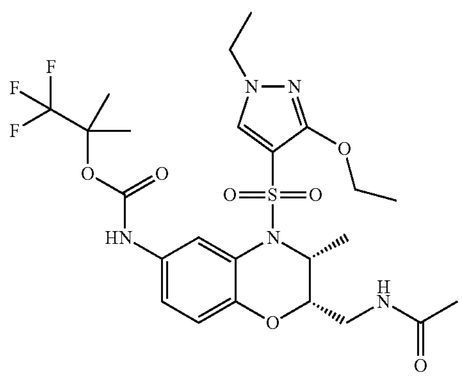 [SMILES: CCOc1nn(CC)cc1S(=O)(=O)N1c2cc(NC(=O)OC(C)(C)C(F)(F)F)ccc2O[C@@H](CNC(C)=O)[C@H]1C] | 2,2,2-trifluoro-1,1-dimethylethyl {(2S,3R)-2-[(acetylamino)methyl]-4-[(3-ethoxy-1-ethyl-1H-pyrazol-4-yl)sulfonyl]-3-methyl-3,4-dihydro-2H-1,4-benzoxazin-6-yl}carbamate | 592 (M + H)+ |
| 52i | 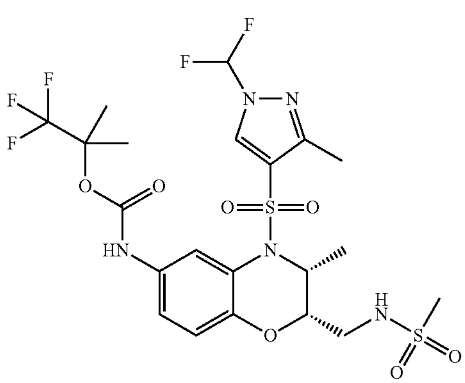 [SMILES: Cc1nn(C(F)F)cc1S(=O)(=O)N1c2cc(NC(=O)OC(C)(C)C(F)(F)F)ccc2O[C@@H](CNS(C)(=O)=O)[C@H]1C] | 2,2,2-trifluoro-1,1-dimethylethyl [(2S,3R)-4-{[1-(difluoromethyl)-3-methyl-1H-pyrazol-4-yl]sulfonyl}-3-methyl-2-{[(methylsulfonyl)amino]methyl}-3,4-dihydro-2H-1,4-benzoxazin-6-yl]carbamate | 620 (M + H)+ |
| 52J | 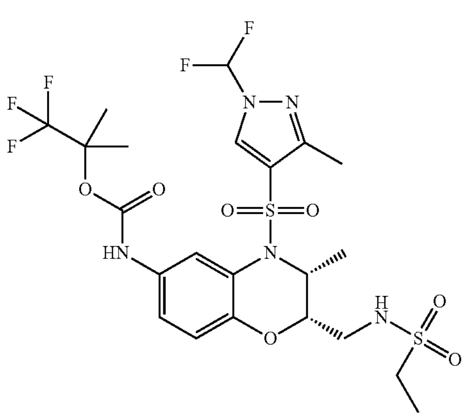 [SMILES: CCS(=O)(=O)NC[C@@H]1Oc2ccc(NC(=O)OC(C)(C)C(F)(F)F)cc2N(S(=O)(=O)c2cn(C(F)F)nc2C)[C@@H]1C] | 2,2,2-trifluoro-1,1-dimethylethyl [(2S,3R)-4-{[1-(difluoromethyl)-3-methyl-1H-pyrazol-4-yl]sulfonyl}-2-{[(ethylsulfonyl)amino]methyl}-3-methyl-3,4-dihydro-2H-1,4-benzoxazin-6-yl]carbamate | 634 (M + H)+ |

TABLE 20-continued

| Ex. No. | Structure | Name | Observed m/z |
|---|---|---|---|
| 52K | 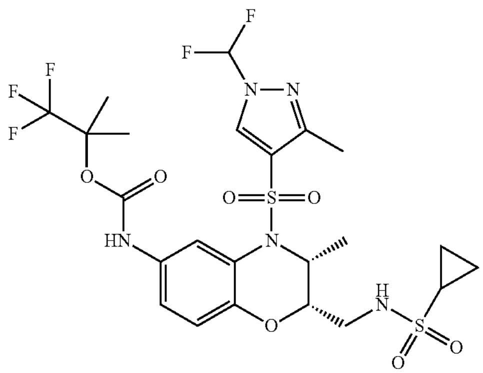 [SMILES: Cc1nn(C(F)F)cc1S(=O)(=O)N1c2cc(NC(=O)OC(C)(C)C(F)(F)F)ccc2O[C@@H](CNS(=O)(=O)C2CC2)[C@H]1C] | 2,2,2-trifluoro-1,1-dimethylethyl [(2S,3R)-2-{[(cyclopropylsulfonyl)amino]methyl}-4-{[1-(difluoromethyl)-3-methyl-1H-pyrazol-4-yl]sulfonyl}-3-methyl-3,4-dihydro-2H-1,4-benzoxazin-6-yl]carbamate | 646 (M + H)+ |
| 52L | 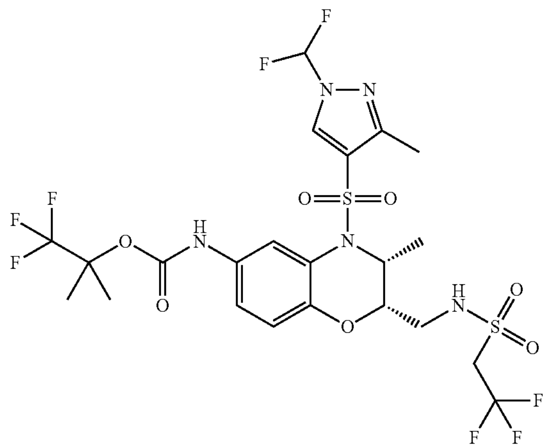 [SMILES: Cc1nn(C(F)F)cc1S(=O)(=O)N1c2cc(NC(=O)OC(C)(C)C(F)(F)F)ccc2O[C@@H](CNS(=O)(=O)CC(F)(F)F)[C@H]1C] | 2,2,2-trifluoro-1,1-dimethylethyl [(2S,3R)-4-{[1-(difluoromethyl)-3-methyl-1H-pyrazol-4-yl]sulfonyl}-3-methyl-2-({[(2,2,2-trifluoroethyl)sulfonyl]amino}methyl)-3,4-dihydro-2H-1,4-benzoxazin-6-yl]carbamate | 688 (M + H)+ |
| 52M | 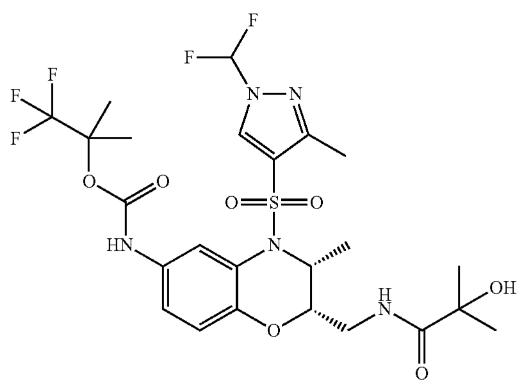 [SMILES: Cc1nn(C(F)F)cc1S(=O)(=O)N1c2cc(NC(=O)OC(C)(C)C(F)(F)F)ccc2O[C@@H](CNC(=O)C(C)(C)O)[C@H]1C] | 2,2,2-trifluoro-1,1-dimethylethyl [(2S,3R)-4-{[1-(difluoromethyl)-3-methyl-1H-pyrazol-4-yl]sulfonyl}-2-{[(2-hydroxy-2-methylpropanoyl)amino]methyl}-3-methyl-3,4-dihydro-2H-1,4-benzoxazin-6-yl]carbamate | 628 (M + H)+ |
| 52N | 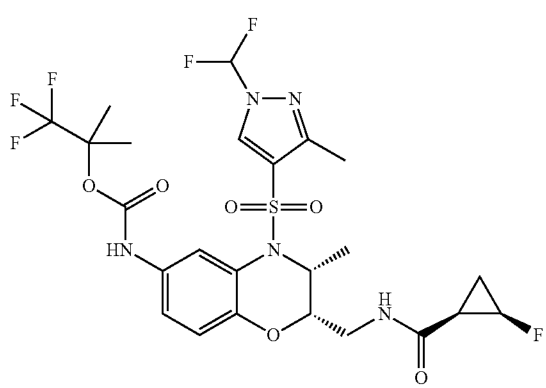 [SMILES: Cc1nn(C(F)F)cc1S(=O)(=O)N1c2cc(NC(=O)OC(C)(C)C(F)(F)F)ccc2O[C@@H](CNC(=O)[C@H]2C[C@H]2F)[C@H]1C] | 2,2,2-trifluoro-1,1-dimethylethyl {(2S,3R)-4-{[1-(difluoromethyl)-3-methyl-1H-pyrazol-4-yl]sulfonyl}-2-[({[(1R,2R)-2-fluorocyclopropyl]carbonyl}amino)methyl]-3-methyl-3,4-dihydro-2H-1,4-benzoxazin-6-yl}carbamate | 628 (M + H)+ |

TABLE 20-continued

| Ex. No. | Structure | Name | Observed m/z |
|---|---|---|---|
| 52o | 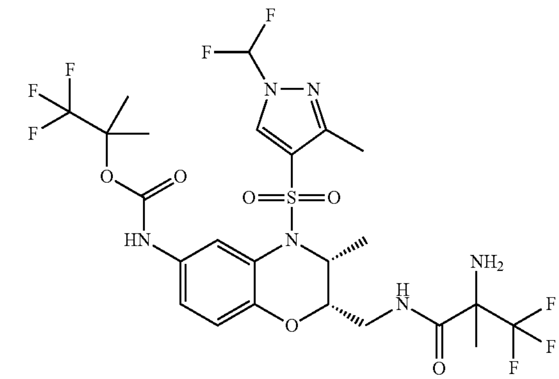 [SMILES: Cc1nn(C(F)F)cc1S(=O)(=O)N1c2cc(NC(=O)OC(C)(C)C(F)(F)F)ccc2O[C@@H](CNC(=O)C(C)(N)C(F)(F)F)[C@H]1C] | 2,2,2-trifluoro-1,1-dimethylethyl [(2S,3R)-2-{[(2R and 2S-amino-3,3,3-trifluoro-2-methylpropanoyl)amino]methyl}-4-{[1-(difluoromethyl)-3-methyl-1H-pyrazol-4-yl]sulfonyl}-3-methyl-3,4-dihydro-2H-1,4-benzoxazin-6-yl]carbamate | 681 (M + H)+ |
| 52P | 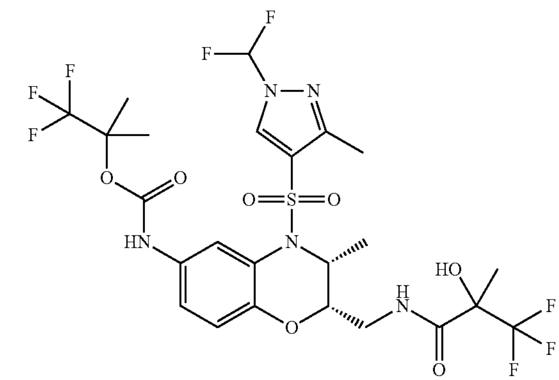 [SMILES: Cc1nn(C(F)F)cc1S(=O)(=O)N1c2cc(NC(=O)OC(C)(C)C(F)(F)F)ccc2O[C@@H](CNC(=O)C(C)(O)C(F)(F)F)[C@H]1C] | 1,1,1-trifluoro-2-methylpropan-2-yl ((2S,3R)-4-((1-(difluoromethyl)-3-methyl-1H-pyrazol-4-yl)sulfonyl)-3-methyl-2-(((R and S)-3,3,3-trifluoro-2-hydroxy-2-methylpropanamido)methyl)-3,4-dihydro-2H-benzo[b][1,4]oxazin-6-yl)carbamate | 682 (M + H)+ |
| 52Q | 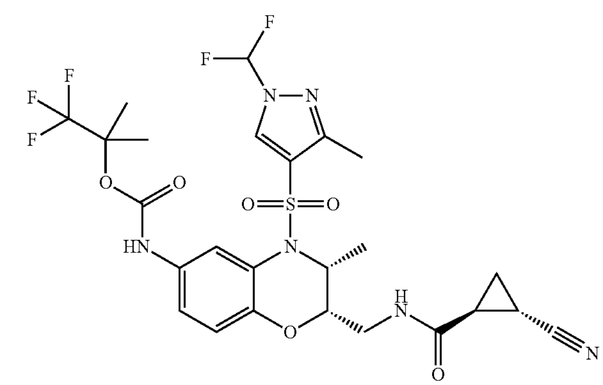 [SMILES: Cc1nn(C(F)F)cc1S(=O)(=O)N1c2cc(NC(=O)OC(C)(C)C(F)(F)F)ccc2O[C@@H](CNC(=O)[C@H]2C[C@@H]2C#N)[C@H]1C] | 2,2,2-trifluoro-1,1-dimethylethyl [(2S,3R)-2-[({[(1S,2S)-2-cyanocyclopropyl]carbonyl}amino)methyl]-4-{[1-(difluoromethyl)-3-methyl-1H-pyrazol-4-yl]sulfonyl}-3-methyl-3,4-dihydro-2H-1,4-benzoxazin-6-yl]carbamate | 635 (M + H)+ |
| 52R | 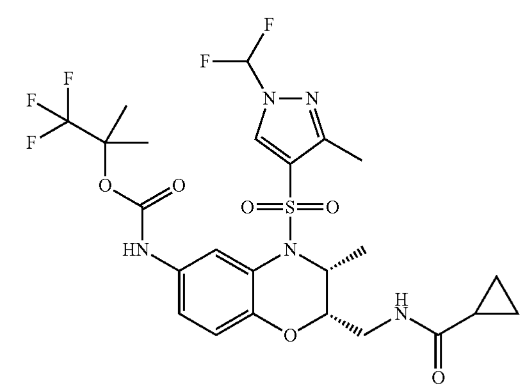 [SMILES: Cc1nn(C(F)F)cc1S(=O)(=O)N1c2cc(NC(=O)OC(C)(C)C(F)(F)F)ccc2O[C@@H](CNC(=O)C2CC2)[C@H]1C] | 2,2,2-trifluoro-1,1-dimethylethyl [(2S,3R)-2-{[(cyclopropylcarbonyl)amino]methyl}-4-{[1-(difluoromethyl)-3-methyl-1H-pyrazol-4-yl]sulfonyl}-3-methyl-3,4-dihydro-2H-1,4-benzoxazin-6-yl]carbamate | 610 (M + H)+ |

TABLE 20-continued

| Ex. No. | Structure | Name | Observed m/z |
|---|---|---|---|
| 52S | 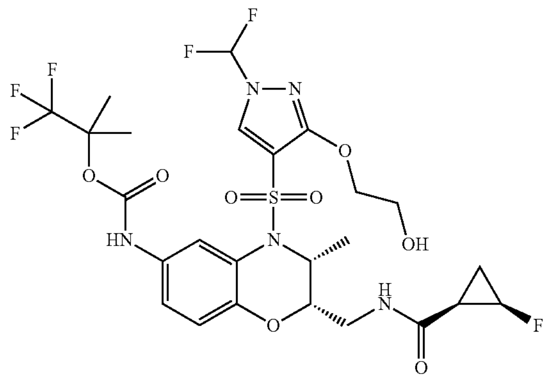 [SMILES: C[C@@H]1[C@H](CNC(=O)[C@H]2C[C@H]2F)Oc2ccc(NC(=O)OC(C)(C)C(F)(F)F)cc2N1S(=O)(=O)c1cn(C(F)F)nc1OCCO] | 2,2,2-trifluoro-1,1-dimethylethyl {(2S,3R)-4-{[1-(difluoromethyl)-3-(2-hydroxyethoxy)-1H-pyrazol-4-yl]sulfonyl}-2-[({[(1R,2R)-2-fluorocyclopropyl]carbonyl}amino)methyl]-3-methyl-3,4-dihydro-2H-1,4-benzoxazin-6-yl}carbamate | 674 (M + H)+ |
| 52T | 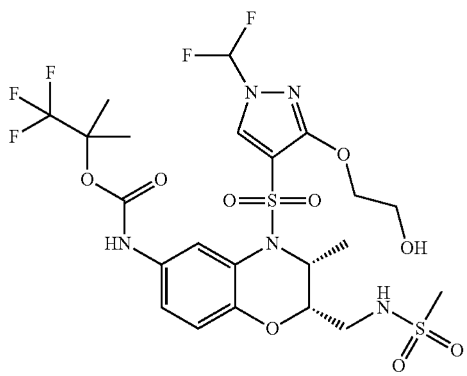 [SMILES: C[C@@H]1[C@H](CNS(C)(=O)=O)Oc2ccc(NC(=O)OC(C)(C)C(F)(F)F)cc2N1S(=O)(=O)c1cn(C(F)F)nc1OCCO] | 2,2,2-trifluoro-1,1-dimethylethyl [(2S,3R)-4-{[1-(difluoromethyl)-3-(2-hydroxyethoxy)-1H-pyrazol-4-yl]sulfonyl}-3-methyl-2-{[(methylsulfonyl)amino]methyl}-3,4-dihydro-2H-1,4-benzoxazin-6-yl]carbamate | 688 (M + Na)+ |
| 52U | 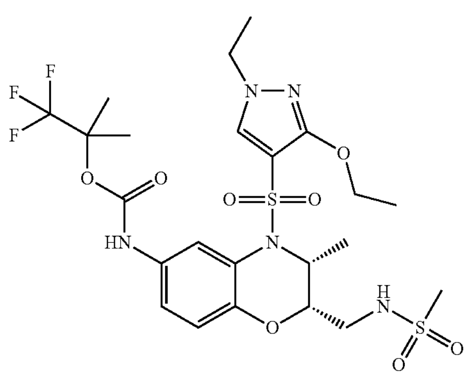 [SMILES: CCOc1nn(CC)cc1S(=O)(=O)N1c2cc(NC(=O)OC(C)(C)C(F)(F)F)ccc2O[C@@H](CNS(C)(=O)=O)[C@H]1C] | 2,2,2-trifluoro-1,1-dimethylethyl [(2S,3R)-4-[(3-ethoxy-1-ethyl-1H-pyrazol-4-yl)sulfonyl]-3-methyl-2-{[(methylsulfonyl)amino]methyl}-3,4-dihydro-2H-1,4-benzoxazin-6-yl]carbamate | 628 (M + H)+ |
| 52V | 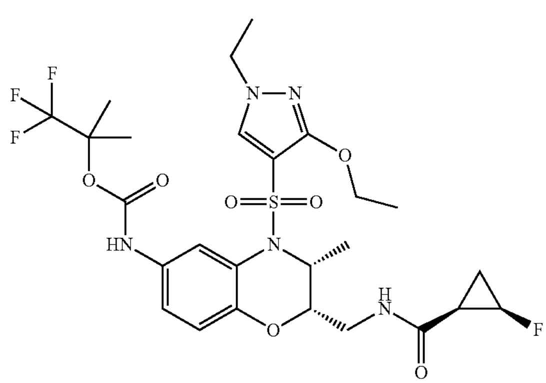 [SMILES: CCOc1nn(CC)cc1S(=O)(=O)N1c2cc(NC(=O)OC(C)(C)C(F)(F)F)ccc2O[C@@H](CNC(=O)[C@H]2C[C@H]2F)[C@H]1C] | 2,2,2-trifluoro-1,1-dimethylethyl {(2S,3R)-4-[(3-ethoxy-1-ethyl-1H-pyrazol-4-yl)sulfonyl]-2-[({[(1R,2R)-2-fluorocyclopropyl]carbonyl}amino)methyl]-3-methyl-3,4-dihydro-2H-1,4-benzoxazin-6-yl}carbamate | 636 (M + H)+ |

TABLE 20-continued

| Ex. No. | Structure | Name | Observed m/z |
|---|---|---|---|
| 52W | 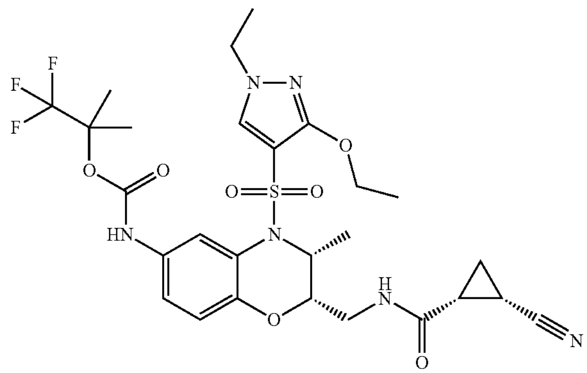 [SMILES: CCOc1nn(CC)cc1S(=O)(=O)N1c2cc(NC(=O)OC(C)(C)C(F)(F)F)ccc2O[C@@H](CNC(=O)[C@@H]2C[C@@H]2C#N)[C@H]1C] | 2,2,2-trifluoro-1,1-dimethylethyl {(2S,3R)-2-[({[(1R,2S)-2-cyanocyclopropyl]carbonyl}amino)methyl]-4-[(3-ethoxy-1-ethyl-1H-pyrazol-4-yl)sulfonyl]-3-methyl-3,4-dihydro-2H-1,4-benzoxazin-6-yl}carbamate | 643 (M + H)+ |
| 52X | 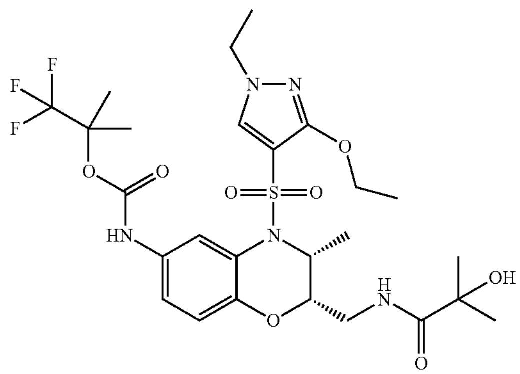 [SMILES: CCOc1nn(CC)cc1S(=O)(=O)N1c2cc(NC(=O)OC(C)(C)C(F)(F)F)ccc2O[C@@H](CNC(=O)C(C)(C)O)[C@H]1C] | 2,2,2-trifluoro-1,1-dimethylethyl [(2S,3R)-4-[(3-ethoxy-1-ethyl-1H-pyrazol-4-yl)sulfonyl]-2-{[(2-hydroxy-2-methylpropanoyl)amino]methyl}-3-methyl-3,4-dihydro-2H-1,4-benzoxazin-6-yl]carbamate | 636 (M + H)+ |
| 52Y | 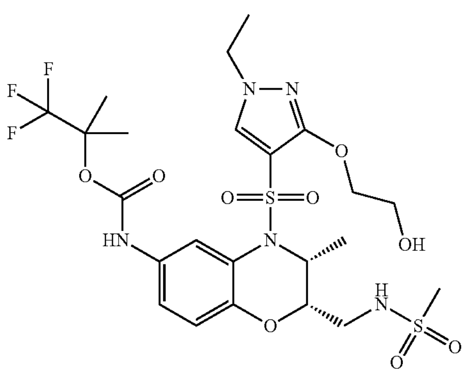 [SMILES: CCn1cc(S(=O)(=O)N2c3cc(NC(=O)OC(C)(C)C(F)(F)F)ccc3O[C@@H](CNS(C)(=O)=O)[C@H]2C)c(OCCO)n1] | 2,2,2-trifluoro-1,1-dimethylethyl [(2S,3R)-4-{[1-ethyl-3-(2-hydroxyethoxy)-1H-pyrazol-4-yl]sulfonyl}-3-methyl-2-{[(methylsulfonyl)amino]methyl}-3,4-dihydro-2H-1,4-benzoxazin-6-yl]carbamate | 644 (M + H)+ |
| 52Z | 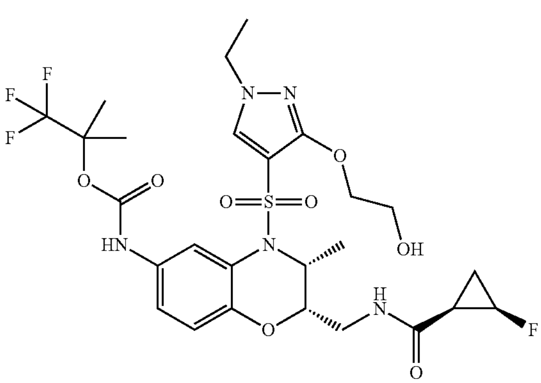 [SMILES: CCn1cc(S(=O)(=O)N2c3cc(NC(=O)OC(C)(C)C(F)(F)F)ccc3O[C@@H](CNC(=O)[C@H]3C[C@H]3F)[C@H]2C)c(OCCO)n1] | 2,2,2-trifluoro-1,1-dimethylethyl {(2S,3R)-4-{[1-ethyl-3-(2-hydroxyethoxy)-1H-pyrazol-4-yl]sulfonyl}-2-[({[(1R,2R)-2-fluorocyclopropyl]carbonyl}amino)methyl]-3-methyl-3,4-dihydro-2H-1,4-benzoxazin-6-yl}carbamate | 652 (M + H)+ |

TABLE 20-continued

| Ex. No. | Structure | Name | Observed m/z |
|---|---|---|---|
| 52AA | 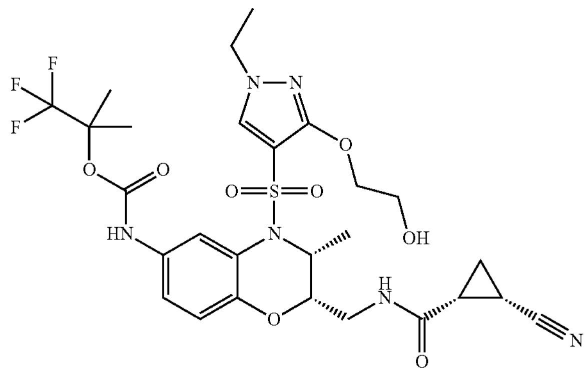 [SMILES: CCn1cc(S(=O)(=O)N2c3cc(NC(=O)OC(C)(C)C(F)(F)F)ccc3O[C@@H](CNC(=O)[C@@H]3C[C@@H]3C#N)[C@H]2C)c(OCCO)n1] | 2,2,2-trifluoro-1,1-dimethylethyl [(2S,3R)-2-[({[(1R,2S)-2-cyanocyclopropyl]carbonyl}amino)methyl]-4-{[1-ethyl-3-(2-hydroxyethoxy)-1H-pyrazol-4-yl]sulfonyl}-3-methyl-3,4-dihydro-2H-1,4-benzoxazin-6-yl]carbamate | 659 (M + H)+ |
| 52AB | 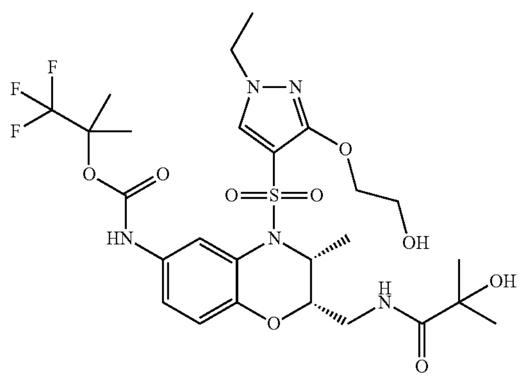 [SMILES: CCn1cc(S(=O)(=O)N2c3cc(NC(=O)OC(C)(C)C(F)(F)F)ccc3O[C@@H](CNC(=O)C(C)(C)O)[C@H]2C)c(OCCO)n1] | 2,2,2-trifluoro-1,1-dimethylethyl [(2S,3R)-4-{[1-ethyl-3-(2-hydroxyethoxy)-1H-pyrazol-4-yl]sulfonyl}-2-{[(2-hydroxy-2-methylpropanoyl)amino]methyl}-3-methyl-3,4-dihydro-2H-1,4-benzoxazin-6-yl]carbamate | 674 (M + Na)+ |
| 52AC | 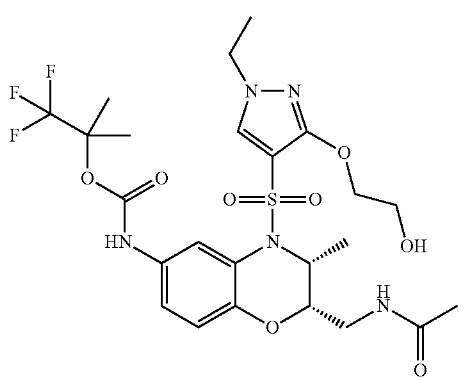 [SMILES: CCn1cc(S(=O)(=O)N2c3cc(NC(=O)OC(C)(C)C(F)(F)F)ccc3O[C@@H](CNC(C)=O)[C@H]2C)c(OCCO)n1] | 2,2,2-trifluoro-1,1-dimethylethyl [(2S,3R)-2-[(acetylamino)methyl]-4-{[1-ethyl-3-(2-hydroxyethoxy)-1H-pyrazol-4-yl]sulfonyl}-3-methyl-3,4-dihydro-2H-1,4-benzoxazin-6-yl]carbamate | 608 (M + Na)+ |

Example 53—Synthesis of 1,1,1-trifluoro-2-methyl-propan-2-yl ((2S,3R)-2-((S)-1-acetamidoethyl)-4-((3,4-difluorophenyl)sulfonyl)-3-methyl-3,4-dihydro-2H-benzo[b][1,4]oxazin-6-yl)carbamate

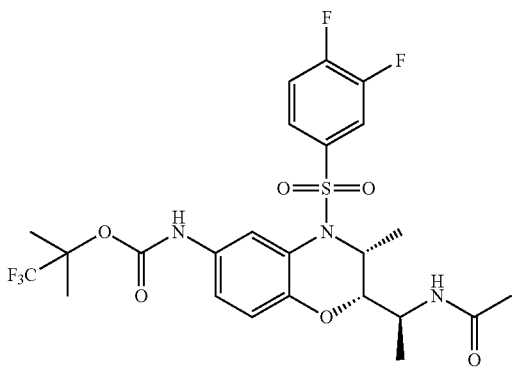 [SMILES: CC(=O)N[C@@H](C)[C@@H]1Oc2ccc(NC(=O)OC(C)(C)C(F)(F)F)cc2N(S(=O)(=O)c2ccc(F)c(F)c2)[C@@H]1C]

Step 1—Synthesis of (2S,3S,4R)-4-((tert-butoxycarbonyl)amino)-3-((tert-butyldimethylsilyl)oxy)-2-methylpentanoic acid

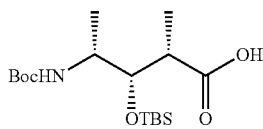

Into a 500-mL 3-necked round-bottom flask purged and maintained under an inert atmosphere of nitrogen, was placed a solution of known (*JACS*, 2003, 8218) (2S,3S,4R)-4-[[(tert-butoxy)carbonyl]amino]-3-hydroxy-2-methylpentanoic acid (9.88 g, 39.95 mmol, 1.00 equiv) in dichloromethane (200 mL), 2,6-dimethylpyridine (12.8 g, 119.46 mmol, 3.00 equiv). This was followed by the addition of TBSOTf (26.4 g, 100.00 mmol, 2.50 equiv) dropwise with stirring at −78° C. The resulting solution was stirred for 60 min at −78° C. The reaction was then quenched by the addition of water/ice. The resulting solution was extracted with 3×200 mL of ethyl acetate and the organic layers combined and concentrated under vacuum. The resulting solution was diluted with 150 mL of methanol. Then 50 mL of K$_2$CO$_3$ (0.5 M) was added. The resulting solution was allowed to react, with stirring, for an additional 60 min at room temperature. The pH value of the solution was adjusted to 2 with hydrogen chloride (1 N). The resulting solution was extracted with 3×300 mL of ethyl acetate and the organic layers combined and concentrated under vacuum. The crude product was applied onto a silica gel column with ethyl acetate/petroleum ether (1:1) to afford (2S,3S,4R)-4-[[(tert-butoxy)carbonyl]amino]-3-[(tert-butyldimethylsilyl)oxy]-2-methylpentanoic acid as a white solid. $^1$H-NMR (CDCl$_3$, 400 MHz) δ 4.48 (br s, 1H), 4.05 (m, 1H), 3.78 (m, 1H), 2.63 (m, 1H), 1.25-1.10 (m, 8H), 0.90 (m, 13H), 0.30 (m, 8H).

Step 2—Synthesis of benzyl tert-butyl ((2R,3S,4S)-3-((tert-butyldimethylsilyl)oxy)pentane-2,4-diyl) dicarbamate

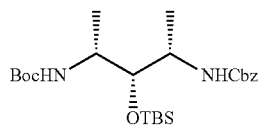

Into a 50-mL round-bottom flask purged and maintained under an inert atmosphere of nitrogen, was placed a solution of (2S,3S,4R)-4-[[(tert-butoxy)carbonyl]amino]-3-[(tert-butyldimethylsilyl)oxy]-2-methylpentanoic acid (1.8 g, 4.98 mmol, 1.00 equiv) in toluene (20 mL), DPPA (1.38 g, 5.01 mmol, 1.00 equiv), TEA (1.0 g, 9.88 mmol, 2.00 equiv). The resulting solution was stirred for 2 h at 60° C. Then phenylmethanol (1.62 g, 14.98 mmol, 3.00 equiv) and TEA (1.0 g, 9.88 mmol, 2.0 eq.) were added. The resulting solution was allowed to react, with stirring, for an additional 3 days at 90° C. The reaction was then quenched by the addition of water. The resulting solution was extracted with 3×50 mL of ethyl acetate and the organic layers combined, then washed with 2×30 mL of brine, dried and concentrated. The crude product was applied onto a silica gel column with ethyl acetate/petroleum ether (1:10) to afford tert-butyl N-[(2S,3S,4S)-4-[[(benzyloxy)carbonyl]amino]-3-[(tert-butyldimethylsilyl)oxy]pentan-2-yl]carbamate as a colorless oil, which was used in the next step without further purification.

Step 3—Synthesis of benzyl tert-butyl ((2R,3S,4S)-3-hydroxypentane-2,4-diyl)dicarbamate

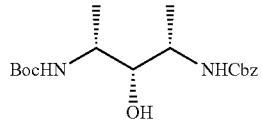 [SMILES: C[C@H](NC(=O)OCc1ccccc1)[C@H](O)[C@@H](C)NC(=O)OC(C)(C)C]

Into a 50-mL round-bottom flask, was placed a solution of tert-butyl N-[(2R,3S,4R)-4-[[(benzyloxy)carbonyl]amino]-3-[(tert-butyldimethylsilyl)oxy]pentan-2-yl]carbamate (1.3 g, 2.79 mmol, 1.00 equiv) in tetrahydrofuran (20 mL), TBAF (1.46 g, 5.58 mmol, 2.00 equiv). The resulting solution was stirred for 2 h at room temperature, then concentrated under vacuum. The crude product was applied onto a silica gel column with ethyl acetate/petroleum ether (1:2) to afford tert-butyl N-[(2S,3S,4R)-4-[[(benzyloxy)carbonyl]amino]-3-hydroxypentan-2-yl]carbamate as a colorless oil, which was used in the next step without further purification.

Step 4—Synthesis of benzyl tert-butyl ((2R,3S,4S)-3-(2-bromo-4-nitrophenoxy)pentane-2,4-diyl)dicarbamate

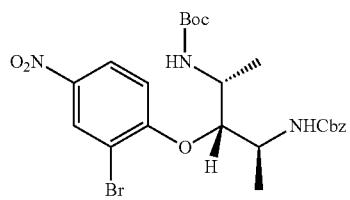 [SMILES: C[C@H](NC(=O)OCc1ccccc1)[C@H](Oc1ccc([N+](=O)[O-])cc1Br)[C@@H](C)NC(=O)OC(C)(C)C]

Into a 50-mL 3-necked round-bottom flask, was placed tert-butyl N-[(2R,3S,4S)-4-[[(benzyloxy)carbonyl]amino]-3-hydroxypentan-2-yl]carbamate (950 mg, 2.70 mmol, 1.00 equiv), followed by the addition of sodium hydride (324 mg, 8.10 mmol, 3.00 equiv) in several portions at 0° C. To this suspension was added tetrahydrofuran (20 mL) and 2-bromo-1-fluoro-4-nitrobenzene (768 mg, 3.49 mmol, 1.30 equiv). The resulting mixture was stirred for 30 min at 0° C. and at room temperature for 12 h. The reaction was then quenched by the addition of 20 mL of water/ice and the resulting mixture was extracted with 3×30 mL of ethyl acetate. The crude product was applied onto a silica gel column with ethyl acetate/petroleum ether (1:20-1:1) to afford tert-butyl N-[(2R,3S,4S)-4-[[(benzyloxy)carbonyl]amino]-3-(2-bromo-4-nitrophenoxy)pentan-2-yl]carbamate as a yellow solid.

Step 5—Synthesis of benzyl ((2S,3R,4R)-4-amino-3-(2-bromo-4-nitrophenoxy)pentan-2-yl)carbamate

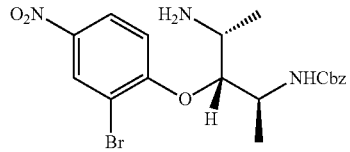 [SMILES: C[C@H](NC(=O)OCc1ccccc1)[C@H](Oc1ccc([N+](=O)[O-])cc1Br)[C@@H](C)N]

Into a 25-mL round-bottom flask was placed a solution of tert-butyl N-[(2R,3S,4S)-4-[[(benzyloxy)carbonyl]amino]-3-(2-bromo-4-nitrophenoxy)pentan-2-yl]carbamate (450 mg, 0.81 mmol, 1.00 equiv) in dichloromethane (10 mL) and $CF_3COOH$ (3 mL). The resulting solution was stirred for 2 h at room temperature, then quenched with saturated $NaHCO_3$ (aq.). The resulting mixture was extracted with DCM (20 mL×3) and the combined organic layers concentrated under vacuum to afford benzyl N-[(2S,3R,4R)-4-amino-3-(2-bromo-4-nitrophenoxy)pentan-2-yl]carbamate as a yellow solid, which was carried forward without further purification.

Step 6—Synthesis of benzyl ((2S,3S,4R)-3-(2-bromo-4-nitrophenoxy)-4-(3,4-difluorophenylsulfonamido)pentan-2-yl)carbamate

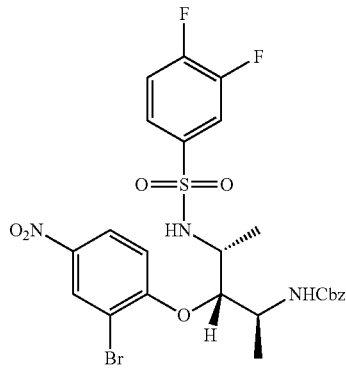 [SMILES: C[C@H](NC(=O)OCc1ccccc1)[C@H](Oc1ccc([N+](=O)[O-])cc1Br)[C@@H](C)NS(=O)(=O)c1ccc(F)c(F)c1]

Into a 25-mL round-bottom flask was placed benzyl N-[(2S,3R,4R)-4-amino-3-(2-bromo-4-nitrophenoxy)pentan-2-yl]carbamate (350 mg, 0.77 mmol, 1.00 equiv), TEA (233 mg, 2.30 mmol, 3.00 equiv), 4-dimethylaminopyridine (9.4 mg, 0.08 mmol, 0.10 equiv) and 3,4-difluorobenzene-1-sulfonyl chloride (246 mg, 1.16 mmol, 1.50 equiv). The resulting mixture was stirred overnight at room temperature, then concentrated under vacuum. The crude product was applied onto a silica gel column with ethyl acetate/petroleum ether (1:20-100:1) to afford benzyl N-[(2S,3S,4R)-3-(2-bromo-4-nitrophenoxy)-4-[(3,4-difluorobenzene)sulfonamido]pentan-2-yl]carbamate as a yellow solid.

Step 7—Synthesis of benzyl ((S)-1-((2S,3R)-4-((3,4-difluorophenyl)sulfonyl)-3-methyl-6-nitro-3,4-dihydro-2H-benzo[b][1,4]oxazin-2-yl)ethyl)carbamate

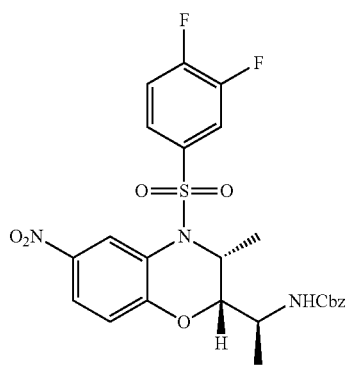

Into a 25-mL round-bottom flask was placed a solution of benzyl N-[(2S,3S,4R)-3-(2-bromo-4-nitrophenoxy)-4-[(3,4-difluorobenzene)sulfonamido]pentan-2-yl]carbamate (320 mg, 0.51 mmol, 1.00 equiv) in MeCN (10 mL), CuI (10 mg, 0.051 mmol, 0.1 equiv), potassium carbonate (140.8 mg, 1.02 mmol, 2.00 equiv) and 1-N,2-N-dimethylcyclohexane-1,2-diamine (14 mg, 0.1 mmol, 0.2 equiv). The resulting solution was stirred overnight at 70° C., then concentrated under vacuum. The crude product was applied onto a silica gel column with ethyl acetate/petroleum ether (1:20-100:1) to afford benzyl N-[(1S)-1-[(2S,3R)-4-[(3,4-difluoroben-

423 zene)sulfonyl]-3-methyl-6-nitro-3,4-dihydro-2H-1,4-benzoxazin-2-yl]ethyl]carbamate as a yellow solid, which was used in the next step without further purification.

Step 8—Synthesis of benzyl ((S)-1-((2S,3R)-6-amino-4-((3,4-difluorophenyl)sulfonyl)-3-methyl-3,4-dihydro-2H-benzo[b][1,4]oxazin-2-yl)ethyl)carbamate

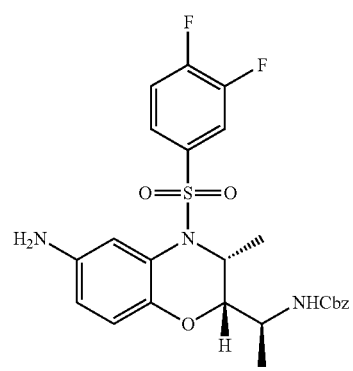 [SMILES: C[C@H](NC(=O)OCc1ccccc1)[C@@H]1Oc2ccc([N+](=O)[O-])cc2N(S(=O)(=O)c2ccc(F)c(F)c2)[C@@H]1C]

Into a 25-mL round-bottom flask was placed benzyl ((S)-1-((2S,3R)-4-((3,4-difluorophenyl)sulfonyl)-3-methyl-6-nitro-3,4-dihydro-2H-benzo[b][1,4]oxazin-2-yl)ethyl]carbamate (110 mg, 0.19 mmol, 1.00 equiv), Raney-Ni (80 mg), methanol (5 mL) and hydrazine hydrate (0.2 mL). The resulting solution was stirred at room temperature for 20 min, then the solids were filtered out and the filtrate concentrated under vacuum to afford the crude title compound as a yellow solid, which was used in the next step without further purification.

Step 9—Synthesis of 1,1,1-trifluoro-2-methylpropan-2-yl N-[(2S,3R)-2-[(1S)-1-[[(benzyloxy)carbonyl]amino]ethyl]-4-[(3,4-difluorobenzene)sulfonyl]-3-methyl-3,4-dihydro-2H-1,4-benzoxazin-6-yl]carbamate

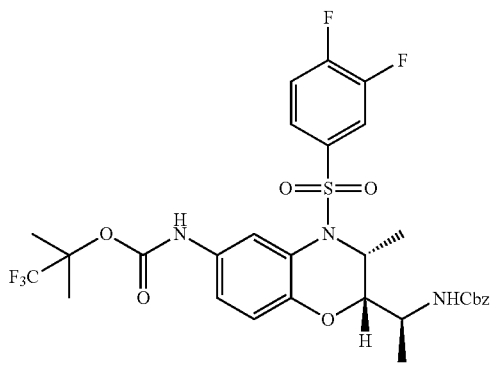 [SMILES: C[C@H](NC(=O)OCc1ccccc1)[C@@H]1Oc2ccc(NC(=O)OC(C)(C)C(F)(F)F)cc2N(S(=O)(=O)c2ccc(F)c(F)c2)[C@@H]1C]

Into a 25-mL round-bottom flask was placed benzyl N-[(1S)-1-[(2S,3R)-6-amino-4-[(3,4-difluorobenzene)sulfonyl]-3-methyl-3,4-dihydro-2H-1,4-benzoxazin-2-yl]ethyl]carbamate (130 mg, 0.25 mmol, 1.00 equiv), TEA (25 mg, 0.25 mmol, 1.00 equiv) and 1,1,1-trifluoro-2-methylpropan-(4-nitrophenyl) carbonate (60 mg, 0.25 mmol, 1.0 eq.) in THF (5 mL). The resulting solution was stirred for 6 days at

424

60° C., then concentrated under vacuum. The crude product was purified by prep-HPLC (MeCN/water using TFA buffer) to afford 1,1,1-trifluoro-2-methylpropan-2-yl N-[(2S,3R)-2-[(1 S)-1-[[(benzyloxy)carbonyl]amino]ethyl]-4-[(3,4-difluorobenzene)sulfonyl]-3-methyl-3,4-dihydro-2H-1,4-benzoxazin-6-yl]carbamate as a white solid. $^1$H-NMR (CD$_3$OD, 400 MHz) δ 8.02 (s, 1H), 7.77 (m, 1H), 7.58 (m, 1H), 7.45-7.32 (m, 6H), 7.08 (m, 1H), 6.80 (m, 1H), 5.20 (m, 2H), 4.68 (m, 1H), 3.65 (m, 1H), 3.27 (m, 1H), 1.79 (s, 6H), 1.26 (m, 3H), 1.13 (m, 3H).

Step 10—Synthesis of 1,1,1-trifluoro-2-methylpropan-2-yl ((2S,3R)-2-((S)-1-aminoethyl)-4-((3,4-difluorophenyl)sulfonyl)-3-methyl-3,4-dihydro-2H-benzo[b][1,4]oxazin-6-yl)carbamate

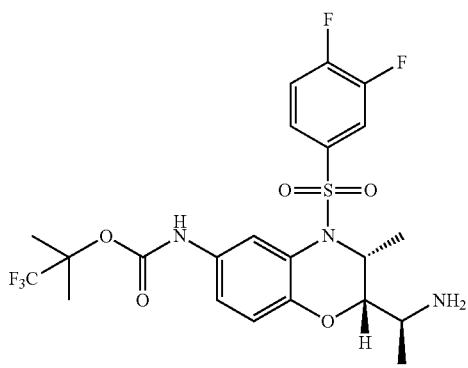 [SMILES: C[C@H](N)[C@@H]1Oc2ccc(NC(=O)OC(C)(C)C(F)(F)F)cc2N(S(=O)(=O)c2ccc(F)c(F)c2)[C@@H]1C]

Into a 25-mL round-bottom flask was placed 1,1,1-trifluoro-2-methylpropan-2-yl N-[(2S,3R)-2-[(1S)-1-[[(benzyloxy)carbonyl]amino]ethyl]-4-[(3,4-difluorobenzene)sulfonyl]-3-methyl-3,4-dihydro-2H-1,4-benzoxazin-6-yl]carbamate (130 mg, 0.19 mmol, 1.00 equiv), Pd/C (80 mg) in methanol (5 mL). The resulting solution was stirred overnight at room temperature under 1 atm of H$_2$, then the solids were filtered out. The filtrate was concentrated under vacuum to afford 1,1,1-trifluoro-2-methylpropan-2-yl N-[(2S,3R)-2-[(1S)-1-aminoethyl]-4-[(3,4-difluorobenzene)sulfonyl]-3-methyl-3,4-dihydro-2H-1,4-benzoxazin-6-yl]carbamate as yellow oil, which was taken to the next step without further purification.

Step 11—Synthesis of 1,1,1-trifluoro-2-methylpropan-2-yl ((2S,3R)-2-((S)-1-acetamidoethyl)-4-((3,4-difluorophenyl)sulfonyl)-3-methyl-3,4-dihydro-2H-benzo[b][1,4]oxazin-6-yl)carbamate

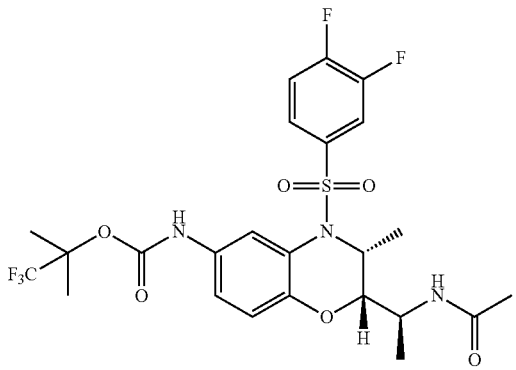 [SMILES: CC(=O)N[C@@H](C)[C@@H]1Oc2ccc(NC(=O)OC(C)(C)C(F)(F)F)cc2N(S(=O)(=O)c2ccc(F)c(F)c2)[C@@H]1C]

425

The title compound was prepared using a similar procedure as described in Example 49, Part VII. ¹H-NMR (CD₃OD, 400 MHz) δ 9.36 (s, 1H), 8.19 (m, 1H), 7.98 (m, 1H), 7.84 (m, 1H), 7.65 (m, 1H), 7.47 (m, 1H), 7.09 (m, 1H), 6.81 (m, 1H), 4.60 (m, 1H), 3.94 (m, 1H), 3.30 (s, 1H), 2.05 (s, 3H), 1.79 (s, 6H), 1.26 (m, 3H), 1.13 (m, 3H).

Example 54—Preparation of 1,1,1-trifluoro-2-methylpropan-2-yl ((R)-2-((S)-1-acetamido-2,2,2-trifluoroethyl)-4-((4-fluorophenyl)sulfonyl)-3,4-dihydro-2H-benzo[b][1,4]oxazin-6-yl)carbamate, 1,1,1-trifluoro-2-methylpropan-2-yl ((R)-2-((R)-1-acetamido-2,2,2-trifluoroethyl)-4-((4-fluorophenyl)sulfonyl)-3,4-dihydro-2H-benzo[b][1,4]oxazin-6-yl)carbamate, 1,1,1-trifluoro-2-methylpropan-2-yl ((S)-2-((S)-1-acetamido-2,2,2-trifluoroethyl)-4-((4-fluorophenyl)sulfonyl)-3,4-dihydro-2H-benzo[b][1,4]oxazin-6-yl)carbamate, 1,1,1-trifluoro-2-methylpropan-2-yl ((S)-2-((R)-1-acetamido-2,2,2-trifluoroethyl)-4-((4-fluorophenyl)sulfonyl)-3,4-dihydro-2H-benzo[b][1,4]oxazin-6-yl)carbamate

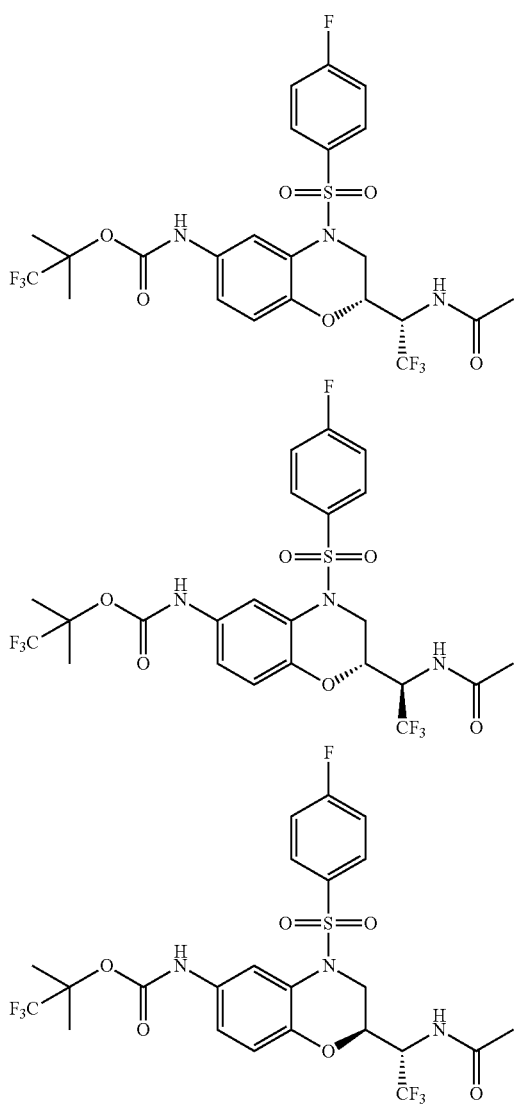

-continued

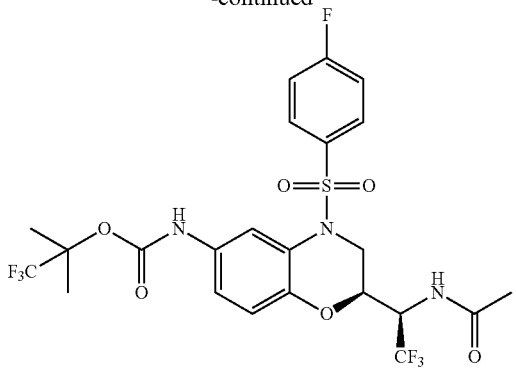

Step 1—Preparation of (R)-4-benzyl-6-nitro-3,4-dihydro-2H-benzo[b][1,4]oxazine-2-carboxylic acid

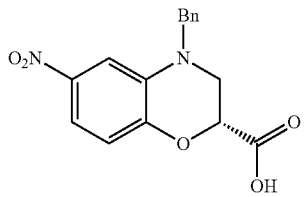 [SMILES: O=C(O)[C@H]1CN(Cc2ccccc2)c2cc([N+](=O)[O-])ccc2O1]

To a mixture of (R)-(4-benzyl-6-nitro-3,4-dihydro-2H-benzo[b][1,4]oxazin-2-yl)methanol (10 g, 33.3 mmol) and iodobenzene diacetate (26.8 g, 83.3 mmol) in 120 mL of MeCN/water (1:1) was added TEMPO (10.4 g, 66.6 mmol) in portions at 0° C. and the resulted mixture was stirred at room temperature for 24 hours. NaOH (13.32 g, 333 mmol) was added into the mixture at 0° C. and then the resulting solution was stirred at room temperature for 5 more hours. Water was added and the aqueous layer was extracted with EtOAc/PE (1:1). The aqueous layer was acidified to pH=3 with 1 N HCl and extracted with EtOAc. The combined organic layers were washed with water, brine, dried over Na₂SO₄ and filtered. The filtrate was concentrated in vacuo to give the title compound as a yellow solid without further purification. LCMS (ESI): calculated for $C_{16}H_{15}N_2O_5$ [M+H]⁺: 315. found: 315; ¹H-NMR (400 MHz, DMSO-d₆) δ 13.3 (1H, br s), 7.48-7.52 (1H, m), 7.26-7.37 (6H, m), 6.99 (1H, d, J=8.8 Hz), 5.18-5.20 (1H, m), 4.51-4.61 (2H, m), 3.60-3.71 (2H, m).

Step 2—Preparation of (R and S)-1-(4-benzyl-6-nitro-3,4-dihydro-2H-benzo[b][1,4]oxazin-2-yl)-2,2,2-trifluoroethanone

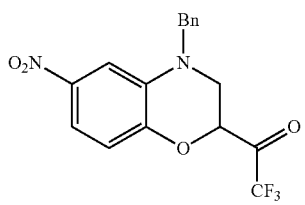 [SMILES: O=C(C1CN(Cc2ccccc2)c2cc([N+](=O)[O-])ccc2O1)C(F)(F)F]

A solution of (R)-4-benzyl-6-nitro-3,4-dihydro-2H-benzo[b][1,4]oxazine-2-carboxylic acid (7.5 g, 23.85 mmol) in 150 mL of DCM was added 2 drops of DMF and 12 mL of (COCl)$_2$ at 0° C. The reaction was stirred at room temperature for 2 hours, then concentrated in vacuo. The crude mixture was re-dissolved in 150 mL of DCM and treated with TFAA (19.5 mL, 143.1 mmol) followed by the slow addition of 15 mL of pyridine at 0° C. The resulting mixture was stirred at room temperature for 24 hours. Upon completion, at 0° C., ice water was added into the reaction slowly and then stirred at room temperature for 1 h. The mixture was extracted with DCM. The combined organic phase was washed with 1 N HCl, brine, dried over Na$_2$SO$_4$ and filtered. The filtrate was concentrated in vacuo to give the titled compound as a red oil after column chromatography on silica gel (petroleum ether:EtOAc=20:1 to 10:1). LCMS (ESI): calculated for C$_{17}$H$_{14}$F$_3$N$_2$O$_4$ [M+H]$^+$: 367. found: 385; $^1$H-NMR (MeOD, 400 MHz) δ 7.53-7.57 (2H, m), 7.28-7.36 (5H, m), 6.90-6.96 (1H, m), 4.57-4.62 (2H, m), 4.38-4.42 (1H, m), 3.52-3.60 (1H, m), 3.41-3.45 (1H, m).

Step 3—Preparation of (R and S)-1-(6-amino-3,4-dihydro-2H-benzo[b][1,4]oxazin-2-yl)-2,2,2-trifluoroethanone

A solution of 1-(4-benzyl-6-nitro-3,4-dihydro-2H-benzo[b][1,4]oxazin-2-yl)-2,2,2-trifluoroethanone (1.0 g, 2.73 mmol) in 30 mL of EtOAc was charged with 1 g of dry Pd/C and a balloon of H$_2$. The reaction was stirred at room temperature for 16 hours, then filtered through CELITE pad. The filtrate was concentrated in vacuo to give the crude titled compound as a dark-white solid without any further purification. LCMS (ESI): calculated for C$_{10}$H$_{10}$F$_3$N$_2$O$_2$ [M+H]$^+$: 247. found: 247; $^1$H-NMR (DMSO-d$_6$, 400 MHz) δ 7.16 (1H, s), 7.11 (1H, s), 7.36 (1H, d, J=8.4 Hz), 5.86 (1H, d, J=2.4 Hz), 5.75-5.77 (1H, m), 5.51 (1H, s), 4.08-4.11 (1H, s), 3.87-3.89 (2H, m), 3.11-3.17 (3H, m).

Step 4—Preparation of (R and S)-1,1,1-trifluoro-2-methylpropan-2-yl (2-(2,2,2-trifluoroacetyl)-3,4-dihydro-2H-benzo[b][1,4]oxazin-6-yl)carbamate

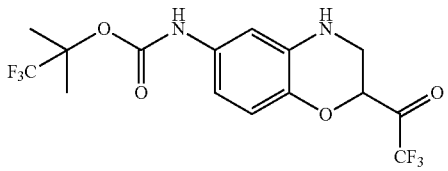 [SMILES: CC(C)(OC(=O)Nc1ccc2c(c1)NCC(C(=O)C(F)(F)F)O2)C(F)(F)F]

To a solution of (R and S)-1-(6-amino-3,4-dihydro-2H-benzo[b][1,4]oxazin-2-yl)-2,2,2-trifluoroethanone (2.8 g, 23.6 mmol) and 1,1,1-trifluoro-2-methylpropan-2-yl 1H-imidazole-1-carboxylate (2.78 g, 25.9 mmol) in 28 mL of DMSO was added 1.1 mL of HCl (13.44 mmol) and the reaction was stirred at 70° C. for 5 hours, then neutralized with saturated aqueous NaHCO$_3$ and extracted with EtOAc. The combined organic layers were washed with brine, dried over Na$_2$SO$_4$ and filtered. The filtrate was concentrated in vacuo and purified by column chromatography (DCM:EtOAc=20:1 to 10:1) to give the titled compound. LCMS (ESI): calculated for C$_{15}$H$_{15}$F$_6$N$_2$O$_4$ [M+H]$^+$: 401. found [M+H$_2$O+H] 419; $^1$H-NMR (CDCl$_3$, 400 MHz) δ 7.00 (1H, br s), 6.82 (1H, d, J=8.80 Hz), 6.59 (1H, s), 6.52-6.55 (1H, m), 4.44-4.45 (1H, m), 3.64-3.68 (1H, m), 3.39-3.43 (1H, m), 1.73 (6H, s).

Step 5—Preparation of (R and S)-1,1,1-trifluoro-2-methylpropan-2-yl (4-((4-fluorophenyl) sulfonyl)-2-(2,2,2-trifluoroacetyl)-3,4-dihydro-2H-benzo[b][1,4]oxazin-6-yl)carbamate

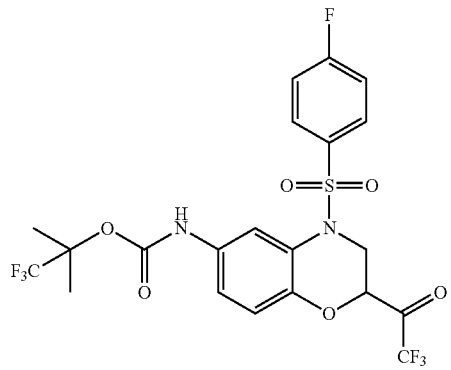 [SMILES: CC(C)(OC(=O)Nc1ccc2c(c1)N(S(=O)(=O)c1ccc(F)cc1)CC(C(=O)C(F)(F)F)O2)C(F)(F)F]

To a solution of (R and S)-1,1,1-trifluoro-2-methylpropan-2-yl (2-(2,2,2-trifluoroacetyl)-3,4-dihydro-2H-benzo[b][1,4]oxazin-6-yl)carbamate (1.0 g, 2.5 mmol) in 15/5 mL of THF/pyridine was added 4-fluorobenzene-1-sulfonyl chloride (972 mg, 5.0 mmol) and the reaction was stirred at room temperature for 16 hours. Upon completion, 1 N of HCl was added until pH=3~4 and the resulting mixture extracted with EtOAc. The combined organic layers were washed with brine, dried over Na$_2$SO$_4$ and concentrated in vacuo to give the titled compound as a yellow oil after column chromatography purification (petroleum ether:EtOAc=20:1 to 10:1). LCMS (ESI): calculated for C$_{21}$H$_{18}$F$_7$N$_2$O$_6$S [M+H]$^+$: 559. found: 559; $^1$H-NMR (MeOD, 400 MHz) δ 7.97 (1H, s), 7.71-7.74 (2H, m), 7.26-7.30 (2H, m), 7.16-7.18 (1H, m), 6.77-6.83 (1H, m), 4.46-4.59 (1H, m), 3.42-3.46 (1H, m), 3.25-3.31 (2H, m), 1.77 (6H, s).

Step 6—Preparation of 1,1,1-trifluoro-2-methylpropan-2-yl ((R and S)-4-((4-fluorophenyl)sulfonyl)-2-((S and R)-2,2,2-trifluoro-1-hydroxyethyl)-3,4-dihydro-2H-benzo[b][1,4]oxazin-6-yl)carbamate

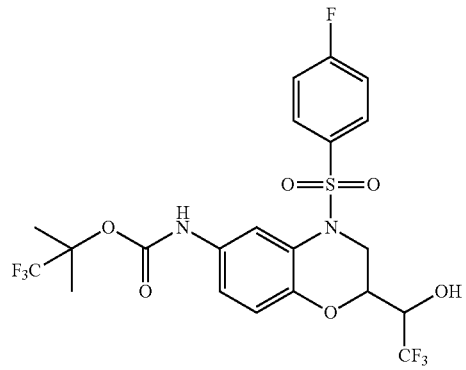 [SMILES: CC(C)(OC(=O)Nc1ccc2c(c1)N(S(=O)(=O)c1ccc(F)cc1)CC(C(O)C(F)(F)F)O2)C(F)(F)F]

To a solution of (R and S)-1,1,1-trifluoro-2-methylpropan-2-yl (4-((4-fluorophenyl)sulfonyl)-2-(2,2,2-trifluoroacetyl)-3,4-dihydro-2H-benzo[b][1,4]oxazin-6-yl)carbamate (300 mg, 0.54 mmol) in 10 mL of MeOH was added NaBH$_4$ (41 mg, 1.07 mmol) and the resulted solution was stirred at room temperature for 2 hours. Upon completion, water was added and the resulting mixture extracted with EtOAc. The combined organic layers were washed with brine, dried over Na$_2$SO$_4$ and filtered. The filtrate was concentrated in vacuo to give the crude title compound as a yellow solid without further purification. $^1$H-NMR (MeOD, 400 MHz) δ 7.98 (1H, s), 7.76-7.79 (2H, m), 7.25-7.30 (2H, m), 7.12-7.14 (1H, m), 6.76-6.79 (1H, m), 4.41-4.55 (1H, m), 4.17-4.18 (1H, m), 3.34-3.54 (2H, m), 1.77 (6H, s).

Step 7—Preparation of (S and R)-2,2,2-trifluoro-1-((R and S)-4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)ethyl trifluoromethanesulfonate

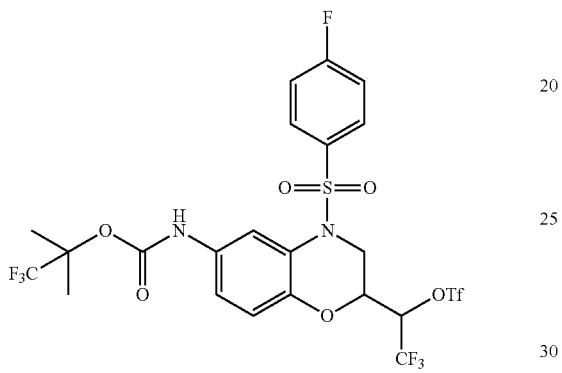

To a solution of 1,1,1-trifluoro-2-methylpropan-2-yl ((R and S)-4-((4-fluorophenyl)sulfonyl)-2-((S and R)-2,2,2-trifluoro-1-hydroxyethyl)-3,4-dihydro-2H-benzo[b][1,4]oxazin-6-yl)carbamate (600 mg, 1.07 mmol) in 25/2.5 mL of DCM/pyridine was added Tf$_2$O (480 mg, 1.70 mmol) at 0° C. and the resulted mixture was stirred at 0° C. for 1 hour. Upon completion, 1 N of HCl was added and the resulting mixture was extracted with DCM. The combined organic layers were washed with brine, dried over Na$_2$SO$_4$ and filtered. The filtrate was concentrated in vacuo to give the crude title compound as a yellow oil without further purification. $^1$H-NMR (MeOD, 400 MHz) δ 7.95-7.97 (1H, m), 7.75-7.82 (2H, m), 7.28-7.33 (2H, m), 7.18-7.19 (1H, m), 6.82-6.84 (1H, m), 5.92-6.01 (1H, m), 4.51-4.57 (1H, m), 3.86-3.91 (1H, m), 3.36-3.44 (1H, m), 1.77 (6H, s).

Step 8—Preparation of 1,1,1-trifluoro-2-methylpropan-2-yl ((R and S)-2-((S and R)-1-azido-2,2,2-trifluoroethyl)-4-((4-fluorophenyl)sulfonyl)-3,4-dihydro-2H-benzo[b][1,4]oxazin-6-yl)carbamate

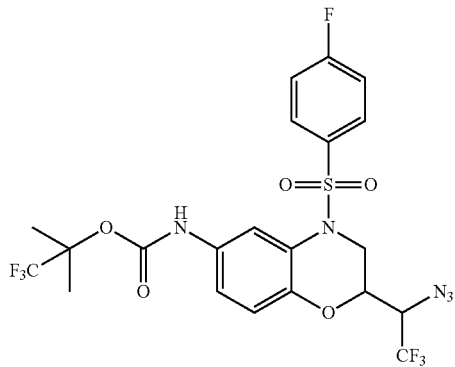 [SMILES: CC(C)(OC(=O)Nc1ccc2c(c1)N(S(=O)(=O)c1ccc(F)cc1)CC(C(N=[N+]=[N-])C(F)(F)F)O2)C(F)(F)F]

To a solution of (S and R)-2,2,2-trifluoro-1-((R and S)-4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)ethyl trifluoromethanesulfonate (600 mg, 0.87 mmol) in 20 mL of DMSO was added NaN$_3$ (120 mg, 1.85 mmol) and the reaction was stirred at room temperature for 16 hours. Upon completion, water was added and the mixture extracted with EtOAc. The aqueous layer was treated with H$_2$O$_2$ followed by Na$_2$SO$_3$ before being discarded. The combined organic layers were washed with water, brine, dried over Na$_2$SO$_4$ and filtered. The filtrate was concentrated in vacuo to give the title compound as a white solid. $^1$H-NMR (MeOD, 400 MHz) δ 7.97 (s, 1H), 7.79-7.82 (m, 2H), 7.21-7.31 (m, 2H), 7.14-7.17 (m, 1H), 6.77-6.79 (m, 1H), 4.39-4.49 (m, 1H), 4.35-4.38 (m, 1H), 3.72-3.75 (m, 1H), 3.40-3.47 (m, 1H), 1.77 (s, 6H).

Step 9—Preparation of 1,1,1-trifluoro-2-methylpropan-2-yl ((R and S)-2-((S and R)-1-amino-2,2,2-trifluoroethyl)-4-((4-fluorophenyl)sulfonyl)-3,4-dihydro-2H-benzo[b][1,4]oxazin-6-yl)carbamate

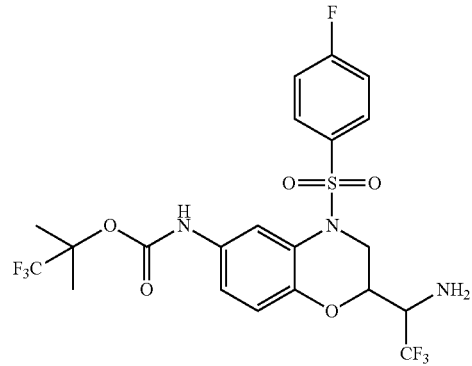 [SMILES: CC(C)(OC(=O)Nc1ccc2c(c1)N(S(=O)(=O)c1ccc(F)cc1)CC(C(N)C(F)(F)F)O2)C(F)(F)F]

A solution of 1,1,1-trifluoro-2-methylpropan-2-yl ((R and S)-2-((S and R)-1-azido-2,2,2-trifluoroethyl)-4-((4-fluorophenyl)sulfonyl)-3,4-dihydro-2H-benzo[b][1,4]oxazin-6-yl)carbamate (300 mg, 0.51 mmol) and one drop of NH$_4$OH in 30 mL of MeOH was charged with 150 mg of Pd/C (wet) and a balloon of H$_2$ and the reaction was stirred at room temperature for 16 hours. Upon completion, the solution was filtered through CELITE and the filtrate concentrated to give the crude title compound as a yellow solid without further purification. LCMS (ESI): calculated for C$_{21}$H$_{21}$F$_7$N$_3$O$_5$S [M+H]$^+$: 560. found: 560; $^1$H-NMR (MeOD, 400 MHz) δ 7.98 (s, 1H), 7.79-7.83 (m, 2H), 7.25-7.30 (m, 2H), 7.10-7.13 (m, 1H), 6.76-6.78 (m, 1H), 4.47-4.51 (m, 1H), 3.56-3.59 (m, 1H), 3.43-3.49 (m, 2H), 1.77 (s, 6H).

Step 10—Preparation of 1,1,1-trifluoro-2-methyl-propan-2-yl ((R)-2-((S)-1-acetamido-2,2,2-trifluoro-ethyl)-4-((4-fluorophenyl)sulfonyl)-3,4-dihydro-2H-benzo[b][1,4]oxazin-6-yl)carbamate, 1,1,1-trifluoro-2-methylpropan-2-yl ((R)-2-((R)-1-acetamido-2,2,2-trifluoroethyl)-4-((4-fluorophenyl)sulfonyl)-3,4-dihydro-2H-benzo[b][1,4]oxazin-6-yl)carbamate, 1,1,1-trifluoro-2-methylpropan-2-yl ((S)-2-((S)-1-acetamido-2,2,2-trifluoroethyl)-4-((4-fluorophenyl)sulfonyl)-3,4-dihydro-2H-benzo[b][1,4]oxazin-6-yl)carbamate, 1,1,1-trifluoro-2-methylpropan-2-yl ((S)-2-((R)-1-acetamido-2,2,2-trifluoroethyl)-4-((4-fluorophenyl)sulfonyl)-3,4-dihydro-2H-benzo[b][1,4]oxazin-6-yl)carbamate

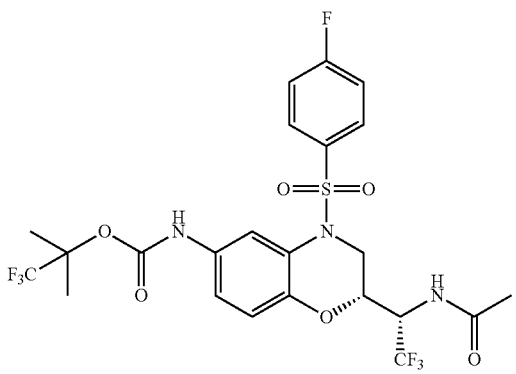

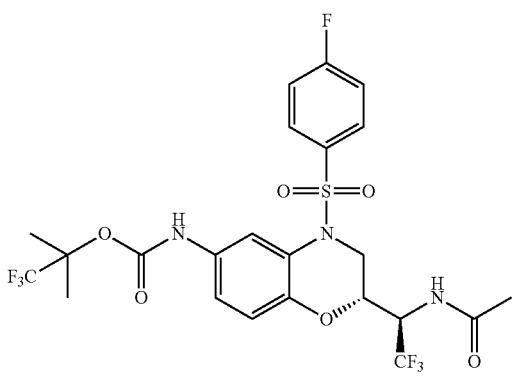

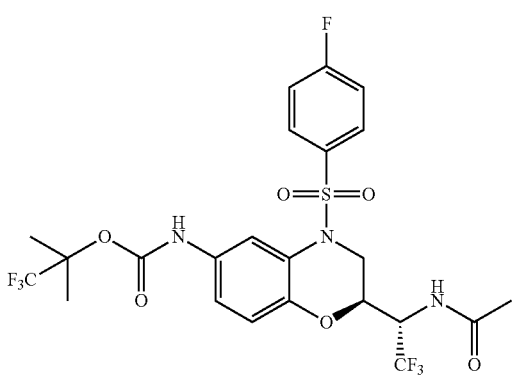

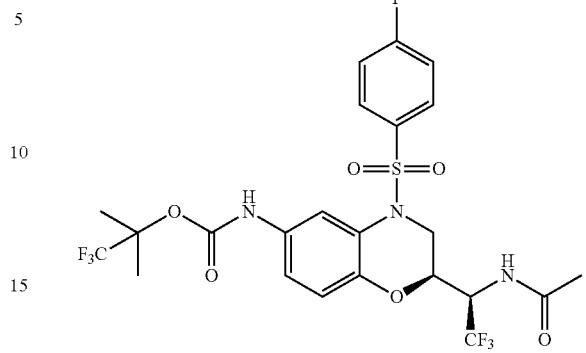

A solution of 1,1,1-trifluoro-2-methylpropan-2-yl ((R and S)-2-((S and R)-1-amino-2,2,2-trifluoroethyl)-4-((4-fluorophenyl)sulfonyl)-3,4-dihydro-2H-benzo[b][1,4]oxazin-6-yl)carbamate (120 mg, 0.21 mmol) and acetic anhydride (44 mg, 0.43 mmol) in DCM (8 mL) was stirred at 30° C. overnight. Upon completion, the mixture was extracted with EtOAc and saturated $NaHCO_3$. The combined organic layers were washed with brine, dried over $Na_2SO_4$ and filtered. The filtrate was concentrated in vacuo and the residue was purified by prep-TLC (petroleum ether:EtOAc=5:1) to give a diastereomeric mixture of the title compound as a white solid. LCMS (ESI): calculated for $C_{23}H_{23}F_7N_3O_6S$ [M+H]$^+$: 602. found: 602.

The mixture was separated by chiral SFC (Chiralcel OD-3 150×4.6 mm I.D., 3 um; Mobile phase: methanol (0.05% DEA) in $CO_2$ from 5% to 40%) to afford 4 isomers.

54A: Isomer 1 (first peak): $^1$H NMR (CDCl$_3$, 400 MHz) δ 7.75-7.65 (3H, m), 7.15 (2H, t, J=8.4 Hz), 6.82 (1H, d, J=8.4 Hz), 6.74 (1H, s), 5.94 (1H, d, J=10.4 Hz), 4.79 (1H, d, J=8.3 Hz), 4.30-4.21 (1H, m), 3.67 (1H, d, J=10.4 Hz), 3.05 (1H, dd, J=10.4, 14.4 Hz), 2.06 (3H, s), 1.77 (6H, s).
54B: Isomer 2 (second peak): $^1$H NMR (CDCl$_3$, 400 MHz) δ 7.75-7.65 (3H, m), 7.15 (2H, t, J=8.4 Hz), 6.82 (1H, d, J=8.4 Hz), 6.74 (1H, s), 5.94 (1H, d, J=10.4 Hz), 4.79 (1H, d, J=8.3 Hz), 4.30-4.21 (1H, m), 3.67 (1H, d, J=10.4 Hz), 3.05 (1H, dd, J=10.4, 14.4 Hz), 2.06 (3H, s), 1.77 (6H, s).
54C: Isomer 3 (third peak): $^1$H NMR (CDCl$_3$, 400 MHz) δ 7.75-7.65 (3H, m), 7.15 (2H, t, J=8.4 Hz), 6.82 (1H, d, J=8.4 Hz), 6.74 (1H, s), 5.94 (1H, d, J=10.4 Hz), 4.79 (1H, d, J=8.3 Hz), 4.30-4.21 (1H, m), 3.67 (1H, d, J=10.4 Hz), 3.05 (1H, dd, J=10.4, 14.4 Hz), 2.05 (3H, s), 1.75 (6H, s). 54D: Isomer 4 (fourth peak): $^1$H NMR (CDCl$_3$, 400 MHz) δ 7.76-7.65 (3H, m), 7.15 (2H, t, J=8.4 Hz), 6.85-6.78 (2H, m), 5.99 (1H, d, J=9.6 Hz), 4.81 (1H, d, J=8.4 Hz), 4.25 (1H, dd, J=1.6, 14.4 Hz), 3.66 (1H, d, J=10.4 Hz), 3.06 (1H, dd, J=10.4, 14.4 Hz), 2.05 (3H, s), 1.75 (6H, s).

Biological Assays

The compounds of the invention inhibit RORgammaT activity. Activation of RORgammaT activity can be measured using, e.g., a biochemical TR-FRET assay. In such an assay, interaction of cofactor-derived peptides with human RORgammaT-Ligand Binding Domain (LBD) can be measured. The TR-FRET technique is a sensitive biochemical proximity assay that will give information concerning the interaction of a ligand with the LBD, in the presence of cofactor-derived peptides (Zhou et al., Methods 25:54-61, 2001).

To identify novel antagonists of RORgammaT, an assay was developed which employs the interaction of RORgammaT with its co-activator peptide SRC1_2. This peptide mimics the recruitment of co-activators to RORgammaT through its interaction with the LXXLL (SEQ ID NO:1) (e.g., NR box) motifs (Xie et al., J. Immunol. 175: 3800-09, 2005; Kurebayashi et al., Biochem. Biophys. Res. Commun. 315: 919-27, 2004; Jin et al., Mol. Endocrinology 24:923-29, 2010). The RORγ-Ligand Binding Domain TR-FRET Assay was run according to the following protocol.

HIS-tagged RORγ-LBD protein was recombinantly expressed in Escherichia coli. The RORγ-LBD protein was purified by $Ni^{2+}$-affinity resin. Purified protein was then diluted in assay buffer (50 mM Tris pH 7.0, 50 mM KCl, 1 mM EDTA, 0.1 mM DTT, 100 μg/mL bovine serum albumin, delipidated) to obtain a RORγ-LBD final concentration of 3 nM. Europium tagged anti-HIS antibody was also added to this solution (1.25 nM). Separately, SF9 cells not expressing any recombinant protein were lysed (32,000 cells per μl in 25 mM Tris, 50 mM NaCl) and the previously frozen lysate was added to the diluted RORγ-LBD solution at a ratio of 0.75 μl SF9 lysate per 15 μl of diluted RORγ-LBD.

Compounds to be tested were injected to the 384-well assay plate using Acoustic Droplet Ejection technology by Echo 550 liquid handler (Labcyte, Calif.).

A stock of biotinylated-LXXLL peptide from coactivator SRC1 (Biotin-SPSSHSSLTERHKILHRLLQEGSP) (SEQ ID NO:2) and APC-conjugated streptavidin (final concentrations 100 nM and 8 nM respectively) were also added to each well.

The final assay mixture was incubated overnight at 4° C., warmed to room temperature and the fluorescence signal was measured on an Envision plate reader: (Excitation filter=340 nm; APC emission=665 nm; Europium emission=615 nm; dichroic mirror=D400/D630; delay time=100 μs, integration time=200 μs). $IC_{50}$ values for test compounds were calculated from the quotient of the fluorescence signal at 665 nm divided by the fluorescence signal at 615 nm.

The $IC_{50}$ values for representative compounds of the invention are set forth below.

| Ex. No. | $IC_{50}$ (nM) |
|---|---|
| 1 | 19.52 |
| 2 | 58.42 |
| 3 | 204.9 |
| 4 | 36.87 |
| 5A | 903.8 |
| 5B | 21.05 |
| 5C | 13.41 |
| 5D | 26.46 |
| 5E | 5.887 |
| 5F | 2059 |
| 5G | 251 |
| 5H | 17.44 |
| 5i | 13.94 |
| 5J | 26.45 |
| 5K | 54.5 |
| 5L | 528.9 |
| 5M | 1831 |
| 5N | 932.6 |
| 5o | 8.789 |
| 5P | 13.1 |
| 5Q | 6.09 |
| 5R | 2.7 |
| 5S | 22.35 |
| 5T | 36 |
| 5U | 14.25 |
| 5V | 9.5 |
| 5W | 5.36 |
| 5X | 7.4 |
| 5Y | 19.1 |
| 5Z | 197 |
| 5AA | 56 |
| 5AB | 8.26 |
| 5AC | 4.25 |
| 5AD | 4.81 |
| 5AE | 3.99 |
| 5AF | 4.59 |
| 5AG | 8.053 |
| 5AH | 198 |
| 5Ai | 3388 |
| 5AJ | 28.17 |
| 5AK | 45.88 |
| 5AL | 29.99 |
| 5AM | 6.263 |
| 5AN | 11.03 |
| 5Ao | 7.565 |
| 5AP | 555.8 |
| 5AQ | 15.17 |
| 5AR | 11.95 |
| 5AS | 45.1 |
| 5AT | 13.62 |
| 5AU | 8895 |
| 5AV | 1533 |
| 5AW | 28.2 |
| 5AX | 28.81 |
| 5AY | 19.18 |
| 5AZ | 42.12 |
| 5BA | 52.32 |
| 5BB | 42.56 |
| 5BC | 68.2 |
| 6 | 9.953 |
| 8 | 469.4 |
| 9 | 53.04 |
| 10A | 10.23 |
| 10B | 2.642 |
| 10C | 4.629 |
| 10D | 3.35 |
| 10E | 2.191 |
| 10F | 2.433 |
| 10G | 6.408 |
| 10H | 9.428 |
| 10i | 4.726 |
| 10J | 48.66 |
| 10K | 9.277 |
| 10L | 43.91 |
| 10M | 43.59 |
| 10N | 17.59 |
| 10o | 4.358 |
| 10P | 346.1 |
| 10Q | 106 |
| 10R | 163.2 |
| 10S | 2.57 |
| 10T | 2.86 |
| 10W | 233 |
| 10X | 53.53 |
| 10Y | 60.66 |
| 10Z | 12.78 |
| 10AA | 490.9 |
| 10AB | 203 |
| 10AC | 28.5 |
| 10AD | 24.37 |
| 10AE | 48.05 |
| 10AF | 27.56 |
| 10AG | 97.11 |
| 10AH | 24.96 |
| 10Ai | 7.401 |
| 10AJ | 3.614 |
| 10AK | 29.4 |
| 10AL | 8.699 |
| 10AM | 5.811 |
| 10AN | 8.818 |
| 10Ao | 4.742 |
| 10AP | 13.04 |
| 10AQ | 10.71 |

| Ex. No. | IC$_{50}$ (nM) |
|---|---|
| 10AR | 6.533 |
| 10AS | 5.261 |
| 10AT | 26.67 |
| 10AU | 13.25 |
| 10AV | 20.53 |
| 10AW | 12.13 |
| 10AX | 25.78 |
| 10AY | 225.4 |
| 10AZ | 4.378 |
| 10BA | 17.81 |
| 10BB | 20.04 |
| 10BC | 1545 |
| 10BD | 156.8 |
| 10BE | 115.1 |
| 10BF | 277.9 |
| 10BG | 1261 |
| 10BH | 14 |
| 10Bi | 1106 |
| 10BJ | 8.525 |
| 10BK | 7.162 |
| 10BL | 75.4 |
| 10BM | 2342 |
| 10BN | 3956 |
| 10Bo | 7341 |
| 10BP | 2666 |
| 10BQ | 3115 |
| 11 | 13.14 |
| 12A | 5.362 |
| 12B | 5.387 |
| 12C | 7.654 |
| 12D | 10.65 |
| 12E | 8.175 |
| 12F | 6.242 |
| 12G | 8.72 |
| 13 | 2.186 |
| 14 | 2.479 |
| 15A | 6.835 |
| 15B | 5.111 |
| 16A | 66.94 |
| 16B | 13.95 |
| 16C | 15.99 |
| 16D | 5.904 |
| 16E | 15.07 |
| 16F | 6.292 |
| 16G | 51.42 |
| 16H | 61.28 |
| 16i | 43.62 |
| 16J | 157.3 |
| 16K | 4.916 |
| 16L | 38.98 |
| 16M | 74.51 |
| 16N | 9.122 |
| 17 | 84.01 |
| 18 | 335.1 |
| 19A | 6.49 |
| 19B | 49.14 |
| 19C | 41.02 |
| 19D | 19.99 |
| 19E | 24.78 |
| 19F | 28.28 |
| 19G | 42.46 |
| 19H | 875 |
| 19i | 73.31 |
| 19J | 13.3 |
| 19K | 60.03 |
| 19L | 8.162 |
| 19M | 404.6 |
| 19N | 21.44 |
| 19o | 100 |
| 19P | 32.87 |
| 19Q | 2192 |
| 20 | 17.3 |
| 21A | 5.1 |
| 21B | 4.6 |
| 21C | 29.26 |
| 21D | 155.6 |
| 21E | 13.1 |
| 21F | 72 |
| 21G | 20.8 |
| 22 | 32.33 |
| 23A | 22.13 |
| 23B | 13.77 |
| 23C | 11.09 |
| 23D | 113 |
| 23E | 24.17 |
| 23F | 8.556 |
| 23G | 11.09 |
| 23H | 18.5 |
| 23i | 3.239 |
| 23J | 13.72 |
| 23K | 28.18 |
| 23L | 23.17 |
| 23M | 56.23 |
| 23N | 39.43 |
| 23o | 7.999 |
| 23P | 7.092 |
| 23Q | 81 |
| 24 | 34.44 |
| 25A | 48.42 |
| 25B | 13.64 |
| 25C | 15.22 |
| 25D | 7.096 |
| 25E | 7.838 |
| 25F | 5.094 |
| 26 | 245.9 |
| 27A | 576.9 |
| 27B | 55.6 |
| 27C | 24.28 |
| 27D | 63.66 |
| 27E | 3.675 |
| 27F | 23.77 |
| 27G | 25.18 |
| 27H | 5.623 |
| 27i | 3.766 |
| 28 | 9.1 |
| 29A | 19.4 |
| 29B | 9.9 |
| 29C | 6.6 |
| 29D | 14.96 |
| 29E | 5.612 |
| 29F | 2.77 |
| 29G | 14.29 |
| 29H | 7.423 |
| 29i | 14.27 |
| 30A | 33.32 |
| 30B | 75.39 |
| 30C | 134.9 |
| 30D | 18.49 |
| 30E | 44.32 |
| 30F | 54.33 |
| 30G | 13.56 |
| 30H | 47.39 |
| 30i | 25.19 |
| 30J | 161.3 |
| 30K | 108.6 |
| 30L | 60.39 |
| 30M | 33.69 |
| 30N | 43.22 |
| 30o | 30.57 |
| 30P | 215.5 |
| 30Q | 24.22 |
| 30R | 11.02 |
| 30S | 15.1 |
| 30T | 8.087 |
| 30U | 5702 |
| 30V | 142 |
| 30W | 891.1 |
| 30X | 7640 |
| 30Y | 4889 |
| 30Z | 334 |
| 30AA | 28.42 |
| 30AB | 303 |

| Ex. No. | IC$_{50}$ (nM) |
|---|---|
| 30AC | 9897 |
| 30AD | 404 |
| 30AE | 13.54 |
| 31 | 10.83 |
| 32A | 5.2 |
| 32B | 10.94 |
| 32C | 7.18 |
| 32D | 9.99 |
| 32E | 7.87 |
| 32F | 9.10 |
| 32G | 6.995 |
| 32H | 11.9 |
| 32i | 16.84 |
| 32J | 15.59 |
| 32K | 6.726 |
| 32L | 6.303 |
| 32M | 9.34 |
| 32N | 9.756 |
| 32o | 8.965 |
| 32P | 8.657 |
| 32Q | 16.73 |
| 32R | 381.6 |
| 32S | 16.6 |
| 32T | 12.57 |
| 32U | 57.65 |
| 32V | 14.64 |
| 33 | 16.45 |
| 34A | 14.07 |
| 34B | 16.45 |
| 34C | 40.87 |
| 34D | 25.57 |
| 34E | 12.55 |
| 34F | 8.87 |
| 34G | 12.41 |
| 34H | 5.696 |
| 34i | 74.7 |
| 34J | 42.15 |
| 34K | 51.04 |
| 34L | 87.94 |
| 34M | 16.94 |
| 34N | 23.2 |
| 34o | 12.11 |
| 34P | 4.924 |
| 34Q | 5.635 |
| 34R | 545.9 |
| 34S | 10.71 |
| 34T | 10.29 |
| 34U | 3.921 |
| 34V | 5.035 |
| 34W | 11.38 |
| 34X | 7.694 |
| 34Y | 26.26 |
| 34Z | 44.66 |
| 34AA | 8.291 |
| 34AB | 26.47 |
| 34AC | 46.52 |
| 34AD | 7.283 |
| 34AE | 17.59 |
| 34AF | 21.39 |
| 34AG | 17.46 |
| 34AH | 13.07 |
| 34Ai | 81.75 |
| 34AJ | 110.3 |
| 34AK | 9.173 |
| 34AL | 9.319 |
| 34AM | 6.104 |
| 34AN | 7.836 |
| 34Ao | 3293 |
| 34AP | 12.74 |
| 34AQ | 13.41 |
| 34AR | 19.95 |
| 34AS | 3.489 |
| 34AT | 12.97 |
| 34AU | 3.944 |
| 34AV | 24.53 |
| 34AW | 14.97 |
| 34AX | 94.97 |
| 34AY | 99.94 |
| 34AZ | 156.1 |
| 34BA | 25.31 |
| 34BB | 58.4 |
| 34BC | 8.142 |
| 34BD | 5.159 |
| 34BE | 4.364 |
| 34BF | 6.842 |
| 34BG | 5.613 |
| 34BH | 4.377 |
| 34Bi | 3.866 |
| 34BJ | 4.511 |
| 34BK | 7.494 |
| 34BL | 46.73 |
| 34BM | 7.636 |
| 34BN | 14.36 |
| 34Bo | 6.805 |
| 34BP | 6.036 |
| 34BQ | 9.711 |
| 34BR | 6.658 |
| 34BS | 5.335 |
| 34BT | 5.254 |
| 34BU | 11.43 |
| 34BV | 6.481 |
| 34BW | 4.911 |
| 34BX | 4.469 |
| 34BY | 5.587 |
| 34BZ | 6.706 |
| 34CA | 5.284 |
| 34CB | 5.442 |
| 34CC | 7.989 |
| 34CD | 6.592 |
| 34CE | 6.033 |
| 34CF | 13.05 |
| 34CG | 6.266 |
| 34CH | 12.51 |
| 34Ci | 5.293 |
| 34CJ | 4.673 |
| 34CK | 6.259 |
| 34CL | 6.256 |
| 34CM | 63.65 |
| 34CN | 7.592 |
| 34Co | 4.595 |
| 34CP | 15.71 |
| 34CQ | 9.23 |
| 34CR | 5.12 |
| 34CS | 7.93 |
| 34CT | 5.37 |
| 34CD | 6.441 |
| 34CV | 4.349 |
| 34CW | 5.838 |
| 34CX | 8.915 |
| 34CY | 3.073 |
| 34CZ | 3.857 |
| 34DA | 5.054 |
| 34DB | 9.634 |
| 34DC | 10.33 |
| 34DD | 21.81 |
| 34DE | 6.007 |
| 35 | 4.141 |
| 36A | 3.819 |
| 36B | 4.377 |
| 36C | 32.75 |
| 36D | 5.935 |
| 36E | 4.989 |
| 36F | 6.39 |
| 36G | 2.986 |
| 36H | 4.156 |
| 36i | 5.258 |
| 36J | 4.267 |
| 36K | 7.89 |
| 36L | 4.597 |
| 36M | 8.448 |

| Ex. No. | IC$_{50}$ (nM) |
|---|---|
| 36N | 4.346 |
| 36o | 2.922 |
| 36P | 130.1 |
| 36Q | 3.958 |
| 36R | 7.329 |
| 36S | 8.611 |
| 36T | 6.735 |
| 36U | 9.369 |
| 36V | 5.233 |
| 36W | 4.916 |
| 36X | 3.838 |
| 36Y | 5.832 |
| 36Z | 9.007 |
| 37A | 5.402 |
| 37B | 18.68 |
| 37C | 4.087 |
| 37D | 13.21 |
| 37E | 11.57 |
| 37F | 11.09 |
| 37G | 3.928 |
| 37H | 2.684 |
| 37i | 13.87 |
| 37J | 3.049 |
| 38A | 7.044 |
| 38B | 14.64 |
| 38C | 11.31 |
| 38D | 9.441 |
| 38E | 6.602 |
| 38F | 5.043 |
| 38G | 7.379 |
| 38H | 55.72 |
| 38i | 29.16 |
| 38J | 94.6 |
| 38K | 10.13 |
| 38L | 7.531 |
| 38M | 12.35 |
| 38N | 4.185 |
| 38o | 24.03 |
| 38P | 12 |
| 38Q | 15.43 |
| 38R | 7.661 |
| 38S | 27.68 |
| 38T | 31.92 |
| 38U | 33.43 |
| 38V | 25.4 |
| 38W | 7.71 |
| 38X | 7.826 |
| 38Y | 18.14 |
| 38Z | 24.34 |
| 38AA | 5.094 |
| 38AB | 14.23 |
| 38AC | 20.41 |
| 38AD | 7.792 |
| 38AE | 14.83 |
| 38AF | 12.32 |
| 38AG | 9.652 |
| 39 | 3.282 |
| 40 | 6.851 |
| 41A | 4.381 |
| 42 | 8.187 |
| 43A | 11.38 |
| 43B | 11.86 |
| 43C | 1642 |
| 44 | 11.82 |
| 45 | 6.221 |
| 46A | 8.428 |
| 46B | 5.701 |
| 46C | 9.258 |
| 46D | 6.491 |
| 46E | 7.103 |
| 46F | 4.869 |
| 47 | 21.86 |
| 48 | 18.58 |
| 49A | >10000 |

| Ex. No. | IC$_{50}$ (nM) |
|---|---|
| 49B | 9.109 |
| 50A | 6.199 |
| 50B | 2155 |
| 51A | 53.72 |
| 51B | >10000 |
| 52A | 57.35 |
| 52B | 6041 |
| 52C | 150 |
| 52D | 10.5 |
| 52E | 5884 |
| 52F | 15.03 |
| 52G | 8.214 |
| 10BR | 16.69 |
| 10BS | 20.79 |
| 10BT | 172.2 |
| 10BU | 101.2 |
| 10BV | 67.53 |
| 10BW | 12.24 |
| 10BX | 53.84 |
| 10BY | 1101 |
| 10BZ | 11.75 |
| 10CA | 20.07 |
| 10CB | 75.54 |
| 10CC | 22.72 |
| 10CD | 432 |
| 10CE | 108 |
| 10CF | 86.21 |
| 10CG | 6751 |
| 10CH | 59.86 |
| 10Ci | 1374 |
| 10CJ | 5810 |
| 10CK | 5.4 |
| 10CL | 188 |
| 10CM | 119.8 |
| 10CN | 22.06 |
| 12H | 7.528 |
| 12i | 17.44 |
| 12J | 7.314 |
| 12K | 8.958 |
| 12L | 6.641 |
| 12M | 19.12 |
| 12N | 8.417 |
| 12o | 22.07 |
| 12P | 3.798 |
| 12Q | 11.59 |
| 12R | 6.463 |
| 12S | 7.117 |
| 12T | 8.253 |
| 12U | 4.014 |
| 16o | 42.15 |
| 16P | 40.94 |
| 16Q | 32.27 |
| 16R | 59.23 |
| 16S | 106.2 |
| 16T | 33.41 |
| 16U | 61.92 |
| 16V | 116.2 |
| 16W | 8.687 |
| 16X | 39.2 |
| 16Y | 7.048 |
| 16Z | 14.25 |
| 16AA | 14.05 |
| 16AB | 12.09 |
| 16AC | 29.35 |
| 34DF | 13.98 |
| 34DG | 303.4 |
| 34DH | 10.63 |
| 34Di | 21.14 |
| 34DJ | 5.388 |
| 34DK | 9.529 |
| 34DL | 93.28 |
| 34DM | 5.604 |
| 34DN | 11.03 |
| 36AA | 13.79 |

-continued

| Ex. No. | IC$_{50}$ (nM) |
|---|---|
| 52H | 10.5 |
| 52i | 16.65 |
| 52J | 15 |
| 52K | 18.26 |
| 52L | 40.79 |
| 52M | 21.91 |
| 52N | 13.23 |
| 52o | 34.75 |
| 52P | 44.66 |
| 52Q | 17.42 |
| 52R | 9.338 |
| 52S | 31.09 |
| 52T | 27.81 |
| 52U | 31.82 |
| 52V | 18.21 |
| 52W | 21.66 |
| 52X | 28.08 |
| 52Y | 33.45 |
| 52Z | 36.11 |
| 52AA | 29.12 |
| 52AB | 67.78 |
| 52AC | 39.61 |
| 53 | 9.162 |
| 54A | 90.94 |
| 54B | 19.58 |
| 54C | 1081 |
| 54D | 236.9 |

While the present invention has been described in conjunction with the specific embodiments set forth above, many alternatives, modifications, and other variations thereof will be apparent to those of ordinary skill in the art in light of the present disclosure. All such alternatives, modifications, and variations are intended to fall within the spirit and scope of the present invention.

What is claimed is:
1. A compound of the Formula (I)

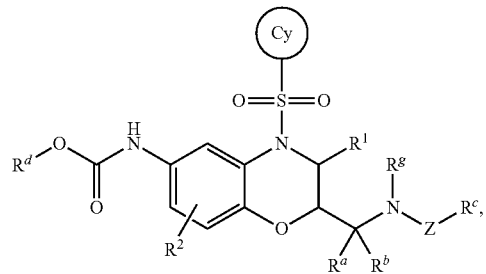

or a pharmaceutically acceptable salt thereof,
wherein:
$R^1$ is H or $C_1$-$C_3$ alkyl,
$R^2$ is H, halo, or $C_1$-$C_3$ alkyl;
$R^a$ and $R^b$ are independently selected from the group consisting of H, $C_1$-$C_6$ alkyl, trifluoromethyl, and cyclopropyl,
Z is —C(O)— or —SO$_2$—;
$R^c$ is selected from the group consisting of
(a.) $C_1$-$C_6$ alkyl, wherein said $C_1$-$C_6$ alkyl of $R^c$ is unsubstituted or independently substituted by 1 to 6 hydroxy, amino, oxo, $C_1$-$C_3$ alkylamino, $C_1$-$C_3$ alkoxy, $C_1$-$C_3$ dialkylamino or fluoro;
(b.) $C_3$-$C_9$ mono- or bicycloalkyl, wherein said $C_3$-$C_9$ mono- or bicycloalkyl of $R^c$ is unsubstituted or independently substituted by 1 to 4 $C_1$-$C_3$ alkyl, $C_1$-$C_3$ alkoxy, fluoro, trifluoromethyl, cyano, amino, $C_1$-$C_3$ alkylamino, or $C_1$-$C_3$ dialkylamino;

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: SRC1_2 peptide
<220> FEATURE:
<221> NAME/KEY: MISC_FEATURE
<222> LOCATION: (2)..(3)
<223> OTHER INFORMATION: Xaa can be any naturally occurring amino acid

<400> SEQUENCE: 1

Leu Xaa Xaa Leu Leu
1               5

<210> SEQ ID NO 2
<211> LENGTH: 24
<212> TYPE: PRT
<213> ORGANISM: Artificial Sequence
<220> FEATURE:
<223> OTHER INFORMATION: SRC1_2 peptide

<400> SEQUENCE: 2

Ser Pro Ser Ser His Ser Ser Leu Thr Glu Arg His Lys Ile Leu His
1               5                   10                  15

Arg Leu Leu Gln Glu Gly Ser Pro
            20
```

(c.) a ring $C^c$ of the formula

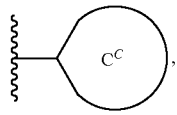

wherein ring $C^c$ is a 3- to 6-membered heterocyclyl, wherein said heterocyclyl is a saturated, partially saturated, or aromatic ring system containing 1 to 3 heteroatoms independently selected from the group consisting of N, O, and S, and is unsubstituted or independently substituted by 1 to 3 $C_1$-$C_6$ alkyl, $C_1$-$C_3$ alkoxy, fluoro, hydroxyl, oxo, cyano, amino, $C_1$-$C_3$ alkylamino, or $C_1$-$C_3$ dialkylamino; and
  (d.) phenyl, wherein said phenyl of $R^c$ is unsubstituted or independently substituted by 1 to 4 $C_1$-$C_3$ alkylsulfonyl;
$R^g$ is H or methyl;
$R^d$ is
  (a.) $C_1$-$C_8$ alkyl, wherein said $C_1$-$C_8$ alkyl of $R^d$ is unsubstituted or independently substituted by 1 to 6 halo, $C_1$-$C_3$ alkoxy, hydroxy, cyano, trimethylsilyl, or methylsulfonyl;
  (b.) $C_2$-$C_8$ alkenyl, wherein said $C_2$-$C_8$ alkenyl of $R^d$ is unsubstituted or independently substituted by 1 to 6 fluoro or cyano; or
  (c.) a group of the formula -M-$R^{CH}$; wherein
    M is
      (i.) a bond; or
      (ii.) $C_1$-$C_6$ alkylene, wherein said $C_1$-$C_6$ alkylene of M is unsubstituted or substituted by 1 to 6 fluoro; and
    $R^{CH}$ is a ring selected from the group consisting of
      (i.) $C_3$-$C_9$ mono- or bicycloalkyl;
      (ii.) phenyl; and
      (iii.) a 3- to 6-membered heterocyclyl, wherein said heterocyclyl of $R^{CH}$ is a saturated or partially saturated ring system containing 1 to 2 heteroatoms independently selected from the group consisting of N, O, and S;
    wherein $R^{CH}$ is unsubstituted or independently substituted by 1 to 4 halo, $C_1$-$C_3$ alkyl, $C_1$-$C_3$ trifluoroalkyl, cyano, $C_1$-$C_4$ alkylcarbonylamino, or oxo;
Cy is
  (a.) phenyl;
  (b.) a 5- to 7-membered, monocyclic heterocyclyl, wherein said heterocyclyl of Cy is a saturated, partially saturated, or aromatic ring system containing 1 to 3 heteroatoms independently selected from the group consisting of N, O, and S; or
  (c.) $C_3$-$C_6$ cycloalkyl;
  wherein Cy is unsubstituted or independently substituted by 1 to 4 $R^k$ moieties selected from the group consisting of:
    (i.) $C_1$-$C_6$ alkyl, wherein $C_1$-$C_6$ alkyl is unsubstituted or independently substituted by 1 to 3 hydroxy or fluoro;
    (ii.) $C_1$-$C_6$ alkoxy, wherein said $C_1$-$C_6$ alkoxy is unsubstituted or independently substituted by 1 to 3 fluoro, hydroxy, methoxy, or phenyl;
    (iii.) —$N(R^e)_2$;
    (iv.) —$O(CH_2)_{n1}C(O)N(R^e)_2$;
    (v.) —$O(CH_2)_{n2}CO_2R^f$;
    (vi.) hydroxyl;
    (vii.) oxo;
    (viii.) halo;
    (ix.) $C_1$-$C_3$ alkylsulfonyl;
    (x.) cyano;
    (xi.) oxetanyl;
    (xii.) cyclopropyl;
    (xiii.) —$(CH_2)_{n1}N(H)C(O)O$—$(C_1$-$C_6$ alkyl); and
    (xiv.) —$SF_5$;
  or alternatively, two $R^k$ moieties, when substituted on adjacent ring atoms of Cy, form a second ring, wherein said second ring is a 5- to 7-membered saturated, partially saturated, or aromatic ring system containing 0, 1, or 2 heteroatoms independently selected from the group consisting of N, O, and S; wherein said second ring is unsubstituted or substituted by 1 to 3 $R^k$ moieties independently selected from (i)-(xiv);
each $R^e$ is independently H or $C_1$-$C_3$ alkyl,
$R^f$ is H or $C_1$-$C_3$ alkyl;
the subscript n1 is 1, 2, or 3; and
the subscript n2 is 1, 2, or 3.

2. The compound of claim 1 or a pharmaceutically acceptable salt thereof, wherein Cy is unsubstituted or independently substituted by 1 to 4 $R^k$ moieties selected from the group consisting of (i.)-(xi.) as set forth in claim 1;
  or alternatively, two $R^k$ moieties, when substituted on adjacent ring atoms of Cy, form a second ring, wherein said second ring is a 5- to 7-membered saturated, partially saturated, or aromatic ring system containing 0, 1, or 2 heteroatoms independently selected from the group consisting of N, O, and S; wherein said second ring is unsubstituted or substituted by 1 to 3 $R^k$ moieties independently selected from (i)-(xi).

3. The compound of claim 2 or a pharmaceutically acceptable salt thereof, wherein Z is —C(O)—.

4. The compound of claim 2 or a pharmaceutically acceptable salt thereof, wherein Z is —$SO_2$—.

5. The compound of claim 2 or a pharmaceutically acceptable salt thereof, wherein $R^1$ is H.

6. The compound of claim 2 or a pharmaceutically acceptable salt thereof, wherein $R^1$ is methyl.

7. The compound of claim 2 or a pharmaceutically acceptable salt thereof, wherein Cy is a group of the formula

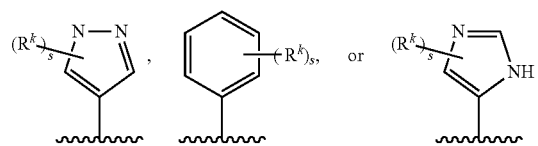

wherein the subscript s is 0, 1, 2, or 3.

8. The compound of claim 2 or a pharmaceutically acceptable salt thereof, wherein $R^d$ is a group of the formula

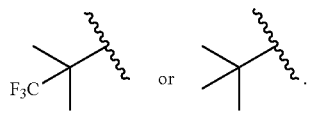

9. The compound of claim 2 or a pharmaceutically acceptable salt thereof, wherein $R^d$ is a group of the formula

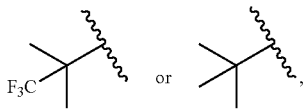

$R^1$ is H,
$R^2$ is H,
$R^g$ is H,
$R^a$ is H or $CH_3$,
$R^b$ is H or $CH_3$,
Z is —C(O)—, and
$R^c$ is $CH_3$.

10. The compound of claim 2 or a pharmaceutically acceptable salt thereof, wherein Cy is

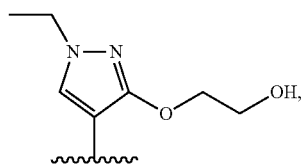 [SMILES: *c1cn(CC)nc1OCCO]

and
$R^d$ is a group of the formula

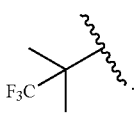

11. The compound of claim 2 or a pharmaceutically acceptable salt thereof, wherein Cy is

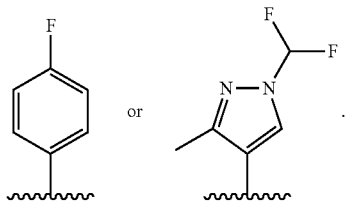

12. The compound of claim 2 or a pharmaceutically acceptable salt thereof, wherein $R^d$ is a group of the formula

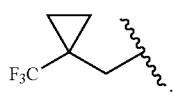

13. The compound of claim 2 or a pharmaceutically acceptable salt thereof, wherein the group —Z—$R^c$ is a group of the formula

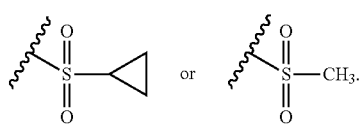 [SMILES: *S(=O)(=O)C1CC1 ; *S(C)(=O)=O]

14. The compound of claim 2 or a pharmaceutically acceptable salt thereof, wherein $R^g$ is H.

15. The compound of claim 2 or a pharmaceutically acceptable salt thereof, wherein
$R^d$ is a group of the formula -M-$R^{CH}$; wherein
M is
(i.) a bond; or
(ii.) $C_1$-$C_6$ alkylene, wherein said $C_1$-$C_6$ alkylene of M is unsubstituted or substituted by 1 to 6 fluoro; and
$R^{CH}$ is a ring selected from the group consisting of
(i.) $C_3$-$C_9$ mono- or bicycloalkyl, wherein said cycloalkyl of $R^{CH}$ is unsubstituted or independently substituted by 1 to 4 fluoro, $C_1$-$C_3$ alkyl, or $C_1$-$C_3$ trifluoroalkyl;
(ii.) phenyl, wherein said phenyl of $R^{CH}$ is unsubstituted or independently substituted by 1 to 3 halo or cyano; and
(iii.) a 3- to 6-membered heterocyclyl, wherein said heterocyclyl of $R^{CH}$ is a saturated or partially saturated ring system containing 1 to 2 heteroatoms independently selected from the group consisting of N, O, and S, wherein said heterocyclyl is unsubstituted or independently substituted by 1 to 2 $C_1$-$C_3$ alkyl, trifluoromethyl, $C_1$-$C_4$ alkylcarbonylamino, or oxo.

16. The compound of claim 2, having the Formula (IB)

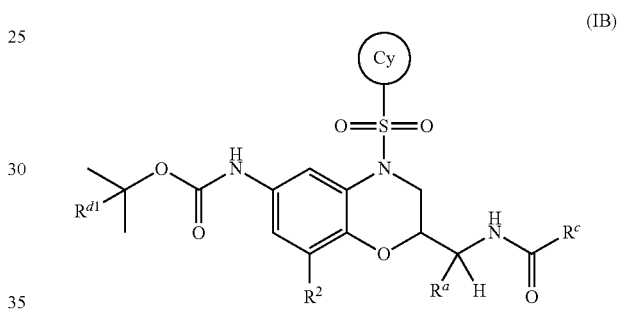

wherein
Cy is

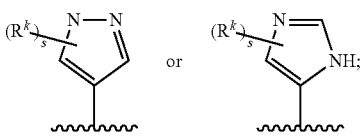

$R^2$ is H or F;
the subscript s is 0, 1, 2, or 3;
$R^{d1}$ is $CH_3$, $CHF_2$, $CH_2F$, or $CF_3$;
$R^a$ is H or $C_1$-$C_3$ alkyl; and
$R^c$ is
(a.) $C_1$-$C_6$ alkyl, wherein said $C_1$-$C_6$ alkyl is unsubstituted or independently substituted by 1 to 4 fluoro or hydroxyl; or
(b.) cyclopropyl, wherein said cyclopropyl is unsubstituted or substituted by 1 to 2 fluoro;
or a pharmaceutically acceptable salt thereof.

17. The compound of claim 16 or a pharmaceutically acceptable salt thereof, wherein each $R^k$ is independently:
(i.) $C_1$-$C_6$ alkyl, wherein said $C_1$-$C_6$ alkyl is unsubstituted or independently substituted by 1 to 3 hydroxy or fluoro;
(ii.) $C_1$-$C_6$ alkoxy, wherein said $C_1$-$C_6$ alkoxy is unsubstituted or independently substituted by 1 to 3 fluoro, hydroxy, methoxy, or phenyl;
(iii). a halo selected from fluoro or chloro; or
alternatively, two $R^k$ moieties, when substituted on adjacent ring atoms of Cy, form a second ring, wherein said second ring is a 5- to 6-membered partially saturated or aromatic ring system that contains 0 or 1 N atom; wherein said second ring is unsubstituted or substituted by 1 to 2 $R^k$ moieties independently selected from (i)-(iii).

18. The compound of claim 2, having the Formula (IB)

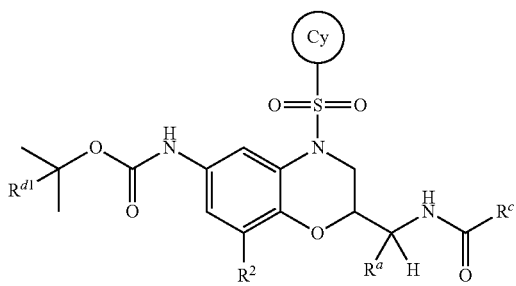

(IB)

wherein Cy is:

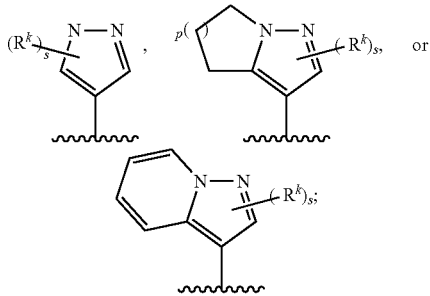

wherein
the subscript p is 1 or 2; and
the subscript s is 0, 1, or 2;
$R^2$ is H or F;
$R^{d1}$ is $CH_3$, $CHF_2$, $CH_2F$, or $CF_3$;
$R^a$ is H or $C_1$-$C_3$ alkyl; and
$R^c$ is
(a.) $C_1$-$C_6$ alkyl, wherein said $C_1$-$C_6$ alkyl is unsubstituted or independently substituted by 1 to 4 fluoro or hydroxyl; or
(b.) cyclopropyl, wherein said cyclopropyl is unsubstituted or substituted by 1 to 2 fluoro;
or a pharmaceutically acceptable salt thereof.

19. The compound of claim 2, having the Formula (IB)

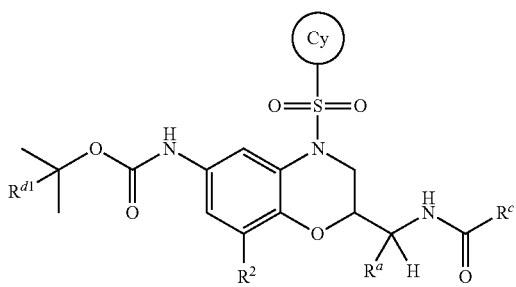

(IB)

wherein Cy is

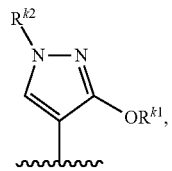

wherein
$R^{k1}$ is $C_1$-$C_6$ alkyl or $CH_2CH_2OH$; and
$R^{k2}$ is $C_1$-$C_3$ alkyl or $CHF_2$;
$R^2$ is H or F;
$R^{d1}$ is $CH_3$, $CHF_2$, $CH_2F$, or $CF_3$;
$R^a$ is H or $C_1$-$C_3$ alkyl; and
$R^c$ is
(a.) $C_1$-$C_6$ alkyl, wherein said $C_1$-$C_6$ alkyl is unsubstituted or independently substituted by 1 to 4 fluoro or hydroxyl; or
(b.) cyclopropyl, wherein said cyclopropyl is unsubstituted or substituted by 1 to 2 fluoro;
or a pharmaceutically acceptable salt thereof.

20. The compound of claim 2, having the Formula (IB)

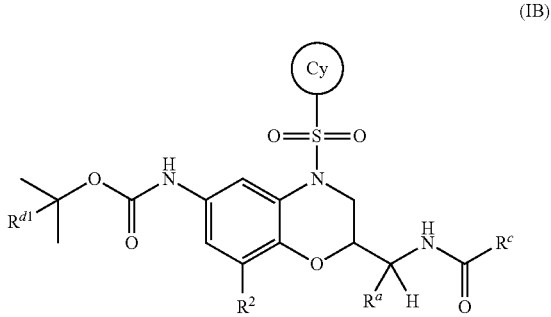

(IB)

wherein Cy is

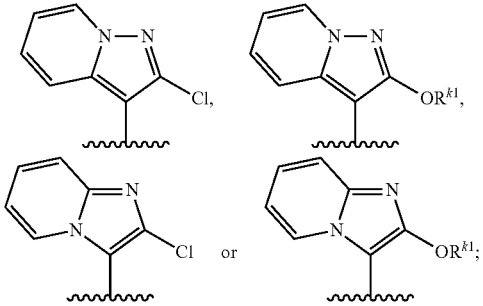

wherein
$R^{k1}$ is $C_1$-$C_6$ alkyl or $CH_2CH_2OH$;
$R^2$ is H or F;
$R^{d1}$ is $CH_3$, $CHF_2$, $CH_2F$, or $CF_3$;
$R^a$ is H or $C_1$-$C_3$ alkyl; and
$R^c$ is
(a.) $C_1$-$C_6$ alkyl, wherein said $C_1$-$C_6$ alkyl is unsubstituted or independently substituted by 1 to 4 fluoro or hydroxyl; or
(b.) cyclopropyl, wherein said cyclopropyl is unsubstituted or substituted by 1 to 2 fluoro;
or a pharmaceutically acceptable salt thereof.

21. The compound of claim 20, having the Formula (IC)

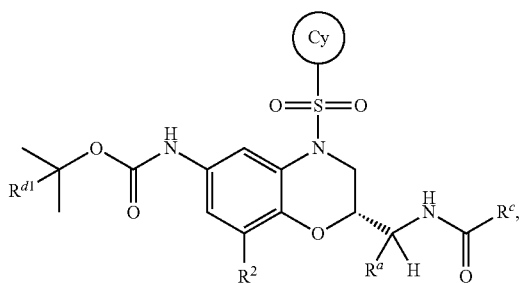

(IC)

or a pharmaceutically acceptable salt thereof.

22. A pharmaceutical composition comprising a therapeutically effective amount of a compound of claim 1 or a pharmaceutically acceptable salt thereof and a pharmaceutically acceptable carrier.

23. A method of treating a disease or condition mediated by RORgammaT comprising administering a therapeutically effective amount of a compound of claim 1 or a pharmaceutically acceptable salt thereof to a patient in need of such treatment, wherein the disease or condition is multiple sclerosis, inflammatory bowel disease, Crohn's disease, ankylosing spondylitis, psoriasis, rheumatoid arthritis, asthma, osteoarthritis, Kawasaki disease, Hashimoto's thyroiditis, or mucosal leishmaniasis.

24. The method of claim 23, wherein the disease or condition is ankylosing spondylitis or psoriasis.

25. The method of claim 24, wherein the compound is a compound of claim 16.

26. A compound selected from the following, or a pharmaceutically acceptable salt thereof:

(S)-tert-butyl (2-(aminomethyl)-4-((4-fluorophenyl)sulfonyl)-3,4-dihydro-2H-benzo[b][1,4]oxazin-6-yl)carbamate;

(S)-tert-butyl (2-(acetamidomethyl)-4-((1-ethyl-3-methyl-1H-pyrazol-4-yl)sulfonyl)-3,4-dihydro-2H-benzo[b][1,4]oxazin-6-yl)carbamate;

(S)-tert-butyl (2-(acetamidomethyl)-4-((1,5-dimethyl-1H-pyrazol-4-yl)sulfonyl)-3,4-dihydro-2H-benzo[b][1,4]oxazin-6-yl)carbamate;

(S)-tert-butyl (2-(acetamidomethyl)-4-(imidazo[1,2-a]pyridin-6-ylsulfonyl)-3,4-dihydro-2H-benzo[b][1,4]oxazin-6-yl)carbamate;

(S)-tert-butyl (2-(acetamidomethyl)-4-(imidazo[1,2-a]pyridin-5-ylsulfonyl)-3,4-dihydro-2H-benzo[b][1,4]oxazin-6-yl)carbamate;

(S)-tert-butyl (2-(acetamidomethyl)-4-((3-cyano-4-methylphenyl)sulfonyl)-3,4-dihydro-2H-benzo[b][1,4]oxazin-6-yl)carbamate;

(S)-tert-butyl (2-(acetamidomethyl)-4-((5-bromo-2-chlorophenyl)sulfonyl)-3,4-dihydro-2H-benzo[b][1,4]oxazin-6-yl)carbamate;

(S)-tert-butyl (2-(acetamidomethyl)-4-((1-(difluoromethyl)-5-methyl-1H-pyrazol-4-yl)sulfonyl)-3,4-dihydro-2H-benzo[b][1,4]oxazin-6-yl)carbamate;

(S)-tert-butyl (2-(acetamidomethyl)-4-((3-chloro-1-ethyl-1H-pyrazol-4-yl)sulfonyl)-3,4-dihydro-2H-benzo[b][1,4]oxazin-6-yl)carbamate;

(S)-tert-butyl (2-(acetamidomethyl)-4-((2-methyl-6,7-dihydro-5H-pyrazolo[5,1-b][1,3]oxazin-3-yl)sulfonyl)-3,4-dihydro-2H-benzo[b][1,4]oxazin-6-yl)carbamate;

(S)-tert-butyl (2-(acetamidomethyl)-4-((5-methoxy-1,3-dimethyl-1H-pyrazol-4-yl)sulfonyl)-3,4-dihydro-2H-benzo[b][1,4]oxazin-6-yl)carbamate;

(S)-tert-butyl (2-(acetamidomethyl)-4-((2-methyl-4,5,6,7-tetrahydropyrazolo[1,5-a]pyridin-3-yl)sulfonyl)-3,4-dihydro-2H-benzo[b][1,4]oxazin-6-yl)carbamate;

(S)-tert-butyl (2-(acetamidomethyl)-4-((3-methoxy-1,5-dimethyl-1H-pyrazol-4-yl)sulfonyl)-3,4-dihydro-2H-benzo[b][1,4]oxazin-6-yl)carbamate;

(S)-tert-butyl (2-(acetamidomethyl)-4-(imidazo[2,1-b]thiazol-5-ylsulfonyl)-3,4-dihydro-2H-benzo[b][1,4]oxazin-6-yl)carbamate;

(S)-tert-butyl (2-(acetamidomethyl)-4-((2,3-dichlorophenyl)sulfonyl)-3,4-dihydro-2H-benzo[b][1,4]oxazin-6-yl)carbamate (S)-tert-butyl (2-(acetamidomethyl)-4-((2-methylimidazo[1,2-a]pyrimidin-3-yl)sulfonyl)-3,4-dihydro-2H-benzo[b][1,4]oxazin-6-yl)carbamate;

(S)-tert-butyl (2-(acetamidomethyl)-4-((6,7-dihydro-5H-pyrazolo[5,1-b][1,3]oxazin-3-yl)sulfonyl)-3,4-dihydro-2H-benzo[b][1,4]oxazin-6-yl)carbamate;

(S)-tert-butyl (2-(acetamidomethyl)-4-((2-methylpyrazolo[1,5-a]pyrimidin-3-yl)sulfonyl)-3,4-dihydro-2H-benzo[b][1,4]oxazin-6-yl)carbamate;

(S)-tert-butyl (2-(acetamidomethyl)-4-((4-chlorophenyl)sulfonyl)-3,4-dihydro-2H-benzo[b][1,4]oxazin-6-yl)carbamate;

(S)-tert-butyl (2-(acetamidomethyl)-4-((2-chloro-4-fluorophenyl)sulfonyl)-3,4-dihydro-2H-benzo[b][1,4]oxazin-6-yl)carbamate;

(S)-tert-butyl (2-(acetamidomethyl)-4-((3-chlorophenyl)sulfonyl)-3,4-dihydro-2H-benzo[b][1,4]oxazin-6-yl)carbamate;

(S)-tert-butyl (2-(acetamidomethyl)-4-((3-(trifluoromethyl)phenyl)sulfonyl)-3,4-dihydro-2H-benzo[b][1,4]oxazin-6-yl)carbamate;

(S)-tert-butyl (2-(acetamidomethyl)-4-((3-cyanophenyl)sulfonyl)-3,4-dihydro-2H-benzo[b][1,4]oxazin-6-yl)carbamate;

(S)-tert-butyl (2-(acetamidomethyl)-4-((3-(methylsulfonyl)phenyl)sulfonyl)-3,4-dihydro-2H-benzo[b][1,4]oxazin-6-yl)carbamate;

(S)-tert-butyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-tert-butyl (2-(acetamidomethyl)-4-((3-cyano-4-fluorophenyl)sulfonyl)-3,4-dihydro-2H-benzo[b][1,4]oxazin-6-yl)carbamate;

(S)-tert-butyl (2-(acetamidomethyl)-4-((4-fluoro-3-methylphenyl)sulfonyl)-3,4-dihydro-2H-benzo[b][1,4]oxazin-6-yl)carbamate;

(S)-tert-butyl (2-(acetamidomethyl)-4-((2-chloro-5-(trifluoromethyl)pyridin-3-yl)sulfonyl)-3,4-dihydro-2H-benzo[b][1,4]oxazin-6-yl)carbamate;

(S)-tert-butyl (2-(acetamidomethyl)-4-((2-chloro-5-methylpyridin-3-yl)sulfonyl)-3,4-dihydro-2H-benzo[b][1,4]oxazin-6-yl)carbamate;

(S)-tert-butyl (2-(acetamidomethyl)-4-((5-methyl-2-oxo-1,2-dihydropyridin-3-yl)sulfonyl)-3,4-dihydro-2H-benzo[b][1,4]oxazin-6-yl)carbamate;

(S)-tert-butyl (2-(acetamidomethyl)-4-((5-methylpyridin-3-yl)sulfonyl)-3,4-dihydro-2H-benzo[b][1,4]oxazin-6-yl)carbamate;

(S)-tert-butyl (2-(acetamidomethyl)-4-((3,4-difluorophenyl)sulfonyl)-3,4-dihydro-2H-benzo[b][1,4]oxazin-6-yl)carbamate;

(S)-tert-butyl (2-(acetamidomethyl)-4-((3-chloro-4-fluorophenyl)sulfonyl)-3,4-dihydro-2H-benzo[b][1,4]oxazin-6-yl)carbamate;
(S)-tert-butyl (2-(acetamidomethyl)-4-((4-fluoro-3-methoxyphenyl)sulfonyl)-3,4-dihydro-2H-benzo[b][1,4]oxazin-6-yl)carbamate;
(S)-tert-butyl (2-(acetamidomethyl)-4-((4-fluoro-3-(trifluoromethyl)phenyl)sulfonyl)-3,4-dihydro-2H-benzo[b][1,4]oxazin-6-yl)carbamate;
(S)-tert-butyl (2-(acetamidomethyl)-4-((5-(trifluoromethyl)pyridin-3-yl)sulfonyl)-3,4-dihydro-2H-benzo[b][1,4]oxazin-6-yl)carbamate;
(S)-tert-butyl (2-(acetamidomethyl)-4-((4-chloro-3-cyanophenyl)sulfonyl)-3,4-dihydro-2H-benzo[b][1,4]oxazin-6-yl)carbamate;
(S)-tert-butyl (2-(acetamidomethyl)-4-((5-cyano-2-methylphenyl)sulfonyl)-3,4-dihydro-2H-benzo[b][1,4]oxazin-6-yl)carbamate;
(S)-tert-butyl (2-(acetamidomethyl)-4-((1-isopropyl-3,5-dimethyl-1H-pyrazol-4-yl)sulfonyl)-3,4-dihydro-2H-benzo[b][1,4]oxazin-6-yl)carbamate;
(S)-tert-butyl (2-(acetamidomethyl)-4-(imidazo[1,2-a]pyridin-3-ylsulfonyl)-3,4-dihydro-2H-benzo[b][1,4]oxazin-6-yl)carbamate;
(S)-tert-butyl (2-(acetamidomethyl)-4-((2-methylimidazo[1,2-a]pyridin-3-yl)sulfonyl)-3,4-dihydro-2H-benzo[b][1,4]oxazin-6-yl)carbamate;
(S)-tert-butyl (2-(acetamidomethyl)-4-((6-methylimidazo[2,1-b]thiazol-5-yl)sulfonyl)-3,4-dihydro-2H-benzo[b][1,4]oxazin-6-yl)carbamate;
(S)-tert-butyl (2-(acetamidomethyl)-4-((2-methoxy-4,5,6,7-tetrahydropyrazolo[1,5-a]pyridin-3-yl)sulfonyl)-3,4-dihydro-2H-benzo[b][1,4]oxazin-6-yl)carbamate;
(S)-tert-butyl (2-(acetamidomethyl)-4-((2-methoxy-5,6-dihydro-4H-pyrrolo[1,2-b]pyrazol-3-yl)sulfonyl)-3,4-dihydro-2H-benzo[b][1,4]oxazin-6-yl)carbamate;
(S)-tert-butyl (2-(acetamidomethyl)-4-((2-chloro-4,5,6,7-tetrahydropyrazolo[1,5-a]pyridin-3-yl)sulfonyl)-3,4-dihydro-2H-benzo[b][1,4]oxazin-6-yl)carbamate;
(S)-tert-butyl (2-(acetamidomethyl)-4-((6-(trifluoromethyl)pyridin-2-yl)sulfonyl)-3,4-dihydro-2H-benzo[b][1,4]oxazin-6-yl)carbamate;
(S)-tert-butyl (2-(acetamidomethyl)-4-((1-ethyl-3-methoxy-1H-pyrazol-4-yl)sulfonyl)-3,4-dihydro-2H-benzo[b][1,4]oxazin-6-yl)carbamate;
(S)-tert-butyl (2-(acetamidomethyl)-4-((3-ethoxy-1-ethyl-1H-pyrazol-4-yl)sulfonyl)-3,4-dihydro-2H-benzo[b][1,4]oxazin-6-yl)carbamate;
(S)-methyl 2-((4-((2-(acetamidomethyl)-6-((tert-butoxycarbonyl)amino)-2H-benzo[b][1,4]oxazin-4(3H)-yl)sulfonyl)-1-ethyl-1H-pyrazol-3-yl)oxy)acetate;
(S)-tert-butyl (2-(acetamidomethyl)-4-((3-(2,2-difluoroethoxy)-1-ethyl-1H-pyrazol-4-yl)sulfonyl)-3,4-dihydro-2H-benzo[b][1,4]oxazin-6-yl)carbamate;
(S)-2-((4-((2-(acetamidomethyl)-6-((tert-butoxycarbonyl)amino)-2H-benzo[b][1,4]oxazin-4(3H)-yl)sulfonyl)-1-ethyl-1H-pyrazol-3-yl)oxy)acetic acid;
(S)-tert-butyl (2-(acetamidomethyl)-4-((1-ethyl-3-(2-(methylamino)-2-oxoethoxy)-1H-pyrazol-4-yl)sulfonyl)-3,4-dihydro-2H-benzo[b][1,4]oxazin-6-yl)carbamate;
(S)-tert-butyl (2-(acetamidomethyl)-4-((1-ethyl-3-(2,2,2-trifluoroethoxy)-1H-pyrazol-4-yl)sulfonyl)-3,4-dihydro-2H-benzo[b][1,4]oxazin-6-yl)carbamate;
(S)-tert-butyl (2-(acetamidomethyl)-4-((1-ethyl-3-(2-hydroxyethoxy)-1H-pyrazol-4-yl)sulfonyl)-3,4-dihydro-2H-benzo[b][1,4]oxazin-6-yl)carbamate;
(S)-tert-butyl (2-(acetamidomethyl)-4-((2-chloro-5,6-dihydro-4H-pyrrolo[1,2-b]pyrazol-3-yl)sulfonyl)-3,4-dihydro-2H-benzo[b][1,4]oxazin-6-yl)carbamate;
(S)-tert-butyl (2-(acetamidomethyl)-4-((1-ethyl-3-(ethylamino)-1H-pyrazol-4-yl)sulfonyl)-3,4-dihydro-2H-benzo[b][1,4]oxazin-6-yl)carbamate;
(S)-tert-butyl (2-(acetamidomethyl)-4-((3-cyclopropyl-1-ethyl-1H-pyrazol-4-yl)sulfonyl)-3,4-dihydro-2H-benzo[b][1,4]oxazin-6-yl)carbamate;
(S)-tert-butyl (2-(acetamidomethyl)-4-((3-(difluoromethoxy)-1-ethyl-1H-pyrazol-4-yl)sulfonyl)-3,4-dihydro-2H-benzo[b][1,4]oxazin-6-yl)carbamate;
(S)-tert-butyl (2-(acetamidomethyl)-4-((3-(dimethylamino)-1-ethyl-1H-pyrazol-4-yl)sulfonyl)-3,4-dihydro-2H-benzo[b][1,4]oxazin-6-yl)carbamate;
(S)-1,1,1-trifluoro-2-methylpropan-2-yl (2-(acetamidomethyl)-4-((4-fluorophenyl)sulfonyl)-3,4-dihydro-2H-benzo[b][1,4]oxazin-6-yl)carbamate;
(S)-1,1,1-trifluoro-2-methylpropan-2-yl (2-(acetamidomethyl)-4-((1-ethyl-3-hydroxy-1H-pyrazol-4-yl)sulfonyl)-3,4-dihydro-2H-benzo[b][1,4]oxazin-6-yl)carbamate;
(S)-1,1,1-trifluoro-2-methylpropan-2-yl (2-(acetamidomethyl)-4-((1-ethyl-3-isopropoxy-1H-pyrazol-4-yl)sulfonyl)-3,4-dihydro-2H-benzo[b][1,4]oxazin-6-yl)carbamate;
(S)-1,1,1-trifluoro-2-methylpropan-2-yl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;
(S)-1,1,1-trifluoro-2-methylpropan-2-yl (2-(acetamidomethyl)-4-((3-chloro-4-fluorophenyl)sulfonyl)-3,4-dihydro-2H-benzo[b][1,4]oxazin-6-yl)carbamate;
(S)-1,1,1-trifluoro-2-methylpropan-2-yl (2-(acetamidomethyl)-4-((3,4-difluorophenyl)sulfonyl)-3,4-dihydro-2H-benzo[b][1,4]oxazin-6-yl)carbamate;
(S)-1,1,1-trifluoro-2-methylpropan-2-yl (2-(acetamidomethyl)-4-((4-fluoro-3-(trifluoromethyl)phenyl)sulfonyl)-3,4-dihydro-2H-benzo[b][1,4]oxazin-6-yl)carbamate;
(S)-1,1,1-trifluoro-2-methylpropan-2-yl (2-(acetamidomethyl)-4-((4-fluoro-3-methylphenyl)sulfonyl)-3,4-dihydro-2H-benzo[b][1,4]oxazin-6-yl)carbamate;
(S)-1,1,1-trifluoro-2-methylpropan-2-yl (2-(acetamidomethyl)-4-((4-fluoro-3-methoxyphenyl)sulfonyl)-3,4-dihydro-2H-benzo[b][1,4]oxazin-6-yl)carbamate;
(S)-1,1,1-trifluoro-2-methylpropan-2-yl (2-(acetamidomethyl)-4-((4-chlorophenyl)sulfonyl)-3,4-dihydro-2H-benzo[b][1,4]oxazin-6-yl)carbamate;
(S)-1,1,1-trifluoro-2-methylpropan-2-yl (2-(acetamidomethyl)-4-((3-cyanophenyl)sulfonyl)-3,4-dihydro-2H-benzo[b][1,4]oxazin-6-yl)carbamate;
(S)-1,1,1-trifluoro-2-methylpropan-2-yl (2-(acetamidomethyl)-4-((4-chloro-3-cyanophenyl)sulfonyl)-3,4-dihydro-2H-benzo[b][1,4]oxazin-6-yl)carbamate;
(S)-1,1,1-trifluoro-2-methylpropan-2-yl (2-(acetamidomethyl)-4-((5-cyano-2-methylphenyl)sulfonyl)-3,4-dihydro-2H-benzo[b][1,4]oxazin-6-yl)carbamate;
(S)-1,1,1-trifluoro-2-methylpropan-2-yl (2-(acetamidomethyl)-4-((3-(methylsulfonyl)phenyl)sulfonyl)-3,4-dihydro-2H-benzo[b][1,4]oxazin-6-yl)carbamate;
(S)-1,1,1-trifluoro-2-methylpropan-2-yl (2-(acetamidomethyl)-4-((2-chloro-5-cyanophenyl)sulfonyl)-3,4-dihydro-2H-benzo[b][1,4]oxazin-6-yl)carbamate;
(S)-1,1,1-trifluoro-2-methylpropan-2-yl (2-(acetamidomethyl)-4-((3-chloro-5-cyanophenyl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-(difluoromethyl)-5-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3-chloro-1-ethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-methyl-3-(trifluoromethyl)-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((2,4-dimethylthiazol-5-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3-ethoxy-4-fluorophenyl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3-(difluoromethoxy)phenyl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3-(trifluoromethoxy)phenyl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3-bromophenyl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3-bromo-4-fluorophenyl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((2-methylthiazol-5-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-ethyl-5-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-ethyl-3,5-dimethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3-methyl-1-propyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((2-methyl-4-(trifluoromethyl)thiazol-5-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3,5-dimethyl-1-propyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3,5-dimethyl-1-(2,2,2-trifluoroethyl)-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-(2,2-difluoroethyl)-3,5-dimethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-ethyl-3-(trifluoromethyl)-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-ethyl-3-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1,5-dimethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (4-((1,5-dimethyl-1H-pyrazol-4-yl)sulfonyl)-2-(methylsulfonamidomethyl)-3,4-dihydro-2H-benzo[b][1,4]oxazin-6-yl)carbamate;

(S)-1,1,1-trifluoro-2-methylpropan-2-yl (2-(acetamidomethyl)-4-((2-methoxy-5,6-dihydro-4H-pyrrolo[1,2-b]pyrazol-3-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((2-methoxy-4,5,6,7-tetrahydropyrazolo[1,5-a]pyridin-3-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-(difluoromethyl)-3,5-dimethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-ethyl-3-methoxy-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3-ethoxy-1-ethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((5-cyclopropylpyridin-3-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((2-chloro-4,5,6,7-tetrahydropyrazolo[1,5-a]pyridin-3-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3-methoxy-1,5-dimethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((2-chloro-5,6-dihydro-4H-pyrrolo[1,2-b]pyrazol-3-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3-(2,2-difluoroethoxy)-1-ethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-(2,2-difluoroethyl)-3-ethoxy-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3-cyclopropyl-1-ethyl-1iH-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3-(difluoromethoxy)-1-ethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-ethyl-3-(methylamino)-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-ethyl-3-(ethylamino)-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-cyclopropyl-3-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-cyclopropyl-5-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-(difluoromethyl)-3-ethoxy-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-(imidazo[1,2-a]pyridin-3-ylsulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3-(benzyloxy)-1-ethyl-1iH-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3-(3-(benzyloxy)propoxy)-1-ethyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-ethyl-3-(3-hydroxypropoxy)-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3-methyl-1-propyl-1H-pyrazol-5-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-(2-methoxyethyl)-3-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-(2-methoxyethyl)-5-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-isopropyl-3-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-isopropyl-5-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((2-(2-hydroxyethoxy)-4,5,6,7-tetrahydropyrazolo[1,5-a]pyridin-3-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3-chloro-1-(difluoromethyl)-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3-methyl-1-(oxetan-3-yl)-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((5-methyl-1-(oxetan-3-yl)-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-(2-hydroxyethyl)-3-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-(2-hydroxyethyl)-5-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-(2-hydroxy-2-methylpropyl)-3-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((1-(2-hydroxy-2-methylpropyl)-5-methyl-1H-pyrazol-4-yl)sulfonyl)-3,4-dihydro-2H-benzo[b][1,4]oxazin-6-yl)carbamate;

(S)-2-((4-((2-(acetamidomethyl)-6-(((((1,1,1-trifluoro-2-methylpropan-2-yl)oxy)carbonyl)amino)-2,3-dihydro-4H-benzo[b][1,4]oxazin-4-yl)sulfonyl)-1-ethyl-1H-pyrazol-3-yl)oxy)acetic acid;

(S)-1,1,1-trifluoro-2-methylpropan-2-yl (2-(cyclopropanecarboxamidomethyl)-4-((1-ethyl-3-(2-hydroxyethoxy)-1H-pyrazol-4-yl)sulfonyl)-3,4-dihydro-2H-benzo[b][1,4]oxazin-6-yl)carbamate;

1,1,1-trifluoro-2-methylpropan-2-yl ((S)-4-((1-ethyl-3-(2-hydroxyethoxy)-1H-pyrazol-4-yl)sulfonyl)-2-(((1S,2S)-2-fluorocyclopropanecarboxamido)methyl)-3,4-dihydro-2H-benzo[b][1,4]oxazin-6-yl)carbamate;

(S)-1,1,1-trifluoro-2-methylpropan-2-yl (4-((1-ethyl-3-(2-hydroxyethoxy)-1H-pyrazol-4-yl)sulfonyl)-2-((2-hydroxy-2-methylpropanamido)methyl)-3,4-dihydro-2H-benzo[b][1,4]oxazin-6-yl)carbamate;

1,1,1-trifluoro-2-methylpropan-2-yl ((2S)-4-((1-ethyl-3-(2-hydroxyethoxy)-1H-pyrazol-4-yl)sulfonyl)-2-((3,3,3-trifluoro-2-hydroxy-2-methylpropanamido)methyl)-3,4-dihydro-2H-benzo[b][1,4]oxazin-6-yl)carbamate;

1,1,1-trifluoro-2-methylpropan-2-yl ((2S)-2-((2-amino-3,3,3-trifluoro-2-methylpropanamido)methyl)-4-((1-ethyl-3-(2-hydroxyethoxy)-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (4-((1-ethyl-3-(2-hydroxyethoxy)-1H-pyrazol-4-yl)sulfonyl)-2-((2,2,2-trifluoroethylsulfonamido)methyl)-3,4-dihydro-2H-benzo[b][1,4]oxazin-6-yl)carbamate;

(S)-1,1,1-trifluoro-2-methylpropan-2-yl (4-((1-ethyl-3-(2-hydroxyethoxy)-1H-pyrazol-4-yl)sulfonyl)-2-(methylsulfonamidomethyl)-3,4-dihydro-2H-benzo[b][1,4]oxazin-6-yl)carbamate;

(S)-1,1,1-trifluoro-2-methylpropan-2-yl (2-(acetamidomethyl)-4-((3-cyclopropyl-4-fluorophenyl)sulfonyl)-3,4-dihydro-2H-benzo[b][1,4]oxazin-6-yl)carbamate;

(S)-1,1,1-trifluoro-2-methylpropan-2-yl (2-(acetamidomethyl)-4-((3-cyclopropylphenyl)sulfonyl)-3,4-dihydro-2H-benzo[b][1,4]oxazin-6-yl)carbamate;

1,1,1-trifluoro-2-methylpropan-2-yl ((R)-2-((R)-1-acetamidoethyl)-4-((3-chloro-4-fluorophenyl)sulfonyl)-3,4-dihydro-2H-benzo[b][1,4]oxazin-6-yl)carbamate;

1,1,1-trifluoro-2-methylpropan-2-yl ((R)-2-((S)-1-acetamidoethyl)-4-((3-chloro-4-fluorophenyl)sulfonyl)-3,4-dihydro-2H-benzo[b][1,4]oxazin-6-yl)carbamate;

1,1,1-trifluoro-2-methylpropan-2-yl ((R)-2-((R or S)-1-acetamidoethyl)-4-((1-(difluoromethyl)-3-methyl-1H-pyrazol-4-yl)sulfonyl)-3,4-dihydro-2H-benzo[b][1,4]oxazin-6-yl)carbamate;

1,1,1-trifluoro-2-methylpropan-2-yl ((R)-2-((S or R)-1-acetamidoethyl)-4-((1-(difluoromethyl)-3-methyl-1H-pyrazol-4-yl)sulfonyl)-3,4-dihydro-2H-benzo[b][1,4]oxazin-6-yl)carbamate;

1,1,1-trifluoro-2-methylpropan-2-yl ((R)-2-((R or S)-1-acetamidoethyl)-4-((3,4-difluorophenyl)sulfonyl)-3,4-dihydro-2H-benzo[b][1,4]oxazin-6-yl)carbamate;

1,1,1-trifluoro-2-methylpropan-2-yl ((R)-2-((S or R)-1-acetamidoethyl)-4-((3,4-difluorophenyl)sulfonyl)-3,4-dihydro-2H-benzo[b][1,4]oxazin-6-yl)carbamate;

1,1,1-trifluoro-2-methylpropan-2-yl ((R)-2-((R or S)-1-acetamidoethyl)-4-((3-chloro-1-ethyl-1H-pyrazol-4-yl)sulfonyl)-3,4-dihydro-2H-benzo[b][1,4]oxazin-6-yl)carbamate;

1,1,1-trifluoro-2-methylpropan-2-yl ((R)-2-((S or R)-1-acetamidoethyl)-4-((3-chloro-1-ethyl-1H-pyrazol-4-yl)sulfonyl)-3,4-dihydro-2H-benzo[b][1,4]oxazin-6-yl)carbamate;

1,1,1-trifluoro-2-methylpropan-2-yl ((R)-2-((R or S)-1-acetamidoethyl)-4-((3-methoxy-1,5-dimethyl-1H-pyrazol-4-yl)sulfonyl)-3,4-dihydro-2H-benzo[b][1,4]oxazin-6-yl)carbamate;

1,1,1-trifluoro-2-methylpropan-2-yl ((R)-2-((S)-1-acetamidoethyl)-4-((3-methoxy-1,5-dimethyl-1H-pyrazol-4-yl)sulfonyl)-3,4-dihydro-2H-benzo[b][1,4]oxazin-6-yl)carbamate;

1,1,1-trifluoro-2-methylpropan-2-yl ((R or S)-2-((S or R)-1-acetamidoethyl)-4-((4-fluorophenyl)sulfonyl)-3,4-dihydro-2H-benzo[b][1,4]oxazin-6-yl)carbamate;

1,1,1-trifluoro-2-methylpropan-2-yl ((S or R)-2-((S or R)-1-acetamidoethyl)-4-((4-fluorophenyl)sulfonyl)-3,4-dihydro-2H-benzo[b][1,4]oxazin-6-yl)carbamate;

1,1,1-trifluoro-2-methylpropan-2-yl ((R or S)-2-((S or R)-1-acetamidoethyl)-4-((4-fluorophenyl)sulfonyl)-3,4-dihydro-2H-benzo[b][1,4]oxazin-6-yl)carbamate;

1,1,1-trifluoro-2-methylpropan-2-yl ((R or S)-2-((R or S)-1-acetamidoethyl)-4-((4-fluorophenyl)sulfonyl)-3,4-dihydro-2H-benzo[b][1,4]oxazin-6-yl)carbamate;

1,1,1-trifluoro-2-methylpropan-2-yl ((R)-2-((R or S)-acetamido(cyclopropyl)methyl)-4-((4-fluorophenyl)sulfonyl)-3,4-dihydro-2H-benzo[b][1,4]oxazin-6-yl)carbamate 1,1,1-trifluoro-2-methylpropan-2-yl ((R)-2-((S or R)-acetamido(cyclopropyl)methyl)-4-((4-fluorophenyl)sulfonyl)-3,4-dihydro-2H-benzo[b][1,4]oxazin-6-yl)carbamate;

(R)-tert-butyl (2-(2-acetamidopropan-2-yl)-4-((4-fluorophenyl)sulfonyl)-3,4-dihydro-2H-benzo[b][1,4]oxazin-6-yl)carbamate;

(S)-tert-butyl (2-(2-acetamidopropan-2-yl)-4-((4-fluorophenyl)sulfonyl)-3,4-dihydro-2H-benzo[b][1,4]oxazin-6-yl)carbamate;

(R)-1,1,1-trifluoro-2-methylpropan-2-yl (2-(2-acetamidopropan-2-yl)-4-((3-chloro-4-fluorophenyl)sulfonyl)-3,4-dihydro-2H-benzo[b][1,4]oxazin-6-yl)carbamate;

(S)-1,1,1-trifluoro-2-methylpropan-2-yl (2-(2-acetamidopropan-2-yl)-4-((3-chloro-4-fluorophenyl)sulfonyl)-3,4-dihydro-2H-benzo[b][1,4]oxazin-6-yl)carbamate;

(R)-1,1,1-trifluoro-2-methylpropan-2-yl (2-(2-acetamidopropan-2-yl)-4-((4-fluorophenyl)sulfonyl)-3,4-dihydro-2H-benzo[b][1,4]oxazin-6-yl)carbamate;

(R)-1,1,1-trifluoro-2-methylpropan-2-yl (4-((3-chloro-4-fluorophenyl)sulfonyl)-2-(2-(methylsulfonamido)propan-2-yl)-3,4-dihydro-2H-benzo[b][1,4]oxazin-6-yl)carbamate;

(R)-1,1,1-trifluoro-2-methylpropan-2-yl (4-((3-chloro-4-fluorophenyl)sulfonyl)-2-(2-(cyclopropanesulfonamido)propan-2-yl)-3,4-dihydro-2H-benzo[b][1,4]oxazin-6-yl)carbamate;

(R)-1,1,1-trifluoro-2-methylpropan-2-yl (4-((3,4-difluorophenyl)sulfonyl)-2-(2-(methylsulfonamido)propan-2-yl)-3,4-dihydro-2H-benzo[b][1,4]oxazin-6-yl)carbamate;

(R)-1,1,1-trifluoro-2-methylpropan-2-yl (4-((4-fluorophenyl)sulfonyl)-2-(2-(methylsulfonamido)propan-2-yl)-3,4-dihydro-2H-benzo[b][1,4]oxazin-6-yl)carbamate;

(R)-1,1,1-trifluoro-2-methylpropan-2-yl (2-(2-(2-(dimethylamino)-2-oxoacetamido)propan-2-yl)-4-((4-fluorophenyl)sulfonyl)-3,4-dihydro-2H-benzo[b][1,4]oxazin-6-yl)carbamate;

(R)-1,1,1-trifluoro-2-methylpropan-2-yl (2-(2-(cyclopropanesulfonamido)propan-2-yl)-4-((4-fluorophenyl)sulfonyl)-3,4-dihydro-2H-benzo[b][1,4]oxazin-6-yl)carbamate;

(R or S)-1,1,1-trifluoro-2-methylpropan-2-yl (2-(2-acetamidopropan-2-yl)-4-((3-chloro-1-ethyl-1H-pyrazol-4-yl)sulfonyl)-3,4-dihydro-2H-benzo[b][1,4]oxazin-6-yl)carbamate;

(R or S)-1,1,1-trifluoro-2-methylpropan-2-yl (2-(2-acetamidopropan-2-yl)-4-((1-(difluoromethyl)-3-methyl-1H-pyrazol-4-yl)sulfonyl)-3,4-dihydro-2H-benzo[b][1,4]oxazin-6-yl)carbamate;

(R or S)-1,1,1-trifluoro-2-methylpropan-2-yl (2-(2-acetamidopropan-2-yl)-4-((4-fluoro-3-(trifluoromethyl)phenyl)sulfonyl)-3,4-dihydro-2H-benzo[b][1,4]oxazin-6-yl)carbamate;

(R or S)-1,1,1-trifluoro-2-methylpropan-2-yl (2-(2-acetamidopropan-2-yl)-4-((3-methoxy-1,5-dimethyl-1H-pyrazol-4-yl)sulfonyl)-3,4-dihydro-2H-benzo[b][1,4]oxazin-6-yl)carbamate;

(R or S)-1,1,1-trifluoro-2-methylpropan-2-yl (2-(2-acetamidopropan-2-yl)-4-((3-chloro-1-ethyl-1H-pyrazol-4-yl)sulfonyl)-3,4-dihydro-2H-benzo[b][1,4]oxazin-6-yl)carbamate;

(R or S)-1,1,1-trifluoro-2-methylpropan-2-yl (2-(2-acetamidopropan-2-yl)-4-((1-(difluoromethyl)-3-methyl-1H-pyrazol-4-yl)sulfonyl)-3,4-dihydro-2H-benzo[b][1,4]oxazin-6-yl)carbamate;

(R or S)-1,1,1-trifluoro-2-methylpropan-2-yl (2-(2-acetamidopropan-2-yl)-4-((4-fluoro-3-(trifluoromethyl)phenyl)sulfonyl)-3,4-dihydro-2H-benzo[b][1,4]oxazin-6-yl)carbamate;

(R or S)-1,1,1-trifluoro-2-methylpropan-2-yl (2-(2-acetamidopropan-2-yl)-4-((3-methoxy-1,5-dimethyl-1H-pyrazol-4-yl)sulfonyl)-3,4-dihydro-2H-benzo[b][1,4]oxazin-6-yl)carbamate;

1,1,1-trifluoro-2-methylbutan-2-yl ((S)-2-(acetamidomethyl)-4-((4-fluorophenyl)sulfonyl)-3,4-dihydro-2H-benzo[b][1,4]oxazin-6-yl)carbamate;

(S)-tert-pentyl (2-(acetamidomethyl)-4-((4-fluorophenyl)sulfonyl)-3,4-dihydro-2H-benzo[b][1,4]oxazin-6-yl)carbamate;

(S)-2,3-dimethylbutan-2-yl (2-(acetamidomethyl)-4-((4-fluorophenyl)sulfonyl)-3,4-dihydro-2H-benzo[b][1,4]oxazin-6-yl)carbamate;

(S)-2,3,3-trimethylbutan-2-yl (2-(acetamidomethyl)-4-((4-fluorophenyl)sulfonyl)-3,4-dihydro-2H-benzo[b][1,4]oxazin-6-yl)carbamate;

2-cyano-1,1,1-trifluoropropan-2-yl ((S)-2-(acetamidomethyl)-4-((4-fluorophenyl)sulfonyl)-3,4-dihydro-2H-benzo[b][1,4]oxazin-6-yl)carbamate;

(S)-1-methylcyclobutyl (2-(acetamidomethyl)-4-((4-fluorophenyl)sulfonyl)-3,4-dihydro-2H-benzo[b][1,4]oxazin-6-yl)carbamate;

(S)-1-methylcyclopropyl (2-(acetamidomethyl)-4-((4-fluorophenyl)sulfonyl)-3,4-dihydro-2H-benzo[b][1,4]oxazin-6-yl)carbamate;

(S)-3,3,4,4,4-pentafluoro-2-methylbutan-2-yl (2-(acetamidomethyl)-4-((4-fluorophenyl)sulfonyl)-3,4-dihydro-2H-benzo[b][1,4]oxazin-6-yl)carbamate;

(S)-2,2,3,3,3-pentafluoropropyl (2-(acetamidomethyl)-4-((4-fluorophenyl)sulfonyl)-3,4-dihydro-2H-benzo[b][1,4]oxazin-6-yl)carbamate;

1-cyclopropyl-2,2,2-trifluoroethyl ((S)-2-(acetamidomethyl)-4-((4-fluorophenyl)sulfonyl)-3,4-dihydro-2H-benzo[b][1,4]oxazin-6-yl)carbamate;

1,1,1-trifluoro-3-methyl-3-phenylbutan-2-yl ((S)-2-(acetamidomethyl)-4-((4-fluorophenyl)sulfonyl)-3,4-dihydro-2H-benzo[b][1,4]oxazin-6-yl)carbamate;

2,2,2-trifluoro-1-(1-methylcyclohexyl)ethyl ((S)-2-(acetamidomethyl)-4-((4-fluorophenyl)sulfonyl)-3,4-dihydro-2H-benzo[b][1,4]oxazin-6-yl)carbamate;

1-cyclohexyl-2,2,2-trifluoroethyl ((S)-2-(acetamidomethyl)-4-((4-fluorophenyl)sulfonyl)-3,4-dihydro-2H-benzo[b][1,4]oxazin-6-yl)carbamate;

1-cyclohexyl-2,2,3,3,3-pentafluoropropyl ((S)-2-(acetamidomethyl)-4-((4-fluorophenyl)sulfonyl)-3,4-dihydro-2H-benzo[b][1,4]oxazin-6-yl)carbamate;

(R)-3,3,4,4,4-pentafluorobutan-2-yl ((S)-2-(acetamidomethyl)-4-((4-fluorophenyl)sulfonyl)-3,4-dihydro-2H-benzo[b][1,4]oxazin-6-yl)carbamate;

(S)-3,3,4,4,4-pentafluorobutan-2-yl ((S)-2-(acetamidomethyl)-4-((4-fluorophenyl)sulfonyl)-3,4-dihydro-2H-benzo[b][1,4]oxazin-6-yl)carbamate;

(S)-1,1,1,3,3,3-hexafluoropropan-2-yl (2-(acetamidomethyl)-4-((4-fluorophenyl)sulfonyl)-3,4-dihydro-2H-benzo[b][1,4]oxazin-6-yl)carbamate;

(S)-1-(trifluoromethyl)cyclohexyl (2-(acetamidomethyl)-4-((4-fluorophenyl)sulfonyl)-3,4-dihydro-2H-benzo[b][1,4]oxazin-6-yl)carbamate;

(S)-4,4-dimethyl-1-(trifluoromethyl)cyclohexyl (2-(acetamidomethyl)-4-((4-fluorophenyl)sulfonyl)-3,4-dihydro-2H-benzo[b][1,4]oxazin-6-yl)carbamate;

2,2,2-trifluoro-1-phenylethyl ((S)-2-(acetamidomethyl)-4-((4-fluorophenyl)sulfonyl)-3,4-dihydro-2H-benzo[b][1,4]oxazin-6-yl)carbamate;

1-(4-chlorophenyl)-2,2,2-trifluoroethyl ((S)-2-(acetamidomethyl)-4-((4-fluorophenyl)sulfonyl)-3,4-dihydro-2H-benzo[b][1,4]oxazin-6-yl)carbamate;

2,2,3,3,3-pentafluoro-1-phenylpropyl ((S)-2-(acetamidomethyl)-4-((4-fluorophenyl)sulfonyl)-3,4-dihydro-2H-benzo[b][1,4]oxazin-6-yl)carbamate;

1,1,1-trifluoro-2-phenylpropan-2-yl ((S)-2-(acetamidomethyl)-4-((4-fluorophenyl)sulfonyl)-3,4-dihydro-2H-benzo[b][1,4]oxazin-6-yl)carbamate;

1,1,1,2,2-pentafluoropentan-3-yl ((S)-2-(acetamidomethyl)-4-((4-fluorophenyl)sulfonyl)-3,4-dihydro-2H-benzo[b][1,4]oxazin-6-yl)carbamate;

1,1,1-trifluoro-3-phenylpropan-2-yl ((S)-2-(acetamidomethyl)-4-((4-fluorophenyl)sulfonyl)-3,4-dihydro-2H-benzo[b][1,4]oxazin-6-yl)carbamate;

(S)-2,2,2-trifluoroethyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-(1-(trifluoromethyl)cyclopropyl)methyl (2-(acetamidomethyl)-4-((4-fluorophenyl)sulfonyl)-3,4-dihydro-2H-benzo[b][1,4]oxazin-6-yl)carbamate;

(S)-(1-(trifluoromethyl)cyclopropyl)methyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-(1-(trifluoromethyl)cyclopropyl)methyl (2-(cyclopropanecarboxamidomethyl)-4-((4-fluorophenyl)sulfonyl)-3,4-dihydro-2H-benzo[b][1,4]oxazin-6-yl)carbamate;

(S)-(1-(trifluoromethyl)cyclopropyl)methyl (2-(acetamidomethyl)-4-((3,4-difluorophenyl)sulfonyl)-3,4-dihydro-2H-benzo[b][1,4]oxazin-6-yl)carbamate;

(S)-(1-(trifluoromethyl)cyclopropyl)methyl (2-(acetamidomethyl)-4-((4-fluoro-3-methoxyphenyl)sulfonyl)-3,4-dihydro-2H-benzo[b][1,4]oxazin-6-yl)carbamate;

(S)-(1-(trifluoromethyl)cyclopropyl)methyl (2-(acetamidomethyl)-4-((4-fluoro-3-methylphenyl)sulfonyl)-3,4-dihydro-2H-benzo[b][1,4]oxazin-6-yl)carbamate;

(S)-(1-(trifluoromethyl)cyclopropyl)methyl (2-(acetamidomethyl)-4-((3-chloro-4-fluorophenyl)sulfonyl)-3,4-dihydro-2H-benzo[b][1,4]oxazin-6-yl)carbamate;

(S)-4,4-difluorocyclohexyl (2-(acetamidomethyl)-4-((4-fluorophenyl)sulfonyl)-3,4-dihydro-2H-benzo[b][1,4]oxazin-6-yl)carbamate;

(2,2-difluorocyclopropyl)methyl ((S)-2-(acetamidomethyl)-4-((4-fluorophenyl)sulfonyl)-3,4-dihydro-2H-benzo[b][1,4]oxazin-6-yl)carbamate;

(S)-cyclopentyl (2-(acetamidomethyl)-4-((4-fluorophenyl)sulfonyl)-3,4-dihydro-2H-benzo[b][1,4]oxazin-6-yl)carbamate;

(S)-cyclopentyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-cyclohexyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

2-(trifluoromethyl)cyclohexyl ((S)-2-(acetamidomethyl)-4-((4-fluorophenyl)sulfonyl)-3,4-dihydro-2H-benzo[b][1,4]oxazin-6-yl)carbamate;

(2S)-bicyclo[2.2.1]heptan-2-yl ((S)-2-(acetamidomethyl)-4-((4-fluorophenyl)sulfonyl)-3,4-dihydro-2H-benzo[b][1,4]oxazin-6-yl)carbamate;

6-(2,2,2-trifluoroethyl)bicyclo[3.1.0]hexan-6-yl ((S)-2-(acetamidomethyl)-4-((4-fluorophenyl)sulfonyl)-3,4-dihydro-2H-benzo[b][1,4]oxazin-6-yl)carbamate;

(1R,2S)-2-(trifluoromethyl)cyclohexyl ((S)-2-(acetamidomethyl)-4-((4-fluorophenyl)sulfonyl)-3,4-dihydro-2H-benzo[b][1,4]oxazin-6-yl)carbamate;

(1 S,2R)-2-(trifluoromethyl)cyclohexyl ((S)-2-(acetamidomethyl)-4-((4-fluorophenyl)sulfonyl)-3,4-dihydro-2H-benzo[b][1,4]oxazin-6-yl)carbamate;

3,3-dimethylbutan-2-yl ((S)-2-(acetamidomethyl)-4-((4-fluorophenyl)sulfonyl)-3,4-dihydro-2H-benzo[b][1,4]oxazin-6-yl)carbamate;

1,1,1-trifluoropropan-2-yl ((S)-2-(acetamidomethyl)-4-((4-fluorophenyl)sulfonyl)-3,4-dihydro-2H-benzo[b][1,4]oxazin-6-yl)carbamate;

(R)-3,3-dimethylbutan-2-yl ((S)-2-(acetamidomethyl)-4-((4-fluorophenyl)sulfonyl)-3,4-dihydro-2H-benzo[b][1,4]oxazin-6-yl)carbamate;

(S)-3,3-dimethylbutan-2-yl ((S)-2-(acetamidomethyl)-4-((4-fluorophenyl)sulfonyl)-3,4-dihydro-2H-benzo[b][1,4]oxazin-6-yl)carbamate;

(S)-3,3-dimethylbutan-2-yl ((S)-2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(R)-1,1,1-trifluoro-3,3-dimethylbutan-2-yl ((S)-2-(acetamidomethyl)-4-((4-fluorophenyl)sulfonyl)-3,4-dihydro-2H-benzo[b][1,4]oxazin-6-yl)carbamate;

(S)-1,1,1-trifluoro-3,3-dimethylbutan-2-yl ((S)-2-(acetamidomethyl)-4-((4-fluorophenyl)sulfonyl)-3,4-dihydro-2H-benzo[b][1,4]oxazin-6-yl)carbamate;

(R)-3,3-dimethylbutan-2-yl ((S)-2-(cyclopropanecarboxamidomethyl)-4-((4-fluorophenyl)sulfonyl)-3,4-dihydro-2H-benzo[b][1,4]oxazin-6-yl)carbamate;

(S)-3,3-dimethylbutan-2-yl ((S)-2-(cyclopropanecarboxamidomethyl)-4-((4-fluorophenyl)sulfonyl)-3,4-dihydro-2H-benzo[b][1,4]oxazin-6-yl)carbamate;

(R)-3,3-dimethylbutan-2-yl ((S)-2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-2,2-difluoro-2-phenylethyl (2-(acetamidomethyl)-4-((4-fluorophenyl)sulfonyl)-3,4-dihydro-2H-benzo[b][1,4]oxazin-6-yl)carbamate;

(2,2,3,3-tetrafluorocyclobutyl)methyl ((S)-2-(acetamidomethyl)-4-((4-fluorophenyl)sulfonyl)-3,4-dihydro-2H-benzo[b][1,4]oxazin-6-yl)carbamate;

(S)-2-cyano-2-methylpropyl (2-(acetamidomethyl)-4-((4-fluorophenyl)sulfonyl)-3,4-dihydro-2H-benzo[b][1,4]oxazin-6-yl)carbamate;

(S)-4-((2-(acetamidomethyl)-6-(((neopentyloxy)carbonyl)amino)-2H-benzo[b][1,4]oxazin-4(3H)-yl)sulfonyl)-1-(difluoromethyl)-3-methyl-1H-pyrazole;

(S)-isobutyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-isobutyl (2-(acetamidomethyl)-4-((4-fluorophenyl)sulfonyl)-3,4-dihydro-2H-benzo[b][1,4]oxazin-6-yl)carbamate;

(S)-(1-methylcyclopropyl)methyl (2-(acetamidomethyl)-4-((4-fluorophenyl)sulfonyl)-3,4-dihydro-2H-benzo[b][1,4]oxazin-6-yl)carbamate;

sec-butyl ((S)-2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-(1-methylcyclopentyl)methyl (2-(acetamidomethyl)-4-((4-fluorophenyl)sulfonyl)-3,4-dihydro-2H-benzo[b][1,4]oxazin-6-yl)carbamate;

(S)-tert-butyl 3-((((2-(acetamidomethyl)-4-((4-fluorophenyl)sulfonyl)-3,4-dihydro-2H-benzo[b][1,4]oxazin-6-yl)carbamoyl)oxy)methyl)-3-methylazetidine-1-carboxylate;

(S)-benzyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-2-chlorobenzyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-2,2-difluoro-3,3-dimethylpentyl (2-(acetamidomethyl)-4-((4-fluorophenyl)sulfonyl)-3,4-dihydro-2H-benzo[b][1,4]oxazin-6-yl)carbamate;

(S)-2,2-difluoro-3,3-dimethylpent-4-en-1-yl (2-(acetamidomethyl)-4-((4-fluorophenyl)sulfonyl)-3,4-dihydro-2H-benzo[b][1,4]oxazin-6-yl)carbamate;

(2,2-difluoro-1-phenylcyclopropyl)methyl ((S)-2-(acetamidomethyl)-4-((4-fluorophenyl)sulfonyl)-3,4-dihydro-2H-benzo[b][1,4]oxazin-6-yl)carbamate;

(S)-3,3,3-trifluoropropyl (2-(acetamidomethyl)-4-((4-fluorophenyl)sulfonyl)-3,4-dihydro-2H-benzo[b][1,4]oxazin-6-yl)carbamate;

(S)-2-(trimethylsilyl)ethyl (2-(acetamidomethyl)-4-((4-fluorophenyl)sulfonyl)-3,4-dihydro-2H-benzo[b][1,4]oxazin-6-yl)carbamate;

(S)-2,2,2-trichloroethyl (2-(acetamidomethyl)-4-((4-fluorophenyl)sulfonyl)-3,4-dihydro-2H-benzo[b][1,4]oxazin-6-yl)carbamate;

(S)-2,2,2-trichloroethyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-2,2,2-trichloroethyl (2-(cyclopropanecarboxamidomethyl)-4-((4-fluorophenyl)sulfonyl)-3,4-dihydro-2H-benzo[b][1,4]oxazin-6-yl)carbamate;

(S)-methyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-isopropyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-phenyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-4-chlorophenyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-2-chlorophenyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-cyclopropylmethyl (2-(acetamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-neopentyl (2-(acetamidomethyl)-4-((4-fluorophenyl)sulfonyl)-3,4-dihydro-2H-benzo[b][1,4]oxazin-6-yl)carbamate;

(S)-cyclopropylmethyl (2-(acetamidomethyl)-4-((4-fluorophenyl)sulfonyl)-3,4-dihydro-2H-benzo[b][1,4]oxazin-6-yl)carbamate;

(S)-2-(methylsulfonyl)ethyl (2-(acetamidomethyl)-4-((4-fluorophenyl)sulfonyl)-3,4-dihydro-2H-benzo[b][1,4]oxazin-6-yl)carbamate;

1-cyclopropylethyl ((S)-2-(acetamidomethyl)-4-((4-fluorophenyl)sulfonyl)-3,4-dihydro-2H-benzo[b][1,4]oxazin-6-yl)carbamate;

3,3,4,4,4-pentafluorobutan-2-yl ((S)-2-(acetamidomethyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((1-fluorocyclopropanecarboxamido)methyl)-4-((4-fluorophenyl)sulfonyl)-3,4-dihydro-2H-benzo[b][1,4]oxazin-6-yl)carbamate;

(S)-tert-butyl (4-((4-fluorophenyl)sulfonyl)-2-(pivalamidomethyl)-3,4-dihydro-2H-benzo[b][1,4]oxazin-6-yl)carbamate;

(S)-tert-butyl (4-((4-fluorophenyl)sulfonyl)-2-((1-methylcyclopropanecarboxamido)methyl)-3,4-dihydro-2H-benzo[b][1,4]oxazin-6-yl)carbamate (S)-tert-butyl (4-((4-fluorophenyl)sulfonyl)-2-(propionamidomethyl)-3,4-dihydro-2H-benzo[b][1,4]oxazin-6-yl)carbamate;

(S)-tert-butyl (2-(butyramidomethyl)-4-((4-fluorophenyl)sulfonyl)-3,4-dihydro-2H-benzo[b][1,4]oxazin-6-yl)carbamate;

(S)-tert-butyl (4-((4-fluorophenyl)sulfonyl)-2-(isobutyramidomethyl)-3,4-dihydro-2H-benzo[b][1,4]oxazin-6-yl)carbamate;

(S)-tert-butyl (2-(cyclopropanecarboxamidomethyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-(cyclopropanecarboxamidomethyl)-4-((4-fluorophenyl)sulfonyl)-3,4-dihydro-2H-benzo[b][1,4]oxazin-6-yl)carbamate;

(S)-tert-butyl (2-(cyclopropanecarboxamidomethyl)-4-((1-(difluoromethyl)-3-methyl-1H-pyrazol-4-yl)sulfonyl)-3,4-dihydro-2H-benzo[b][1,4]oxazin-6-yl)carbamate;

(S)-neopentyl (2-(cyclopropanecarboxamidomethyl)-4-((4-fluorophenyl)sulfonyl)-3,4-dihydro-2H-benzo[b][1,4]oxazin-6-yl)carbamate (S)-neopentyl (2-(cyclopropanecarboxamidomethyl)-;4-((1-(difluoromethyl)-3-methyl-1H-pyrazol-4-yl)sulfonyl)-3,4-dihydro-2H-benzo[b][1,4]oxazin-6-yl)carbamate;

1,1,1-trifluoro-2-methylpropan-2-yl ((S)-2-(((1 S,2S)-2-fluorocyclopropanecarboxamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((3-fluorocyclobutanecarboxamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((3,3-difluorocyclobutanecarboxamido)methyl)-4-((4-fluorophenyl)sulfonyl)-3,4-dihydro-2H-benzo[b][1,4]oxazin-6-yl)carbamate;

1,1,1-trifluoro-2-methylpropan-2-yl ((2S)-4-((4-fluorophenyl)sulfonyl)-2-((2-methylcyclopropanecarboxamido)methyl)-3,4-dihydro-2H-benzo[b][1,4]oxazin-6-yl)carbamate;

1,1,1-trifluoro-2-methylpropan-2-yl ((2S)-2-((2,2-difluorocyclopropanecarboxamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((bicyclo[1.1.1]pentane-1-carboxamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((1-methylcyclopropanecarboxamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((3-methylcyclobutanecarboxamido)methyl)-3,4-dihydro-2H-benzo[b][1,4]oxazin-6-yl)carbamate;

1,1,1-trifluoro-2-methylpropan-2-yl ((2S)-2-((2,2-dimethylcyclopropanecarboxamido)methyl)-4-((4-fluorophenyl)sulfonyl)-3,4-dihydro-2H-benzo[b][1,4]oxazin-6-yl)carbamate;

1,1,1-trifluoro-2-methylpropan-2-yl ((S)-2-(((1R,2S)-2-fluorocyclopropanecarboxamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((1-(dimethylamino)cyclopropanecarboxamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((1-methylcyclobutanecarboxamido)methyl)-3,4-dihydro-2H-benzo[b][1,4]oxazin-6-yl)carbamate;

(S)-1,1,1-trifluoro-2-methylpropan-2-yl (2-((2-amino-2-methylpropanamido)methyl)-4-((4-fluorophenyl)sulfonyl)-3,4-dihydro-2H-benzo[b][1,4]oxazin-6-yl)carbamate;

1,1,1-trifluoro-2-methylpropan-2-yl ((2S)-4-((4-fluorophenyl)sulfonyl)-2-((3,3,3-trifluoro-2-hydroxypropanamido)methyl)-3,4-dihydro-2H-benzo[b][1,4]oxazin-6-yl)carbamate;

1,1,1-trifluoro-2-methylpropan-2-yl ((2S)-2-((2-amino-3,3,3-trifluoro-2-methylpropanamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((1-aminocyclopentanecarboxamido)methyl)-4-((4-fluorophenyl)sulfonyl)-3,4-dihydro-2H-benzo[b][1,4]oxazin-6-yl)carbamate;

1,1,1-trifluoro-2-methylpropan-2-yl ((2S)-2-((2-amino-3-fluoro-3-methylbutanamido)methyl)-4-((4-fluorophenyl)sulfonyl)-3,4-dihydro-2H-benzo[b][1,4]oxazin-6-yl)carbamate;

1,1,1-trifluoro-2-methylpropan-2-yl ((2S)-2-((2-amino-3,3,3-trifluoropropanamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((1-aminocyclopropanecarboxamido)methyl)-4-((4-fluorophenyl)sulfonyl)-3,4-dihydro-2H-benzo[b][1,4]oxazin-6-yl)carbamate;

1,1,1-trifluoro-2-methylpropan-2-yl ((2S)-4-((4-fluorophenyl)sulfonyl)-2-((3,3,3-trifluoro-2-hydroxy-2-methylpropanamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((2-hydroxy-2-methylpropanamido)methyl)-3,4-dihydro-2H-benzo[b][1,4]oxazin-6-yl)carbamate;

1,1,1-trifluoro-2-methylpropan-2-yl ((2S)-2-((2-(dimethylamino)propanamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((2-(dimethylamino)-2-oxoacetamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((2-(dimethylamino)-2-methylpropanamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((2-methyl-2-(methylamino)propanamido)methyl)-3,4-dihydro-2H-benzo[b][1,4]oxazin-6-yl)carbamate;

1,1,1-trifluoro-2-methylpropan-2-yl ((2S)-2-((1-(tert-butyl)azetidine-2-carboxamido)methyl)-4-((4-fluorophenyl)sulfonyl)-3,4-dihydro-2H-benzo[b][1,4]oxazin-6-yl)carbamate;

1,1,1-trifluoro-2-methylpropan-2-yl ((2S)-4-((4-fluorophenyl)sulfonyl)-2-((spiro[2.3]hexane-1-carboxamido)methyl)-3,4-dihydro-2H-benzo[b][1,4]oxazin-6-yl)carbamate;

1,1,1-trifluoro-2-methylpropan-2-yl ((2S)-2-((2,2-difluoro-1-methylcyclopropanecarboxamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((oxetane-3-carboxamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((3-methyloxetane-3-carboxamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((1-methylazetidine-3-carboxamido)methyl)-3,4-dihydro-2H-benzo[b][1,4]oxazin-6-yl)carbamate;

(S)-1,1,1-trifluoro-2-methylpropan-2-yl (2-((3-aminooxetane-3-carboxamido)methyl)-4-((4-fluorophenyl)sulfonyl)-3,4-dihydro-2H-benzo[b][1,4]oxazin-6-yl)carbamate;

1,1,1-trifluoro-2-methylpropan-2-yl ((2S)-4-((4-fluorophenyl)sulfonyl)-2-((tetrahydro-2H-pyran-3-carboxamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((2-(tetrahydro-2H-pyran-4-yl)acetamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((tetrahydro-2H-pyran-4-carboxamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((1-methyl-1H-pyrazole-4-carboxamido)methyl)-3,4-dihydro-2H-benzo[b][1,4]oxazin-6-yl)carbamate;

(S)-1,1,1-trifluoro-2-methylpropan-2-yl (2-((1H-pyrazole-4-carboxamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((1-(trifluoromethyl)cyclopropanecarboxamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((1-methyl-1H-pyrrole-2-carboxamido)methyl)-3,4-dihydro-2H-benzo[b][1,4]oxazin-6-yl)carbamate;

(S)-1,1,1-trifluoro-2-methylpropan-2-yl (2-((1-cyanocyclopropanecarboxamido)methyl)-4-((4-fluorophenyl)sulfonyl)-3,4-dihydro-2H-benzo[b][1,4]oxazin-6-yl)carbamate;

(S)-5-(((4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)carbamoyl)isoxazole;

(S)-4-(((4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)carbamoyl)-1H-imidazole;

(S)-1,1,1-trifluoro-2-methylpropan-2-yl (4-((4-fluorophenyl)sulfonyl)-2-((1-hydroxycyclopropanecarboxamido)methyl)-3,4-dihydro-2H-benzo[b][1,4]oxazin-6-yl)carbamate;

(S)-2-(((4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)carbamoyl)-1H-imidazole;

(S)-3-(((4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)carbamoyl)-1H-1,2,4-triazole;

(S)-5-(((4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)carbamoyl)-1H-1,2,3-triazole;

(S)-1,1,1-trifluoro-2-methylpropan-2-yl (4-((4-fluorophenyl)sulfonyl)-2-((furan-2-carboxamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((furan-2-carboxamido)methyl)-3,4-dihydro-2H-benzo[b][1,4]oxazin-6-yl)carbamate;

(S)-3-(((4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)carbamoyl)azetidine;

1,1,1-trifluoro-2-methylpropan-2-yl ((2S)-4-((4-fluorophenyl)sulfonyl)-2-((tetrahydrofuran-2-carboxamido)methyl)-3,4-dihydro-2H-benzo[b][1,4]oxazin-6-yl)carbamate 1,1,1-trifluoro-2-methylpropan-2-yl ((2S)-4-((4-fluorophenyl)sulfonyl)-2-((2-methyl-5-;oxopyrrolidine-2-carboxamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((1-hydroxycyclobutanecarboxamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((3-methoxycyclobutanecarboxamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((1-isopropylazetidine-3-carboxamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((1-methylcyclopentanecarboxamido)methyl)-3,4-dihydro-2H-benzo[b][1,4]oxazin-6-yl)carbamate;

1,1,1-trifluoro-2-methylpropan-2-yl ((2S)-4-((4-fluorophenyl)sulfonyl)-2-((oxetane-2-carboxamido)methyl)-3,4-dihydro-2H-benzo[b][1,4]oxazin-6-yl)carbamate;

(S)-1,1,1-trifluoro-2-methylpropan-2-yl (2-((4H-1,2,4-triazole-3-carboxamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((2-hydroxy-2-methylpropanamido)methyl)-3,4-dihydro-2H-benzo[b][1,4]oxazin-6-yl)carbamate;

(S)-1,1,1-trifluoro-2-methylpropan-2-yl (2-((2-(3,5-dimethylisoxazol-4-yl)acetamido)methyl)-4-((4-fluorophenyl)sulfonyl)-3,4-dihydro-2H-benzo[b][1,4]oxazin-6-yl)carbamate;

1,1,1-trifluoro-2-methylpropan-2-yl ((S)-2-(((1R,2S)-2-cyanocyclopropanecarboxamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((1H-pyrrole-2-carboxamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((3,5-dimethylisoxazole-4-carboxamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((4-methyl-1H-imidazole-5-carboxamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((2-methyl-1H-imidazole-4-carboxamido)methyl)-3,4-dihydro-2H-benzo[b][1,4]oxazin-6-yl)carbamate;

(S)-1,1,1-trifluoro-2-methylpropan-2-yl (2-((3-(ethylsulfonyl)benzamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((4-(ethylsulfonyl)benzamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((2-(4-(ethylsulfonyl)phenyl)acetamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((2-methoxy-2-methylpropanamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((tetrahydro-2H-pyran-4-carboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((oxetane-3-carboxamido)methyl)-3,4-dihydro-2H-benzo[b][1,4]oxazin-6-yl)carbamate;

(S)-1,1,1-trifluoro-2-methylpropan-2-yl (4-((1-ethyl-3-methoxy-1H-pyrazol-4-yl)sulfonyl)-2-((oxetane-3-carboxamido)methyl)-3,4-dihydro-2H-benzo[b][1,4]oxazin-6-yl)carbamate;

(S)-1,1,1-trifluoro-2-methylpropan-2-yl (4-((2-methoxy-5,6-dihydro-4H-pyrrolo[1,2-b]pyrazol-3-yl)sulfonyl)-2-((oxetane-3-carboxamido)methyl)-3,4-dihydro-2H-benzo[b][1,4]oxazin-6-yl)carbamate;

1,1,1-trifluoro-2-methylpropan-2-yl ((S)-4-((3-chloro-4-fluorophenyl)sulfonyl)-2-(((1S,2S)-2-fluorocyclopropanecarboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((3-methyloxetane-3-carboxamido)methyl)-3,4-dihydro-2H-benzo[b][1,4]oxazin-6-yl)carbamate;

(S)-1,1,1-trifluoro-2-methylpropan-2-yl (2-((3-aminooxetane-3-carboxamido)methyl)-4-((3-chloro-4-fluorophenyl)sulfonyl)-3,4-dihydro-2H-benzo[b][1,4]oxazin-6-yl)carbamate;

1,1,1-trifluoro-2-methylpropan-2-yl ((2S)-4-((3-chloro-4-fluorophenyl)sulfonyl)-2-((2-methyltetrahydrofuran-2-carboxamido)methyl)-3,4-dihydro-2H-benzo[b][1,4]oxazin-6-yl)carbamate;

1,1,1-trifluoro-2-methylpropan-2-yl ((2S)-4-((3-chloro-4-fluorophenyl)sulfonyl)-2-((2-isopropyltetrahydro-2H-pyran-4-carboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((4-cyanotetrahydro-2H-pyran-4-carboxamido)methyl)-3,4-dihydro-2H-benzo[b][1,4]oxazin-6-yl)carbamate;

1,1,1-trifluoro-2-methylpropan-2-yl ((2S)-4-((3-chloro-4-fluorophenyl)sulfonyl)-2-((2-methyltetrahydro-2H-pyran-2-carboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((1-methyl-1H-pyrazole-4-carboxamido)methyl)-3,4-dihydro-2H-benzo[b][1,4]oxazin-6-yl)carbamate;

(S)-1,1,1-trifluoro-2-methylpropan-2-yl (2-((1H-pyrazole-4-carboxamido)methyl)-4-((3-chloro-4-fluorophenyl)sulfonyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((1-(trifluoromethyl)cyclopropanecarboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((1-methylcyclopropanecarboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((1-cyanocyclopropanecarboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((1-hydroxycyclopropanecarboxamido)methyl)-3,4-dihydro-2H-benzo[b][1,4]oxazin-6-yl)carbamate;

(S)-1,1,1-trifluoro-2-methylpropan-2-yl (2-((1H-imidazole-2-carboxamido)methyl)-4-((3-chloro-4-fluorophenyl)sulfonyl)-3,4-dihydro-2H-benzo[b][1,4]oxazin-6-yl)carbamate;

1,1,1-trifluoro-2-methylpropan-2-yl ((2S)-4-((3-chloro-4-fluorophenyl)sulfonyl)-2-((2-methylcyclopropanecarboxamido)methyl)-3,4-dihydro-2H-benzo[b][1,4]oxazin-6-yl)carbamate;

1,1,1-trifluoro-2-methylpropan-2-yl ((S)-4-((3-chloro-4-fluorophenyl)sulfonyl)-2-(((S)-tetrahydrofuran-2-carboxamido)methyl)-3,4-dihydro-2H-benzo[b][1,4]oxazin-6-yl)carbamate;

1,1,1-trifluoro-2-methylpropan-2-yl ((2S)-4-((3-chloro-4-fluorophenyl)sulfonyl)-2-((tetrahydrofuran-2-carboxamido)methyl)-3,4-dihydro-2H-benzo[b][1,4]oxazin-6-yl)carbamate;

1,1,1-trifluoro-2-methylpropan-2-yl ((S)-4-((3-chloro-4-fluorophenyl)sulfonyl)-2-(((1R,2S)-2-cyanocyclopropanecarboxamido)methyl)-3,4-dihydro-2H-benzo[b][1,4]oxazin-6-yl)carbamate;

1,1,1-trifluoro-2-methylpropan-2-yl ((2S)-4-((3-chloro-4-fluorophenyl)sulfonyl)-2-((2-methyl-5-oxopyrrolidine-2-carboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((1-hydroxycyclobutanecarboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((3-methoxycyclobutanecarboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((3,3-difluorocyclobutanecarboxamido)methyl)-3,4-dihydro-2H-benzo[b][1,4]oxazin-6-yl)carbamate;

(S)-1,1,1-trifluoro-2-methylpropan-2-yl (2-((bicyclo[1.1.1]pentane-1-carboxamido)methyl)-4-((3-chloro-4-fluorophenyl)sulfonyl)-3,4-dihydro-2H-benzo[b][1,4]oxazin-6-yl)carbamate;

1,1,1-trifluoro-2-methylpropan-2-yl ((2S)-4-((3-chloro-4-fluorophenyl)sulfonyl)-2-((tetrahydro-2H-pyran-3-carboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((1-methylcyclopentanecarboxamido)methyl)-3,4-dihydro-2H-benzo[b][1,4]oxazin-6-yl)carbamate;

1,1,1-trifluoro-2-methylpropan-2-yl ((S)-4-((3-chloro-4-fluorophenyl)sulfonyl)-2-(((1R,2S)-2-fluorocyclopropanecarboxamido)methyl)-3,4-dihydro-2H-benzo[b][1,4]oxazin-6-yl)carbamate;

1,1,1-trifluoro-2-methylpropan-2-yl ((2S)-4-((3-chloro-4-fluorophenyl)sulfonyl)-2-((2,2-dimethyltetrahydro-2H-pyran-4-carboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((4-methyltetrahydro-2H-pyran-4-carboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((3-ethyloxetane-3-carboxamido)methyl)-3,4-dihydro-2H-benzo[b][1,4]oxazin-6-yl)carbamate (S)-1,1,1-trifluoro-2-methylpropan-2-yl (4-((3-chloro-4-fluorophenyl)sulfonyl)-2-((4-fluorotetrahydro-2H-pyran-4-carboxamido)methyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((1-methylcyclobutanecarboxamido)methyl)-3,4-dihydro-2H-benzo[b][1,4]oxazin-6-yl)carbamate;

(S)-1,1,1-trifluoro-2-methylpropan-2-yl (4-((1-ethyl-3-methyl-1H-pyrazol-4-yl)sulfonyl)-2-((oxetane-3-carboxamido)methyl)-3,4-dihydro-2H-benzo[b][1,4]oxazin-6-yl)carbamate;

(S)-1,1,1-trifluoro-2-methylpropan-2-yl (4-((3,4-difluorophenyl)sulfonyl)-2-((oxetane-3-carboxamido)methyl)-3,4-dihydro-2H-benzo[b][1,4]oxazin-6-yl)carbamate;

1,1,1-trifluoro-2-methylpropan-2-yl ((S)-2-(((1R,2S)-2-cyanocyclopropanecarboxamido)methyl)-4-((3,4-difluorophenyl)sulfonyl)-3,4-dihydro-2H-benzo[b][1,4]oxazin-6-yl)carbamate;

1,1,1-trifluoro-2-methylpropan-2-yl ((S)-2-(((1R,2S)-2-cyanocyclopropanecarboxamido)methyl)-4-((1-ethyl-3-methyl-1H-pyrazol-4-yl)sulfonyl)-3,4-dihydro-2H-benzo[b][1,4]oxazin-6-yl)carbamate;

1,1,1-trifluoro-2-methylpropan-2-yl ((S)-4-((3,4-difluorophenyl)sulfonyl)-2-(((1R,2S)-2-fluorocyclopropanecarboxamido)methyl)-3,4-dihydro-2H-benzo[b][1,4]oxazin-6-yl)carbamate;

(S)-1,1,1-trifluoro-2-methylpropan-2-yl (4-((3-chloro-1-ethyl-1H-pyrazol-4-yl)sulfonyl)-2-((oxetane-3-carboxamido)methyl)-3,4-dihydro-2H-benzo[b][1,4]oxazin-6-yl)carbamate;

1,1,1-trifluoro-2-methylpropan-2-yl ((2S)-4-((3-chloro-4-fluorophenyl)sulfonyl)-2-((2-(tetrahydro-2H-pyran-3-yl)acetamido)methyl)-3,4-dihydro-2H-benzo[b][1,4]oxazin-6-yl)carbamate;

1,1,1-trifluoro-2-methylpropan-2-yl ((2S)-4-((3-chloro-4-fluorophenyl)sulfonyl)-2-((2-methyltetrahydrofuran-3-carboxamido)methyl)-3,4-dihydro-2H-benzo[b][1,4]oxazin-6-yl)carbamate;

(S)-1,1,1-trifluoro-2-methylpropan-2-yl (4-((3-ethoxy-1-ethyl-1H-pyrazol-4-yl)sulfonyl)-2-((oxetane-3-carboxamido)methyl)-3,4-dihydro-2H-benzo[b][1,4]oxazin-6-yl)carbamate;

1,1,1-trifluoro-2-methylpropan-2-yl ((S)-4-((3-(difluoromethoxy)-1-ethyl-1H-pyrazol-4-yl)sulfonyl)-2-(((1S,2S)-2-fluorocyclopropanecarboxamido)methyl)-3,4-dihydro-2H-benzo[b][1,4]oxazin-6-yl)carbamate;

(S)-1,1,1-trifluoro-2-methylpropan-2-yl (4-((3-(difluoromethoxy)-1-ethyl-1H-pyrazol-4-yl)sulfonyl)-2-((2-hydroxy-2-methylpropanamido)methyl)-3,4-dihydro-2H-benzo[b][1,4]oxazin-6-yl)carbamate;

1,1,1-trifluoro-2-methylpropan-2-yl ((2S)-2-((2-amino-3,3,3-trifluoro-2-methylpropanamido)methyl)-4-((3-(difluoromethoxy)-1-ethyl-1H-pyrazol-4-yl)sulfonyl)-3,4-dihydro-2H-benzo[b][1,4]oxazin-6-yl)carbamate;

1,1,1-trifluoro-2-methylpropan-2-yl ((S)-4-((1-(difluoromethyl)-3-ethoxy-1H-pyrazol-4-yl)sulfonyl)-2-(((1S,2S)-2-fluorocyclopropanecarboxamido)methyl)-3,4-dihydro-2H-benzo[b][1,4]oxazin-6-yl)carbamate (S)-1,1,1-trifluoro-2-methylpropan-2-yl (4-((1-(difluoromethyl)-3-ethoxy-1H-pyrazol-4-yl)sulfonyl)-2-((2-hydroxy-2-methylpropanamido)methyl)-3,4-dihydro-2H-benzo[b][1,4]oxazin-6-yl)carbamate;

1,1,1-trifluoro-2-methylpropan-2-yl ((2S)-2-((2-amino-3,3,3-trifluoro-2-methylpropanamido)methyl)-4-((1-(difluoromethyl)-3-ethoxy-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (4-((3-(2,2-difluoroethoxy)-1-ethyl-1H-pyrazol-4-yl)sulfonyl)-2-((2-hydroxy-2-methylpropanamido)methyl)-3,4-dihydro-2H-benzo[b][1,4]oxazin-6-yl)carbamate;

(S)-1,1,1-trifluoro-2-methylpropan-2-yl (4-((1-(2,2-difluoroethyl)-3-ethoxy-1H-pyrazol-4-yl)sulfonyl)-2-((2-hydroxy-2-methylpropanamido)methyl)-3,4-dihydro-2H-benzo[b][1,4]oxazin-6-yl)carbamate;

(S)-1,1,1-trifluoro-2-methylpropan-2-yl (4-((1-ethyl-3-methyl-1H-pyrazol-4-yl)sulfonyl)-2-((2-hydroxy-2-methylpropanamido)methyl)-3,4-dihydro-2H-benzo[b][1,4]oxazin-6-yl)carbamate;

(S)-1,1,1-trifluoro-2-methylpropan-2-yl (2-((2-hydroxy-2-methylpropanamido)methyl)-4-((2-methoxy-5,6-dihydro-4H-pyrrolo[1,2-b]pyrazol-3-yl)sulfonyl)-3,4-dihydro-2H-benzo[b][1,4]oxazin-6-yl)carbamate;

(S)-1,1,1-trifluoro-2-methylpropan-2-yl (2-(cyclopropanesulfonamidomethyl)-4-((4-fluorophenyl)sulfonyl)-3,4-dihydro-2H-benzo[b][1,4]oxazin-6-yl)carbamate;

(S)-4-((2-(cyclopropanesulfonamidomethyl)-6-((((1,1,1-trifluoro-2-methylpropan-2-yl)oxy)carbonyl)amino)-2H-benzo[b][1,4]oxazin-4(3H)-yl)sulfonyl)-1-(difluoromethyl)-3-methyl-1H-pyrazole;

(S)-1,1,1-trifluoro-2-methylpropan-2-yl (2-(cyclopropanesulfonamidomethyl)-4-((3,4-difluorophenyl)sulfonyl)-3,4-dihydro-2H-benzo[b][1,4]oxazin-6-yl)carbamate;

(S)-1,1,1-trifluoro-2-methylpropan-2-yl (2-(cyclopropanesulfonamidomethyl)-4-((3-ethoxy-4-fluorophenyl)sulfonyl)-3,4-dihydro-2H-benzo[b][1,4]oxazin-6-yl)carbamate;

(S)-tert-butyl (2-(cyclopropanesulfonamidomethyl)-4-((1-(difluoromethyl)-5-methyl-1H-pyrazol-4-yl)sulfonyl)-3,4-dihydro-2H-benzo[b][1,4]oxazin-6-yl)carbamate;

(S)-4-((6-(((tert-butoxycarbonyl)amino)-2-(cyclopropanesulfonamidomethyl)-2H-benzo[b][1,4]oxazin-4(3H)-yl)sulfonyl)-3-chloro-1-ethyl-1H-pyrazole;

(S)-1,1,1-trifluoro-2-methylpropan-2-yl (2-(cyclopropanesulfonamidomethyl)-4-((3-(methylsulfonyl)phenyl)sulfonyl)-3,4-dihydro-2H-benzo[b][1,4]oxazin-6-yl)carbamate;

(S)-1,1,1-trifluoro-2-methylpropan-2-yl (2-(cyclopropanesulfonamidomethyl)-4-((4-fluoro-3-methoxyphenyl)sulfonyl)-3,4-dihydro-2H-benzo[b][1,4]oxazin-6-yl)carbamate;

(S)-tert-butyl (2-(cyclopropanesulfonamidomethyl)-4-((3,4-difluorophenyl)sulfonyl)-3,4-dihydro-2H-benzo[b][1,4]oxazin-6-yl)carbamate;

(S)-tert-butyl (2-(cyclopropanesulfonamidomethyl)-4-((4-fluoro-3-methoxyphenyl)sulfonyl)-3,4-dihydro-2H-benzo[b][1,4]oxazin-6-yl)carbamate;

(S)-1,1,1-trifluoro-2-methylpropan-2-yl (4-((3-cyanophenyl)sulfonyl)-2-(cyclopropanesulfonamidomethyl)-3,4-dihydro-2H-benzo[b][1,4]oxazin-6-yl)carbamate;

(S)-tert-butyl (2-(cyclopropanesulfonamidomethyl)-4-((4-fluorophenyl)sulfonyl)-3,4-dihydro-2H-benzo[b][1,4]oxazin-6-yl)carbamate;

(S)-tert-butyl (4-((3-cyanophenyl)sulfonyl)-2-(cyclopropanesulfonamidomethyl)-3,4-dihydro-2H-benzo[b][1,4]oxazin-6-yl)carbamate;

(S)-tert-butyl (2-(cyclopropanesulfonamidomethyl)-4-((3-(methylsulfonyl)phenyl)sulfonyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-(cyclopropanesulfonamidomethyl)-3,4-dihydro-2H-benzo[b][1,4]oxazin-6-yl)carbamate;

(S)-tert-butyl (4-((3-chloro-4-fluorophenyl)sulfonyl)-2-(cyclopropanesulfonamidomethyl)-3,4-dihydro-2H-benzo[b][1,4]oxazin-6-yl)carbamate (S)-(1-(trifluoromethyl)cyclopropyl)methyl (2-(cyclopropanesulfonamidomethyl)-4-((4-fluorophenyl)sulfonyl)-3,4-dihydro-2H-benzo[b][1,4]oxazin-6-yl)carbamate;

(S)-4-((6-((tert-butoxycarbonyl)amino)-2-(cyclopropanesulfonamidomethyl)-2H-benzo[b][1,4]oxazin-4(3H)-yl)sulfonyl)-1-(difluoromethyl)-3-methyl-1H-pyrazole;

3-(((S)-2-(cyclopropanesulfonamidomethyl)-6-((((1,1,1-trifluoro-2-methylpropan-2-yl)oxy)carbonyl)amino)-2H-benzo[b][1,4]oxazin-4(3H)-yl)sulfonyl)-2-methoxy-5,6,7,8-tetrahydro-4H-pyrazolo[1,5-a]pyridine;

4-(((S)-2-(cyclopropanesulfonamidomethyl)-6-((((1,1,1-trifluoro-2-methylpropan-2-yl)oxy)carbonyl)amino)-2H-benzo[b][1,4]oxazin-4(3H)-yl)sulfonyl)-1-ethyl-3-methoxy-1H-pyrazole;

3-(((S)-2-(cyclopropanesulfonamidomethyl)-6-((((1,1,1-trifluoro-2-methylpropan-2-yl)oxy)carbonyl)amino)-2H-benzo[b][1,4]oxazin-4(3H)-yl)sulfonyl)-2-methoxy-4,5,6,7-tetrahydropyrrolo[1,2-b]pyrazole;

(S)-1,1,1-trifluoro-2-methylpropan-2-yl (2-(cyclopropanesulfonamidomethyl)-4-((1-ethyl-3-methyl-1H-pyrazol-4-yl)sulfonyl)-3,4-dihydro-2H-benzo[b][1,4]oxazin-6-yl)carbamate;

(S)-4-((2-(cyclopropanesulfonamidomethyl)-6-((((1,1,1-trifluoro-2-methylpropan-2-yl)oxy)carbonyl)amino)-2H-benzo[b][1,4]oxazin-4(3H)-yl)sulfonyl)-3-ethoxy-1-ethyl-1H-pyrazole;

(S)-3-chloro-4-((2-(cyclopropanesulfonamidomethyl)-6-((((1,1,1-trifluoro-2-methylpropan-2-yl)oxy)carbonyl)amino)-2H-benzo[b][1,4]oxazin-4(3H)-yl)sulfonyl)-1-ethyl-1H-pyrazole;

(S)-4-((2-(cyclopropanesulfonamidomethyl)-6-((((1,1,1-trifluoro-2-methylpropan-2-yl)oxy)carbonyl)amino)-2H-benzo[b][1,4]oxazin-4(3H)-yl)sulfonyl)-1-(difluoromethyl)-3-ethoxy-1H-pyrazole;

(S)-4-((2-(cyclopropanesulfonamidomethyl)-6-((((1,1,1-trifluoro-2-methylpropan-2-yl)oxy)carbonyl)amino)-2H-benzo[b][1,4]oxazin-4(3H)-yl)sulfonyl)-3-(difluoromethoxy)-1-ethyl-1H-pyrazole;

(S)-4-((2-(cyclopropanesulfonamidomethyl)-6-((((1,1,1-trifluoro-2-methylpropan-2-yl)oxy)carbonyl)amino)-2H-benzo[b][1,4]oxazin-4(3H)-yl)sulfonyl)-1-ethyl-3-(2-methoxy-2-oxoethoxy)-1H-pyrazole;

(S)-tert-butyl (4-((3,4-difluorophenyl)sulfonyl)-2-(methylsulfonamidomethyl)-3,4-dihydro-2H-benzo[b][1,4]oxazin-6-yl)carbamate;

(S)-tert-butyl (2-(methylsulfonamidomethyl)-4-((3-(methylsulfonyl)phenyl)sulfonyl)-3,4-dihydro-2H-benzo[b][1,4]oxazin-6-yl)carbamate;

(S)-tert-butyl (4-((4-fluoro-3-methoxyphenyl)sulfonyl)-2-(methylsulfonamidomethyl)-3,4-dihydro-2H-benzo[b][1,4]oxazin-6-yl)carbamate;

(S)-4-((6-((tert-butoxycarbonyl)amino)-2-(methylsulfonamidomethyl)-2H-benzo[b][1,4]oxazin-4(3H)-yl)sulfonyl)-1-(difluoromethyl)-3-methyl-1H-pyrazole;

(S)-tert-butyl (4-((3-cyanophenyl)sulfonyl)-2-(methylsulfonamidomethyl)-3,4-dihydro-2H-benzo[b][1,4]oxazin-6-yl)carbamate;

(S)-tert-butyl (4-((4-fluorophenyl)sulfonyl)-2-(methylsulfonamidomethyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-(methylsulfonamidomethyl)-3,4-dihydro-2H-benzo[b][1,4]oxazin-6-yl)carbamate;

(S)-tert-butyl (4-((3-chloro-4-fluorophenyl)sulfonyl)-2-(methylsulfonamidomethyl)-3,4-dihydro-2H-benzo[b][1,4]oxazin-6-yl)carbamate;

(S)-1,1,1-trifluoro-2-methylpropan-2-yl (4-((1-ethyl-3-methyl-1H-pyrazol-4-yl)sulfonyl)-2-(methylsulfonamidomethyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-(methylsulfonamidomethyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((pyridine-3-sulfonamido)methyl)-3,4-dihydro-2H-benzo[b][1,4]oxazin-6-yl)carbamate;

(S)-5-(N-((4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)sulfamoyl)-2-methylthiazole;

(S)-1,1,1-trifluoro-2-methylpropan-2-yl (4-((4-fluorophenyl)sulfonyl)-2-((1-methyl-1H-imidazole-4-sulfonamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((thiophene-2-sulfonamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((1-methylcyclopropanesulfonamido)methyl)-3,4-dihydro-2H-benzo[b][1,4]oxazin-6-yl)carbamate (S)-1,1,1-trifluoro-2-methylpropan-2-yl (2-(ethylsulfonamidomethyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((2,2,2-trifluoroethylsulfonamido)methyl)-3,4-dihydro-2H-benzo[b][1,4]oxazin-6-yl)carbamate;

(S)-1,1,1-trifluoro-2-methylpropan-2-yl (4-((4-fluorophenyl)sulfonyl)-2-((trifluoromethylsulfonamido)methyl)-3,4-dihydro-2H-benzo[b][1,4]oxazin-6-yl)carbamate;

(S)-5-(N-((4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)sulfamoyl)-2,4-dimethylthiazole;

(S)-1,1,1-trifluoro-2-methylpropan-2-yl (2-((cyclohexyl-methylsulfonamido)methyl)-4-((4-fluorophenyl)sulfo-nyl)-3,4-dihydro-2H-benzo[b][1,4]oxazin-6-yl)car-bamate;

(S)-4-(N-((4-((4-fluorophenyl)sulfonyl)-6-(((((1,1,1-trif-luoro-2-methylpropan-2-yl)oxy)carbonyl)amino)-3,4-dihydro-2H-benzo[b][1,4]oxazin-2-yl)methyl)sulfa-moyl)-3,5-dimethylisoxazole;

(S)-1,1,1-trifluoro-2-methylpropan-2-yl (4-((4-fluorophe-nyl)sulfonyl)-2-(propylsulfonamidomethyl)-3,4-di-hydro-2H-benzo[b][1,4]oxazin-6-yl)carbamate;

(S)-1,1,1-trifluoro-2-methylpropan-2-yl (4-((4-fluorophe-nyl)sulfonyl)-2-(phenylsulfonamidomethyl)-3,4-di-hydro-2H-benzo[b][1,4]oxazin-6-yl)carbamate;

(S)-1,1,1-trifluoro-2-methylpropan-2-yl (2-((chlorometh-ylsulfonamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((5-chlorothi-ophene-2-sulfonamido)methyl)-4-((4-fluorophenyl)sulfonyl)-3,4-dihydro-2H-benzo[b][1,4]oxazin-6-yl)carbamate;

(S)-2-((N-((4-((4-fluorophenyl)sulfonyl)-6-(((((1,1,1-trif-luoro-2-methylpropan-2-yl)oxy)carbonyl)amino)-3,4-dihydro-2H-benzo[b][1,4]oxazin-2-yl)methyl)sulfa-moyl)methyl)pyridine;

(S)-3-((N-((4-((4-fluorophenyl)sulfonyl)-6-(((((1,1,1-trif-luoro-2-methylpropan-2-yl)oxy)carbonyl)amino)-3,4-dihydro-2H-benzo[b][1,4]oxazin-2-yl)methyl)sulfa-moyl)methyl)pyridine;

(S)-1,1,1-trifluoro-2-methylpropan-2-yl (4-((4-fluorophe-nyl)sulfonyl)-2-((2-methylpropylsulfonamido)methyl)-3,4-dihydro-2H-benzo[b][1,4]oxazin-6-yl)car-bamate;

(S)-4-(N-((4-((4-fluorophenyl)sulfonyl)-6-(((((1,1,1-trif-luoro-2-methylpropan-2-yl)oxy)carbonyl)amino)-3,4-dihydro-2H-benzo[b][1,4]oxazin-2-yl)methyl)sulfa-moyl)-1-methyl-3-(trifluoromethyl)-1H-pyrazole;

(S)-1,1,1-trifluoro-2-methylpropan-2-yl (4-((4-fluorophe-nyl)sulfonyl)-2-((phenyl methylsulfonamido)methyl)-3,4-dihydro-2H-benzo[b][1,4]oxazin-6-yl)carbamate (S)-1,1,1-trifluoro-2-methylpropan-2-yl (2-((2-cyanophe-nylsulfonamido)methyl)-4-((4-fluorophenyl)sulfonyl)-3,4-dihydro-2H-benzo[b][1,4]oxazin-6-yl)carbamate;

(S)-1-(difluoromethyl)-4-(N-((4-((4-fluorophenyl)sulfo-nyl)-6-(((((1,1,1-trifluoro-2-methylpropan-2-yl)oxy)carbonyl)amino)-3,4-dihydro-2H-benzo[b][1,4]ox-azin-2-yl)methyl)sulfamoyl)-5-methyl-1H-pyrazole;

(S)-1,1,1-trifluoro-2-methylpropan-2-yl (4-((3-chloro-4-fluorophenyl)sulfonyl)-2-((2,2,2-trifluoroethylsulfona-mido)methyl)-3,4-dihydro-2H-benzo[b][1,4]oxazin-6-yl)carbamate;

1,1,1-trifluoro-2-methylpropan-2-yl ((2S)-2-((2-ethylcy-clopropanesulfonamido)methyl)-4-((4-fluorophenyl)sulfonyl)-3,4-dihydro-2H-benzo[b][1,4]oxazin-6-yl)carbamate;

(S)-1,1,1-trifluoro-2-methylpropan-2-yl (2-((2-ethoxyeth-ylsulfonamido)methyl)-4-((4-fluorophenyl)sulfonyl)-3,4-dihydro-2H-benzo[b][1,4]oxazin-6-yl)carbamate;

1,1,1-trifluoro-2-methylpropan-2-yl ((2S)-4-((4-fluoro-phenyl)sulfonyl)-2-(((tetrahydro-2H-pyran-2-yl)meth-ylsulfonamido)methyl)-3,4-dihydro-2H-benzo[b][1,4]oxazin-6-yl)carbamate;

(S)-1,1,1-trifluoro-2-methylpropan-2-yl (2-((cyclopropyl-methylsulfonamido)methyl)-4-((4-fluorophenyl)sulfo-nyl)-3,4-dihydro-2H-benzo[b][1,4]oxazin-6-yl)car-bamate;

1,1,1-trifluoro-2-methylpropan-2-yl ((2S)-4-((3-chloro-4-fluorophenyl)sulfonyl)-2-((2-ethylcyclopropanesulfo-namido)methyl)-3,4-dihydro-2H-benzo[b][1,4]oxazin-6-yl)carbamate;

(S)-4-(N-((4-((3-chloro-4-fluorophenyl)sulfonyl)-6-(((((1,1,1-trifluoro-2-methylpropan-2-yl)oxy)carbonyl)amino)-3,4-dihydro-2H-benzo[b][1,4]oxazin-2-yl)methyl)sulfamoyl)-3,5-dimethylisoxazole;

(S)-1,1,1-trifluoro-2-methylpropan-2-yl (4-((3-chloro-4-fluorophenyl)sulfonyl)-2-(propylsulfonamidomethyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-(phenylsulfonamidomethyl)-3,4-dihydro-2H-benzo[b][1,4]oxazin-6-yl)carbamate;

(S)-1,1,1-trifluoro-2-methylpropan-2-yl (4-((3-chloro-4-fluorophenyl)sulfonyl)-2-((2-methylpropylsulfona-mido)methyl)-3,4-dihydro-2H-benzo[b][1,4]oxazin-6-yl)carbamate;

(S)-1,1,1-trifluoro-2-methylpropan-2-yl (4-((3-ethoxy-1-ethyl-1H-pyrazol-4-yl)sulfonyl)-2-((2,2,2-trifluoroeth-ylsulfonamido)methyl)-3,4-dihydro-2H-benzo[b][1,4]oxazin-6-yl)carbamate;

(S)-1,1,1-trifluoro-2-methylpropan-2-yl (4-((4-fluorophe-nyl)sulfonyl)-2-((N-methylmethylsulfonamido)methyl)-3,4-dihydro-2H-benzo[b][1,4]oxazin-6-yl)car-bamate;

(S)-1,1,1-trifluoro-2-methylpropan-2-yl (2-((1,1-dioxido-isothiazolidin-2-yl)methyl)-4-((4-fluorophenyl)sulfo-nyl)-3,4-dihydro-2H-benzo[b][1,4]oxazin-6-yl)car-bamate;

(S)-1,1,1-trifluoro-2-methylpropan-2-yl (4-((3-chloro-4-fluorophenyl)sulfonyl)-2-((N-methylmethylsulfona-mido)methyl)-3,4-dihydro-2H-benzo[b][1,4]oxazin-6-yl)carbamate;

(S)-tert-butyl (2-(acetamidomethyl)-4-((4-(trifluorom-ethyl)piperidin-1-yl)sulfonyl)-3,4-dihydro-2H-benzo[b][1,4]oxazin-6-yl)carbamate;

tert-butyl ((2S)-2-(acetamidomethyl)-4-((3-(trifluorom-ethyl)pyrrolidin-1-yl)sulfonyl)-3,4-dihydro-2H-benzo[b][1,4]oxazin-6-yl)carbamate;

tert-butyl ((2S)-2-(acetamidomethyl)-4-((3-(trifluorom-ethyl)piperidin-1-yl)sulfonyl)-3,4-dihydro-2H-benzo[b][1,4]oxazin-6-yl)carbamate;

(S)-tert-butyl (2-(acetamidomethyl)-4-((4-fluoropiperi-din-1-yl)sulfonyl)-3,4-dihydro-2H-benzo[b][1,4]ox-azin-6-yl)carbamate;

(S)-tert-butyl (2-(acetamidomethyl)-8-fluoro-4-((4-fluo-rophenyl)sulfonyl)-3,4-dihydro-2H-benzo[b][1,4]ox-azin-6-yl)carbamate;

(S)-1,1,1-trifluoro-2-methylpropan-2-yl (2-(acetamidom-ethyl)-8-fluoro-4-((4-fluorophenyl)sulfonyl)-3,4-di-hydro-2H-benzo[b][1,4]oxazin-6-yl)carbamate;

(S)-4-((6-(((tert-butoxycarbonyl)amino)-8-fluoro-2-(methylsulfonamidomethyl)-2H-benzo[b][1,4]oxazin-4(3H)-yl)sulfonyl)-1-(difluoromethyl)-3-methyl-1H-pyrazole;

(S)-tert-butyl (2-(cyclopropanesulfonamidomethyl)-8-fluoro-4-((4-fluorophenyl)sulfonyl)-3,4-dihydro-2H-benzo[b][1,4]oxazin-6-yl)carbamate;

(S)-tert-butyl (2-(cyclopropanesulfonamidomethyl)-4-((1-(difluoromethyl)-3-methyl-1H-pyrazol-4-yl)sulfo-nyl)-8-fluoro-3,4-dihydro-2H-benzo[b][1,4]oxazin-6-yl)carbamate;

(S)-tert-butyl (8-fluoro-4-((4-fluorophenyl)sulfonyl)-2-(methylsulfonamidomethyl)-3,4-dihydro-2H-benzo[b][1,4]oxazin-6-yl)carbamate;

(S)-tert-butyl (2-(acetamidomethyl)-4-((3,4-difluorophenyl)sulfonyl)-8-fluoro-3,4-dihydro-2H-benzo[b][1,4]oxazin-6-yl)carbamate;

(S)-1,1,1-trifluoro-2-methylpropan-2-yl (2-(acetamidomethyl)-4-((3,4-difluorophenyl)sulfonyl)-8-fluoro-3,4-dihydro-2H-benzo[b][1,4]oxazin-6-yl)carbamate;

(S)-1,1,1-trifluoro-2-methylpropan-2-yl (2-(acetamidomethyl)-8-chloro-4-((4-fluorophenyl)sulfonyl)-3,4-dihydro-2H-benzo[b][1,4]oxazin-6-yl)carbamate;

(S)-1,1,1-trifluoro-2-methylpropan-2-yl (8-chloro-4-((4-fluorophenyl)sulfonyl)-2-(methylsulfonamidomethyl)-3,4-dihydro-2H-benzo[b][1,4]oxazin-6-yl)carbamate tert-butyl (cis-2-(acetamidomethyl)-4-((4-fluorophenyl)sulfonyl)-3-methyl-3,4-dihydro-2H-benzo[b][1,4]oxazin-6-yl)carbamate;

(R,S) 1,1,1-trifluoro-2-methylpropan-2-yl (cis-2-(acetamidomethyl)-4-((4-fluorophenyl)sulfonyl)-3-methyl-3,4-dihydro-2H-benzo[b][1,4]oxazin-6-yl)carbamate;

(S,R) 1,1,1-trifluoro-2-methylpropan-2-yl (cis-2-(acetamidomethyl)-4-((4-fluorophenyl)sulfonyl)-3-methyl-3,4-dihydro-2H-benzo[b][1,4]oxazin-6-yl)carbamate;

tert-butyl-2-(acetamidomethyl)-4-(4-fluorophenylsulfonyl)-3-methyl-3,4-dihydro-2H-benzo[b][1,4]oxazin-6-ylcarbamate;

1,1,1-trifluoro-2-methylpropan-2-yl ((2S,3S)-2-(acetamidomethyl)-4-((4-fluorophenyl)sulfonyl)-3-methyl-3,4-dihydro-2H-benzo[b][1,4]oxazin-6-yl)carbamate;

1,1,1-trifluoro-2-methylpropan-2-yl (2R,3R)-2-(acetamidomethyl)-4-((4-fluorophenyl)sulfonyl)-3-methyl-3,4-dihydro-2H-benzo[b][1,4]oxazin-6-yl)carbamate;

1,1,1-trifluoro-2-methylpropan-2-yl (2-(acetamidomethyl)-3-ethyl-4-((4-fluorophenyl)sulfonyl)-3,4-dihydro-2H-benzo[b][1,4]oxazin-6-yl)carbamate;

1,1,1-trifluoro-2-methylpropan-2-yl ((2S,3R or 2R, 3S)-2-(acetamidomethyl)-4-((3-ethoxy-1-ethyl-1H-pyrazol-4-yl)sulfonyl)-3-methyl-3,4-dihydro-2H-benzo[b][1,4]oxazin-6-yl)carbamate;

1,1,1-trifluoro-2-methylpropan-2-yl ((2R,3S or 2S,3R)-2-(acetamidomethyl)-4-((1-(difluoromethyl)-3-methyl-1H-pyrazol-4-yl)sulfonyl)-3-methyl-3,4-dihydro-2H-benzo[b][1,4]oxazin-6-yl)carbamate;

1,1,1-trifluoro-2-methylpropan-2-yl ((2S,3R or 2R,3S)-4-((4-fluorophenyl)sulfonyl)-2-((2-hydroxy-2-methylpropanamido)methyl)-3-methyl-3,4-dihydro-2H-benzo[b][1,4]oxazin-6-yl)carbamate;

1,1,1-trifluoro-2-methylpropan-2-yl ((2S,3R)-2-(acetamidomethyl)-4-((1-(difluoromethyl)-3-methyl-1H-pyrazol-4-yl)sulfonyl)-3-methyl-3,4-dihydro-2H-benzo[b][1,4]oxazin-6-yl)carbamate;

1,1,1-trifluoro-2-methylpropan-2-yl ((2R,3S or 2S,3R)-2-(acetamidomethyl)-4-((1-(difluoromethyl)-3-methyl-1H-pyrazol-4-yl)sulfonyl)-3-methyl-3,4-dihydro-2H-benzo[b][1,4]oxazin-6-yl)carbamate;

1,1,1-trifluoro-2-methylpropan-2-yl ((2S,3R or 2R,3S)-4-((4-fluorophenyl)sulfonyl)-2-((2-hydroxy-2-methylpropanamido)methyl)-3-methyl-3,4-dihydro-2H-benzo[b][1,4]oxazin-6-yl)carbamate;

1,1,1-trifluoro-2-methylpropan-2-yl ((2S,3R)-2-(acetamidomethyl)-4-((1-(difluoromethyl)-3-methyl-1H-pyrazol-4-yl)sulfonyl)-3-methyl-3,4-dihydro-2H-benzo[b][1,4]oxazin-6-yl)carbamate;

2,2,2-trifluoro-1,1-dimethylethyl [(2S)-2-[({[(1R,2S)-2-cyanocyclopropyl]carbonyl}amino)methyl]-4-{[1-(difluoromethyl)-3-(2-hydroxyethoxy)-1H-pyrazol-4-yl]sulfonyl}-3,4-dihydro-2H-1,4-benzoxazin-6-yl]carbamate;

2,2,2-trifluoro-1, 1-dimethylethyl [(2S)-4-{[1-(difluoromethyl)-3-(2-hydroxyethoxy)-1H-pyrazol-4-yl]sulfonyl}-2-({[(2,2,2-trifluoroethyl)sulfonyl]amino}methyl)-3,4-dihydro-2H-1,4-benzoxazin-6-yl]carbamate;

2,2,2-trifluoro-1, 1-dimethylethyl [(2S)-4-{[1-(difluoromethyl)-3-(2-hydroxyethoxy)-1H-pyrazol-4-yl]sulfonyl}-2-{[(2-hydroxy-2-methylpropanoyl)amino]methyl}-3,4-dihydro-2H-1,4-benzoxazin-6-yl]carbamate;

2,2,2-trifluoro-1,1-dimethylethyl [(2S)-2-{[(2S and 2R-amino-3,3,3-trifluoro-2-methylpropanoyl)amino]methyl}-4-{[1-(difluoromethyl)-3-(2-hydroxyethoxy)-1H-pyrazol-4-yl]sulfonyl}-3,4-dihydro-2H-1,4-benzoxazin-6-yl]carbamate;

2,2,2-trifluoro-1, 1-dimethylethyl {(2S)-4-{[1-(difluoromethyl)-3-(2-hydroxyethoxy)-1H-pyrazol-4-yl]sulfonyl}-2-[({[(1R,2R)-2-fluorocyclopropyl]carbonyl}amino)methyl]-3,4-dihydro-2H-1,4-benzoxazin-6-yl}carbamate;

2,2,2-trifluoro-1,1-dimethylethyl [(2S)-4-{[3-(2-hydroxyethoxy)-1-(1-methylethyl)-1H-pyrazol-4-yl]sulfonyl}-2-{[(2-hydroxy-2-methylpropanoyl)amino]methyl}-3,4-dihydro-2H-1,4-benzoxazin-6-yl]carbamate;

2,2,2-trifluoro-1,1-dimethylethyl [(2S)-2-[(acetylamino)methyl]-4-{[1-cyclopropyl-3-(2-hydroxyethoxy)-1H-pyrazol-4-yl]sulfonyl}-3,4-dihydro-2H-1,4-benzoxazin-6-yl]carbamate;

2,2,2-trifluoro-1, 1-dimethylethyl [(2S)-4-{[1-cyclopropyl-3-(2-hydroxyethoxy)-1H-pyrazol-4-yl]sulfonyl}-2-{[(2-hydroxy-2-methylpropanoyl)amino]methyl}-3,4-dihydro-2H-1,4-benzoxazin-6-yl]carbamate;

2,2,2-trifluoro-1, 1-dimethylethyl [(2S)-4-{[2-(2-hydroxyethoxy)pyrazolo[1,5-a]pyridin-3-yl]sulfonyl}-2-{[(2-hydroxy-2-methyl}-3,4-dihydro-2H-1,4-benzoxazin-6-yl]carbamate;

2,2,2-trifluoro-1,1-dimethylethyl [(2S)-4-{[1-ethyl-3-(2-hydroxyethoxy)-1H-pyrazol-4-yl]sulfonyl}-2-{[(oxetan-3-ylcarbonyl)amino]methyl}-3,4-dihydro-2H-1,4-benzoxazin-6-yl]carbamate;

2,2,2-trifluoro-1,1-dimethylethyl [(2S)-2-{[(cyclopropylsulfonyl)amino]methyl}-4-{[1-ethyl-3-(2-hydroxyethoxy)-1H-pyrazol-4-yl]sulfonyl}-3,4-dihydro-2H-1,4-benzoxazin-6-yl]carbamate;

2,2,2-trifluoro-1,1-dimethylethyl [(2S)-2-[(acetylamino)methyl]-4-{[1-(difluoromethyl)-3-(2-hydroxyethoxy)-1H-pyrazol-4-yl]sulfonyl}-3,4-dihydro-2H-1,4-benzoxazin-6-yl]carbamate;

2,2,2-trifluoro-1,1-dimethylethyl [(2S)-2-[(acetylamino)methyl]-4-{[3-(2-hydroxyethoxy)-1-(1-methylethyl)-1H-pyrazol-4-yl]sulfonyl}-3,4-dihydro-2H-1,4-benzoxazin-6-yl]carbamate;

2,2,2-trifluoro-1,1-dimethylethyl [(2S)-2-[(acetylamino)methyl]-4-{[2-(2-hydroxyethoxy)pyrazolo[1,5-a]pyridin-3-yl]sulfonyl}-3,4-dihydro-2H-1,4-benzoxazin-6-yl]carbamate;

methyl 2-((4-(((R)-2-((R or S)-acetamido(cyclopropyl)methyl)-6-((((1,1,1-trifluoro-2-methylpropan-2-yl)oxy)carbonyl)amino)-2H-benzo[b][1,4]oxazin-4(3H)-yl)sulfonyl)-1-ethyl-1H-pyrazol-3-yl)oxy)acetate;

1,1,1-trifluoro-2-methylpropan-2-yl ((R)-2-((R or S)-acetamido(cyclopropyl)methyl)-4-((1-ethyl-3-(2-hydroxyethoxy)-1H-pyrazol-4-yl)sulfonyl)-3,4-dihydro-2H-benzo[b][1,4]oxazin-6-yl)carbamate;

methyl 2-((4-(((R)-2-((R or S)-acetamido(cyclopropyl)methyl)-6-((((1,1,1-trifluoro-2-methylpropan-2-yl)

oxy)carbonyl)amino)-2H-benzo[b][1,4]oxazin-4(3H)-yl)sulfonyl)-1-ethyl-1H-pyrazol-3-yl)oxy)acetate;

1,1,1-trifluoro-2-methylpropan-2-yl ((R)-2-((R or S)-acetamido(cyclopropyl)methyl)-4-((1-ethyl-3-(2-hydroxyethoxy)-1H-pyrazol-4-yl)sulfonyl)-3,4-dihydro-2H-benzo[b][1,4]oxazin-6-yl)carbamate;

1,1,1-trifluoro-2-methylpropan-2-yl ((R)-2-((R or S)-cyclopropyl(2-hydroxy-2-methylpropanamido)methyl)-4-((1-ethyl-3-(2-hydroxyethoxy)-1H-pyrazol-4-yl)sulfonyl)-3,4-dihydro-2H-benzo[b][1,4]oxazin-6-yl)carbamate;

1,1,1-trifluoro-2-methylpropan-2-yl ((R)-2-((R or S)-cyclopropyl(2-hydroxy-2-methylpropanamido)methyl)-4-((1-ethyl-3-(2-hydroxyethoxy)-1H-pyrazol-4-yl)sulfonyl)-3,4-dihydro-2H-benzo[b][1,4]oxazin-6-yl)carbamate;

methyl 2-((4-(((R)-2-((R or S)-cyclopropyl(2-hydroxy-2-methylpropanamido)methyl)-6-((((1,1,1-trifluoro-2-methylpropan-2-yl)oxy)carbonyl)amino)-2H-benzo[b][1,4]oxazin-4(3H)-yl)sulfonyl)-1-ethyl-1H-pyrazol-3-yl)oxy)acetate;

methyl 2-((4-(((R)-2-((R or S)-cyclopropyl(2-hydroxy-2-methylpropanamido)methyl)-6-((((1,1,1-trifluoro-2-methylpropan-2-yl)oxy)carbonyl)amino)-2H-benzo[b][1,4]oxazin-4(3H)-yl)sulfonyl)-1-ethyl-1H-pyrazol-3-yl)oxy)acetate;

2,2,2-trifluoro-1,1-dimethylethyl [(2R)-2-[(1S or 1R)-1-(acetylamino)ethyl]-4-{[1-(difluoromethyl)-3-(2-hydroxyethoxy)-1H-pyrazol-4-yl]sulfonyl}-3,4-dihydro-2H-1,4-benzoxazin-6-yl]carbamate;

1,1,1-trifluoro-2-methylpropan-2-yl ((R)-2-((R or S)-1-acetamidopropyl)-4-((4-fluorophenyl)sulfonyl)-3,4-dihydro-2H-benzo[b][1,4]oxazin-6-yl)carbamate;

1,1,1-trifluoro-2-methylpropan-2-yl ((R)-2-((R or S)-1-acetamidopropyl)-4-((4-fluorophenyl)sulfonyl)-3,4-dihydro-2H-benzo[b][1,4]oxazin-6-yl)carbamate;

2,2,2-trifluoro-1,1-dimethylethyl [(2R)-2-[(1R or S)-1-(acetylamino)ethyl]-4-{[1-(difluoromethyl)-3-ethoxy-1H-pyrazol-4-yl]sulfonyl}-3,4-dihydro-2H-1,4-benzoxazin-6-yl]carbamate;

2,2,2-trifluoro-1,1-dimethylethyl [(2R)-2-[(1R or S)-1-(acetylamino)ethyl]-4-{[1-(difluoromethyl)-3-ethoxy-1H-pyrazol-4-yl]sulfonyl}-3,4-dihydro-2H-1,4-benzoxazin-6-yl]carbamate;

2,2,2-trifluoro-1,1-dimethylethyl [(2R)-2-[(1R or S)-1-(acetylamino)ethyl]-4-{[1-ethyl-3-(2-hydroxyethoxy)-1H-pyrazol-4-yl]sulfonyl}-3,4-dihydro-2H-1,4-benzoxazin-6-yl]carbamate;

2,2,2-trifluoro-1,1-dimethylethyl [(2R)-2-[(1R or S)-1-(acetylamino)ethyl]-4-{[1-ethyl-3-(2-hydroxyethoxy)-1H-pyrazol-4-yl]sulfonyl}-3,4-dihydro-2H-1,4-benzoxazin-6-yl]carbamate;

(S)-1,1,1-trifluoro-2-methylpropan-2-yl (2-((2-hydroxy-2-methylpropanamido)methyl)-4-((1-isopropyl-3-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (2-((2-hydroxy-2-methylpropanamido)methyl)-4-((1-isopropyl-5-methyl-1H-pyrazol-4-yl)sulfonyl)-3,4-dihydro-2H-benzo[b][1,4]oxazin-6-yl)carbamate;

(S)-1,1,1-trifluoro-2-methylpropan-2-yl (4-((1-cyclopropyl-3-methyl-1H-pyrazol-4-yl)sulfonyl)-2-((2-hydroxy-2-methylpropanamido)methyl)-3,4-dihydro-2H-benzo[b][1,4]oxazin-6-yl)carbamate;

(S)-1,1,1-trifluoro-2-methylpropan-2-yl (4-((1-cyclopropyl-5-methyl-1H-pyrazol-4-yl)sulfonyl)-2-((2-hydroxy-2-methylpropanamido)methyl)-3,4-dihydro-2H-benzo[b][1,4]oxazin-6-yl)carbamate;

2,2,2-trifluoro-1,1-dimethylethyl [(2S)-4-[(6-chloroimidazo[2,1-b][1,3]thiazol-5-yl)sulfonyl]-2-{[(2-hydroxy-2-methylpropanoyl)amino]methyl}-3,4-dihydro-2H-1,4-benzoxazin-6-yl]carbamate;

2,2,2-trifluoro-1,1-dimethylethyl [(2S)-2-{[(2-hydroxy-2-methylpropanoyl)amino]methyl}-4-{[3-(pentafluoro-lambda~6~-sulfanyl)phenyl]sulfonyl}-3,4-dihydro-2H-1,4-benzoxazin-6-yl]carbamate;

2,2,2-trifluoro-1,1-dimethylethyl {(2S)-2-{[(2-hydroxy-2-methylpropanoyl)amino]methyl}-4-[(1-methyl-1H-pyrazol-5-yl)sulfonyl]-3,4-dihydro-2H-1,4-benzoxazin-6-yl}carbamate;

2,2,2-trifluoro-1,1-dimethylethyl [(2S)-4-{[1-ethyl-3-(ethylamino)-1H-pyrazol-4-yl]sulfonyl}-2-{[(2-hydroxy-2-methylpropanoyl)amino]methyl}-3,4-dihydro-2H-1,4-benzoxazin-6-yl]carbamate;

2,2,2-trifluoro-1,1-dimethylethyl [(2S)-4-{[1-(difluoromethyl)-3-methyl-1H-pyrazol-4-yl]sulfonyl}-2-{[(2-hydroxy-2-methylpropanoyl)amino]methyl}-3,4-dihydro-2H-1,4-benzoxazin-6-yl]carbamate;

2,2,2-trifluoro-1,1-dimethylethyl [(2S)-2-{[(cyclopropylsulfonyl)amino]methyl}-4-{[3-(pentafluoro-lambda~6~-sulfanyl)phenyl]sulfonyl}-3,4-dihydro-2H-1,4-benzoxazin-6-yl]carbamate;

2,2,2-trifluoro-1,1-dimethylethyl {(2S,3R)-2-[(acetylamino)methyl]-4-[(3-ethoxy-1-ethyl-1iH-pyrazol-4-yl)sulfonyl]-3-methyl-3,4-dihydro-2H-1,4-benzoxazin-6-yl}carbamate;

2,2,2-trifluoro-1,1-dimethylethyl [(2S,3R)-4-{[1-(difluoromethyl)-3-methyl-1H-pyrazol-4-yl]sulfonyl}-3-methyl-2-{[(methylsulfonyl)amino]methyl}-3,4-dihydro-2H-1,4-benzoxazin-6-yl]carbamate;

2,2,2-trifluoro-1,1-dimethylethyl [(2S,3R)-4-{[1-(difluoromethyl)-3-methyl-1H-pyrazol-4-yl]sulfonyl}-2-{[(ethylsulfonyl)amino]methyl}-3-methyl-3,4-dihydro-2H-1,4-benzoxazin-6-yl]carbamate;

2,2,2-trifluoro-1,1-dimethylethyl [(2S,3R)-2-{[(cyclopropylsulfonyl)amino]methyl}-4-{[1-(difluoromethyl)-3-methyl-1H-pyrazol-4-yl]sulfonyl}-3-methyl-3,4-dihydro-2H-1,4-benzoxazin-6-yl]carbamate;

2,2,2-trifluoro-1,1-dimethylethyl [(2S,3R)-4-{[1-(difluoromethyl)-3-methyl-1H-pyrazol-4-yl]sulfonyl}-3-methyl-2-({[(2,2,2-trifluoroethyl)sulfonyl]amino}methyl)-3,4-dihydro-2H-1,4-benzoxazin-6-yl]carbamate;

2,2,2-trifluoro-1,1-dimethylethyl [(2S,3R)-4-{[1-(difluoromethyl)-3-methyl-1H-pyrazol-4-yl]sulfonyl}-2-{[(2-hydroxy-2-methylpropanoyl)amino]methyl}-3-methyl-3,4-dihydro-2H-1,4-benzoxazin-6-yl]carbamate;

2,2,2-trifluoro-1, 1-dimethylethyl {(2S,3R)-4-{[1-(difluoromethyl)-3-methyl-1H-pyrazol-4-yl]sulfonyl}-2-[({[(1R,2R)-2-fluorocyclopropyl]carbonyl}amino)methyl]-3-methyl-3,4-dihydro-2H-1,4-benzoxazin-6-yl}carbamate;

2,2,2-trifluoro-1,1-dimethylethyl [(2S,3R)-2-{[(2R and 2S-amino-3,3,3-trifluoro-2-methylpropanoyl)amino]methyl}-4-{[1-(difluoromethyl)-3-methyl-1H-pyrazol-4-yl]sulfonyl}-3-methyl-3,4-dihydro-2H-1,4-benzoxazin-6-yl]carbamate;

1,1,1-trifluoro-2-methylpropan-2-yl ((2S,3R)-4-((1-(difluoromethyl)-3-methyl-1H-pyrazol-4-yl)sulfonyl)-3-methyl-2-(((R and S)-3,3,3-trifluoro-2-hydroxy-2-methylpropanamido)methyl)-3,4-dihydro-2H-benzo[b][1,4]oxazin-6-yl)carbamate;

2,2,2-trifluoro-1,1-dimethylethyl [(2S,3R)-2-[({[(1S,2S)-2-cyanocyclopropyl]carbonyl}amino)methyl]-4-{[1-(difluoromethyl)-3-methyl-1H-pyrazol-4-yl]sulfonyl}-3-methyl-3,4-dihydro-2H-1,4-benzoxazin-6-yl]carbamate;

2,2,2-trifluoro-1,1-dimethylethyl [(2S,3R)-2-{[(cyclopropylcarbonyl)amino]methyl}-4-{[1-(difluoromethyl)-3-methyl-1H-pyrazol-4-yl]sulfonyl}-3-methyl-3,4-dihydro-2H-1,4-benzoxazin-6-yl]carbamate;

2,2,2-trifluoro-1,1-dimethylethyl {(2S,3R)-4-{[1-(difluoromethyl)-3-(2-hydroxyethoxy)-1H-pyrazol-4-yl]sulfonyl}-2-[({[(1R,2R)-2-fluorocyclopropyl]carbonyl}amino)methyl]-3-methyl-3,4-dihydro-2H-1,4-benzoxazin-6-yl}carbamate;

2,2,2-trifluoro-1,1-dimethylethyl [(2S,3R)-4-{[1-(difluoromethyl)-3-(2-hydroxyethoxy)-1H-pyrazol-4-yl]sulfonyl}-3-methyl-2-{[(methylsulfonyl)amino]methyl}-3,4-dihydro-2H-1,4-benzoxazin-6-yl]carbamate;

2,2,2-trifluoro-1,1-dimethylethyl [(2S,3R)-4-[(3-ethoxy-1-ethyl-1H-pyrazol-4-yl)sulfonyl]-3-methyl-2-{[(methylsulfonyl)amino]methyl}-3,4-dihydro-2H-1,4-benzoxazin-6-yl]carbamate;

2,2,2-trifluoro-1,1-dimethylethyl {(2S,3R)-4-[(3-ethoxy-1-ethyl-1H-pyrazol-4-yl)sulfonyl]-2-[({[(1R,2R)-2-fluorocyclopropyl]carbonyl}amino)methyl]-3-methyl-3,4-dihydro-2H-1,4-benzoxazin-6-yl}carbamate;

2,2,2-trifluoro-1,1-dimethylethyl {(2S,3R)-2-[({[(1R,2S)-2-cyanocyclopropyl]carbonyl}amino)methyl]-4-[(3-ethoxy-1-ethyl-1H-pyrazol-4-yl)sulfonyl]-3-methyl-3,4-dihydro-2H-1,4-benzoxazin-6-yl}carbamate;

2,2,2-trifluoro-1,1-dimethylethyl [(2S,3R)-4-[(3-ethoxy-1-ethyl-1H-pyrazol-4-yl)sulfonyl]-2-{[(2-hydroxy-2-methylpropanoyl)amino]methyl}-3-methyl-3,4-dihydro-2H-1,4-benzoxazin-6-yl]carbamate;

2,2,2-trifluoro-1,1-dimethylethyl [(2S,3R)-4-{[1-ethyl-3-(2-hydroxyethoxy)-1H-pyrazol-4-yl]sulfonyl}-3-methyl-2-{[(methylsulfonyl)amino]methyl}-3,4-dihydro-2H-1,4-benzoxazin-6-yl]carbamate;

2,2,2-trifluoro-1,1-dimethylethyl {(2S,3R)-4-{[1-ethyl-3-(2-hydroxyethoxy)-1H-pyrazol-4-yl]sulfonyl}-2-[({[(1R,2R)-2-fluorocyclopropyl]carbonyl}amino)methyl]-3-methyl-3,4-dihydro-2H-1,4-benzoxazin-6-yl}carbamate;

2,2,2-trifluoro-1,1-dimethylethyl [(2S,3R)-2-[({[(1R,2S)-2-cyanocyclopropyl]carbonyl}amino)methyl]-4-{[1-ethyl-3-(2-hydroxyethoxy)-1H-pyrazol-4-yl]sulfonyl}-3-methyl-3,4-dihydro-2H-1,4-benzoxazin-6-yl]carbamate;

2,2,2-trifluoro-1,1-dimethylethyl [(2S,3R)-4-{[1-ethyl-3-(2-hydroxyethoxy)-1H-pyrazol-4-yl]sulfonyl}-2-{[(2-hydroxy-2-methylpropanoyl)amino]methyl}-3-methyl-3,4-dihydro-2H-1,4-benzoxazin-6-yl]carbamate;

2,2,2-trifluoro-1,1-dimethylethyl [(2S,3R)-2-[(acetylamino)methyl]-4-{[1-ethyl-3-(2-hydroxyethoxy)-1H-pyrazol-4-yl]sulfonyl}-3-methyl-3,4-dihydro-2H-1,4-benzoxazin-6-yl]carbamate;

1,1,1-trifluoro-2-methylpropan-2-yl ((2S,3R)-2-((S)-1-acetamidoethyl)-4-((3,4-difluorophenyl)sulfonyl)-3-methyl-3,4-dihydro-2H-benzo[b][1,4]oxazin-6-yl)carbamate;

1,1,1-trifluoro-2-methylpropan-2-yl ((R)-2-((S)-1-acetamido-2,2,2-trifluoroethyl)-4-((4-fluorophenyl)sulfonyl)-3,4-dihydro-2H-benzo[b][1,4]oxazin-6-yl)carbamate;

1,1,1-trifluoro-2-methylpropan-2-yl ((R)-2-((R)-1-acetamido-2,2,2-trifluoroethyl)-4-((4-fluorophenyl)sulfonyl)-3,4-dihydro-2H-benzo[b][1,4]oxazin-6-yl)carbamate;

1,1,1-trifluoro-2-methylpropan-2-yl ((S)-2-((S)-1-acetamido-2,2,2-trifluoroethyl)-4-((4-fluorophenyl)sulfonyl)-3,4-dihydro-2H-benzo[b][1,4]oxazin-6-yl)carbamate; and 1,1,1-trifluoro-2-methylpropan-2-yl ((S)-2-((R)-1-acetamido-2,2,2-trifluoroethyl)-4-((4-fluorophenyl)sulfonyl)-3,4-dihydro-2H-benzo[b][1,4]oxazin-6-yl)carbamate.

* * * * *